(12) United States Patent
Velaparthi et al.

(10) Patent No.: US 9,556,179 B2
(45) Date of Patent: Jan. 31, 2017

(54) SUBSTITUTED IMIDAZOLES AS CASEIN KINASE 1 D/E INHIBITORS

(71) Applicant: BRISTOL-MYERS SQUIBB COMPANY, Princeton, NJ (US)

(72) Inventors: Upender Velaparthi, Cheshire, CT (US); Chetan Padmakar Darne, Orange, CT (US); Dharmpal S. Dodd, Princeton, NJ (US); Anthony J. Sampognaro, Meriden, CT (US); Mark D. Wittman, Wallingford, CT (US); Selvakumar Kumaravel, Bangalore (IN); Dibakar Mullick, Howrah District (IN); Peiying Liu, Madison, CT (US); Chandrasekhar Reddy Rachamreddy, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/653,895

(22) PCT Filed: Dec. 20, 2013

(86) PCT No.: PCT/US2013/076795
§ 371 (c)(1),
(2) Date: Jun. 19, 2015

(87) PCT Pub. No.: WO2014/100533
PCT Pub. Date: Jun. 26, 2014

(65) Prior Publication Data
US 2015/0344481 A1      Dec. 3, 2015

Related U.S. Application Data

(60) Provisional application No. 61/740,564, filed on Dec. 21, 2012.

(51) Int. Cl.
*C07D 487/04*   (2006.01)
*C07D 519/00*   (2006.01)

(52) U.S. Cl.
CPC ........... *C07D 487/04* (2013.01); *C07D 519/00* (2013.01)

(58) Field of Classification Search
CPC .................................................. C07D 487/04
See application file for complete search history.

(56) References Cited

U.S. PATENT DOCUMENTS

| | | |
|---|---|---|
| 7,820,665 B2 | 10/2010 | Booker et al. |
| 8,455,491 B2 | 6/2013 | Puech et al. |
| 2007/0078136 A1 | 4/2007 | Vaccaro et al. |
| 2010/0029619 A1 | 2/2010 | Uchikawa et al. |
| 2013/0190314 A1 | 7/2013 | Chiang et al. |

FOREIGN PATENT DOCUMENTS

| | | |
|---|---|---|
| EP | 2 058 309 A1 | 5/2009 |
| WO | WO 2010/070238 A1 | 6/2010 |
| WO | WO 2010/091409 A1 | 8/2010 |
| WO | WO 2014/100540 A1 | 6/2014 |

OTHER PUBLICATIONS

U.S. Appl. No. 14/653,878, filed Jun. 19, 2015.*
Pinedo et al. (2000).*
McMahon et al. (2000).*

* cited by examiner

*Primary Examiner* — Paul V Ward
(74) *Attorney, Agent, or Firm* — Hong Liu; Elliott Korsen

(57) ABSTRACT

The invention provides compounds of Formula (I) and pharmaceutically acceptable salts thereof. The compounds of Formula (I) inhibit protein kinase activity thereby making them useful as anticancer agents.

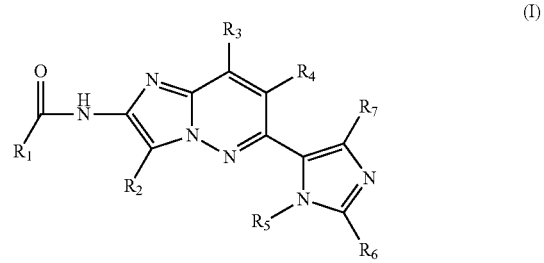

15 Claims, No Drawings

SUBSTITUTED IMIDAZOLES AS CASEIN KINASE 1 D/E INHIBITORS

CROSS REFERENCES TO RELATED APPLICATIONS

This application is a 371 of International Application No. PCT/US2013/076795, filed on Dec. 20, 2013, which claims the benefit of U.S. Provisional Application Ser. No. 61/740,564 filed on Dec. 21, 2012 which is incorporated herein by reference.

FIELD OF THE INVENTION

The invention relates to novel substituted imidazoles useful as protein kinase inhibitors. This invention also relates to methods of using the compounds in the treatment of proliferative and other types of diseases and to pharmaceutical compositions containing the compounds.

BACKGROUND OF THE INVENTION

The invention relates to substituted imidazole compounds which inhibit protein kinase enzymes, compositions which contain protein kinase inhibiting compounds and methods of using inhibitors of protein kinase enzymes to treat diseases which are characterized by an overexpression or upregulation of protein kinases. Protein kinases mediate intracellular signal transduction by affecting a phosphoryl transfer from a nucleoside triphosphate to a protein acceptor that is involved in a signaling pathway. There are a number of kinases and pathways through which extracellular and other stimuli cause a variety of cellular responses to occur inside the cell. An extracellular stimulus may affect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Serine/threonine kinases are a class of protein kinases that are among the most promising drug targets for future small molecule inhibitors. Inhibition of serine/threonine kinases is likely to have relevance to the treatment of cancer, diabetes and a variety of inflammatory disorders. The successful development of GLEEVEC® as a Bcr/Abl protein kinase inhibitor has provided further evidence that protein kinases are valid drug targets for potential cancer therapies.

Casein kinase 1 (CK1) belongs to the serine/threonine kinase family. In mammals, the enzyme exists in seven isozymic forms: $\alpha$, $\beta$, $\gamma1$, $\gamma2$, $\gamma3$, $\delta$, and $\epsilon$. By phosphorylating different substrate proteins, these isoforms are able to activate, inactivate, stabilize, or destabilize the functions of the proteins, regulating the functions of various types of different organisms. For example, a tumor suppressor factor p53 and an oncogene mdm2, which are both important proteins for controlling abnormal cell growth, are substrates of casein kinase 1.

Mammalian casein kinase 1δ and casein kinase 1ε are key regulators of diverse cellular growth and survival processes including Wnt signaling, DNA repair and circadian rhythms. They have a kinase domain that is similar to those of other isoforms. However, the N-terminal and C-terminal domains thereof are different from those of other isoforms. The C-terminal domain has a plurality of autophosphorylation sites, and it is considered to be involved in regulation of autoenzyme activity. Phosphorylation of p53 by casein kinase 1δ or casein kinase 1ε leads to a consequent change in the interaction between p53 and mdm2. It has also been known that casein kinase 1ε or casein kinase 1δ is involved in a regulatory protein associated with the formation of a spindle as a central body during cell division, and that the casein kinase 1δ or casein kinase 1ε is involved in apoptosis mediated by TRAIL (tumor necrosis factor-related apoptosis inducing factor) and Fas. It has been further reported that inhibition of casein kinase 1ε or casein kinase 1δ by a nonselective casein kinase 1 inhibitory compound IC261 reduces pancreatic tumor cell growth in vitro and in vivo (Brockschmidt et al., *Gut*, 57(6):799-806 (2008)). Hence, a medicament inhibiting the function of casein kinase 1δ or casein kinase 1ε would be expected to exert important phenotypic and therapeutic effects broadly in development and disease, especially cancer.

The present invention relates to a new class substituted imidazoles found to be effective in inhibiting casein kinase 1δ or casein kinase 1ε. These novel compounds are provided to be useful as pharmaceuticals with desirable stability, bioavailability, therapeutic index and toxicity values that are important to their drugability.

SUMMARY OF THE INVENTION

The invention is directed to substituted imidazole compounds of Formulae (I)-(VI) or stereoisomers, tautomers, pharmaceutically acceptable salts, solvates or prodrugs thereof, which inhibit protein kinase enzymes, especially protein kinase CK1 for the treatment of cancer.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides methods for inhibiting the activity of protein kinase CK1 comprising administering to a host in need of such treatment a therapeutically effective amount of at least one of the compounds of the present invention or stereoisomers, tautomers, pharmaceutically acceptable salts, solvates, or prodrugs thereof. The present invention also provides methods for treating cancers comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, in preparing a medicament for the treatment of cancer in a human patient, particularly a cancer receptive to treatment via inhibition of the CK1 enzyme.

These and other features of the invention will be set forth in the expanded form as the disclosure continues.

DETAILED DESCRIPTION OF THE INVENTION

The invention provides for novel substituted imidazole compounds useful as therapeutic agents, pharmaceutical compositions employing such novel compounds and for methods of using such compounds.

In accordance with the invention, there are disclosed compounds of Formula (I) including enantiomers, diastereomers, tautomers, pharmaceutically-acceptable salts, prodrugs, hydrates, or solvates thereof,

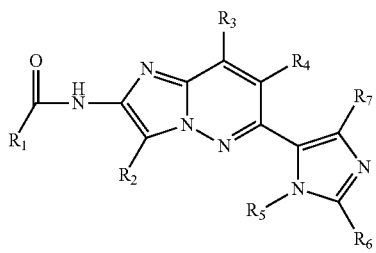

(I)

wherein:
$R_1$ is selected from $NR_aR_a$, $C_{1-4}$alkyl optionally substituted with OH, CN, and aryl, $C_{2-4}$alkenyl optionally substituted with OH, CN, and aryl, $-(CR_dR_d)_r$-carbocyclyl substituted with 0-5 $R_{11}$, and $-(CR_dR_d)_r$-heterocyclyl comprising carbon atoms and 1 to 3 heteroatoms selected from N, $NR_{12}$, O, S, and substituted with 0-5 $R_{11}$;
$R_2$ is selected from H, $C_{1-4}$alkyl, F, Cl, Br, and CN;
$R_3$ is selected from H and $C_{1-4}$alkyl;
$R_4$ is selected from H, $C_{1-4}$alkyl, F, Cl, Br, and CN;
$R_5$ is selected from H, $C_{1-4}$alkyl substituted with 0-4 $R_e$, $-(CH_2)_r$-$C_{3-6}$ carbocyclyl substituted with 0-4 $R_e$, and $-(CH_2)_r$-heterocyclyl comprising carbon atoms and 1 to 3 heteroatoms selected from N, $NR_8$, O, S, and substituted with 0-4 $R_e$;
$R_6$, is selected from H, $C_{1-6}$alkyl substituted with 0-3 $R_e$, and $C_{3-6}$carbocyclyl substituted with 0-3 $R_e$; or
$R_5$ and $R_6$ together with the nitrogen atom and the adjacent carbon atom to which they are respectively attached form a heterocyclic ring substituted with 0-5 $R_9$;
$R_7$ is aryl substituted with 0-3 $R_e$;
$R_8$ is selected from H, $C_{1-4}$ alkyl substituted with 0-3 $R_e$, $-(CH_2)_rOR_b$, $(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rC(=O)(CH_2)_rNR_aR_a$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_2NR_aR_a$, $-(CH_2)_rNR_aS(O)_2NR_aR_a$, $-(CH_2)_rNR_aS(O)_2R_c$, $(CH_2)_r$-$C_{3-6}$ carbocyclyl substituted with 0-3 $R_e$, and $-(CH_2)_r$-heterocyclyl substituted with 0-3 $R_e$;
$R_9$ is selected from $C_{1-4}$ alkyl substituted with 0-3 $R_e$, $-(CH_2)_rNR_aR_a$, $-(CH_2)_rC(=O)R_b$, $-(CH_2)_rC(=O)OR_b$, $-(CH_2)_rC(=O)NR_aR_a$, $S(O)_pR_c$, $(CH_2)_r$-$C_{3-6}$ carbocyclyl substituted with 0-3 $R_e$, and $-(CH_2)_r$-heterocyclyl substituted with 0-3 $R_e$;

$R_{11}$, at each occurrence, is independently selected from H, F, Cl, Br, =O, CN, $NO_2$, $-OR_b$, $-S(O)_pR_c$, $-C(=O)R_b$, $-(CR_dR_a)_rNR_aR_a$, $-(CR_dR_d)_rC(=O)NR_aR_a$, $-NR_aC(=O)R_b$, $-NR_aC(=O)OR_b$, $-OC(=O)NR_aR_a$, $-NR_aC(=O)NR_aR_a$, $-(CR_dR_d)_rC(=O)OR_b$, $-S(O)_2NR_aR_a$, $-NR_aS(O)_2NR_aR_a$, $-NR_aS(O)_2R_c$, $C_{1-6}$ alkyl substituted with 0-5 $R_e$, $-(CR_dR_d)_r$-$C_{3-6}$carbocyclyl substituted with 0-5 $R_e$, and $-(CR_dR_d)_r$-heterocyclyl substituted with 0-5 $R_e$;
$R_{12}$ is selected from H, $-C(=O)R_b$, $C_{1-6}$ alkyl substituted with 0-5 $R_e$, $-(CH_2)_r$-$C_{3-6}$carbocyclyl substituted with 0-5 $R_e$, and $-(CH_2)_r$-heterocyclyl substituted with 0-5 $R_e$;
$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r$-$C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r$-$C_{3-10}$carbocyclyl substituted with 0-5 $R_e$, and $-(CH_2)_r$-heterocyclyl substituted with 0-5 $R_e$;
$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;
$R_d$, at each occurrence, is independently selected from H and $C_{1-4}$alkyl substituted with 0-5 $R_e$;
$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r$-$C_{3-6}$ cycloalkyl, F, Cl, Br, CN, $NO_2$, =O, $CO_2H$, $-(CH_2)_rOC_{1-5}$ alkyl, $-(CH_2)_rOR_f$, $S(O)_pR_f$, $S(O)_pNR_fR_f$, and $-(CH_2)_rNR_fR_f$;
$R_f$, at each occurrence, is independently selected from H, $C_{1-5}$-alkyl, $C_{3-6}$cycloalkyl, and phenyl, or $R_f$ and $R_f$ together with the nitrogen atom to which they are both attached form a heterocyclic ring optionally substituted with $C_{1-4}$alkyl;
p, at each occurrence, is independently selected from zero, 1, and 2; and
r, at each occurrence, is independently selected from zero, 1, 2, 3, and 4.

In another aspect, there are disclosed compounds of Formula (II) including enantiomers, diastereomers, tautomers, pharmaceutically-acceptable salts, prodrugs, hydrates, or solvates thereof,

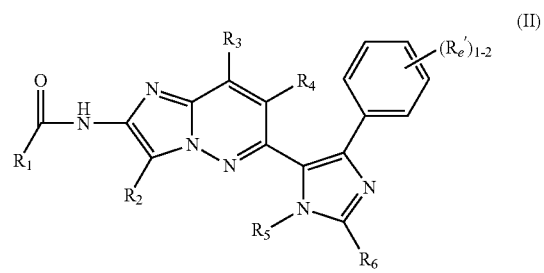

(II)

wherein:
$R_e'$ is selected from F, Cl, Br, $OC_{1-6}$ alkyl, and $C_{1-6}$ alkyl substituted with 0-5 $R_f$;
$R_5$ is selected from H, $C_{1-4}$alkyl substituted with 0-3 $R_e$, $-(CH_2)_r C_{3-6}$ carbocyclyl substituted with 0-3 $R_e$, and —(CH₂)ᵣ-heterocyclyl comprising carbon atoms and 1 to 3 heteroatoms selected from N, NR₈, O, S, and substituted with 0-3 R_e;

R₆, is selected from H, C₁₋₆alkyl substituted with 0-2 R_e, and C₃₋₆cycloalkyl substituted with 0-2 R_e; or R₅ and R₆ together with the nitrogen atom and the adjacent carbon atom to which they are respectively attached form a heterocyclic ring substituted with 0-4 R₉; and R₈ is selected from H, C₁₋₄ alkyl substituted with 0-3 R_e, —(CH₂)ᵣS(O)_pR_c, —(CH₂)ᵣCN, —(CH₂)ᵣOR_b, (CH₂)ᵣS(O)_pR_c, —(CH₂)ᵣC(=O)R_b, —(CH₂)ᵣNR_aR_a, (CH₂)ᵣC(=O)NR_aR_a, —(CH₂)ᵣC(=O)(CH₂)ᵣNR_aR_a, —(CH₂)ᵣNR_aC(=O)R_d, —(CH₂)ᵣNR_aC(=O)OR_b, —(CH₂)ᵣOC(=O)NR_aR_a, —(CH₂)ᵣNR_aC(=O)NR_aR_a, —(CH₂)ᵣC(=O)OR_b, —(CH₂)ᵣS(O)₂NR_eR_a, —(CH₂)ᵣNR_aS(O)₂R_c, —(CH₂)ᵣ—C₃₋₆ carbocyclyl substituted with 0-3 R_e, and —(CH₂)ᵣ-heterocyclyl substituted with 0-3 R_e;

other variables are as defined in Formula (I) above.

In another embodiment, there are disclosed compounds of Formula (II) including enantiomers, diastereomers, tautomers, pharmaceutically-acceptable salts, prodrugs, hydrates, or solvates thereof, wherein:

R₅ is selected from H, C₁₋₄alkyl substituted with 0-1 R_e, C₃₋₆cycloalkyl, aryl, and —(CH₂)ᵣ-heterocyclyl selected from pyridyl, pyrimidinyl, pyrazinyl, pyridazinyl, triazinyl, furyl, thienyl, imidazolyl, thiazolyl, indolyl, pyrrolyl, oxazolyl, isoxazolyl, pyrazolyl, triazolyl, tetrazolyl, indazolyl, 1,2,4-thiadiazolyl, isothiazolyl, azetidinyl, pyrrolidinyl, piperidinyl, piperazinyl, and morpholinyl;

other variables are as defined in Formula (I) above.

In another embodiment, there are disclosed compounds of Formula (II) including enantiomers, diastereomers, tautomers, pharmaceutically-acceptable salts, prodrugs, hydrates, or solvates thereof, wherein:

R₅ is selected from H,

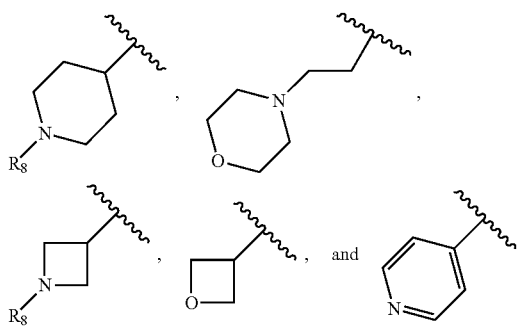

R₈ is selected from H, C₁₋₄ alkyl substituted with 0-3 R_e, —(CH₂)ᵣS(O)_pR_c, —(CH₂)ᵣOR_b, —(CH₂)ᵣC(=O)R_b, —(CH₂)ᵣNR_aR_a, —(CH₂)ᵣC(=O)NR_aR_a, —(CH₂)ᵣ(C=O)CH₂NR_aR_a, —(CH₂)ᵣNR_aC(=O)R_b, —(CH₂)ᵣN-R_aC(=O)OR_b, —(CH₂)ᵣC(=O)OR_b, and —(CH₂)ᵣ-heterocyclyl substituted with 0-3 R_e;

R_a, at each occurrence, is independently selected from H, C₁₋₆ alkyl substituted with 0-5 R_e, —(CH₂)ᵣ—C₃₋₁₀carbocyclyl substituted with 0-5 R_e, and —(CH₂)ᵣ-heterocyclyl substituted with 0-5 R_e; or R_a and R_a together with the nitrogen atom to which they are both attached form a heterocyclic ring substituted with 0-5 R_e;

R_b, at each occurrence, is independently selected from H, C₁₋₆ alkyl substituted with 0-5 R_e, —(CH₂)ᵣ—C₃₋₁₀carbocyclyl substituted with 0-5 R_e, and —(CH₂)ᵣ-heterocyclyl substituted with 0-5 R_e;

R_c, at each occurrence, is independently selected from C₁₋₆ alkyl substituted with 0-5 R_e, C₃₋₆carbocyclyl, and heterocyclyl;

R_e, at each occurrence, is independently selected from C₁₋₆ alkyl substituted with 0-5 R_f, —(CH₂)ᵣ—C₃₋₆ cycloalkyl, F, Cl, Br, CN, NO₂, =O, CO₂H, —(CH₂)ᵣOC₁₋₅alkyl, —(CH₂)ᵣOH, SH, and —(CH₂)ᵣNR_fR_f;

R_f, at each occurrence, is independently selected from H, C₁₋₅ alkyl, and phenyl, or R_f and R_f together with the nitrogen atom to which they are both attached form a heterocyclic ring;

other variables are as defined in Formula (I) above.

In another embodiment, there are disclosed compounds of formula (I) including enantiomers, diastereomers, tautomers, pharmaceutically-acceptable salts, prodrugs, hydrates, or solvates thereof, wherein:

R₅ and R₆ together with the nitrogen atom and the adjacent carbon atom to which they are respectively attached form a heterocyclic ring having 1 to 3 heteroatoms selected from N, O, S, and substituted with 0-3 R₉;

other variables are as defined in Formula (I) above.

In another embodiment, there are disclosed compounds of formula (III) including enantiomers, diastereomers, tautomers, pharmaceutically-acceptable salts, prodrugs, hydrates, or solvates thereof,

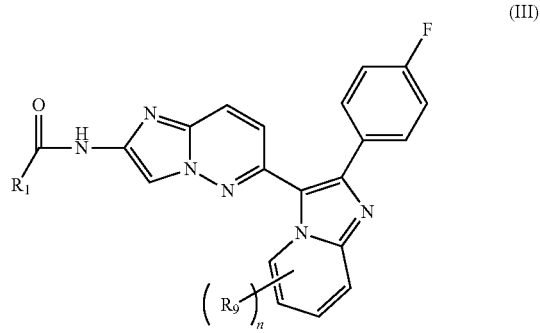

(III)

wherein:

R₉ is selected from NR_aR_a, SR_c, and —(CH₂)ᵣ-heterocyclyl substituted with 0-3 R_e;

R_a, at each occurrence, is independently selected from H, C₁₋₆ alkyl substituted with 0-5 R_e, C₃₋₁₀carbocyclyl substituted with 0-5 R_e, heterocyclyl substituted with 0-5 R_e; or R_a and R_a together with the nitrogen atom to which they are both attached form a heterocyclic ring substituted with 0-5 R_e;

R_c is C₁₋₄ alkyl substituted with 0-5 R_e;

R_e, at each occurrence, is independently selected from C₁₋₆ alkyl, F, Cl, Br, CN, NO₂, =O, CO₂H, and OH; and n, at each occurrence, is independently selected from zero, 1, and 2;

other variables are as defined in Formula (I) above.

In another embodiment, there are disclosed compounds of formula (IV) including enantiomers, diastereomers, tautomers, pharmaceutically-acceptable salts, prodrugs, hydrates, or solvates thereof, (IV)

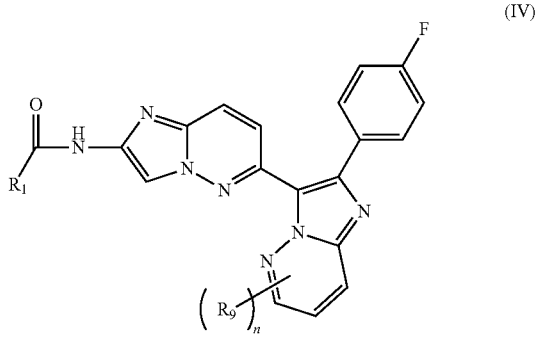

wherein:
R$_9$ is selected from NR$_a$R$_a$, SR$_c$, and —(CH$_2$)$_r$-heterocyclyl substituted with 0-3 R$_e$;
R$_a$, at each occurrence, is independently selected from H, C$_{1-6}$ alkyl substituted with 0-5 R$_e$, C$_{3-10}$carbocyclyl substituted with 0-5 R$_e$, heterocyclyl substituted with 0-5 R$_e$; or R$_a$ and R$_a$ together with the nitrogen atom to which they are both attached form a heterocyclic ring substituted with 0-5 R$_e$;
R$_c$ is C$_{1-4}$ alkyl substituted with 0-5 R$_e$;
R$_e$, at each occurrence, is independently selected from C$_{1-6}$ alkyl, F, Cl, Br, CN, NO$_2$, =O, CO$_2$H, and OH; and
n, at each occurrence, is independently selected from zero, 1, and 2;
other variables are as defined in Formula (I) above.

In another embodiment, there are disclosed compounds of formula (V) including enantiomers, diastereomers, tautomers, pharmaceutically-acceptable salts, prodrugs, hydrates, or solvates thereof, (V)

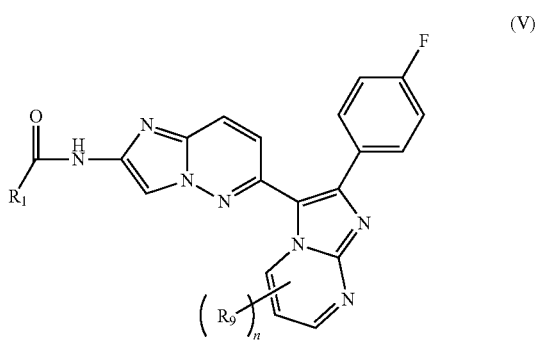

wherein:
R$_9$ is selected from NR$_a$R$_a$, SR$_c$, and —(CH$_2$)$_r$-heterocyclyl substituted with 0-3 R$_e$;
R$_a$, at each occurrence, is independently selected from H, C$_{1-6}$ alkyl substituted with 0-5 R$_e$, C$_{3-10}$carbocyclyl substituted with 0-5 R$_e$, heterocyclyl substituted with 0-5 R$_e$; or R$_a$ and R$_a$ together with the nitrogen atom to which they are both attached form a heterocyclic ring substituted with 0-5 R$_e$;
R$_c$ is C$_{1-4}$ alkyl substituted with 0-5 R$_e$;
R$_e$, at each occurrence, is independently selected from C$_{1-6}$ alkyl F, Cl, Br, CN, NO$_2$, =O, CO$_2$H, and OH; and
n, at each occurrence, is independently selected from zero, 1, and 2;
other variables are as defined in Formula (I) above.

In another embodiment, there are disclosed compounds of Formula (II) including enantiomers, diastereomers, tautomers, pharmaceutically-acceptable salts, prodrugs, hydrates, or solvates thereof, wherein:
R$_1$ is selected from C$_{1-4}$alkyl substituted with OH and CN, —CH=CH(CH$_2$)$_r$-aryl substituted with 0-4 R$_{11}$, —(CH$_2$)$_r$-aryl substituted with 0-4 R$_{11}$, —(CH$_2$)$_r$-cycloalkyl substituted with 0-4 R$_{11}$, and —(CH$_2$)$_r$-heterocyclyl comprising carbon atoms and 1 to 4 heteroatoms selected from N, NR$_{12}$, O, S and substituted with 0-4 R$_{11}$;
R$_{11}$, at each occurrence, is independently selected from H, F, Cl, Br, =O, CN, NO$_2$, —OR$_b$, —S(O)$_p$R$_c$, —C(=O)R$_b$, —(CH$_2$)$_r$NR$_a$R$_a$, —(CH$_2$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CH$_2$)$_r$C(=O)OR$_b$, C$_{1-6}$ alkyl substituted with 0-5 R$_e$, —(CH$_2$)$_r$—C$_{3-6}$carbocyclyl substituted with 0-5 R$_e$, and —(CH$_2$)$_r$-heterocyclyl substituted with 0-5 R$_e$;
R$_{12}$ is independently selected from H, —C(=O)R$_b$, C$_{1-6}$ alkyl substituted with 0-5 R$_e$, —(CH$_2$)$_r$—C$_{3-6}$carbocyclyl substituted with 0-5 R$_e$, and —(CH$_2$)$_r$-heterocyclyl substituted with 0-5 R$_e$;
R$_a$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;
R$_b$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;
R$_e$, at each occurrence, is independently selected from C$_{1-6}$ alkyl substituted with 0-5 R$_f$, —(CH$_2$)$_r$—C$_{3-6}$ cycloalkyl, F, Cl, Br, CN, NO$_2$, =O, CO$_2$H, —(CH$_2$)$_r$OC$_{1-5}$alkyl, —(CH$_2$)$_r$OH, SH, and —(CH$_2$)$_r$NR$_f$R$_f$; and
R$_f$, at each occurrence, is independently selected from H, C$_{1-5}$ alkyl, and phenyl, or R$_f$ and R$_f$ together with the nitrogen atom to which they are both attached form a heterocyclic ring;
other variables are as defined in Formula (I) above.

In another embodiment, there are disclosed compounds of Formula (II) including enantiomers, diastereomers, tautomers, pharmaceutically-acceptable salts, prodrugs, hydrates, or solvates thereof, wherein:
R$_1$ is heterocyclyl selected from pyridyl, pyrimidinyl, pyrazinyl, pyridazinyl, triazinyl, furyl, quinolinyl, quinoxalinyl, dihydroquinolinyl, tetrahydroquinolinyl, tetrahydropyranyl, isoquinolinyl, thienyl, imidazolyl, thiazolyl, indolyl, pyrrolyl, oxazolyl, benzofuryl, benzothienyl, benzothiazolyl, benzoxazinyl, isoxazolyl, pyrazolyl, triazolyl, tetrazolyl, indazolyl, 1,2,3-thiadiazolyl, 1,2,4-thiadiazolyl, isothiazolyl, purinyl, carbazolyl, benzimidazolyl, indolinyl, benzodioxolanyl, benzodioxane, 1,5-naphthyridinyl, imidazopyridinyl, azetidinyl, pyrrolidinyl, piperidinyl, piperazinyl, and morpholinyl;
other variables in the formula are as defined above.

In another embodiment, there are disclosed compounds of Formula (II) including enantiomers, diastereomers, tautomers, pharmaceutically-acceptable salts, prodrugs, hydrates, or solvates thereof, wherein:
R$_1$ is selected from carbocyclyl substituted with 0-4 R$_{11}$, and —(CH$_2$)$_r$-5- to 10-membered heterocyclyl comprising carbon atoms and 1 to 4 heteroatoms selected from N, NR$_9$, O, S and substituted with 0-4 R$_{11}$;

R$_5$ is selected from H, C$_{1-4}$alkyl substituted with 0-3 R$_e$ and —(CH$_2$)$_r$-heterocyclyl comprising carbon atoms and 1 to 3 heteroatoms selected from N, NR$_8$, O, S, and substituted with 0-3 R$_e$;

R$_6$ is selected from H, C$_{1-6}$alkyl substituted with 0-2 R$_e$, and C$_{3-6}$cycloalkyl substituted with 0-3 R$_e$;

R$_8$ is selected from H, C$_{1-4}$ alkyl substituted with 0-3 R$_e$, —(CH$_2$)$_r$C(=O)R$_b$, and —(CH$_2$)$_r$-heterocyclyl substituted with 0-3 R$_e$;

R$_{11}$, at each occurrence, is independently selected from H, F, Cl, CN, —OR$_b$, —(CH$_2$)$_r$NR$_a$R$_a$, —NR$_a$C(=O)R$_b$, C$_{1-6}$ alkyl substituted with 0-5 R$_e$, —(CH$_2$)$_r$—C$_{3-6}$carbocyclyl substituted with 0-5 R$_e$, and —(CH$_2$)$_r$-5- to 10-membered heterocyclyl substituted with 0-5 R$_e$;

R$_a$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_e$, at each occurrence, is independently selected from C$_{1-6}$ alkyl substituted with 0-5 R$_f$, —(CH$_2$)$_r$—C$_{3-6}$ cycloalkyl, F, Cl, Br, CN, NO$_2$, =O, CO$_2$H, —(CH$_2$)$_r$OC$_{1-5}$alkyl, —(CH$_2$)$_r$OH, S(O)$_2$C$_{1-4}$alkyl, and —(CH$_2$)$_r$NR$_f$R$_f$;

R$_f$, at each occurrence, is independently selected from H, C$_{1-5}$ alkyl, and phenyl, or R$_f$ and R$_f$ together with the nitrogen atom to which they are both attached form a heterocyclic ring; and r, at each occurrence, is independently selected from zero, 1, 2, 3, and 4.

In another embodiment, there are disclosed compounds of Formula (II) including enantiomers, diastereomers, tautomers, pharmaceutically-acceptable salts, prodrugs, hydrates, or solvates thereof, wherein:

R$_1$ is selected from

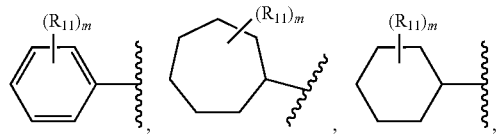

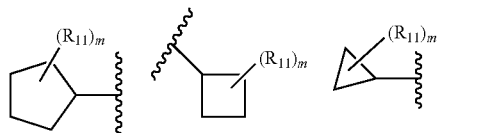

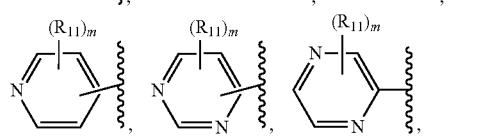

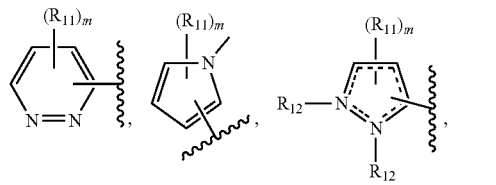

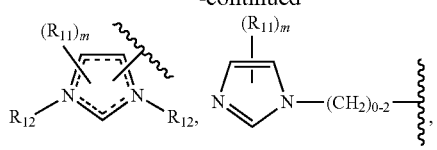

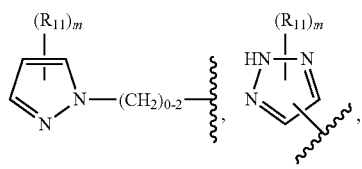

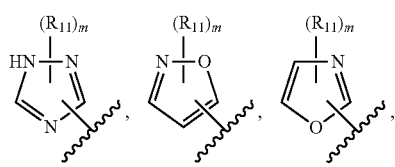

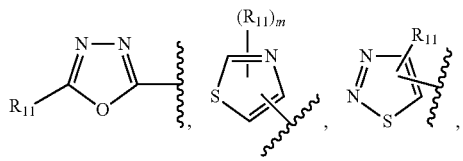

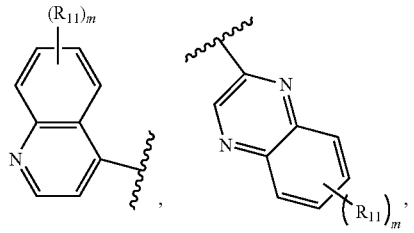

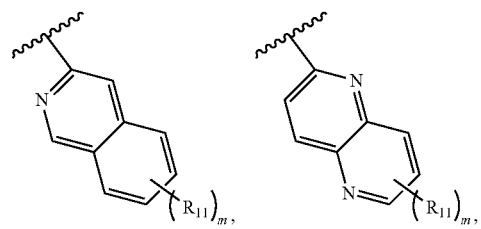

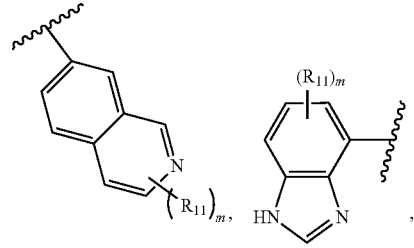

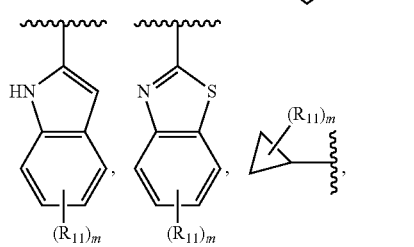

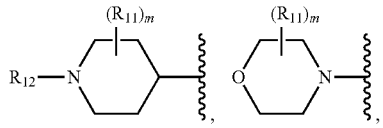

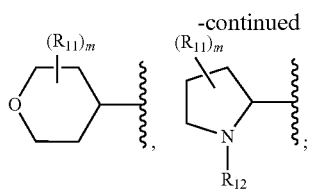

---- represents an optional bond;
R$_{11}$, at each occurrence, is independently selected from H, F, Cl, Br, =O, CN, —OR$_b$, —C(=O)R$_b$, —(CH$_2$)$_r$NR$_a$R$_a$, —(CH$_2$)$_r$C(=O)NR$_a$R$_a$, —NR$_a$C(=O)R$_b$, —(CH$_2$)$_r$C(=O)OR$_b$, C$_{1-6}$ alkyl substituted with 0-5 R$_e$, —(CH$_2$)$_r$—C$_{3-6}$carbocyclyl substituted with 0-5 R$_e$, and —(CH$_2$)$_r$-heterocyclyl substituted with 0-5 R$_e$;
R$_{12}$, at each occurrence, is independently selected from H, —C(=O)R$_b$, C$_{1-6}$ alkyl substituted with 0-5 R$_e$; and
m, at each occurrence, is independently selected from zero, 1, and 2
other variables in the formula are as defined above.

In another embodiment, there are disclosed compounds of Formula (II) including enantiomers, diastereomers, tautomers, pharmaceutically-acceptable salts, prodrugs, hydrates, or solvates thereof, wherein:
R$_1$ is selected from —CH=CH(CH$_2$)$_r$-aryl, aryl substituted with 0-4 R$_{11}$, cycloalkyl substituted with 0-4 R$_{11}$, and —(CH$_2$)$_r$5- to 10-membered heterocyclyl comprising carbon atoms and 1 to 4 heteroatoms selected from N, NR$_{12}$, O, S and substituted with 0-4 R$_{11}$;
R$_5$ is selected from H, C$_{1-4}$alkyl substituted with 0-3 R$_e$ and —(CH$_2$)$_r$-heterocyclyl comprising carbon atoms and 1 to 3 heteroatoms selected from N, NR$_8$, O, S, and substituted with 0-3 R$_e$;
R$_6$, is selected from H, C$_{1-6}$alkyl substituted with 0-2 R$_e$, and C$_{3-6}$cycloalkyl substituted with 0-3 R$_e$; or
R$_5$ and R$_6$ together with the nitrogen atom and the adjacent carbon atom to which they are respectively attached form a heterocyclic ring substituted with 0-5 R$_9$; and
R$_8$ is selected from H, C$_{1-4}$ alkyl substituted with 0-3 R$_e$, —(CH$_2$)$_r$OR$_b$, —(CH$_2$)$_r$C(=O)R$_b$, —(CH$_2$)$_r$NR$_a$R$_a$, —(CH$_2$)$_r$C(=O)NR$_a$R$_a$, and —(CH$_2$)$_r$-heterocyclyl substituted with 0-3 R$_e$;
R$_{11}$, at each occurrence, is independently selected from H, F, Cl, CN, —OR$_b$, —(CH$_2$)$_r$NR$_a$R$_a$, —NR$_a$C(=O)R$_b$, C$_{1-6}$ alkyl substituted with 0-5 R$_e$, —(CH$_2$)$_r$—C$_{3-6}$carbocyclyl substituted with 0-5 R$_e$, and —(CH$_2$)$_r$-5- to 10-membered heterocyclyl substituted with 0-5 R$_e$;
R$_a$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;
R$_b$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;
R$_e$, at each occurrence, is independently selected from C$_{1-6}$ alkyl substituted with 0-5 R$_f$, —(CH$_2$)$_r$—C$_{3-6}$ cycloalkyl, F, Cl, Br, CN, NO$_2$, =O, CO$_2$H, —(CH$_2$)$_r$OC$_{1-5}$alkyl, —(CH$_2$)$_r$OH, SH, and —(CH$_2$)$_r$NR$_f$R$_f$; and
R$_f$, at each occurrence, is independently selected from H, C$_{1-5}$ alkyl, and phenyl, or R$_f$ and R$_f$ together with the nitrogen atom to which they are both attached form a heterocyclic ring.

In another embodiment, there are disclosed compounds of Formula (II) including enantiomers, diastereomers, tautomers, pharmaceutically-acceptable salts, prodrugs, hydrates, or solvates thereof, wherein:
R$_1$ is selected from

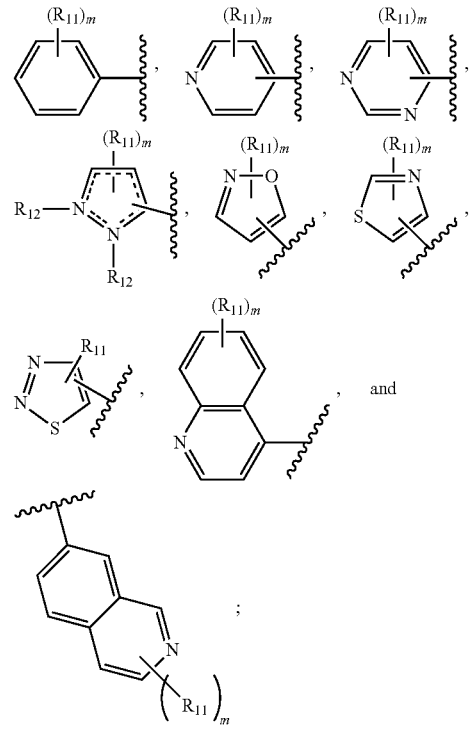

R$_5$ is selected from H, C$_{1-4}$alkyl substituted with 0-3 R$_e$,

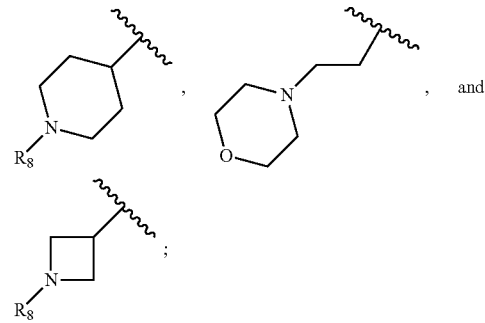

R$_6$, is selected from H, C$_{1-4}$alkyl, and C$_{3-6}$cycloalkyl; or
R$_5$ and R$_6$ together with the nitrogen atom and the adjacent carbon atom to which they are respectively attached form a heterocyclic ring comprising carbon atoms and 1 to 3 nitrogen atoms;
R$_8$ is selected from H, C$_{1-4}$alkyl, —(CH$_2$)$_r$CN, —(CH$_2$)$_r$OH, —(CH$_2$)$_r$C(=O)NH$_2$, —C(=O)CH$_2$NH$_2$, —C(=O)CH$_2$CN, —C(=O)CH$_2$CF$_3$, C(=O)CH$_2$OH, and C(=O)-isoxazolyl;
R$_{11}$, at each occurrence, is independently selected from F, Cl, CN, —NR$_a$R$_a$, —NHC(=O)R$_b$, C$_{1-4}$ alkyl substituted with 0-5 R$_e$,

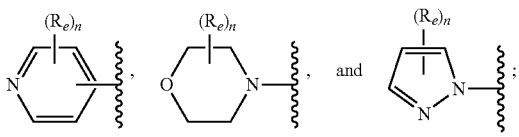

$R_{12}$, at each occurrence, is independently selected from H and $C_{1-4}$ alkyl;

$R_a$, at each occurrence, is independently selected from H, $C_{1-4}$ alkyl substituted with 0-5 $R_e$;

$R_b$, at each occurrence, is independently selected from H, $C_{1-4}$ alkyl substituted with 0-5 $R_e$;

$R_e$, at each occurrence, is independently selected from $C_{1-6}$ alkyl substituted with 0-5 $R_f$, —$(CH_2)_r$—$C_{3-6}$ cycloalkyl, F, Cl, Br, CN, $NO_2$, =O, $CO_2H$, —$(CH_2)_rOC_{1-5}$alkyl, —$(CH_2)_rOH$, SH, and $NH_2$;

m, at each occurrence, is independently selected from zero, 1, and 2 n, at each occurrence, is independently selected from zero and 1; and r, at each occurrence, is independently selected from zero, 1, and 2;

other variables are as defined in Formula (I) above.

In another embodiment, there are disclosed compounds of Formula (VI)

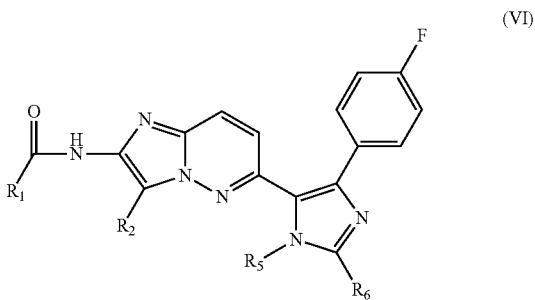

(VI)

including enantiomers, diastereomers, tautomers, pharmaceutically-acceptable salts, prodrugs, hydrates, or solvates thereof, wherein:

$R_1$ is selected from aryl substituted with 0-4 $R_{11}$, cycloalkyl substituted with 0-4 $R_{11}$, and —$(CH_2)_r$-5- to 10-membered heterocyclyl comprising carbon atoms and 1 to 4 heteroatoms selected from N, $NR_{12}$, O, S and substituted with 0-4 $R_{11}$;

$R_2$ is selected from H, $C_{1-4}$alkyl, F, Cl, Br, and CN;

$R_5$ is selected from H, $C_{1-4}$alkyl substituted with 0-3 $R_e$, —$(CH_2)_r$—$C_{3-6}$ carbocyclyl substituted with 0-3 $R_e$, and —$(CH_2)_r$-heterocyclyl comprising carbon atoms and 1 to 3 heteroatoms selected from N, $NR_8$, O, S, and substituted with 0-3 $R_e$;

$R_6$, is selected from H, $C_{1-6}$alkyl substituted with 0-2 $R_e$, and $C_{3-6}$cycloalkyl substituted with 0-2 $R_e$; and $R_8$ is selected from H, $C_{1-4}$ alkyl substituted with 0-3 $R_e$—$(CH_2)_rCN$, —$(CH_2)_rOR_b$, $(CH_2)_rS(O)_pR_c$, —$(CH_2)_rNR_aR_a$, —$(CH_2)_rC(=O)NR_aR_a$, —$(CH_2)_rC(=O)(CH_2)_rNR_aR_a$, —$(CH_2)_rNR_aC(=O)R_d$, —$(CH_2)_rNR_aC(=O)OR_b$, —$(CH_2)_r$—$OC(=O)NR_aR_a$, —$(CH_2)_rNR_aC(=O)NR_aR_a$, —$(CH_2)_rC(=O)OR_b$, —$(CH_2)_rS(O)_2NR_aR_a$, —$(CH_2)_rNR_aS(O)_2R_c$, —$(CH_2)_r$—$C_{3-6}$ carbocyclyl substituted with 0-3 $R_e$, and —$(CH_2)_r$-heterocyclyl substituted with 0-3 $R_e$;

other variables in the formula are as defined in Formula (I).

In another embodiment of the compounds of Formulae (I) and (II), $R_1$ is heterocyclyl selected from pyridyl, pyrimidinyl, pyrazinyl, pyridazinyl, triazinyl, furyl, quinolinyl, dihydroquinolinyl, tetrahydroquinolinyl, isoquinolinyl, thienyl, imidazolyl, thiazolyl, indolyl, pyrrolyl, oxazolyl, benzofuryl, benzothienyl, benzthiazolyl, benzoxazinyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane, each of which is substituted with 0-4 $R_{11}$.

In still another embodiment, $R_1$ is $C_{1-4}$ alkyl and $C_{3-6}$ cycloalkyl substituted with 0-4 $R_{11}$.

In another embodiment, $R_1$ is substituted with 0-4 $R_{11}$ and is heteroaryl selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, isoquinolinyl, tetrahydroquinolinyl, and tetrahydroisoquinolinyl.

All aspects of the compounds, including individual variable definitions, may be combined with other aspects to form additional compounds. For example, in one embodiment of Formula (I), $R_1$ is heteroaryl and $R_5$ is hydrogen. In another embodiment, $R_1$ is $C_{3-6}$ cycloalkyl and $R_5$ is hydrogen. In still another embodiment, $R_1$ is heteroaryl and $R_5$ is heterocyclyl.

In certain embodiments, the present invention includes compounds of Formula (I), or stereoisomers, tautomers, pharmaceutically acceptable salts, solvates, or prodrugs thereof, wherein:

$R_1$ is selected from —$(CR_dR_d)_r$-carbocyclyl substituted with 0-5 $R_{11}$, and —$(CR_dR_d)_r$-heterocyclyl comprising carbon atoms and 1 to 4 heteroatoms selected from N, $NR_{12}$, O, S, and substituted with 0-5 $R_{11}$;

$R_2$ is H;

$R_3$ is H;

$R_4$ is H;

$R_5$ is selected from H, $C_{1-4}$alkyl substituted with 0-4 $R_e$, —$(CH_2)_r$—$C_{3-6}$ carbocyclyl substituted with 0-4 $R_e$, and —$(CH_2)_r$-heterocyclyl comprising carbon atoms and 1 to 3 heteroatoms selected from N, $NR_8$, O, S, and substituted with 0-4 $R_e$;

$R_6$ is selected from H, $C_{1-6}$alkyl substituted with 0-3 $R_e$, and $C_{3-6}$carbocyclyl substituted with 0-3 $R_e$; or $R_5$ and $R_6$ together with the nitrogen atom and the adjacent carbon atom to which they are respectively attached form a heterocyclic ring substituted with 0-5 $R_9$;

$R_7$ is aryl substituted with 0-3 $R_e$;

$R_8$ is selected from H, $C_{1-4}$ alkyl substituted with 0-3 $R_e$, —$(CH_2)_rCN$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)$—$C_{1-4}$ alkyl substituted with 0-3 $R_e$, —$(CH_2)_r$—$NR_aC(=O)R_b$, —$(CH_2)_rNR_aC(=O)OR_b$, —$(CH_2)_r$—$OC(=O)NR_aR_a$, —$(CH_2)_rNR_aC(=O)$ $NR_aR_a$, —$(CH_2)_rC(=O)OR_b$, —$(CH_2)_rS(O)_2NR_aR_a$, —$(CH_2)_rNR_aS(O)_2NR_aR_a$, —$(CH_2)_rNR_aS(O)_2R_c$, $(CH_2)_r$-carbocyclyl substituted with 0-3 $R_e$, and —$(CH_2)_r$-heterocyclyl substituted with 0-3 $R_e$;

$R_{11}$, at each occurrence, is independently selected from H, F, Cl, Br, =O, CN, $NO_2$, —$OR_b$, —$S(O)_pR_c$, —$C(=O)R_b$, —$(CR_dR_d)_rNR_aR_a$, —$(CR_dR_d)_rC(=O)NR_aR_a$, —$NR_aC(=O)R_b$, —$NR_aC(=O)OR_b$, —$OC(=O)NR_aR_a$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$carbocyclyl substituted with 0-5 $R_e$, and —$(CR_dR_d)_r$-heterocyclyl substituted with 0-5 $R_e$;

$R_{12}$ is selected from H, —C(=O)$R_b$, $C_{1-6}$ alkyl substituted with 0-5 $R_e$, —$(CH_2)_r$—$C_{3-6}$carbocyclyl substituted with 0-5 $R_e$, and —$(CH_2)_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOR_f$, $S(O)_pR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_1$ alkyl;

p, at each occurrence, is independently selected from zero, 1, and 2; and r, at each occurrence, is independently selected from zero, 1, 2, 3, and 4.

In certain embodiments, the present invention includes compounds of Formula (I), or stereoisomers, tautomers, pharmaceutically acceptable salts, solvates, or prodrugs thereof, wherein:

$R_1$ is heterocyclyl selected from pyridyl, pyrimidinyl, pyrazinyl, pyridazinyl, triazinyl, furyl, quinolinyl, quinoxalinyl, dihydroquinolinyl, tetrahydroquinolinyl, tetrahydropyranyl, isoquinolinyl, thienyl, imidazolyl, thiazolyl, indolyl, pyrrolyl, oxazolyl, benzofuryl, benzothienyl, benzothiazolyl, benzoxazinyl, isoxazolyl, pyrazolyl, triazolyl, tetrazolyl, indazolyl, 1,2,3-thiadiazolyl, 1,2,4-thiadiazolyl, isothiazolyl, purinyl, carbazolyl, benzimidazolyl, indolinyl, benzodioxolanyl, benzodioxane, 1,5-naphthyridinyl, imidazopyridinyl, azetidinyl, pyrrolidinyl, piperidinyl, piperazinyl, and morpholinyl, each heterocyclyl substituted with 0-5 $R_{11}$;

$R_2$ is H;
$R_3$ is H;
$R_4$ is H;
$R_5$ is heterocyclyl comprising carbon atoms and 1 to 3 heteroatoms selected from N, $NR_8$, O, S, and substituted with 0-4 &;
$R_6$ is selected from H, $C_{1-6}$alkyl substituted with 0-3 $R_e$, and $C_{3-6}$carbocyclyl substituted with 0-3 $R_e$; or
$R_5$ and $R_6$ together with the nitrogen atom and the adjacent carbon atom to which they are respectively attached form a heterocyclic ring substituted with 0-5 $R_9$;
$R_7$ is aryl substituted with 0-2 $R_e$;

$R_{12}$ is selected from H, —C(=O)$R_b$, $C_{1-6}$ alkyl substituted with 0-5 $R_e$, —$(CH_2)_r$—$C_{3-6}$carbocyclyl substituted with 0-5 $R_e$, and —$(CH_2)_r$-heterocyclyl substituted with 0-5 $R_e$;

$R_{11}$, at each occurrence, is independently selected from H, F, Cl, Br, =O, CN, $NO_2$, —$OR_b$, —$S(O)_pR_c$, —C(=O)$R_b$, —$(CR_dR_d)_rNR_aR_a$, —$(CR_dR_d)_rC(=O)NR_aR_a$, —$NR_aC(=O)R_b$, —$NR_aC(=O)OR_b$, —$OC(=O)NR_aR_a$, —$NR_aC(=O)NR_aR_a$, —$(CR_dR_d)_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_dR_d)_r$—$C_{3-6}$carbocyclyl substituted with 0-5 $R_e$, and —$(CR_dR_d)_r$-heterocyclyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOR_f$, $S(O)_pR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_1$ alkyl;

p, at each occurrence, is independently selected from zero, 1, and 2; and r, at each occurrence, is independently selected from zero, 1, 2, 3, and 4.

In certain embodiments, the present invention includes compounds of Formula (I), or stereoisomers, tautomers, pharmaceutically acceptable salts, solvates, or prodrugs thereof, wherein:

$R_1$ is heterocyclyl selected from pyridyl, pyrimidinyl, pyrazinyl, pyridazinyl, triazinyl, furyl, quinolinyl, quinoxalinyl, dihydroquinolinyl, tetrahydroquinolinyl, tetrahydropyranyl, isoquinolinyl, thienyl, imidazolyl, thiazolyl, indolyl, pyrrolyl, oxazolyl, benzofuryl, benzothienyl, benzothiazolyl, benzoxazinyl, isoxazolyl, pyrazolyl, triazolyl, tetrazolyl, indazolyl, 1,2,3-thiadiazolyl, 1,2,4-thiadiazolyl, isothiazolyl, purinyl, carbazolyl, benzimidazolyl, indolinyl, benzodioxolanyl, benzodioxane, 1,5-naphthyridinyl, imidazopyridinyl, azetidinyl, pyrrolidinyl, piperidinyl, piperazinyl, and morpholinyl, each heterocyclyl substituted with 0-5

$R_2$ is H;
$R_3$ is H;
$R_4$ is H;
$R_5$ is H,

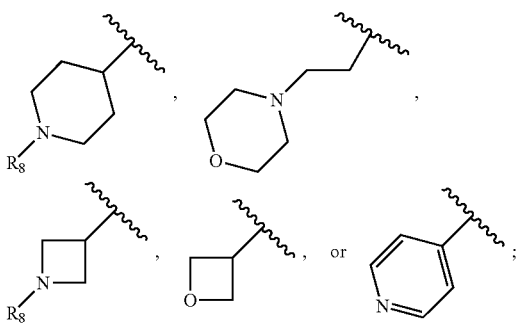

R$_6$ is selected from H, C$_{1-6}$alkyl substituted with 0-3 R$_e$, and C$_{3-6}$carbocyclyl substituted with 0-3 R$_e$; or R$_7$ is aryl substituted with 0-3 R$_e$;

R$_8$ is selected from H, C$_{1-4}$ alkyl substituted with 0-3 R$_e$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)—C$_{1-4}$ alkyl substituted with 0-3 R$_e$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, (CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, (CH$_2$)$_r$-carbocyclyl substituted with 0-3 R$_e$, and —(CH$_2$)$_r$-heterocyclyl substituted with 0-3 R$_e$;

R$_{11}$, at each occurrence, is independently selected from H, F, Cl, Br, =O, CN, NO$_2$, —OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, C$_{1-6}$ alkyl substituted with 0-5 R$_e$, —(CR$_d$R$_d$)$_r$—C$_{3-6}$carbocyclyl substituted with 0-5 R$_e$, and —(CR$_d$R$_d$)$_r$-heterocyclyl substituted with 0-5 R$_e$;

R$_{12}$ is selected from H, —C(=O)R$_b$, C$_{1-6}$ alkyl substituted with 0-5 R$_e$, —(CH$_2$)$_r$—C$_{3-6}$carbocyclyl substituted with 0-5 R$_e$, and —(CH$_2$)$_r$-heterocyclyl substituted with 0-5 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, F, Cl, Br, CN, NO$_2$, =O, CO$_2$H, —(CH$_2$)$_r$OR$_f$, S(O)$_p$R$_f$, and —(CH$_2$)$_r$NR$_f$R$_f$;

R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

In other embodiments, the present invention includes compounds of Formula (I), or stereoisomers, tautomers, pharmaceutically acceptable salts, solvates, or prodrugs thereof, wherein:

R$_1$ is selected from

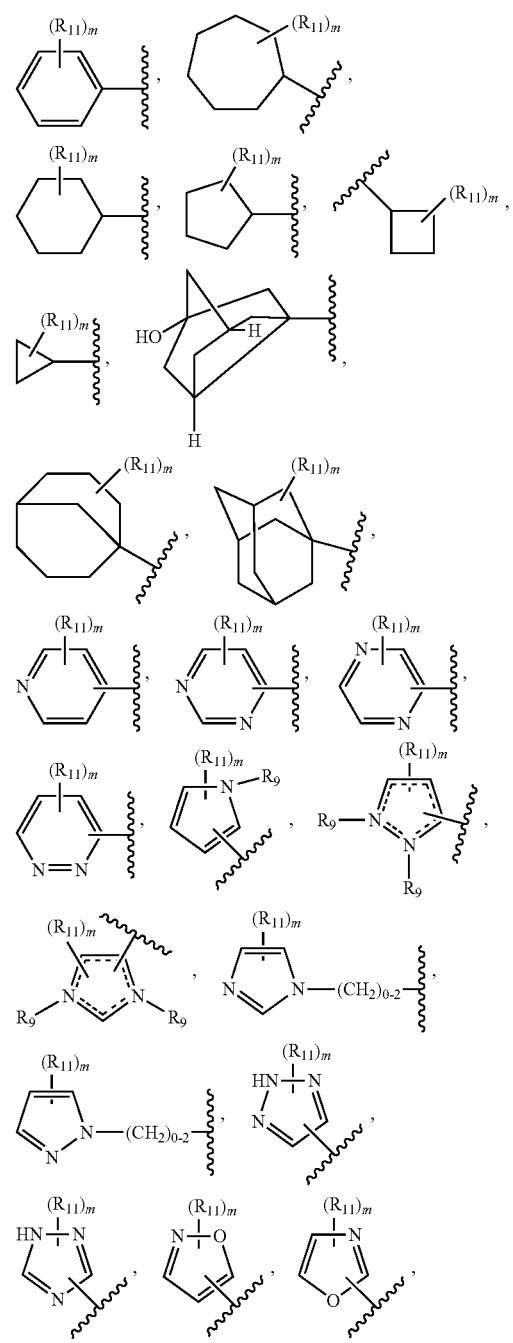

-continued

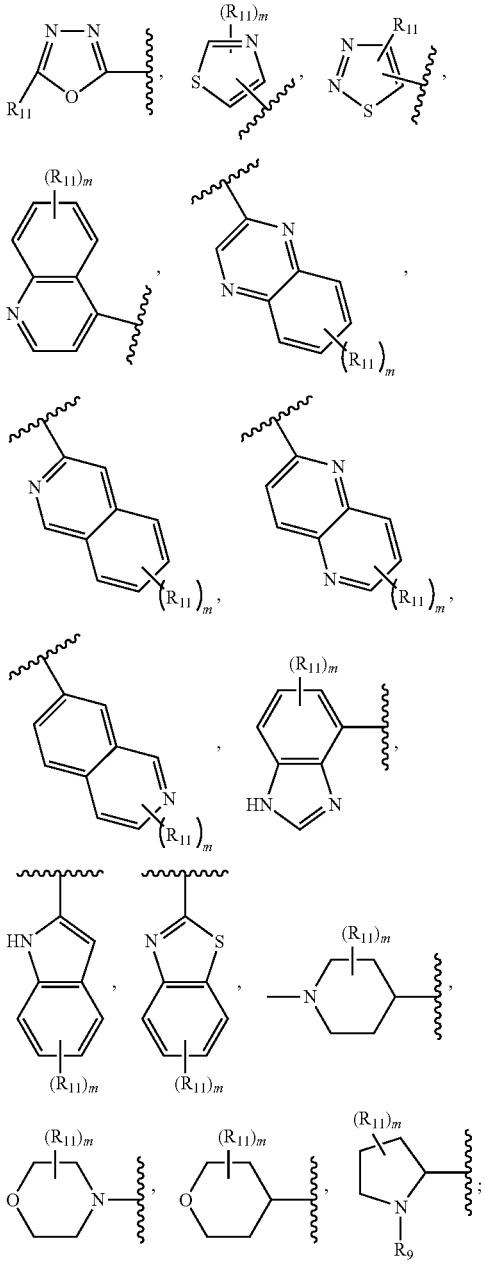

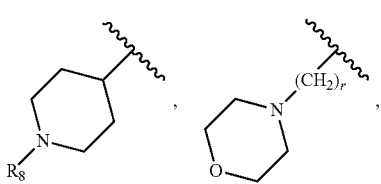

---- represents an optional bond;
R$_2$ is H;
R$_3$ is H;
R$_4$ is H;
R$_5$ is selected from H, -continued

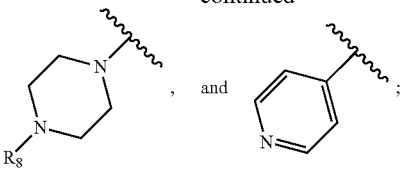

R$_6$ is selected from H, C$_{1-6}$alkyl substituted with 0-3 R$_e$, and C$_{3-6}$carbocyclyl substituted with 0-3 R$_e$; or R$_8$ is selected from H, C$_{1-4}$ alkyl substituted with 0-3 R$_e$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)—C$_{1-4}$ alkyl substituted with 0-3 R$_e$, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$NR$_a$R$_a$, —(CH$_2$)$_r$NR$_a$S(O)$_2$R$_c$, (CH$_2$)$_r$-carbocyclyl substituted with 0-3 R$_e$, and —(CH$_2$)$_r$-heterocyclyl substituted with 0-3 R$_e$;

R$_{11}$, at each occurrence, is independently selected from H, F, Cl, Br, =O, CN, NO$_2$, —OR$_b$, —S(O)$_p$R$_c$, —C(=O)R$_b$, —(CR$_d$R$_d$)$_r$NR$_a$R$_a$, —(CR$_d$R$_d$)$_r$C(=O)NR$_a$R$_a$, —NR$_a$C(=O)R$_b$, —NR$_a$C(=O)OR$_b$, —OC(=O)NR$_a$R$_a$, —NR$_a$C(=O)NR$_a$R$_a$, —(CR$_d$R$_d$)$_r$C(=O)OR$_b$, —S(O)$_2$NR$_a$R$_a$, —NR$_a$S(O)$_2$NR$_a$R$_a$, —NR$_a$S(O)$_2$R$_c$, C$_{1-6}$ alkyl substituted with 0-5 R$_e$, —(CR$_d$R$_d$)$_r$—C$_{3-6}$carbocyclyl substituted with 0-5 R$_e$, and —(CR$_d$R$_d$)$_r$-heterocyclyl substituted with 0-5 R$_e$;

R$_{12}$ is selected from H, —C(=O)R$_b$, C$_{1-6}$ alkyl substituted with 0-5 R$_e$, —(CH$_2$)$_r$—C$_{3-6}$carbocyclyl substituted with 0-5 R$_e$, and —(CH$_2$)$_r$-heterocyclyl substituted with 0-5 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, F, Cl, Br, CN, NO$_2$, =O, CO$_2$H, —(CH$_2$)$_r$OR$_f$, S(O)$_p$R$_f$, and —(CH$_2$)$_r$NR$_f$R$_f$;

R$_f$, at each occurrence, is independently selected from H, C$_{1-5}$ alkyl, C$_{3-6}$ cycloalkyl, and phenyl, or R$_f$ and R$_f$ together with the nitrogen atom to which they are both attached form a heterocyclic ring optionally substituted with C$_1$ alkyl;

p, at each occurrence, is independently selected from zero, 1, and 2; and r, at each occurrence, is independently selected from zero, 1, 2, 3, and 4.

The compounds of Formulae (I)-(VI) may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for Formulae (I)-(VI) may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

The present invention is also intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the Formulae (I)-(VI) may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:

a) *Design of Prodrugs*, Bundgaard, H., ed., Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and c) Bundgaard, H., *Adv. Drug Deliv. Rev.*, 8:1-38 (1992).

It should further be understood that solvates (e.g., hydrates) of the compounds of Formulae (I)-(VI) are also within the scope of the invention. Methods of solvation are generally known in the art. The inventive compounds may either be in the free or hydrate form.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

DEFINITIONS

The following are definitions of terms used in this specification and appended claims. The initial definition provided for a group or term herein applies to that group or term throughout the specification and claims, individually or as part of another group, unless otherwise indicated.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

As used herein, the term "alkyl" or "alkylene" is intended to include both branched and straight-chain saturated aliphatic hydrocarbon groups having the specified number of carbon atoms. For example, "C$_{1-10}$ alkyl" (or alkylene), is intended to include C$_1$, C$_2$, C$_3$, C$_4$, C$_5$, C$_6$, C$_7$, C$_8$, C$_9$, and C$_{10}$ alkyl groups. Additionally, for example, "C$_1$-C$_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "halogen" or "halo" refers to fluorine (F), chlorine (Cl), bromine (Br) and iodine.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle", "carbocyclic residue", or "carbocyclyl" is intended to mean any stable 3-, 4-, 5-, 6-, or 7-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle", "carbocyclic residue", or "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

The term "aryl" refers to monocyclic, bicyclic, tricyclic aromatic hydrocarbon groups having 6 to 15 carbon atoms in the ring portion, such as phenyl, naphthyl, biphenyl and diphenyl groups, each of which may be substituted. Aryl groups which are bicyclic or tricyclic must include at least one fully aromatic ring but the other fused ring or rings may be aromatic or non-aromatic. When an aryl is substituted with a further heterocyclic ring, said ring may be attached to the aryl through a carbon atom or a heteroatom and said ring in turn is optionally substituted with one to two substituents as valence allows.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "cycloalkyl" refers to an optionally substituted, saturated cyclic hydrocarbon ring systems, preferably containing 1 to 3 rings and 3 to 7 carbons per ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

As used herein, the term "heterocycle", "heterocyclyl", "heterocyclic ring" or "heterocyclic group" is intended to mean a stable 4-, 5-, 6-, or 7-membered monocyclic or bicyclic or 7-, 8-, 9-, 10-, 11-, 12-, 13-, or 14-membered bicyclic heterocyclic ring which is saturated, partially unsaturated or fully unsaturated or aromatic, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on a carbon atom or on a nitrogen atom if the resulting compound is stable. A nitrogen atom in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle", "heterocyclyl", "heterocyclic ring" or "heterocyclic group" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and Spiro compounds containing, for example, the above heterocycles.

Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (0, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, dihydroisoquinolinyl, tetrahydroquinolinyl, isoquinolinyl, benzimidazolyl, benzopyranyl, benzoxazinyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and the like.

Exemplary tricyclic heteroaryl groups include carbazolyl, benzidolyl, phenanthrollinyl, acridinyl, phenanthridinyl, xanthenyl and the like.

The term "heteroatoms" shall include oxygen, sulfur and nitrogen.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

When any variable occurs more than one time in any constituent or formula for a compound, its definition at each occurrence is independent of its definition at every other occurrence. Thus, for example, if a group is shown to be substituted with 0-3 $R_e$, then said group may optionally be substituted with up to three $R_e$ groups and $R_e$ at each occurrence is selected independently from the definition of $R_e$. Also, combinations of substituents and/or variables are permissible only if such combinations result in stable compounds.

Utility

The compounds of the invention may be used to modulate kinase activities.

Applicants have discovered that compounds of Formulae (I)-(VI) have particular utility in treating conditions associated with the modulation of the serine/threonine kinase activity, especially that of casein kinase 1δ or casein kinase 1ε. The diseases, with the pathological conditions of which the activation mechanism of casein kinase 1δ or casein kinase 1ε associated, are not limited. Examples of such diseases include circadian rhythm disorder (including sleep disorder), neurodegenerative disease, and proliferative disorder (cancer).

In the present specification, the type of circadian rhythm disorder is not limited. The circadian rhythm disorder includes mood disorder and sleep disorder. Such sleep disorder is circadian rhythm sleep disorder, and the circadian rhythm sleep disorder includes a disease selected from the group consisting of shift work sleep disorder, jet lag syndrome, advanced sleep phase syndrome, and delayed sleep phase syndrome. Moreover, the sleep disorder includes a disease selected from the group consisting of insomnia, sleep-related breathing disorder, central hypersomnia, parasomnia, and sleep-related movement disorder. Furthermore, the above-described mood disorder is selected from either depressive disorder or bipolar disorder, and the depressive disorder is major depressive disorder. Further, the mood disorder is selected from either depressive disorder or bipolar disorder, and the bipolar disorder is selected from the group consisting of bipolar type-I disorder or bipolar type-II disorder. Still further, examples of the disease in the present invention include insomnia, sleep-related breathing disorder, central hypersomnia, circadian rhythm sleep disorder, parasomnia, sleep-related movement disorder, and sleep disorder caused by other reasons.

In the present specification, insomnia includes psychophysiologic insomnia caused by stress or the like, insomnia caused by medical disease, and the like. Sleep-related breathing disorder includes central sleep apnea syndrome, obstructive sleep apnea syndrome, sleep-related hypoventilation/anoxemia syndrome, and the like. Central hypersomnia includes narcolepsy, idiopathic hypersomnia, recurrent hypersomnia, and the like. Circadian rhythm sleep disorder includes shift work sleep disorder, jet lag syndrome, advanced sleep phase syndrome, delayed sleep phase syndrome, and the like. Parasomnia includes sleep walking, REM sleep behavior disorder, and the like. Sleep-related movement disorder includes restless legs syndrome, periodic limb movement disorder, and the like.

In the present specification, the type of neurodegenerative disease is not limited, Examples of central neurodegenerative disease include: neurodegenerative disease caused by Alzheimer's disease, Parkinson's disease or Down's syndrome; nerve degeneration caused by physical nerve damage (brain tissue damage such as brain contusion, and nerve damage caused by head injury and the like); and nerve degeneration caused by nerve damage occurred after ischemia or ischemic reperfusion include: stroke, cerebral infarction, cerebral hemorrhage, cerebral ischemia, subarachnoid hemorrhage, aneurysmal hemorrhage, myocardial infarction, hypoxia, anoxia and nerve damage caused by grand mal/cerebral ischemia.

The compounds of the present invention can be used to treat proliferative disorders associated with abnormal kinase activity. As used herein, the terms "treating" and "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

Accordingly, one aspect of the invention is the use of a compound of the Formulae (I)-(VI), or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of Formulae (I)-(VI) or a pharmaceutically acceptable salt thereof as defined herein before.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. Compounds of Formulae (I)-(VI) may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisene, hydroxyprogesterone, aminoglutethimide, estramustine, medroxyprogesteroneacetate, leuprolide, flutamide, toremifene, ZOLADEX®; matrix metalloproteinase inhibitors; VEGF inhibitors, such as anti-VEGF antibodies (AVASTIN®) and small molecules such as ZD6474 and SU6668; Vatalanib, BAY-43-9006, SU11248, CP-547632, and CEP-7055; HER 1 and HER 2 inhibitors including anti-HER2 antibodies (HERCEPTIN®); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g., GLEEVEC® and dasatinib; CASODEX® (bicalutamide, Astra Zeneca), Tamoxifen; MEK-1 kinase inhibitors, MAPK kinase inhibitors, PI3 kinase inhibitors; PDGF inhibitors, such as imatinib; antiangiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (ixabepilone), [15-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; other CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g., 6-thioguanine and 6-mercaptopurine; glutamine antagonists, e.g., DON (AT-125; d-oxonorleucine); ribonucleotide reductase inhibitors; mTOR inhibitors; and haematopoietic growth factors.

Additional cytotoxic agents include cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein may be surgery, radiotherapy or chemotherapy. Such chemotherapy may cover three main categories of therapeutic agent:

(i) antiangiogenic agents that work by different mechanisms from those defined herein before (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as AVASTIN® (bevacizumab) and ERBITUX® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); intercalating antitumor antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide, nitrosoureas, thiotepa; antimitotic agents (for example, vinca alkaloids like vincristine, vinorelbine, vinblastine and vinflunine) and taxoids such as TAXOL® (paclitaxel), Taxotere (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as VELCADE® (bortezomib).

As stated above, the Formulae (I)-(VI) compounds of the invention are of interest for their antiproliferative effects. More specifically, the compounds of Formulae (I)-(VI) are useful in the treatment of a variety of cancers, including (but not limited to) the following:

carcinoma, including that of the prostate, pancreatic ductal adenocarcinoma, breast, colon, lung, ovary, pancreas, and thyroid;

tumors of the central and peripheral nervous system, including neuroblastoma, glioblastoma, and medulloblastoma; and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neurofibromatosis, pulmonary fibrosis, arthritis, psoriasis, glomerulonephritis, restenosis following angioplasty or vascular surgery, hypertrophic scar formation and inflammatory bowel disease.

The compounds of Formulae (I)-(VI) are especially useful in treatment of tumors having a high incidence of serine/threonine kinase activity, such as prostate, colon, lung, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

Compounds of Formulae (I)-(VI) may also be useful in the treatment of other cancerous diseases (such as acute myelogenous leukemia) that may be associated with signal transduction pathways operating through kinases such as DYRK1a, CDK, and GSK3β. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formulae (I)-(VI) and a pharmaceutically acceptable carrier.

A "pharmaceutically acceptable carrier" refers to media generally accepted in the art for the delivery of biologically active agents to animals, in particular, mammals Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS® Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

The compounds of Formulae (I)-(VI) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

When a compound according to this invention is administered into a human subject, the daily dosage will normally be determined by the prescribing physician with the dosage generally varying according to the age, weight, sex and response of the individual patient, as well as the severity of the patient's symptoms. Exemplary dosage amounts for a mammal may include from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of protein kinase enzyme levels.

If formulated as a fixed dose, a combination product can, for example, utilize a dosage of the compound of Formulae (I)-(VI) within the dosage range described above and the dosage of another anti-cancer agent/treatment within the approved dosage range for such known anti-cancer agent/treatment. If a combination product is inappropriate, the compounds of Formulae (I)-(VI) and the other anti-cancer agent/treatment can, for example, be administered simultaneously or sequentially. If administered sequentially, the present invention is not limited to any particular sequence of administration. For example, compounds of Formulae (I)-(VI) can be administered either prior to, or after, administration of the known anti-cancer agent or treatment.

Biological Assays

CK1ε and CK1δ Kinase Assays

The kinase assay was performed in V-bottom 384-well plates. The final assay volume was 30 μl prepared from 15 μl additions of enzyme, substrates (fluoresceinated peptide FL-AHA-KRRRAL-PSER-VASLPGL-OH and ATP) and test compounds in assay buffer (20 mM HEPES pH 7.4, 30 mM $MgCl_2$, 0.015% Brij35 and 4 mM DTT). The reaction was incubated at room temperature for 22 hours and terminated by adding 45 μl of 35 mM EDTA to each sample. The reaction mixture was analyzed on the Caliper LAB-CHIP®3000 (Caliper, Hopkinton, Mass.) by electrophoretic separation of the unphosphorylated substrate and phosphorylated product. Inhibition data were calculated by comparison of the no enzyme control reactions for 100% inhibition and vehicle-only reactions for 0% inhibition. The final concentration of reagents in the assay were 200 pM CK1ε or CK1δ, 50 μM ATP, 1.5 μM FL-AHA-KRRRAL-PSER-VASLPGL-OH, and 1.6% DMSO. Dose response curves were generated to determine the concentration required to inhibit 50% of the kinase activity ($IC_{50}$). Compounds were dissolved at 10 mM in dimethylsulfoxide (DMSO) and evaluated at eleven concentrations. $IC_{50}$ values were derived by non-linear regression analysis.

The following compounds were found to have the $IC_{50}$ described in Table A when measured in the assays described above.

TABLE A

| Example No. | CK1ε ($IC_{50}$, μM) | CK1δ ($IC_{50}$, μM) |
| --- | --- | --- |
| 1 | 0.000943 | 0.000064 |
| 2 | 0.002456 | 0.002540 |
| 3 | 0.000298 | 0.000306 |
| 4 | 0.002248 | 0.000302 |
| 5 | 0.001418 | 0.000379 |
| 6 | 0.001173 | 0.000264 |
| 7 | 0.001774 | 0.000284 |
| 8 | 0.000225 | 0.000195 |
| 9 | 0.000681 | 0.000920 |
| 10 | 0.002268 | 0.000847 |
| 11 | 0.000654 | 0.000847 |
| 12 | 0.000283 | 0.000847 |
| 13 | 0.000610 | 0.000214 |
| 14 | 0.003905 | 0.000624 |
| 15 | 0.014150 | 0.000215 |
| 16 | 0.003055 | 0.000295 |
| 17 | 0.021770 | 0.002141 |
| 18 | 0.000599 | 0.000259 |
| 19 | — | 0.000611 |
| 20 | 0.001775 | 0.000280 |
| 21 | 0.005559 | 0.000170 |
| 22 | 0.001293 | 0.000101 |
| 23 | 0.000675 | 0.000183 |
| 24 | 0.000183 | 0.000165 |
| 25 | — | 0.000532 |
| 26 | 0.002229 | 0.000449 |
| 27 | 0.001133 | 0.000265 |
| 28 | 0.001273 | 0.000207 |
| 29 | 0.000676 | 0.000226 |
| 30 | 0.001998 | 0.000295 |
| 31 | 0.011170 | 0.000742 |
| 32 | 0.010650 | 0.000602 |
| 33 | 0.001896 | 0.000378 |
| 34 | 0.012390 | 0.000136 |
| 35 | 0.007218 | 0.000527 |
| 36 | 0.001577 | 0.000197 |
| 37 | 0.001273 | 0.000296 |
| 38 | 0.000305 | 0.000292 |
| 39 | 0.002217 | 0.001926 |
| 40 | 0.000984 | 0.000085 |
| 41 | 0.001009 | 0.000128 |
| 42 | 0.002934 | 0.002792 |
| 43 | 0.000952 | 0.000234 |
| 44 | 0.001232 | 0.000295 |
| 45 | 0.016420 | 0.001975 |
| 46 | 0.000743 | 0.000198 |
| 47 | 0.001097 | 0.000225 |
| 48 | 0.001450 | 0.000220 |
| 49 | 0.007331 | 0.001059 |
| 50 | 0.001105 | 0.000278 |
| 51 | 0.002576 | 0.000240 |
| 52 | 0.001438 | 0.000347 |
| 53 | 0.001562 | 0.000191 |
| 54 | 0.003091 | 0.000446 |
| 55 | 0.001047 | 0.000178 |
| 56 | 0.000297 | 0.000130 |
| 57 | 0.003420 | 0.000321 |
| 58 | 0.000457 | 0.000233 |
| 59 | 0.001974 | 0.000579 |
| 60 | 0.000545 | 0.000213 |
| 61 | 0.001261 | 0.000186 |
| 62 | 0.000256 | 0.000313 |
| 63 | 0.000391 | 0.000239 |
| 64 | 0.000798 | 0.000361 |
| 65 | 0.001371 | 0.000256 |
| 66 | 0.007198 | 0.000928 |
| 67 | 0.000233 | 0.000116 |
| 68 | 0.000811 | 0.000193 |
| 69 | — | — |
| 70 | 0.000493 | 0.000143 |
| 71 | 0.000676 | 0.000172 |
| 72 | 0.000559 | 0.000183 |
| 73 | 0.000608 | 0.000354 |
| 74 | 0.001520 | 0.000675 |
| 75 | 0.003486 | 0.001402 |
| 76 | 0.001805 | 0.000251 |
| 77 | 0.014000 | 0.000744 |
| 78 | 0.002228 | 0.000295 |
| 79 | 0.001914 | 0.000376 |
| 80 | 0.000809 | 0.000171 |
| 81 | 0.001634 | 0.000311 |
| 82 | 0.001590 | 0.000247 |
| 83 | 0.000461 | 0.000142 |
| 84 | 0.000967 | 0.000179 |
| 85 | 0.002342 | 0.000309 |
| 86 | 0.000851 | 0.000286 |
| 87 | 0.001053 | 0.000402 |
| 88 | 0.002558 | 0.000380 |
| 89 | 0.001095 | 0.000146 |
| 90 | 0.005683 | 0.000650 |
| 91 | 0.000796 | 0.000296 |
| 92 | 0.007876 | 0.001446 |
| 93 | 0.002473 | 0.000393 |
| 94 | 0.001267 | 0.000338 |
| 95 | 0.000170 | 0.000060 |
| 96 | 0.000966 | — |
| 97 | 0.000095 | 0.000034 |
| 98 | 0.003879 | 0.000268 |
| 99 | 0.001261 | 0.000329 |
| 100 | 0.000128 | 0.000091 |
| 101 | 0.001242 | 0.000334 |
| 102 | 0.000484 | 0.000243 |
| 103 | 0.000356 | 0.000267 |
| 104 | 0.001223 | 0.000847 |
| 105 | 0.000096 | — |
| 106 | 0.003125 | 0.000732 |
| 107 | 0.001918 | 0.000467 |
| 108 | 0.003303 | 0.000306 |
| 109 | 0.001025 | 0.000557 |
| 110 | 0.003267 | 0.000650 |
| 111 | 0.000564 | 0.000233 |
| 112 | 0.000886 | 0.000494 |
| 113 | 0.001510 | 0.000438 |

TABLE A-continued

| Example No. | CK1ε (IC$_{50}$, μM) | CK1δ (IC$_{50}$, μM) |
|---|---|---|
| 115 | 0.003884 | 0.000159 |
| 116 | 0.000372 | 0.000173 |
| 117 | 0.000424 | 0.000175 |
| 118 | 0.000182 | 0.000194 |
| 119 | 0.008269 | 0.001211 |
| 120 | 0.016650 | 0.001516 |
| 121 | 0.010810 | 0.000489 |
| 122 | 0.002861 | 0.000446 |
| 123 | 0.016690 | 0.002865 |
| 124 | 0.027070 | 0.003724 |
| 125 | 0.006034 | 0.000950 |
| 126 | 0.009024 | 0.001662 |
| 127 | 0.010050 | 0.001752 |
| 128 | 0.006412 | 0.000301 |
| 129 | 0.019140 | 0.002281 |
| 130 | 0.053280 | 0.003323 |
| 131 | 0.020690 | 0.001966 |
| 132 | 0.014180 | 0.001699 |
| 133 | 0.013110 | 0.000907 |
| 134 | 0.007825 | 0.000542 |
| 135 | 0.002603 | 0.000745 |
| 136 | 0.008897 | 0.000514 |
| 137 | 0.005783 | 0.000203 |
| 138 | 0.011020 | 0.001564 |
| 139 | — | — |
| 140 | 0.022200 | 0.002285 |
| 141 | 0.016000 | 0.001027 |
| 142 | 0.002548 | 0.000414 |
| 143 | 0.000656 | 0.000112 |
| 144 | 0.001555 | 0.000254 |
| 145 | 0.009510 | 0.000962 |
| 146 | 0.024750 | 0.002241 |
| 147 | 0.004905 | 0.000529 |
| 148 | 0.009872 | 0.000608 |
| 149 | 0.002836 | 0.002193 |
| 150 | 0.003806 | 0.000034 |
| 151 | — | — |
| 152 | 0.003072 | — |
| 153 | 0.005295 | 0.000204 |
| 154 | 0.008642 | 0.000915 |
| 155 | 0.007483 | 0.000451 |
| 156 | 0.000976 | 0.000249 |
| 157 | 0.009934 | 0.000587 |
| 158 | 0.002732 | 0.000854 |
| 159 | 0.005598 | 0.001314 |
| 160 | 0.003211 | 0.000306 |
| 161 | 0.002505 | 0.000415 |
| 162 | 0.002418 | 0.000311 |
| 163 | 0.000936 | 0.000242 |
| 164 | 0.067300 | 0.004366 |
| 165 | 0.053570 | 0.004645 |
| 166 | 0.001304 | 0.000192 |
| 167 | 0.000687 | 0.000104 |
| 168 | 0.001727 | 0.000110 |
| 169 | 0.005237 | 0.000492 |
| 170 | 0.008429 | 0.000743 |
| 171 | 0.007676 | 0.001977 |
| 172 | — | — |
| 173 | 0.003482 | 0.000315 |
| 174 | 0.607100 | 0.073680 |
| 175 | 0.019350 | 0.003934 |
| 176 | 0.047410 | 0.005684 |
| 177 | 0.024170 | 0.006798 |
| 178 | 1.520000 | 0.199600 |
| 179 | 0.002932 | 0.000206 |
| 180 | 0.012120 | 0.001601 |
| 181 | 0.010800 | 0.004012 |
| 182 | 0.006134 | 0.000530 |
| 183 | 0.003821 | 0.000207 |
| 184 | 0.077220 | 0.007527 |
| 185 | 0.010200 | 0.003799 |
| 186 | 0.011360 | 0.010340 |
| 187 | 0.030270 | 0.010480 |
| 188 | 0.009803 | 0.003565 |
| 189 | 0.032090 | 0.017080 |
| 190 | 0.006054 | 0.004771 |
| 191 | 0.003020 | 0.002111 |
| 192 | 0.001056 | 0.000096 |
| 193 | 0.001277 | 0.000111 |
| 194 | 0.013780 | 0.000715 |
| 195 | 0.004874 | 0.000603 |
| 196 | 0.005907 | 0.003648 |
| 197 | 0.008982 | 0.002995 |
| 198 | 0.034570 | 0.003875 |
| 199 | 0.016260 | 0.003237 |
| 200 | 0.004609 | 0.001780 |
| 201 | 0.003044 | 0.001214 |
| 202 | 0.028110 | 0.009839 |
| 203 | 0.003676 | 0.000447 |
| 204 | 0.001826 | 0.002094 |
| 205 | 0.004349 | 0.002038 |
| 206 | — | — |
| 207 | 0.018090 | 0.002352 |
| 208 | 0.017010 | 0.001593 |
| 209 | 0.029500 | 0.001828 |
| 210 | 0.075150 | 0.017600 |
| 211 | 0.006774 | 0.001959 |
| 212 | 0.005979 | 0.000640 |
| 213 | 0.017240 | 0.001615 |
| 214 | 0.022330 | 0.002195 |
| 215 | 0.017130 | 0.001673 |
| 216 | 0.026710 | 0.002950 |
| 217 | 0.012230 | 0.000833 |
| 218 | 0.178200 | 0.060660 |
| 219 | 0.001224 | 0.001148 |
| 220 | 0.011370 | 0.000734 |
| 221 | 0.042160 | 0.004057 |
| 222 | 0.043640 | 0.030740 |
| 223 | 0.010100 | 0.006845 |
| 224 | 0.002814 | 0.000694 |
| 225 | 0.010410 | 0.002817 |
| 226 | 0.010120 | 0.004939 |
| 227 | 0.036940 | 0.012470 |
| 228 | 0.001817 | 0.002073 |
| 229 | 0.002572 | 0.000474 |
| 230 | 0.003376 | 0.000452 |
| 231 | 0.002905 | 0.000417 |
| 232 | 0.001536 | 0.000322 |
| 233 | 0.001173 | 0.000306 |
| 234 | 0.002310 | 0.000456 |
| 235 | 0.002820 | 0.000295 |
| 236 | 0.001147 | 0.000266 |
| 237 | 0.001350 | 0.000365 |
| 238 | 0.000412 | 0.000223 |
| 239 | 0.005180 | 0.000547 |
| 240 | 0.005891 | 0.000694 |
| 241 | 0.001399 | 0.000362 |
| 242 | 0.011980 | 0.002156 |
| 243 | 0.005964 | 0.000652 |
| 244 | — | 0.000204 |
| 245 | 0.007430 | 0.000899 |
| 246 | 0.005959 | 0.000769 |
| 247 | 0.459500 | 0.061390 |
| 248 | 0.034310 | 0.001805 |
| 249 | 0.001105 | 0.000371 |
| 250 | 0.008383 | 0.000292 |
| 251 | 0.005375 | 0.000385 |
| 252 | 0.002513 | 0.000347 |
| 253 | 0.018000 | 0.001151 |
| 254 | 0.018670 | 0.001115 |
| 255 | 0.002447 | 0.000386 |
| 256 | 0.230400 | 0.010220 |
| 257 | 0.002287 | 0.000325 |
| 258 | 0.006564 | 0.000393 |
| 259 | 0.003171 | 0.000314 |
| 260 | 0.005525 | 0.000403 |
| 261 | 0.014780 | 0.000403 |
| 262 | 0.003476 | 0.000331 |
| 263 | 0.005403 | 0.000436 |
| 264 | 0.156300 | 0.041530 |
| 265 | 0.000719 | 0.000147 |
| 266 | 0.014110 | 0.000416 |
| 267 | 0.001773 | 0.000287 |
| 268 | 0.007571 | 0.000419 |

TABLE A-continued

| Example No. | CK1ε (IC$_{50}$, μM) | CK1δ (IC$_{50}$, μM) |
| --- | --- | --- |
| 269 | 0.009393 | 0.001080 |
| 270 | 0.072530 | 0.009454 |
| 271 | 0.005973 | 0.000897 |
| 272 | 0.016590 | 0.001650 |
| 273 | 0.001008 | 0.000257 |
| 274 | 0.008985 | 0.000635 |
| 275 | 0.004233 | 0.000545 |
| 276 | 0.035900 | 0.003878 |
| 277 | 0.003817 | 0.000238 |
| 278 | 0.005432 | 0.000444 |
| 279 | 0.000887 | 0.000169 |
| 280 | 0.002493 | 0.000520 |
| 281 | 0.007786 | 0.001809 |
| 282 | 0.013180 | 0.000766 |
| 283 | 0.007616 | 0.000545 |
| 284 | 0.002022 | 0.000384 |
| 285 | 0.001222 | 0.000245 |
| 286 | 0.006778 | 0.000727 |
| 287 | 0.009169 | 0.000776 |
| 288 | 0.000222 | 0.000110 |
| 289 | 0.001269 | 0.000613 |
| 290 | 0.001886 | 0.000412 |
| 291 | 0.002640 | 0.000388 |
| 292 | 0.001806 | 0.000208 |
| 293 | 0.001283 | 0.000109 |
| 294 | 0.004031 | 0.000208 |
| 295 | 0.005950 | 0.000126 |
| 296 | 0.010170 | 0.000519 |
| 297 | 0.002264 | 0.000354 |
| 298 | 0.005295 | 0.000714 |
| 299 | 0.000760 | 0.000186 |
| 300 | 0.034310 | 0.001805 |
| 301 | 0.005293 | 0.000413 |
| 302 | 0.0326 | 0.0072 |
| 303 | 0.0044 | 0.0039 |
| 304 | 0.048480 | 0.003441 |
| 305 | — | — |
| 306 | 0.006467 | 0.003167 |
| 307 | 0.003682 | 0.001362 |
| 308 | 0.005262 | 0.000322 |
| 309 | 0.013660 | 0.000964 |
| 310 | 0.008372 | 0.001033 |
| 311 | 0.046870 | 0.033890 |
| 312 | 0.019580 | 0.008379 |
| 313 | 0.001886 | 0.000691 |
| 314 | 0.003103 | 0.000479 |
| 315 | 0.375300 | 0.019750 |
| 316 | 0.039360 | 0.003091 |
| 317 | — | 0.001207 |
| 318 | 0.024250 | 0.002968 |
| 319 | 0.012080 | 0.001733 |
| 320 | 0.001858 | 0.000274 |
| 321 | 0.001968 | 0.000152 |
| 322 | 0.004762 | 0.000473 |
| 323 | 0.002684 | 0.000401 |
| 324 | 0.001906 | 0.000344 |
| 325 | 0.001442 | 0.000323 |
| 326 | 0.012330 | 0.002678 |
| 327 | 0.006081 | 0.000676 |
| 328 | 0.002132 | 0.000335 |
| 329 | 0.018530 | 0.003466 |
| 330 | 0.003345 | 0.000373 |
| 331 | 0.001448 | 0.000249 |
| 332 | 0.006862 | 0.000870 |
| 333 | 0.003282 | 0.001327 |
| 334 | 0.000966 | 0.000824 |
| 335 | 0.002572 | 0.000476 |
| 336 | 0.002200 | 0.000507 |
| 337 | 0.002582 | 0.000271 |
| 338 | 0.000768 | 0.000368 |
| 339 | 0.001613 | 0.000187 |
| 340 | 0.006275 | 0.000400 |
| 341 | 0.008846 | 0.001322 |
| 342 | 0.004894 | 0.001408 |
| 343 | 0.002172 | 0.000921 |
| 344 | 0.113200 | 0.014460 |
| 345 | 0.016260 | 0.005798 |
| 346 | 0.008299 | 0.001763 |
| 347 | 0.001191 | 0.000379 |
| 348 | 0.005766 | 0.001619 |
| 349 | 0.006894 | 0.000698 |
| 350 | 0.002318 | 0.000343 |
| 351 | 0.002010 | 0.000534 |
| 352 | 0.003242 | 0.000593 |
| 353 | 0.074220 | 0.004944 |
| 354 | 0.010620 | 0.001417 |
| 355 | 0.038710 | 0.003798 |
| 356 | 0.001909 | 0.000513 |
| 357 | 0.017640 | 0.001488 |
| 358 | 0.003919 | 0.000534 |
| 359 | 0.003168 | 0.000599 |
| 360 | 0.005379 | 0.000520 |
| 361 | 1.261000 | 0.074810 |
| 362 | 0.087530 | 0.006338 |
| 363 | 0.026160 | 0.002363 |
| 364 | 0.004013 | 0.000566 |
| 365 | 1.106000 | 0.103400 |
| 366 | 0.025080 | 0.001723 |
| 367 | 0.049670 | 0.003652 |
| 368 | 0.048390 | 0.004860 |
| 369 | 0.008745 | 0.001408 |
| 370 | 0.016200 | 0.001124 |
| 371 | 0.019810 | 0.002505 |
| 372 | 0.028290 | 0.002194 |
| 373 | 0.176500 | 0.018470 |
| 374 | 0.003954 | 0.000399 |
| 375 | 0.016340 | 0.001911 |
| 376 | 0.078060 | 0.008875 |
| 377 | 0.004044 | 0.000656 |
| 378 | 0.059970 | 0.006193 |
| 379 | 0.004938 | 0.000569 |
| 380 | 0.036100 | 0.005226 |
| 381 | 0.003738 | 0.000754 |
| 382 | 0.102600 | 0.021850 |
| 383 | 0.017280 | 0.006341 |
| 384 | 0.029060 | 0.008514 |
| 385 | 0.002520 | 0.001757 |
| 386 | 0.055080 | 0.010500 |
| 387 | 0.011890 | 0.006780 |
| 388 | 0.019420 | 0.007116 |
| 389 | 0.270500 | 0.035200 |
| 390 | 0.032560 | 0.007198 |
| 391 | 0.010490 | 0.004453 |
| 392 | 0.054500 | 0.016720 |
| 393 | — | — |
| 394 | 0.015300 | 0.006813 |
| 395 | 0.010620 | 0.005460 |
| 396 | 0.004412 | 0.003881 |
| 397 | 0.006648 | 0.002744 |
| 398 | 0.002702 | 0.000660 |
| 399 | 0.005288 | 0.002127 |
| 400 | 0.023260 | 0.006757 |
| 401 | 0.034210 | 0.012990 |
| 402 | 0.007474 | 0.000463 |
| 403 | 0.001615 | 0.000582 |
| 404 | 0.004213 | 0.001038 |
| 405 | 0.004213 | 0.001038 |
| 406 | 0.002943 | 0.000349 |
| 407 | 0.059840 | 0.034940 |
| 408 | 0.295700 | 0.012950 |
| 409 | 0.030790 | 0.058030 |
| 410 | 0.151200 | 0.007571 |
| 411 | 0.019380 | 0.001613 |
| 412 | 0.026610 | 0.002249 |
| 413 | 0.019640 | 0.001140 |
| 414 | 0.004346 | 0.000438 |
| 415 | 0.008710 | 0.001210 |
| 416 | 0.0574 | 0.0025 |
| 417 | 0.0116 | 0.0014 |
| 418 | 0.0792 | 0.0064 |
| 419 | 0.0352 | 0.0031 |
| 420 | 0.0185 | 0.0036 |
| 421 | 0.0122 | 0.0012 |
| 422 | 0.0117 | 0.0010 |

TABLE A-continued

| Example No. | CK1ε (IC$_{50}$, μM) | CK1δ (IC$_{50}$, μM) |
|---|---|---|
| 423 | 0.0180 | 0.0011 |
| 424 | 0.0136 | 0.0010 |
| 425 | 0.0110 | 0.0011 |
| 426 | 0.0104 | 0.0009 |
| 427 | 0.0065 | 0.0007 |
| 428 | 0.0091 | 0.0009 |
| 429 | 0.0068 | 0.0008 |
| 430 | 0.0123 | 0.0011 |
| 431 | 0.0011 | 0.0002 |
| 432 | 0.0008 | 0.0002 |
| 433 | 0.0012 | 0.0002 |
| 434 | 0.0018 | 0.0003 |
| 435 | 0.0014 | 0.0002 |
| 436 | 0.0020 | 0.0004 |
| 437 | 0.0024 | 0.0004 |
| 438 | 0.0021 | 0.0003 |
| 439 | 0.0033 | 0.0013 |
| 440 | 0.0013 | 0.0004 |
| 441 | 0.0054 | 0.0008 |
| 442 | 0.0025 | 0.0004 |
| 443 | 0.0027 | 0.0004 |
| 444 | 0.0024 | 0.0002 |
| 445 | 0.0047 | 0.0004 |
| 446 | 0.0018 | 0.0003 |
| 447 | 0.0058 | 0.0004 |
| 448 | 0.0036 | 0.0004 |
| 449 | 0.0090 | 0.0007 |
| 450 | 0.0069 | 0.0007 |
| 451 | 0.0046 | 0.0004 |
| 452 | 0.0015 | 0.0003 |
| 453 | 0.0015 | 0.0003 |
| 454 | — | — |
| 455 | 0.0048 | 0.0007 |
| 456 | 0.0070 | 0.0009 |
| 457 | 0.0085 | 0.0005 |
| 458 | 0.0037 | 0.0003 |
| 459 | 0.0026 | 0.0003 |
| 460 | 0.0037 | 0.0006 |
| 461 | 0.0026 | 0.0006 |
| 462 | 0.0065 | 0.0012 |
| 463 | 0.0038 | 0.0005 |
| 464 | 0.0023 | 0.0001 |
| 465 | 0.0050 | 0.0006 |
| 466 | 0.0015 | 0.0002 |
| 467 | 0.0061 | 0.0008 |
| 468 | 0.0039 | 0.0005 |
| 469 | 0.0129 | 0.0023 |
| 470 | 0.0081 | 0.0011 |
| 471 | 0.0035 | 0.0005 |
| 472 | 0.0045 | 0.0006 |
| 473 | 0.0029 | 0.0005 |
| 474 | 0.0093 | 0.0010 |
| 475 | 0.0081 | 0.0007 |
| 476 | 0.0025 | 0.0003 |
| 477 | 0.0078 | 0.0006 |
| 478 | 0.0023 | 0.0004 |
| 479 | 0.0080 | 0.0008 |
| 480 | 0.0104 | 0.0005 |
| 481 | 0.0054 | 0.0006 |
| 482 | 0.0119 | 0.0011 |
| 483 | 0.0039 | 0.0004 |
| 484 | 0.0067 | 0.0006 |
| 485 | 0.0045 | 0.0005 |
| 486 | 0.0064 | 0.0007 |
| 487 | 0.0051 | 0.0004 |

Methods of Preparation

The compounds of the present invention may be prepared by methods such as those illustrated in the following schemes. Solvents, temperatures, pressures, and other reaction conditions may readily be selected by one of ordinary skill in the art. Starting materials are commercially available or readily prepared by one of ordinary skill in the art. These schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). All documents cited herein are incorporated herein by reference in their entirety.

In general, the time taken to complete a reaction procedure will be judged by the person performing the procedure, preferably with the aid of information obtained by may be performed in an alternate sequence or order to give the desired compound(s). All documents cited herein are incorporated herein by reference in their entirety.

In general, the time taken to complete a reaction procedure will be judged by the person performing the procedure, preferably with the aid of information obtained by monitoring the reaction by methods such as HPLC or TLC. A reaction does not have to go to completion to be useful to this invention. The methods for the preparation of various heterocycles used to this invention can be found in standard organic reference books, for example, Katritzky, A. R. et al., eds., *Comprehensive Heterocyclic Chemistry, The Structure, Reactions, Synthesis and Uses, of Heterocyclic Compounds*, First Edition, Pergamon Press, New York (1984), and Katritzky, A. R. et al., eds., *Comprehensive Heterocyclic Chemistry II, A Review of the Literature* 1982-1995: *The Structure, Reactions, Synthesis and Uses, of Heterocyclic Compounds*, Pergamon Press, New York (1996).

Unless otherwise specified, the various substituents of the compounds are defined in the same manner as the Formula (I) compound of the invention.

For ease of reference, the following abbreviations are used herein:

Ac acetyl
AcCl acetyl chloride
AcOH acetic acid
NH$_4$OAc ammonium acetate
NH$_4$OH ammonium hydroxide
(Boc)$_2$O di t-butyl dicarbonate
CH$_2$Cl$_2$ or DCM dichloromethane
CHCl$_3$ chloroform
CH$_3$CN or MeCN acetonitrile
DIBAL-H diisobutylaluminum hydride
DIPEA or Hunig's base diisopropylethylamine
DMA dimethylacetamide
DMAP dimethylaminopyridine
DME dimethoxyethane
DMF dimethylformamide
DMSO dimethylsulfoxide
Et$_2$O diethyl ether
EtOAc ethyl acetate
EtOH ethanol
Et$_3$N or TEA triethylamine
HATU 2-(1H-7-azabenzotriazol-1-yl)-1,1,3,3-tetramethyl-uroniumhexafluorophosphate
HCl hydrochloric acid
K$_2$CO$_3$ potassium carbonate
KOAc potassium acetate
K$_3$PO$_4$ potassium phosphate, tribasic
MeLi methyllithium
MeOH methanol
MsCl methanesulfonyl chloride
MTBE methyl tert-butyl ether
Na$_2$CO$_3$ sodium carbonate
NaH sodium hydride
NaHCO$_3$ sodium bicarbonate NaHMDS sodium hexamethyldisilazide
NBS N-bromosuccinimide
NCS N-chlorosuccinimide
NMP N-methyl-2-pyrrolidone
NaOH sodium hydroxide
OXONE® Potassium peroxymonosulfate
PdCl$_2$(dppf) [1,1'-bis(diphenylphosphino)ferrocene]dichloropalladium(II) dichloromethane
PdCl$_2$(dppf) CH$_2$Cl$_2$ [1,1'-bis(diphenylphosphino)ferrocene]dichloropalladium(II) dichloromethane adduct
TFA trifluoroacetic acid
THF tetrahydrofuran
TMS-Cl trimethylsilyl chloride
TosMIC tosylmethyl isocyanate
h hour(s)
min minute(s)
L liter
mL milliliter
μL microliter
g gram(s)
mg milligram(s)
mmol millimole(s)
rt room temperature
ret time HPLC retention time
satd saturated
aq. aqueous
HPLC high performance liquid chromatography
Prep HPLC preparative reverse phase HPLC
LC/MS liquid chromatography/mass spectrometry
MS mass spectrometry
NMR nuclear magnetic resonance Analytical HPLC/LC-MS retention time reported for each example and intermediate uses one of the following general Analytical HPLC/LC-MS Methods:

Method A:
PHENOMENEX® Luna 2.0×50 mm 3 μm column; flow rate 0.8 mL/min; gradient time 4 min; 100% Solvent A to 100% Solvent B and holding 100% Solvent B for 1.0 min; monitoring at 220 nm (Solvent A: 10% MeOH, 90% H$_2$O, 0.1% TFA; Solvent B: 90% MeOH, 10% H$_2$O, 0.1% TFA).

Method B:
Waters BEH C18 2.0×50 mm 1.7 μm column; flow rate 1.0 mL/min; monitoring at 220 nm; Solvent A: 5:95 CH$_3$CN:H$_2$O with 10 mM NH$_4$OAc; Solvent B: 95:5 CH$_3$CN:H$_2$O with 10 mM NH$_4$OAc; Gradient: 0.5 mM hold at 0% B, 0%-100% B over 4 min.

Method C:
Waters BEH C18 2.0×50 mm 1.7 μm column; flow rate 1.0 mL/min; monitoring at 220 nm; Solvent A: 5:95 MeOH:H$_2$O with 10 mM NH$_4$OAc; Solvent B: 95:5 MeOH:H$_2$O with 10 mM NH$_4$OAc; Gradient: 0.5 mM. hold at 0% B, 0%-100% B over 4 min.

Method D:
PHENOMENEX® Luna C18, 2.0×30 mm, 3 μm column; flow rate 1.0 mL/min; gradient time 2.0 min; 100% Solvent A to 100% Solvent B and holding 100% Solvent B for 1 min; monitoring at 220 nm (Solvent A: 5% MeOH, 95% H$_2$O, 10 mM ammonium acetate; Solvent B: 95% MeOH, 5% H$_2$O, 10 mM ammonium acetate).

Method E:
PHENOMENEX® Luna 2.0×30 mm, 3 μm column; flow rate 1.0 mL/min; gradient time 2.0 min; 100% Solvent A to 100% Solvent B and holding 100% Solvent B for 1 min; monitoring at 220 nm (Solvent A: 10% MeOH, 90% H$_2$O, 0.1% TFA; Solvent B: 90% MeOH, 10% H$_2$O, 0.1% TFA).

Method F:
PHENOMENEX® Luna C18, 2.0×50 mm, 3 μm column; flow rate 0.8 mL/min; gradient time 4.0 min; 100% Solvent A to 100% Solvent B and holding 100% Solvent B for 1 min; monitoring at 220 nm (Solvent A: 5% MeOH, 95% H$_2$O, 10 mM ammonium acetate; Solvent B: 95% MeOH, 5% H$_2$O, 10 mM ammonium acetate).

Method G:
Waters Acquity UPLC BEH C18, 2.1×50 mm, 1.7-μm column; flow rate 0.8 mL/min; gradient time 2.20 min.; 100% Solvent A to 100% Solvent B and holding 100% Solvent B for 1 min; monitoring at 220 nm (Solvent A: 100% H$_2$O with 0.05% TFA; Solvent B: 100% CH$_3$CN with 0.05% TFA).

Method H:
PHENOMENEX® Luna C18, 2.0×50 mm, 3 μm column; flow rate 0.8 mL/min; gradient time 4.0 mM; 100% Solvent A to 100% Solvent B and holding 100% Solvent B for 1 min; monitoring at 220 nm (Solvent A: 5% MeOH, 95% H$_2$O, 10 mM ammonium acetate; Solvent B: 95% MeOH, 5% H$_2$O, 10 mM ammonium acetate).

Method I:
SUPELCO® Ascentis Express 4.6×50 mm 2.7 μm C18 column; flow rate 4.0 mL/min, gradient time 4.0 min; 100% Solvent A to 100% Solvent B and holding 100% Solvent B for 1 min; monitoring at 220 nm (Solvent A: 5% acetonitrile, 95% H$_2$O, 10 mM ammonium acetate; Solvent B: 95% acetonitrile, 5% H$_2$O, 10 mM ammonium acetate).

Method J:
Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Method K:
SunFire C18 4.6 mm×150 mm, 3.5μ column; flow rate 1 mL/min; gradient time 15 min; 10% Solvent B to 100% Solvent B; monitoring at 254 nm and 220 nm (Solvent A: 5% acetonitrile, 95% water, 0.05% TFA; Solvent B: 95% acetonitrile, 5% water, 0.05% TFA)

Method L:
XBridge Phenyl 4.6 mm×150 mm, 3.5μ column; flow rate 1 mL/min; gradient time 15 min; 10% Solvent B to 100% Solvent B; monitoring at 254 nm and 220 nm (Solvent A: 5% acetonitrile, 95% water, 0.05% TFA; Solvent B: 95% acetonitrile, 5% water, 0.05% TFA)

Method M:
SunFire C 8 4.6 mm×150 mm, 3.5μ column; flow rate 1 mL/min; gradient time 23 min; 100% Solvent A to 100% Solvent B and holding 100% Solvent B for 5 min. Monitoring at 254 nm and 220 nm (Solvent A: 5% acetonitrile, 95% water, 0.05% TFA Solvent B: 95% acetonitrile, 5% water, 0.05% TFA)

Method N:
XBridge Phenyl 4.6 mm×150 mm, 3.5μ column; flow rate 1 mL/min; gradient time 23 min; 100% mobile phase A to 100% mobile phase B and holding 100% Solvent B for 5 min. Monitoring at 254 nm and 220 nm (Solvent A: 5% acetonitrile, 95% water, 0.05% TFA; Solvent B: 95% acetonitrile, 5% water, 0.05% TFA)

Scheme 1

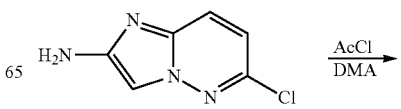

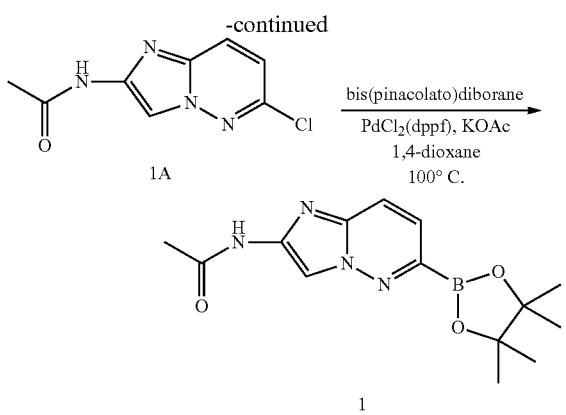

Intermediate 1

N-(6-(4,4,5,5-tetramethyl-1,3,2-dioxaborolan-2-yl)imidazo[1,2-b]pyridazin-2-yl)acetamide

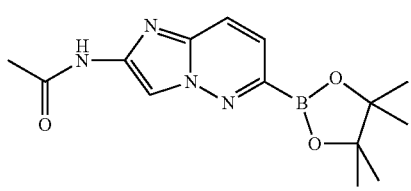 [SMILES: CC(=O)Nc1cn2nc(B3OC(C)(C)C(C)(C)O3)ccc2n1]

Intermediate 1A: N-(6-(4,4,5,5-tetramethyl-1,3,2-dioxaborolan-2-yl)imidazo[1,2-b]pyridazin-2-yl)acetamide

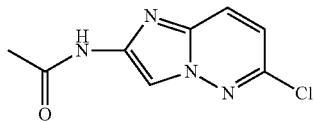

To a solution of 6-chloroimidazo[1,2-b]pyridazin-2-amine (12.0 g, 71.2 mmol) in DMA (119 mL) was added acetyl chloride (5.57 mL, 78 mmol) and the reaction mixture was stirred at rt for 1 h. It was quenched with satd. aq. NaHCO$_3$ to pH ~8. The resultant precipitate was filtered off and the filter cake was washed with water. The crude product was air-dried, followed by drying on the high-vac to afford Intermediate 1A (14 g, 93%) as a tan solid. HPLC Ret. Time: 2.68 min (Method A). MS(ES): m/z=211.07 [M+H]$^+$.

Intermediate 1: N-(6-(4,4,5,5-tetramethyl-1,3,2-dioxaborolan-2-yl)imidazo[1,2-b]pyridazin-2-yl)acetamide

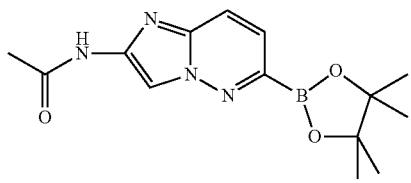

To a degassed suspension of Intermediate 1A (8.68 g, 41.2 mmol), 4,4,4',4',5,5,5',5'-octamethyl-2,2'-bi(1,3,2-dioxaborolane) (12.69 g, 49.5 mmol) and potassium acetate (10.11 g, 103 mmol) in 1,4-dioxane (137 mL) was added PdCl$_2$(dppf) (3.02 g, 4.12 mmol). The reaction mixture was degassed again for 5 min A reflux condenser was attached to the round bottom flask and the reaction was heated in an oil-bath at 100° C. for 16 h. It was then cooled to rt and passed through CELITE®. The filter cake was washed with copious amounts of MeOH. To the combined filtrate was added activated charcoal and the solution was again passed through CELITE®. The filtrate was evaporated to near dryness under reduced pressure to provide a residue, to which was added a 1:1 mixture of hexanes:Et$_2$O to precipitate out a solid that was filtered off. This solid was then suspended in minimum amount of CH$_2$Cl$_2$ and the suspension was filtered off to provide Intermediate 1 as a white solid. HPLC Ret. Time: 1.44 min. (Method A). MS(ES): m/z=221.10 [M+H]$^+$ of the corresponding boronic acid. $^1$H NMR (400 MHz, DMSO-d$_6$) δ ppm 10.96 (s, 1H), 8.30 (s, 1H), 7.92 (d, J=9.3 Hz, 1H), 7.35 (d, J=9.0 Hz, 1H), 2.11 (s, 3H), 1.35 (s, 12H).

Scheme 2

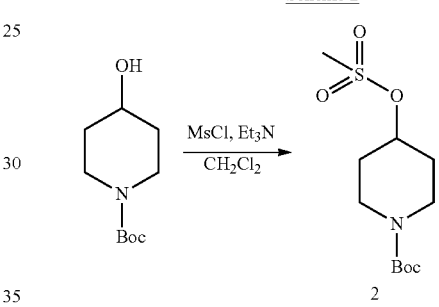

Intermediate 2 tert-butyl 4-((methylsulfonyl)oxy)piperidine-1-carboxylate

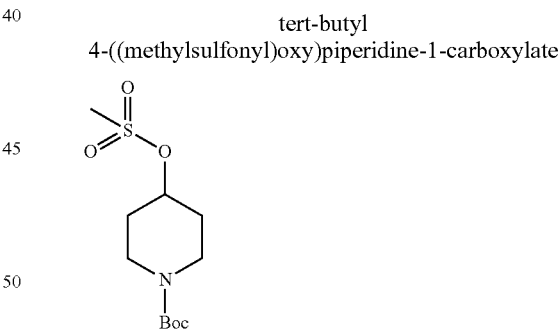

To a solution of tert-butyl 4-hydroxypiperidine-1-carboxylate (50.0 g, 248 mmol) in CH$_2$Cl$_2$ (500 mL) was added Et$_3$N (41.6 mL, 298 mmol), followed by a dropwise addition of methanesulfonyl chloride (21.30 mL, 273 mmol) at 0° C. The reaction mixture was stirred at rt for 1 h and then quenched with satd. aq. NaHCO$_3$ (200 mL). The two layers were separated and the organic layer was washed with water (3×100 mL) and brine. The organic phase was dried over anhydrous magnesium sulfate, filtered and concentrated under reduced pressure to provide Intermediate 2 (67.3 g, 97% yield) as a buff solid. HPLC Ret. Time: 3.23 min. (Method A). MS(ES): m/z=302.1 [M+Na]$^+$. $^1$H NMR (400 MHz, chloroform-d) δ ppm 4.88 (dt, J=7.7, 4.0 Hz, 1H), 3.70 (ddd, J=13.4, 7.2, 4.0 Hz, 2H), 3.30 (ddd, J=13.6, 8.2, 3.8 Hz, 2H), 3.04 (s, 3H), 2.02-1.91 (m, 2H), 1.82 (ddd, J=12.7, 8.7, 4.0 Hz, 2H), 1.46 (s, 9H).

Scheme 3

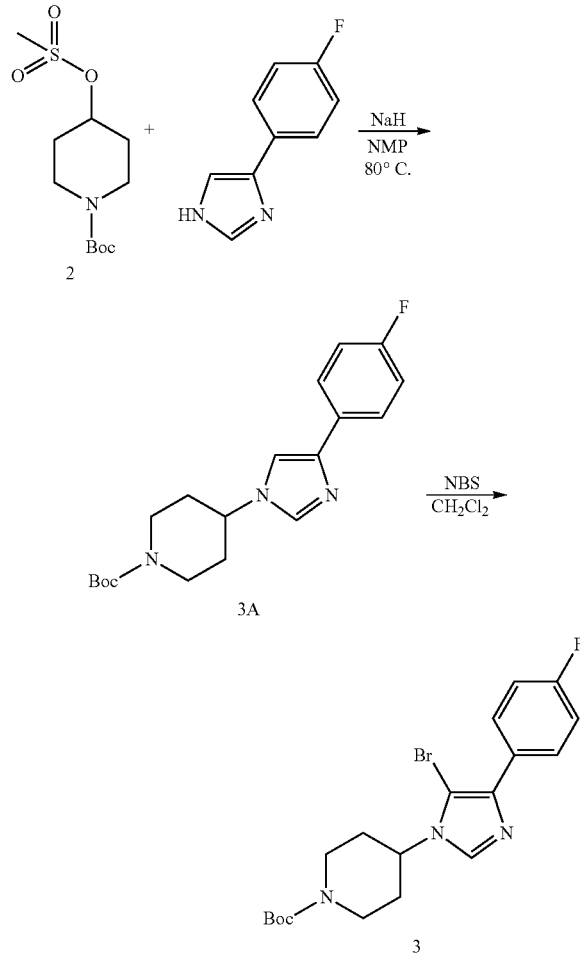

Intermediate 3 tert-butyl 4-(5-bromo-4-(4-fluorophenyl)-1H-imidazol-1-yl)piperidine-1-carboxylate Intermediate 3A: tert-butyl 4-(4-(4-fluorophenyl)-1H-imidazol-1-yl)piperidine-1-carboxylate

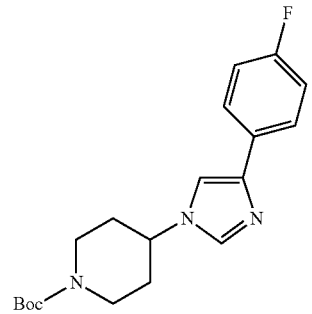 [SMILES: CC(C)(C)OC(=O)N1CCC(n2cnc(-c3ccc(F)cc3)c2)CC1]

Intermediate 3A was synthesized according to the procedure described in PCT Publication No. WO 2010/091409 (PCT/US2010/023637). To a solution of 4-(4-fluorophenyl)-1H-imidazole (10.0 g, 61.7 mmol) in NMP (154 mL) was added NaH (60% suspension in mineral oil, 10.61 g, 265 mmol) and the reaction mixture was stirred at rt for 45 min. To this was added, dropwise over 20 min., a solution of Intermediate 2 (79 g, 284 mmol) in NMP (150 mL). The resultant mixture was heated in an oil-bath at 80° C. for 16 h. It was then cooled to rt, diluted with ~1 L water and extracted with EtOAc (4×200 mL). The combined organics were washed with water (5×100 mL) and brine. The organic phase was dried over anhydrous magnesium sulfate, filtered, concentrated under reduced pressure and purified by silica gel chromatography (300 g Thomson BIOTAGE® column, eluting with 5% EtOAc in $CH_2Cl_2$ to isolate unreacted Intermediate 2, and then 5% MeOH in $CH_2Cl_2$) to provide the desired Intermediate 3A (19.5 g, 92% yield) as a buff solid. HPLC Ret. Time: 3.06 min. (Method A). MS(ES): m/z 346.14 [M+H]$^+$. $^1$H NMR (400 MHz, chloroform-d) δ ppm 8.02 (s, 1H), 7.83-7.72 (m, 2H), 7.23 (d, J=1.5 Hz, 1H), 7.15-7.04 (m, 2H), 4.44-4.20 (m, 3H), 3.93-3.80 (m, 1H), 3.03 (ddd, J=13.4, 9.9, 3.3 Hz, 1H), 2.96-2.80 (m, 2H), 2.15 (d, J=12.3 Hz, 2H), 1.89 (qd, J=12.4, 4.3 Hz, 2H), 1.55-1.48 (m, 9H).

Intermediate 3: tert-butyl 4-(5-bromo-4-(4-fluorophenyl)-1H-imidazol-1-yl)piperidine-1-carboxylate

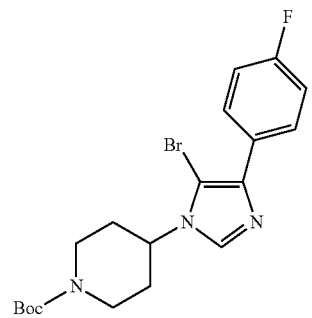 [SMILES: CC(C)(C)OC(=O)N1CCC(n2cnc(-c3ccc(F)cc3)c2Br)CC1]

To a solution of Intermediate 3A (10.47 g, 30.3 mmol) in CH$_2$Cl$_2$ (152 mL) was added N-bromosuccinimide (5.93 g, 33.3 mmol) and the reaction was stirred at rt for 40 min., after which the solvent was evaporated under reduced pressure. The crude material was purified by silica gel chromatography (300 g Thomson BIOTAGE® column, eluting with 50% EtOAc in CH$_2$Cl$_2$) to provide Intermediate 3 (8.12 g, 63.2% yield) as a white solid. HPLC Ret. Time: 3.62 min. (Method A). MS(ES): m/z=424.0 [M+H]$^+$. $^1$H NMR (400 MHz, chloroform-d) δ ppm 8.04 (s, 1H), 7.99-7.90 (m, 2H), 7.20-7.09 (m, 2H), 4.37 (br. S., 1H), 4.28 (tt, J=12.0, 3.8 Hz, 2H), 2.91 (br. S., 2H), 2.18 (d, J=12.8 Hz, 2H), 1.89 (qd, J=12.5, 4.5 Hz, 2H), 1.55-1.46 (m, 9H).

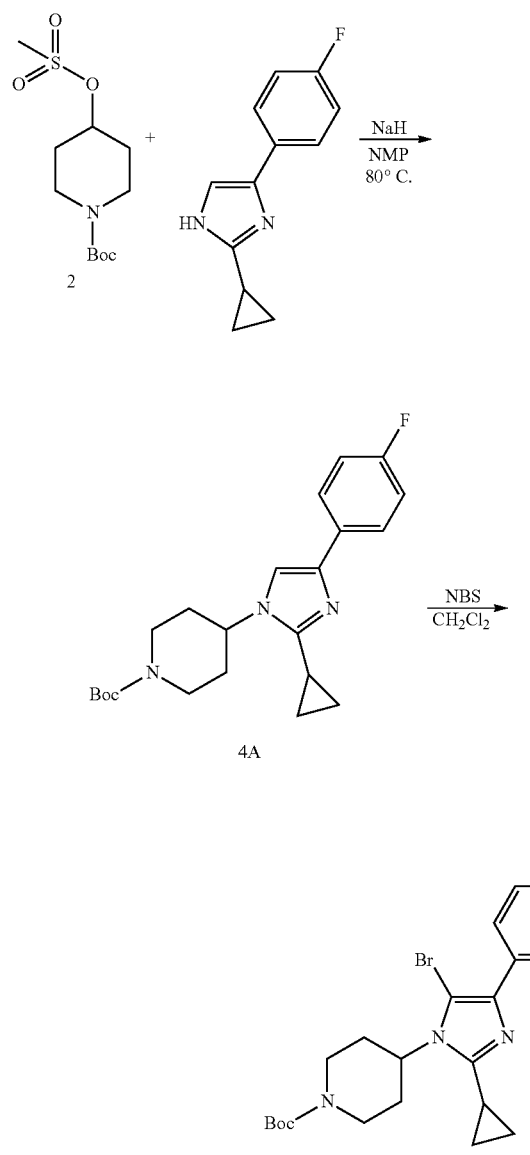

Scheme 3

Intermediate 4 tert-butyl 4-(5-bromo-2-cyclopropyl-4-(4-fluorophenyl)-1H-imidazol-1-yl)piperidine-1-carboxylate

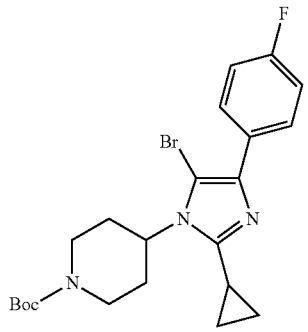 [SMILES: CC(C)(C)OC(=O)N1CCC(n2c(C3CC3)nc(-c3ccc(F)cc3)c2Br)CC1]

Intermediate 4A: tert-butyl 4-(2-cyclopropyl-4-(4-fluorophenyl)-1H-imidazol-1-yl)piperidine-1-carboxylate

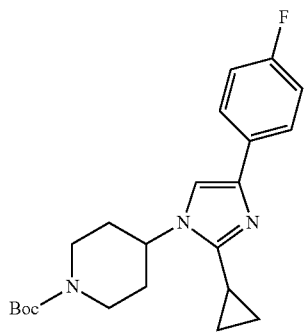

Intermediate 4A was synthesized analogous to Intermediate 3A by reacting 2-cyclopropyl-4-(4-fluorophenyl)-1H-imidazole with Intermediate 2. HPLC Ret. Time: 3.29 min. (Method A). MS(ES): m/z=386.22 [M+H]$^+$.

Intermediate 4: tert-butyl 4-(5-bromo-2-cyclopropyl-4-(4-fluorophenyl)-1H-imidazol-1-yl)piperidine-1-carboxylate

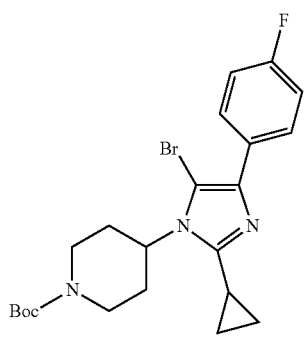 [SMILES: CC(C)(C)OC(=O)N1CCC(n2c(C3CC3)nc(-c3ccc(F)cc3)c2Br)CC1]

Intermediate 4 was synthesized analogous to Intermediate 3 by reacting Intermediate 4A with N-bromosuccinimide. HPLC Ret. Time: 3.63 min. (Method A). MS(ES): m/z 464.0 [M+H]$^+$. $^1$H NMR (400 MHz, DMSO-d$_6$) δ ppm 7.90-7.79 (m, 2H), 7.32-7.19 (m, 2H), 4.68 (br. s., 1H), 4.13 (d, J=10.3 Hz, 2H), 2.93 (br. s., 2H), 2.45-2.26 (m, 2H), 2.22-2.06 (m, 1H), 1.89 (d, J=10.0 Hz, 2H), 1.48-1.39 (m, 9H), 1.02-0.95 (m, 3H).

Scheme 5

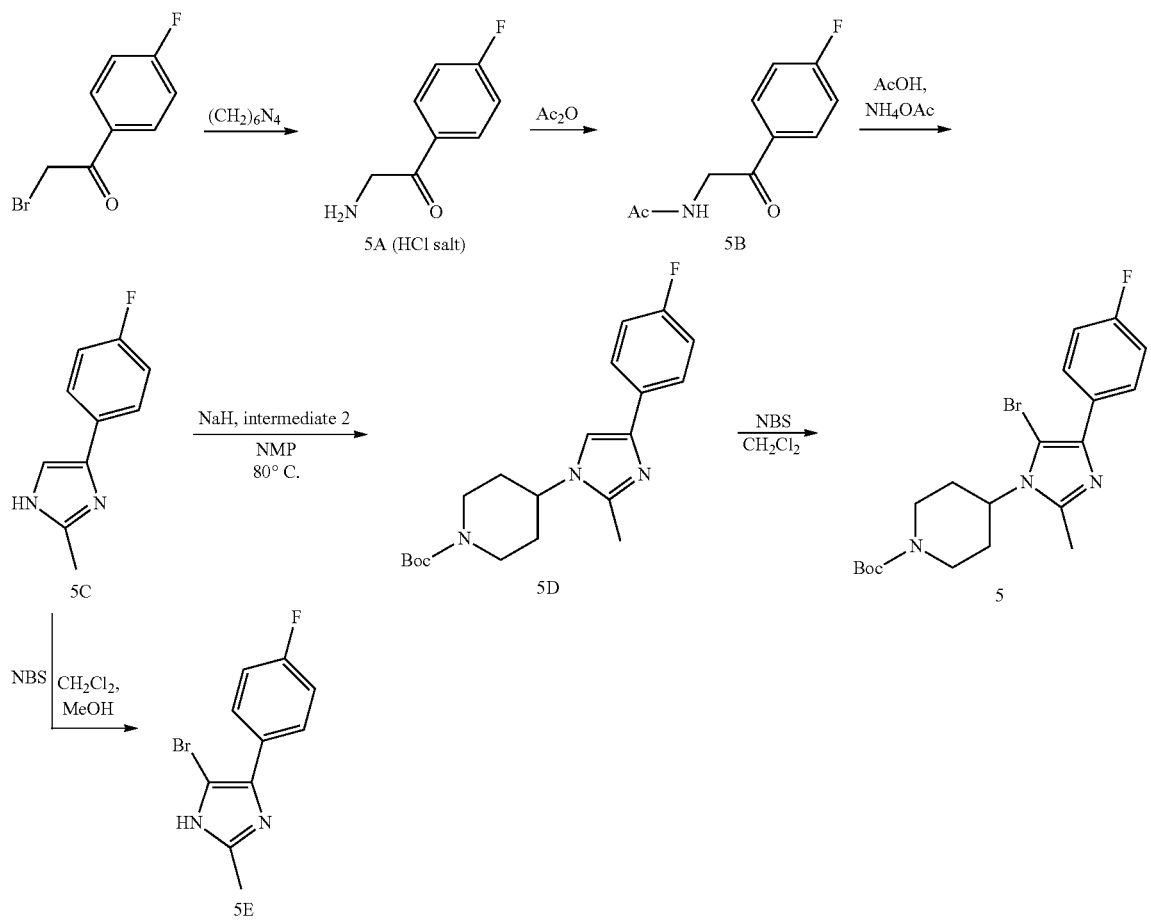

Intermediate 5 tert-butyl 4-(5-bromo-4-(4-fluorophenyl)-2-methyl-1H-imidazol-1-yl)piperidine-1-carboxylate

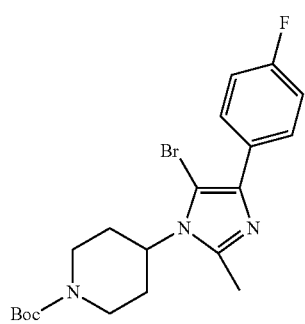 [SMILES: Cc1nc(-c2ccc(F)cc2)c(Br)n1C1CCN(C(=O)OC(C)(C)C)CC1]

Intermediate 5A:
2-amino-1-(4-fluorophenyl)ethanone, HCl

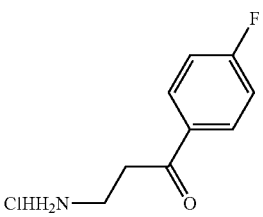

Intermediate 5A was synthesized according to the procedure described in PCT Publication No. WO 2009/137081 (PCT/US2009/002845). To a solution of 2-bromo-1-(4-fluorophenyl)ethanone (6.57 g, 30.3 mmol) in CHCl$_3$ (65.5 mL) was added hexamethylenetetramine (4.37 g, 30.8 mmol). The reaction mixture was stirred at rt for 16 h and then filtered off. The white solid thus collected, was suspended in MeOH (130 mL) and to it was added conc. HCl (~8.6 mL). This homogenous reaction mixture was refluxed for 4 h. Upon cooling, the inorganics were filtered off and the filter cake was washed with MeOH (~30 mL). The combined filtrate was concentrated under reduced pressure to afford a solid that was dried on high vac for 2 h. It was then purified by silica gel chromatography (Thomson BIOTAGE® column, eluting with a gradient of 5% to 20% solution of MeOH in CH$_2$Cl$_2$) to provide the desired product as a red solid. This solid was suspended in min. amount of CH$_2$Cl$_2$ and filtered off to provide Intermediate 5A as a colorless solid (5.44 g, 95% yield). HPLC Ret. Time: 0.90 min (Method D). MS(ES): m/z=136.05 [M+H]$^+$.

Intermediate 5B:
N-(2-(4-fluorophenyl)-2-oxoethyl)acetamide

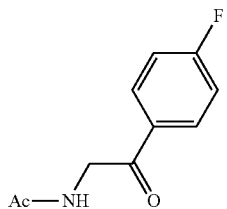 [SMILES: CC(=O)NCC(=O)c1ccc(F)cc1]

Intermediate 5B was synthesized according to the procedure described in PCT Publication No. WO 2009/137081 (PCT/US2009/002845). To a suspension of 2-amino-1-(4-fluorophenyl)ethanone, HCl, Intermediate 5A (5.442 g, 28.7 mmol) in THF (115 mL) was added TEA (8.00 mL, 57.4 mmol), followed by Ac$_2$O (4.52 mL, 47.9 mmol). The reaction mixture was stirred at rt for 1 h and then filtered off to remove the inorganics. The filtrate was taken in a separatory funnel and washed with water (×3) and brine. The organic phase was dried over anhydrous magnesium sulfate, filtered and concentrated under reduced pressure to afford Intermediate 5B as a solid (4.25 g, 76% yield). HPLC Ret. Time: 1.63 min. (Method A). MS(ES): m/z 218.07 [M+Na]$^+$.

Intermediate 5C:
4-(4-fluorophenyl)-2-methyl-1H-imidazole

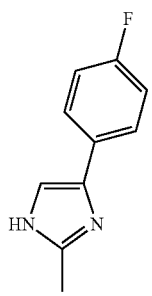

Intermediate 5C was synthesized according to the procedure described in PCT Publication No. WO 2009/137081 (PCT/US2009/002845). A suspension of Intermediate 5B (4.254 g, 21.79 mmol), AcONH$_4$ (10.73 g, 139 mmol) and AcOH (20.48 mL, 358 mmol) in xylene (325 mL) was refluxed for 14 h under Dean and Stark conditions to azeotropically distill off water. The reaction mixture was then concentrated to dryness under reduced pressure. The resultant crude oil was quenched with satd. aq. NaHCO$_3$. The aq. layer was extracted with EtOAc (×3) and the combined organics were washed with water and brine. The organic phase was dried over anhydrous magnesium sulfate, filtered, concentrated under reduced pressure and purified by silica gel chromatography (240 g Thomson BIOTAGE® column, eluting with a gradient of 1% to 5% solution of MeOH in CH$_2$Cl$_2$) to provide Intermediate 5C (2.7 g, 70.3% yield) as a solid. HPLC Ret. Time: 2.18 min. (Method A). MS(ES): m/z=177.11 [M+H]$^+$.

Intermediate 5D: tert-butyl 4-(4-(4-fluorophenyl)-2-methyl-1H-imidazol-1-yl)piperidine-1-carboxylate

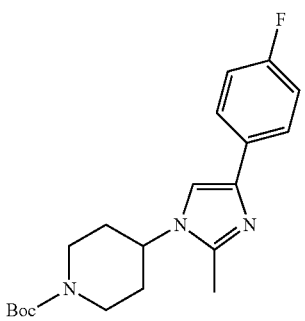 [SMILES: Cc1nc(-c2ccc(F)cc2)cn1C1CCN(C(=O)OC(C)(C)C)CC1]

Intermediate 5D was synthesized analogous to Intermediate 3A by reacting Intermediate 5C with Intermediate 2. HPLC Ret. Time: 3.048 min. (Method A). MS(ES): m/z=360.14 [M+H]$^+$.

Intermediate 5: tert-butyl 4-(5-bromo-4-(4-fluorophenyl)-2-methyl-1H-imidazol-1-yl)piperidine-1-carboxylate

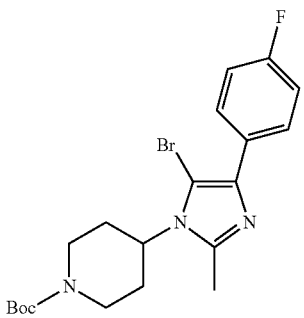 [SMILES: Cc1nc(-c2ccc(F)cc2)c(Br)n1C1CCN(C(=O)OC(C)(C)C)CC1]

Intermediate 5 was synthesized analogous to Intermediate 3 by reacting Intermediate 5D with N-bromosuccinimide. HPLC Ret. Time: 3.331 min. (Method A). MS(ES): m/z 439.97 [M+H]$^+$.

Intermediate 5E:
5-bromo-4-(4-fluorophenyl)-2-methyl-1H-imidazole

Intermediate 5E was synthesized analogous to Intermediate 3 by reacting Intermediate 5C with N-bromosuccinimide. HPLC Ret. Time 2.68 min (Method A). MS(ES): m/z=257.04 [M+H]$^+$. $^1$H NMR (400 MHz, DMSO-d$_6$) δ ppm 12.51 (br. s, 1H), 7.73 (dd, J=8.2, 5.6 Hz, 2H), 7.32 (t, J=8.9 Hz, 2H), 2.31 (s, 3H).

Scheme 6

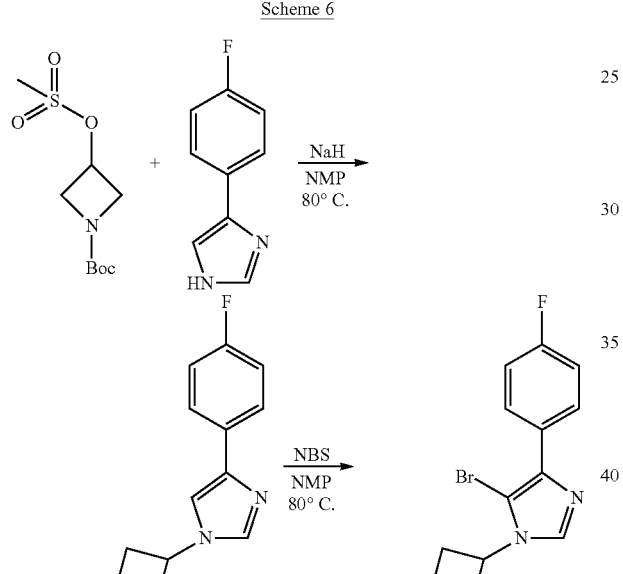

Intermediate 6 tert-butyl 3-(5-bromo-4-(4-fluorophenyl)-1H-imidazol-1-yl)azetidine-1-carboxylate

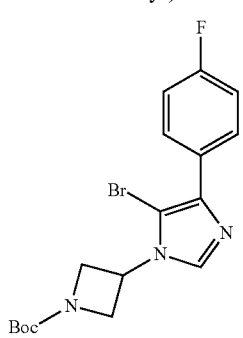

Intermediate 6A: tert-butyl 3-(4-(4-fluorophenyl)-1H-imidazol-1-yl)azetidine-1-carboxylate

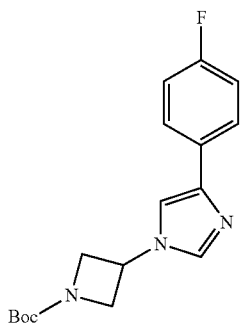 [SMILES: CC(C)(C)OC(=O)N1CC(n2cnc(-c3ccc(F)cc3)c2)C1]

Intermediate 6A was synthesized analogous to Intermediate 3A by reacting 4-(4-fluorophenyl)-1H-imidazole with commercially available tert-butyl 3-((methylsulfonyl)oxy)azetidine-1-carboxylate. HPLC Ret. Time 3.00 min. (Method A). MS(ES): m/z=318.22 [M+H]$^+$. $^1$H NMR (400 MHz, chloroform-d) δ ppm 8.24 (s, 1H), 7.87-7.74 (m, 2H), 7.47 (d, J=1.3 Hz, 1H), 7.17-7.06 (m, 2H), 5.15 (s, 1H), 4.52 (dd, J=9.7, 8.2 Hz, 2H), 4.14 (dd, J=9.9, 4.6 Hz, 2H), 1.54-1.46 (m, 10H).

Intermediate 6: tert-butyl 3-(5-bromo-4-(4-fluorophenyl)-1H-imidazol-1-yl)azetidine-1-carboxylate Intermediate 6 was synthesized analogous to Intermediate 3 by reacting Intermediate 6A with N-bromosuccinimide. HPLC Ret. Time 3.73 min. (Method A). MS(ES): m/z=398.13 [M+H]$^+$. $^1$H NMR (400 MHz, chloroform-d) δ ppm 8.24 (s, 1H), 7.98-7.87 (m, 2H), 7.20-7.09 (m, 2H), 5.17-5.03 (m, 1H), 4.60-4.48 (m, 2H), 4.29 (dd, J=9.7, 5.4 Hz, 2H), 1.56-1.45 (m, 9H).

Scheme 7

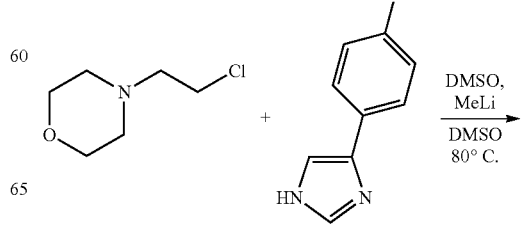

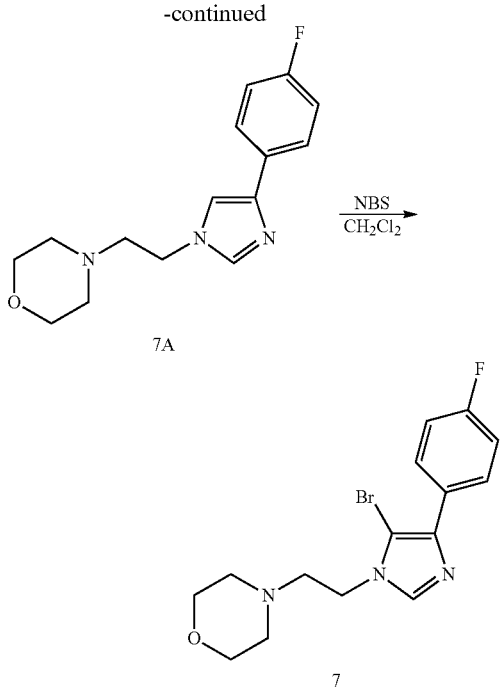

Intermediate 7

4-(2-(5-bromo-4-(4-fluorophenyl)-1H-imidazol-1-yl)ethyl)morpholine

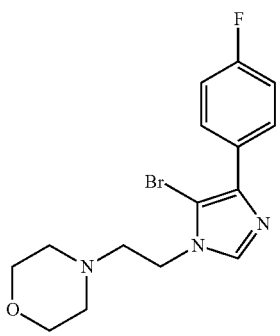 [SMILES: Fc1ccc(-c2ncn(CCN3CCOCC3)c2Br)cc1]

Intermediate 7A: 4-(2-(4-(4-fluorophenyl)-1H-imidazol-1-yl)ethyl)morpholine

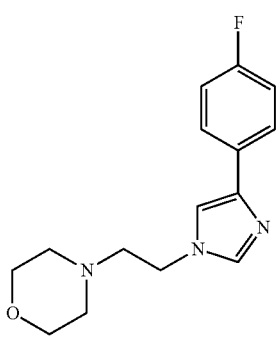 [SMILES: Fc1ccc(-c2cn(CCN3CCOCC3)cn2)cc1]

Intermediate 7A was synthesized according to the procedure described in PCT Publication No. WO 2009/152825 (PCT/DK2009/050134). A 250 mL round-bottom flask was charged under nitrogen with DMSO (83 mL, 1172 mmol). To it was added methyllithium (8.48 mL, 13.57 mmol) in a dropwise manner. This mixture was stirred at rt for 40 min. so as to generate dimsyl anion. Simultaneously, in another round-bottom flask was prepared a solution of 4-(4-fluorophenyl)-1H-imidazole (2.0 g, 12.33 mmol) and 4-(2-chloroethyl)morpholine (2.214 g, 14.80 mmol) in DMSO (24.67 mL). The latter solution was added dropwise to the generated dimsyl anion at rt. The resultant reaction mixture was heated at 80° C. for 16 h. It was then cooled to rt, diluted with ~1 L water and extracted with EtOAc (3×150 mL) The combined organics were washed with water (5×100 mL) and brine. The organic phase was dried over anhydrous magnesium sulfate, filtered, concentrated under reduced pressure and purified by silica gel chromatography (240 g Thomson BIOTAGE® column, eluting with 20% EtOAc in $CH_2Cl_2$ to isolate unreacted 4-(4-fluorophenyl)-1H-imidazole, and then with 100% EtOAc) to provide Intermediate 7A (1.763 g, 51.9% yield) as a brown solid. HPLC Ret. Time 1.48 min. (Method A). MS(ES): m/z=276.16 [M+H]$^+$. $^1$H NMR (400 MHz, chloroform-d) δ ppm 7.87 (s, 1H), 7.81-7.72 (m, 2H), 7.33-7.23 (m, 1H), 7.15-7.03 (m, 2H), 4.15 (t, J=6.3 Hz, 2H), 3.80-3.69 (m, 4H), 2.79 (t, J=6.1 Hz, 2H), 2.60-2.49 (m, 4H).

Intermediate 7: 4-(2-(5-bromo-4-(4-fluorophenyl)-1H-imidazol-1-yl)ethyl)morpholine

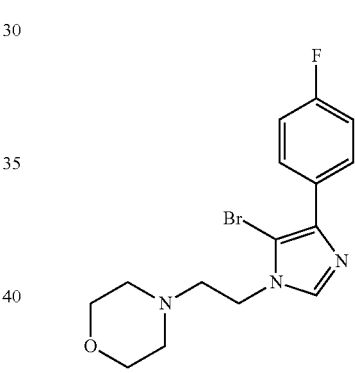

Intermediate 7 was synthesized analogous to Intermediate 3 by reacting Intermediate 7A with N-bromosuccinimide. HPLC Ret. Time 2.40 min. (Method A). MS(ES): m/z 355.99 [M+H]$^+$.

Scheme 8

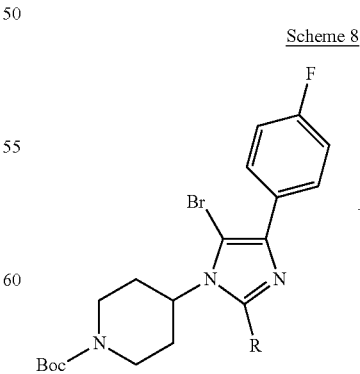

3. R = H
4. R = cyclopropyl
5. R = Me

-continued

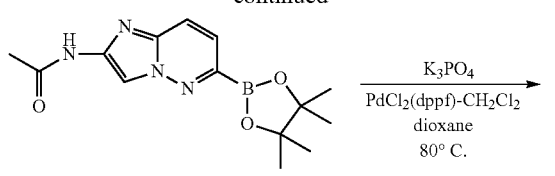

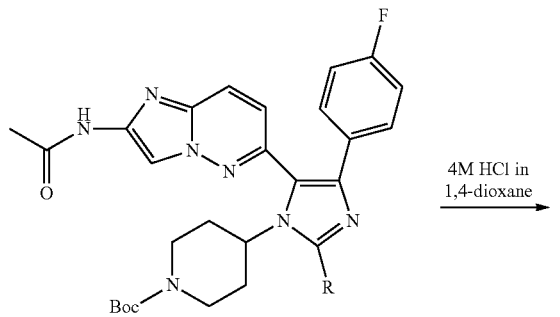

8A: R = H
9A: R = cyclopropyl
10A: Me

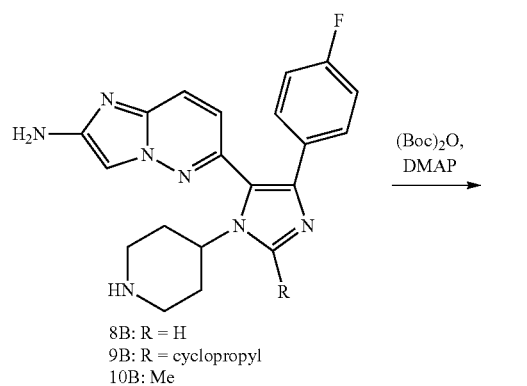

8B: R = H
9B: R = cyclopropyl
10B: Me

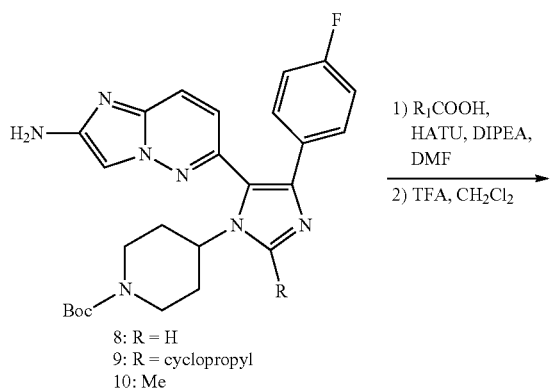

8: R = H
9: R = cyclopropyl
10: Me

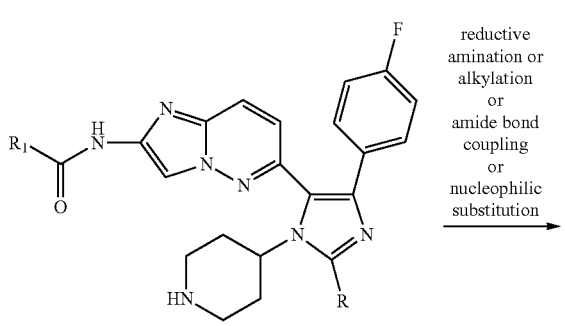

-continued

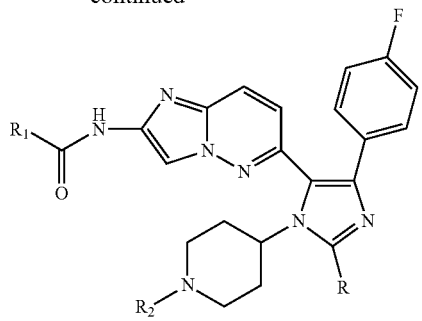

Intermediate 8 tert-butyl 4-(5-(2-aminoimidazo[1,2-b]pyridazin-6-yl)-4-(4-fluorophenyl)-1H-imidazol-1-yl)piperidine-1-carboxylate

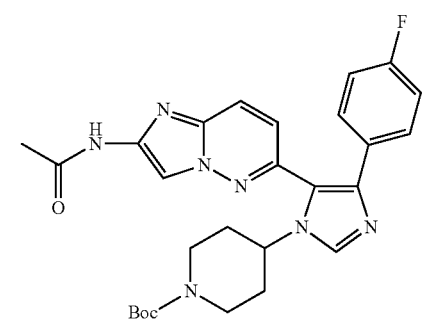 [SMILES: CC(=O)Nc1cn2nc(-c3c(-c4ccc(F)cc4)ncn3C3CCN(C(=O)OC(C)(C)C)CC3)ccc2n1]

Intermediate 8A: tert-butyl 4-(5-(2-acetamidoimidazo[1,2-b]pyridazin-6-yl)-4-(4-fluorophenyl)-1H-imidazol-1-yl)piperidine-1-carboxylate To a degassed mixture of Intermediate 3 (5.75 g, 13.55 mmol), Intermediate 1 (7.37 g, 24.39 mmol) and 2M aq. solution of K₃PO₄ (20.33 mL, 40.7 mmol) in 1,4-dioxane (108 mL) was added PdCl₂(dppf)-CH₂Cl₂ adduct (0.553 g, 0.678 mmol). The reaction mixture was degassed again for 5 min. A reflux condenser was attached to the round bottom flask and the reaction was heated in an oil-bath at 80° C. for 16 h. The reaction was cooled to rt and the inorganics were filtered off. The filter cake was washed with 1,4-dioxane and a solution of 5% MeOH in CH₂Cl₂. The combined filtrate was concentrated under reduced pressure to near dryness. The resultant residue was diluted with water and extracted with a 5% solution of MeOH in CH$_2$Cl$_2$ (3×60 mL). The combined organics were washed with brine. The organic phase was dried over anhydrous magnesium sulfate, filtered, concentrated under reduced pressure and purified by silica gel chromatography (300 g Thomson BIOTAGE® column, eluting with a solution of 5% MeOH in CH$_2$Cl$_2$) to provide a brown solid. It was triturated with a minimum amount of CH$_2$Cl$_2$ to afford Intermediate 8A (2.90 g, 41.2% yield) as a white solid. HPLC Ret. Time 3.28 min. (Method A). MS(ES): m/z 520.19 [M+H]$^+$. $^1$H NMR (400 MHz, DMSO-d$_6$) δ ppm 11.01 (s, 1H), 8.36 (s, 1H), 8.19 (s, 1H), 8.01 (dd, J=9.3, 0.8 Hz, 1H), 7.53-7.37 (m, 2H), 7.18-7.02 (m, 3H), 4.32-4.19 (m, 1H), 4.05 (d, J=8.5 Hz, 2H), 3.18 (d, J=5.3 Hz, 1H), 2.13 (s, 3H), 2.03 (d, J=10.3 Hz, 2H), 1.95-1.79 (m, 2H), 1.48-1.36 (m, 10H).

Intermediate 8B: 6-(4-(4-fluorophenyl)-1-(piperidin-4-yl)-1H-imidazol-5-yl)imidazo[1,2-b]pyridazin-2-amine

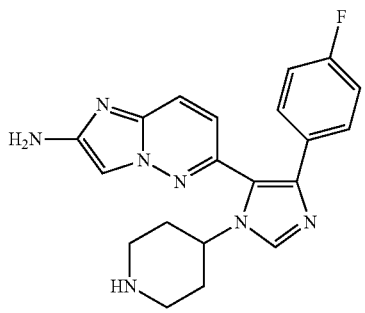 [SMILES: Nc1cn2nc(-c3c(-c4ccc(F)cc4)ncn3C3CCNCC3)ccc2n1]

To a solution of Intermediate 8A (2.96 g, 5.69 mmol) in MeOH (56.9 mL) was added hydrogen chloride (4M solution in 1,4-dioxane, 42.7 mL, 171 mmol) and the reaction mixture was stirred at rt for 16 h. The volatiles were evaporated under reduced pressure and the residue was carefully quenched with satd. aq. NaHCO$_3$ to pH ~8. The aq. layer was extracted with a solution of 5% MeOH in CH$_2$Cl$_2$ (2×50 mL) and the combined organics were washed with brine. The organic phase was dried over anhydrous magnesium sulfate and concentrated under reduced pressure to provide Intermediate 8B (1.99 g, 93%) as a yellowish brown solid. HPLC Ret. Time: 2.00 min (Method A). MS(ES): m/z=378.13 [M+H]$^+$.

Intermediate 8: tert-butyl 4-(5-(2-aminoimidazo[1,2-b]pyridazin-6-yl)-4-(4-fluorophenyl)-1H-imidazol-1-yl)piperidine-1-carboxylate

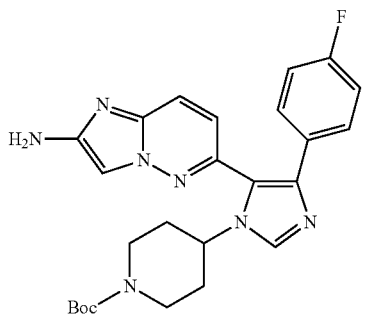 [SMILES: CC(C)(C)OC(=O)N1CCC(n2cnc(-c3ccc(F)cc3)c2-c2ccc3nc(N)cn3n2)CC1]

To a solution of Intermediate 8B (1.99 g, 5.27 mmol) in CH$_2$Cl$_2$ (52.7 mL) was added (Boc)$_2$O (1.15 g, 5.27 mmol) and DMAP (0.064 g, 0.527 mmol). The reaction mixture was stirred at rt for 45 min. and quenched with satd. aq. NaHCO$_3$. The two layers were separated and the aq. layer was back-extracted with a solution of 5% MeOH in CH$_2$Cl$_2$ (3×30 mL). The combined organics were washed with brine. The organic phase was dried over anhydrous magnesium sulfate, filtered and concentrated under reduced pressure to provide Intermediate 8 (2.40 g, 95% yield) as a yellowish brown solid. HPLC Ret. Time: 2.99 min. (Method A). MS(ES): m/z=478.13 [M+H]$^+$. $^1$H NMR (400 MHz, DMSO-d$_6$) δ 8.13 (s, 1H), 7.70 (dd, J=9.0, 0.8 Hz, 1H), 7.48-7.36 (m, 3H), 7.19-7.06 (m, 2H), 6.90 (d, J=9.0 Hz, 1H), 4.08 (d, J=12.3 Hz, 3H), 2.00 (d, J=10.3 Hz, 2H), 1.86 (dd, J=12.2, 4.4 Hz, 2H), 1.41 (s, 9H).

Intermediate 9 tert-butyl 4-(5-(2-aminoimidazo[1,2-b]pyridazin-6-yl)-2-cyclopropyl-4-(4-fluorophenyl)-1H-imidazol-1-yl)piperidine-1-carboxylate

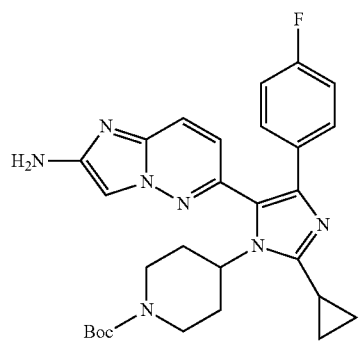 [SMILES: CC(C)(C)OC(=O)N1CCC(n2c(C3CC3)nc(-c3ccc(F)cc3)c2-c2ccc3nc(N)cn3n2)CC1]

Intermediate 9A: tert-butyl 4-(5-(2-acetamidoimidazo[1,2-b]pyridazin-6-yl)-2-cyclopropyl-4-(4-fluorophenyl)-1H-imidazol-1-yl)piperidine-1-carboxylate

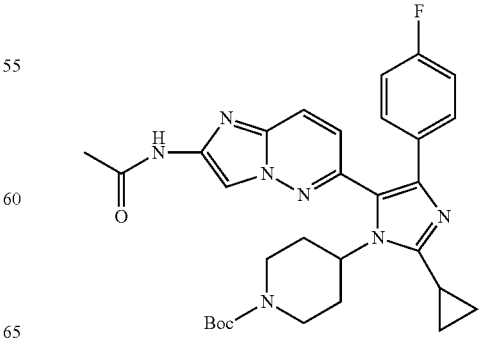

Intermediate 9A was synthesized analogous to Intermediate 8A by reacting Intermediate 1 with Intermediate 4. HPLC Ret. Time: 3.22 min. (Method A). MS(ES): m/z=560.18 [M+H]⁺.

Intermediate 9B: 6-(2-cyclopropyl-4-(4-fluorophenyl)-1-(piperidin-4-yl)-1H-imidazol-5-yl)imidazo[1,2-b]pyridazin-2-amine

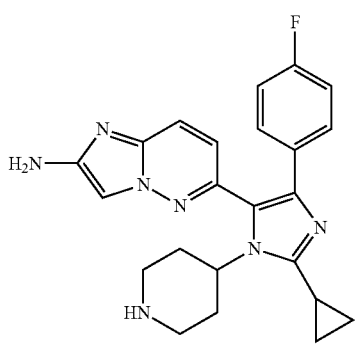 [SMILES: Nc1cn2nc(-c3c(-c4ccc(F)cc4)nc(C4CC4)n3C3CCNCC3)ccc2n1]

Intermediate 9B was synthesized analogous to Intermediate 8B by reacting Intermediate 9A with hydrogen chloride (4M solution in 1,4-dioxane). HPLC Ret. Time: 2.03 min. (Method A). MS(ES): m/z=418.17 [M+H]⁺.

Intermediate 9: tert-butyl 4-(5-(2-aminoimidazo[1,2-b]pyridazin-6-yl)-2-cyclopropyl-4-(4-fluorophenyl)-1H-imidazol-1-yl)piperidine-1-carboxylate

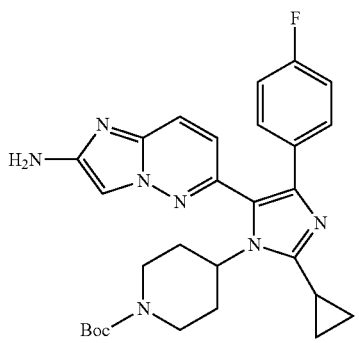 [SMILES: CC(C)(C)OC(=O)N1CCC(n2c(C3CC3)nc(-c3ccc(F)cc3)c2-c2ccc3nc(N)cn3n2)CC1]

Intermediate 9 was synthesized analogous to Intermediate 8 by reacting Intermediate 9B with (Boc)₂O. HPLC Ret. Time: 3.77 min. (Method P). MS(ES): m/z=518.40 [M+H]⁺. ¹H NMR (400 MHz, DMSO-d₆) δ ppm 7.73-7.64 (m, 1H), 7.38 (s, 1H), 7.33-7.23 (m, 2H), 7.10-6.99 (m, 2H), 6.90 (d, J=9.0 Hz, 1H), 5.78 (s, 1H), 5.67 (s, 2H), 4.43 (br. s., 1H), 2.75 (br. s., 2H), 2.19-2.07 (m, 1H), 1.90 (br. s., 4H), 1.34-1.23 (m, 9H), 1.10-0.94 (m, 4H).

Intermediate 10 tert-butyl 4-(5-(2-aminoimidazo[1,2-b]pyridazin-6-yl)-4-(4-fluorophenyl)-2-methyl-1H-imidazol-1-yl)piperidine-1-carboxylate

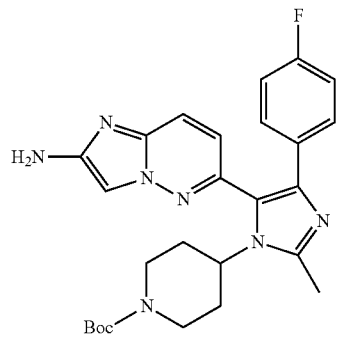 [SMILES: Cc1nc(-c2ccc(F)cc2)c(-c2ccc3nc(N)cn3n2)n1C1CCN(C(=O)OC(C)(C)C)CC1]

Intermediate 10A: tert-butyl 4-(5-(2-acetamidoimidazo[1,2-b]pyridazin-6-yl)-4-(4-fluorophenyl)-2-methyl-1H-imidazol-1-yl)piperidine-1-carboxylate

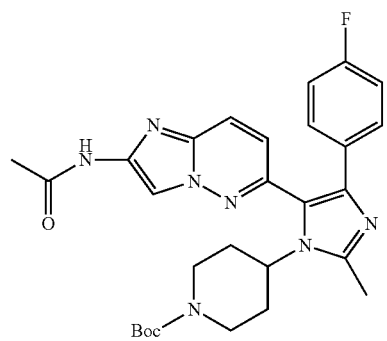 [SMILES: CC(=O)Nc1cn2nc(-c3c(-c4ccc(F)cc4)nc(C)n3C3CCN(C(=O)OC(C)(C)C)CC3)ccc2n1]

Intermediate 10A was synthesized analogous to Intermediate 8A by reacting Intermediate 1 with Intermediate 5. HPLC Ret. Time: 3.04 min. (Method A). MS(ES): m/z=534.16 [M+H]⁺.

Intermediate 10B: 6-(4-(4-fluorophenyl)-2-methyl-1-(piperidin-4-yl)-1H-imidazol-5-yl)imidazo[1,2-b]pyridazin-2-amine

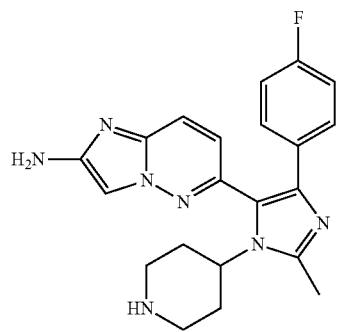 [SMILES: Cc1nc(-c2ccc(F)cc2)c(-c2ccc3nc(N)cn3n2)n1C1CCNCC1]

Intermediate 10B was synthesized analogous to Intermediate 8B by reacting Intermediate 10A with hydrogen chloride (4M solution in 1,4-dioxane). HPLC Ret. Time: 1.90 min. (Method A). MS(ES): m/z=392.12 [M+H]+.

Intermediate 10: tert-butyl 4-(5-(2-aminoimidazo[1,2-b]pyridazin-6-yl)-4-(4-fluorophenyl)-2-methyl-1H-imidazol-1-yl)piperidine-1-carboxylate

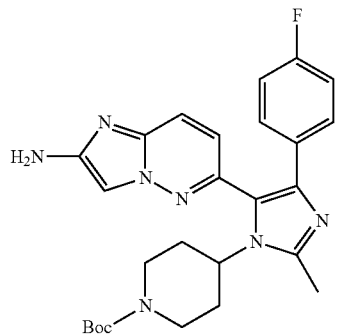 [SMILES: Cc1nc(-c2ccc(F)cc2)c(-c2ccc3nc(N)cn3n2)n1C1CCN(C(=O)OC(C)(C)C)CC1]

Intermediate 10 was synthesized analogous to Intermediate 8 by reacting Intermediate 10B with (Boc)₂O. HPLC Ret. Time: 2.58 min. (Method A). MS(ES): m/z 492.18 [M+H]+.

Scheme 9

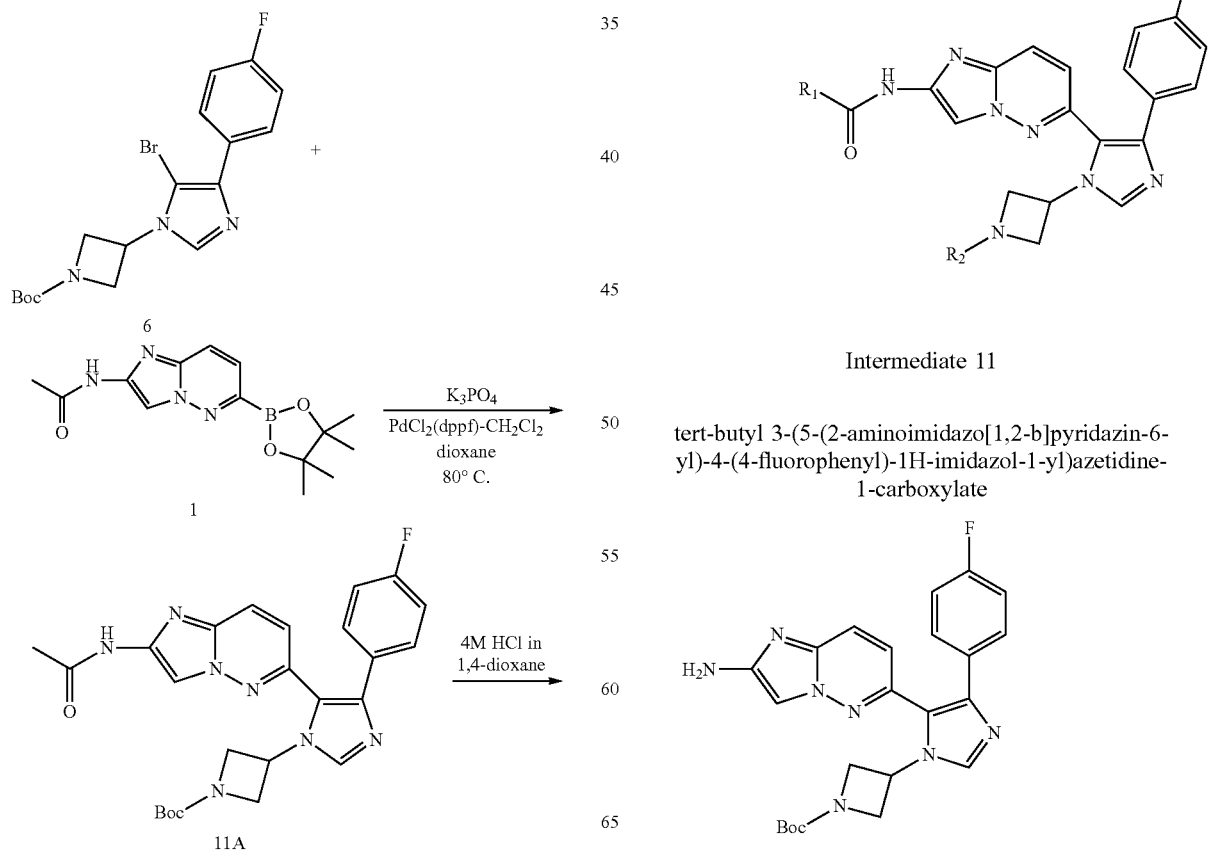

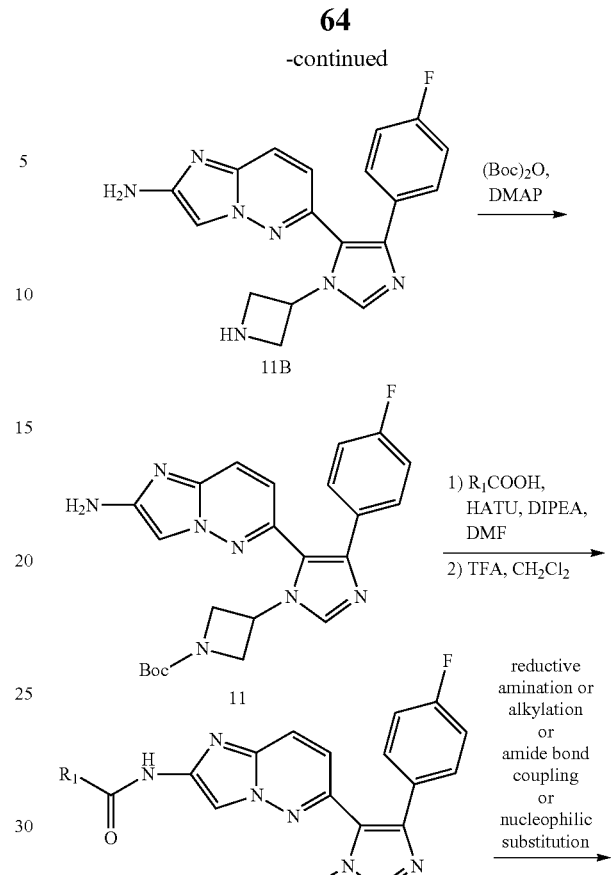

Intermediate 11 tert-butyl 3-(5-(2-aminoimidazo[1,2-b]pyridazin-6-yl)-4-(4-fluorophenyl)-1H-imidazol-1-yl)azetidine-1-carboxylate

Intermediate 11A: tert-butyl 3-(5-(2-acetamidoimidazo[1,2-b]pyridazin-6-yl)-4-(4-fluorophenyl)-1H-imidazol-1-yl)azetidine-1-carboxylate

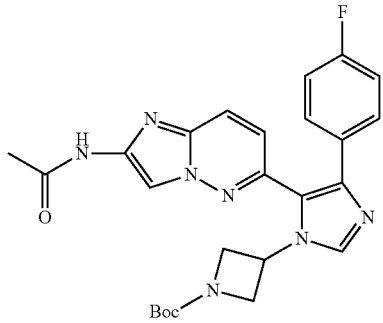 [SMILES: CC(=O)Nc1cn2nc(-c3c(-c4ccc(F)cc4)ncn3C3CN(C(=O)OC(C)(C)C)C3)ccc2n1]

Intermediate 11A was synthesized analogously to Intermediate 8A by reacting Intermediate 1 with Intermediate 6. HPLC Ret. Time 3.26 min. (Method A). MS(ES): m/z 392.24 [M+H]+.

Intermediate 11B: 6-(1-(azetidin-3-yl)-4-(4-fluorophenyl)-1H-imidazol-5-yl)imidazo[1,2-b]pyridazin-2-amine

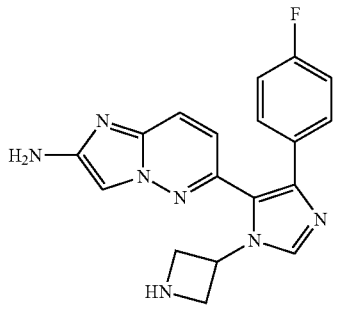 [SMILES: Nc1cn2nc(-c3c(-c4ccc(F)cc4)ncn3C3CNC3)ccc2n1]

Intermediate 11B was synthesized analogously to Intermediate 8B by reacting Intermediate 11A with hydrogen chloride (4M solution in 1,4-dioxane). HPLC Ret. Time 2.09 min. (Method A). MS(ES): m/z 350.20 [M+H]+.

Intermediate 11: tert-butyl 3-(5-(2-aminoimidazo[1,2-b]pyridazin-6-yl)-4-(4-fluorophenyl)-1H-imidazol-1-yl)azetidine-1-carboxylate

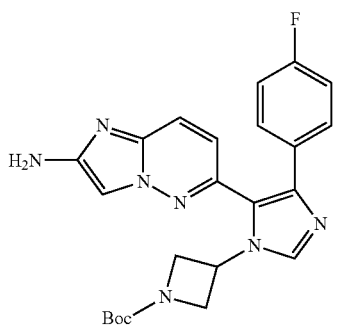 [SMILES: CC(C)(C)OC(=O)N1CC(n2cnc(-c3ccc(F)cc3)c2-c2ccc3nc(N)cn3n2)C1]

Intermediate 11 was synthesized analogous to Intermediate 8 by reacting Intermediate 11B with (Boc)$_2$O. HPLC Ret. Time 2.80 min. (Method A). MS(ES): m/z=450.24 [M+H]+.

Scheme 10

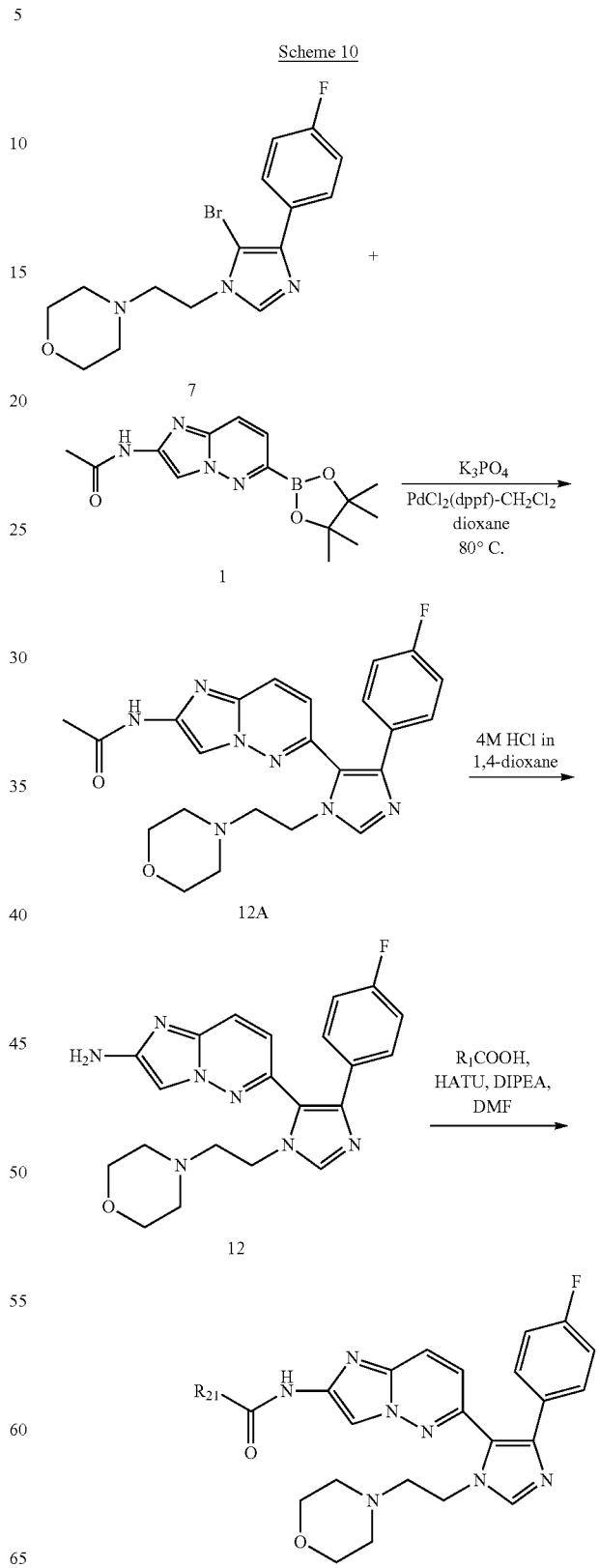

Intermediate 12

6-(4-(4-fluorophenyl)-1-(2-morpholinoethyl)-1H-imidazol-5-yl)imidazo[1,2-b]pyridazin-2-amine

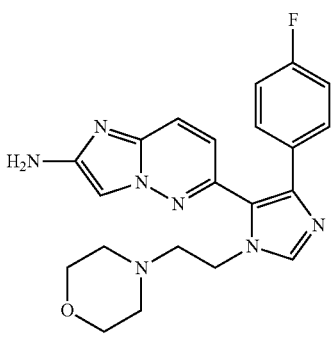 [SMILES: Nc1cn2nc(-c3c(-c4ccc(F)cc4)ncn3CCN3CCOCC3)ccc2n1]

Intermediate 12A: N-(6-(4-(4-fluorophenyl)-1-(2-morpholinoethyl)-1H-imidazol-5-yl)imidazo[1,2-b]pyridazin-2-yl)acetamide

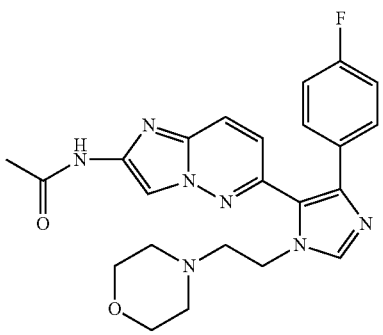 [SMILES: CC(=O)Nc1cn2nc(-c3c(-c4ccc(F)cc4)ncn3CCN3CCOCC3)ccc2n1]

Intermediate 12A was synthesized analogous to Intermediate 8A by reacting Intermediate 1 with Intermediate 7. HPLC Ret. Time 2.53 min. (Method A). MS(ES): m/z=450.11 [M+H]+.

Intermediate 12: 6-(4-(4-fluorophenyl)-1-(2-morpholinoethyl)-1H-imidazol-5-yl)imidazo[1,2-b]pyridazin-2-amine

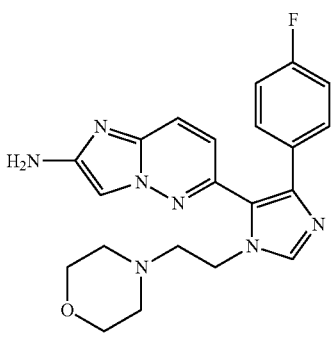 [SMILES: Nc1cn2nc(-c3c(-c4ccc(F)cc4)ncn3CCN3CCOCC3)ccc2n1]

To a solution of Intermediate 12A (0.6 g, 1.335 mmol) in MeOH (13.35 mL) was added hydrogen chloride (4M solution in dioxane, 10.01 mL, 40.0 mmol) and the reaction mixture was stirred at rt for 16 h. The volatiles were evaporated under reduced pressure and the residue was quenched with satd. aq. NaHCO$_3$. The aq. layer was extracted with a 10% solution of MeOH in CH$_2$Cl$_2$ (3×30 mL) The combined organics were washed with brine. The organic phase was dried over anhydrous magnesium sulfate and concentrated under reduced pressure to provide Intermediate 12 as a brown solid (0.517 g, 95% yield). HPLC Ret. Time 2.02 min (Method A). MS(ES): m/z=408.08 [M+H]+. $^1$H NMR (400 MHz, DMSO-d$_6$) δ ppm 7.94 (s, 1H), 7.68 (d, J=9.0 Hz, 1H), 7.51-7.37 (m, 3H), 7.12 (t, J=9.0 Hz, 2H), 6.86 (d, J=9.0 Hz, 1H), 5.66 (s, 2H), 4.14 (t, J=6.4 Hz, 2H), 3.44 (t, J=4.5 Hz, 4H), 2.28 (br. s., 4H).

Scheme 11

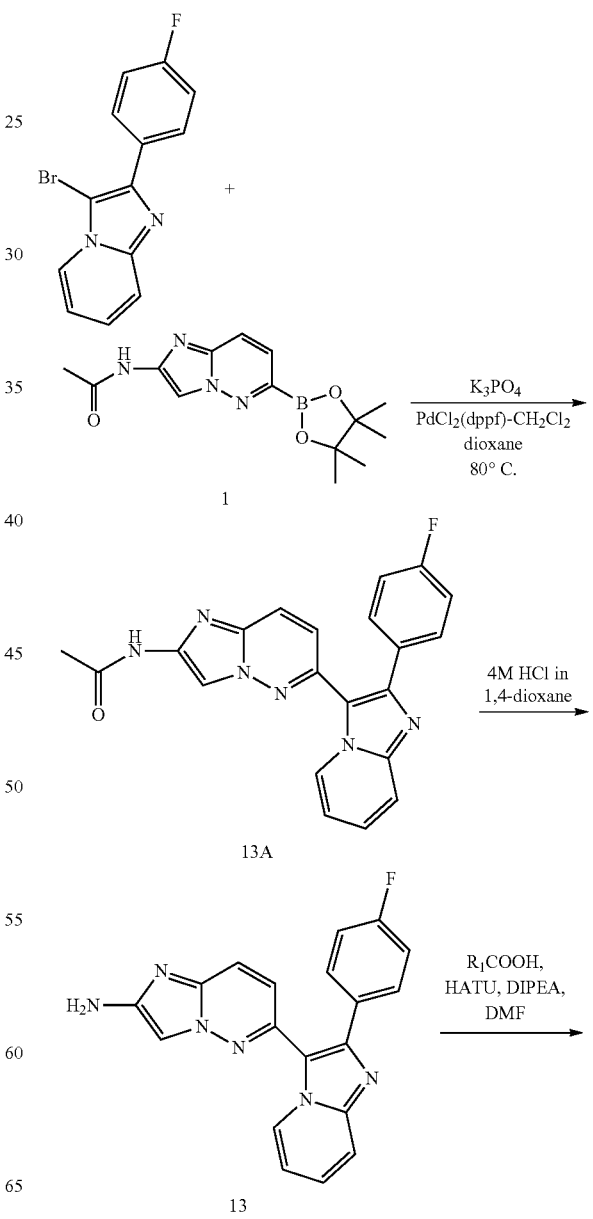

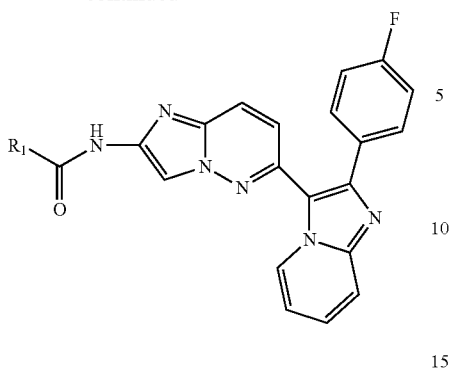

Intermediate 13

6-(2-(4-fluorophenyl)imidazo[1,2-a]pyridin-3-yl)imidazo[1,2-b]pyridazin-2-amine

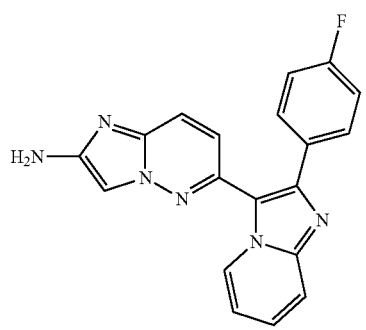 [SMILES: Nc1cn2nc(-c3c(-c4ccc(F)cc4)nc4ccccn34)ccc2n1]

Intermediate 13A: N-(6-(2-(4-fluorophenyl)imidazo[1,2-a]pyridin-3-yl)imidazo[1,2-b]pyridazin-2-yl)acetamide

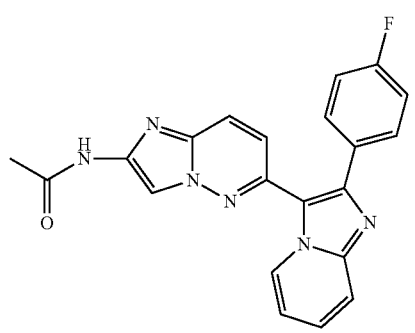 [SMILES: CC(=O)Nc1cn2nc(-c3c(-c4ccc(F)cc4)nc4ccccn34)ccc2n1]

Intermediate 13A was synthesized analogous to Intermediate 8A by reacting Intermediate 1 with commercially available 3-bromo-2-(4-fluorophenyl)imidazo[1,2-a]pyridine. HPLC Ret. Time 2.76 min. (Method A). MS(ES): m/z=387.14 [M+H]$^+$.

Intermediate 13: 6-(2-(4-fluorophenyl)imidazo[1,2-a]pyridin-3-yl)imidazo[1,2-b]pyridazin-2-amine

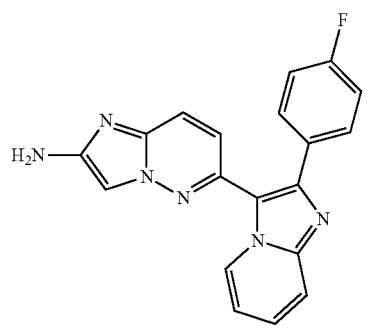 [SMILES: Nc1cn2nc(-c3c(-c4ccc(F)cc4)nc4ccccn34)ccc2n1]

Intermediate 13 was synthesized analogous to Intermediate 12 by reacting Intermediate 13A with hydrogen chloride (4M solution in 1,4-dioxane). HPLC Ret. Time 2.205 min. (Method A). MS(ES): m/z=345.16 [M+H]$^+$.

Scheme 12

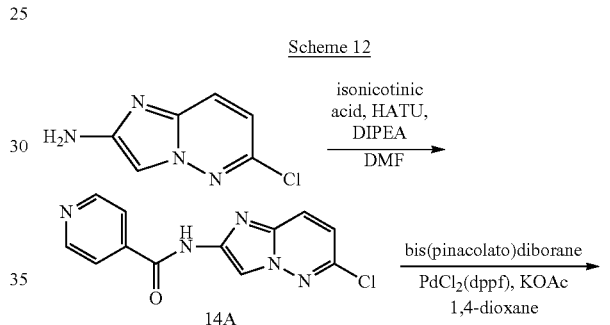

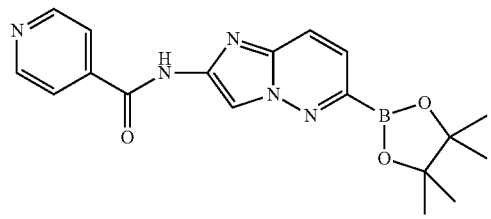

Intermediate 14

(2-(isonicotinamido)imidazo[1,2-b]pyridazin-6-yl)boronic acid

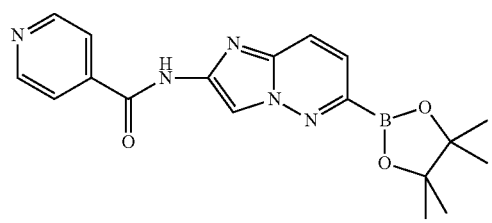 [SMILES: CC1(C)OB(c2ccc3nc(NC(=O)c4ccncc4)cn3n2)OC1(C)C]

Intermediate 14A: N-(6-chloroimidazo[1,2-b]pyridazin-2-yl)isonicotinamide

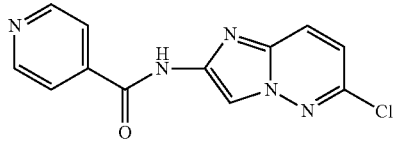 [SMILES: O=C(Nc1cn2nc(Cl)ccc2n1)c1ccncc1]

To a solution of 6-chloroimidazo[1,2-b]pyridazin-2-amine (1.0 g, 5.75 mmol) in DMF (16.44 mL) was added isonicotinic acid (1.417 g, 11.51 mmol), HATU (4.38 g, 11.51 mmol) and Hunig's base (4.02 ml, 23.02 mmol). The reaction mixture was stirred at rt for 16 h and then diluted with water (200 mL). The generated precipitate was filtered off, washed with copious amounts of water and then dried on high vac to afford the desired product 14A (1.49 g, 95% yield) as a yellowish solid. HPLC Ret. Time 2.552 min. (Method A). MS(ES): m/z 274.11 [M+H]$^+$.

Intermediate 14: (2-(isonicotinamido)imidazo[1,2-b]pyridazin-6-yl)boronic acid

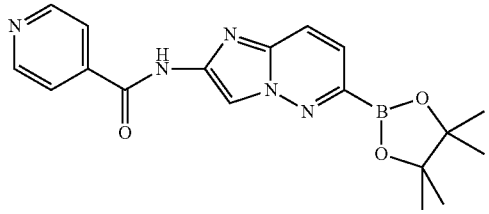 [SMILES: CC1(C)OB(c2ccc3nc(NC(=O)c4ccncc4)cn3n2)OC1(C)C]

To a degassed suspension of Intermediate 14 A (1.49 g, 5.44 mmol), 4,4,4',4',5,5,5',5'-octamethyl-2,2'-bi(1,3,2-dioxaborolane) (2.074 g, 8.17 mmol) and potassium acetate (1.336 g, 13.61 mmol) in 1,4-dioxane (36.3 mL) was added PdCl$_2$(dppf)-CH$_2$Cl$_2$ adduct (0.445 g, 0.544 mmol). The reaction mixture was degassed again for 5 min. A reflux condenser was attached to the round bottom flask and the reaction was heated in an oil-bath at 100° C. for 16 h. The reaction mixture was then cooled to rt and used in the Suzuki coupling step without any work up. HPLC Ret. Time 0.45 min. (Method A). MS(ES): m/z=284.12 [M+H]$^+$.

Scheme 13

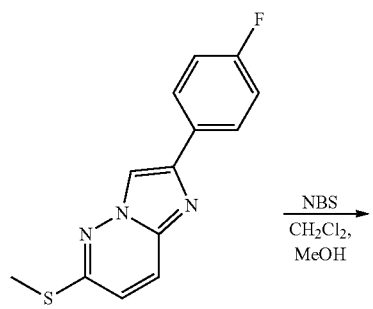

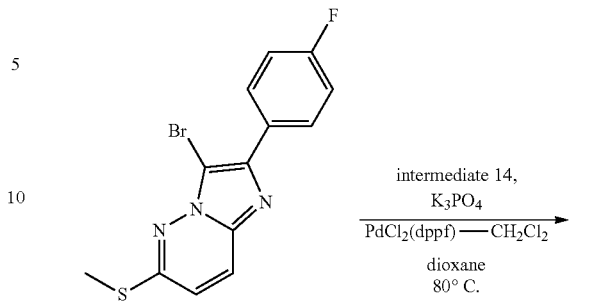

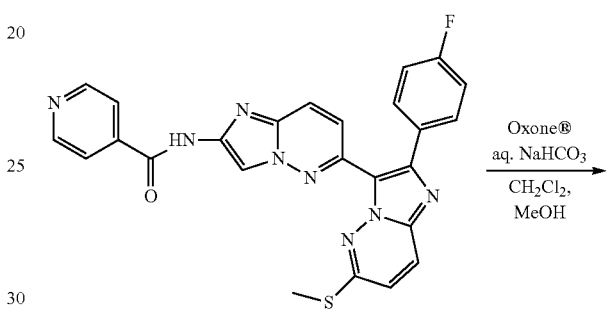

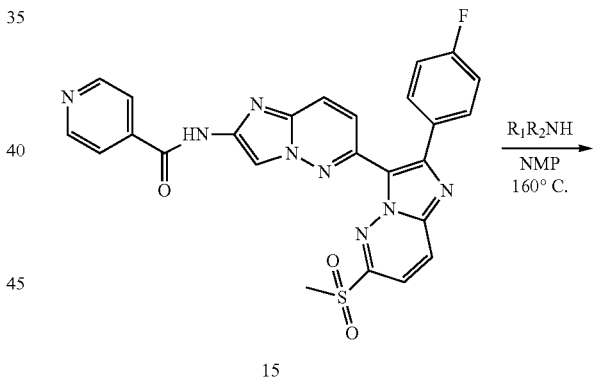

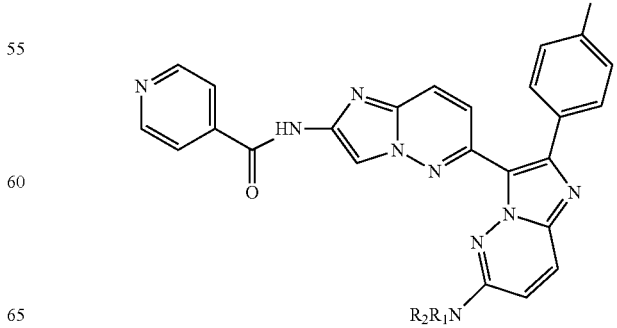

Intermediate 15

N-(2-(4-fluorophenyl)-6-(methylsulfonyl)-[3,6'-biimidazo[1,2-b]pyridazin]-2'-yl)isonicotinamide

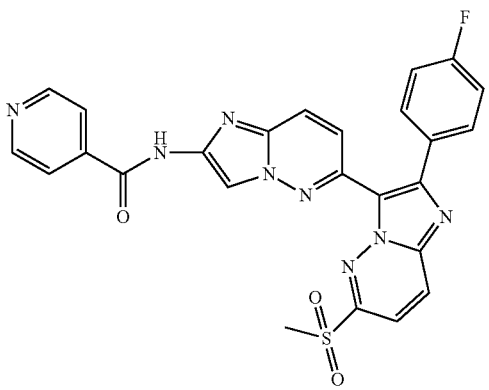 [SMILES: CS(=O)(=O)c1ccc2nc(-c3ccc(F)cc3)c(-c3ccc4nc(NC(=O)c5ccncc5)cn4n3)n2n1]

Intermediate 15A: 3-bromo-2-(4-fluorophenyl)-6-(methylthio)imidazo[1,2-b]pyridazine

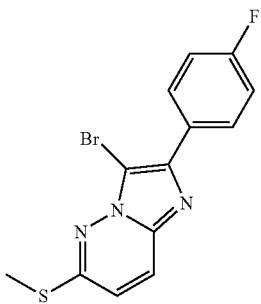 [SMILES: CSc1ccc2nc(-c3ccc(F)cc3)c(Br)n2n1]

Intermediate 15A was synthesized analogous to Intermediate 3 by reacting commercially available 2-(4-fluorophenyl)-6-(methylthio)imidazo[1,2-b]pyridazine with N-bromosuccinimide. HPLC Ret. Time 4.216 min. (Method A). MS(ES): m/z=338.06 [M+H]$^+$.

Intermediate 15 B: N-(2-(4-fluorophenyl)-6-(methylthio)-[3,6'-biimidazo[1,2-b]pyridazin]-2'-yl)isonicotinamide

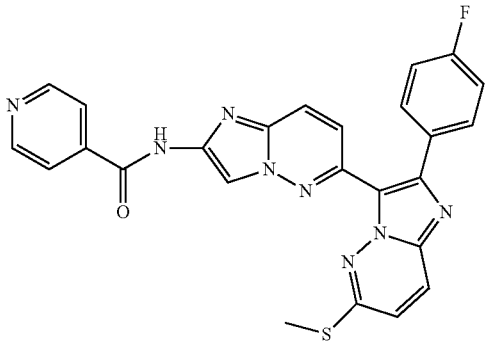 [SMILES: CSc1ccc2nc(-c3ccc(F)cc3)c(-c3ccc4nc(NC(=O)c5ccncc5)cn4n3)n2n1]

Intermediate 15B was synthesized analogous to Intermediate 8A by reacting Intermediate 15A with Intermediate 14. HPLC Ret. Time 3.596 min. (Method A). MS(ES): m/z=497.20 [M+H]$^+$.

Intermediate 15: N-(2-(4-fluorophenyl)-6-(methylsulfonyl)-[3,6'-biimidazo[1,2-b]pyridazin]-2'-yl)isonicotinamide

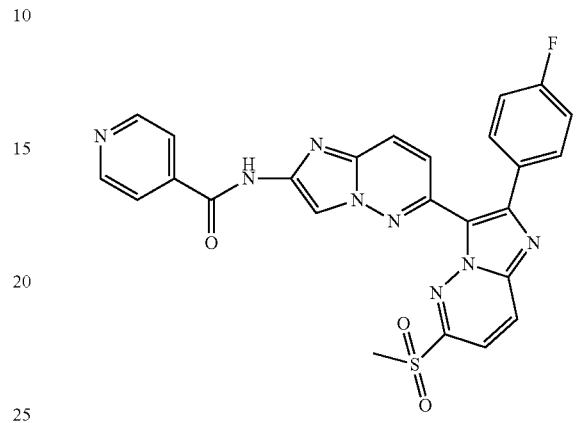

To a solution of Intermediate 15B (0.27 g, 0.544 mmol) in CH$_2$Cl$_2$ (15 mL) and MeOH (15 mL) were sequentially added, satd. aq. NaHCO$_3$ (6.75 mL, 0.544 mmol) and OXONE® (1.504 g, 2.447 mmol). The reaction mixture was stirred at rt for 16 h and then transferred to a separatory funnel. The two layers were separated and the aq. layer was extracted thrice with CH$_2$Cl$_2$. The combined organics were washed with brine. The organic phase was dried over anhydrous magnesium sulfate and concentrated under reduced pressure to provide Intermediate 15 (0.282 g, 98% yield) as a brown solid. HPLC Ret. Time 3.396 min. (Method H). MS(ES): m/z=529.20 [M+H]$^+$.

Compound 1

N-(6-(4-(4-fluorophenyl)-1-(piperidin-4-yl)-1H-imidazol-5-yl)imidazo[1,2-b]pyridazin-2-yl)isonicotinamide

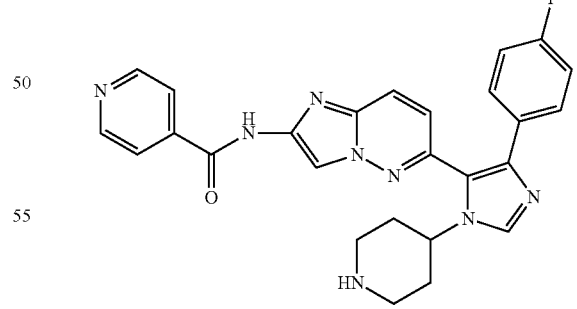

To a solution of Intermediate 8 (0.425 g, 0.890 mmol), isonicotinic acid (0.219 g, 1.780 mmol) and HATU (0.677 g, 1.780 mmol) in DMF (8.90 mL) was added Hunig's base (0.622 mL, 3.56 mmol) and the reaction was stirred at rt for 16 h. It was then quenched with satd. aq. NaHCO$_3$ and the generated precipitate was filtered off. The filter cake was washed with water and then air-dried to provide the intermediate amide.

To a solution of this amide in CH$_2$Cl$_2$ (4 mL) was added TFA (1 mL) and the reaction was stirred at rt for 30 min. The volatiles were evaporated under reduced pressure, the residue dissolved in DMF and the material purified via preparative LC/MS with the following conditions: Column: Waters XBridge C18, 19×150 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 5-100% B over 30 minutes, then a 5-minute hold at 100% B; Flow: 20 mL/min. Fractions containing the desired product (0.095 g, 21% yield) were combined and dried via centrifugal evaporation. HPLC Ret. Time 1.94 min., 3.31 min (Methods B and C respectively). MS(ES): m/z=483.40 [M+H]$^+$. $^1$H NMR (400 MHz, DMSO-d$_6$) δ ppm 12.12 (s, 1H), 9.26 (s, 1H), 9.01-8.88 (m, 3H), 8.75 (s, 1H), 8.62 (d, J=10.0 Hz, 1H), 8.25-8.11 (m, 3H), 7.60-7.45 (m, 2H), 7.38-7.23 (m, 2H), 7.14 (d, J=9.3 Hz, 1H), 4.81-4.63 (m, 1H), 3.47 (br. S., 1H), 3.14-2.96 (m, 2H), 2.38 (d, J=12.0 Hz, 2H), 2.30-2.13 (m, 2H).

Compound 2

N-(6-(4-(4-fluorophenyl)-1-(1-methylpiperidin-4-yl)-1H-imidazol-5-yl)imidazo[1,2-b]pyridazin-2-yl)isonicotinamide

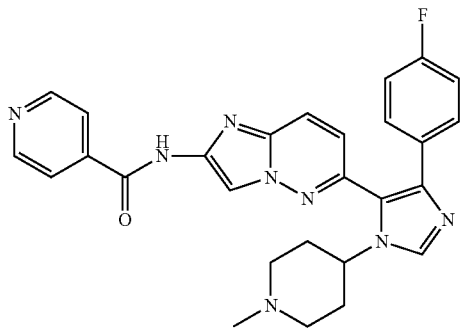 [SMILES: CN1CCC(n2cnc(-c3ccc(F)cc3)c2-c2ccc3nc(NC(=O)c4ccncc4)cn3n2)CC1]

To a solution of compound 1 (0.033 g, 0.068 mmol) and formaldehyde (37% aq. solution, 0.031 mL, 0.410 mmol) in MeOH (0.68 mL) and CH$_2$Cl$_2$ (0.68 mL) was added sodium cyanoborohydride (0.036 g, 0.547 mmol) and acetic acid (3.92 μL, 0.068 mmol). The reaction mixture was stirred for 16 h at rt and the volatiles were evaporated under reduced pressure. The residue was dissolved in DMF and purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 10-100% B over 20 minutes, then a 4-minute hold at 100% B; Flow: 25 mL/min. Fractions containing the desired product (0.0245 g, 72.1% yield) were combined and dried via centrifugal evaporation. HPLC Ret. Time 1.80 min., 3.87 min. (Methods B and C respectively). MS(ES): m/z 497.27 [M+H]$^+$. $^1$H NMR (500 MHz, DMSO-d$_6$) δ ppm 8.82 (d, J=5.8 Hz, 2H), 8.60 (s, 1H), 8.18 (s, 1H), 8.09 (d, J=9.5 Hz, 1H), 8.02 (d, J=6.1 Hz, 2H), 7.97 (s, 1H), 7.46 (dd, J=8.5, 5.5 Hz, 2H), 7.18-7.08 (m, 3H), 4.14-4.02 (m, 1H), 2.91 (s, 2H), 2.85 (d, J=11.9 Hz, 2H), 2.75 (s, 2H), 2.17 (s, 3H).

The compounds described in Table 1 were synthesized analogous to compound 2 by reacting compound 1 with the corresponding aldehydes.

TABLE 1

| Compound No. | Structure | Name | [M + H]$^+$ | Ret. Time | HPLC Method |
|---|---|---|---|---|---|
| 3 | 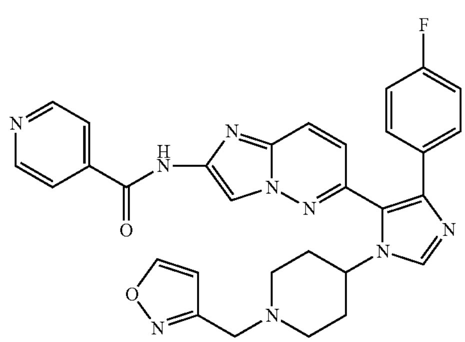 [SMILES: O=C(Nc1cn2nc(-c3c(-c4ccc(F)cc4)ncn3C3CCN(Cc4ccon4)CC3)ccc2n1)c1ccncc1] | N-(6-(4-(4-fluorophenyl)-1-(1-(isoxazol-3-ylmethyl)piperidin-4-yl)-1H-imidazol-5-yl)imidazo[1,2-b]pyridazin-2-yl)isonicotinamide | 564.3 | 2.30, 3.72 | B, C |

TABLE 1-continued

| Compound No. | Structure | Name | [M + H]⁺ | Ret. Time | HPLC Method |
|---|---|---|---|---|---|
| 4 | 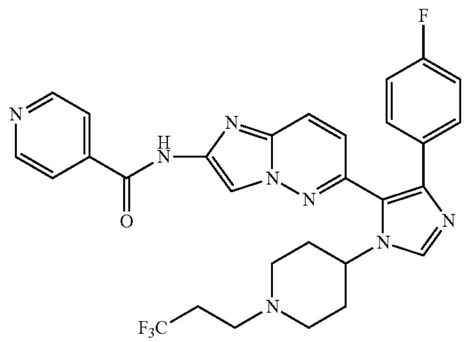 [SMILES: O=C(Nc1cn2nc(-c3c(-c4ccc(F)cc4)ncn3C3CCN(CCC(F)(F)F)CC3)ccc2n1)c1ccncc1] | N-(6-(4-(4-fluorophenyl)-1-(1-(3,3,3-trifluoropropyl)piperidin-4-yl)-1H-imidazol-5-yl)imidazo[1,2-b]pyridazin-2-yl)isonicotinamide | 579.3 | 2.41, 389 | B, C |

Compound 5

N-(6-(4-(4-fluorophenyl)-1-(1-(isoxazole-3-carbonyl)piperidin-4-yl)-1H-imidazol-5-yl)imidazo[1,2-b]pyridazin-2-yl)isonicotinamide

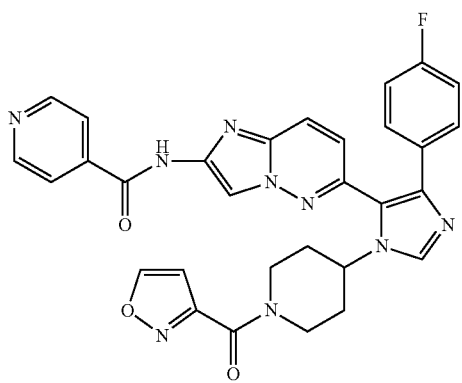 [SMILES: O=C(Nc1cn2nc(-c3c(-c4ccc(F)cc4)ncn3C3CCN(C(=O)c4ccon4)CC3)ccc2n1)c1ccncc1]

To a solution of compound 1 (0.035 g, 0.073 mmol), isoxazole-3-carboxylic acid (0.016 g, 0.145 mmol) and HATU (0.055 g, 0.145 mmol) in DMF (1.451 mL) was added Hunig's base (0.051 mL, 0.290 mmol) and the reaction mixture was stirred at rt for 16 h. It was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 45-85% B over 20 minutes, then a 5-minute hold at 100% B; Flow: 20 mL/min. Fractions containing the desired product (0.0128 g, 30.6% yield) were combined and dried via centrifugal evaporation. HPLC Ret. Time 2.16 min., 3.55 min. (Methods B and C respectively). MS(ES): m/z=578.20 [M+H]⁺. ¹H NMR (500 MHz, DMSO-d₆) δ ppm 11.86 (br. s, 1H), 9.12 (d, J=1.5 Hz, 1H), 8.88-8.78 (m, 2H), 8.64 (s, 1H), 8.24 (s, 1H), 8.10 (d, J=9.2 Hz, 1H), 8.06-7.98 (m, 2H), 7.52-7.41 (m, 2H), 7.21-7.10 (m, 3H), 6.86 (d, J=1.5 Hz, 1H), 4.63 (d, J=13.1 Hz, 1H), 4.53-4.39 (m, 1H), 4.03 (d, J=14.6 Hz, 1H), 3.92 (s, 1H), 3.30-3.16 (m, 1H), 2.95-2.84 (m, 1H), 2.21 (d, J=11.3 Hz, 1H), 2.18-2.11 (m, 1H), 2.11-1.96 (m, 2H).

The compound described in Table 2 was synthesized analogous to compound 5 by reacting compound 1 with the corresponding carboxylic acid.

TABLE 2

| Compound No. | Structure | Name | [M + H]⁺ | Ret. Time | HPLC Method |
|---|---|---|---|---|---|
| 6 | 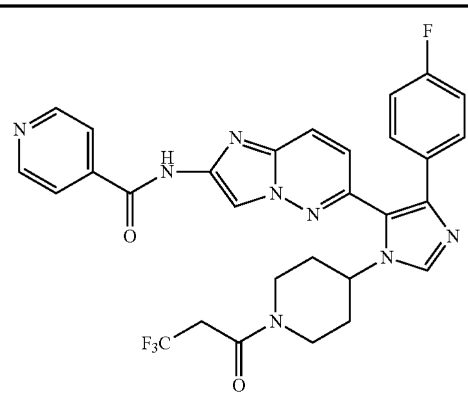 | N-(6-(4-(4-fluorophenyl)-1-(1-(3,3,3-trifluoropropanoyl)piperidin-4-yl)-1H-imidazol-5-yl)imidazo[1,2-b]pyridazin-2-yl)isonicotinamide | 593.2 | 2.25, 3.59 | B, C |

Compound 7

(R)—N-(6-(4-(4-fluorophenyl)-1-(1-(3,3,3-trifluoro-2-hydroxypropyl)piperidin-4-yl)-1H-imidazol-5-yl)imidazo[1,2-b]pyridazin-2-yl)isonicotinamide

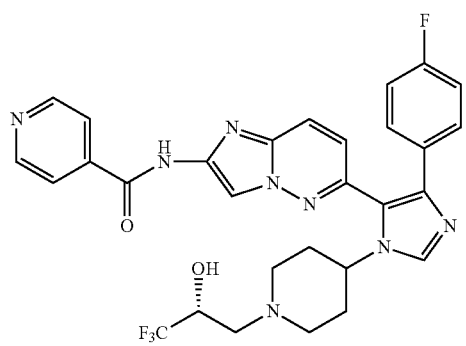 [SMILES: O=C(Nc1cn2nc(-c3c(-c4ccc(F)cc4)ncn3C3CCN(C[C@@H](O)C(F)(F)F)CC3)ccc2n1)c1ccncc1]

A solution of compound 1 (0.035 g, 0.073 mmol) and (R)-2-(trifluoromethyl)oxirane (0.041 g, 0.363 mmol) in DMF (1.451 mL) was stirred at rt for 16 h. It was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 45-85% B over 20 minutes, then a 5-minute hold at 100% B; Flow: 20 mL/min. Fractions containing the desired product (0.018 g, 41.7% yield) were combined and dried via centrifugal evaporation. HPLC Ret. Time 3.77 min. (Method C). MS(ES): m/z=595.20 [M+H]$^+$. $^1$H NMR (500 MHz, DMSO-d$_6$) δ ppm 8.86-8.78 (m, 2H), 8.60 (s, 1H), 8.19 (s, 1H), 8.14-8.05 (m, 1H), 8.05-7.96 (m, 2H), 7.47 (dd, J=8.9, 5.8 Hz, 2H), 7.19-7.09 (m, 3H), 4.17-4.04 (m, 2H), 3.92 (s, 1H), 3.01 (t, J=9.9 Hz, 2H), 2.20-1.98 (m, 6H), 1.90 (s, 2H).

The compound described in Table 3 was synthesized analogous to compound 7 by reacting compound 1 with the corresponding epoxide.

Compound 9

2-fluoro-N-(6-(4-(4-fluorophenyl)-1-(piperidin-4-yl)-1H-imidazol-5-yl)imidazo[1,2-b]pyridazin-2-yl)isonicotinamide

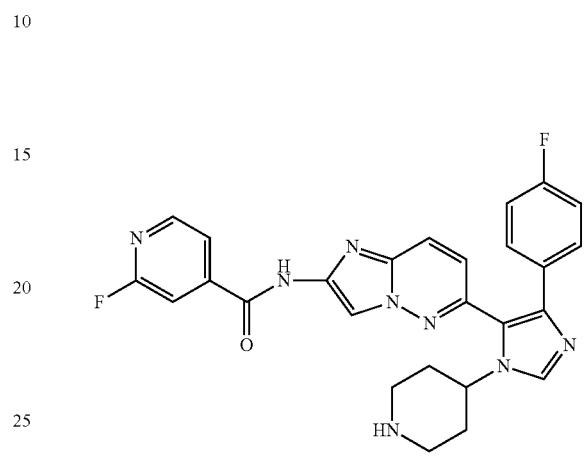

Compound 9 was synthesized analogous to compound 1 by reacting Intermediate 8 with 2-fluoroisonicotinic acid, followed by the deprotection of the Boc group with TFA. HPLC Ret. Time 1.96 min., 3.40 min. (Methods B and C respectively). MS(ES): m/z 501.40 [M+H]$^+$. $^1$H NMR (500 MHz, DMSO-d$_6$) δ ppm 8.59 (s, 1H), 8.48 (d, J=5.2 Hz, 1H), 8.19-8.06 (m, 2H), 7.98 (d, J=4.9 Hz, 1H), 7.82 (s, 1H), 7.51-7.39 (m, 2H), 7.20-7.07 (m, 3H), 4.15 (tt, J=11.8, 3.7 Hz, 1H), 3.01 (d, J=12.2 Hz, 2H), 2.46 (t, J=11.4 Hz, 2H), 1.96 (d, J=9.5 Hz, 2H), 1.92-1.78 (m, 3H).

TABLE 3

| Compound No. | Structure | Name | [M + H]$^+$ | Ret. Time | HPLC Method |
|---|---|---|---|---|---|
| 8 | 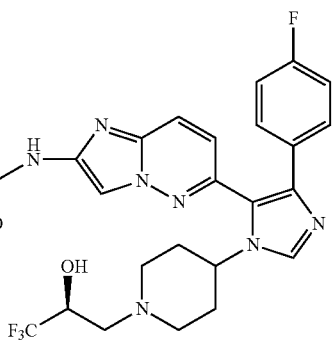 | (S)-N-(6-(4-(4-fluorophenyl)-1-(1-(3,3,3-trifluoro-2-hydroxypropyl)piperidin-4-yl)-1H-imidazol-5-yl)imidazo[1,2-b]pyridazin-2-yl)isonicotinamide | 593.0 | 2.25, 1.75 | B, C |

Compound 10

2-fluoro-N-(6-(4-(4-fluorophenyl)-1-(1-(3,3,3-trifluoropropyl)piperidin-4-yl)-1H-imidazol-5-yl)imidazo[1,2-b]pyridazin-2-yl)isonicotinamide

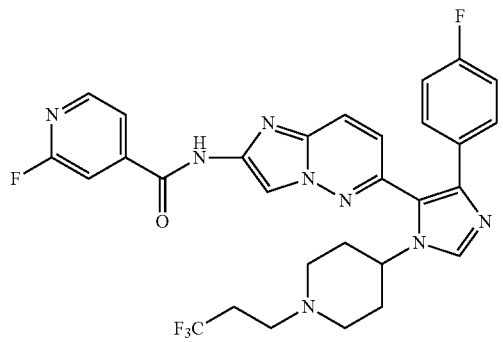 [SMILES: O=C(Nc1cn2nc(-c3c(-c4ccc(F)cc4)ncn3C3CCN(CCC(F)(F)F)CC3)ccc2n1)c1ccnc(F)c1]

Compound 10 was synthesized analogous to compound 2 by reacting compound 9 with 3,3,3-trifluoropropanal. HPLC Ret. Time 2.65 min., 4.10 min. (Methods B and C respectively). MS(ES): m/z=597.42 [M+H]$^+$. $^1$H NMR (400 MHz, DMSO-d$_6$) δ ppm 12.02 (s, 1H), 8.75-8.62 (m, 2H), 8.50 (d, J=5.3 Hz, 1H), 8.21-8.09 (m, 1H), 7.99 (dt, J=5.3, 1.5 Hz, 1H), 7.83 (s, 1H), 7.58-7.42 (m, 2H), 7.24 (t, J=8.8 Hz, 2H), 7.13 (d, J=9.3 Hz, 1H), 4.60 (br. s., 1H), 3.70 (br. s., 1H), 3.37 (br. s, 1H), 3.16 (br. s, 1H), 2.97-2.78 (m, 2H), 2.42 (br. s., 1H), 2.30 (br. s., 1H).

The compounds described in Table 4 were synthesized analogous to compound 10 by reacting compound 9 with the corresponding aldehydes.

TABLE 4

| Compound No. | Structure | Name | [M + H]$^+$ | Ret. Time | HPLC Method |
| --- | --- | --- | --- | --- | --- |
| 11 | 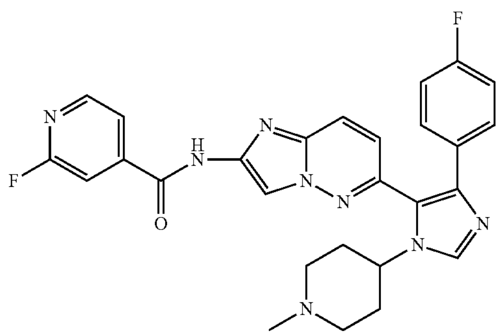 [SMILES: CN1CCC(n2cnc(-c3ccc(F)cc3)c2-c2ccc3nc(NC(=O)c4ccnc(F)c4)cn3n2)CC1] | N-(6-(4-(4-fluorophenyl)-1-(1-methylpiperidin-4-yl)-1H-imidazol-5-yl)imidazo[1,2-b]pyridazin-2-yl)isonicotinamide | 515.4 | 2.19, 3.75 | B, C |
| 12 | 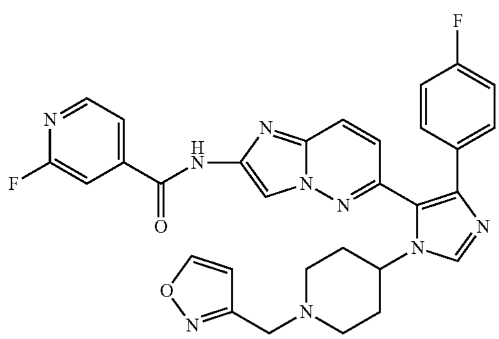 [SMILES: O=C(Nc1cn2nc(-c3c(-c4ccc(F)cc4)ncn3C3CCN(Cc4ccon4)CC3)ccc2n1)c1ccnc(F)c1] | N-(6-(4-(4-fluorophenyl)-1-(1-(isoxazol-3-ylmethyl)piperidin-4-yl)-1H-imidazol-5-yl)imidazo[1,2-b]pyridazin-2-yl)isonicotinamide | 582.40 | 2.56, 3.89 | B, C |
| 13 | 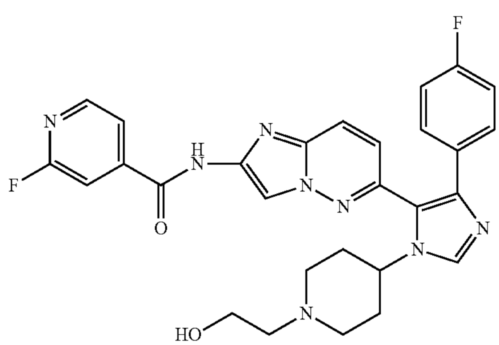 [SMILES: O=C(Nc1cn2nc(-c3c(-c4ccc(F)cc4)ncn3C3CCN(CCO)CC3)ccc2n1)c1ccnc(F)c1] | 2-fluoro-N-(6-(4-(4-fluorophenyl)-1-(1-(2-hydroxyethyl)piperidin-4-yl)-1H-imidazol-5-yl)imidazo[1,2-b]pyridazin-2-yl)isonicotinamide | 545.40 | 2.12, 3.65 | B, C |

TABLE 4-continued

| Compound No. | Structure | Name | [M + H]+ | Ret. Time | HPLC Method |
|---|---|---|---|---|---|
| 14 | 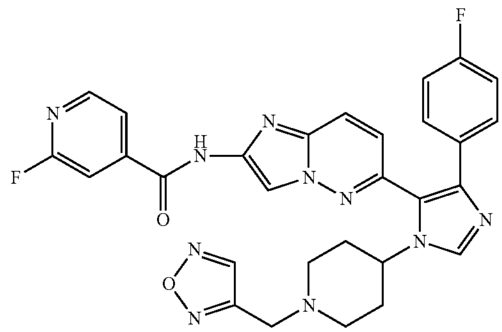 [SMILES: O=C(Nc1cn2nc(-c3c(-c4ccc(F)cc4)ncn3C3CCN(Cc4cnon4)CC3)ccc2n1)c1ccnc(F)c1] | N-(6-(1-(1-(1,2,5-oxadiazole-3-carbonyl)piperidin-4-yl)-4-(4-fluorophenyl)-1H-imidazol-5-yl)imidazo[1,2-b]pyridazin-2-yl)-2-fuoroisonicotinamide | 597.30 | 2.11, 3.42 | B, C |
| 15 | 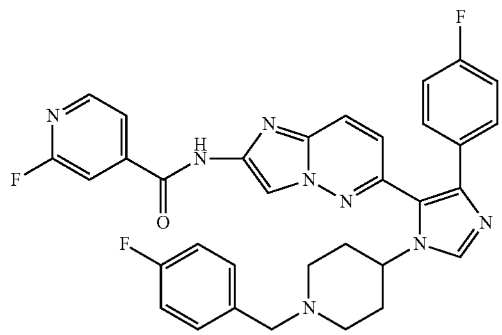 [SMILES: O=C(Nc1cn2nc(-c3c(-c4ccc(F)cc4)ncn3C3CCN(Cc4ccc(F)cc4)CC3)ccc2n1)c1ccnc(F)c1] | 2-fluoro-N-(6-(1-(1-(4-fluorobenzyl)piperidin-4-yl)-4-(4-fluorophenyl)-1H-imidazol-5-yl)imidazo[1,2-b]pyridazin-2-yl)isonicotinamide | 609.28 | 2.73 | B |
| 16 | 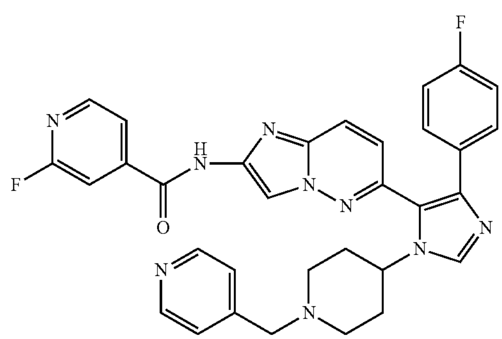 [SMILES: O=C(Nc1cn2nc(-c3c(-c4ccc(F)cc4)ncn3C3CCN(Cc4ccncc4)CC3)ccc2n1)c1ccnc(F)c1] | 2-fluoro-N-(6-(4-(4-fluorophenyl)-1-(1-(pyridin-4-ylmethyl)piperidin-4-yl)-1H-imidazol-5-yl)imidazo[1,2-b]pyridazin-2-yl)isonicotinamide | 592.30 | 2.36 | B |
| 17 | 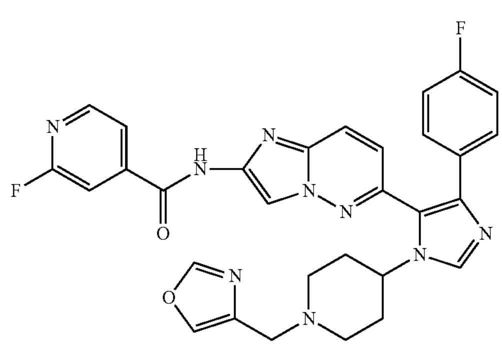 [SMILES: O=C(Nc1cn2nc(-c3c(-c4ccc(F)cc4)ncn3C3CCN(Cc4cocn4)CC3)ccc2n1)c1ccnc(F)c1] | 2-fluoro-N-(6-(4-(4-fluorophenyl)-1-(1-(oxazol-4-ylmethyl)piperidin-4-yl)-1H-imidazol-5-yl)imidazo[1,2-b]pyridazin-2-yl)isonicotinamide | 582.29 | 3.84 | C |

TABLE 4-continued

| Compound No. | Structure | Name | [M + H]⁺ | Ret. Time | HPLC Method |
|---|---|---|---|---|---|
| 18 | 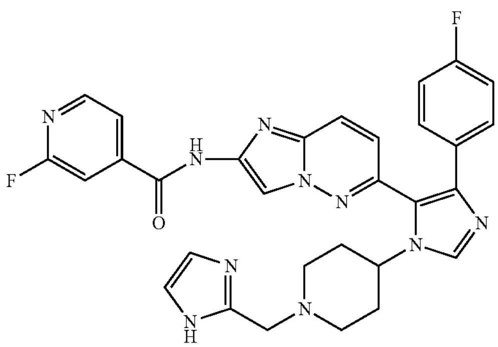 [SMILES: O=C(Nc1cn2nc(-c3c(-c4ccc(F)cc4)ncn3C3CCN(Cc4ncc[nH]4)CC3)ccc2n1)c1ccnc(F)c1] | N-(6-(1-(1-((1H-imidazol-2-yl)methyl)piperidin-4-yl)-4-(4-fluorophenyl)-1H-imidazol-5-yl)imidazo[1,2-b]pyridazin-2-yl)-2-fluoroisonicotinamide | 581.30 | 2.10 | B |
| 19 | 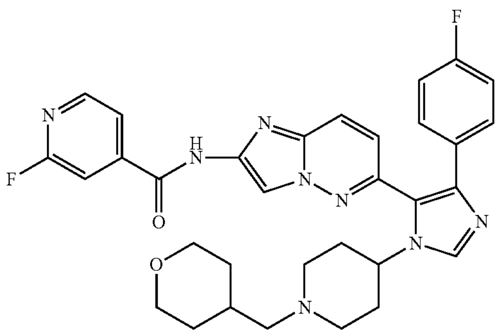 [SMILES: O=C(Nc1cn2nc(-c3c(-c4ccc(F)cc4)ncn3C3CCN(CC4CCOCC4)CC3)ccc2n1)c1ccnc(F)c1] | 2-fluoro-N-(6-(4-(4-fluorophenyl)-1-(1-((tetrahydro-2H-pyran-4-yl)methyl)piperidin-4-yl)-1H-imidazol-5-yl)imidazo[1,2-b]pyridazin-2-yl)isonicotinamide | 599.31 | 4.01 | C |
| 20 | 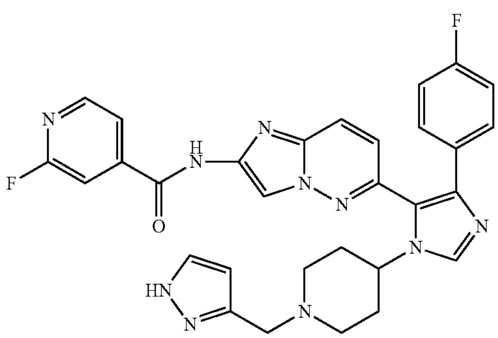 [SMILES: O=C(Nc1cn2nc(-c3c(-c4ccc(F)cc4)ncn3C3CCN(Cc4cc[nH]n4)CC3)ccc2n1)c1ccnc(F)c1] | N-(6-(1-(1-((1H-pyrazol-3-yl)methyl)piperidin-4-yl)-4-(4-fluorophenyl)-1H-imidazol-5-yl)imidazo[1,2-b]pyridazin-2-yl)-2-fluoroisonicotinamide | 581.27 | 3.83 | C |
| 21 | 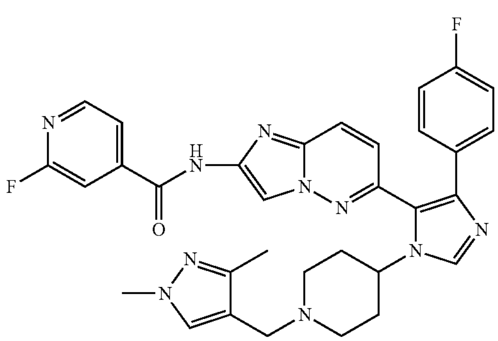 [SMILES: Cc1nn(C)cc1CN1CCC(n2cnc(-c3ccc(F)cc3)c2-c2ccc3nc(NC(=O)c4ccnc(F)c4)cn3n2)CC1] | N-(6-(1-(1-((1H-pyrazol-5-yl)methyl)piperidin-4-yl)-4-(4-fluorophenyl)-1H-imidazol-5-yl)imidazo[1,2-b]pyridazin-2-yl)-2-fluoroisonicotinamide | 609.31 | 3.90 | C |

TABLE 4-continued

| Compound No. | Structure | Name | [M + H]+ | Ret. Time | HPLC Method |
|---|---|---|---|---|---|
| 22 | 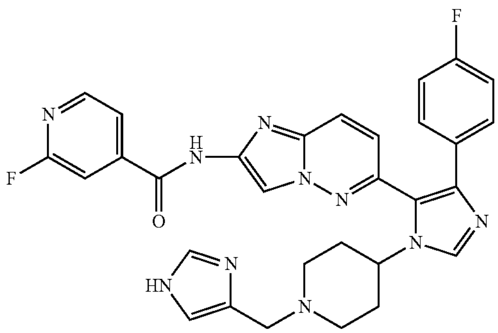 [SMILES: O=C(Nc1cn2nc(-c3c(-c4ccc(F)cc4)ncn3C3CCN(Cc4c[nH]cn4)CC3)ccc2n1)c1ccnc(F)c1] | N-(6-(1-(1-((1,3-dimethyl-1H-pyrazol-4-yl)methyl)piperidin-4-yl)-4-(4-fluorophenyl)-1H-imidazol-5-yl)imidazo[1,2-b]pyridazin-2-yl)-2-fluoroisonicotinamide | 581.55 | 1.94 | B |
| 23 | 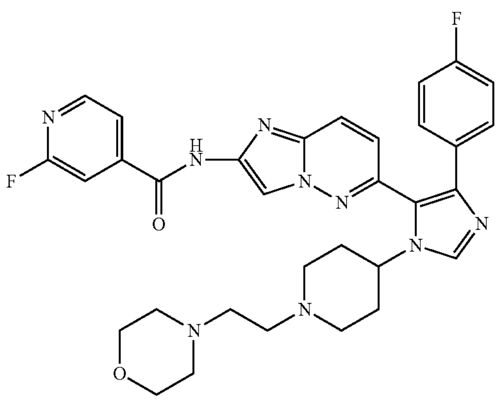 [SMILES: O=C(Nc1cn2nc(-c3c(-c4ccc(F)cc4)ncn3C3CCN(CCN4CCOCC4)CC3)ccc2n1)c1ccnc(F)c1] | 2-fluoro-N-(6-(4-(4-fluorophenyl)-1-(1-(2-morpholinoethyl)piperidin-4-yl)-1H-imidazol-5-yl)imidazo[1,2-b]pyridazin-2-yl)isonicotinamide | 614.36 | 2.08 | B |
| 24 | 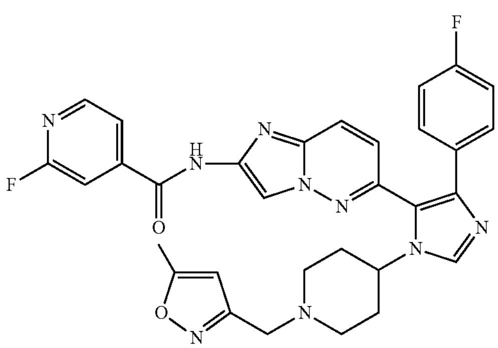 [SMILES: Cc1cc(CN2CCC(n3cnc(-c4ccc(F)cc4)c3-c3ccc4nc(NC(=O)c5ccnc(F)c5)cn4n3)CC2)no1] | 2-fluoro-N-(6-(4-(4-fluorophenyl)-1-(1-((5-methylisoxazol-3-yl)methyl)piperidin-4-yl)-1H-imidazol-5-yl)imidazo[1,2-b]pyridazin-2-yl)isonicotinamide | 581.30 | 2.11 | B |
| 25 | 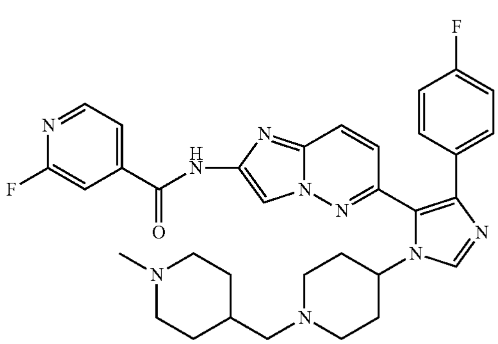 [SMILES: CN1CCC(CN2CCC(n3cnc(-c4ccc(F)cc4)c3-c3ccc4nc(NC(=O)c5ccnc(F)c5)cn4n3)CC2)CC1] | 2-fluoro-N-(6-(4-(4-fluorophenyl)-1-(1-((1-methylpiperidin-4-yl)methyl)piperidin-4-yl)-1H-imidazol-5-yl)imidazo[1,2-b]pyridazin-2-yl)isonicotinamide | 612.32 | 3.69 | C |

TABLE 4-continued

| Compound No. | Structure | Name | [M + H]+ | Ret. Time | HPLC Method |
|---|---|---|---|---|---|
| 26 | 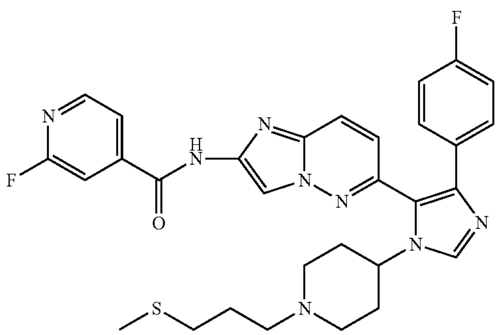 [SMILES: CSCCCN1CCC(n2cnc(-c3ccc(F)cc3)c2-c2ccc3nc(NC(=O)c4ccnc(F)c4)cn3n2)CC1] | 2-fluoro-N-(6-(4-(4-fluorophenyl)-1-(1-(3-(methylthio)propyl)piperidin-4-yl)-1H-imidazol-5-yl)imidazo[1,2-b]pyridazin-2-yl)isonicotinamide | 589.01 | 4.02 | C |
| 27 | 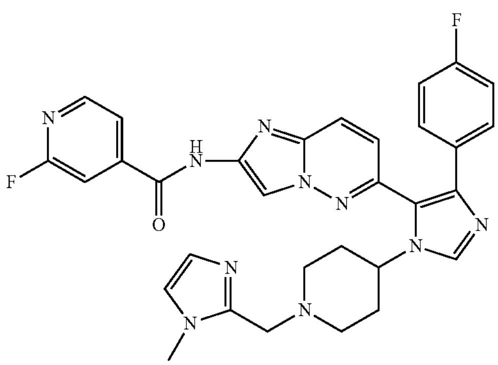 [SMILES: Cn1ccnc1CN1CCC(n2cnc(-c3ccc(F)cc3)c2-c2ccc3nc(NC(=O)c4ccnc(F)c4)cn3n2)CC1] | 2-fluoro-N-(6-(4-(4-fluorophenyl)-1-(1-((1-methyl-1H-imidazol-2-yl)methyl)piperidin-4-yl)-1H-imidazol-5-yl)imidazo[1,2-b]pyridazin-2-yl)isonicotinamide | 595.26 | 3.88 | C |
| 28 | 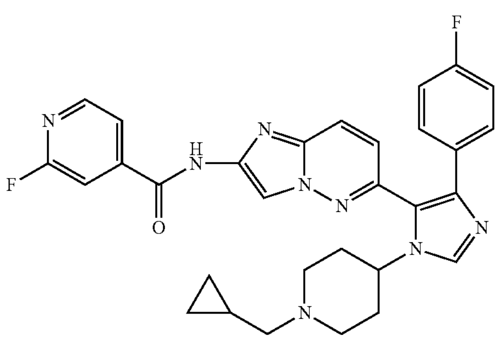 [SMILES: O=C(Nc1cn2nc(-c3c(-c4ccc(F)cc4)ncn3C3CCN(CC4CC4)CC3)ccc2n1)c1ccnc(F)c1] | N-(6-(1-(1-(cyclopropylmethyl)piperidin-4-yl)-4-(4-fluorophenyl)-1H-imidazol-5-yl)imidazo[1,2-b]pyridazin-2-yl)-2-fluoroisonicotinamide | 555.31 | 3.94 | C |
| 29 | 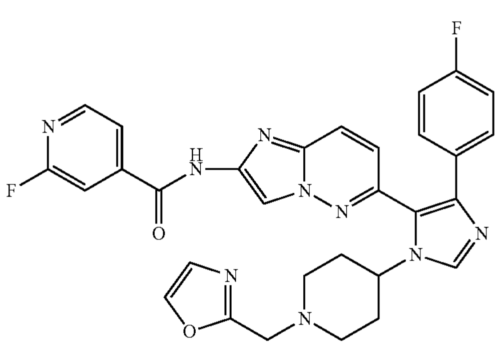 [SMILES: O=C(Nc1cn2nc(-c3c(-c4ccc(F)cc4)ncn3C3CCN(Cc4ncco4)CC3)ccc2n1)c1ccnc(F)c1] | 2-fluoro-N-(6-(4-(4-fluorophenyl)-1-(1-(oxazol-2-ylmethyl)piperidin-4-yl)-1H-imidazol-5-yl)imidazo[1,2-b]pyridazin-2-yl)isonicotinamide | 582.29 | 2.31 | B |

TABLE 4-continued

| Compound No. | Structure | Name | [M + H]+ | Ret. Time | HPLC Method |
|---|---|---|---|---|---|
| 30 | 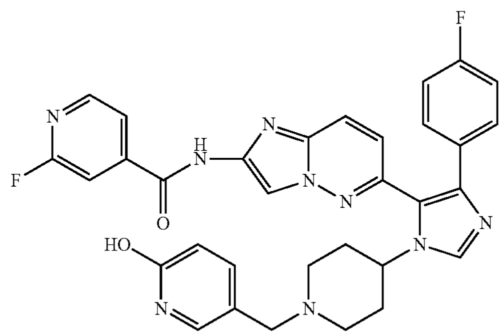 [SMILES: O=C(Nc1cn2nc(-c3c(-c4ccc(F)cc4)ncn3C3CCN(Cc4ccc(O)nc4)CC3)ccc2n1)c1ccnc(F)c1] | 2-fluoro-N-(6-(4-(4-fluorophenyl)-1-(1-((6-hydroxypyridin-3-yl)methyl)piperidin-4-yl)-1H-imidazol-5-yl)imidazo[1,2-b]pyridazin-2-yl)isonicotinamide | 608.19 | 2.09 | B |
| 31 | 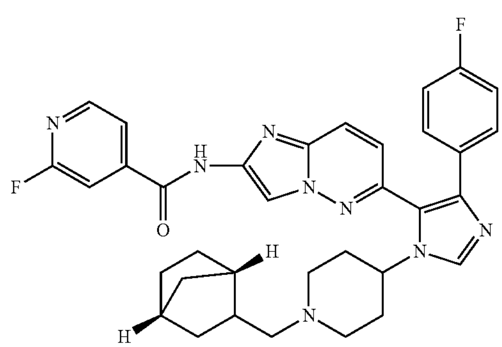 [SMILES: O=C(Nc1cn2nc(-c3c(-c4ccc(F)cc4)ncn3C3CCN(CC4C[C@@H]5CC[C@H]4C5)CC3)ccc2n1)c1ccnc(F)c1] | N-(6-(1-(1-(((1S,4R)-bicyclo[2.2.1]heptan-2-ylmethyl)piperidin-4-yl)-4-(4-fluorophenyl)-1H-imidazol-5-yl)imidazo[1,2-6]pyridazin-2-yl)-2-fluoroisonicotinamide | 609.36 | 4.52 | C |
| 32 | 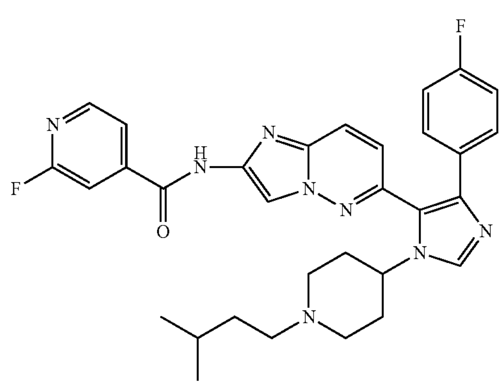 [SMILES: CC(C)CCN1CCC(n2cnc(-c3ccc(F)cc3)c2-c2ccc3nc(NC(=O)c4ccnc(F)c4)cn3n2)CC1] | 2-fluoro-N-(6-(4-(4-fluorophenyl)-1-(1-isopentylpiperidin-4-yl)-1H-imidazol-5-yl)imidazo[1,2-b]pyridazin-2-yl)isonicotinamide | 571.29 | 2.54, 4.17 | B, C |

Compound 33

2-fluoro-N-(6-(4-(4-fluorophenyl)-1-(1-(3-fluoropropyl)piperidin-4-yl)-1H-imidazol-5-yl)imidazo[1,2-b]pyridazin-2-yl)isonicotinamide

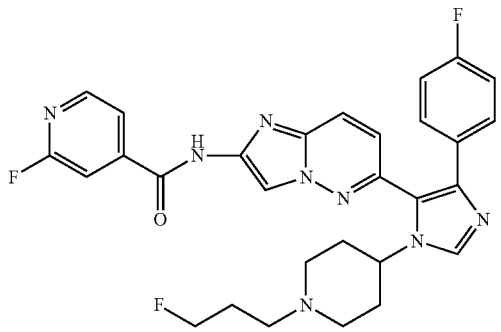 [SMILES: O=C(Nc1cn2nc(-c3c(-c4ccc(F)cc4)ncn3C3CCN(CCCF)CC3)ccc2n1)c1ccnc(F)c1]

To a solution of compound 9 (0.035 g, 0.070 mmol) and 1-fluoro-3-iodopropane (0.066 g, 0.350 mmol) in DMF (1.40 mL) was added Hunig's base (0.073 mL 0.420 mmol) and the reaction mixture was stirred at rt for 3 h. It was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 40-100% B over 20 minutes, then a 4-minute hold at 100% B; Flow: 25 mL/min. Fractions containing the desired product (0.012 g, 28.7% yield) were combined and dried via centrifugal evaporation. HPLC Ret. Time 2.19 min., 3.91 min. (Methods B and C respectively). MS(ES): m/z=561.30 [M+H]$^+$. $^1$H NMR (500 MHz, DMSO-$d_6$) δ ppm 8.59 (s, 1H), 8.48 (d, J=4.9 Hz, 1H), 8.19 (s, 1H), 8.10 (d, J=9.2 Hz, 1H), 7.98 (d, J=5.2 Hz, 1H), 7.82 (s, 1H), 7.47 (dd, J=8.5, 5.8 Hz, 2H), 7.21-7.08 (m, 3H), 4.53 (t, J=6.1 Hz, 1H), 4.43 (t, J=6.0 Hz, 1H), 4.10 (t, J=7.6 Hz, 1H), 2.95 (d, J=10.7 Hz, 2H), 2.38 (t, J=7.2 Hz, 2H), 2.08-1.89 (m, 6H), 1.89-1.72 (m, 3H).

The compounds described in Table 5 were synthesized analogous to compound 33 by reacting compound 9 with the corresponding alkyl halides.

TABLE 5

| Compound No. | Structure | Name | [M + H]$^+$ | HPLC Ret. Time | HPLC Method |
|---|---|---|---|---|---|
| 34 | 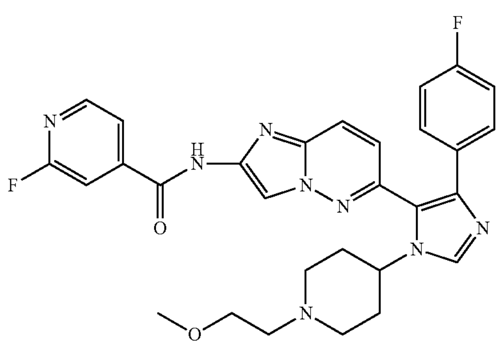 [SMILES: COCCN1CCC(n2cnc(-c3ccc(F)cc3)c2-c2ccc3nc(NC(=O)c4ccnc(F)c4)cn3n2)CC1] | 2-fluoro-N-(6-(4-(4-fluorophenyl)-1-(1-(2-methoxyethyl)piperidin-4-yl)-1H-imidazol-5-yl)imidazo[1,2-b]pyridazin-2-yl)isonicotinamide | 559.40 | 2.09, 3.81 | B, C |
| 35 | 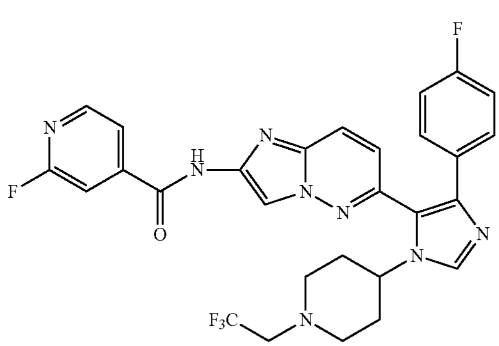 [SMILES: O=C(Nc1cn2nc(-c3c(-c4ccc(F)cc4)ncn3C3CCN(CC(F)(F)F)CC3)ccc2n1)c1ccnc(F)c1] | 2-fluoro-N-(6-(4-(4-fluorophenyl)-1-(1-(2,2,2-trifluoroethyl)piperidin-4-yl)-1H-imidazol-5-yl)imidazo[1,2-b]pyridazin-2-yl)isonicotinamide | 583.20 | 2.84, 4.10 | B, C |

Compound 36

N-(6-(1-(1-(2-cyanoethyl)piperidin-4-yl)-4-(4-fluorophenyl)-1H-imidazol-5-yl)imidazo[1,2-b]pyridazin-2-yl)-2-fluoroisonicotinamide

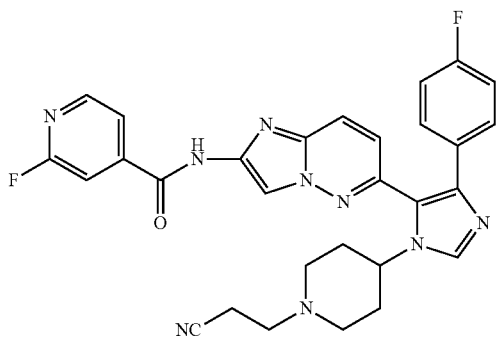

To a solution of compound 9 (0.018 g, 0.036 mmol) in EtOH (0.719 ml) was added acrylonitrile (9.82 µL, 0.144 mmol) and Hunig's base (0.038 mL, 0.216 mmol). The reaction mixture was heated in an oil bath at 60° C. for 16 h. The generated precipitate was filtered off and the filter cake was purified via preparative LC/MS with the following conditions: Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 methanol:water with 20-mM ammonium acetate; Gradient: 50-100% B over 13 minutes, then a 4-minute hold at 100% B; Flow: 20 mL/min. Fractions containing the desired product (0.01 g, 48.2% yield) were combined and dried via centrifugal evaporation. HPLC Ret. Time 2.32 min., 3.77 min (Methods B and C respectively). MS(ES): m/z=554.28 [M+H]$^+$. $^1$H NMR (500 MHz, DMSO-d$_6$) δ ppm 8.59 (s, 1H), 8.48 (d, J=5.2 Hz, 1H), 8.21 (s, 1H), 8.09 (d, J=9.5 Hz, 1H), 8.04-7.94 (m, 1H), 7.82 (s, 1H), 7.55-7.41 (m, 2H), 7.18-7.07 (m, 3H), 4.10 (br. s., 1H), 2.99 (d, J=5.8 Hz, 2H), 2.91 (s, 1H), 2.75 (s, 1H), 2.67 (t, J=6.4 Hz, 2H), 2.59 (t, J=6.6 Hz, 2H), 2.11-1.94 (m, 6H).

Compound 37

(R)-2-fluoro-N-(6-(4-(4-fluorophenyl)-1-(1-(3,3,3-trifluoro-2-hydroxypropyl)piperidin-4-yl)-1H-imidazol-5-yl)imidazo[1,2-b]pyridazin-2-yl)isonicotinamide

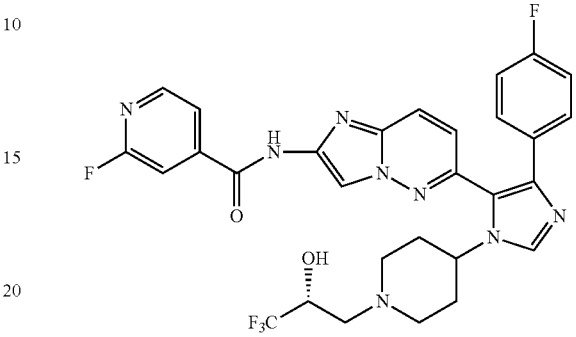

To a solution of compound 9 (0.035 g, 0.070 mmol) in DMF was added (R)-2-(trifluoromethyl)oxirane (0.039 g, 0.350 mmol) and the reaction mixture was stirred at rt for 3 h. The crude material was purified via preparative LC/MS with the following conditions: Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 40-80% B over 12 minutes, then a 5-minute hold at 100% B; Flow: 20 mL/min. Fractions containing the desired product (0.011 g, 24.51% yield) were combined and dried via centrifugal evaporation. HPLC Ret. Time 2.49 min., 3.98 min. (Methods B and C respectively). MS(ES): m/z=613.20 [M+H]$^+$. $^1$H NMR (500 MHz, DMSO-d$_6$) δ ppm 8.60 (s, 1H), 8.48 (d, J=5.2 Hz, 1H), 8.19 (s, 1H), 8.09 (d, J=9.5 Hz, 1H), 8.04-7.94 (m, 1H), 7.82 (s, 1H), 7.47 (dd, J=8.7, 5.6 Hz, 2H), 7.21-7.08 (m, 3H), 6.15 (br. s., 1H), 4.11 (d, J=7.3 Hz, 2H), 3.01 (t, J=9.8 Hz, 2H), 2.19-1.97 (m, 6H).

The compound described in Table 6 was synthesized analogous to compound 37 by reacting compound 9 with the corresponding epoxide.

TABLE 6

| Compound No. | Structure | Name | [M + H]$^+$ | HPLC Ret. Time | Method |
|---|---|---|---|---|---|
| 38 | (structure shown) | (S)-2-fluoro-N-(6-(4-(4-fluorophenyl)-1-(1-(3,3,3-trifluoro-2-hydroxypropyl)piperidin-4-yl)-1H-imidazol-5-yl)imidazo[1,2-b]pyridazin-2-yl)isonicotinamide | 613.20 | 2.60, 3.98 | B, C |

Compound 39

2-fluoro-N-(6-(4-(4-fluorophenyl)-1-(1-(isoxazole-3-carbonyl)piperidin-4-yl)-1H-imidazol-5-yl)imidazo[1,2-b]pyridazin-2-yl)isonicotinamide

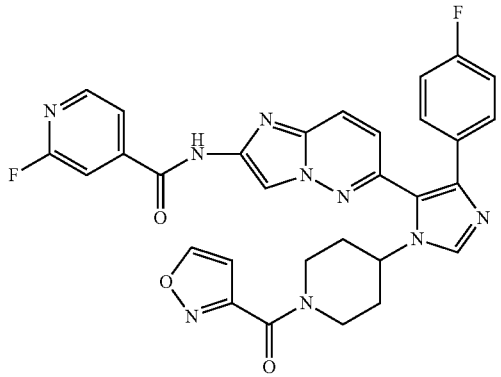

Compound 39 was synthesized analogous to compound 5 by reacting compound 9 with isoxazole 3-carboxylic acid. HPLC Ret. Time 2.39 min., 3.76 min. (Methods B and C respectively). MS(ES): m/z=596.20 [M+H]$^+$. $^1$H NMR (500 MHz, DMSO-d$_6$) δ ppm 9.12 (d, J=1.5 Hz, 1H), 8.64 (s, 1H), 8.48 (d, J=5.2 Hz, 1H), 8.24 (s, 1H), 8.11 (d, J=9.2 Hz, 1H), 7.98 (d, J=5.2 Hz, 1H), 7.83 (s, 1H), 7.53-7.40 (m, 2H), 7.21-7.07 (m, 3H), 6.86 (d, J=1.5 Hz, 1H), 4.63 (d, J=13.1 Hz, 1H), 4.54-4.41 (m, 1H), 4.03 (d, J=13.7 Hz, 1H), 3.29-3.14 (m, 1H), 2.96-2.83 (m, 1H), 2.21 (d, J=11.0 Hz, 1H), 2.14 (d, J=11.3 Hz, 1H), 2.10-1.96 (m, 2H).

The compounds described in Table 7 were synthesized analogous to compound 39 by reacting compound 9 with the corresponding carboxylic acids.

TABLE 7

| Compound No. | Structure | Name | [M + H]$^+$ | HPLC Ret. Time | HPLC Method |
|---|---|---|---|---|---|
| 40 | 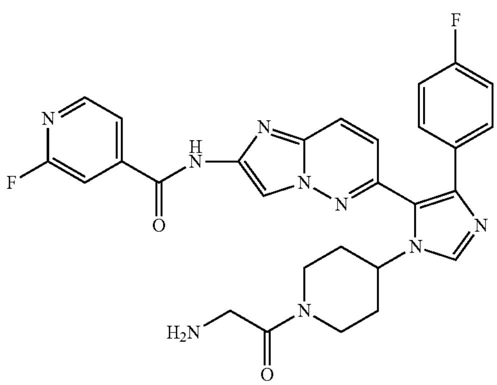 [SMILES: NCC(=O)N1CCC(n2cnc(-c3ccc(F)cc3)c2-c2ccc3nc(NC(=O)c4ccnc(F)c4)cn3n2)CC1] | N-(6-(1-(1-(2-aminoacetyl)piperidin-4-yl)-4-(4-fluorophenyl)-1H-imidazol-5-yl)imidazo[1,2-b]pyridazin-2-yl)-2-fluoroisonicotinamide | 558.40 | 1.95, 3.49 | B, C |
| 41 | 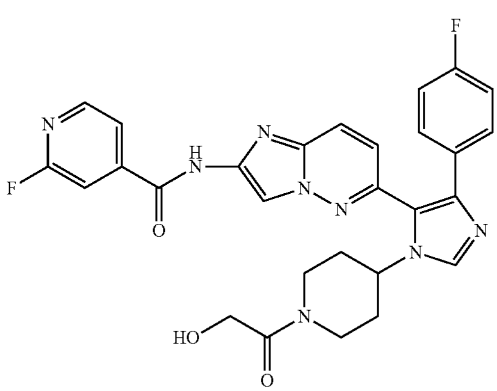 | 2-fluoro-N-(6-(4-(4-fluorophenyl)-1-(1-(2-hydroxyacetyl)piperidin-4-yl)-1H-imidazol-5-yl)imidazo[1,2-6]pyridazin-2-yl)isonicotinamide | 557.30 | 2.19, 3.59 | B, C |

TABLE 7-continued

| Compound No. | Structure | Name | [M + H]+ | Ret. Time | HPLC Method |
|---|---|---|---|---|---|
| 42 | 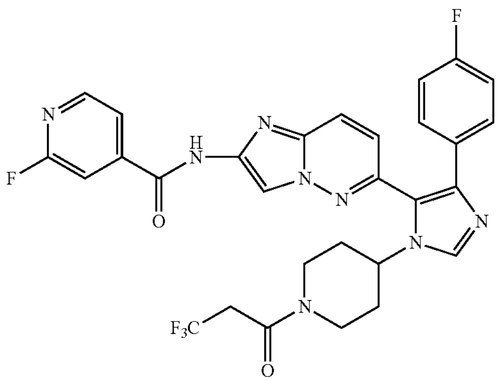 [SMILES: O=C(Nc1cn2nc(-c3c(-c4ccc(F)cc4)ncn3C3CCN(C(=O)CC(F)(F)F)CC3)ccc2n1)c1ccnc(F)c1] | 2-fluoro-N-(6-(4-(4-fluorophenyl)-1-(1-(3,3,3-trifluoropropanoyl)piperidin-4-yl)-1H-imidazol-5-yl)imidazo[1,2-b]pyridazin-2-yl)isonicotinamide | 611.20 | 2.50, 3.79 | B, C |
| 43 | 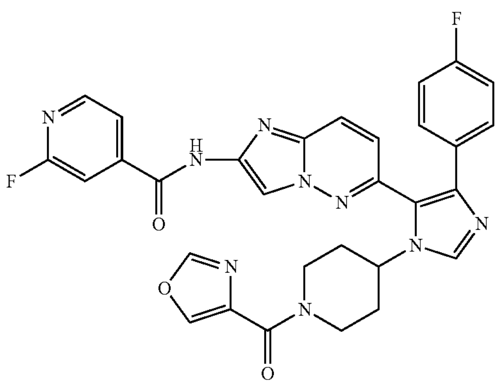 [SMILES: O=C(Nc1cn2nc(-c3c(-c4ccc(F)cc4)ncn3C3CCN(C(=O)c4cocn4)CC3)ccc2n1)c1ccnc(F)c1] | 2-fluoro-N-(6-(4-(4-fluorophenyl)-1-(1-(oxazole-4-carbonyl)piperidin-4-yl)-1H-imidazol-5-yl)imidazo[1,2-6]pyridazin-2-yl)isonicotinamide | 596.20 | 2.27, 3.69 | B, C |
| 44 | 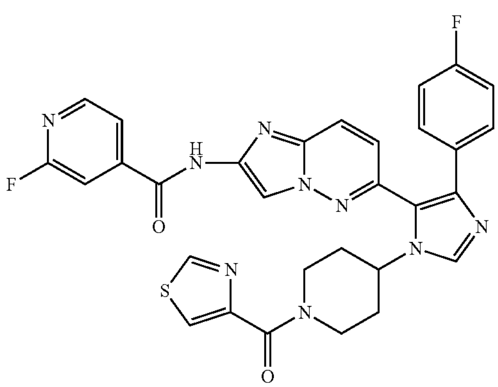 [SMILES: O=C(Nc1cn2nc(-c3c(-c4ccc(F)cc4)ncn3C3CCN(C(=O)c4cscn4)CC3)ccc2n1)c1ccnc(F)c1] | 2-fluoro-N-(6-(4-(4-fluorophenyl)-1-(1-(thiazole-4-carbonyl)piperidin-4-yl)-1H-imidazol-5-yl)imidazo[1,2-b]pyridazin-2-yl)isonicotinamide | 612.20 | 2.31, 3.75 | B, C |
| 45 | 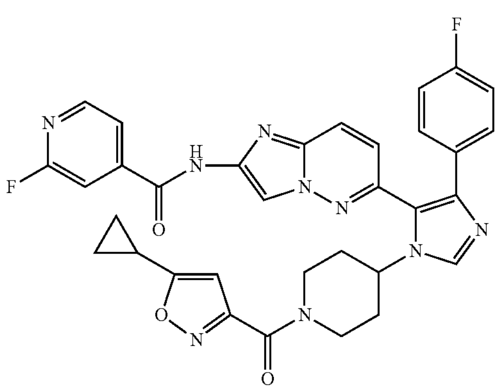 [SMILES: O=C(Nc1cn2nc(-c3c(-c4ccc(F)cc4)ncn3C3CCN(C(=O)c4cc(C5CC5)on4)CC3)ccc2n1)c1ccnc(F)c1] | N-(6-(1-(1-(5-cyclopropylisoxazole-3-carbonyl)piperidin-4-yl)-4-(4-fluorophenyl)-1H-imidazol-5-yl)imidazo[1,2-b]pyridazin-2-yl)-2-fluoroisonicotinamide | 636.20 | 2.66, 4.02 | B, C |

TABLE 7-continued

| Compound No. | Structure | Name | [M + H]+ | Ret. Time | HPLC Method |
|---|---|---|---|---|---|
| 46 | 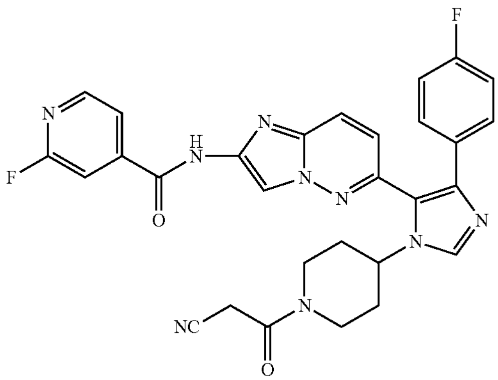 [SMILES: N#CCC(=O)N1CCC(n2cnc(-c3ccc(F)cc3)c2-c2ccc3nc(NC(=O)c4ccnc(F)c4)cn3n2)CC1] | N-(6-(1-(1-(2-cyanoacetyl)piperidin-4-yl)-4-(4-fluorophenyl)-1H-imidazol-5-yl)imidazo[1,2-b]pyridazin-2-yl)-2-fluoroisonicotinamide | 568.50 | 2.38, 3.57 | B, C |
| 47 | 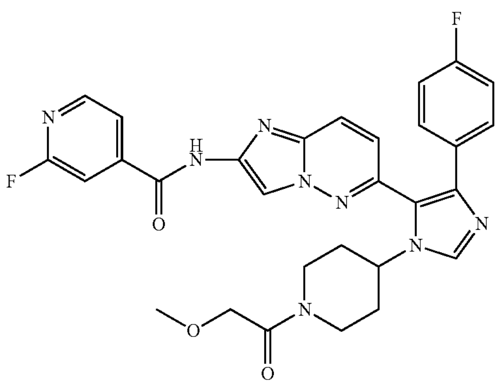 [SMILES: COCC(=O)N1CCC(n2cnc(-c3ccc(F)cc3)c2-c2ccc3nc(NC(=O)c4ccnc(F)c4)cn3n2)CC1] | 2-fluoro-N-(6-(4-(4-fluorophenyl)-1-(1-(2-methoxyacetyl)piperidin-4-yl)-1H-imidazol-5-yl)imidazo[1,2-b]pyridazin-2-yl)isonicotinamide | 573.50 | 2.32, 3.65 | B, C |
| 48 | 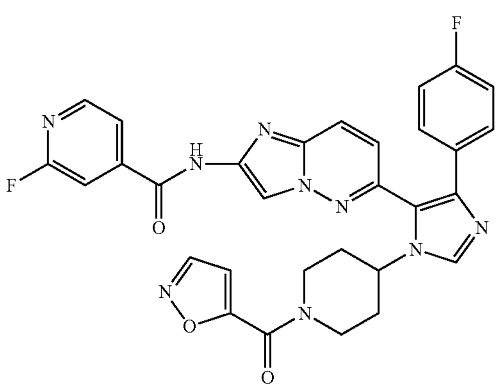 [SMILES: O=C(Nc1cn2nc(-c3c(-c4ccc(F)cc4)ncn3C3CCN(C(=O)c4ccno4)CC3)ccc2n1)c1ccnc(F)c1] | 2-fluoro-N-(6-(4-(4-fluorophenyl)-1-(1-(isoxazole-5-carbonyl)piperidin-4-yl)-1H-imidazol-5-yl)imidazo[1,2-b]pyridazin-2-yl)isonicotinamide | 596.30 | 2.00, 3.48 | B, C |
| 49 | 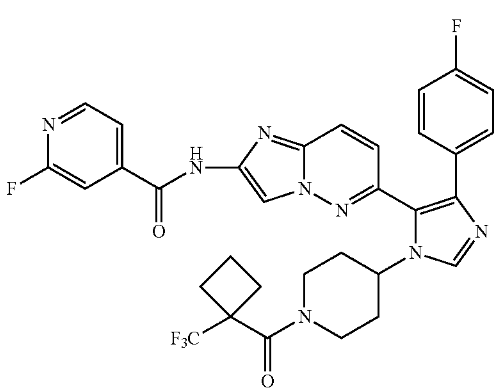 [SMILES: O=C(Nc1cn2nc(-c3c(-c4ccc(F)cc4)ncn3C3CCN(C(=O)C4(C(F)(F)F)CCC4)CC3)ccc2n1)c1ccnc(F)c1] | 2-fluoro-N-(6-(4-(4-fluorophenyl)-1-(1-(1-(trifluoromethyl)cyclobutanecarbonyl)piperidin-4-yl)-1H-imidazol-5-yl)imidazo[1,2-b]pyridazin-2-yl)isonicotinamide | 651.30 | 2.77, 4.12 | B, C |

TABLE 7-continued

| Compound No. | Structure | Name | [M + H]⁺ | Ret. Time | HPLC Method |
|---|---|---|---|---|---|
| 50 | 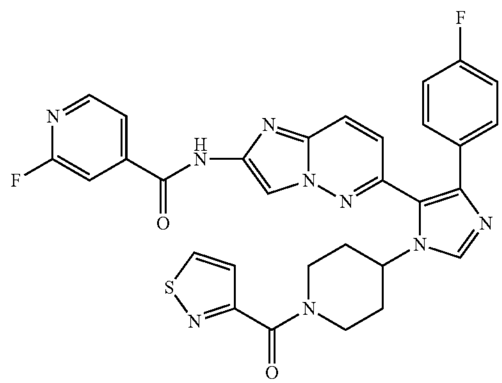 [SMILES: O=C(Nc1cn2nc(-c3c(-c4ccc(F)cc4)ncn3C3CCN(C(=O)c4ccsn4)CC3)ccc2n1)c1ccnc(F)c1] | 2-fluoro-N-(6-(4-(4-fluorophenyl)-1-(1-(isothiazole-3-carbonyl)piperidin-4-yl)-1H-imidazol-5-yl)imidazo[1,2-b]pyridazin-2-yl)isonicotinamide | 612.20 | 2.43, 3.82 | B, C |
| 51 | 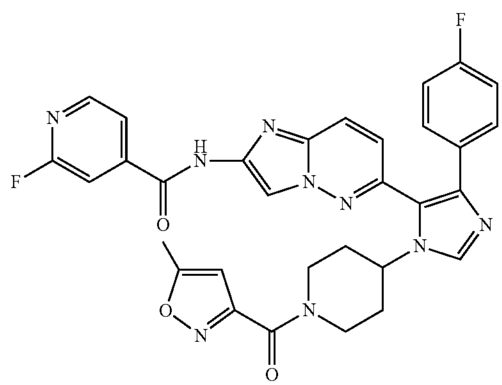 [SMILES: Cc1cc(C(=O)N2CCC(n3cnc(-c4ccc(F)cc4)c3-c3ccc4nc(NC(=O)c5ccnc(F)c5)cn4n3)CC2)no1] | 2-fluoro-N-(6-(4-(4-fluorophenyl)-1-(1-(5-methylisoxazole-3-carbonyl)piperidin-4-yl)-1H-imidazol-5-yl)imidazo[1,2-b]pyridazin-2-yl)isonicotinamide | 610.26 | 2.52 | B |
| 52 | 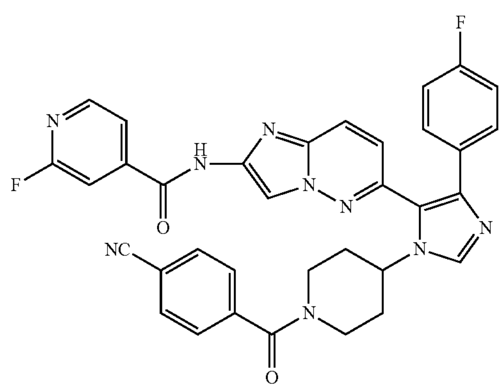 [SMILES: N#Cc1ccc(C(=O)N2CCC(n3cnc(-c4ccc(F)cc4)c3-c3ccc4nc(NC(=O)c5ccnc(F)c5)cn4n3)CC2)cc1] | N-(6-(1-(1-(4-cyanobenzoyl)piperidin-4-yl)-4-(4-fluorophenyl)-1H-imidazol-5-yl)imidazo[1,2-b]pyridazin-2-yl)-2-fluoroisonicotinamide | 630.01 | 3.8 | C |
| 53 | 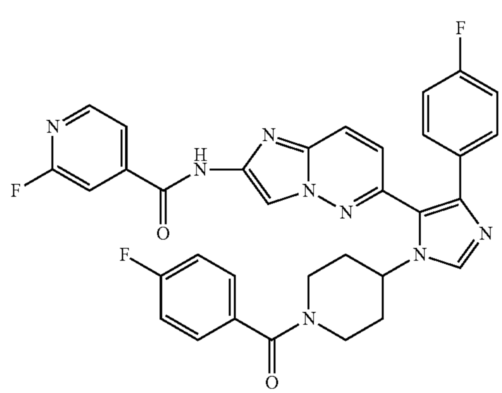 [SMILES: O=C(Nc1cn2nc(-c3c(-c4ccc(F)cc4)ncn3C3CCN(C(=O)c4ccc(F)cc4)CC3)ccc2n1)c1ccnc(F)c1] | 2-fluoro-N-(6-(1-(1-(4-fluorobenzoyl)piperidin-4-yl)-4-(4-fluorophenyl)-1H-imidazol-5-yl)imidazo[1,2-b]pyridazin-2-yl)isonicotinamide | 622.99 | 2.64 | B |

TABLE 7-continued

| Compound No. | Structure | Name | [M + H]+ | Ret. Time | HPLC Method |
|---|---|---|---|---|---|
| 54 | 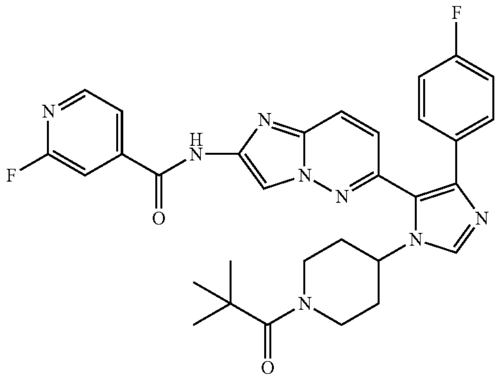 [SMILES: CC(C)(C)C(=O)N1CCC(n2cnc(-c3ccc(F)cc3)c2-c2ccc3nc(NC(=O)c4ccnc(F)c4)cn3n2)CC1] | 2-fluoro-N-(6-(4-(4-fluorophenyl)-1-(1-pivaloylpiperidin-4-yl)-1H-imidazol-5-yl)imidazo[1,2-b]pyridazin-2-yl)isonicotinamide | 585.02 | 2.62 | B |
| 55 | 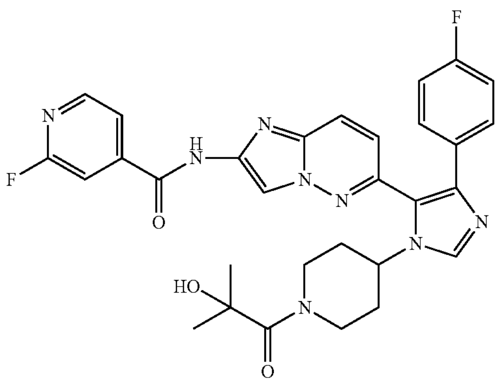 [SMILES: CC(C)(O)C(=O)N1CCC(n2cnc(-c3ccc(F)cc3)c2-c2ccc3nc(NC(=O)c4ccnc(F)c4)cn3n2)CC1] | 2-fluoro-N-(6-(4-(4-fluorophenyl)-1-(1-(2-hydroxy-2-methylpropanoyl)piperidin-4-yl)-1H-imidazol-5-yl)imidazo[1,2-b]pyridazin-2-yl)isonicotinamide | 587.31 | 2.24 | B |
| 56 | 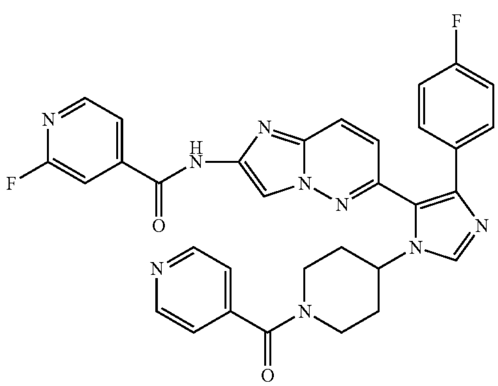 [SMILES: O=C(Nc1cn2nc(-c3c(-c4ccc(F)cc4)ncn3C3CCN(C(=O)c4ccncc4)CC3)ccc2n1)c1ccnc(F)c1] | 2-fluoro-N-(6-(4-(4-fluorophenyl)-1-(1 isonicotinoylpiperidin-4-yl)-1H-imidazol-5-yl)imidazo[1,2-b]pyridazin-2-yl)isonicotinamide | 606.02 | 3.65 | C |
| 57 | 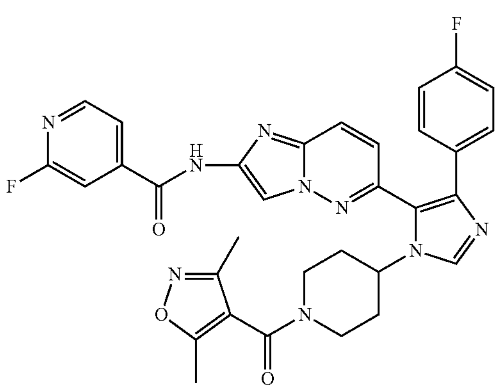 [SMILES: Cc1noc(C)c1C(=O)N1CCC(n2cnc(-c3ccc(F)cc3)c2-c2ccc3nc(NC(=O)c4ccnc(F)c4)cn3n2)CC1] | N-(6-(1-(1-(3,5-dimethylisoxazole-4-carbonyl)piperidin-4-yl)-4-(4-fluorophenyl)-1H-imidazol-5-yl)imidazo[1,2-b]pyridazin-2-yl)-2-fluoroisonicotinamide | 624.03 | 3.75 | C |

TABLE 7-continued

| Compound No. | Structure | Name | [M + H]+ | Ret. Time | HPLC Method |
|---|---|---|---|---|---|
| 58 | 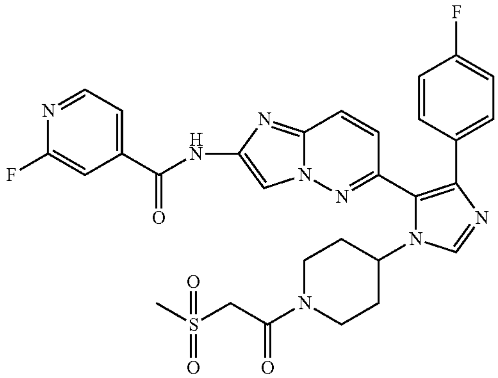 [SMILES: CS(=O)(=O)CC(=O)N1CCC(n2cnc(-c3ccc(F)cc3)c2-c2ccc3nc(NC(=O)c4ccnc(F)c4)cn3n2)CC1] | 2-fluoro-N-(6-(4-(4-fluorophenyl)-1-(1-(2-(methylsulfonyl)acetyl)piperidin-4-yl)-1H-imidazol-5-yl)imidazo[1,2-b]pyridazin-2-yl)isonicotinamide | 621.19 | 2.22 | B |
| 59 | 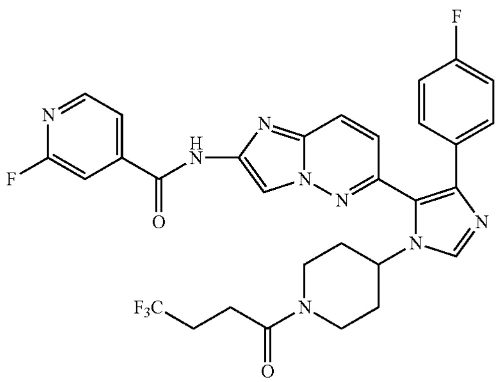 | 2-fluoro-N-(6-(4-(4-fluorophenyl)-1-(1-(4,4,4-trifluorobutanoyl)piperidin-4-yl)-1H-imidazol-5-yl)imidazo[1,2-b]pyridazin-2-yl)isonicotinamide | 624.99 | 2.63 | B |
| 60 | 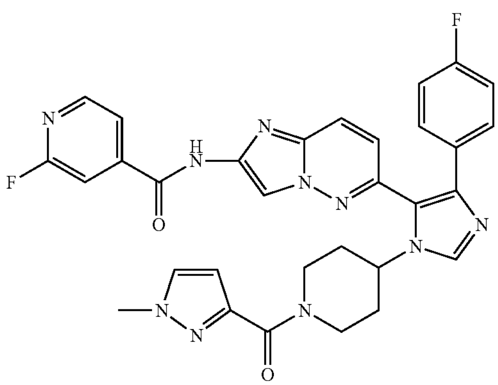 [SMILES: Cn1ccc(C(=O)N2CCC(n3cnc(-c4ccc(F)cc4)c3-c3ccc4nc(NC(=O)c5ccnc(F)c5)cn4n3)CC2)n1] | 2-fluoro-N-(6-(4-(4-fluorophenyl)-1-(1-(1-methyl-1H-pyrazole-3-carbonyl)piperidin-4-yl)-1H-imidazol-5-yl)imidazo[1,2-b]pyridazin-2-yl)isonicotinamide | 609.01 | 2.32 | B |
| 61 | 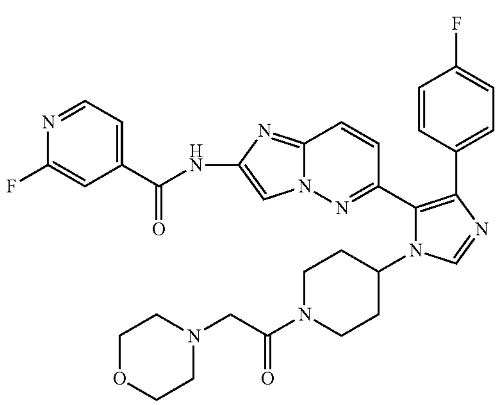 [SMILES: O=C(Nc1cn2nc(-c3c(-c4ccc(F)cc4)ncn3C3CCN(C(=O)CN4CCOCC4)CC3)ccc2n1)c1ccnc(F)c1] | 2-fluoro-N-(6-(4-(4-fluorophenyl)-1-(1-(2-morpholinoacetyl)piperidin-4-yl)-1H-imidazol-5-yl)imidazo[1,2-b]pyridazin-2-yl)isonicotinamide | 628.33 | 3.74 | C |

TABLE 7-continued

| Compound No. | Structure | Name | [M + H]+ | Ret. Time | HPLC Method |
|---|---|---|---|---|---|
| 62 | 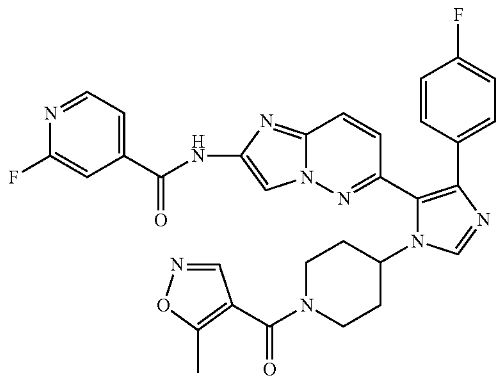 [SMILES: Cc1oncc1C(=O)N1CCC(n2cnc(-c3ccc(F)cc3)c2-c2ccc3nc(NC(=O)c4ccnc(F)c4)cn3n2)CC1] | 2-fluoro-N-(6-(4-(4-fluorophenyl)-1-(1-(5-methylisoxazole-4-carbonyl)piperidin-4-yl)-1H-imidazol-5-yl)imidazo[1,2-b]pyridazin-2-yl)isonicotinamide | 610.26 | 3.76 | C |
| 63 | 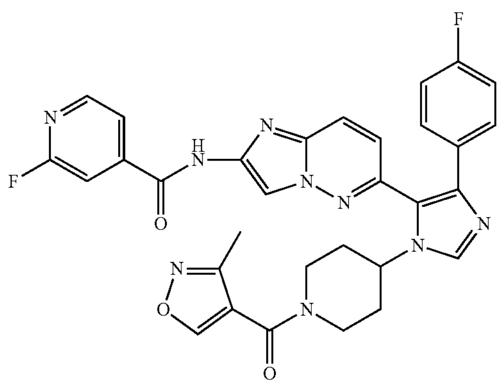 [SMILES: Cc1nocc1C(=O)N1CCC(n2cnc(-c3ccc(F)cc3)c2-c2ccc3nc(NC(=O)c4ccnc(F)c4)cn3n2)CC1] | 2-fluoro-N-(6-(4-(4-fluorophenyl)-1-(1-(3-methylisoxazole-4-carbonyl)piperidm-4-yl)-1H-imidazol-5-yl)imidazo[1,2-6]pyridazin-2-yl)isonicotinamide | 610.23 | 2.39 | B |
| 64 | 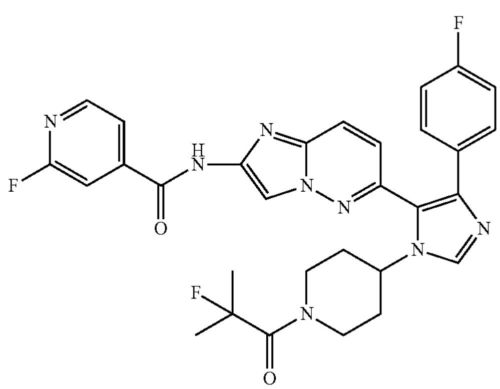 [SMILES: CC(C)(F)C(=O)N1CCC(n2cnc(-c3ccc(F)cc3)c2-c2ccc3nc(NC(=O)c4ccnc(F)c4)cn3n2)CC1] | 2-fluoro-N-(6-(1-(1-(2-fluoro-2-methylpropanoyl)piperidin-4-yl)-4-(4-fluorophenyl)-1H-imidazol-5-yl)imidazo[1,2-6]pyridazin-2-yl)isonicotinamide | 589.01 | 2.58 | B |
| 65 | 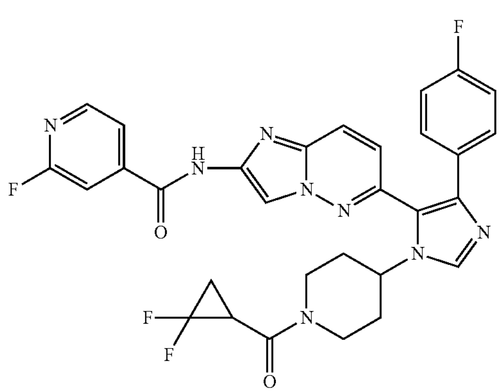 [SMILES: O=C(Nc1cn2nc(-c3c(-c4ccc(F)cc4)ncn3C3CCN(C(=O)C4CC4(F)F)CC3)ccc2n1)c1ccnc(F)c1] | N-(6-(1-(1-(2,2-difluorocyclopropanecarbonyl)piperidin-4-yl)-4-(4-fluorophenyl)-1H-imidazol-5-yl)imidazo[1,2-b]pyridazin-2-yl)-2-fluoroisonicotinamide | 605.26 | 3.85 | C |

TABLE 7-continued

| Compound No. | Structure | Name | [M + H]+ | Ret. Time | HPLC Method |
|---|---|---|---|---|---|
| 66 | 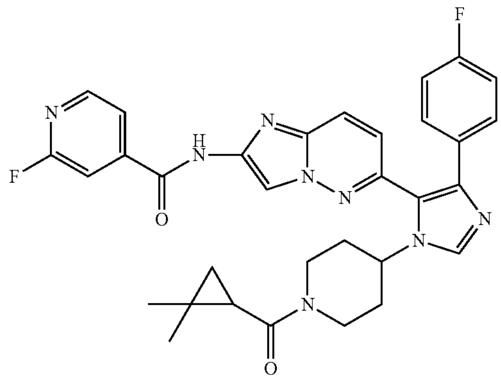 [SMILES: CC1(C)CC1C(=O)N1CCC(n2cnc(-c3ccc(F)cc3)c2-c2ccc3nc(NC(=O)c4ccnc(F)c4)cn3n2)CC1] | N-(6-(1-(1-(2,2-dimethylcyclopropanecarbonyl)piperidin-4-yl)-4-(4-fluorophenyl)-1H-imidazol-5-yl)imidazo[1,2-6]pyridazin-2-yl)-2-fluoroisonicotinamide | 597.3 | 2.62 | C |
| 67 | 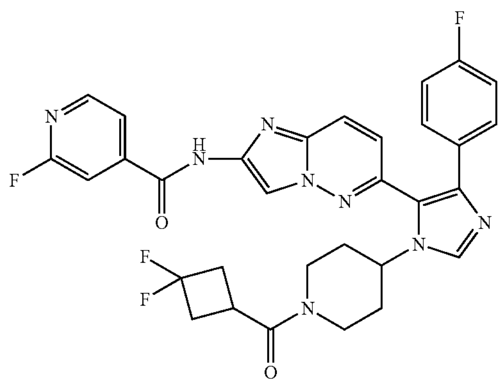 [SMILES: O=C(Nc1cn2nc(-c3c(-c4ccc(F)cc4)ncn3C3CCN(C(=O)C4CC(F)(F)C4)CC3)ccc2n1)c1ccnc(F)c1] | N-(6-(1-(1-(3,3-difluorocyclobutanecarbonyl)piperidin-4-yl)-4-(4-fluorophenyl)-1H-imidazol-5-yl)imidazo[1,2-b]pyridazin-2-yl)-2-fluoroisonicotinamide | 619.02 | 3.82 | C |
| 68 | 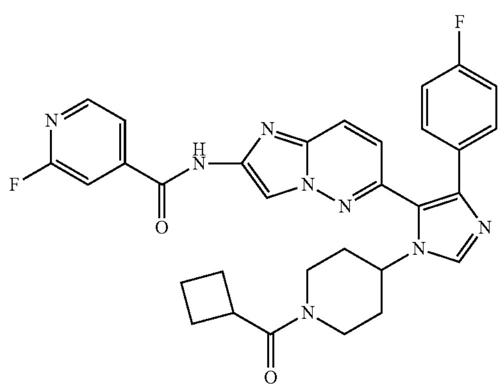 [SMILES: O=C(Nc1cn2nc(-c3c(-c4ccc(F)cc4)ncn3C3CCN(C(=O)C4CCC4)CC3)ccc2n1)c1ccnc(F)c1] | N-(6-(1-(1-(cyclobutanecarbonyl)piperidin-4-yl)-4-(4-fluorophenyl)-1H-imidazol-5-yl)imidazo[1,2-b]pyridazin-2-yl)-2-fluoroisonicotinamide | 583.28 | 2.53 | B |
| 69 | 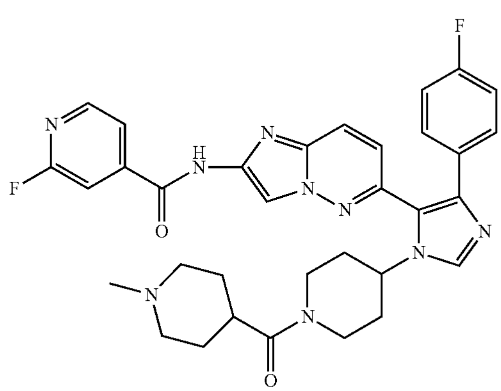 [SMILES: CN1CCC(C(=O)N2CCC(n3cnc(-c4ccc(F)cc4)c3-c3ccc4nc(NC(=O)c5ccnc(F)c5)cn4n3)CC2)CC1] | 2-fluoro-N-(6-(4-(4-fluorophenyl)-1-(1-(1-methylpiperidine-4-carbonyl)piperidin-4-yl)-1H-imidazol-5-yl)imidazo[1,2-6]pyridazin-2-yl)isonicotinamide | 626.09 | 2.07 | B |

TABLE 7-continued

| Compound No. | Structure | Name | [M + H]⁺ | Ret. Time | HPLC Method |
|---|---|---|---|---|---|
| 70 | 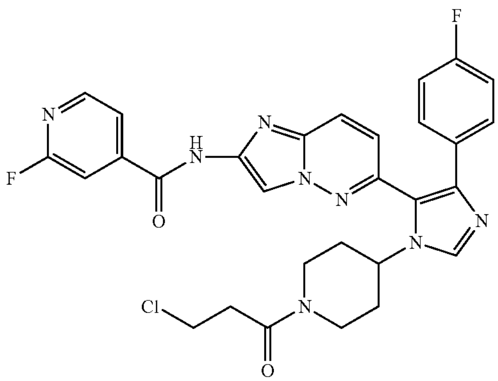 [SMILES: O=C(Nc1cn2nc(-c3c(-c4ccc(F)cc4)ncn3C3CCN(C(=O)CCCl)CC3)ccc2n1)c1ccnc(F)c1] | N-(6-(1-(1-(3-chloropropanoyl)piperidin-4-yl)-4-(4-fluorophenyl)-1H-imidazol-5-yl)imidazo[1,2-b]pyridazin-2-yl)-2-fluoroisonicotinamide | 590.99 | 2.46 | B |
| 71 | 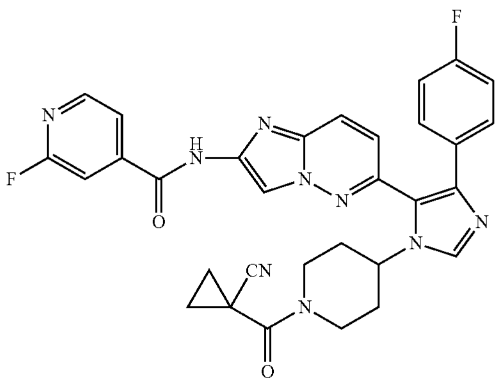 [SMILES: N#CC1(C(=O)N2CCC(n3cnc(-c4ccc(F)cc4)c3-c3ccc4nc(NC(=O)c5ccnc(F)c5)cn4n3)CC2)CC1] | N-(6-(1-(1-(1-cyanocyclopropanecarbonyl)piperidin-4-yl)-4-(4-fluorophenyl)-1H-imidazol-5-yl)imidazo[1,2-b]pyridazin-2-yl)-2-fluoroisonicotinamide | 594.29 | 2.43 | B |
| 72 | 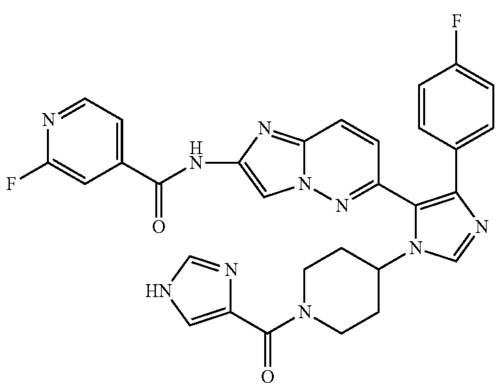 [SMILES: O=C(Nc1cn2nc(-c3c(-c4ccc(F)cc4)ncn3C3CCN(C(=O)c4c[nH]cn4)CC3)ccc2n1)c1ccnc(F)c1] | N-(6-(1-(1-(1H-imidazole-4-carbonyl)piperidin-4-yl)-4-(4-fluorophenyl)-1H-imidazol-5-yl)imidazo(1,2-b]pyridazin-2-yl)-2-fluoroisonicotinamide | 595.21 | 2.16 | B |
| 73 | 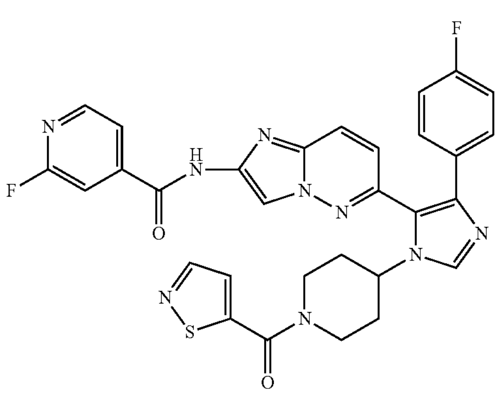 [SMILES: O=C(Nc1cn2nc(-c3c(-c4ccc(F)cc4)ncn3C3CCN(C(=O)c4ccns4)CC3)ccc2n1)c1ccnc(F)c1] | 2-fluoro-N-(6-(4-(4-fluorophenyl)-1-(1-(isothiazole-5-carbonyl)piperidin-4-yl)-1H-imidazol-5-yl)imidazo[1,2-b]pyridazin-2-yl)isonicotinamide | 611.95 | 3.73 | C |

Compound 74

N-(6-(1-(1-(cyclopropylsulfonyl)piperidin-4-yl)-4-(4-fluorophenyl)-1H-imidazol-5-yl)imidazo[1,2-b]pyridazin-2-yl)-2-fluoroisonicotinamide

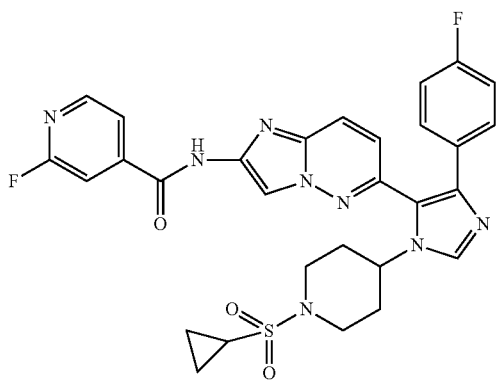 [SMILES: O=C(Nc1cn2nc(-c3c(-c4ccc(F)cc4)ncn3C3CCN(S(=O)(=O)C4CC4)CC3)ccc2n1)c1ccnc(F)c1]

To a solution of compound 9 (0.035 g, 0.070 mmol) and cyclopropanesulfonyl chloride (0.020 g, 0.140 mmol) in DMF (1.40 mL) was added Hunig's base (0.037 mL, 0.210 mmol) and the reaction mixture was stirred at rt for 3 h. It was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 30-70% B over 12 minutes, then a 5-minute hold at 100% B; Flow: 20 mL/min. Fractions containing the desired product (0.014 g, 29.5% yield) were combined and dried via centrifugal evaporation. HPLC Ret. Time 2.49 min., 3.79 min. (Methods B and C respectively). MS(ES): m/z=605.20 [M+H]$^+$. $^1$H NMR (500 MHz, DMSO-d$_6$) δ ppm 11.96 (br. s, 1H), 8.63 (s, 1H), 8.49 (d, J=5.2 Hz, 1H), 8.25 (s, 1H), 8.11 (d, J=9.5 Hz, 1H), 8.04-7.93 (m, 1H), 7.83 (s, 1H), 7.46 (dd, J=8.9, 5.5 Hz, 2H), 7.22-7.06 (m, 3H), 4.38-4.19 (m, 1H), 3.71 (d, J=12.2 Hz, 2H), 3.02-2.87 (m, 3H), 2.67-2.54 (m, 2H), 2.23-2.02 (m, 4H), 1.06-0.85 (m, 4H).

Compound 75 neopentyl 4-(5-(2-(2-fluoroisonicotinamido)imidazo[1,2-b]pyridazin-6-yl)-4-(4-fluorophenyl)-1H-imidazol-1-yl)piperidine-1-carboxylate

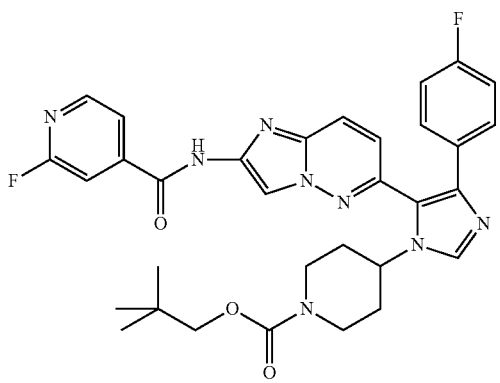 [SMILES: CC(C)(C)COC(=O)N1CCC(n2cnc(-c3ccc(F)cc3)c2-c2ccc3nc(NC(=O)c4ccnc(F)c4)cn3n2)CC1]

To a solution of compound 9 (0.035 g, 0.070 mmol) and neopentyl carbonochloridate (0.032 g, 0.210 mmol) in DMF (1.40 mL) was added Hunig's base (0.049 mL, 0.280 mmol) and the reaction mixture was stirred at rt for 3 h. It purified via preparative LC/MS with the following conditions: Column: Waters XBridge C18, 19×200 mm, 5-μm particles; Guard Column: Waters XBridge C18, 19×10 mm, particles; Mobile Phase A: water; Mobile Phase B: methanol; Buffer: 20-mM ammonium acetate; Gradient: 30-95% B over 19.5 minutes, then a 14.0 minute hold at 95% B; Flow: 20 mL/min Fractions containing the desired product (0.0105 g, 24.43% yield) were combined and dried via centrifugal evaporation. HPLC Ret. Time 2.97 min., 4.30 min. (Methods B and C respectively). MS(ES): m/z 615.30 [M+H]$^+$. $^1$H NMR (500 MHz, DMSO-d$_6$) δ ppm 11.96 (br. s, 1H), 8.63 (s, 1H), 8.49 (d, J=4.9 Hz, 1H), 8.21 (s, 1H), 8.10 (d, J=9.5 Hz, 1H), 8.04-7.90 (m, 1H), 7.82 (s, 1H), 7.46 (dd, J=8.9, 5.5 Hz, 2H), 7.21-7.06 (m, 3H), 4.44-4.27 (m, 1H), 4.12 (d, J=13.4 Hz, 2H), 3.71 (br. s., 2H), 2.90 (s, 2H), 2.84 (br. s., 1H), 2.75 (s, 1H), 2.08 (d, J=11.0 Hz, 2H), 2.02-1.85 (m, 2H), 0.92 (s, 9H).

The compounds described in Table 8 were synthesized analogous to compound 75 by reacting compound 5 with the corresponding chloroformate.

TABLE 8

| Compound No. | Structure | Name | [M + H]$^+$ | Ret. Time | HPLC Method |
|---|---|---|---|---|---|
| 76 | 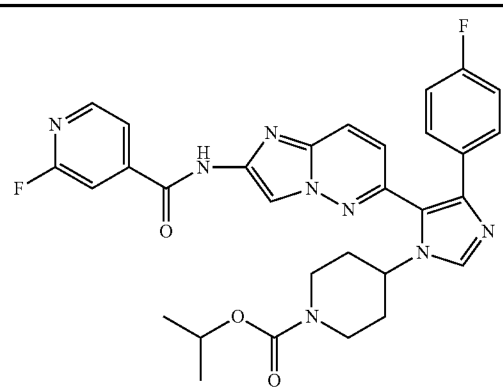 | isopropyl 4-(5-(2-(2-fluoroisonicotinamido)imidazo[1,2-b]pyridazin-6-yl)-4-(4-fluorophenyl)-1H-imidazol-1-yl)piperidine-1-carboxylate | 587.0 | 2.77, 2.65 | B, C |

TABLE 8-continued

| Compound No. | Structure | Name | [M + H]+ | Ret. Time | HPLC Method |
|---|---|---|---|---|---|
| 77 | 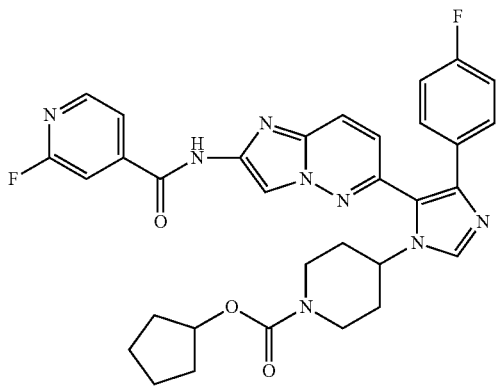 [SMILES: O=C(Nc1cn2nc(-c3c(-c4ccc(F)cc4)ncn3C3CCN(C(=O)OC4CCCC4)CC3)ccc2n1)c1ccnc(F)c1] | cyclopentyl 4-(5-(2-(2-fluoroisonicotinamido)imidazo[1,2-b]pyridazin-6-yl)-4-(4-fluorophenyl)-1H-imidazol-1-yl)piperidine-1-carboxylate | 613.30 | 2.86, 4.24 | B, C |

Compound 78 cyclopropylmethyl 4-(5-(2-(2-fluoroisonicotinamido)imidazo[1,2-b]pyridazin-6-yl)-4-(4-fluorophenyl)-1H-imidazol-1-yl)piperidine-1-carboxylate

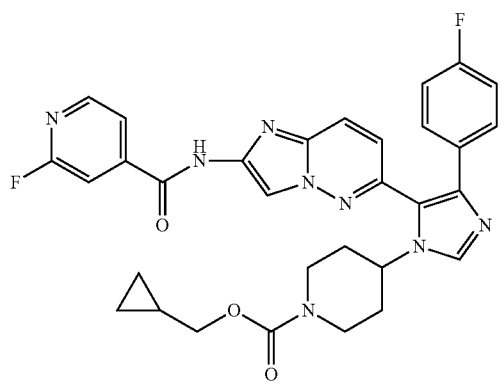 [SMILES: O=C(Nc1cn2nc(-c3c(-c4ccc(F)cc4)ncn3C3CCN(C(=O)OCC4CC4)CC3)ccc2n1)c1ccnc(F)c1]

To a solution of cyclopropylmethanol (8.29 μl, 0.105 mmol) in THF (1.40 mL) were sequentially added Hunig's base (0.037 mL, 0.210 mmol) and 4-nitrophenyl carbonochloridate (0.022 g, 0.105 mmol) and the reaction was stirred at rt for 16 h. To this solution was then addition a solution of compound 9 (0.035 g, 0.070 mmol) in DMF (1 mL) The resultant reaction mixture was stirred for 90 min. and then purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 30-100% B over 20 minutes, then a 4-minute hold at 100% B; Flow: 20 mL/min Fractions containing the desired product (14.3 mg, 34.2% yield) were combined and dried via centrifugal evaporation. HPLC Ret. Time 2.76 min., 4.16 min. (Methods B and C respectively). MS(ES): m/z=599.20 [M+H]+.

The compounds described in Table 9 were synthesized analogous to compound 78 by reacting compound 9 with the corresponding chloroformates generated in situ by reacting 4-nitrophenyl carbonochloridate with the corresponding alcohols.

TABLE 9

| Compound No. | Structure | Name | [M + H]+ | Ret. Time | HPLC Method |
|---|---|---|---|---|---|
| 79 | 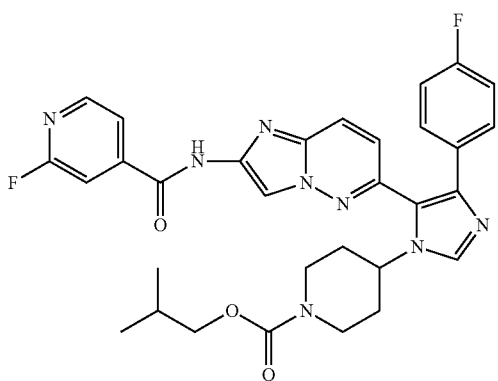 [SMILES: CC(C)COC(=O)N1CCC(n2cnc(-c3ccc(F)cc3)c2-c2ccc3nc(NC(=O)c4ccnc(F)c4)cn3n2)CC1] | isobutyl 4-(5-(2-(2-fluoroisonicotinamido)imidazo[1,2-b]pyridazin-6-yl)-4-(4-fluorophenyl)-1H-imidazol-1-yl)piperidine-1-carboxylate | 601.21 | 2.90, 4.24 | B, C |

TABLE 9-continued

| Compound No. | Structure | Name | [M + H]⁺ | Ret. Time | HPLC Method |
|---|---|---|---|---|---|
| 80 | 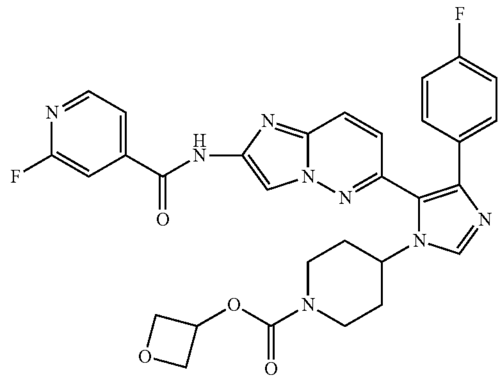 [SMILES: O=C(Nc1cn2nc(-c3c(-c4ccc(F)cc4)ncn3C3CCN(C(=O)OC4COC4)CC3)ccc2n1)c1ccnc(F)c1] | oxetan-3-yl 4-(5-(2-(2-fluoroisonicotinamido)imidazo[1,2-b]pyridazin-6-yl)-4-(4-fluorophenyl)-1H-imidazol-1-yl)piperidine-1-carboxylate | 601.14 | 2.36, 3.77 | B, C |
| 81 | 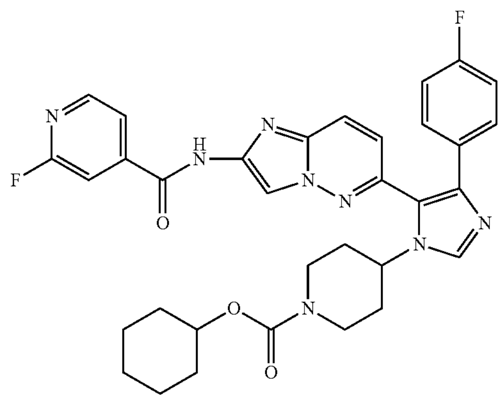 [SMILES: O=C(Nc1cn2nc(-c3c(-c4ccc(F)cc4)ncn3C3CCN(C(=O)OC4CCCCC4)CC3)ccc2n1)c1ccnc(F)c1] | tetrahydro-2H-pyran-4-yl 4-(5-(2-(2-fluoroisonicotinamido)imidazo[1,2-b]pyridazin-6-yl)-4-(4-fluorophenyl)-1H-imidazol-1-yl)piperidine-1-carboxylate | 629.17 | 2.52, 3.94 | B, C |
| 82 | 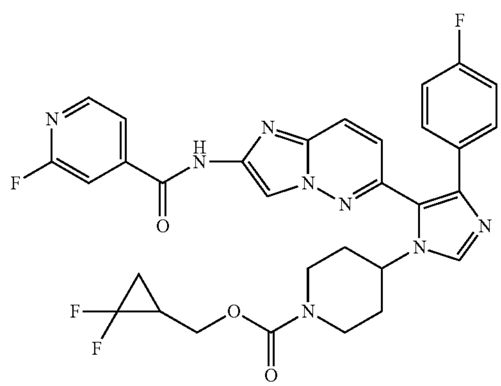 [SMILES: O=C(Nc1cn2nc(-c3c(-c4ccc(F)cc4)ncn3C3CCN(C(=O)OCC4CC4(F)F)CC3)ccc2n1)c1ccnc(F)c1] | (2,2-difluorocyclopropyl)methyl 4-(5-(2-(2-fluoroisonicotinamido)imidazo[1,2-b]pyridazin-6-yl)-4-(4-fluorophenyl)-1H-imidazol-1-yl)piperidine-1-carboxylate | 635.15 | 2.76, 4.07 | B, C |
| 83 | 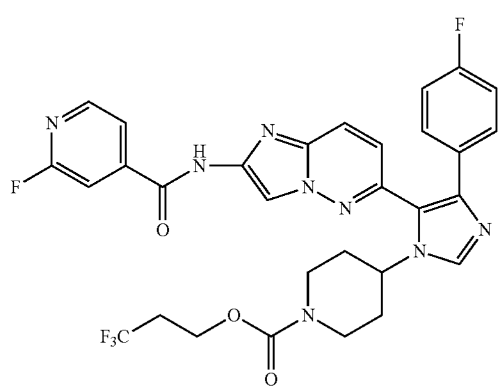 [SMILES: O=C(Nc1cn2nc(-c3c(-c4ccc(F)cc4)ncn3C3CCN(C(=O)OCCC(F)(F)F)CC3)ccc2n1)c1ccnc(F)c1] | 3,3,3-trifluoropropyl 4-(5-(2-(2-fluoroisonicotinamido)imidazo[1,2-b]pyridazin-6-yl)-4-(4-fluorophenyl)-1H-imidazol-1-yl)piperidine-1-carboxylate | 641.12 | 2.78, 4.09 | B, C |

TABLE 9-continued

| Compound No. | Structure | Name | [M + H]+ | HPLC Ret. Time | Method |
|---|---|---|---|---|---|
| 84 | 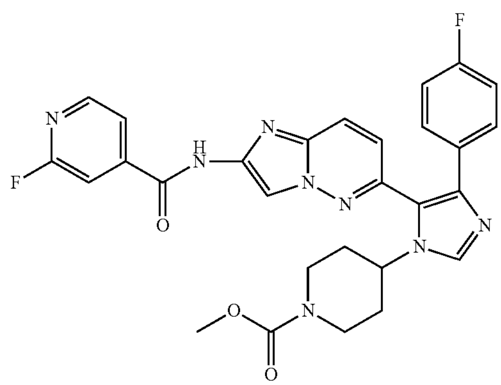 [SMILES: COC(=O)N1CCC(n2cnc(-c3ccc(F)cc3)c2-c2ccc3nc(NC(=O)c4ccnc(F)c4)cn3n2)CC1] | methyl 4-(5-(2-(2-fluoroisonicotinamido)imidazo[1,2-b]pyridazin-6-yl)-4-(4-fluorophenyl)-1H-imidazol-1-yl)piperidine-1-carboxylate | 559.22 | 2.20, 3.24 | B, C |
| 85 | 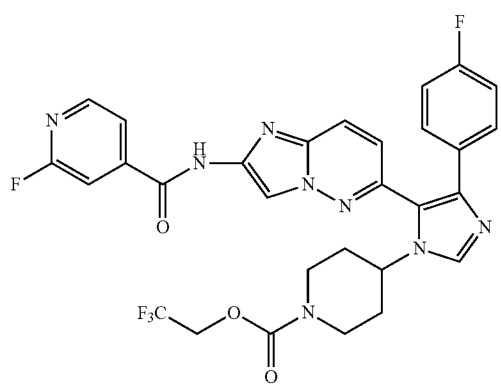 [SMILES: O=C(Nc1cn2nc(-c3c(-c4ccc(F)cc4)ncn3C3CCN(C(=O)OCC(F)(F)F)CC3)ccc2n1)c1ccnc(F)c1] | 2,2,2-trifluoroethyl 4-(5-(2-(2-fluoroisonicotinamido)imidazo[1,2-b]pyridazin-6-yl)-4-(4-fluorophenyl)-1H-imidazol-1-yl)piperidine-1-carboxylate | 627.11 | 2.72, 4.00 | B, C |
| 86 | 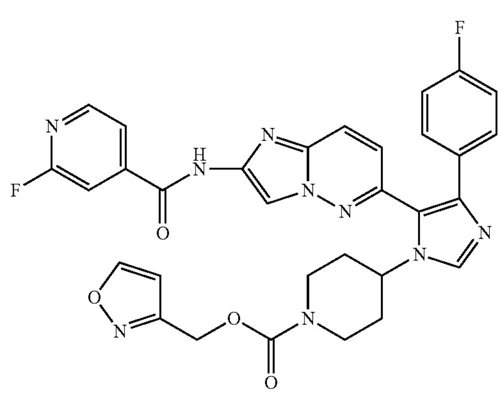 [SMILES: O=C(Nc1cn2nc(-c3c(-c4ccc(F)cc4)ncn3C3CCN(C(=O)OCc4ccon4)CC3)ccc2n1)c1ccnc(F)c1] | isoxazol-3-ylmethyl 4-(5-(2-(2-fluoroisonicotinamido)imidazo[1,2-b]pyridazin-6-yl)-4-(4-fluorophenyl)-1H-imidazol-1-yl)piperidine-1-carboxylate | 626.20 | 2.53, 3.83 | B, C |

Compound 87

2,6-difluoro-N-(6-(4-(4-fluorophenyl)-1-(piperidin-4-yl)-1H-imidazol-5-yl)imidazo[1,2-b]pyridazin-2-yl)isonicotinamide

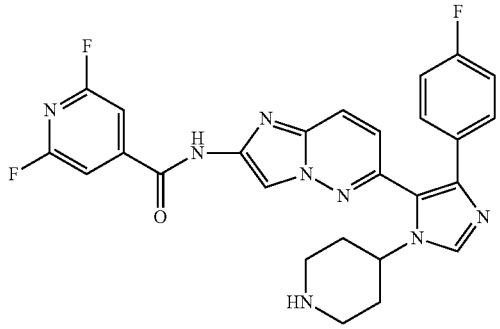 [SMILES: O=C(Nc1cn2nc(-c3c(-c4ccc(F)cc4)ncn3C3CCNCC3)ccc2n1)c1cc(F)nc(F)c1]

Compound 87 was synthesized analogous to compound 1 by reacting Intermediate 8 with 2,6-difluoroisonicotinic acid, followed by the deprotection of the Boc group with TFA. HPLC Ret. Time 3.18 min. (Method A). MS(ES): m/z=519.21 [M+H]$^+$. $^1$H NMR (400 MHz, DMSO-d$_6$) δ ppm 12.07 (s, 1H), 8.75 (d, J=8.8 Hz, 1H), 8.68 (s, 1H), 8.49-8.31 (m, 1H), 8.20-8.04 (m, 1H), 7.88-7.76 (m, 2H), 7.55-7.42 (m, 2H), 7.25-7.09 (m, 3H), 4.65-4.49 (m, 1H), 3.43 (br. s., 1H), 3.03 (q, J=12.0 Hz, 2H), 2.31 (d, J=13.1 Hz, 2H), 2.24-2.06 (m, 2H).

Compound 88

2,6-difluoro-N-(6-(4-(4-fluorophenyl)-1-(1-(3-fluoropropyl)piperidin-4-yl)-1H-imidazol-5-yl)imidazo[1,2-b]pyridazin-2-yl)isonicotinamide

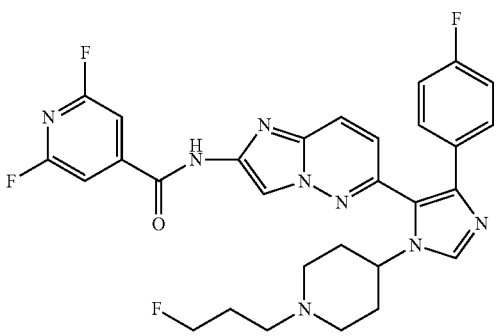 [SMILES: O=C(Nc1cn2nc(-c3c(-c4ccc(F)cc4)ncn3C3CCN(CCCF)CC3)ccc2n1)c1cc(F)nc(F)c1]

Compound 88 was synthesized analogous to compound 33 by reacting compound 87 with 1-fluoro-3-iodopropane. HPLC Ret. Time 2.53 min., 4.13 min. (Methods B and C respectively). MS(ES): m/z=579.30 [M+H]$^+$. $^1$H NMR (500 MHz, DMSO-d$_6$) δ ppm 12.02 (br. s, 1H), 8.59 (s, 1H), 8.23-8.14 (m, 1H), 8.11 (d, J=9.2 Hz, 1H), 7.82 (s, 2H), 7.52-7.40 (m, 2H), 7.20-7.08 (m, 3H), 4.53 (t, J=6.1 Hz, 1H), 4.43 (t, J=6.0 Hz, 1H), 4.10 (dt, J=15.3, 7.9 Hz, 1H), 3.02-2.87 (m, 2H), 2.38 (t, J=7.2 Hz, 2H), 2.10-1.88 (m, 8H), 1.87-1.71 (m, 2H).

The compound described in Table 10 was synthesized analogous to compound 88 by reacting compound 87 with the corresponding alkyl halide.

TABLE 10

| Compound No. | Structure | Name | [M + H]$^+$ | HPLC Ret. Time | Method |
|---|---|---|---|---|---|
| 89 | 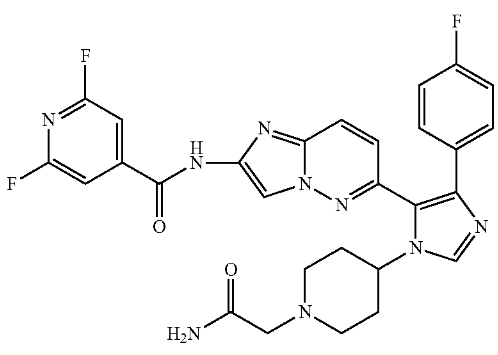 [SMILES: NC(=O)CN1CCC(n2cnc(-c3ccc(F)cc3)c2-c2ccc3nc(NC(=O)c4cc(F)nc(F)c4)cn3n2)CC1] | N-(6-(1-(1-(2-amino-2-oxoethyl)piperidin-4-yl)-4-(4-fluorophenyl)-1H-imidazol-5-yl)imidazo[1,2-b]pyridazin-2-yl)-2,6-difluoroisonicotinamide | 576.4 | 2.34, 3.91 | B, C |

125

Compound 90

(R)-2,6-difluoro-N-(6-(4-(4-fluorophenyl)-1-(1-(3,3,3-trifluoro-2-hydroxypropyl)piperidin-4-yl)-1H-imidazol-5-yl)imidazo[1,2-b]pyridazin-2-yl)isonicotinamide

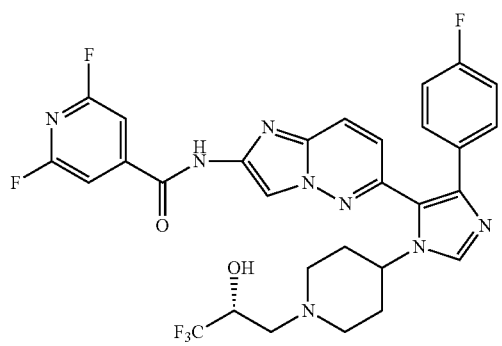 [SMILES: O=C(Nc1cn2nc(-c3c(-c4ccc(F)cc4)ncn3C3CCN(C[C@@H](O)C(F)(F)F)CC3)ccc2n1)c1cc(F)nc(F)c1]

Compound 90 was synthesized analogous to compound 7 by reacting compound 87 with (R)-2-(trifluoromethyl)oxirane. HPLC Ret. Time 2.73 min., 4.17 min. (Methods B and C respectively). MS(ES): m/z=631.20 [M+H]$^+$. $^1$H NMR (500 MHz, DMSO-d$_6$) ppm 8.59 (s, 1H), 8.19 (s, 1H), 8.11 (d, J=9.2 Hz, 1H), 7.82 (s, 2H), 7.52-7.41 (m, 2H), 7.24-7.06 (m, 3H), 6.14 (d, J=6.1 Hz, 1H), 4.11 (br. s, 2H), 3.01 (t, J=9.9 Hz, 2H), 2.60-2.53 (m, 1H), 2.19-1.97 (m, 6H).

The compound described in Table 11 was synthesized analogous to compound 90 by reacting compound 87 with the corresponding epoxide.

126

Compound 92

2,6-difluoro-N-(6-(4-(4-fluorophenyl)-1-(1-(3,3,3-trifluoropropyl)piperidin-4-yl)-1H-imidazol-5-yl)imidazo[1,2-b]pyridazin-2-yl)isonicotinamide

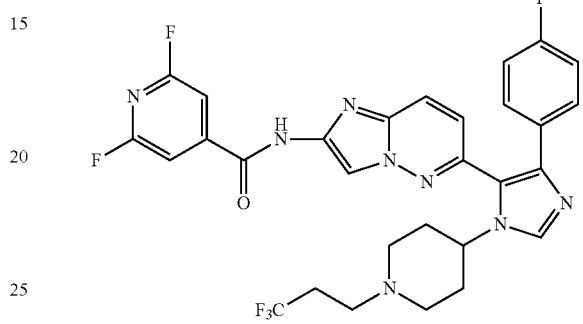

Compound 92 was synthesized analogous to compound 2 by reacting compound 87 with 3,3,3-trifluoropropanal. HPLC Ret. Time 2.91 min., 4.29 min. (Methods B and C respectively). MS(ES): m/z=615.30 [M+H]$^+$. $^1$H NMR (500 MHz, DMSO-d$_6$) δ ppm 12.03 (br. s, 1H), 8.59 (s, 1H), 8.20 (s, 1H), 8.11 (d, J=9.2 Hz, 1H), 7.97 (s, 1H), 7.82 (s, 2H), 7.56-7.40 (m, 2H), 7.23-7.05 (m, 3H), 4.11 (br. s., 1H), 3.07-2.94 (m, 2H), 2.90 (s, 4H), 2.75 (s, 3H), 2.50-2.37 (m, 3H), 2.02 (d, J=6.7 Hz, 7H).

TABLE 11

| Compound No. | Structure | Name | [M + H]$^+$ | Ret. Time | HPLC Method |
|---|---|---|---|---|---|
| 91 | 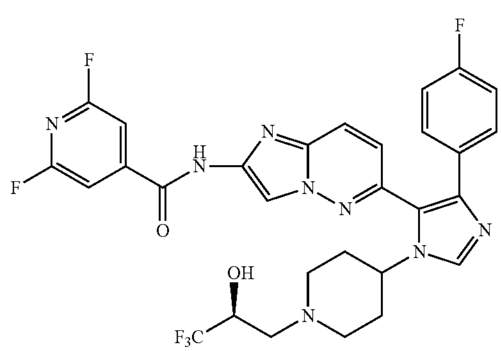 | (S)-2,6-difluoro-N-(6-(4-(4-fluorophenyl)-1-(1-(3,3,3-trifluoro-2-hydroxypropyl)piperidin-4-yl)-1H-imidazol-5-yl)imidazo[1,2-b]pyridazin-2-yl)isonicotinamide | 631.0 | 2.77, 2.41 | B, C |

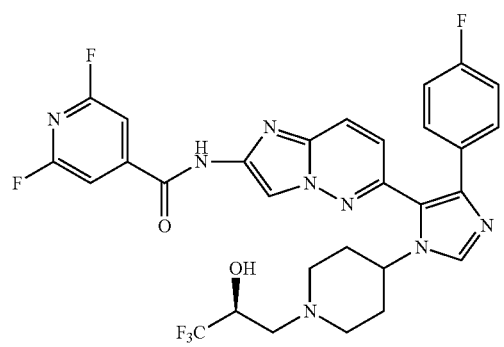 [SMILES: O=C(Nc1cn2nc(-c3c(-c4ccc(F)cc4)ncn3C3CCN(C[C@H](O)C(F)(F)F)CC3)ccc2n1)c1cc(F)nc(F)c1]

Compound 93

2,6-difluoro-N-(6-(4-(4-fluorophenyl)-1-(1-(isoxazole-3-carbonyl)piperidin-4-yl)-1H-imidazol-5-yl)imidazo[1,2-b]pyridazin-2-yl)isonicotinamide

Compound 95

N-(6-(4-(4-fluorophenyl)-1-(piperidin-4-yl)-1H-imidazol-5-yl)imidazo[1,2-b]pyridazin-2-yl)-4-methyl-2-(pyridin-3-yl)thiazole-5-carboxamide

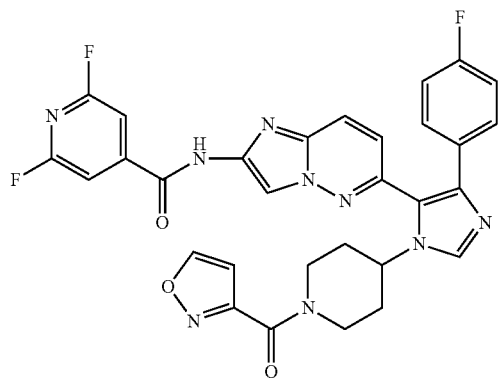 [SMILES: O=C(Nc1cn2nc(-c3c(-c4ccc(F)cc4)ncn3C3CCN(C(=O)c4ccon4)CC3)ccc2n1)c1cc(F)nc(F)c1]

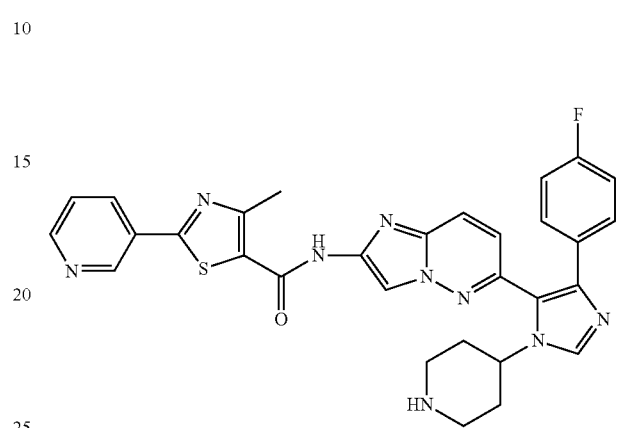

Compound 93 was synthesized analogous to compound 5 by reacting compound 87 with isoxazole 3-carboxylic acid. HPLC Ret. Time 2.61 min., 3.67 min (Methods B and C respectively). MS(ES): m/z 614.20 [M+H]$^+$. $^1$H NMR (500 MHz, DMSO-d$_6$) δ ppm 12.02 (s, 1H), 9.12 (d, J=1.5 Hz, 1H), 8.64 (s, 1H), 8.24 (s, 1H), 8.12 (d, J=9.5 Hz, 1H), 7.82 (s, 2H), 7.47 (dd, J=8.9, 5.5 Hz, 2H), 7.18-7.08 (m, 4H), 6.86 (d, J=1.5 Hz, 1H), 4.63 (d, J=13.1 Hz, 1H), 4.56-4.42 (m, 1H), 4.03 (d, J=13.4 Hz, 1H), 3.24 (t, J=12.1 Hz, 1H), 2.95-2.83 (m, 1H), 2.21 (d, J=11.6 Hz, 1H), 2.14 (d, J=10.4 Hz, 1H), 2.11-1.95 (m, 2H).

The compounds described in Table 12 was synthesized analogous to compound 93 by reacting compound 87 with the corresponding carboxylic acid.

Compound 95 was synthesized analogous to compound 1 by reacting Intermediate 8 with 4-methyl-2-(pyridin-3-yl)thiazole-5-carboxylic acid, followed by the deprotection of the Boc group with TFA. HPLC Ret. Time 3.20 min. (Method A). MS(ES): m/z 580.20 [M+H]$^+$. $^1$H NMR (400 MHz, DMSO-d$_6$) δ ppm 11.71 (s, 1H), 9.22 (dd, J=2.3, 0.8 Hz, 1H), 8.91 (s, 1H), 8.86-8.74 (m, 2H), 8.65 (s, 1H), 8.49-8.37 (m, 1H), 8.19-8.08 (m, 1H), 7.66 (ddd, J=8.0, 4.9, 0.9 Hz, 1H), 7.55-7.42 (m, 2H), 7.30-7.21 (m, 2H), 7.12 (d, J=9.3 Hz, 1H), 4.73-4.55 (m, 1H), 3.44 (d, J=11.8 Hz, 2H), 3.05 (d, J=10.8 Hz, 2H), 2.75 (s, 3H), 2.35 (d, J=11.3 Hz, 2H), 2.25-2.08 (m, 2H).

TABLE 12

| Compound No. | Structure | Name | [M + H]$^+$ | Ret. Time | HPLC Method |
|---|---|---|---|---|---|
| 94 | 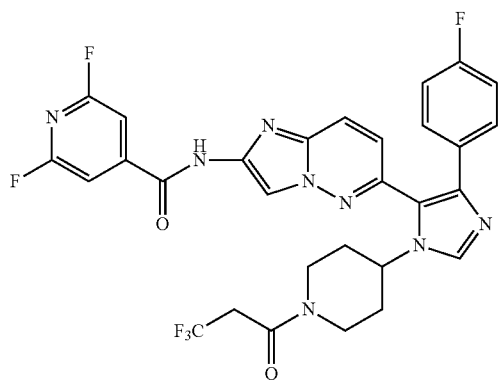 [SMILES: O=C(Nc1cn2nc(-c3c(-c4ccc(F)cc4)ncn3C3CCN(C(=O)CC(F)(F)F)CC3)ccc2n1)c1cc(F)nc(F)c1] | 2,6-difluoro-N-(6-(4-(4-fluorophenyl)-1-(1-(3,3,3-trifluoropropanoyl)piperidin-4-yl)-1H-imidazol-5-yl)imidazo[1,2-b]pyridazin-2-yl)isonicotinamide | 629.20 | 2.70, 3.99 | B, C |

Compound 96

N-(6-(4-(4-fluorophenyl)-1-(1-methylpiperidin-4-yl)-1H-imidazol-5-yl)imidazo[1,2-b]pyridazin-2-yl)-4-methyl-2-(pyridin-3-yl)thiazole-5-carboxamide

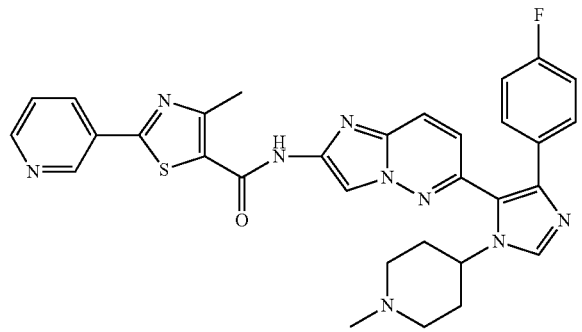 [SMILES: Cc1nc(-c2cccnc2)sc1C(=O)Nc1cn2nc(-c3c(-c4ccc(F)cc4)ncn3C3CCNCC3)ccc2n1]

Compound 96 was synthesized analogous to compound 2 by reacting compound 95 with formaldehyde (37% aq. solution). HPLC Ret. Time 2.29 min., 4.0 min. (Methods B and C respectively). MS(ES): m/z=594.50 [M+H]$^+$. $^1$H NMR (500 MHz, DMSO-d$_6$) δ ppm 9.19 (d, J=2.1 Hz, 1H), 8.75 (dd, J=4.7, 1.4 Hz, 1H), 8.53 (s, 1H), 8.37 (dt, J=7.9, 2.0 Hz, 1H), 8.17 (s, 1H), 8.08 (d, J=9.2 Hz, 1H), 7.61 (dd, J=7.9, 4.9 Hz, 1H), 7.46 (dd, J=8.7, 5.6 Hz, 2H), 7.21-7.04 (m, 3H), 4.14-4.00 (m, 1H), 2.85 (d, J=11.6 Hz, 2H), 2.74 (s, 3H), 2.17 (s, 3H), 2.11-1.97 (m, 4H), 1.97-1.86 (m, 3H).

The compounds described in Table 13 were synthesized analogous to compound 96 by reacting compound 95 with the corresponding aldehyde.

TABLE 13

| Compound No. | Structure | Name | [M + H]$^+$ | HPLC Ret. Time | Method |
|---|---|---|---|---|---|
| 97 | 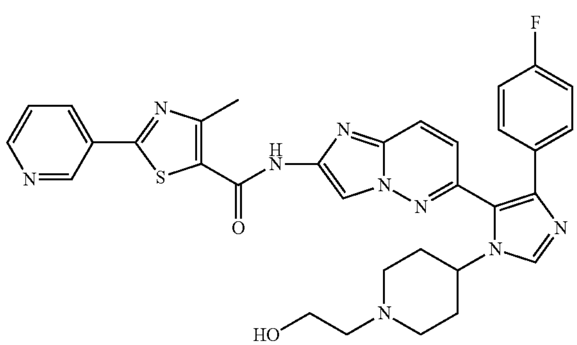 [SMILES: Cc1nc(-c2cccnc2)sc1C(=O)Nc1cn2nc(-c3c(-c4ccc(F)cc4)ncn3C3CCN(CCO)CC3)ccc2n1] | N-(6-(4-(4-fluorophenyl)-1-(1-(2-hydroxyethyl)piperidin-4-yl)-1H-imidazol-5-yl)imidazo[1,2-b]pyridazin-2-yl)-4-methyl-2-(pyridin-3-yl)thiazole-5-carboxamide | 624.42 | 2.08, 3.88 | B, C |
| 98 | 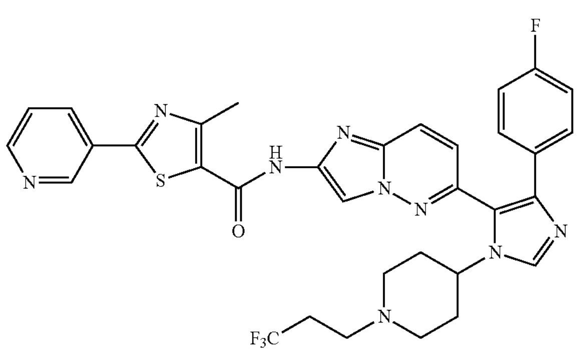 [SMILES: Cc1nc(-c2cccnc2)sc1C(=O)Nc1cn2nc(-c3c(-c4ccc(F)cc4)ncn3C3CCN(CCC(F)(F)F)CC3)ccc2n1] | N-(6-(4-(4-fluorophenyl)-1-(1-(3,3,3-trifluoropropyl)piperidin-4-yl)-1H-imidazol-5-yl)imidazo[1,2-b]pyridazin-2-yl)-4-methyl-2-(pyridin-3-yl)thiazole-5-carboxamide | 676.51 | 2.73, 4.24 | B, C |

131
Compound 99

(S)—N-(6-(4-(4-fluorophenyl)-1-(1-(3,3,3-trifluoro-2-hydroxypropyl)piperidin-4-yl)-1H-imidazol-5-yl)imidazo[1,2-b]pyridazin-2-yl)-4-methyl-2-(pyridin-3-yl)thiazole-5-carboxamide

132
Compound 101

N-(6-(4-(4-fluorophenyl)-1-(1-(isoxazole-3-carbonyl)piperidin-4-yl)-1H-imidazol-5-yl)imidazo[1,2-b]pyridazin-2-yl)-4-methyl-2-(pyridin-3-yl)thiazole-5-carboxamide

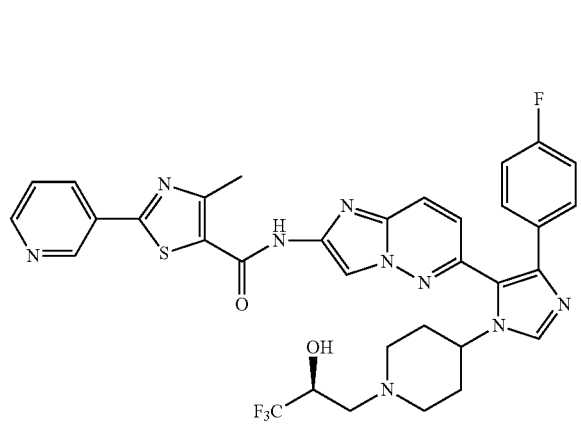

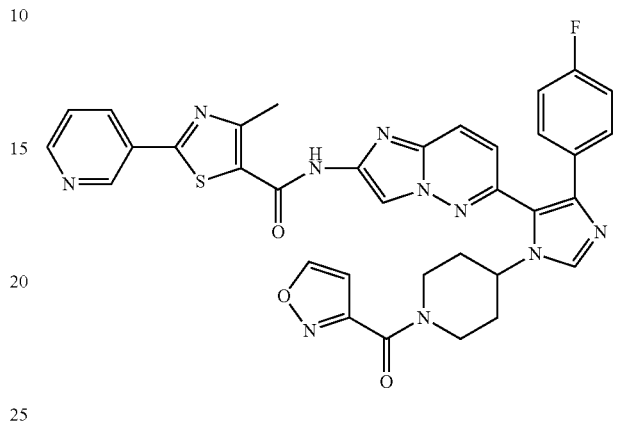

Compound 99 was synthesized analogous to compound 7 by reacting compound 95 with (S)-2-(trifluoromethyl)oxirane. HPLC Ret. Time 2.55 min., 4.10 min. (Methods B and C respectively). MS(ES): m/z=692.30 [M+H]$^1$. $^1$H NMR (500 MHz, DMSO-d$_6$) δ ppm 9.28-9.17 (m, 1H), 8.77 (d, J=4.6 Hz, 1H), 8.57 (s, 1H), 8.41 (d, J=7.9 Hz, 1H), 8.20 (s, 1H), 8.08 (d, J=9.2 Hz, 1H), 7.65 (dd, J=7.9, 4.9 Hz, 2H), 7.50 (dd, J=8.4, 5.6 Hz, 3H), 7.27-7.06 (m, 4H), 4.15 (d, J=7.6 Hz, 3H), 3.64 (br. s., 2H), 3.05 (t, J=10.7 Hz, 3H), 2.78 (s, 4H), 2.25-2.09 (m, 3H), 2.06 (d, J=5.2 Hz, 5H).

The compounds described in Table 14 was synthesized analogous to compound 99 by reacting compound 95 with the corresponding alkyl halide.

Compound 101 was synthesized analogous to compound 5 by reacting compound 95 with isoxazole 3-carboxylic acid. HPLC Ret. Time 2.43 min., 3.90 min. (Methods B and C respectively). MS(ES): m/z=675.30 [M+H]$^+$. $^1$H NMR (500 MHz, DMSO-d$_6$) δ ppm 11.61 (br. s, 1H), 9.19 (d, J=2.1 Hz, 1H), 9.12 (d, J=1.8 Hz, 1H), 8.75 (dd, J=4.7, 1.4 Hz, 1H), 8.58 (s, 1H), 8.37 (dt, J=7.9, 2.0 Hz, 1H), 8.23 (s, 1H), 8.08 (d, J=9.2 Hz, 1H), 7.61 (dd, J=7.9, 4.9 Hz, 1H), 7.54-7.40 (m, 2H), 7.22-7.08 (m, 3H), 6.86 (d, J=1.8 Hz, 1H), 4.63 (d, J=13.7 Hz, 1H), 4.55-4.41 (m, 1H), 4.03 (d, J=13.4 Hz, 1H), 3.24 (t, J=12.1 Hz, 1H), 2.91 (t, J=11.7 Hz, 1H), 2.74 (s, 3H), 2.21 (d, J=11.9 Hz, 1H), 2.14 (d, J=11.6 Hz, 1H), 2.10-1.96 (m, 2H).

The compound described in Table 15 was synthesized analogous to compound 101 by reacting compound 95 with the corresponding carboxylic acid.

TABLE 14

| Compound No. | Structure | Name | [M + H]$^+$ | Ret. Time | HPLC Method |
|---|---|---|---|---|---|
| 100 | 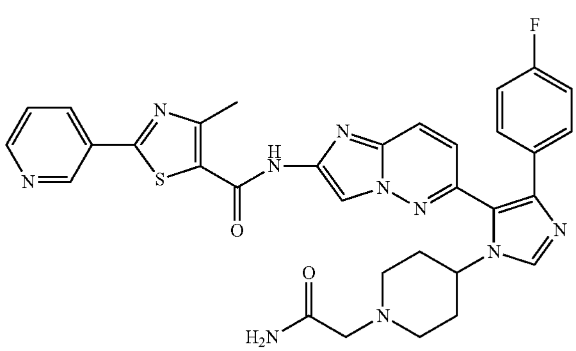 [SMILES: Cc1nc(-c2cccnc2)sc1C(=O)Nc1cn2nc(-c3c(-c4ccc(F)cc4)ncn3C3CCN(CC(N)=O)CC3)ccc2n1] | N-(6-(1-(1-(2-amino-2-oxoethyl)piperidin-4-yl)-4-(4-fluorophenyl)-1H-imidazol-5-yl)imidazo[1,2-b]pyridazin-2-yl)-4-methyl-2-(pyridin-3-yl)thiazole-5-carboxamide | 637.50 | 2.46, 3.94 | B, C |

TABLE 15

| Compound No. | Structure | Name | [M + H]⁺ | Ret. Time | HPLC Method |
|---|---|---|---|---|---|
| 102 | 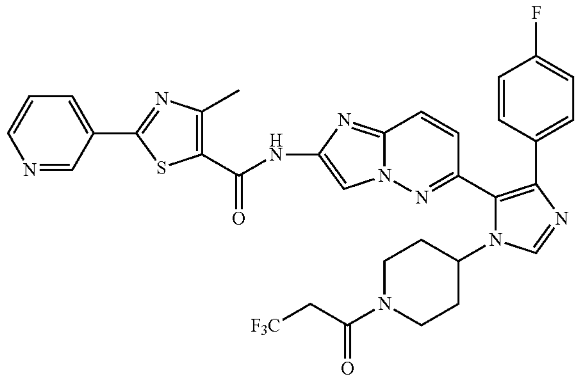 [SMILES: Cc1nc(-c2cccnc2)sc1C(=O)Nc1cn2nc(-c3c(-c4ccc(F)cc4)ncn3C3CCN(C(=O)CC(F)(F)F)CC3)ccc2n1] | N-(6-(4-(4-fluorophenyl)-1-(1-(3,3,3-trifluoropropanoyl)piperidin-4-yl)-1H-imidazol-5-yl)imidazo[1,2-b]pyridazin-2-yl)-4-methyl-2-(pyridin-3-yl)thiazole-5-carboxamide | 690.30 | 2.53, 3.91 | B, C |

Compound 103

N-(6-(4-(4-fluorophenyl)-1-(piperidin-4-yl)-1H-imidazol-5-yl)imidazo[1,2-b]pyridazin-2-yl)-4-methyl-2-(pyridin-4-yl)thiazole-5-carboxamide

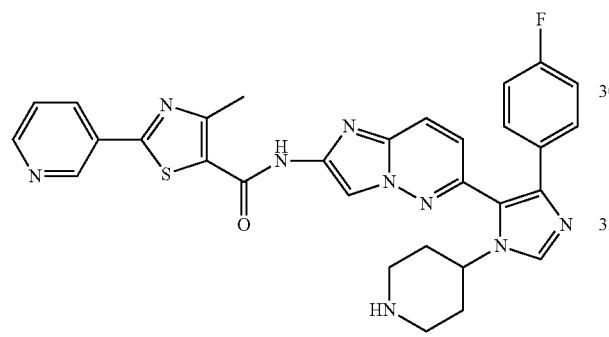

Compound 104

N-(6-(4-(4-fluorophenyl)-1-(1-methylpiperidin-4-yl)-1H-imidazol-5-yl)imidazo[1,2-b]pyridazin-2-yl)-4-methyl-2-(pyridin-4-yl)thiazole-5-carboxamide

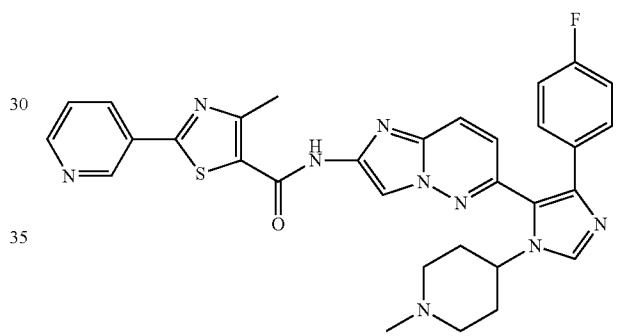

Compound 103 was synthesized analogous to compound 1 by reacting Intermediate 8 with 4-methyl-2-(pyridin-4-yl)thiazole-5-carboxylic acid, followed by the deprotection of the Boc group with TFA. HPLC Ret. Time 2.89 min. (Method A). MS(ES): m/z=580.30 [M+H]⁺. ¹H NMR (400 MHz, DMSO-d₆) δ ppm 11.75 (s, 1H), 8.90-8.75 (m, 3H), 8.63 (s, 1H), 8.42 (s, 1H), 8.18-8.07 (m, 1H), 8.07-7.97 (m, 3H), 7.56-7.43 (m, 2H), 7.20 (t, J=8.9 Hz, 2H), 7.12 (d, J=9.3 Hz, 1H), 3.84-3.72 (m, 1H), 3.42 (d, J=12.3 Hz, 2H), 3.04 (d, J=11.3 Hz, 1H), 2.81-2.71 (m, 4H), 2.39-2.25 (m, 2H), 2.23-2.08 (m, 1H).

Compound 104 was synthesized analogous to compound 2 by reacting compound 103 with formaldehyde (37% aq. solution). HPLC Ret. Time 2.29 min., 4.0 min. (Methods B and C respectively). MS(ES): m/z=594.50 [M+H]⁺. ¹H NMR (500 MHz, DMSO-d₆) δ ppm 8.82-8.71 (m, 2H), 8.54 (s, 1H), 8.17 (s, 1H), 8.08 (d, J=9.5 Hz, 1H), 8.00-7.91 (m, 2H), 7.51-7.41 (m, 2H), 7.19-7.06 (m, 314), 4.15-4.01 (m, 1H), 3.92 (s, 2H), 2.85 (d, J=11.6 Hz, 2H), 2.17 (s, 3H), 2.08-1.97 (m, 4H), 1.97-1.86 (m, 4H).

The compound described in Table 16 was synthesized analogous to compound 104 by reacting compound 103 with the corresponding aldehyde.

TABLE 16

| Compound No. | Structure | Name | [M + H]⁺ | Ret. Time | HPLC Method |
|---|---|---|---|---|---|
| 105 | 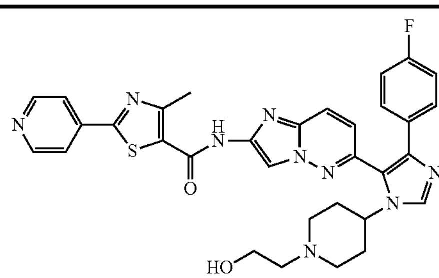 | N-(6-(4-(4-fluorophenyl)-1-(1-(2-hydroxyethyl)piperidin-4-yl)-1H-imidazol-5-yl)imidazo[1,2-b]pyridazin-2-yl)-4-methyl-2-(pyridin-4-yl)thiazole-5-carboxamide | 624.30 | 2.26, 3.95 | B, C |

Compound 106

N-(6-(4-(4-fluorophenyl)-1-(piperidin-4-yl)-1H-imidazol-5-yl)imidazo[1,2-b]pyridazin-2-yl)-2-morpholinoisonicotinamide

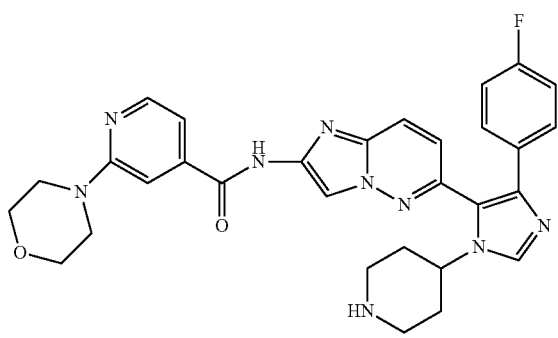 [SMILES: O=C(Nc1cn2nc(-c3c(-c4ccc(F)cc4)ncn3C3CCNCC3)ccc2n1)c1ccnc(N2CCOCC2)c1]

Compound 106 was synthesized analogous to compound 1 by reacting Intermediate 8 with 2-morpholinoisonicotinic acid hydrochloride, followed by the deprotection of the Boc group with TFA. HPLC Ret. Time 1.98 min., 3.55 min. (Methods B and C respectively). MS(ES): m/z=568.36 [M+H]$^+$. $^1$H NMR (500 MHz, DMSO-d$_6$) δ ppm 8.58 (s, 1H), 8.32 (d, J=5.2 Hz, 1H), 8.18-8.02 (m, 2H), 7.53 (s, 1H), 7.46 (dd, J=8.7, 5.6 Hz, 2H), 7.26 (d, J=5.2 Hz, 1H), 7.20-7.07 (m, 3H), 4.23-4.07 (m, 1H), 3.78-3.71 (m, 4H), 3.62-3.53 (m, 4H), 3.43 (br. s., 1H), 3.02 (d, J=12.2 Hz, 2H), 2.50-2.42 (m, 2H), 1.97 (d, J=10.1 Hz, 2H), 1.93-1.78 (m, 4H).

Compound 107

N-(6-(4-(4-fluorophenyl)-1-(1-(3,3,3-trifluoropropyl)piperidin-4-yl)-1H-imidazol-5-yl)imidazo[1,2-b]pyridazin-2-yl)-2-morpholinoisonicotinamide

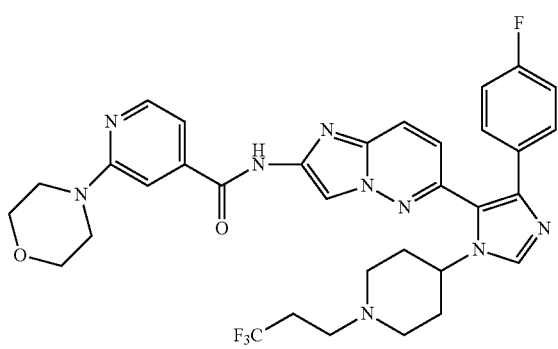 [SMILES: O=C(Nc1cn2nc(-c3c(-c4ccc(F)cc4)ncn3C3CCN(CCC(F)(F)F)CC3)ccc2n1)c1ccnc(N2CCOCC2)c1]

Compound 107 was synthesized analogous to compound 2 by reacting compound 106 with 3,3,3-trifluoropropanal. HPLC Ret. Time 2.47 min., 3.79 min (Methods B and C respectively). MS(ES): m/z=664.22 [M+H]$^+$. $^1$H NMR (500 MHz, DMSO-d$_6$) δ ppm 11.72 (br. s, 1H), 9.12 (d, J=1.8 Hz, 1H), 8.62 (s, 1H), 8.32 (d, J=5.2 Hz, 1H), 8.23 (s, 1H), 8.08 (d, J=9.5 Hz, 1H), 7.54 (s, 1H), 7.47 (dd, J=8.9, 5.5 Hz, 3H), 7.26 (d, J=5.2 Hz, 1H), 7.19-7.07 (m, 4H), 6.86 (d, J=1.8 Hz, 1H), 4.61 (br. s., 1H), 4.47 (br. s., 1H), 4.02 (br. s., 1H), 3.83-3.72 (m, 5H), 3.64-3.54 (m, 5H), 3.24 (s, 1H), 2.91 (s, 2H), 2.19 (br. s., 1H), 2.13 (br. s., 1H), 2.04 (dt, J=11.7, 5.7 Hz, 3H).

Compound 108

N-(6-(4-(4-fluorophenyl)-1-(1-(3,3,3-trifluoropropanoyl)piperidin-4-yl)-1H-imidazol-5-yl)imidazo[1,2-b]pyridazin-2-yl)-2-morpholinoisonicotinamide

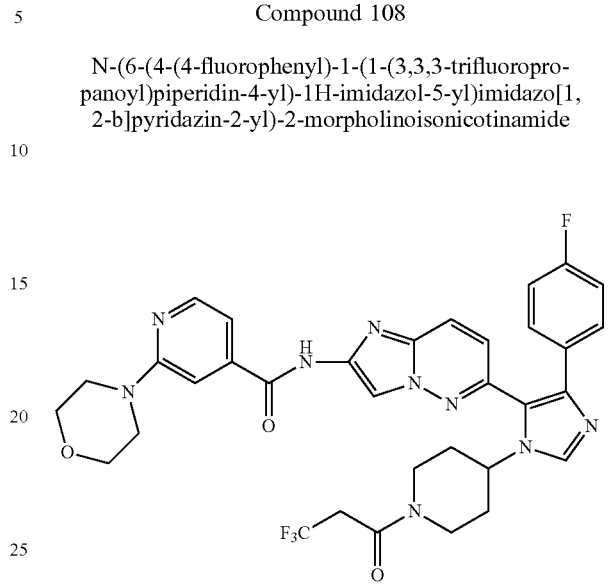

Compound 108 was synthesized analogous to compound 5 by reacting compound 106 with 3,3,3-trifluoropropanoic acid. HPLC Ret. Time 2.56 min., 2.58 min. (Methods B and C respectively). MS(ES): m/z=678.10 [M+H]$^+$. $^1$H NMR (500 MHz, DMSO-d$_6$) δ ppm 11.73 (br. s, 1H), 8.61 (s, 1H), 8.32 (d, J=4.9 Hz, 1H), 8.17 (s, 1H), 8.08 (d, J=9.5 Hz, 1H), 7.54 (s, 1H), 7.51-7.40 (m, 3H), 7.26 (dd, J=5.0, 1.1 Hz, 1H), 7.21-7.07 (m, 4H), 4.52 (d, J=13.1 Hz, 1H), 4.46-4.32 (m, 1H), 4.00-3.86 (m, 3H), 3.83-3.61 (m, 8H), 3.61-3.52 (m, 6H), 3.10 (t, J=12.1 Hz, 1H), 2.65 (t, J=11.9 Hz, 1H), 2.10 (br. s., 3H), 2.05-1.86 (m, 3H).

Compound 109

N-(6-(4-(4-fluorophenyl)-1-(piperidin-4-yl)-1H-imidazol-5-yl)imidazo[1,2-b]pyridazin-2-yl)quinoline-4-carboxamide

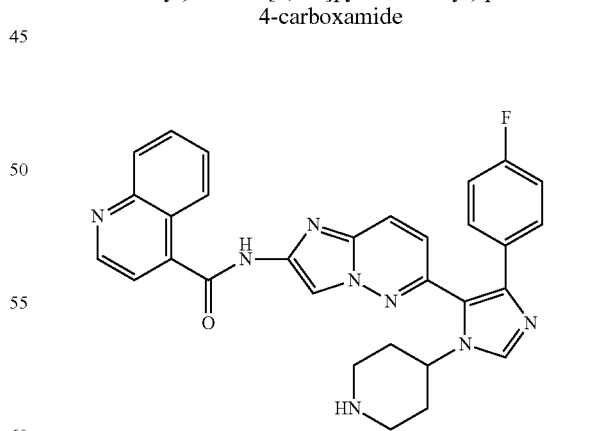

Compound 109 was synthesized analogous to compound 1 by reacting Intermediate 8 with quinoline-4-carboxylic acid, followed by the deprotection of the Boc group with TFA. HPLC Ret. Time 1.96 min., 3.52 min. (Methods B and C respectively). MS(ES): m/z=533.39 [M+H]$^+$. $^1$H NMR (500 MHz, DMSO-d$_6$) δ ppm 9.08 (d, J=4.3 Hz, 1H), 8.67

(s, 1H), 8.25-8.07 (m, 4H), 7.88 (td, J=7.6, 1.2 Hz, 1H), 7.82-7.69 (m, 2H), 7.53-7.42 (m, 2H), 7.25-7.04 (m, 3H), 4.21-4.10 (m, 1H), 3.03 (d, J=12.2 Hz, 2H), 2.47 (s, 1H), 2.02-1.93 (m, 2H), 1.92-1.80 (m, 4H).

Compound 110

N-(6-(4-(4-fluorophenyl)-1-(1-methylpiperidin-4-yl)-1H-imidazol-5-yl)imidazo[1,2-b]pyridazin-2-yl)quinoline-4-carboxamide

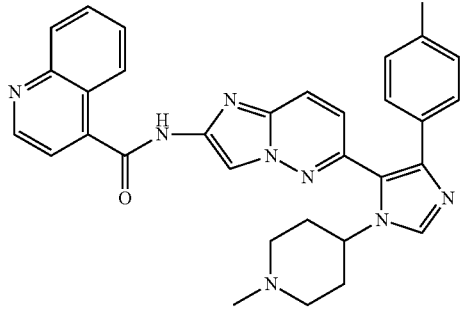

Compound 110 was synthesized analogous to compound 2 by reacting compound 109 with formaldehyde (37% aq. solution). HPLC Ret. Time 2.08 min., 3.71 min. (Methods B and C respectively). MS(ES): m/z=547.30 [M+H]$^+$. $^1$H NMR (500 MHz, DMSO-d$_6$) δ ppm 9.08 (d, J=4.3 Hz, 1H), 8.66 (s, 1H), 8.28-8.06 (m, 4H), 7.88 (t, J=7.6 Hz, 1H), 7.80-7.69 (m, 2H), 7.47 (dd, J=8.7, 5.6 Hz, 2H), 7.21-7.09 (m, 3H), 3.92 (s, 1H), 2.86 (d, J=11.0 Hz, 2H), 2.18 (s, 3H), 2.08-1.99 (m, 4H), 1.99-1.89 (m, 2H), 1.82 (s, 2H).

The compound described in Table 17 was synthesized analogous to compound 110 by reacting compound 109 with the corresponding aldehyde.

Compound 112

N-(6-(1-(1-(2-amino-2-oxoethyl)piperidin-4-yl)-4-(4-fluorophenyl)-1H-imidazol-5-yl)imidazo[1,2-b]pyridazin-2-yl)quinoline-4-carboxamide

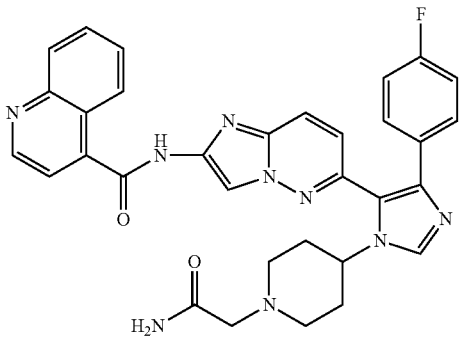 [SMILES: NC(=O)CN1CCC(n2cnc(-c3ccc(F)cc3)c2-c2ccc3nc(NC(=O)c4ccnc5ccccc45)cn3n2)CC1]

Compound 112 was synthesized analogous to compound 33 by reacting compound 109 with 2-bromoacetamide. HPLC Ret. Time 2.18 min., 3.70 min. (Methods B and C respectively). MS(ES): m/z=590.40 [M+H]$^+$. $^1$H NMR (500 MHz, DMSO-d$_6$) δ ppm 9.08 (d, J=4.3 Hz, 1H), 8.67 (s, 1H), 8.21 (d, J=8.2 Hz, 1H), 8.18-8.06 (m, 3H), 7.88 (t, J=7.2 Hz, 1H), 7.82-7.68 (m, 2H), 7.47 (dd, J=8.9, 5.5 Hz, 2H), 7.23 (br. s., 1H), 7.15 (dt, J=9.2, 4.3 Hz, 4H), 4.16-4.06 (m, 1H), 3.92 (s, 1H), 2.96-2.86 (m, 4H), 2.25-2.06 (m, 4H), 2.06-1.97 (m, 2H), 1.77 (s, 1H).

The compound described in Table 18 was synthesized analogous to compound 112 by reacting compound 109 with the corresponding alkene.

TABLE 17

| Compound No. | Structure | Name | [M + H]$^+$ | Ret. Time | HPLC Method |
|---|---|---|---|---|---|
| 111 | 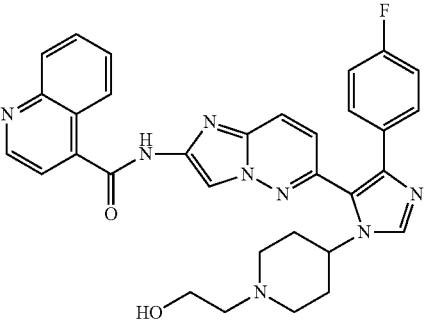 [SMILES: N#CCCN1CCC(n2cnc(-c3ccc(F)cc3)c2-c2ccc3nc(NC(=O)c4ccnc5ccccc45)cn3n2)CC1] | N-(6-(4-(4-fluorophenyl)-1-(1-(2-hydroxyethyl)piperidin-4-yl)-1H-imidazol-5-yl)imidazo[1,2-b]pyridazin-2-yl)quinoline-4-carboxamide | 577.4 | 2.06, 3.65 | B, C |

TABLE 18

| Compound No. | Structure | Name | [M + H]+ | Ret. Time | HPLC Method |
|---|---|---|---|---|---|
| 113 | 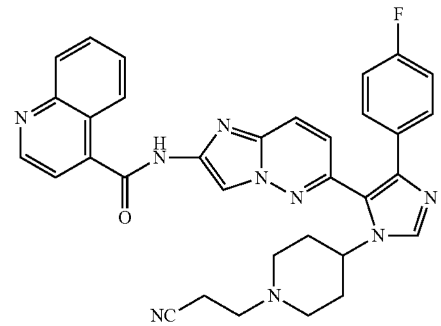 | N-(6-(1-(1-(2-cyanoethyl) piperidin-4-yl)-4-(4-fluorophenyl)-1H-imidazol-5-yl)imidazo[1,2-b]pyridazin-2-yl)quinoline-4-carboxamide | 586.40 | 2.38, 3.75 | B, C |

Compound 114

N-(6-(4-(4-fluorophenyl)-1-(piperidin-4-yl)-1H-imidazol-5-yl)imidazo[1,2-b]pyridazin-2-yl)thiazole-5-carboxamide

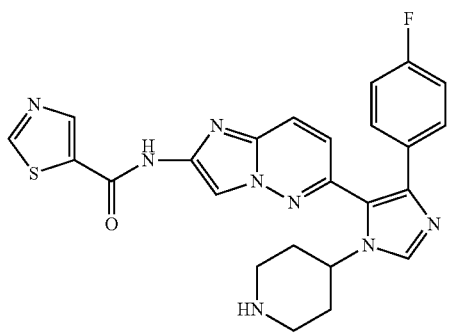 [SMILES: O=C(Nc1cn2nc(-c3c(-c4ccc(F)cc4)ncn3C3CCNCC3)ccc2n1)c1cncs1]

Compound 114 was synthesized analogous to compound 1 by reacting Intermediate 8 with thiazole-5-carboxylic acid, followed by the deprotection of the Boc group with TFA. HPLC Ret. Time 2.83 min (Method A). MS(ES): m/z=489.09 [M+H]+.

Compound 115

N-(6-(4-(4-fluorophenyl)-1-(1-(3,3,3-trifluoropropyl)piperidin-4-yl)-1H-imidazol-5-yl)imidazo[1,2-b]pyridazin-2-yl)thiazole-5-carboxamide

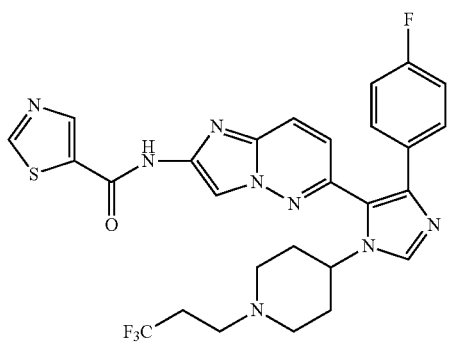 [SMILES: O=C(Nc1cn2nc(-c3c(-c4ccc(F)cc4)ncn3C3CCN(CCC(F)(F)F)CC3)ccc2n1)c1cncs1]

Compound 115 was synthesized analogous to compound 2 by reacting compound 114 with 3,3,3-trifluoropropanal. HPLC Ret. Time 2.42 min., 3.90 min. (Methods B and C respectively). MS(ES): m/z=585.20 [M+H]+. $^1$H NMR (500 MHz, DMSO-$d_6$) δ ppm 11.93 (s, 1H), 9.36 (s, 1H), 8.93 (s, 1H), 8.49 (s, 1H), 8.19 (s, 1H), 8.08 (d, J=9.2 Hz, 1H), 7.55-7.41 (m, 3H), 7.20-7.06 (m, 4H), 4.10 (br. s., 1H), 2.97 (d, J=4.6 Hz, 2H), 2.50-2.33 (m, 3H), 2.10-1.94 (m, 7H).

Compound 116

N-(6-(4-(4-fluorophenyl)-1-(1-(isoxazole-3-carbonyl)piperidin-4-yl)-1H-imidazol-5-yl)imidazo[1,2-b]pyridazin-2-yl)thiazole-5-carboxamide

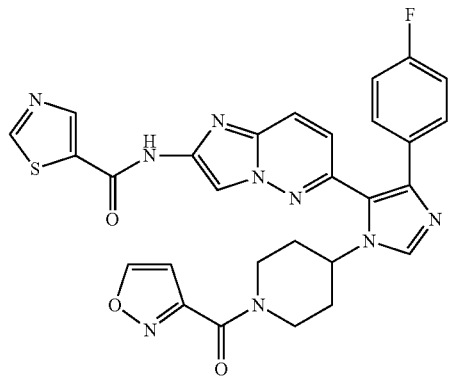 [SMILES: O=C(Nc1cn2nc(-c3c(-c4ccc(F)cc4)ncn3C3CCN(C(=O)c4ccon4)CC3)ccc2n1)c1cncs1]

Compound 116 was synthesized analogous to compound 5 by reacting compound 114 with isoxazole 3-carboxylic acid. HPLC Ret. Time 2.27 min., 2.20 min. (Methods B and C respectively). MS(ES): m/z=583.90 [M+H]+. $^1$H NMR (500 MHz, DMSO-$d_6$) δ ppm 11.91 (br. s, 1H), 9.36 (s, 1H), 9.12 (d, J=1.5 Hz, 1H), 8.93 (s, 1H), 8.54 (s, 1H), 8.23 (s, 1H), 8.09 (d, J=9.2 Hz, 1H), 7.51-7.43 (m, 2H), 7.22-7.08 (m, 3H), 6.86 (d, J=1.5 Hz, 1H), 4.62 (d, J=12.5 Hz, 1H), 4.55-4.40 (m, 1H), 4.03 (d, J=13.7 Hz, 1H), 3.23 (t, J=11.9 Hz, 1H), 2.96-2.84 (m, 1H), 2.20 (d, J=12.8 Hz, 1H), 2.17-2.10 (m, 1H), 2.10-1.96 (m, 2H), 1.23 (d, J=6.7 Hz, 1H).

The compound described in Table 19 was synthesized analogous to compound 116 by reacting compound 114 with the corresponding carboxylic acid.

TABLE 19

| Compound No. | Structure | Name | [M + H]+ | Ret. Time | HPLC Method |
|---|---|---|---|---|---|
| 117 | 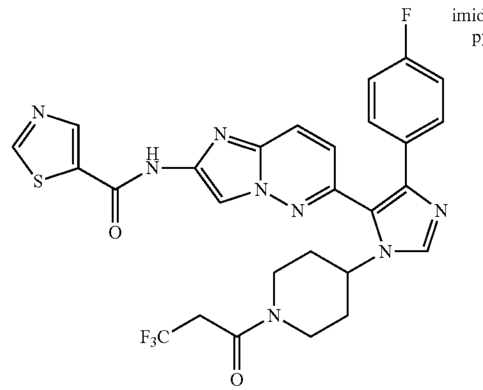 | N-(6-(4-(4-fluorophenyl)-1-(1-(3,3,3-trifluoropropanoyl)piperidin-4-yl)-1H-imidazol-5-yl)imidazo[1,2-b]pyridazin-2-yl)thiazole-5-carboxamide | 599.00 | 2.35, 2.28 | B, C |

Compound 118

(S)—N-(6-(4-(4-fluorophenyl)-1-(1-(3,3,3-trifluoro-2-hydroxypropyl)piperidin-4-yl)-1H-imidazol-5-yl)imidazo[1,2-b]pyridazin-2-yl)thiazole-5-carboxamide Compound 119

N-(6-(2-cyclopropyl-4-(4-fluorophenyl)-1-(piperidin-4-yl)-1H-imidazol-5-yl)imidazo[1,2-b]pyridazin-2-yl)-2-fluoroisonicotinamide

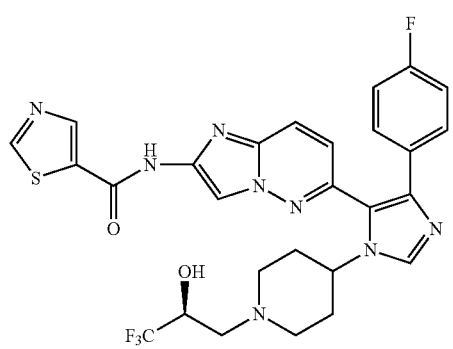 [SMILES: O=C(Nc1cn2nc(-c3c(-c4ccc(F)cc4)ncn3C3CCN(C[C@H](O)C(F)(F)F)CC3)ccc2n1)c1cncs1]

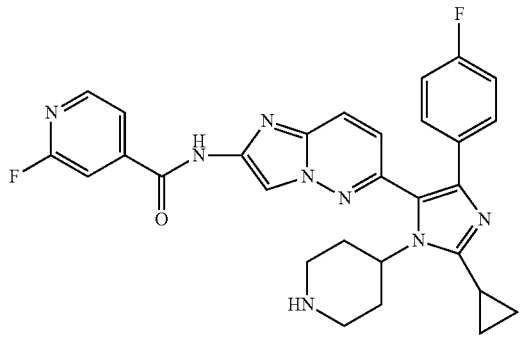 [SMILES: O=C(Nc1cn2nc(-c3c(-c4ccc(F)cc4)nc(C4CC4)n3C3CCNCC3)ccc2n1)c1ccnc(F)c1]

Compound 118 was synthesized analogous to compound 7 by reacting compound 114 with (S)-2-(trifluoromethyl)oxirane. HPLC Ret. Time 2.32 min., 2.0 min. (Methods B and C respectively). MS(ES): m/z=601.0 [M+H]+. $^1$H NMR (500 MHz, DMSO-d$_6$) δ ppm 11.93 (br. s., 1H), 9.36 (s, 1H), 8.93 (s, 1H), 8.50 (s, 1H), 8.19 (s, 1H), 8.08 (d, J=9.5 Hz, 1H), 7.46 (dd, J=8.7, 5.6 Hz, 2H), 7.22-7.06 (m, 3H), 6.14 (d, J=6.7 Hz, 1H), 4.11 (dd, J=10.7, 5.5 Hz, 2H), 3.01 (t, J=9.8 Hz, 2H), 2.19-1.98 (m, 6H).

Compound 119 was synthesized analogous to compound 1 by reacting Intermediate 9 with 2-fluoroisonicotinic acid, followed by the deprotection of the Boc group with TFA. HPLC Ret. Time 2.12 min., 3.59 min. (Methods B and C respectively). MS(ES): m/z=541.42 [M+H]+. $^1$H NMR (500 MHz, DMSO-d$_6$) δ ppm 8.59 (s, 1H), 8.49 (d, J=5.2 Hz, 1H), 8.11 (d, J=9.5 Hz, 1H), 7.98 (d, J=5.2 Hz, 1H), 7.82 (s, 1H), 7.33 (dd, J=8.7, 5.6 Hz, 2H), 7.19 (d, J=9.2 Hz, 1H), 7.07 (t, J=8.9 Hz, 2H), 4.27 (t, J=11.7 Hz, 1H), 2.99 (d, J=12.2 Hz, 2H), 2.46 (t, J=11.3 Hz, 3H), 2.28-2.19 (m, 1H), 2.13-1.96 (m, 2H), 1.88 (s, 6H), 1.13-0.98 (m, 4H).

Compound 120

N-(6-(2-cyclopropyl-4-(4-fluorophenyl)-1-(1-(2-methoxyethyl)piperidin-4-yl)-1H-imidazol-5-yl)imidazo[1,2-b]pyridazin-2-yl)-2-fluoroisonicotinamide

Compound 122

N-(6-(1-(1-(2-cyanoethyl)piperidin-4-yl)-2-cyclopropyl-4-(4-fluorophenyl)-1H-imidazol-5-yl)imidazo[1,2-b]pyridazin-2-yl)-2-fluoroisonicotinamide

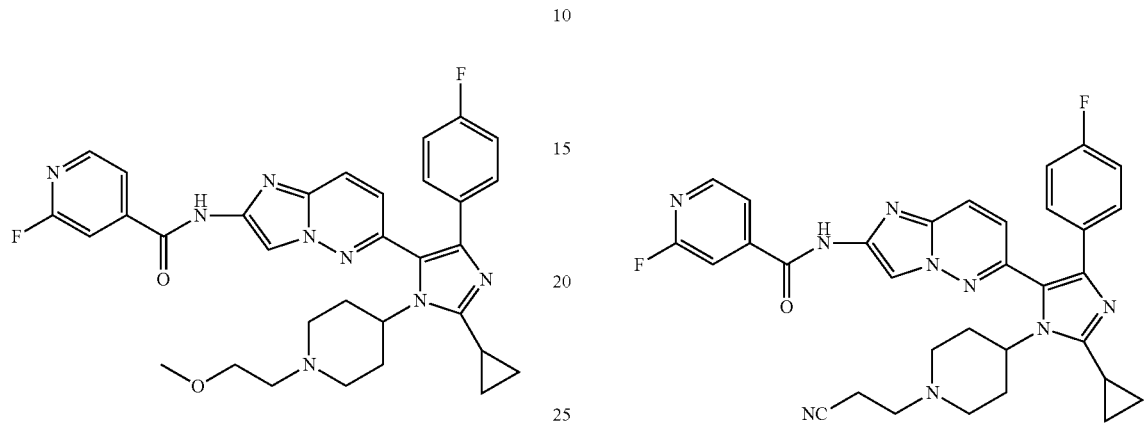

Compound 120 was synthesized analogous to compound 33 by reacting compound 119 with 1-bromo-2-methoxyethane. HPLC Ret. Time 2.45 min., 4.0 min. (Methods B and C respectively). MS(ES): m/z=599.50 [M+H]$^+$. $^1$H NMR (500 MHz, DMSO-d$_6$) δ ppm 8.59 (s, 1H), 8.48 (d, J=5.2 Hz, 1H), 8.12 (d, J=9.2 Hz, 1H), 7.98 (d, J=5.2 Hz, 1H), 7.82 (s, 1H), 7.33 (dd, J=8.9, 5.5 Hz, 2H), 7.20 (d, J=9.2 Hz, 1H), 7.07 (t, J=8.9 Hz, 2H), 4.18 (t, J=12.5 Hz, 1H), 3.19 (s, 3H), 2.95 (d, J=11.0 Hz, 2H), 2.43 (t, J=5.8 Hz, 2H), 2.24-2.09 (m, 3H), 2.09-1.96 (m, 2H), 1.96-1.84 (m, 3H), 1.12-1.00 (m, 5H).

The compounds described in Table 20 were synthesized analogous to compound 120 by reacting compound 119 with appropriate reactants.

Compound 122 was synthesized analogous to compound 37 by reacting compound 119 with acrylonitrile. HPLC Ret. Time 2.65 min., 3.95 min. (Methods B and C respectively). MS(ES): m/z 594.40 [M+H]$^+$. $^1$H NMR (500 MHz, DMSO-d$_6$) δ ppm 8.59 (s, 1H), 8.48 (d, J=5.2 Hz, 1H), 8.12 (d, J=9.2 Hz, 1H), 7.97 (d, J=5.2 Hz, 1H), 7.82 (s, 1H), 7.40-7.28 (m, 2H), 7.20 (d, J=9.2 Hz, 1H), 7.07 (t, J=8.9 Hz, 2H), 4.27-4.12 (m, 1H), 3.92 (s, 1H), 2.95 (d, J=11.0 Hz, 2H), 2.68-2.53 (m, 4H), 2.26-2.12 (m, 3H), 2.12-2.02 (m, 2H), 1.95 (d, J=10.7 Hz, 2H), 1.12-0.99 (m, 4H).

TABLE 20

| Compound No. | Structure | Name | [M + H]$^+$ | Ret. Time | HPLC Method |
|---|---|---|---|---|---|
| 121 | 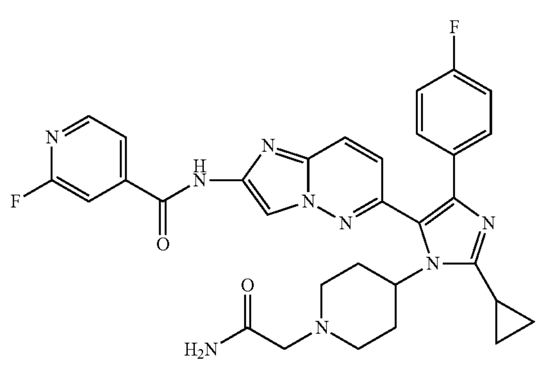 [SMILES: NC(=O)CN1CCC(n2c(C3CC3)nc(-c3ccc(F)cc3)c2-c2ccc3nc(NC(=O)c4ccnc(F)c4)cn3n2)CC1] | N-(6-(1-(1-(2-amino-2-oxoethyl)piperidin-4-yl)-2-cyclopropyl-4-(4-fluorophenyl)-1H-imidazol-5-yl)imidazo[1,2-b]pyridazin-2-yl)-2-fluoroisonicotinamide | 598.32 | 2.42, 3.86 | B, C |

Compound 123

N-(6-(2-cyclopropyl-4-(4-fluorophenyl)-1-(1-(pyridin-4-yl)piperidin-4-yl)-1H-imidazol-5-yl)imidazo[1,2-b]pyridazin-2-yl)-2-fluoroisonicotinamide

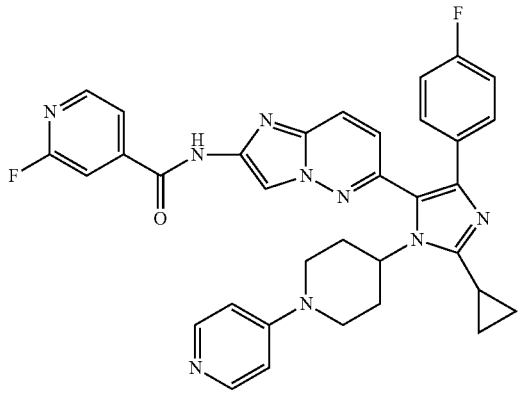 [SMILES: O=C(Nc1cn2nc(-c3c(-c4ccc(F)cc4)nc(C4CC4)n3C3CCN(c4ccncc4)CC3)ccc2n1)c1ccnc(F)c1]

To a solution of compound 119 (0.023 g, 0.043 mmol) in NMP (0.85 mL) was added 4-chloropyridine, HCl (0.032 g, 0.213 mmol), followed by Hunig's base (0.059 mL, 0.340 mmol). The reaction mixture was heated in a sealed tube in an oil-bath at 100° C. for 16 h. The material was purified via preparative LC/MS with the following conditions: Column: Waters XBridge Phenyl, 19×200 mm, 5-μm particles; Guard Column: Waters XBridge C18, 19×10 mm, 5-μm particles; Mobile Phase A: water; Mobile Phase B: acetonitrile; Buffer: 20-mM ammonium acetate; Gradient: 20-95% B over 20.5 minutes, then a 7.0 minute hold at 95% B; Flow: 25 mL/min. Fractions containing the desired product (0.004 g, 15.34% yield) were combined and dried via centrifugal evaporation. HPLC Ret. Time 2.31 min., 3.75 min (Methods B and C respectively). MS(ES): m/z=618.35 [M+H]$^+$. $^1$H NMR (500 MHz, DMSO-d$_6$) δ ppm 8.48 (d, J=4.9 Hz, 1H), 8.38 (s, 1H), 8.07-7.94 (m, 4H), 7.82 (s, 1H), 7.32 (dd, J=8.5, 5.5 Hz, 2H), 7.15-7.00 (m, 3H), 6.70 (d, J=6.4 Hz, 2H), 4.01 (d, J=11.9 Hz, 2H), 2.95 (t, J=12.4 Hz, 2H), 2.11 (d, J=8.2 Hz, 2H), 1.97 (d, J=12.8 Hz, 2H), 1.82 (s, 3H), 1.05 (d, J=2.4 Hz, 2H), 1.03-0.91 (m, 2H).

Compound 124

N-(6-(2-cyclopropyl-1-(1-(cyclopropylsulfonyl)piperidin-4-yl)-4-(4-fluorophenyl)-1H-imidazol-5-yl)imidazo[1,2-b]pyridazin-2-yl)-2-fluoroisonicotinamide

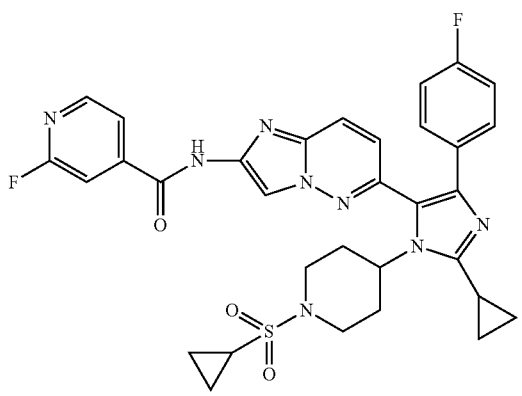 [SMILES: O=C(Nc1cn2nc(-c3c(-c4ccc(F)cc4)nc(C4CC4)n3C3CCN(S(=O)(=O)C4CC4)CC3)ccc2n1)c1ccnc(F)c1]

To a solution of compound 119 (0.023 g, 0.043 mmol) in CH$_2$Cl$_2$ (0.85 mL) was added cyclopropanesulfonyl chloride (8.97 mg, 0.064 mmol), followed by Hunig's base (0.015 mL, 0.085 mmol). The reaction mixture was stirred at rt for 16 h and then the solvent was evaporated under reduced pressure. The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 40-100% B over 14 minutes, then a 4-minute hold at 100% B; Flow: 20 mL/min. Fractions containing the desired product (0.01 g, 35% yield) were combined and dried via centrifugal evaporation. HPLC Ret. Time 2.77 min., 3.95 min (Methods B and C respectively). MS(ES): 645.29 [M+H]$^+$. $^1$H NMR (500 MHz, DMSO-d$_6$) δ ppm 11.98 (s, 1H), 8.62 (s, 1H), 8.48 (d, J=5.2 Hz, 1H), 8.13 (d, J=9.2 Hz, 1H), 7.98 (d, J=5.2 Hz, 1H), 7.82 (s, 1H), 7.32 (dd, J=8.7, 5.6 Hz, 2H), 7.20 (d, J=9.5 Hz, 1H), 7.08 (t, J=8.9 Hz, 2H), 4.44 (br. s., 1H), 3.92 (s, 1H), 3.70 (d, J=12.2 Hz, 2H), 3.18 (s, 1H), 2.96 (t, J=11.6 Hz, 2H), 2.32-2.14 (m, 3H), 2.08 (d, J=10.7 Hz, 2H), 1.13-0.99 (m, 4H), 0.92-0.76 (m, 4H).

Compound 125

N-(6-(2-cyclopropyl-4-(4-fluorophenyl)-1-(1-(pyridin-4-ylcarbamoyl)piperidin-4-yl)-1H-imidazol-5-yl)imidazo[1,2-b]pyridazin-2-yl)-2-fluoroisonicotinamide

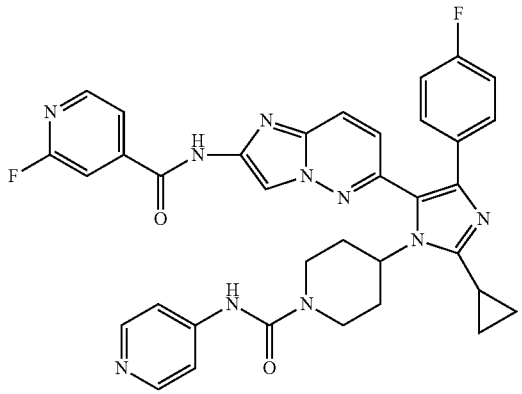 [SMILES: O=C(Nc1cn2nc(-c3c(-c4ccc(F)cc4)nc(C4CC4)n3C3CCN(C(=O)Nc4ccncc4)CC3)ccc2n1)c1ccnc(F)c1]

To a solution of compound 119 (0.022 g, 0.041 mmol) in CH$_2$Cl$_2$ (0.74 mL) and DMF (0.074 mL) were added 4-isocyanatopyridine (0.0073 g, 0.061 mmol), followed by TEA (0.014 mL, 0.102 mmol). The reaction mixture was stirred at rt for 16 h and then the volatiles were evaporated under reduced pressure. The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 40-80% B over 12 minutes, then a 5-minute hold at 100% B; Flow: 20 mL/min. Fractions containing the desired product (0.008 g, 27.7% yield) were combined and dried via centrifugal evaporation. HPLC Ret. Time 2.40 min., 3.81 min (Methods B and C respectively). MS(ES): m/z=661.43 [M+H]$^+$. $^1$H NMR (500 MHz, DMSO-d$_6$) δ ppm 11.90 (br. s, 1H), 8.92 (s, 1H), 8.61-8.43 (m, 2H), 8.20 (d, J=6.1 Hz, 2H), 8.09 (d, J=9.5 Hz, 1H), 7.96 (d, J=5.2 Hz, 1H), 7.80 (s, 1H), 7.41-7.27 (m, 5H), 7.15 (d, The compound described in Table 21 was synthesized analogous to compound 126 by reacting compound 119 with the corresponding carboxylic acid.

TABLE 21

| Compound No. | Structure | Name | [M + H]$^+$ | Ret. Time | HPLC Method |
|---|---|---|---|---|---|
| 127 | 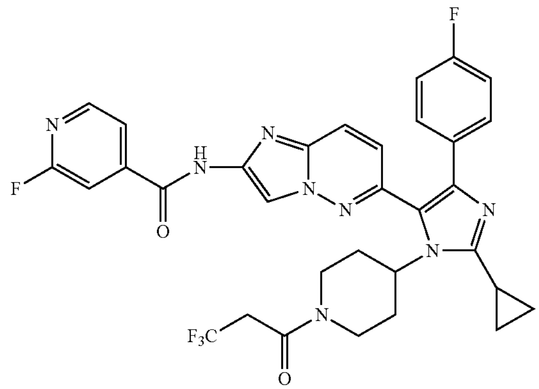 [SMILES: O=C(Nc1cn2nc(-c3c(-c4ccc(F)cc4)nc(C4CC4)n3C3CCN(C(=O)CC(F)(F)F)CC3)ccc2n1)c1ccnc(F)c1] | N-(6-(2-cyclopropyl-4-(4-fluorophenyl)-1-(1-(3,3,3-trifluoropropanoyl)piperidin-4-yl)-1H-imidazol-5-yl)imidazo[1,2-b]pyridazin-2-yl)-2-fluoroisonicotinamide | 651.50 | 2.56, 3.90 | B, C |

J=9.2 Hz, 1H), 7.07 (t, J=9.0 Hz, 2H), 4.19 (d, J=13.1 Hz, 2H), 2.97-2.84 (m, 2H), 2.30-2.16 (m, 1H), 2.12 (d, J=13.4 Hz, 2H), 2.00 (d, J=9.8 Hz, 2H), 1.92 (s, 2H), 1.15-0.98 (m, 5H).

Compound 126

N-(6-(2-cyclopropyl-4-(4-fluorophenyl)-1-(1-(isoxazole-3-carbonyl)piperidin-4-yl)-1H-imidazol-5-yl)imidazo[1,2-b]pyridazin-2-yl)-2-fluoroisonicotinamide Compound 126 was synthesized analogous to compound 5 by reacting compound 119 with isoxazole 3-carboxylic acid. HPLC Ret. Time 2.68 min., 3.90 min. (Methods B and C respectively). MS(ES): m/z=636.30 [M+H]$^+$. $^1$H NMR (500 MHz, DMSO-d$_6$) δ ppm 11.95 (br. s, 1H), 9.07 (d, J=1.5 Hz, 1H), 8.57 (s, 1H), 8.48 (d, J=5.2 Hz, 1H), 8.09 (d, J=9.2 Hz, 1H), 7.98 (d, J=5.2 Hz, 1H), 7.82 (s, 1H), 7.34 (dd, J=8.9, 5.5 Hz, 2H), 7.19-7.03 (m, 3H), 6.81-6.68 (m, 1H), 4.65 (br. s., 1H), 4.58 (d, J=11.6 Hz, 1H), 4.01 (d, J=13.7 Hz, 1H), 3.92 (s, 1H), 3.24 (t, J=12.4 Hz, 1H), 2.98-2.84 (m, 1H), 2.30-2.16 (m, 3H), 2.16-2.09 (m, 1H), 2.05 (d, J=11.3 Hz, 1H), 1.17-0.98 (m, 4H).

Compound 128

N-(6-(2-cyclopropyl-4-(4-fluorophenyl)-1-(1-(isoxazol-3-ylmethyl)piperidin-4-yl)-1H-imidazol-5-yl)imidazo[1,2-b]pyridazin-2-yl)-2-fluoroisonicotinamide Compound 128 was synthesized analogous to compound 2 by reacting compound 119 with isoxazole-3-carbaldehyde. HPLC Ret. Time 2.70 min., 4.04 min. (Methods B and C respectively). MS(ES): m/z=622.40 [M+H]$^+$. $^1$H NMR (500 MHz, DMSO-d$_6$) δ ppm 8.84 (d, J=1.5 Hz, 1H), 8.60 (s, 1H), 8.48 (d, J=5.2 Hz, 1H), 8.11 (d, J=9.2 Hz, 1H), 7.99 (d, J=5.2 Hz, 1H), 7.83 (s, 1H), 7.38-7.27 (m, 2H), 7.17 (d, J=9.2 Hz, 1H), 7.07 (t, J=8.9 Hz, 2H), 6.49 (d, J=1.8 Hz, 1H), 4.21 (t, J=12.4 Hz, 1H), 3.92 (s, 1H), 3.57 (s, 2H), 2.88 (d, J=11.0 Hz, 2H), 2.26-2.14 (m, 3H), 2.14-2.03 (m, 2H), 1.94 (d, J=9.8 Hz, 2H), 1.11-1.00 (m, 4H).

The compounds described in Table 22 were synthesized analogous to compound 128 by reacting compound 119 with the corresponding aldehyde or a ketone.

TABLE 22

| Compound No. | Structure | Name | [M + H]+ | Ret. Time | HPLC Method |
|---|---|---|---|---|---|
| 129 | 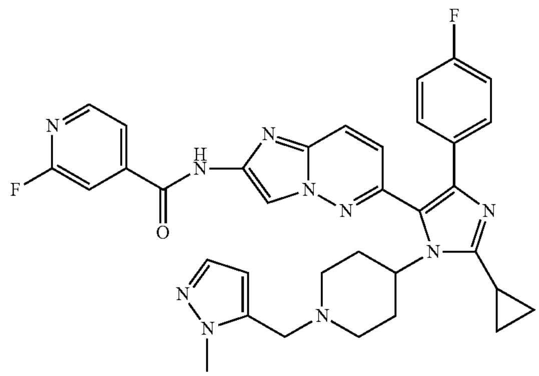 [SMILES: Cn1nccc1CN1CCC(n2c(C3CC3)nc(-c3ccc(F)cc3)c2-c2ccc3nc(NC(=O)c4ccnc(F)c4)cn3n2)CC1] | N-(6-(2-cyclopropyl-4-(4-fluorophenyl)-1-(1-((1-methyl-1H-pyrazol-5-yl)methyl)piperidin-4-yl)-1H-imidazol-5-yl)imidazo[1,2-b]pyridazin-2-yl)-2-fluoroisonicotinamide | 635.40 | 2.71, 4.13 | B, C |
| 130 | 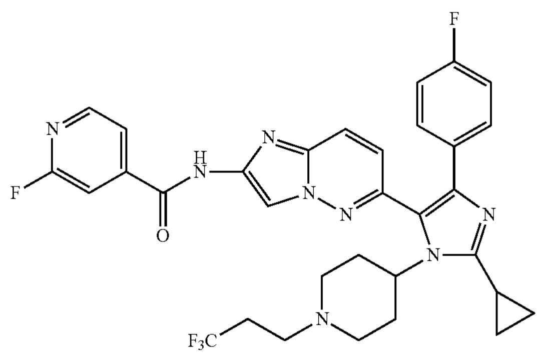 [SMILES: O=C(Nc1cn2nc(-c3c(-c4ccc(F)cc4)nc(C4CC4)n3C3CCN(CCC(F)(F)F)CC3)ccc2n1)c1ccnc(F)c1] | N-(6-(2-cyclopropyl-4-(4-fluorophenyl)-1-(1-(3,3,3-trifluoropropyl)piperidin-4-yl)-1H-imidazol-5-yl)imidazo[1,2-b]pyridazin-2-yl)-2-fluoroisonicotinamide | 637.50 | 3.04, 4.22 | B, C |
| 131 | 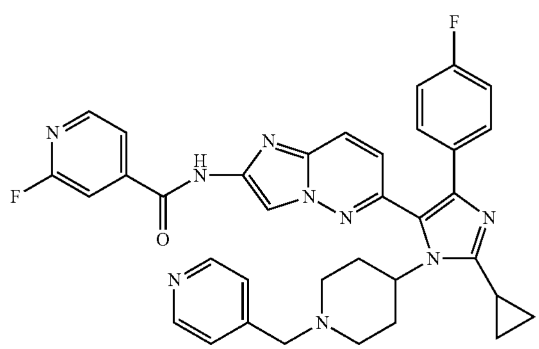 [SMILES: O=C(Nc1cn2nc(-c3c(-c4ccc(F)cc4)nc(C4CC4)n3C3CCN(Cc4ccncc4)CC3)ccc2n1)c1ccnc(F)c1] | N-(6-(2-cyclopropyl-4-(4-fluorophenyl)-1-(1-(pyridin-4-ylmethyl)piperidin-4-yl)-1H-imidazol-5-yl)imidazo[1,2-b]pyridazin-2-yl)-2-fluoroisonicotinamide | 632.37 | 2.69, 4.11 | B, C |
| 132 | 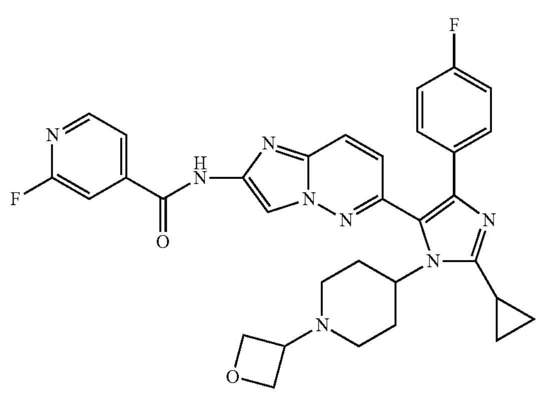 [SMILES: O=C(Nc1cn2nc(-c3c(-c4ccc(F)cc4)nc(C4CC4)n3C3CCN(C4COC4)CC3)ccc2n1)c1ccnc(F)c1] | N-(6-(2-cyclopropyl-4-(4-fluorophenyl)-1-(1-(oxetan-3-yl)piperidin-4-yl)-1H-imidazol-5-yl)imidazo[1,2-b]pyridazin-2-yl)-2-fluoroisonicotinamide | 597.35 | 2.47, 3.90 | B, C |

TABLE 22-continued

| Compound No. | Structure | Name | [M + H]+ | Ret. Time | HPLC Method |
|---|---|---|---|---|---|
| 133 | 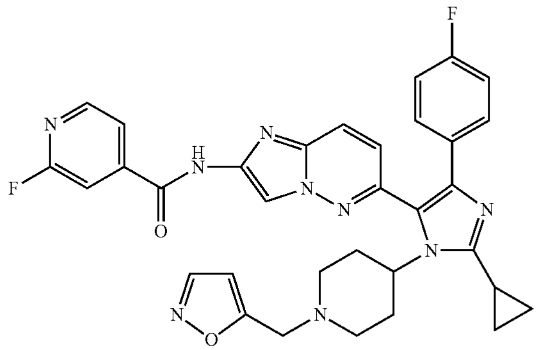 [SMILES: O=C(Nc1cn2nc(-c3c(-c4ccc(F)cc4)nc(C4CC4)n3C3CCN(Cc4ccno4)CC3)ccc2n1)c1ccnc(F)c1] | N-(6-(2-cyclopropyl-4-(4-fluorophenyl)-1-(1-(isoxazol-5-ylmethyl)piperidin-4-yl)-1H-imidazol-5-yl)imidazo[1,2-b]pyridazin-2-yl)-2-fluoroisonicotinamide | 622.39 | 2.67, 3.98 | B, C |
| 134 | 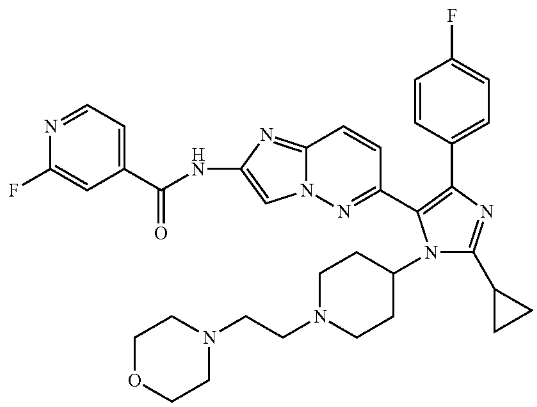 [SMILES: O=C(Nc1cn2nc(-c3c(-c4ccc(F)cc4)nc(C4CC4)n3C3CCN(CCN4CCOCC4)CC3)ccc2n1)c1ccnc(F)c1] | N-(6-(2-cyclopropyl-4-(4-fluorophenyl)-1,1-(2-morpholinoethyl)piperidin-4-yl)-1H-imidazol-5-yl)imidazo[1,2-b]pyridazin-2-yl)-2-fluoroisonicotinamide | 654.50 | 2.37, 3.95 | B, C |

Compound 135

N-(6-(2-cyclopropyl-4-(4-fluorophenyl)-1-(piperidin-4-yl)-1H-imidazol-5-yl)imidazo[1,2-b]pyridazin-2-yl)-3-(pyridin-3-yl)benzamide Compound 135 was synthesized analogous to compound 1 by reacting Intermediate 9 with 3-(pyridin-3-yl)benzoic acid, followed by the deprotection of the Boc group with TFA. HPLC Ret. Time 2.33 min., 3.79 min. (Methods B and C respectively). MS(ES): m/z-=599.40 [M+H]+. $^1$H NMR (500 MHz, DMSO-$d_6$) δ ppm 9.10 (d, J=2.1 Hz, 1H), 8.65 (dd, J=4.7, 1.4 Hz, 1H), 8.61 (s, 1H), 8.56 (s, 1H), 8.28 (d, J=7.9 Hz, 1H), 8.20-8.06 (m, 2H), 8.02 (d, J=7.9 Hz, 1H), 7.71 (t, J=7.8 Hz, 1H), 7.58 (dd, J=7.9, 4.6 Hz, 1H), 7.33 (dd, J=8.7, 5.6 Hz, 2H), 7.18 (d, J=9.2 Hz, 1H), 7.07 (t, J=9.0 Hz, 2H), 4.27 (s, 1H), 3.00 (d, J=11.0 Hz, 2H), 2.46 (t, J=11.6 Hz, 2H), 2.24 (s, 1H), 2.06 (d, J=9.8 Hz, 2H), 1.94-1.83 (m, 4H), 1.14-0.98 (m, 4H).

Compound 136

N-(6-(1-(1-(2-cyanoethyl)piperidin-4-yl)-2-cyclopropyl-4-(4-fluorophenyl)-1H-imidazol-5-yl)imidazo[1,2-b]pyridazin-2-yl)-3-(pyridin-3-yl)benzamide Compound 136 was synthesized analogous to compound 36 by reacting compound 135 with acrylonitrile. HPLC Ret. Time 2.76 min., 4.03 min (Methods B and C respectively). MS(ES): m/z=652.50 [M+H]+. $^1$H NMR (500 MHz, DMSO-$d_6$) δ ppm 11.76 (s, 1H), 9.10 (d, J=2.1 Hz, 1H), 8.65 (dd, J=4.9, 1.5 Hz, 1H), 8.61 (s, 1H), 8.55 (s, 1H), 8.28 (dt, J=7.9, 2.0 Hz, 1H), 8.20-8.06 (m, 2H), 8.02 (d, J=7.6 Hz, 1H), 7.71 (t, J=7.8 Hz, 1H), 7.58 (dd, J=7.9, 4.9 Hz, 1H), 7.39-7.26 (m, 2H), 7.19 (d, J=9.5 Hz, 1H), 7.08 (t, J=8.9 Hz, 2H), 4.20 (t, J=12.1 Hz, 1H), 3.92 (s, 2H), 2.96 (d, J=11.3 Hz, 2H), 2.70-2.53 (m, 5H), 2.27-2.13 (m, 4H), 2.13-2.01 (m, 2H), 1.96 (d, J=9.8 Hz, 2H), 1.89 (s, 1H), 1.11-1.00 (m, 5H).

Compound 137

N-(6-(1-(1-(2-aminoacetyl)piperidin-4-yl)-2-cyclopropyl-4-(4-fluorophenyl)-1H-imidazol-5-yl)imidazo[1,2-b]pyridazin-2-yl)-3-(pyridin-3-yl)benzamide

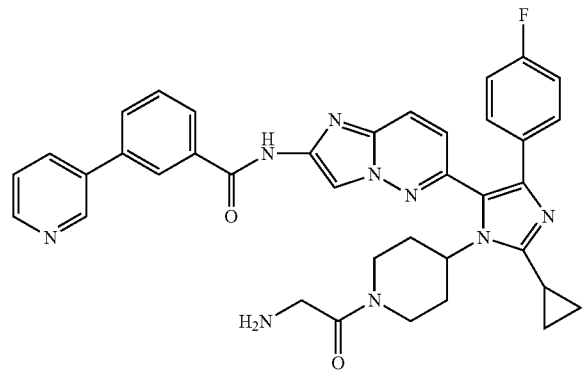 [SMILES: NCC(=O)N1CCC(n2c(C3CC3)nc(-c3ccc(F)cc3)c2-c2ccc3nc(NC(=O)c4cccc(-c5cccnc5)c4)cn3n2)CC1]

Compound 137 was synthesized analogous to compound 5 by reacting compound 135 with 2-((tert-butoxycarbonyl)amino)acetic acid, followed by the deprotection of the Boc group with TFA. HPLC Ret. Time 2.33 min., 3.82 min. (Methods B and C respectively). MS(ES): m/z=656.50 [M+H]$^+$. $^1$H NMR (500 MHz, DMSO-d$_6$) δ ppm 9.10 (d, J=2.1 Hz, 1H), 8.65 (dd, J=4.9, 1.5 Hz, 1H), 8.60 (s, 1H), 8.56 (s, 1H), 8.35-8.23 (m, 1H), 8.17-7.98 (m, 3H), 7.71 (t, J=7.8 Hz, 1H), 7.58 (dd, J=7.8, 4.7 Hz, 1H), 7.35 (dd, J=8.9, 5.8 Hz, 2H), 7.17-6.99 (m, 3H), 4.60-4.39 (m, 2H), 3.92 (s, 1H), 3.84 (d, J=11.3 Hz, 2H), 3.03 (t, J=12.8 Hz, 2H), 2.26-2.12 (m, 2H), 2.00 (br. s., 3H), 1.91 (s, 4H), 1.14-0.96 (m, 5H).

Compound 138

N-(6-(2-cyclopropyl-4-(4-fluorophenyl)-1-(1-(isoxazol-3-ylmethyl)piperidin-4-yl)-1H-imidazol-5-yl)imidazo[1,2-b]pyridazin-2-yl)-3-(pyridin-3-yl)benzamide

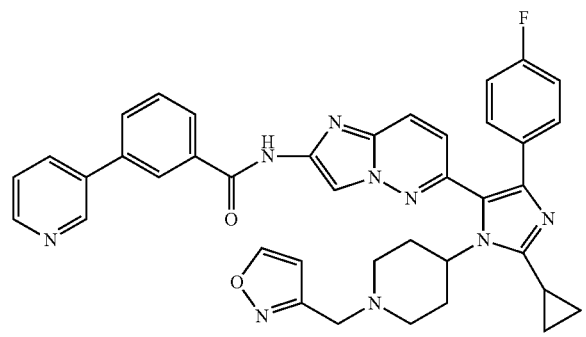 [SMILES: O=C(Nc1cn2nc(-c3c(-c4ccc(F)cc4)nc(C4CC4)n3C3CCN(Cc4ccon4)CC3)ccc2n1)c1cccc(-c2cccnc2)c1]

Compound 138 was synthesized analogous to compound 2 by reacting compound 135 with isoxazole-3-carbaldehyde. HPLC Ret. Time 4.1 min. (Method C). MS(ES): m/z 680.50 [M+H]$^+$. $^1$H NMR (500 MHz, DMSO-d$_6$) δ ppm 11.77 (br. s, 1H), 9.11 (d, J=2.1 Hz, 2H), 8.83 (d, J=1.2 Hz, 2H), 8.75-8.59 (m, 3H), 8.56 (s, 2H), 8.28 (dt, J=7.9, 1.8 Hz, 2H), 8.21-8.06 (m, 3H), 8.02 (d, J=7.9 Hz, 2H), 7.71 (t, J=7.8 Hz, 2H), 7.58 (dd, J=8.1, 4.7 Hz, 2H), 7.39-7.25 (m, 3H), 7.17 (d, J=9.2 Hz, 2H), 7.08 (t, J=8.9 Hz, 3H), 6.49 (d, J=1.5 Hz, 2H), 4.22 (t, J=11.7 Hz, 1H), 2.97-2.79 (m, 3H), 2.31-2.14 (m, 5H), 2.14-2.02 (m, 3H), 1.95 (d, J=10.7 Hz, 3H), 1.85 (s, 4H), 1.12-1.00 (m, 6H).

Compound 139

2-fluoro-N-(6-(4-(4-fluorophenyl)-2-methyl-1-(piperidin-4-yl)-1H-imidazol-5-yl)imidazo[1,2-b]pyridazin-2-yl)isonicotinamide

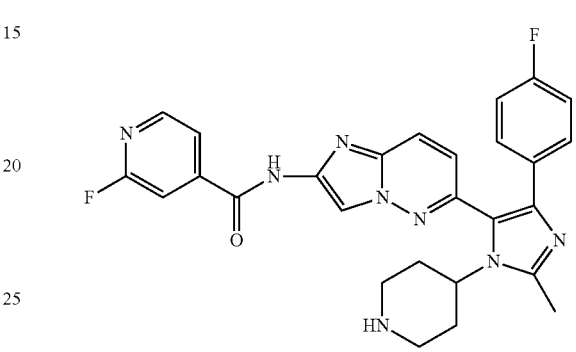

Compound 139 was synthesized analogous to compound 1 by reacting Intermediate 11 with 2-fluoroisonicotinic acid, followed by the deprotection of the Boc group with TFA. HPLC Ret. Time 2.75 min. (Method A). MS(ES): m/z 515.22.

Compound 140

2-fluoro-N-(6-(4-(4-fluorophenyl)-1-(1-(3-fluoropropyl)piperidin-4-yl)-2-methyl-1H-imidazol-5-yl)imidazo[1,2-b]pyridazin-2-yl)isonicotinamide

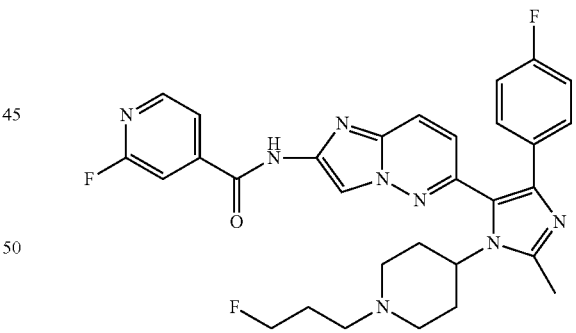

Compound 140 was synthesized analogous to compound 33 by reacting compound 139 with 1-fluoro-3-iodopropane. HPLC Ret. Time 2.15 min., 3.91 min. (Methods B and C respectively). MS(ES): 575.18 [M+H]$^+$. $^1$H NMR (500 MHz, DMSO-d$_6$) δ ppm 11.96 (br. s, 1H), 8.59 (s, 1H), 8.49 (d, J=5.2 Hz, 1H), 8.13 (d, J=9.5 Hz, 1H), 7.98 (d, J=5.2 Hz, 1H), 7.82 (s, 1H), 7.42-7.31 (m, 3H), 7.19 (d, J=9.2 Hz, 1H), 7.14-7.01 (m, 3H), 4.45 (t, J=6.0 Hz, 1H), 4.36 (t, J=6.0 Hz, 1H), 4.03 (td, J=11.6, 3.7 Hz, 1H), 2.89 (d, J=9.5 Hz, 2H), 2.60-2.53 (m, 4H), 2.32 (t, J=7.2 Hz, 3H), 2.05-1.82 (m, 8H), 1.82-1.64 (m, 3H).

The compound described in Table 23 was synthesized analogous to compound 140 by reacting compound 139 with the corresponding alkyl halide.

TABLE 23

| Compound No. | Structure | Name | [M + H]+ | Ret. Time | HPLC Method |
|---|---|---|---|---|---|
| 141 | 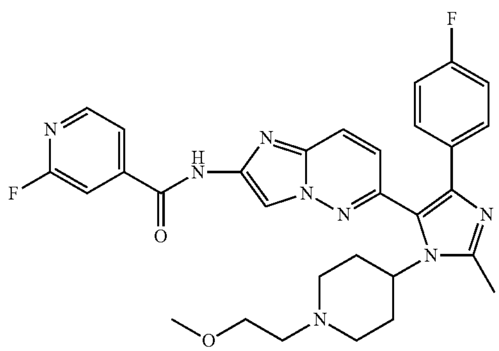 [SMILES: COCCN1CCC(n2c(C)nc(-c3ccc(F)cc3)c2-c2ccc3nc(NC(=O)c4ccnc(F)c4)cn3n2)CC1] | 2-fluoro-N-(6-(4-(4-fluorophenyl)-1-(1-(2-methoxyethyl)piperidin-4-yl)-2-methyl-1H-imidazol-5-yl)imidazo[1,2-b]pyridazin-2-yl)isonicotinamide | 573.22 | 2.26, 3.79 | B, C |

Compound 142

(R)-2-fluoro-N-(6-(4-(4-fluorophenyl)-2-methyl-1-(1-(3,3,3-trifluoro-2-hydroxypropyl)piperidin-4-yl)-1H-imidazol-5-yl)imidazo[1,2-b]pyridazin-2-yl)isonicotinamide

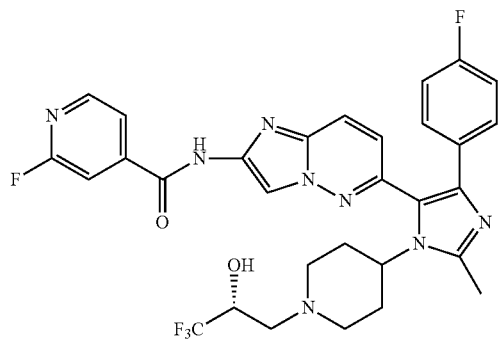 [SMILES: Cc1nc(-c2ccc(F)cc2)c(-c2ccc3nc(NC(=O)c4ccnc(F)c4)cn3n2)n1C1CCN(C[C@@H](O)C(F)(F)F)CC1]

Compound 142 was synthesized analogous to compound 7 by reacting compound 139 with acrylonitrile. HPLC Ret. Time 2.53 min., 3.96 min. (Methods B and C respectively). MS(ES): m/z=627.18 [M+H]+. $^1$H NMR (500 MHz, DMSO-$d_6$) δ ppm 8.59 (s, 1H), 8.49 (d, J=5.2 Hz, 1H), 8.13 (d, J=9.2 Hz, 1H), 7.98 (d, J=5.2 Hz, 1H), 7.82 (s, 1H), 7.41-7.29 (m, 2H), 7.21 (d, J=9.2 Hz, 1H), 7.08 (t, J=8.9 Hz, 2H), 6.06 (d, J=5.2 Hz, 1H), 4.14-3.96 (m, 2H), 2.96 (br. s., 2H), 2.56 (s, 3H), 2.48-2.36 (m, 2H), 2.20-2.04 (m, 2H), 2.04-1.94 (m, 2H), 1.94-1.81 (m, 2H).

The compound described in Table 24 was synthesized analogous to compound 142 by reacting compound 139 with the corresponding epoxide.

TABLE 24

| Compound No. | Structure | Name | [M + H]+ | Ret. Time | HPLC Method |
|---|---|---|---|---|---|
| 143 | 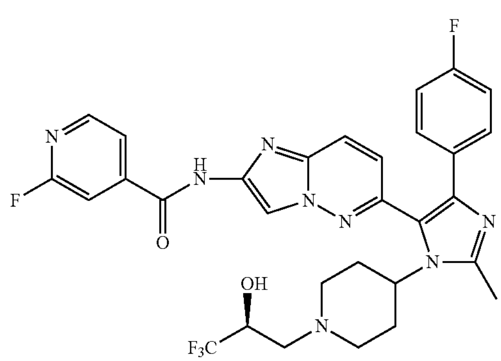 [SMILES: Cc1nc(-c2ccc(F)cc2)c(-c2ccc3nc(NC(=O)c4ccnc(F)c4)cn3n2)n1C1CCN(C[C@H](O)C(F)(F)F)CC1] | (S)-2-fluoro-N-(6-(4-(4-fluorophenyl)-2-methyl-1-(1-(3,3,3-trifluoro-2-hydroxypropyl)piperidin-4-yl)-1H-imidazol-5-yl)imidazo[1,2-b]pyridazin-2-yl)isonicotinamide | 627.26 | 2.56, 3.85 | B, C |

Compound 144

N-(6-(1-(1-(2-cyanoethyl)piperidin-4-yl)-4-(4-fluorophenyl)-2-methyl-1H-imidazol-5-yl)imidazo[1,2-b]pyridazin-2-yl)-2-fluoroisonicotinamide

Compound 145

2-fluoro-N-(6-(4-(4-fluorophenyl)-2-methyl-1-(1-(3,3,3-trifluoropropyl)piperidin-4-yl)-1H-imidazol-5-yl)imidazo[1,2-b]pyridazin-2-yl)isonicotinamide

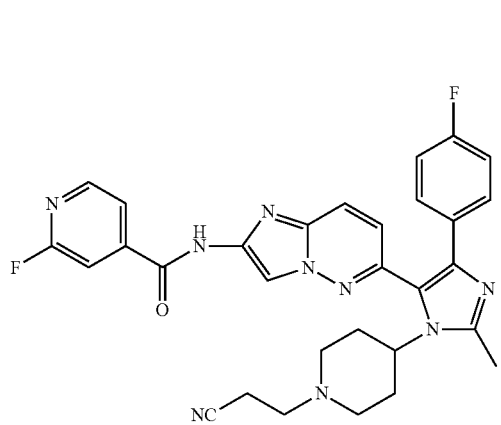 [SMILES: Cc1nc(-c2ccc(F)cc2)c(-c2ccc3nc(NC(=O)c4ccnc(F)c4)cn3n2)n1C1CCN(CCC#N)CC1]

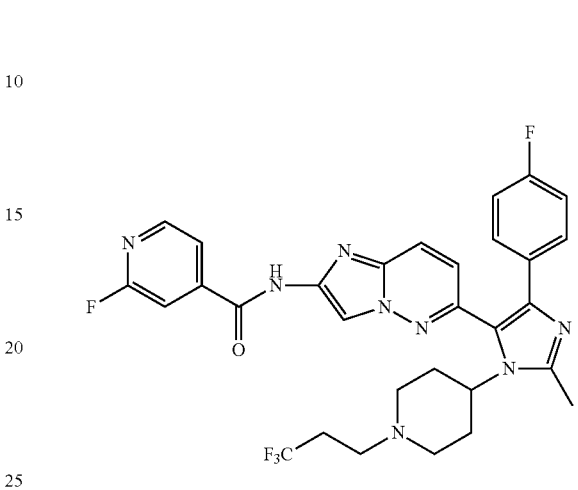

Compound 144 was synthesized analogous to compound 36 by reacting compound 139 with acrylonitrile. HPLC Ret. Time 2.43 min., 3.66 min. (Methods B and C respectively). MS(ES): m/z=568.28 [M+H]$^+$. $^1$H NMR (500 MHz, DMSO-d$_6$) δ ppm 11.97 (s, 1H), 8.59 (s, 1H), 8.49 (d, J=5.2 Hz, 1H), 8.13 (d, J=9.2 Hz, 1H), 7.97 (d, J=5.2 Hz, 1H), 7.82 (s, 1H), 7.41-7.29 (m, 2H), 7.21 (d, J=9.2 Hz, 1H), 7.08 (t, J=9.0 Hz, 2H), 3.00-2.85 (m, 2H), 2.63-2.53 (m, 6H), 2.06 (d, J=11.3 Hz, 2H), 1.98 (d, J=12.2 Hz, 2H), 1.94-1.80 (m, 2H).

Compound 145 was synthesized analogous to compound 2 by reacting compound 139 with 3,3,3-trifluoropropanal. HPLC Ret. Time 2.72 min., 4.12 min. (Methods B and C respectively). MS(ES): m/z=611.20 [M+H]$^+$. $^1$H NMR (500 MHz, DMSO-d$_6$) δ ppm 11.98 (br. s, 1H), 8.59 (s, 1H), 8.49 (d, J=5.2 Hz, 1H), 8.13 (d, J=9.2 Hz, 1H), 7.97 (d, J=5.2 Hz, 1H), 7.82 (s, 1H), 7.41-7.27 (m, 2H), 7.21 (d, J=9.2 Hz, 1H), 7.15-7.00 (m, 2H), 4.05 (d, J=4.0 Hz, 1H), 2.91 (d, J=9.8 Hz, 2H), 2.55 (s, 3H), 2.43-2.30 (m, 2H), 2.05-1.82 (m, 7H).

The compound described in Table 25 was synthesized analogous to compound 145 by reacting compound 139 with the corresponding aldehyde.

TABLE 25

| Compound No. | Structure | Name | [M + H]$^+$ | HPLC Ret. Time | Method |
|---|---|---|---|---|---|
| 146 | 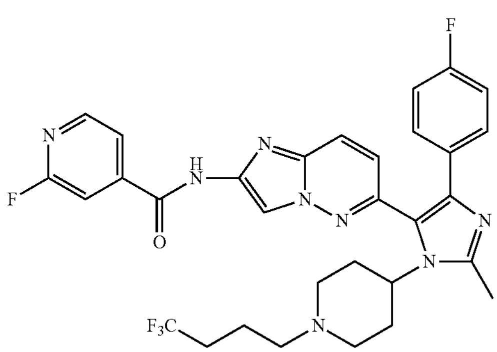 [SMILES: Cc1nc(-c2ccc(F)cc2)c(-c2ccc3nc(NC(=O)c4ccnc(F)c4)cn3n2)n1C1CCN(CCCC(F)(F)F)CC1] | 2-fluoro-N-(6-(4-(4-fluorophenyl)-2-methyl-1-(1-(4,4,4-trifluorobutyl)piperidin-4-yl)-1H-imidazol-5-yl)imidazo[1,2-b]pyridazin-2-yl)isonicotinamide | 625.23 | 2.59, 4.17 | B, C |

Compound 147

2-fluoro-N-(6-(4-(4-fluorophenyl)-1-(1-(isothiazole-3-carbonyl)piperidin-4-yl)-2-methyl-1H-imidazol-5-yl)imidazo[1,2-b]pyridazin-2-yl)isonicotinamide

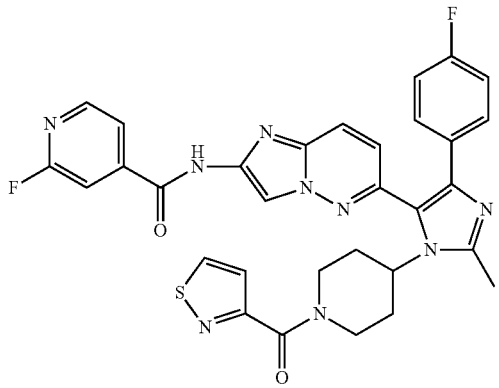 [SMILES: Cc1nc(-c2ccc(F)cc2)c(-c2ccc3nc(NC(=O)c4ccnc(F)c4)cn3n2)n1C1CCN(C(=O)c2ccsn2)CC1]

Compound 147 was synthesized analogous to compound 5 by reacting compound 139 with isothiazole-3-carboxylic acid. HPLC Ret. Time 2.45 min., 3.76 min. (Methods B and C respectively). MS(ES): m/z=626.13 [M+H]$^+$. $^1$H NMR (500 MHz, DMSO-d$_6$) δ ppm 9.18-9.05 (m, 1H), 8.56 (s, 1H), 8.49 (d, J=5.2 Hz, 1H), 8.10 (d, J=9.2 Hz, 1H), 7.98 (d, J=5.2 Hz, 1H), 7.82 (s, 1H), 7.44-7.30 (m, 3H), 7.19-7.02 (m, 3H), 4.61-4.39 (m, 2H), 4.05 (d, J=14.6 Hz, 1H), 3.26-3.11 (m, 1H), 2.94-2.79 (m, 1H), 2.57 (s, 3H), 2.10-1.90 (m, 4H), 1.29-1.17 (m, 2H).

Compound 148

N-(6-(1-(azetidin-3-yl)-4-(4-fluorophenyl)-1H-imidazol-5-yl)imidazo[1,2-b]pyridazin-2-yl)-2-fluoroisonicotinamide

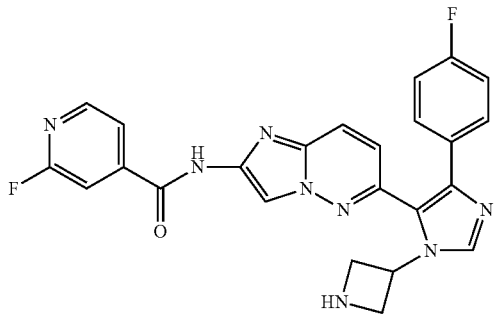 [SMILES: O=C(Nc1cn2nc(-c3c(-c4ccc(F)cc4)ncn3C3CNC3)ccc2n1)c1ccnc(F)c1]

Compound 148 was synthesized analogous to compound 1 by reacting Intermediate 11 with 2-fluoroisonicotinic acid, followed by the deprotection of the Boc group with TFA. HPLC Ret. Time 3.02 min. (Method A). MS(ES): m/z 473.21 [M+H]$^+$. $^1$H NMR (400 MHz, DMSO-d$_6$) δ ppm 12.00 (s, 1H), 8.76 (s, 1H), 8.68 (s, 1H), 8.49 (d, J=5.0 Hz, 1H), 8.10 (d, J=9.5 Hz, 1H), 7.99 (d, J=5.0 Hz, 1H), 7.83 (s, 1H), 7.55 (dd, J=8.5, 5.5 Hz, 2H), 7.24 (t, J=8.9 Hz, 2H), 7.04 (d, J=9.3 Hz, 1H), 5.42 (d, J=7.5 Hz, 1H), 4.56 (d, J=6.5 Hz, 2H), 4.41 (d, J=7.5 Hz, 2H).

Compound 149

2-fluoro-N-(6-(4-(4-fluorophenyl)-1-(1-methylazetidin-3-yl)-1H-imidazol-5-yl)imidazo[1,2-b]pyridazin-2-yl)isonicotinamide

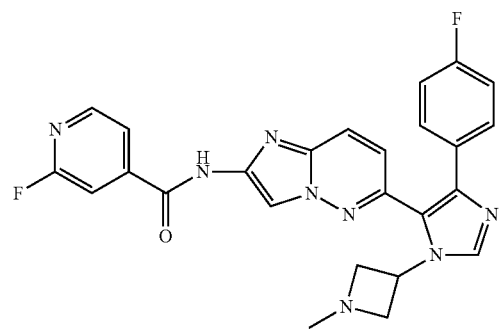 [SMILES: CN1CC(n2cnc(-c3ccc(F)cc3)c2-c2ccc3nc(NC(=O)c4ccnc(F)c4)cn3n2)C1]

Compound 149 was synthesized analogous to compound 2 by reacting compound 148 with formaldehyde (37% aq. solution). HPLC Ret. Time 2.05 min., 3.65 min (Methods B and C respectively). MS(ES): m/z=487.40 [M+H]$^+$. $^1$H NMR (500 MHz, DMSO-d$_6$) δ ppm 11.95 (br. s, 1H), 8.60 (s, 1H), 8.48 (d, J=5.2 Hz, 1H), 8.28 (s, 1H), 8.07 (d, J=9.2 Hz, 1H), 7.98 (d, J=5.2 Hz, 1H), 7.82 (s, 1H), 7.56-7.45 (m, 2H), 7.16 (t, J=8.9 Hz, 2H), 7.08 (d, J=9.2 Hz, 1H), 4.85 (quin, J=6.6 Hz, 1H), 3.66-3.51 (m, 2H), 2.29 (s, 3H).

The compound described in Table 26 was synthesized analogous to compound 149 by reacting compound 148 with the corresponding aldehyde.

TABLE 26

| Compound No. | Structure | Name | [M + H]$^+$ | Ret. Time | HPLC Method |
|---|---|---|---|---|---|
| 150 | 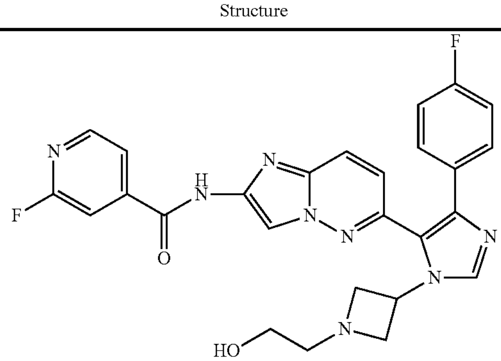 | 2-fluoro-N-(6-(4-(4-fluorophenyl)-1-(1-(2-hydroxyethyl)azetidin-3-yl)-1H-imidazol-5-yl)imidazo[1,2-b]pyridazin-2-yl)isonicotinamide | 517.4 | 2.16, 3.63 | B, C |

Compound 151

N-(6-(1-(azetidin-3-yl)-4-(4-fluorophenyl)-1H-imidazol-5-yl)imidazo[1,2-b]pyridazin-2-yl)-4-methyl-2-(pyridin-4-yl)thiazole-5-carboxamide

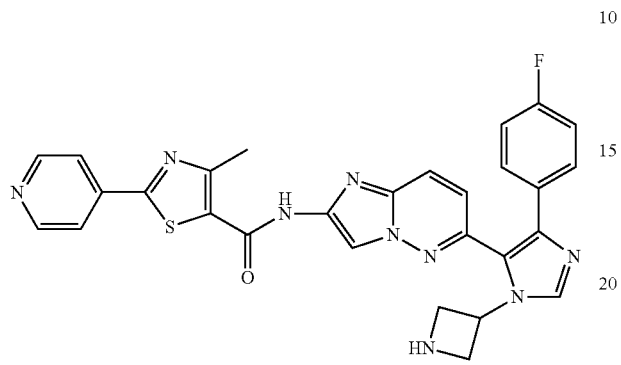

Compound 151 was synthesized analogous to compound 1 by reacting Intermediate 11 with 2-(pyridin-4-yl)thiazole-5-carboxylic acid, followed by the deprotection of the Boc group with TFA. HPLC Ret. Time 3.74 min. (Method F). MS(ES): m/z 552.30 [M+H]$^+$.

Compound 152

N-(6-(4-(4-fluorophenyl)-1-(1-(2-hydroxyethyl)azetidin-3-yl)-1H-imidazol-5-yl)imidazo[1,2-b]pyridazin-2-yl)-4-methyl-2-(pyridin-4-yl)thiazole-5-carboxamide

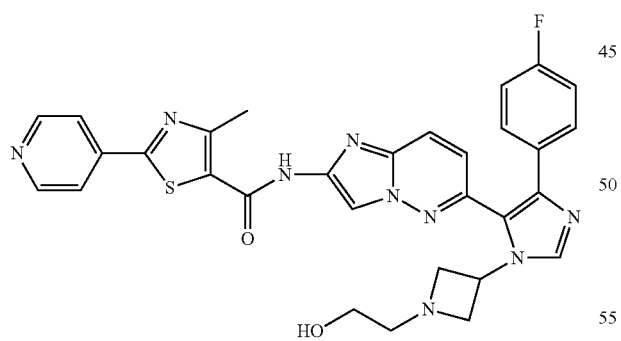

Compound 152 was synthesized analogous to compound 2 by reacting compound 151 with 2-hydroxyacetaldehyde. HPLC Ret. Time 2.12 min., 3.84 min. (Methods B and C respectively). MS(ES): m/z=596.50 [M+H]$^+$. $^1$H NMR (500 MHz, DMSO-d$_6$) δ ppm 8.83-8.73 (m, 2H), 8.54 (s, 1H), 8.28 (s, 1H), 8.04 (d, J=9.2 Hz, 1H), 8.00-7.89 (m, 2H), 7.59-7.46 (m, 2H), 7.16 (t, J=8.9 Hz, 2H), 7.07 (d, J=9.5 Hz, 1H), 4.88 (t, J=6.6 Hz, 1H), 4.44 (br. s., 1H), 3.63 (t, J=7.6 Hz, 2H), 2.91 (s, 1H), 2.78-2.72 (m, 4H), 1.89 (s, 1H).

Compound 153

N-(6-(1-(azetidin-3-yl)-4-(4-fluorophenyl)-1H-imidazol-5-yl)imidazo[1,2-b]pyridazin-2-yl)-4-methyl-2-(pyridin-3-yl)thiazole-5-carboxamide

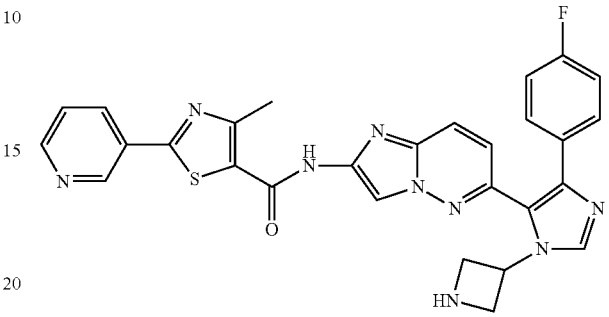

Compound 153 was synthesized analogous to compound 1 by reacting Intermediate 11 with 2-(pyridin-3-yl)thiazole-5-carboxylic acid, followed by the deprotection of the Boc group with TFA. HPLC Ret. Time 2.0 min., 3.66 min (Methods B and C respectively). MS(ES): m/z=552.35 [M+H]$^+$.

Compound 154

N-(6-(4-(4-fluorophenyl)-1-(1-methylazetidin-3-yl)-1H-imidazol-5-yl)imidazo[1,2-b]pyridazin-2-yl)-4-methyl-2-(pyridin-3-yl)thiazole-5-carboxamide

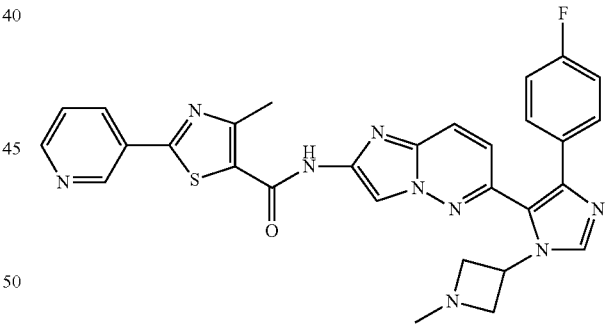

Compound 154 was synthesized analogous to compound 2 by reacting compound 153 with formaldehyde (37% aq. solution). HPLC Ret. Time 2.34 min., 3.94 min. (Methods B and C respectively). MS(ES): m/z=566.40 [M+H]$^+$. $^1$H NMR (500 MHz, DMSO-d$_6$) δ ppm 9.19 (d, J=2.1 Hz, 1H), 8.75 (dd, J=4.7, 1.4 Hz, 1H), 8.54 (s, 1H), 8.37 (d, J=7.9 Hz, 1H), 8.31 (s, 1H), 8.05 (d, J=9.2 Hz, 1H), 7.61 (dd, J=7.9, 4.9 Hz, 1H), 7.51 (dd, J=8.7, 5.6 Hz, 2H), 7.16 (t, J=8.9 Hz, 2H), 7.07 (d, J=9.2 Hz, 1H), 5.09 (s, 1H), 3.83 (t, J=7.8 Hz, 2H), 3.70 (t, J=8.1 Hz, 2H), 2.74 (s, 3H), 1.89 (s, 2H).

The compound described in Table 27 was synthesized analogous to compound 154 by reacting compound 153 with the corresponding aldehyde.

TABLE 27

| Compound No. | Structure | Name | [M + H]+ | Ret. Time | HPLC Method |
|---|---|---|---|---|---|
| 155 | 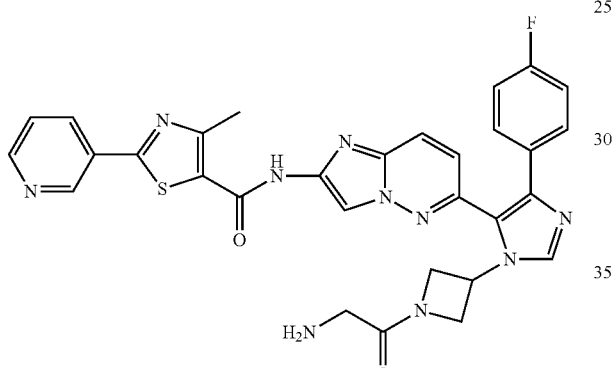 | N-(6-(4-(4-fluorophenyl)-1-(1-(2-hydroxyethyl)azetidin-3-yl)-1H-imidazol-5-yl)imidazo[1,2-b]pyridazin-2-yl)-4-methyl-2-(pyridin-3-yl)thiazole-5-carboxamide | 596.40 | 2.35, 3.86 | B, C |

Compound 156

N-(6-(1-(1-(2-aminoacetyl)azetidin-3-yl)-4-(4-fluorophenyl)-1H-imidazol-5-yl)imidazo[1,2-b]pyridazin-2-yl)-4-methyl-2-(pyridin-3-yl)thiazole-5-carboxamide

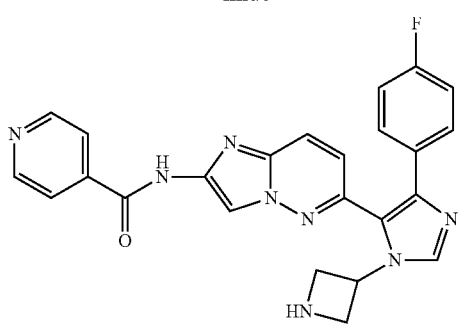

Compound 156 was synthesized analogous to compound 5 by reacting compound 153 with 2-((tert-butoxycarbonyl)amino)acetic acid, followed by Boc deprotection with TFA. HPLC Ret. Time 1.99 min., 3.63 min. (Methods B and C respectively). MS(ES): m/=609.37 [M+H]+. $^1$H NMR (500 MHz, DMSO-d$_6$) δ ppm 9.19 (d, J=2.4 Hz, 1H), 8.75 (dd, J=4.9, 1.5 Hz, 1H), 8.59 (s, 1H), 8.43 (s, 1H), 8.37 (dt, J=8.1, 1.9 Hz, 1H), 8.05 (d, J=9.2 Hz, 1H), 7.61 (dd, J=7.9, 4.9 Hz, 1H), 7.56-7.46 (m, 2H), 7.18 (t, J=8.9 Hz, 2H), 7.06 (d, J=9.2 Hz, 1H), 5.27 (s, 1H), 4.58-4.51 (m, 1H), 4.48 (d, J=5.8 Hz, 1H), 4.35-4.23 (m, 2H), 3.19-3.12 (m, 3H), 2.74 (s, 4H), 1.91 (s, 1H).

Compound 157

N-(6-(1-(azetidin-3-yl)-4-(4-fluorophenyl)-1H-imidazol-5-yl)imidazo[1,2-b]pyridazin-2-yl)isonicotinamide Compound 157 was synthesized analogous to compound 1 by reacting Intermediate 11 with isonicotinic acid, followed by the deprotection of the Boc group with TFA. HPLC Ret. Time 2.51 min. (Method A). MS(ES): m/z=455.17 [M+H]+. $^1$H NMR (400 MHz, DMSO-d$_6$) δ ppm 12.01 (s, 1H), 8.95-8.86 (m, 4H), 8.83 (s, 1H), 8.70 (s, 1H), 8.19-8.05 (m, 5H), 7.59-7.49 (m, 7H), 7.32-7.20 (m, 6H), 7.04 (d, J=9.5 Hz, 2H), 5.44 (s, 1H), 4.57 (d, J=7.0 Hz, 3H), 4.49-4.31 (m, 2H).

Compound 158

N-(6-(4-(4-fluorophenyl)-1-(1-methylazetidin-3-yl)-1H-imidazol-5-yl)imidazo[1,2-b]pyridazin-2-yl)isonicotinamide

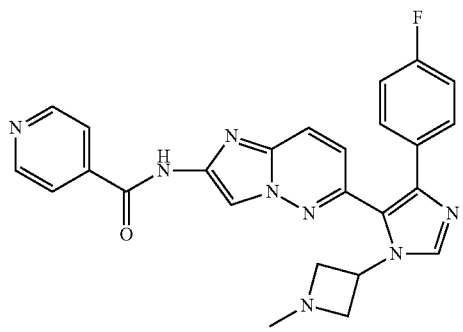 [SMILES: CN1CC(n2cnc(-c3ccc(F)cc3)c2-c2ccc3nc(NC(=O)c4ccncc4)cn3n2)C1]

Compound 158 was synthesized analogous to compound 2 by reacting compound 157 with formaldehyde (37% aq. solution). HPLC Ret. Time 1.78 min., 3.48 min. (Methods B and C respectively). MS(ES): m/z=469.37 [M+H]+. $^1$H NMR (500 MHz, DMSO-d$_6$) δ ppm 8.86-8.78 (m, 2H), 8.60 (s, 1H), 8.29 (s, 1H), 8.11-7.98 (m, 3H), 7.56-7.45 (m, 2H), 7.16 (t, J=8.9 Hz, 2H), 7.08 (d, J=9.2 Hz, 1H), 4.85 (t, J=6.7 Hz, 1H), 3.60 (t, J=7.5 Hz, 2H), 3.18 (s, 3H), 2.29 (s, 3H), 1.89 (s, 2H).

The compound described in Table 28 was synthesized analogous to compound 158 by reacting compound 157 with the corresponding aldehyde.

TABLE 28

| Compound No. | Structure | Name | [M + H]+ | Ret. Time | HPLC Method |
|---|---|---|---|---|---|
| 159 | 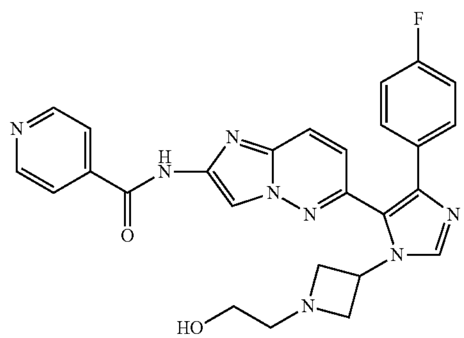 [SMILES: O=C(Nc1cn2nc(-c3c(-c4ccc(F)cc4)ncn3C3CN(CCO)C3)ccc2n1)c1ccncc1] | N-(6-(4-(4-fluorophenyl)-1-(1-(2-hydroxyethyl)azetidin-3-yl)-1H-imidazol-5-yl)imidazo[1,2-b]pyridazin-2-yl)isonicotinamide | 499.35 | 1.77, 3.40 | B, C |

Compound 160

N-(6-(4-(4-fluorophenyl)-1-(2-morpholinoethyl)-1H-imidazol-5-yl)imidazo[1,2-b]pyridazin-2-yl)isonicotinamide

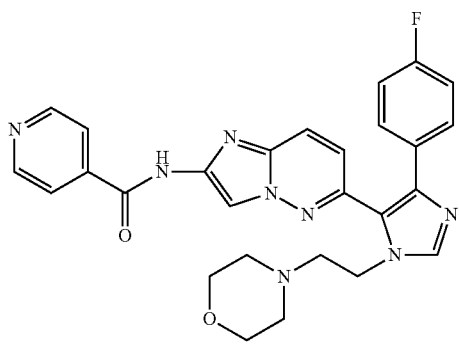 [SMILES: O=C(Nc1cn2nc(-c3c(-c4ccc(F)cc4)ncn3CCN3CCOCC3)ccc2n1)c1ccncc1]

To a solution of Intermediate 12 (0.03 g, 0.074 mmol), isonicotinic acid (0.018 g, 0.147 mmol) and HATU (0.056 g, 0.147 mmol) in DMF (0.491 mL) was added Hunig's base (0.051 mL, 0.295 mmol) and the reaction was stirred at rt for 16 h. It was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 40-100% B over 20 minutes, then a 5-minute hold at 100% B; Flow: 20 mL/min. Fractions containing the desired product (0.013 g, 31.7% yield) were combined and dried via centrifugal evaporation. HPLC Ret. Time 2.02 min., 3.50 min (Methods B and C respectively). MS(ES): m/z 513.30 [M+H]+. 1H NMR (500 MHz, DMSO-$d_6$) δ ppm 11.85 (br. s, 1H), 8.89-8.76 (m, 2H), 8.60 (s, 1H), 8.08 (d, J=9.5 Hz, 1H), 8.05-7.98 (m, 4H), 7.50 (dd, J=8.9, 5.5 Hz, 3H), 7.22-7.03 (m, 4H), 4.27 (t, J=6.1 Hz, 2H), 3.92 (s, 1H), 3.43 (t, J=4.3 Hz, 5H), 2.57 (t, J=6.3 Hz, 2H), 2.31 (br. s, 4H).

The compounds described in Table 29 were synthesized analogous to compound 160 by reacting Intermediate 12 with the corresponding carboxylic acids.

TABLE 29

| Compound No. | Structure | Name | [M + H]+ | Ret. Time | HPLC Method |
|---|---|---|---|---|---|
| 161 | 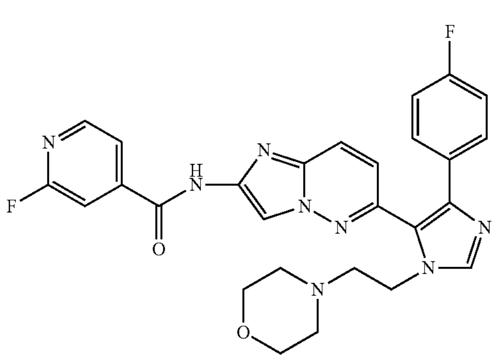 [SMILES: O=C(Nc1cn2nc(-c3c(-c4ccc(F)cc4)ncn3CCN3CCOCC3)ccc2n1)c1ccnc(F)c1] | 2-fluoro-N-(6-(4-(4-fluorophenyl)-1-(2-morpholinoethyl)-1H-imidazol-5-yl)imidazo[1,2-b]pyridazin-2-yl)isonicotinamide | 531.30 | 2.25, 3.69 | B, C |

TABLE 29-continued

| Compound No. | Structure | Name | [M + H]+ | Ret. Time | HPLC Method |
|---|---|---|---|---|---|
| 162 | 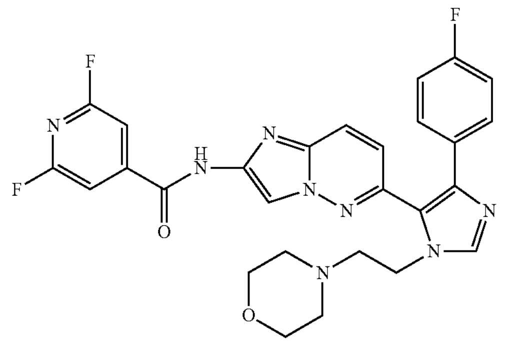 [SMILES: O=C(Nc1cn2nc(-c3c(-c4ccc(F)cc4)ncn3CCN3CCOCC3)ccc2n1)c1cc(F)nc(F)c1] | 2,6-difluoro-N-(6-(4-(4-fluorophenyl)-1-(2-morpholinoethyl)-1H-imidazol-5-yl)imidazo[1,2-b]pyridazin-2-yl)isonicotinamide | 549.30 | 2.50, 3.93 | B, C |
| 163 | 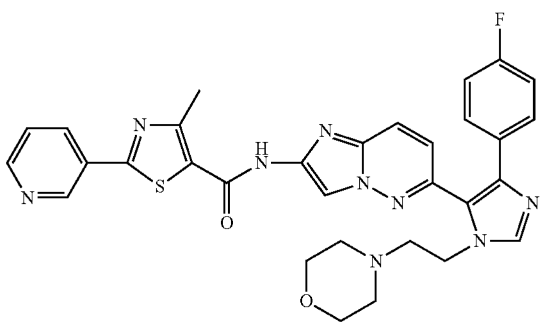 [SMILES: Cc1nc(-c2cccnc2)sc1C(=O)Nc1cn2nc(-c3c(-c4ccc(F)cc4)ncn3CCN3CCOCC3)ccc2n1] | N-(6-(4-(4-fluorophenyl)-1-(2-morpholinoethyl)-1H-imidazol-5-yl)imidazo[1,2-b]pyridazin-2-yl)-4-methyl-2-(pyridin-3-yl)thiazole-5-carboxamide | 610.26 | 2.37, 3.93 | B, C |
| 164 | 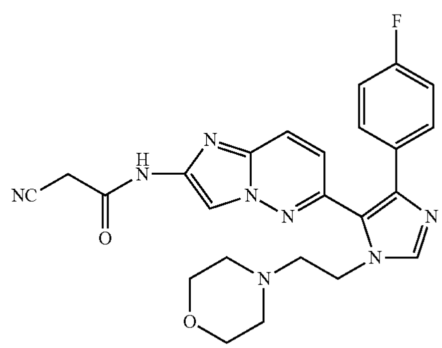 | 2-cyano-N-(6-(4-(4-fluorophenyl)-1-(2-morpholinoethyl)-1H-imidazol-5-yl)imidazo[1,2-b]pyridazin-2-yl)acetamide | 473.29 | 1.88, 3.20 | B, C |
| 165 | 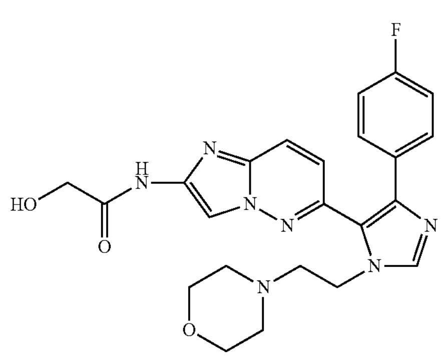 [SMILES: N#CCC(=O)Nc1cn2nc(-c3c(-c4ccc(F)cc4)ncn3CCN3CCOCC3)ccc2n1] | N-(6-(4-(4-fluorophenyl)-1-(2-morpholinoethyl)-1H-imidazol-5-yl)imidazo[1,2-b]pyridazin-2-yl)-2-hydroxyacetamide | 466.27 | 1.72, 3.14 | B, C |

TABLE 29-continued

| Compound No. | Structure | Name | [M + H]+ | Ret. Time | HPLC Method |
|---|---|---|---|---|---|
| 166 | 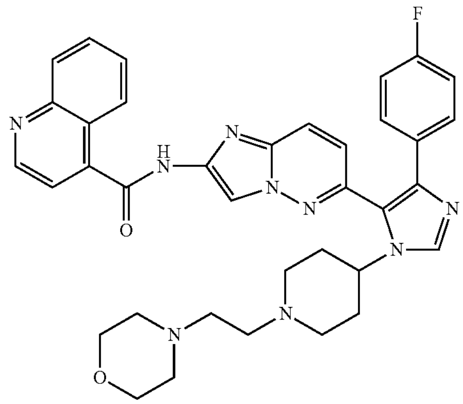 [SMILES: O=C(Nc1cn2nc(-c3c(-c4ccc(F)cc4)ncn3C3CCN(CCN4CCOCC4)CC3)ccc2n1)c1ccnc2ccccc12] | N-(6-(4-(4-fluorophenyl)-1-(2-morpholinoethyl)-1H-imidazol-5-yl)imidazo[1,2-b]pyridazin-2-yl)quinoline-4-carboxamide | 563.27 | 2.25, 3.78 | B, C |
| 167 | 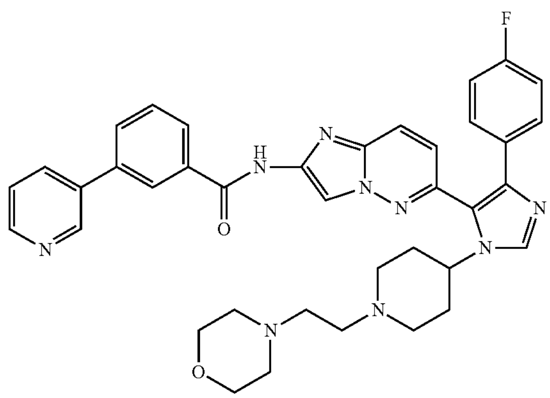 [SMILES: O=C(Nc1cn2nc(-c3c(-c4ccc(F)cc4)ncn3C3CCN(CCN4CCOCC4)CC3)ccc2n1)c1cccc(-c2cccnc2)c1] | N-(6-(4-(4-fluorophenyl)-1-(2-morpholinoethyl)-1H-imidazol-5-yl)imidazo[1,2-b]pyridazin-2-yl)-3-(pyridin-3-yl)benzamide | 589.30 | 2.48, 3.93 | B, C |
| 168 | 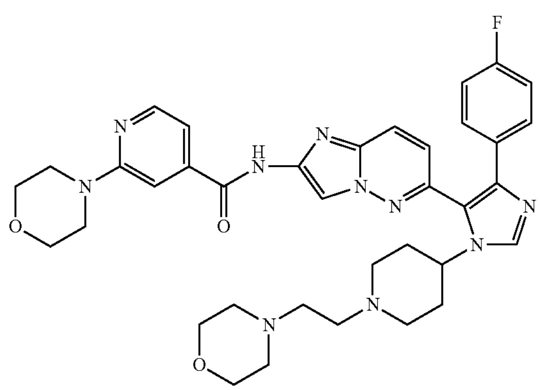 [SMILES: O=C(Nc1cn2nc(-c3c(-c4ccc(F)cc4)ncn3C3CCN(CCN4CCOCC4)CC3)ccc2n1)c1ccnc(N2CCOCC2)c1] | N-(6-(4-(4-fluorophenyl)-1-(2-morpholinoethyl)-1H-imidazol-5-yl)imidazo[1,2-b]pyridazin-2-yl)-2-morpholinoisonicotinamide | 598.40 | 2.31, 3.88 | B, C |

Compound 169

2,6-difluoro-N-(6-(2-(4-fluorophenyl)imidazo[1,2-a]pyridin-3-yl)imidazo[1,2-b]pyridazin-2-yl)isonicotinamide

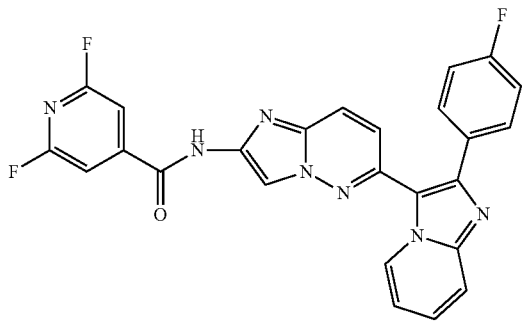 [SMILES: O=C(Nc1cn2nc(-c3c(-c4ccc(F)cc4)nc4ccccn34)ccc2n1)c1cc(F)nc(F)c1]

Compound 169 was synthesized analogous to compound 160 by reacting Intermediate 13 with 2,6-difluoroisonicotinic acid. HPLC Ret. Time 3.43 min. (Method A). MS(ES): m/z=486.04 [M+H]$^+$. $^1$H NMR (400 MHz, DMSO-d$_6$) δ ppm 12.05 (s, 1H), 9.26-9.15 (m, 1H), 8.70 (s, 1H), 8.14 (dd, J=9.3, 0.5 Hz, 1H), 7.92 (d, J=9.0 Hz, 1H), 7.83 (s, 2H), 7.79-7.69 (m, 4H), 7.42-7.26 (m, 3H), 7.13 (d, J=9.5 Hz, 1H).

The compounds described in Table 30 were synthesized analogous to compound 169 by reacting Intermediate 13 with the corresponding carboxylic acids.

TABLE 30

| Compound No. | Structure | Name | [M + H]$^+$ | Ret. Time | HPLC Method |
|---|---|---|---|---|---|
| 170 | 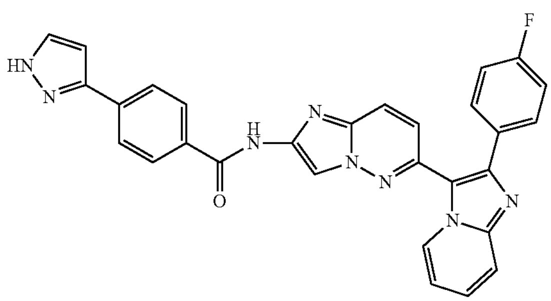 [SMILES: O=C(Nc1cn2nc(-c3c(-c4ccc(F)cc4)nc4ccccn34)ccc2n1)c1ccc(-c2cc[nH]n2)cc1] | N-(6-(2-(4-fluorophenyl)imidazo[1,2-a]pyridin-3-yl)imidazo[1,2-b]pyridazin-2-yl)-4-(1H-pyrazol-3-yl)benzamide | 515.30 | 2.58, 3.98 | B, C |
| 171 | 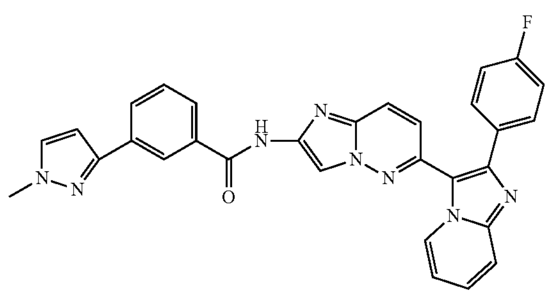 [SMILES: Cn1ccc(-c2cccc(C(=O)Nc3cn4nc(-c5c(-c6ccc(F)cc6)nc6ccccn56)ccc4n3)c2)n1] | N-(6-(2-(4-fluorophenyl)imidazo[1,2-a]pyridin-3-yl)imidazo[1,2-b]pyridazin-2-yl)-3-(1-methyl-1H-pyrazol-3-yl)benzamide | 529.26 | 2.73, 4.07 | B, C |
| 172 | 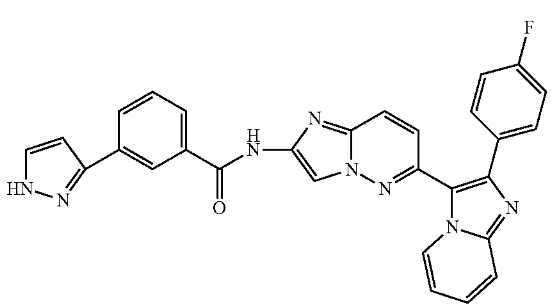 [SMILES: O=C(Nc1cn2nc(-c3c(-c4ccc(F)cc4)nc4ccccn34)ccc2n1)c1cccc(-c2cc[nH]n2)c1] | N-(6-(2-(4-fluorophenyl)imidazo[1,2-a]pyridin-3-yl)imidazo[1,2-b]pyridazin-2-yl)-3-(1H-pyrazol-3-yl)benzamide | 515.23 | 2.53, 3.97 | B, C |

TABLE 30-continued

| Compound No. | Structure | Name | [M + H]+ | Ret. Time | HPLC Method |
|---|---|---|---|---|---|
| 173 | 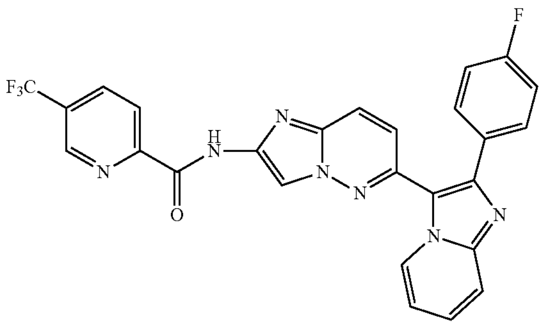 [SMILES: O=C(Nc1cn2nc(-c3c(-c4ccc(F)cc4)nc4ccccn34)ccc2n1)c1ccc(C(F)(F)F)cn1] | N-(6-(2-(4-fluorophenyl) imidazo[1,2-a]pyridin-3-yl) imidazo[1,2-b]pyridazin-2-yl)-6-(trifluoromethyl) nicotinamide | 518.10 | 2.86, 4.10 | B, C |
| 174 | 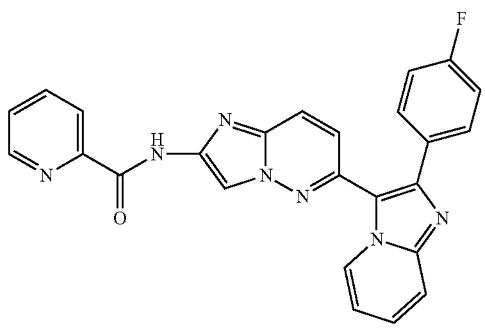 [SMILES: O=C(Nc1cn2nc(-c3c(-c4ccc(F)cc4)nc4ccccn34)ccc2n1)c1ccccn1] | N-(6-(2-(4-fluorophenyl) imidazo[1,2-a]pyridin-3-yl) imidazo[1,2-b]pyridazin-2-yl)-2-pyridinecarboxamide | 451.05 | 3.38 | C |
| 175 | 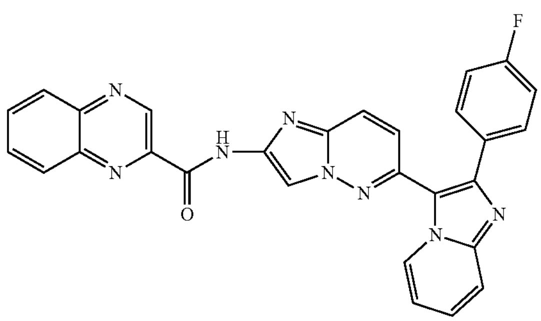 [SMILES: O=C(Nc1cn2nc(-c3c(-c4ccc(F)cc4)nc4ccccn34)ccc2n1)c1cnc2ccccc2n1] | N-(6-(2-(4-fluorophenyl) imidazo[1,2-a]pyridin-3-yl) imidazo[1,2-b]pyridazin-2-yl)-2-quinoxalinecarboxamide | 501.65 | 2.92 | B |
| 176 | 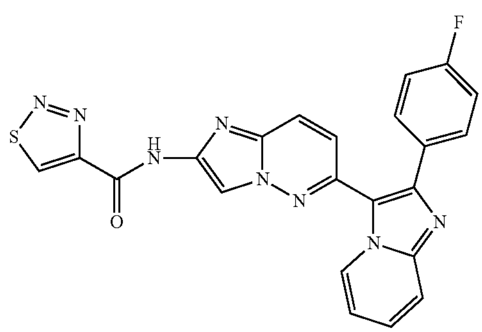 [SMILES: O=C(Nc1cn2nc(-c3c(-c4ccc(F)cc4)nc4ccccn34)ccc2n1)c1csnn1] | N-(6-(2-(4-fluorophenyl) imidazo[1,2-a]pyridin-3-yl) imidazo[1,2-b]pyridazin-2-yl)-1,2,3-thiadiazole-4-carboxamide | 456.91 | 2.41 | B |

TABLE 30-continued

| Compound No. | Structure | Name | [M + H]+ | Ret. Time | HPLC Method |
|---|---|---|---|---|---|
| 177 | 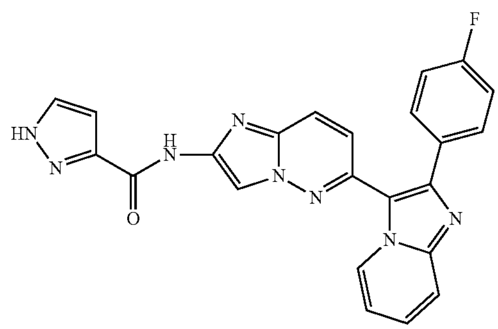 [SMILES: O=C(Nc1cn2nc(-c3c(-c4ccc(F)cc4)nc4ccccn34)ccc2n1)c1cc[nH]n1] | N-(6-(2-(4-fluorophenyl) imidazo[1,2-a]pyridin-3-yl) imidazo[1,2-b]pyridazin-2-yl)-1H-pyrazole-3-carboxamide | 439.30 | 3.74 | C |
| 178 | 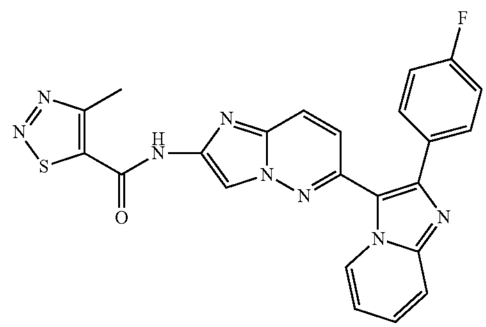 [SMILES: Cc1nnsc1C(=O)Nc1cn2nc(-c3c(-c4ccc(F)cc4)nc4ccccn34)ccc2n1] | N-(6-(2-(4-fluorophenyl) imidazo[1,2-a]pyridin-3-yl) imidazo[1,2-b]pyridazin-2-yl)-4-methyl-1,2,3-thiadiazole-5-carboxamide | 471.18 | 3.48 | C |
| 179 | 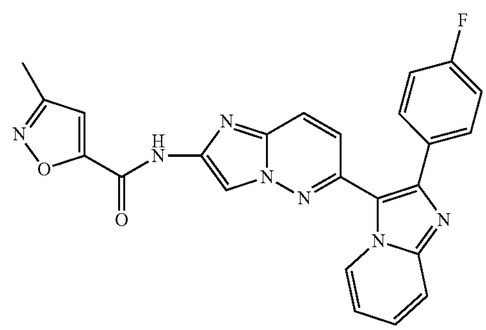 [SMILES: Cc1cc(C(=O)Nc2cn3nc(-c4c(-c5ccc(F)cc5)nc5ccccn45)ccc3n2)on1] | N-(6-(2-(4-fluorophenyl) imidazo[1,2-a]pyridin-3-yl) imidazo[1,2-b]pyridazin-2-yl)-3-methyl-5-isoxazolecarboxamide | 454.15 | 3.89 | C |
| 180 | 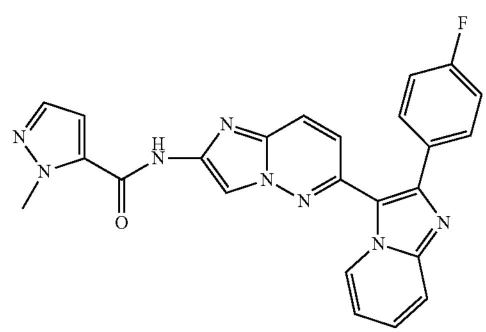 [SMILES: Cn1nccc1C(=O)Nc1cn2nc(-c3c(-c4ccc(F)cc4)nc4ccccn34)ccc2n1] | N-(6-(2-(4-fluorophenyl) imidazo[1,2-a]pyridin-3-yl) imidazo[1,2-b]pyridazin-2-yl)-1-methyl-1H-pyrazole-5-carboxamide | 453.15 | 3.91 | C |

TABLE 30-continued

| Compound No. | Structure | Name | [M + H]+ | Ret. Time | HPLC Method |
|---|---|---|---|---|---|
| 181 | 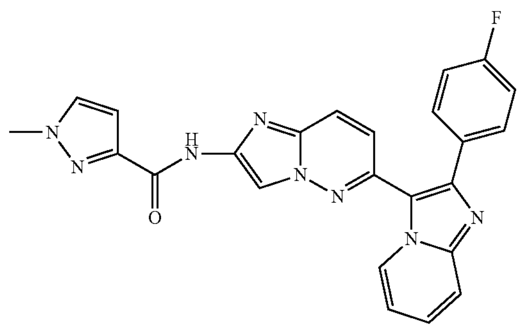 [SMILES: Cn1ccc(C(=O)Nc2cn3nc(-c4c(-c5ccc(F)cc5)nc5ccccn45)ccc3n2)n1] | N-(6-(2-(4-fluorophenyl)imidazo[1,2-a]pyridin-3-yl)imidazo[1,2-b]pyridazin-2-yl)-1-methyl-1H-pyrazole-3-carboxamide | 453.17 | 3.82 | C |
| 182 | 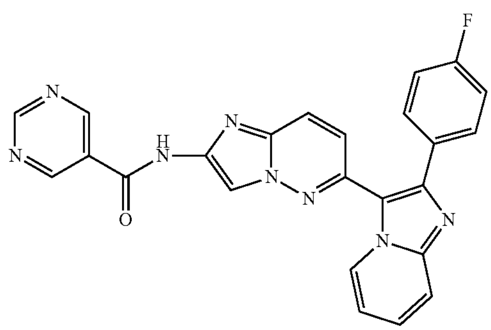 [SMILES: O=C(Nc1cn2nc(-c3c(-c4ccc(F)cc4)nc4ccccn34)ccc2n1)c1cncnc1] | N-(6-(2-(4-fluorophenyl)imidazo[1,2-a]pyridin-3-yl)imidazo[1,2-b]pyridazin-2-yl)-5-pyrimidinecarboxamide | 451.23 | 2.19 | B |
| 183 | 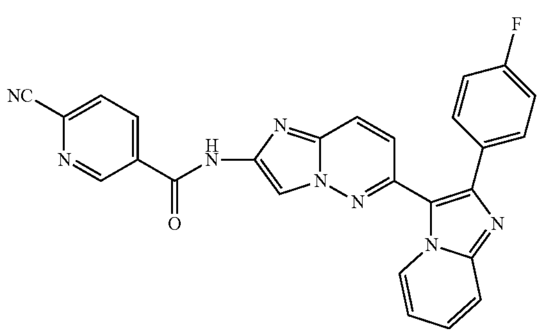 [SMILES: N#Cc1ccc(C(=O)Nc2cn3nc(-c4c(-c5ccc(F)cc5)nc5ccccn45)ccc3n2)cn1] | 6-cyano-N-(6-(2-(4-fluorophenyl)imidazo[1,2-a]pyridin-3-yl)imidazo[1,2-b]pyridazin-2-yl)nicotinamide | 475.37 | 3.90 | C |
| 184 | 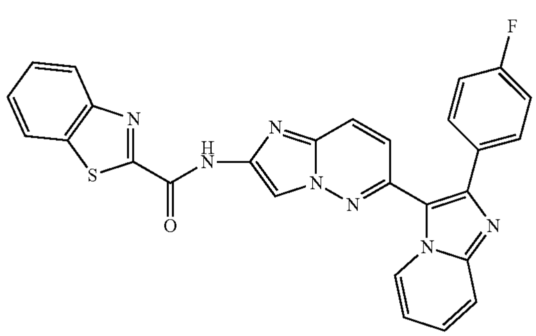 [SMILES: O=C(Nc1cn2nc(-c3c(-c4ccc(F)cc4)nc4ccccn34)ccc2n1)c1nc2ccccc2s1] | N-(6-(2-(4-fluorophenyl)imidazo[1,2-a]pyridin-3-yl)imidazo[1,2-b]pyridazin-2-yl)-1,3-benzothiazole-2-carboxamide | 506.18 | 4.50 | C |

TABLE 30-continued

| Compound No. | Structure | Name | [M + H]+ | Ret. Time | HPLC Method |
|---|---|---|---|---|---|
| 185 | 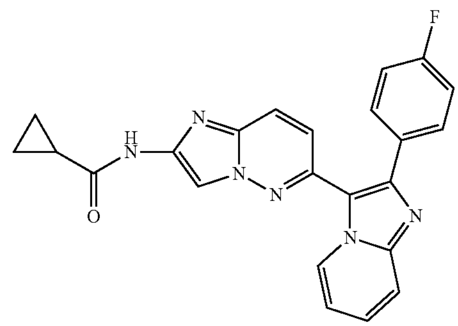 [SMILES: O=C(Nc1cn2nc(-c3c(-c4ccc(F)cc4)nc4ccccn34)ccc2n1)C1CC1] | N-(6-(2-(4-fluorophenyl)imidazo[1,2-a]pyridin-3-yl)imidazo[1,2-b]pyridazin-2-yl)cyclopropanecarboxamide | 413.19 | 3.08 | A |
| 186 | 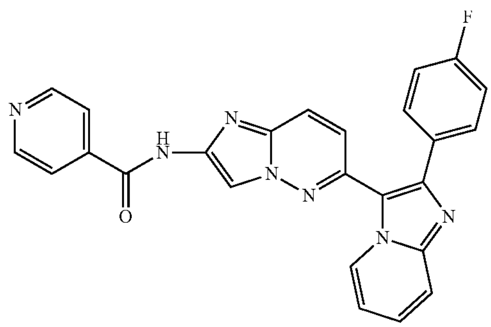 [SMILES: O=C(Nc1cn2nc(-c3c(-c4ccc(F)cc4)nc4ccccn34)ccc2n1)c1ccncc1] | N-(6-(2-(4-fluorophenyl)imidazo[1,2-a]pyridin-3-yl)imidazo[1,2-b]pyridazin-2-yl)isonicotinamide | 450.20 | 2.74 | A |
| 187 | 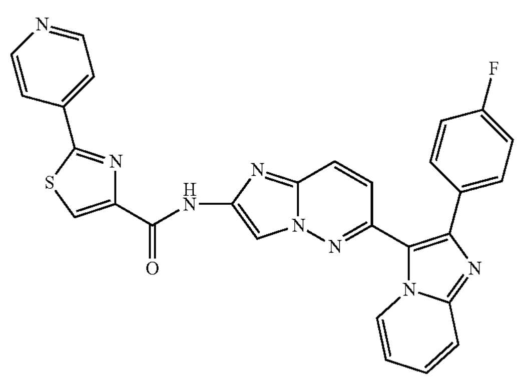 [SMILES: O=C(Nc1cn2nc(-c3c(-c4ccc(F)cc4)nc4ccccn34)ccc2n1)c1csc(-c2ccncc2)n1] | N-(6-(2-(4-fluorophenyl)imidazo[1,2-a]pyridin-3-yl)imidazo[1,2-b]pyridazin-2-yl)-2-(pyridin-4-yl)thiazole-4-carboxamide | 533.30 | 3.00 | P |
| 188 | 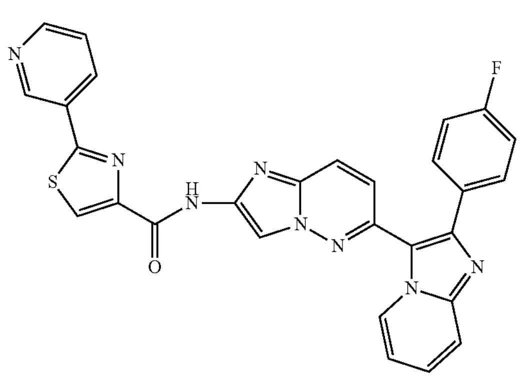 [SMILES: O=C(Nc1cn2nc(-c3c(-c4ccc(F)cc4)nc4ccccn34)ccc2n1)c1csc(-c2cccnc2)n1] | N-(6-(2-(4-fluorophenyl)imidazo[1,2-a]pyridin-3-yl)imidazo[1,2-b]pyridazin-2-yl)-2-(pyridin-3-yl)thiazole-4-carboxamide | 533.18 | 3.23 | A |

TABLE 30-continued

| Compound No. | Structure | Name | [M + H]+ | Ret. Time | HPLC Method |
|---|---|---|---|---|---|
| 189 | 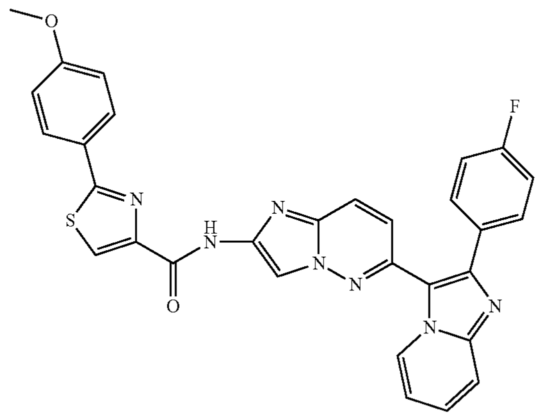 [SMILES: COc1ccc(-c2nc(C(=O)Nc3cn4nc(-c5c(-c6ccc(F)cc6)nc6ccccn56)ccc4n3)cs2)cc1] | N-(6-(2-(4-fluorophenyl) imidazo[1,2-a]pyridin-3-yl) imidazo[1,2-b]pyridazin-2-yl)-2-(4-methoxyphenyl) thiazole-4-carboxamide, 3 HCl | 562.08 | 0.95 | G |
| 190 | 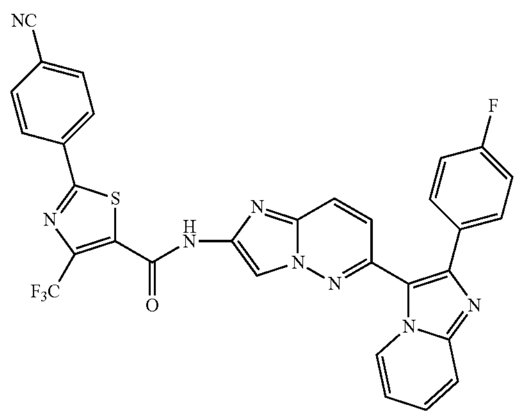 [SMILES: N#Cc1ccc(-c2nc(C(F)(F)F)c(C(=O)Nc3cn4nc(-c5c(-c6ccc(F)cc6)nc6ccccn56)ccc4n3)s2)cc1] | 2-(4-cyanophenyl)-N-(6-(2-(4-fluorophenyl)imidazo [1,2-a]pyridin-3-yl)imidazo [1,2-b]pyridazin-2-yl)-4-(trifluoromethyl)thiazole-5-carboxamide | 625.22 | 3.49 | A |
| 191 | 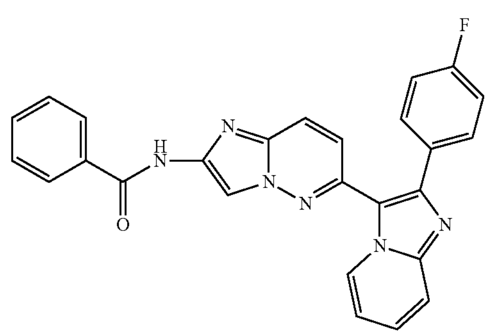 [SMILES: O=C(Nc1cn2nc(-c3c(-c4ccc(F)cc4)nc4ccccn34)ccc2n1)c1ccccc1] | N-(6-(2-(4-fluorophenyl) imidazo[1,2-a]pyridin-3-yl) imidazo[1,2-b]pyridazin-2-yl)benzamide | 449.20 | 3.29 | A |
| 192 | 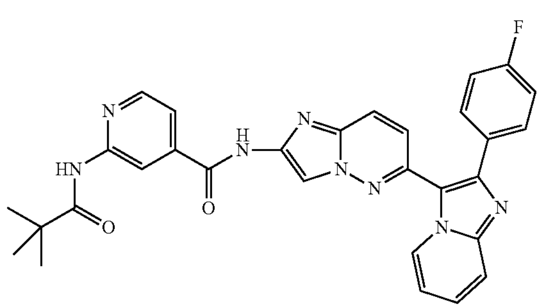 [SMILES: CC(C)(C)C(=O)Nc1cc(C(=O)Nc2cn3nc(-c4c(-c5ccc(F)cc5)nc5ccccn45)ccc3n2)ccn1] | N-(6-(2-(4-fluorophenyl) imidazo[1,2-a]pyridin-3-yl) imidazo[1,2-b]pyridazin-2-yl)-2-pivalamidoisonicotinamide | 549.40 | 2.72, 4.18 | B, C |

TABLE 30-continued

| Compound No. | Structure | Name | [M + H]+ | Ret. Time | HPLC Method |
|---|---|---|---|---|---|
| 193 | 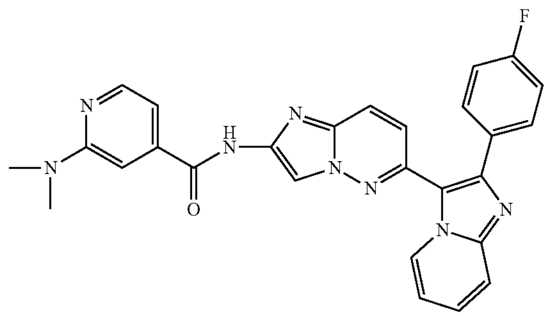 [SMILES: CN(C)c1cc(C(=O)Nc2cn3nc(-c4c(-c5ccc(F)cc5)nc5ccccn45)ccc3n2)ccn1] | 2-(dimethylamino)-N-(6-(2-(4-fluorophenyl)imidazo[1,2-a]pyridin-3-yl)imidazo[1,2-b]pyridazin-2-yl) isonicotinamide | 493.30 | 2.70, 4.12 | B, C |
| 194 | 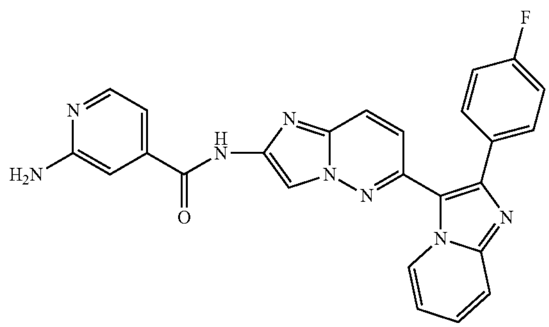 [SMILES: Nc1cc(C(=O)Nc2cn3nc(-c4c(-c5ccc(F)cc5)nc5ccccn45)ccc3n2)ccn1] | 2-amino-N-(6-(2-(4-fluorophenyl)imidazo[1,2-a]pyridin-3-yl)imidazo[1,2-b]pyridazin-2-yl) isonicotinamide | 465.04 | 2.57 | A |
| 195 | 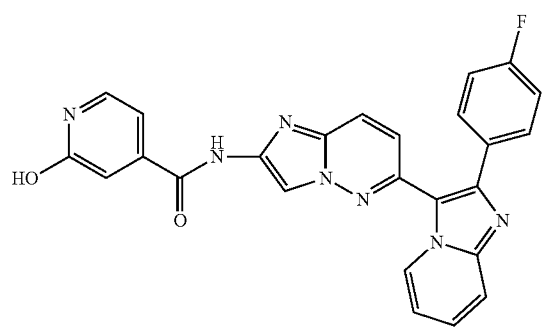 [SMILES: O=C(Nc1cn2nc(-c3c(-c4ccc(F)cc4)nc4ccccn34)ccc2n1)c1ccnc(O)c1] | N-(6-(2-(4-fluorophenyl)imidazo[1,2-a]pyridin-3-yl)imidazo[1,2-b]pyridazin-2-yl)-2-hydroxyisonicotinamide | 466.13 | 2.16, 3.68 | B, C |
| 196 | 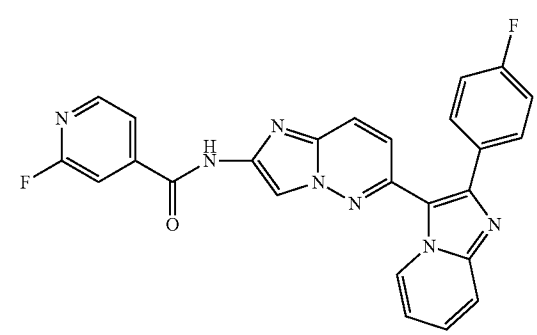 [SMILES: O=C(Nc1cn2nc(-c3c(-c4ccc(F)cc4)nc4ccccn34)ccc2n1)c1ccnc(F)c1] | 2-fluoro-N-(6-(2-(4-fluorophenyl)imidazo[1,2-a]pyridin-3-yl)imidazo[1,2-b]pyridazin-2-yl)isonicotinamide | 468.15 | 3.24 | A |

TABLE 30-continued

| Compound No. | Structure | Name | [M + H]+ | Ret. Time | HPLC Method |
|---|---|---|---|---|---|
| 197 | 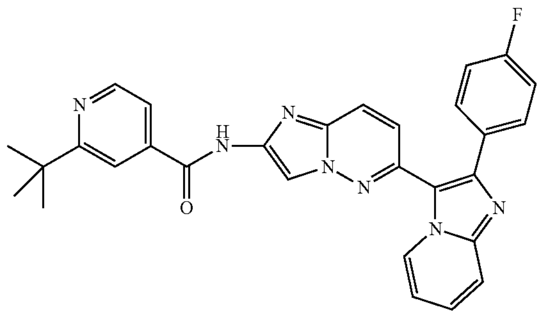 [SMILES: CC(C)(C)c1cc(C(=O)Nc2cn3nc(-c4c(-c5ccc(F)cc5)nc5ccccn45)ccc3n2)ccn1] | 2-(tert-butyl)-N-(6-(2-(4-fluorophenyl)imidazo[1,2-a]pyridin-3-yl)imidazo[1,2-b]pyridazin-2-yl)isonicotinamide | 506.32 | 3.05, 4.42 | B, C |
| 198 | 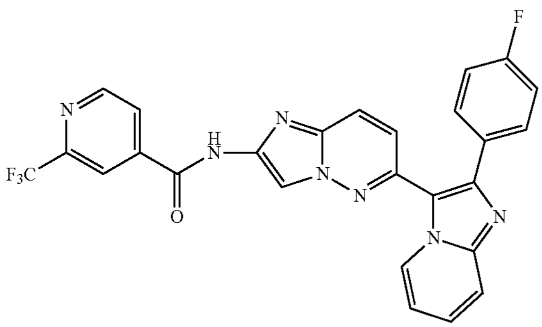 [SMILES: O=C(Nc1cn2nc(-c3c(-c4ccc(F)cc4)nc4ccccn34)ccc2n1)c1ccnc(C(F)(F)F)c1] | N-(6-(2-(4-fluorophenyl)imidazo[1,2-a]pyridin-3-yl)imidazo[1,2-b]pyridazin-2-yl)-2-(trifluoromethyl)isonicotinamide | 518.03 | 2.83 | B |
| 199 | 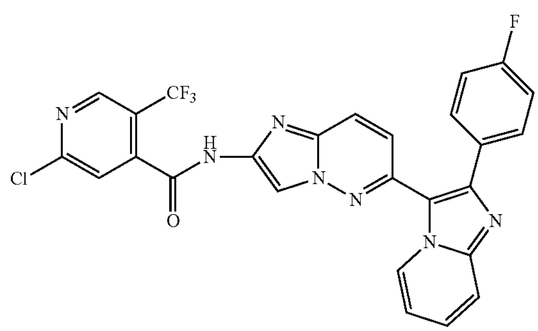 [SMILES: O=C(Nc1cn2nc(-c3c(-c4ccc(F)cc4)nc4ccccn34)ccc2n1)c1cc(Cl)ncc1C(F)(F)F] | 2-chloro-N-(6-(2-(4-fluorophenyl)imidazo[1,2-a]pyridin-3-yl)imidazo[1,2-b]pyridazin-2-yl)-5-(trifluoromethyl)isonicotinamide | 552.12 | 2.86, 4.22 | B, C |
| 200 | 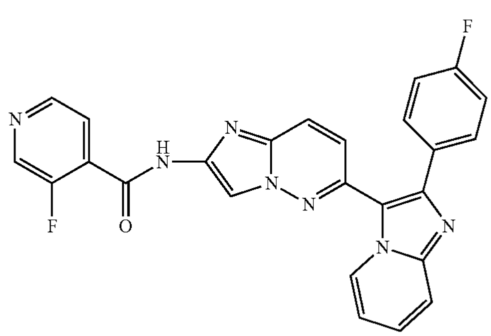 [SMILES: O=C(Nc1cn2nc(-c3c(-c4ccc(F)cc4)nc4ccccn34)ccc2n1)c1ccncc1F] | 3-fluoro-N-(6-(2-(4-fluorophenyl)imidazo[1,2-a]pyridin-3-yl)imidazo[1,2-b]pyridazin-2-yl)isonicotinamide | 468.22 | 3.13 | A |

TABLE 30-continued

| Compound No. | Structure | Name | [M + H]+ | Ret. Time | HPLC Method |
|---|---|---|---|---|---|
| 201 | 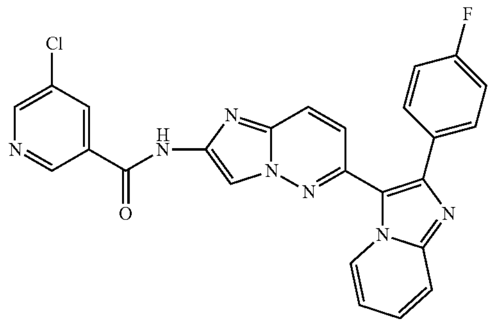 [SMILES: O=C(Nc1cn2nc(-c3c(-c4ccc(F)cc4)nc4ccccn34)ccc2n1)c1cncc(Cl)c1] | 5-chloro-N-(6-(2-(4-fluorophenyl)imidazo[1,2-a]pyridin-3-yl)imidazo[1,2-b]pyridazin-2-yl)nicotinamide | 484.18 | 2.71, 4.21 | B, C |
| 202 | 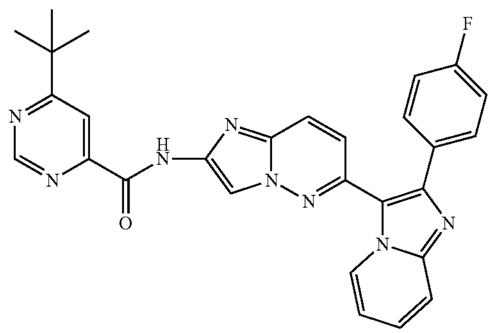 [SMILES: CC(C)(C)c1cc(C(=O)Nc2cn3nc(-c4c(-c5ccc(F)cc5)nc5ccccn45)ccc3n2)ncn1] | 6-(tert-butyl)-N-(6-(2-(4-fluorophenyl)imidazo[1,2-a]pyridin-3-yl)imidazo[1,2-b]pyridazin-2-yl)pyrimidine-4-carboxamide | 507.20 | 3.20, 4.57 | B, C |
| 203 | 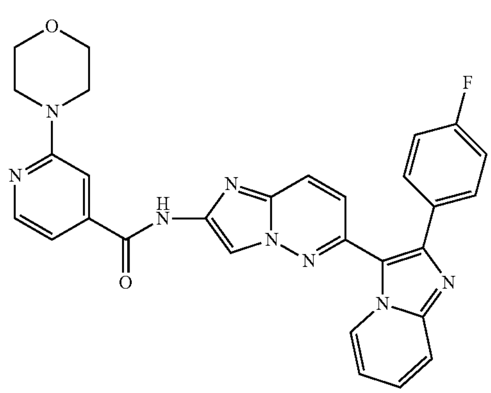 [SMILES: O=C(Nc1cn2nc(-c3c(-c4ccc(F)cc4)nc4ccccn34)ccc2n1)c1ccnc(N2CCOCC2)c1] | N-(6-(2-(4-fluorophenyl)imidazo[1,2-a]pyridin-3-yl)imidazo[1,2-b]pyridazin-2-yl)-2-morpholinoisonicotinamide | 535.26 | 2.76, 4.16 | B, C |
| 204 | 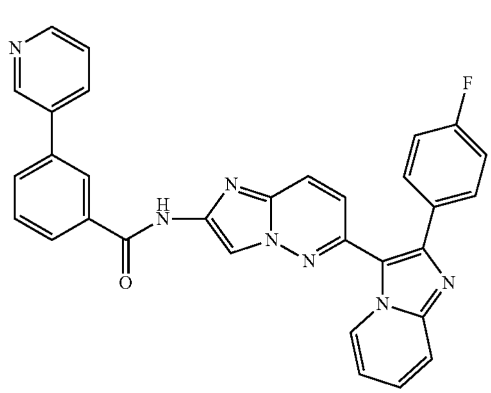 [SMILES: O=C(Nc1cn2nc(-c3c(-c4ccc(F)cc4)nc4ccccn34)ccc2n1)c1cccc(-c2cccnc2)c1] | N-(6-(2-(4-fluorophenyl)imidazo[1,2-a]pyridin-3-yl)imidazo[1,2-b]pyridazin-2-yl)-3-(pyridin-3-yl)benzamide | 526.30 | 2.76, 4.16 | B, C |

TABLE 30-continued

| Compound No. | Structure | Name | [M + H]+ | Ret. Time | HPLC Method |
|---|---|---|---|---|---|
| 205 | 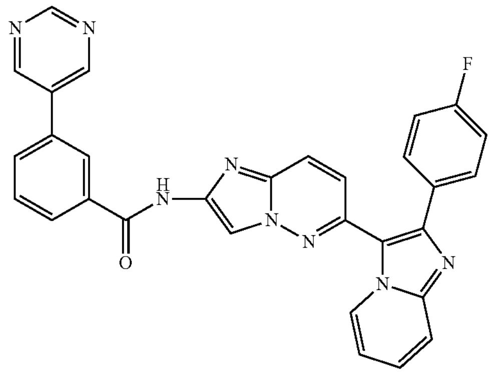 [SMILES: O=C(Nc1cn2nc(-c3c(-c4ccc(F)cc4)nc4ccccn34)ccc2n1)c1cccc(-c2cncnc2)c1] | N-(6-(2-(4-fluorophenyl) imidazo[1,2-a]pyridin-3-yl) imidazo[1,2-b]pyridazin-2-yl)-3-(pyrimidin-5-yl)benzamide | 527.15 | 2.64, 4.06 | B, C |
| 206 | 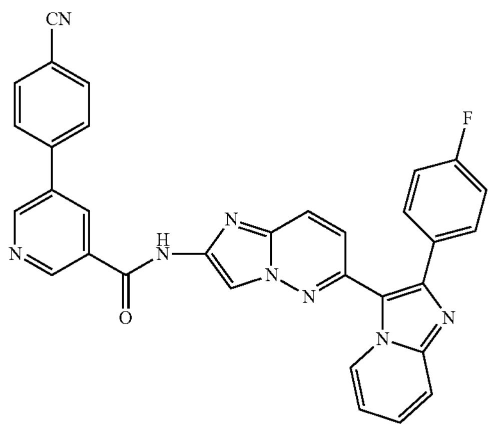 [SMILES: N#Cc1ccc(-c2cncc(C(=O)Nc3cn4nc(-c5c(-c6ccc(F)cc6)nc6ccccn56)ccc4n3)c2)cc1] | 5-(4-cyanophenyl)-N-(6-(2-(4-fluorophenyl)imidazo[1,2-a]pyridin-3-yl)imidazo[1,2-b]pyridazin-2-yl)nicotinamide | 551.25 | 3.45 | A |
| 207 | 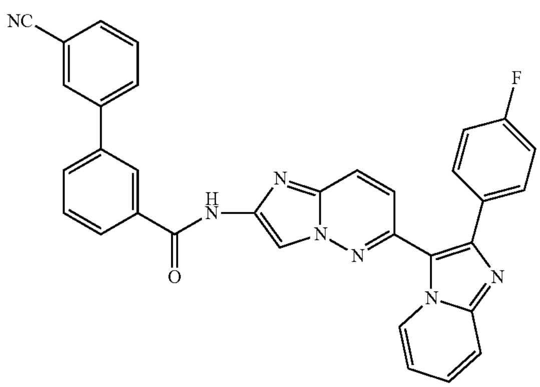 [SMILES: N#Cc1cccc(-c2cccc(C(=O)Nc3cn4nc(-c5c(-c6ccc(F)cc6)nc6ccccn56)ccc4n3)c2)c1] | 3'-cyano-N-(6-(2-(4-fluorophenyl)imidazo[1,2-a]pyridin-3-yl]imidazo[1,2-b]pyridazin-2-yl)-[1,1'-biphenyl]-3-carboxamide | 550.25 | 3.22, 4.38 | B, C |
| 208 | 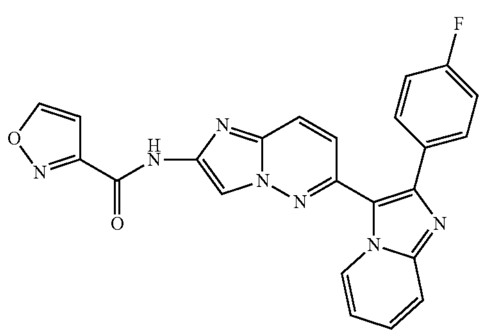 [SMILES: O=C(Nc1cn2nc(-c3c(-c4ccc(F)cc4)nc4ccccn34)ccc2n1)c1ccon1] | N-(6-(2-(4-fluorophenyl) imidazo[1,2-a]pyridin-3-yl) imidazo[1,2-b]pyridazin-2-yl)isoxazole-3-carboxamide | 440.10 | 2.53, 3.86 | B, C |

TABLE 30-continued

| Compound No. | Structure | Name | [M + H]+ | Ret. Time | HPLC Method |
|---|---|---|---|---|---|
| 209 | 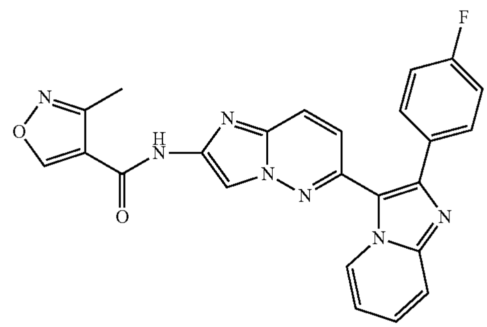 [SMILES: Cc1nocc1C(=O)Nc1cn2nc(-c3c(-c4ccc(F)cc4)nc4ccccn34)ccc2n1] | N-(6-(2-(4-fluorophenyl) imidazo[1,2-a]pyridin-3-yl) imidazo[1,2-b]pyridazin-2-yl)-3-methylisoxazole-4-carboxamide | 454.10 | 2.58, 3.99 | B, C |
| 210 | 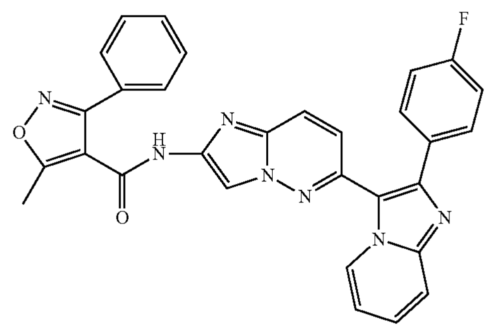 [SMILES: Cc1onc(-c2ccccc2)c1C(=O)Nc1cn2nc(-c3c(-c4ccc(F)cc4)nc4ccccn34)ccc2n1] | N-(6-(2-(4-fluorophenyl) imidazo[1,2-a]pyridin-3-yl) imidazo[1,2-b]pyridazin-2-yl)-5-methyl-3-phenylisoxazole-4-carboxamide | 530.26 | 3.48 | A |
| 211 | 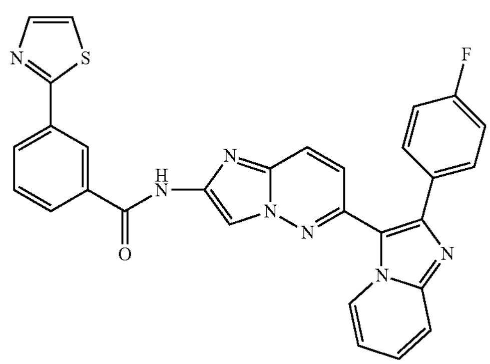 [SMILES: O=C(Nc1cn2nc(-c3c(-c4ccc(F)cc4)nc4ccccn34)ccc2n1)c1cccc(-c2nccs2)c1] | N-(6-(2-(4-fluorophenyl) imidazo[1,2-a]pyridin-3-yl) imidazo[1,2-b]pyridazin-2-yl)-3-(thiazol-2-yl)benzamide | 532.20 | 2.94, 4.29 | B, C |
| 212 | 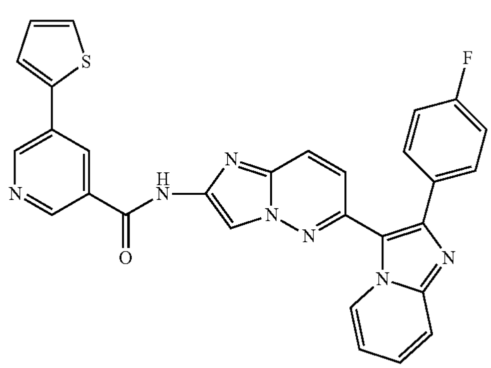 [SMILES: O=C(Nc1cn2nc(-c3c(-c4ccc(F)cc4)nc4ccccn34)ccc2n1)c1cncc(-c2cccs2)c1] | N-(6-(2-(4-fluorophenyl) imidazo[1,2-a]pyridin-3-yl) imidazo[1,2-b]pyridazin-2-yl)-5-(thiophen-2-yl) nicotinamide | 532.30 | 2.88, 4.32 | B, C |

TABLE 30-continued

| Compound No. | Structure | Name | [M + H]+ | Ret. Time | HPLC Method |
|---|---|---|---|---|---|
| 213 | 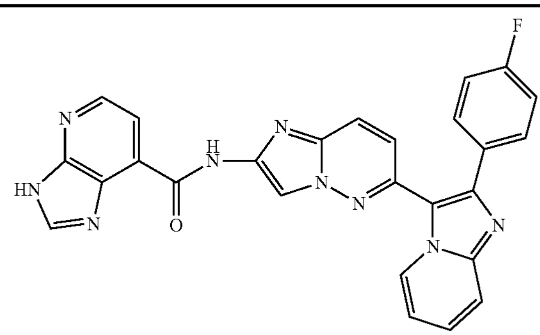 | N-(6-(2-(4-fluorophenyl) imidazo[1,2-a]pyridin-3-yl) imidazo[1,2-b]pyridazin-2-yl)-3H-imidazo[4,5-b] pyridine-7-carboxamide | 490.02 | 2.43, 4.00 | B, C |
| 214 | 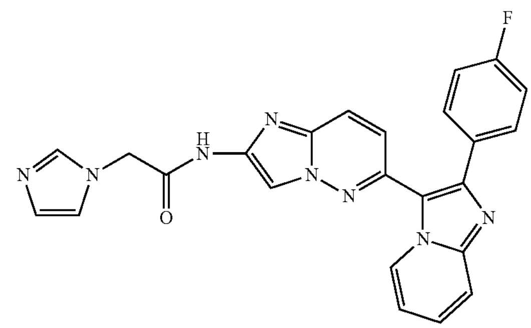 [SMILES: O=C(Cn1ccnc1)Nc1cn2nc(-c3c(-c4ccc(F)cc4)nc4ccccn34)ccc2n1] | N-(6-(2-(4-fluorophenyl) imidazo[1,2-a]pyridin-3-yl) imidazo[1,2-b]pyridazin-2-yl)-2-(1H-imidazol-1-yl) acetamide | 453.06 | 2.04, 3.56 | B, C |
| 215 | 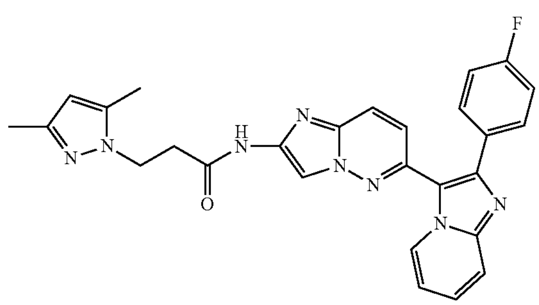 [SMILES: Cc1cc(C)n(CCC(=O)Nc2cn3nc(-c4c(-c5ccc(F)cc5)nc5ccccn45)ccc3n2)n1] | 3-(3,5-dimethyl-1H-pyrazol-1-yl)-N-(6-(2-(4-fluorophenyl) imidazo[1,2-a]pyridin-3-yl)imidazo[1,2-b]pyridazin-2-yl)propanamide | 495.30 | 2.47, 4.10 | B, C |
| 216 | 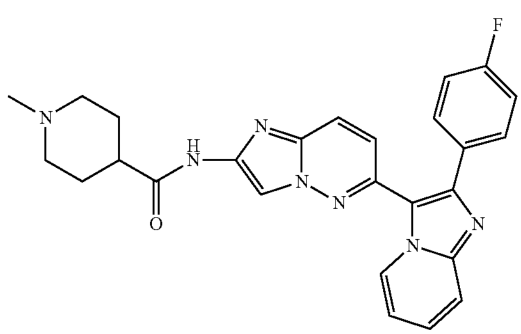 [SMILES: CN1CCC(C(=O)Nc2cn3nc(-c4c(-c5ccc(F)cc5)nc5ccccn45)ccc3n2)CC1] | N-(6-(2-(4-fluorophenyl) imidazo[1,2-a]pyridin-3-yl) imidazo[1,2-b]pyridazin-2-yl)-1-methylpiperidine-4-carboxamide | 470.30 | 1.94, 3.36 | B, C |
| 217 | 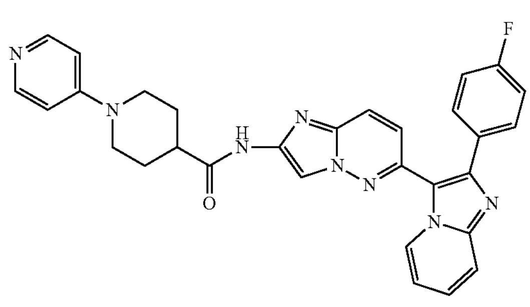 [SMILES: O=C(Nc1cn2nc(-c3c(-c4ccc(F)cc4)nc4ccccn34)ccc2n1)C1CCN(c2ccncc2)CC1] | N-(6-(2-(4-fluorophenyl) imidazo[1,2-a]pyridin-3-yl) imidazo[1,2-b]pyridazin-2-yl)-1-(pyridin-4-yl)piperidine-4-carboxamide | 533.30 | 2.00, 3.54 | B, C |

TABLE 30-continued

| Compound No. | Structure | Name | [M + H]+ | Ret. Time | HPLC Method |
|---|---|---|---|---|---|
| 218 | 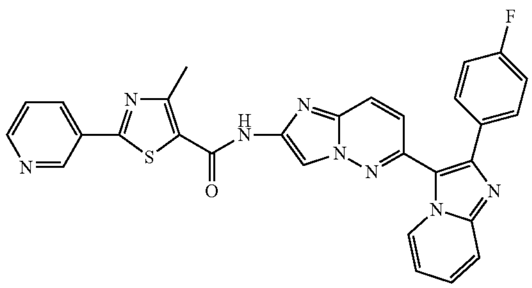 [SMILES: Cc1nc(-c2cccnc2)sc1C(=O)Nc1cn2nc(-c3c(-c4ccc(F)cc4)nc4ccccn34)ccc2n1] | N-(6-(2-(4-fluorophenyl) imidazo[1,2-a]pyridin-3-yl) imidazo[1,2-b]pyridazin-2-yl)-4-methyl-2-(pyridin-3-yl) thiazole-5-carboxamide | 547.21 | 2.93 | A |
| 219 | 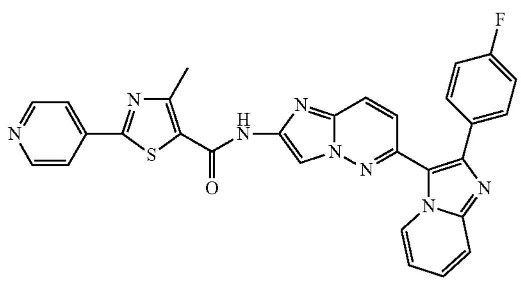 [SMILES: Cc1nc(-c2ccncc2)sc1C(=O)Nc1cn2nc(-c3c(-c4ccc(F)cc4)nc4ccccn34)ccc2n1] | N-(6-(2-(4-fluorophenyl) imidazo[1,2-a]pyridin-3-yl) imidazo[1,2-b]pyridazin-2-yl)-4-methyl-2-(pyridin-4-yl) thiazole-5-carboxamide | 547.27 | 3.14 | A |
| 220 | 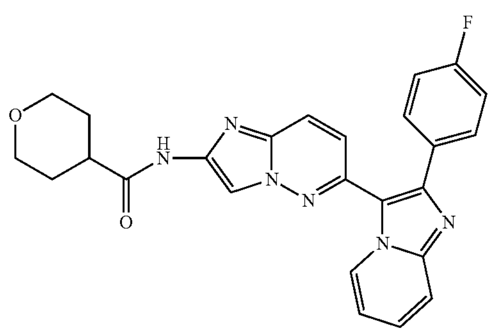 [SMILES: O=C(Nc1cn2nc(-c3c(-c4ccc(F)cc4)nc4ccccn34)ccc2n1)C1CCOCC1] | N-(6-(2-(4-fluorophenyl) imidazo[1,2-a]pyridin-3-yl) imidazo[1,2-b]pyridazin-2-yl)tetrahydro-2H-pyran-4-carboxamide | 457.20 | 2.24, 3.82 | B, C |
| 221 | 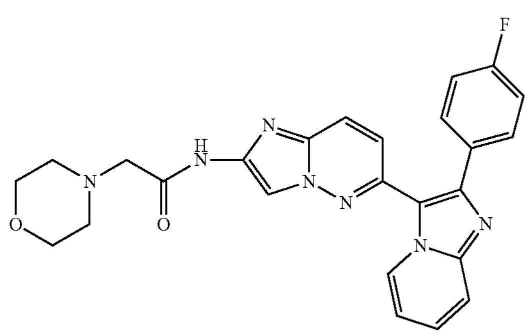 [SMILES: O=C(CN1CCOCC1)Nc1cn2nc(-c3c(-c4ccc(F)cc4)nc4ccccn34)ccc2n1] | N-(6-(2-(4-fluorophenyl) imidazo[1,2-a]pyridin-3-yl) imidazo[1,2-b]pyridazin-2-yl)-2-morpholinoacetamide | 472.20 | 2.23, 3.81 | B, C |

Compound 222

N-(2-(4-fluorophenyl)-6-(pyrrolidin-1-yl)-[3,6'-bi-imidazo[1,2-b]pyridazin]-2'-yl)isonicotinamide

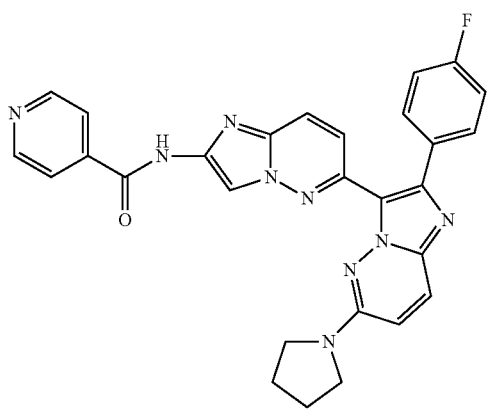 [SMILES: O=C(Nc1cn2nc(-c3c(-c4ccc(F)cc4)nc4ccc(N5CCCC5)nn34)ccc2n1)c1ccncc1]

A solution of Intermediate 15 (0.035 g, 0.066 mmol) and pyrrolidine (0.047 g, 0.662 mmol) in NMP (0.662 mL) was heated in a microwave oven at 160° C. for 12 h. The crude material was purified via preparative LC/MS with the following conditions: Column: Waters XBridge C18, 19×150 mm, 5-μm particles; Guard Column: Waters) (Bridge C18, 19×10 mm, 5-μm particles; Mobile Phase A: water with 20-mM ammonium acetate; Mobile Phase B: 95:5 methanol:water with 20-mM ammonium acetate; Gradient: 40-100% B over 30 minutes, then a 5-minute hold at 100% B; Flow: 20 mL/min. Fractions containing the desired product (0.0034 g, 9.29% yield) were combined and dried via centrifugal evaporation. HPLC Ret. Time 2.65 min. and 4.06 min. (Methods B and C respectively). MS(ES): m/z=520.30 [M+H]$^+$. $^1$H NMR (500 MHz, DMSO-d$_6$) δ ppm 11.85 (s, 1H), 8.82 (d, J=6.1 Hz, 2H), 8.46 (s, 1H), 8.22 (d, J=9.5 Hz, 1H), 8.07-7.95 (m, 3H), 7.82-7.70 (m, 3H), 7.22 (t, J=8.9 Hz, 2H), 7.06 (d, J=10.1 Hz, 1H), 1.95 (t, J=6.4 Hz, 5H).

The compounds described in Table 31 were synthesized analogous to compound 222 by reacting Intermediate 15 with the corresponding amines.

TABLE 31

| Compound No. | Structure | Name | [M + H]$^+$ | Ret. Time | HPLC Method |
|---|---|---|---|---|---|
| 223 | 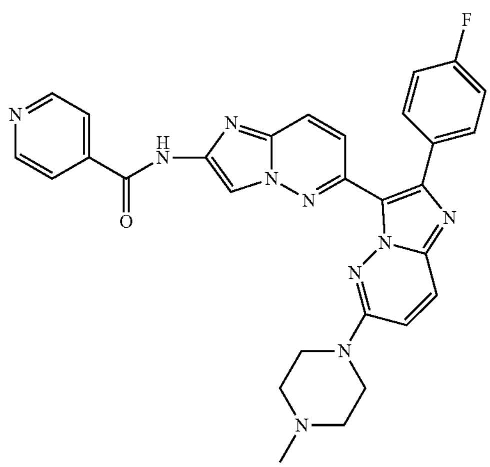 [SMILES: CN1CCN(c2ccc3nc(-c4ccc(F)cc4)c(-c4ccc5nc(NC(=O)c6ccncc6)cn5n4)n3n2)CC1] | N-(2-(4-fluorophenyl)-6-(4-methylpiperazin-1-yl)-[3,6'-biimidazo[1,2-b]pyridazin]-2'-yl)isonicotinamide | 549.34 | 3.83 | C |
| 224 | 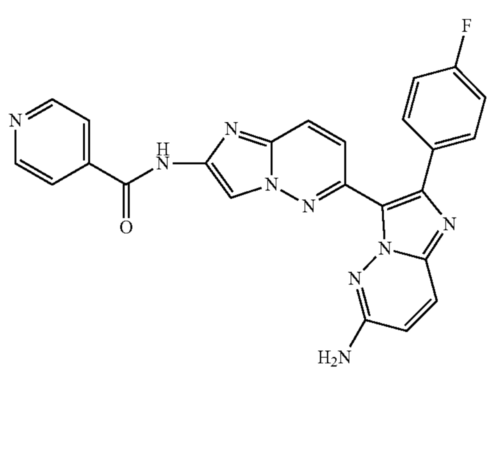 [SMILES: Nc1ccc2nc(-c3ccc(F)cc3)c(-c3ccc4nc(NC(=O)c5ccncc5)cn4n3)n2n1] | N-(6-amino-2-(4-fluorophenyl)-[3,6'-biimidazo[1,2-b]pyridazin]-2'-yl)isonicotinamide | 466.21 | 2.02, 3.57 | B, C |

TABLE 31-continued

| Compound No. | Structure | Name | [M + H]+ | Ret. Time | HPLC Method |
|---|---|---|---|---|---|
| 225 | 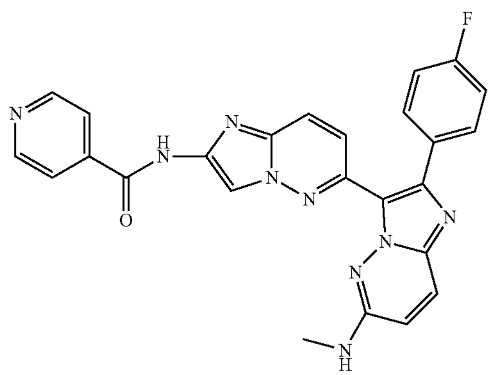 [SMILES: CNc1ccc2nc(-c3ccc(F)cc3)c(-c3ccc4nc(NC(=O)c5ccncc5)cn4n3)n2n1] | N-(2-(4-fluorophenyl)-6-(methyl-amino)-[3,6'-biimidazo[1,2-b]pyridazin]-2'-yl)isonicotinamide | 480.30 | 2.27, 3.76 | B, C |
| 226 | 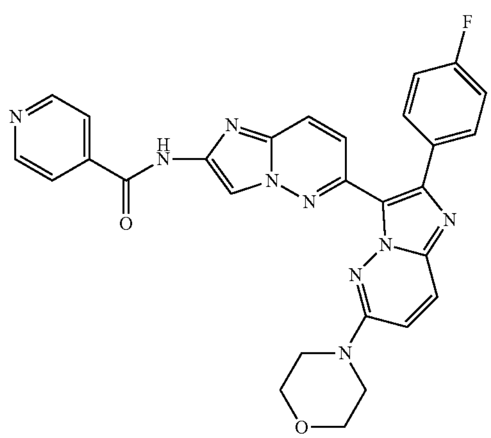 [SMILES: O=C(Nc1cn2nc(-c3c(-c4ccc(F)cc4)nc4ccc(N5CCOCC5)nn34)ccc2n1)c1ccncc1] | N-(2-(4-fluorophenyl)-6-morpholino-[3,6'-biimidazo[1,2-b]pyridazin]-2'-yl)isonicotinamide | 536.31 | 236, 386 | B, C |
| 227 | 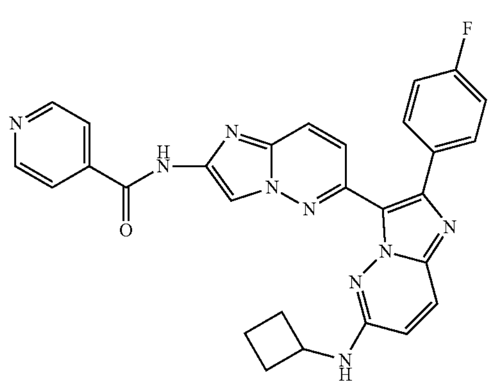 [SMILES: O=C(Nc1cn2nc(-c3c(-c4ccc(F)cc4)nc4ccc(NC5CCC5)nn34)ccc2n1)c1ccncc1] | N-(6-cyclobutylamino)-2-(4-fluorophenyl)-[3,6'-biimidazo[1,2-b]pyridazin]-2'-yl)isonicotinamide | 520.30 | 2.49, 4.06 | B, C |

Compound 228

N-(6-(4-(4-fluorophenyl)-2-methyl-1H-imidazol-5-yl)imidazo[1,2-b]pyridazin-2-yl)isonicotinamide

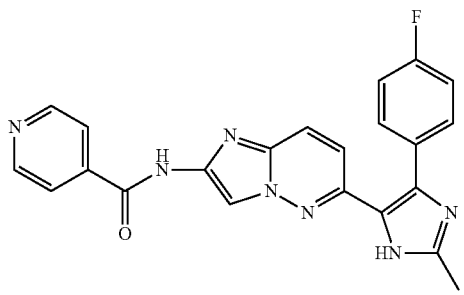 [SMILES: Cc1nc(-c2ccc(F)cc2)c(-c2ccc3nc(NC(=O)c4ccncc4)cn3n2)[nH]1]

Intermediate 5E (1.35 g, 5.29 mmol) and 2M solution of aq. K₃PO₄ (7.94 mL, 15.88 mmol) were added to a crude reaction mixture of Intermediate 14. The suspension was degassed for a few minutes and then PdCl₂(dppf)-CH₂Cl₂ adduct (0.432 g, 0.529 mmol) was added to it. The resultant mixture was degassed again for 5 min. A reflux condenser was attached to the round bottom flask and the reaction was heated in an oil-bath at 80° C. for 16 h. It was then cooled to rt and the inorganics were filtered off. The filter cake was washed with 1,4-dioxane and a solution of 5% MeOH in CH₂Cl₂. The combined filtrate was concentrated under reduced pressure to near dryness. The resultant residue was diluted with water and extracted with a 5% solution of MeOH in CH₂Cl₂ (3×60 mL) The combined organics were washed with brine. The organic phase was dried over anhydrous magnesium sulfate, filtered, concentrated under reduced pressure and purified by silica gel chromatography (240 g Thomson BIOTAGE® column, eluting with a gradient of 5-20% MeOH in CH₂Cl₂) to provide the desired product (0.15 g, 6.72% yield) a brown solid. HPLC Ret. Time 2.192 min (Method H). MS(ES): m/z=414.20 [M+H]⁺.

Scheme 14

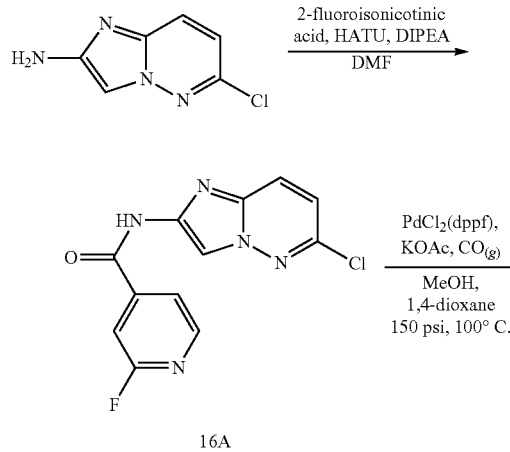

16A

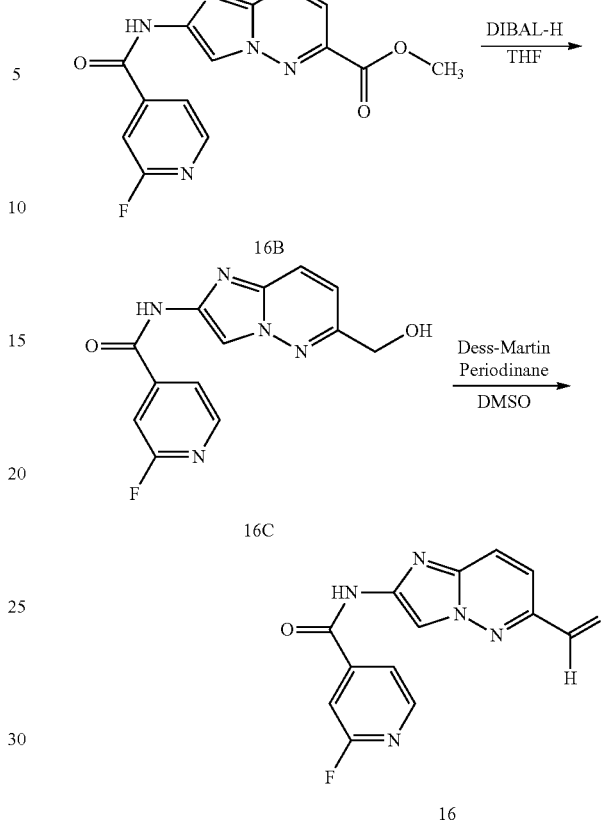

Intermediate 16

2-Fluoro-N-(6-formylimidazo[1,2-b]pyridazin-2-yl)isonicotinamide

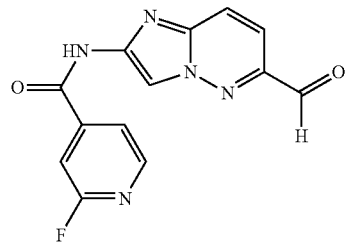 [SMILES: O=Cc1ccc2nc(NC(=O)c3ccnc(F)c3)cn2n1]

Intermediate 16A: N-(6-Chloroimidazo[1,2-b]pyridazin-2-yl)-2-fluoroisonicotinamide

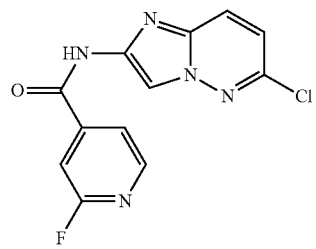 [SMILES: O=C(Nc1cn2nc(Cl)ccc2n1)c1ccnc(F)c1]

DMF (90 mL) and DIPEA (6.22 mL, 35.6 mmol) were added to a mixture of 6-chloroimidazo[1,2-b]pyridazin-2-amine (3.00 g, 17.80 mmol) and 2-fluoroisonicotinic acid (2.76 g, 19.57 mmol). HATU (7.78 g, 20.46 mmol) was added, and the reaction was stirred at room temperature for 4.5 h. The reaction was diluted with water to 1 L total volume, and the resulting solids were filtered off and dried in a warm vacuum oven to provide 16A (5.31 g, 100%). MS(ES): m/z=292.1 [M+H]$^+$. HPLC retention time (Method D): 1.842 min. $^1$H NMR (400 MHz, DMSO-d$_6$) δ 11.93 (s, 1H), 8.53 (s, 1H), 8.47 (d, J=5.0 Hz, 1H), 8.18 (dd, J=9.5, 0.5 Hz, 1H), 7.95 (dt, J=5.1, 1.6 Hz, 1H), 7.80 (s, 1H), 7.43 (d, J=9.3 Hz, 1H).

Intermediate 16B: 2-Fluoro-N-(6-formylimidazo[1,2-b]pyridazin-2-yl)isonicotinamide

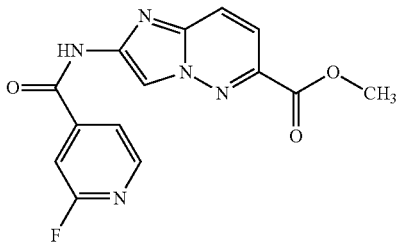 [SMILES: COC(=O)c1ccc2nc(NC(=O)c3ccnc(F)c3)cn2n1]

In a steel Parr pressure reactor, dioxane (170 mL) and MeOH (30 mL) were added to a mixture of 16A (5.00 g, 17.14 mmol), KOAc (6.73 g, 68.6 mmol), and PdCl$_2$(dppf) (2.509 g, 3.43 mmol). The reactor was pressurized to 150 psi with carbon monoxide and heated to 100° C. overnight with stirring. The reaction was cooled to room temperature and the reactor was depressurized. The reaction was diluted with methanol to a total volume of 600 mL and filtered. The filtrate was concentrated in vacuo, and the residue was triturated in 4:1 DCM/hexanes. The solids were filtered off, then suspended in water and re-filtered. The solids were dried to give 16B (3.90 g, 72%). MS(ES): m/z=316.1 [M+H]$^+$. HPLC retention time (Method D): 1.670 min. $^1$H NMR (400 MHz, DMSO-d$_6$) δ 12.02 (br. s., 1H), 8.63 (s, 1H), 8.48 (d, J=5.3 Hz, 1H), 8.22 (d, J=9.3 Hz, 1H), 7.97 (d, J=5.0 Hz, 1H), 7.84-7.76 (m, 2H), 3.98 (s, 3H).

Intermediate 16C: 2-Fluoro-N-(6-(hydroxymethyl)imidazo[1,2-b]pyridazin-2-yl)isonicotinamide

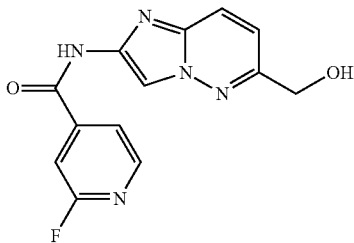 [SMILES: O=C(Nc1cn2nc(CO)ccc2n1)c1ccnc(F)c1]

A suspension of 16B (3.58 g, 11.36 mmol) in THF (120 mL) was cooled in a dry ice/acetonitrile bath. DIBAL-H (1.0 M/CH$_2$Cl$_2$) (39.7 mL, 39.7 mmol) was slowly added, and the reaction was stirred cold for 30 min., then warmed to rt for 3 h. The reaction was re-cooled in the dry ice/acetonitrile bath and quenched by slow addition of 1 N NaOH (15 mL). Water (300 mL) and EtOAc (300 mL) were added. The mixture was filtered over CELITE®. The layers of the filtrate were separated, and the aqueous layer was extracted with more EtOAc (300 mL) The combined organics were washed with brine (500 mL), dried (MgSO$_4$), filtered, and concentrated in vacuo to give 16C (2.82 g, 86%). MS(ES): m/z=288.1 [M+H]$^+$. HPLC retention time (Method D): 1.447 min. $^1$H NMR (400 MHz, DMSO-d$_6$) δ 11.83 (br. s., 1H), 8.47 (d, J=5.3 Hz, 1H), 8.43 (d, J=0.5 Hz, 1H), 8.06 (d, J=9.3 Hz, 1H), 7.96 (dt, J=5.1, 1.7 Hz, 1H), 7.80 (s, 1H), 7.36 (d, J=9.3 Hz, 1H), 5.72 (t, J=6.1 Hz, 1H), 4.63 (d, J=6.0 Hz, 2H).

Intermediate 16: 2-Fluoro-N-(6-formylimidazo[1,2-b]pyridazin-2-yl)isonicotinamide

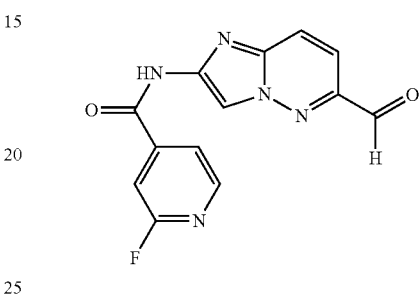

Dess-Martin Periodinane (4.98 g, 11.74 mmol) was added to a solution of 16C (2.81 g, 9.78 mmol) in DMSO (70 mL). After 1 h, the reaction was diluted with water (1 L). The solids were filtered off and dried in a warm vacuum oven, then triturated in ethanol to provide Intermediate 16 (2.29 g, 82%). MS(ES): m/z=284.2 [M–H]$^-$. HPLC retention time (Method D): 1.570 min. $^1$H NMR (500 MHz, DMSO-d$_6$) δ 12.03 (s, 1H), 10.00 (s, 1H), 8.67 (s, 1H), 8.47 (d, J=5.2 Hz, 1H), 8.24 (d, J=9.3 Hz, 1H), 7.96 (d, J=5.0 Hz, 1H), 7.81 (s, 1H), 7.68 (d, J=9.3 Hz, 1H).

Compound 229

2-Fluoro-N-(6-(4-(4-fluorophenyl)-1-propyl-1H-imidazol-5-yl)imidazo[1,2-b]pyridazin-2-yl)isonicotinamide

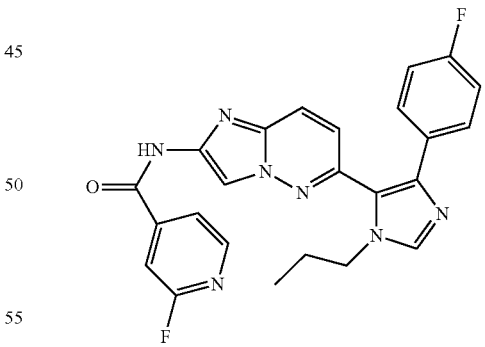

DMF (600 μl) was added to Intermediate 16 (40 mg, 0.140 mmol) and propan-1-amine (11.05 mg, 0.187 mmol). The reaction was stirred overnight at room temperature, then 1-fluoro-4-(isocyano(tosyl)methyl)benzene (27.0 mg, 0.093 mmol) and K$_2$CO$_3$ (16.80 mg, 0.122 mmol) were added. The reaction was stirred overnight, then diluted with DMF (1.4 mL) and filtered. The reaction mixture was purified by prep. HPLC to provide Compound 229 (17.3 mg, 37.9%). MS(ES): m/z=460.3 [M+H]$^+$. HPLC retention time (Method B): 2.54 min. $^1$H NMR (500 MHz, DMSO-d$_6$) δ 11.95 (br.

s., 1H), 8.59 (s, 1H), 8.49 (d, J=4.9 Hz, 1H), 8.09 (d, J=9.5 Hz, 1H), 8.00 (s, 1H), 7.98 (d, J=5.2 Hz, 1H), 7.82 (s, 1H), 7.53-7.46 (m, 2H), 7.19-7.10 (m, 3H), 4.10 (t, J=7.2 Hz, 2H), 1.62 (sxt, J=7.3 Hz, 2H), 0.79 (t, J=7.3 Hz, 3H).

The following compounds in Table 32 were prepared by the procedure described for the preparation of compound 229 using Intermediate 16 with the corresponding amines and TosMIC reagents.

TABLE 32

| Compound No. | Structure | Name | [M + H]⁺ | Retention Time | HPLC Method |
|---|---|---|---|---|---|
| 230 | 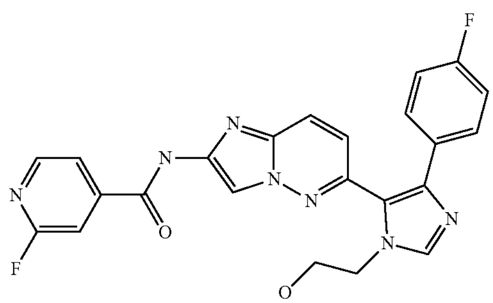 [SMILES: O=C(Nc1cn2nc(-c3c(-c4ccc(F)cc4)ncn3CCO)ccc2n1)c1ccnc(F)c1] | 2-fluoro-N-(6-(4-(4-fluorophenyl)-1-(2-hydroxyethyl)-1H-imidazol-5-yl)imidazo[1,2-b]pyridazin-2-yl)isonicotinamide | 462.3 | 3.55 | B |
| 231 | 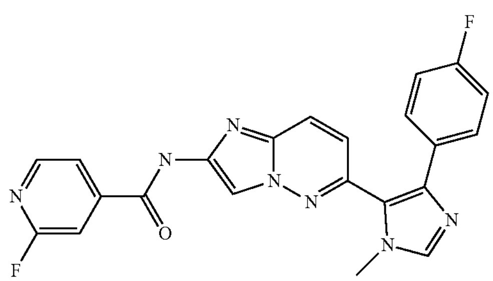 [SMILES: Cn1cnc(-c2ccc(F)cc2)c1-c1ccc2nc(NC(=O)c3ccnc(F)c3)cn2n1] | 2-fluoro-N-(6-(4-(4-fluorophenyl)-1-methyl-1H-imidazol-5-yl)imidazo[1,2-b]pyridazin-2-yl)isonicotinamide | 432.1 | 2.31 | B |
| 232 | 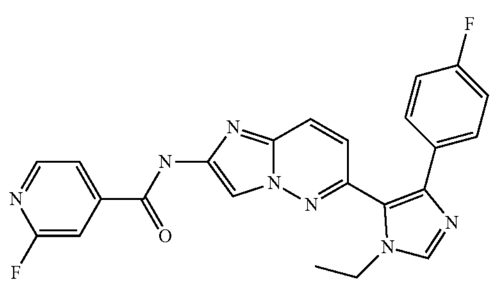 [SMILES: CCn1cnc(-c2ccc(F)cc2)c1-c1ccc2nc(NC(=O)c3ccnc(F)c3)cn2n1] | N-(6-(1-ethyl-4-(4-fluorophenyl)-1H-imidazol-5-yl)imidazo[1,2-b]pyridazin-2-yl)-2-fluoroisonicotinamide | 446.2 | 2.42 | B |
| 233 | 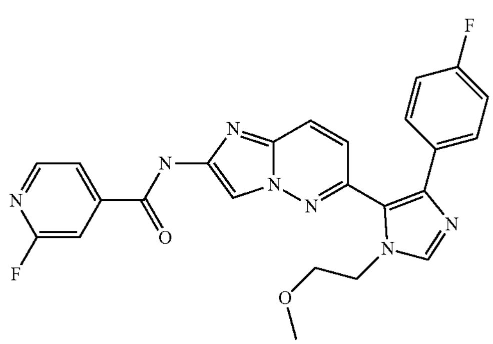 [SMILES: COCCn1cnc(-c2ccc(F)cc2)c1-c1ccc2nc(NC(=O)c3ccnc(F)c3)cn2n1] | 2-fluoro-N-(6-(4-(4-fluorophenyl)-1-(2-methoxyethyl)-1H-imidazol-5-yl)imidazo[1,2-b]pyridazin-2-yl)isonicotinamide | 476.3 | 2.37 | B |

TABLE 32-continued

| Compound No. | Structure | Name | [M + H]+ | Retention Time | HPLC Method |
|---|---|---|---|---|---|
| 234 | 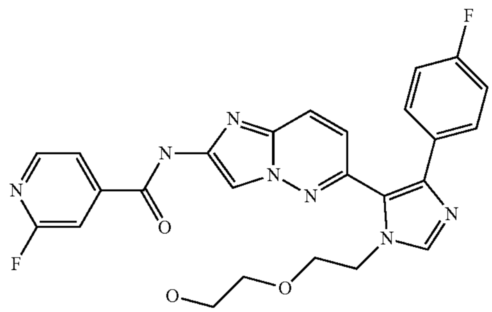 [SMILES: O=C(Nc1cn2nc(-c3c(-c4ccc(F)cc4)ncn3CCOCCO)ccc2n1)c1ccnc(F)c1] | 2-fluoro-N-(6-(4-(4-fluorophenyl)-1-(2-(2-hydroxyethoxy)ethyl-1H-imidazol-5-yl)imidazo[1,2-b]pyridazin-2-yl)isonicotinamide | 506.3 | 2.16 | B |
| 235 | 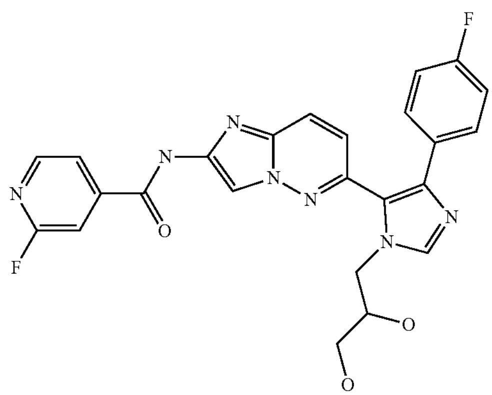 [SMILES: O=C(Nc1cn2nc(-c3c(-c4ccc(F)cc4)ncn3CC(O)CO)ccc2n1)c1ccnc(F)c1] | N-(6-(1-(2,3-dihydroxypropyl)-4-(4-fluorophenyl)-1H-imidazol-5-yl)imidazo[1,2-b]pyridazin-2-yl)-2-fluoroisonicotinamide, dimethylformamide | 492.2 | 2.04 | B |
| 236 | 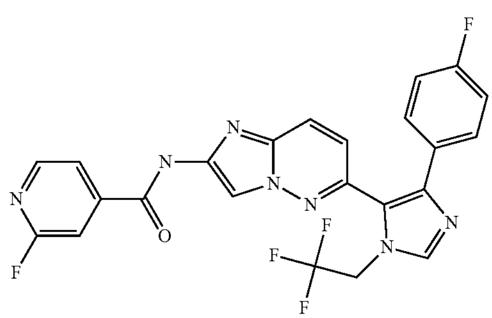 [SMILES: O=C(Nc1cn2nc(-c3c(-c4ccc(F)cc4)ncn3CC(F)(F)F)ccc2n1)c1ccnc(F)c1] | 2-fluoro-N-(6-(4-(4-fluorophenyl)-1-(2,2,2-trifluoroethyl)-1H-imidazol-5-yl)imidazo[1,2-b]pyridazin-2-yl-isonicotinamide | 500.3 | 2.54 | B |
| 237 | 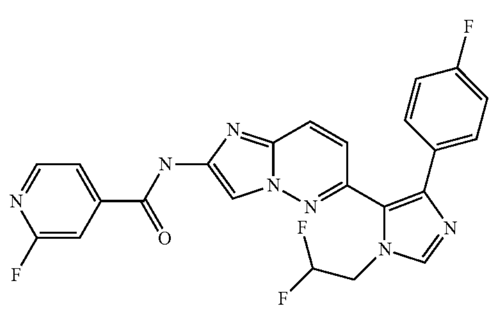 [SMILES: O=C(Nc1cn2nc(-c3c(-c4ccc(F)cc4)ncn3CC(F)F)ccc2n1)c1ccnc(F)c1] | N-(6-(1-(2,2-difluoroethyl)-4-(4-fluorophenyl)-1H-imidazol-5-yl)imidazo[1,2-b]pyridazin-2-yl)-2-fluoroisonicotinamide | 482.2 | 2.43 | B |

| Compound No. | Structure | Name | [M + H]+ | Retention Time | HPLC Method |
|---|---|---|---|---|---|
| 238 | 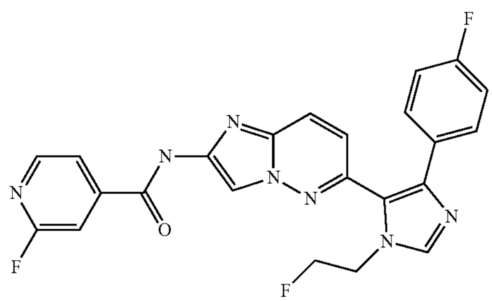 | 2-fluoro-N-(6-(1-(2-fluoroethyl)-4-(4-fluorophenyl)-1H-imidazol-5-yl)imidazo[1,2-b]pyridazin-2-yl)isonicotinamide | 463.1 | 2.30 | B |
| 239 | 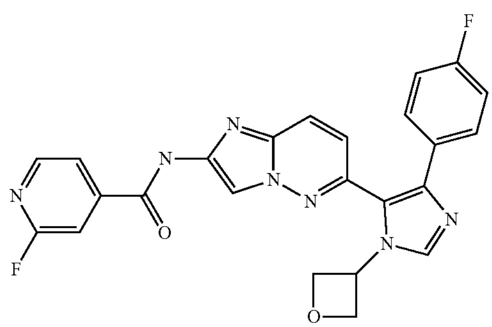 [SMILES: O=C(Nc1cn2nc(-c3c(-c4ccc(F)cc4)ncn3C3COC3)ccc2n1)c1ccnc(F)c1] | 2-fluoro-N-(6-(4-(4-fluorophenyl)-1-(oxetan-3-yl)-1H-imidazol-5-yl)imidazo[1,2-b]pyridazin-2-yl)isonicotinamide | 474.2 | 2.23 | B |
| 240 | 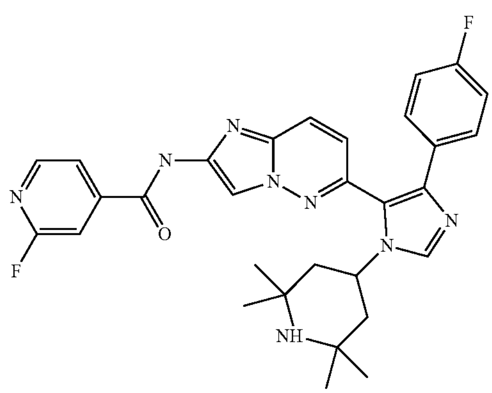 [SMILES: CC1(C)CC(n2cnc(-c3ccc(F)cc3)c2-c2ccc3nc(NC(=O)c4ccnc(F)c4)cn3n2)CC(C)(C)N1] | 2-fluoro-N-(6-(4-(4-fluorophenyl-1-(2,2,6,6-tetramethylpiperidin-4-yl)-1H-imidazol-5-yl)imidazo[1,2-b]pyridazin-2-yl)isonicotinamide | 556.3 | 2.01 | B |
| 241 | 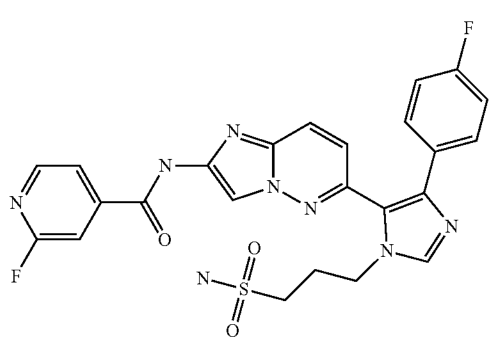 [SMILES: NS(=O)(=O)CCCn1cnc(-c2ccc(F)cc2)c1-c1ccc2nc(NC(=O)c3ccnc(F)c3)cn2n1] | 2-fluoro-N-(6-(4-(4-fluorophenyl-1-(3-sulfamoylpropyl)-1H-imidazol-5-yl)imidazo[1,2-b]pyridazin-2-yl)isonicotinamide | 539.4 | 2.26 | B |

TABLE 32-continued

| Compound No. | Structure | Name | [M + H]+ | Retention Time | HPLC Method |
|---|---|---|---|---|---|
| 242 | 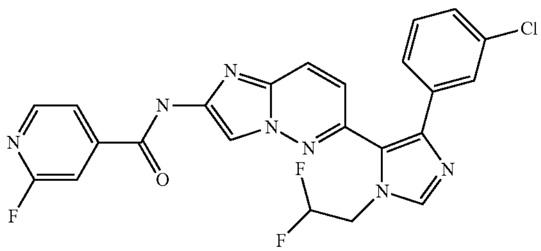 [SMILES: O=C(Nc1cn2nc(-c3c(-c4cccc(Cl)c4)ncn3CC(F)F)ccc2n1)c1ccnc(F)c1] | N-(6-(4-(3-chlorophenyl)-1-(2,2-difluoroethyl)-1H-imidazol-5-yl)imidazo[1,2-b]pyridazin-2-yl)-2-fluoroisonicotinamide | 498.3, 500.3 | 2.73 | B |
| 243 | 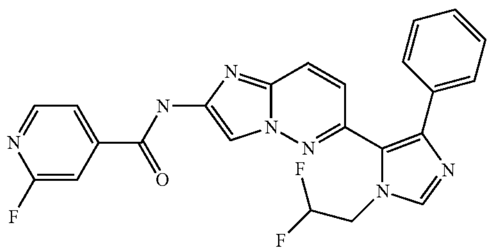 [SMILES: O=C(Nc1cn2nc(-c3c(-c4ccccc4)ncn3CC(F)F)ccc2n1)c1ccnc(F)c1] | N-(6-(1-(2,2-difluoroethyl)-4-phenyl-1H-imidazol-5-yl)imidazo[1,2-b]pyridazin-2-yl)-2-fluoroisonicotinamide | 464.4 | 2.41 | B |
| 244 | 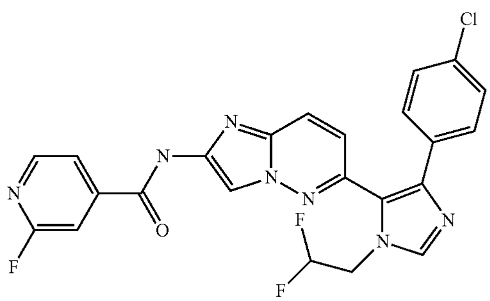 | N-(6-(4-(4-chlorophenyl)-1-(2,2-difluoroethyl)-1H-imidazol-5-yl)imidazo[1,2-b]pyridazin-2-yl)-2-fluoroisonicotinamide | 498.3, 500.3 | 3.07 | B |
| 245 | 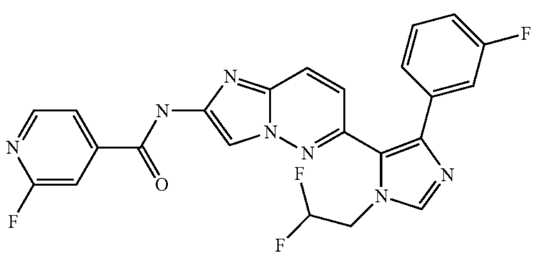 [SMILES: O=C(Nc1cn2nc(-c3c(-c4cccc(F)c4)ncn3CC(F)F)ccc2n1)c1ccnc(F)c1] | N-(6-(1-(2,2-difluoroethyl)-4-(3-fluorophenyl)-1H-imidazol-5-yl)imidazo[1,2-b]pyridazin-2-yl)-2-fluoroisonicotinamide | 482.2 | 2.39 | B |
| 246 | 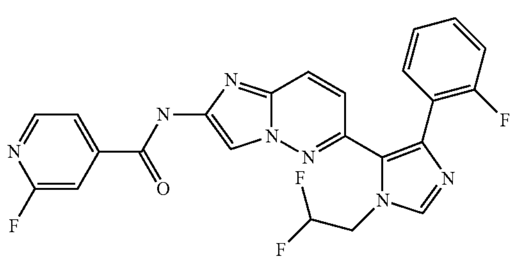 [SMILES: O=C(Nc1cn2nc(-c3c(-c4ccccc4F)ncn3CC(F)F)ccc2n1)c1ccnc(F)c1] | N-(6-(1,(2,2-difluoroethyl)-4-(2-fluorophenyl)-1H-imidazol-5-yl)imidazo[1,2-b]pyridazin-2-yl)-2-fluoroisonicotinamide | 482.3 | 2.27 | B |

TABLE 32-continued

| Compound No. | Structure | Name | [M + H]+ | Retention Time | HPLC Method |
|---|---|---|---|---|---|
| 247 | 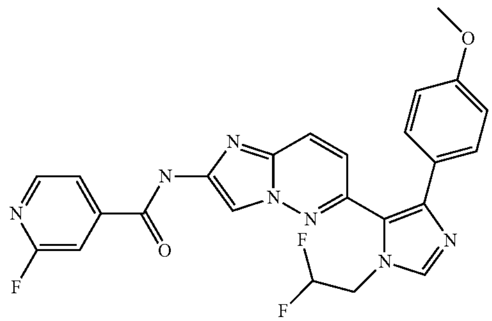 [SMILES: COc1ccc(-c2ncn(CC(F)F)c2-c2ccc3nc(NC(=O)c4ccnc(F)c4)cn3n2)cc1] | N-(6-(1-(2,2-difluoroethyl)-4-(4-methoxyphenyl)-1H-imidazol-5-yl)imidazo[1,2-b]pyridazin-2-yl)-2-fluoroisonicotinamide | 494.9 | 2.33 | B |
| 248 | | N-(6-(1,2-dimethyl-4-(p-tolyl)-1H-imidazol-5-yl)imidazo[1,2-b]pyridazin-2-yl)-2-fluoroisonicotinamide | 442.30 | 2.34 | B |
| 249 | 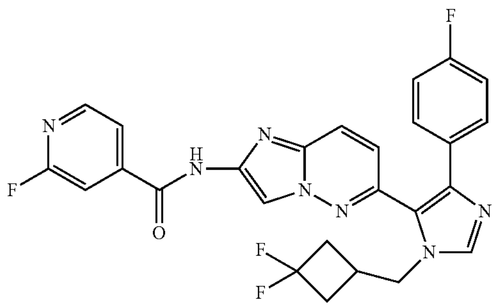 [SMILES: O=C(Nc1cn2nc(-c3c(-c4ccc(F)cc4)ncn3CC3CC(F)(F)C3)ccc2n1)c1ccnc(F)c1] | N-(6-(1-((3,3-difluorocyclobutyl)methyl)-4-(4-fluorophenyl)-1H-imidazol-5-yl)imidazo[1,2-b]pyridazin-2-yl)-2-fluoroisonicotinamide | 522.40 | 3.84 | C |
| 250 | 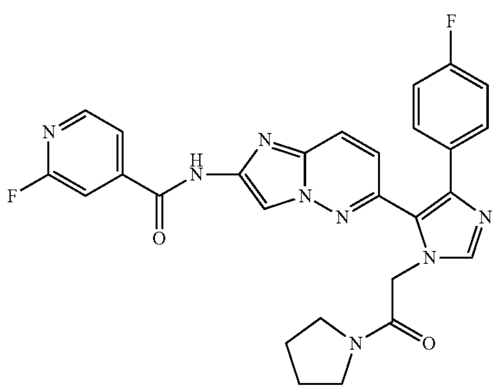 [SMILES: O=C(Nc1cn2nc(-c3c(-c4ccc(F)cc4)ncn3CC(=O)N3CCCC3)ccc2n1)c1ccnc(F)c1] | 2-fluoro-N-(6-(4-(4-fluorophenyl)-1-(2-oxo-2-(1-pyrrolidinyl)ethyl)-1H-imidazol-5-yl)imidazo[1,2-b]pyridazin-2-yl)isonicotinamide | 529.30 | 3.23 | C |
| 251 | 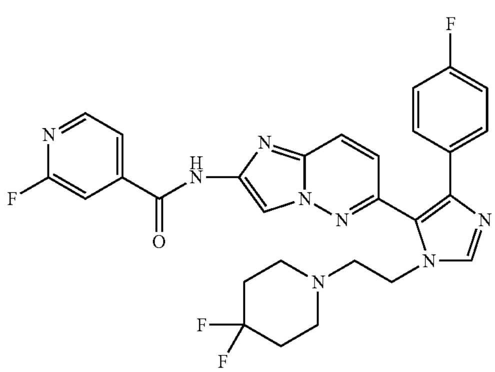 [SMILES: O=C(Nc1cn2nc(-c3c(-c4ccc(F)cc4)ncn3CCN3CCC(F)(F)CC3)ccc2n1)c1ccnc(F)c1] | N-(6-(1-(2-(4,4-difluoro-1-piperidinyl)ethyl)-4-(4-fluorophenyl)-1H-imidazol-5-yl)imidazo[1,2-b]pyridazin-2-yl)-2-fluoroisonicotinamide | 565.30 | 3.97 | C |

TABLE 32-continued

| Compound No. | Structure | Name | [M + H]+ | Retention Time | HPLC Method |
|---|---|---|---|---|---|
| 252 | 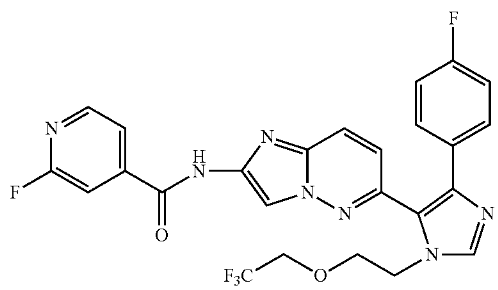 [SMILES: O=C(Nc1cn2nc(-c3c(-c4ccc(F)cc4)ncn3CCOCC(F)(F)F)ccc2n1)c1ccnc(F)c1] | 2-fluoro-N-(6-(4-(4-fluorophenyl)-1-(2-(2,2,2-trifluoroethoxy)ethyl)-1H-imidazol-5-yl)imidazo[1,2-b]pyridazin-2-yl)isonicotinamide | 544.30 | 3.85 | C |
| 253 | 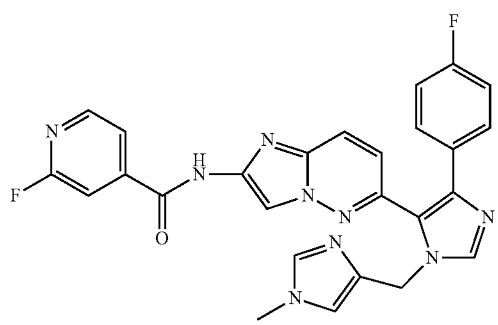 [SMILES: Cn1cnc(Cn2cnc(-c3ccc(F)cc3)c2-c2ccc3nc(NC(=O)c4ccnc(F)c4)cn3n2)c1] | 2-fluoro-N-(6-(4-(4-fluorophenyl)-1-((1-methyl-1H-imidazol-4-yl)methyl)-1H-imidazol-5-yl)imidazo[1,2-b]pyridazin-2-yl)isonicotinamide | 512.30 | 3.56 | C |
| 254 | 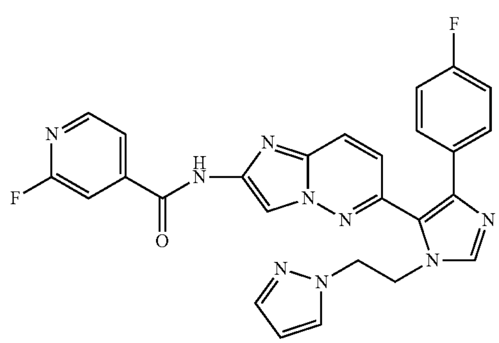 [SMILES: O=C(Nc1cn2nc(-c3c(-c4ccc(F)cc4)ncn3CCn3cccn3)ccc2n1)c1ccnc(F)c1] | 2-fluoro-N-(6-(4-(4-fluorophenyl)-1-(2-(1H-pyrazol-1-yl)ethyl)-1H-imidazol-5-yl)imidazo[1,2-b]pyridazin-2-yl)isonicotinamide | 512.30 | 2.38 | B |
| 255 | 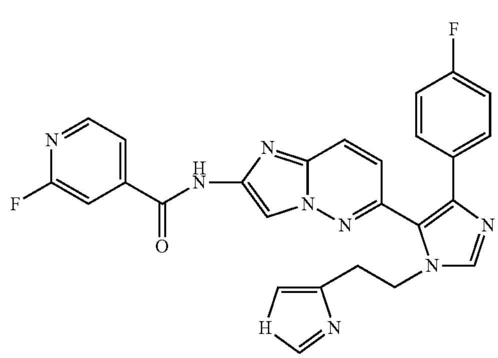 | 2-fluoro-N-(6-(4-(4-fluorophenyl)-1-(2-(1H-imidazol-4-yl)ethyl)-1H-imidazol-5-yl)imidazo[1,2-b]pyridazin-2-yl)isonicotinamide | 512.30 | 3.53 | C |

TABLE 32-continued

| Compound No. | Structure | Name | [M + H]+ | Retention Time | HPLC Method |
|---|---|---|---|---|---|
| 256 | 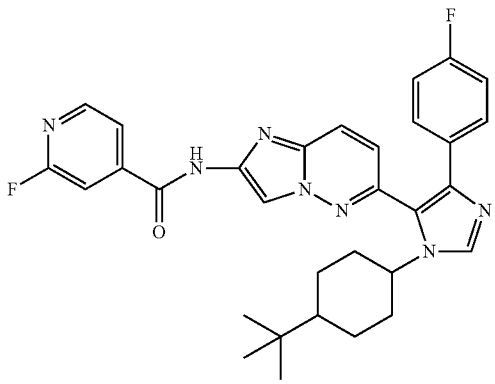 [SMILES: CC(C)(C)C1CCC(n2cnc(-c3ccc(F)cc3)c2-c2ccc3nc(NC(=O)c4ccnc(F)c4)cn3n2)CC1] | N-(6-(1-(4-tert-butylcyclohexyl)-4-(4-fluorophenyl)-1H-imidazol-5-yl)imidazo[1,2-b]pyridazin-2-yl)-2-fluoroisonicotinamide | 556.50 | 4.56 | C |
| 257 | 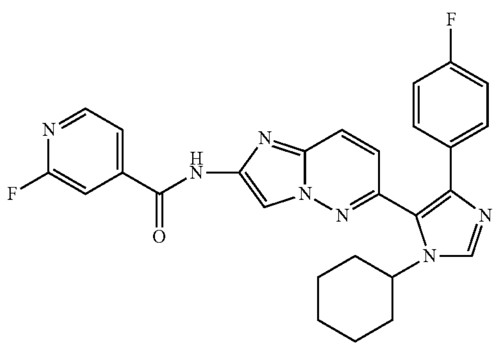 [SMILES: O=C(Nc1cn2nc(-c3c(-c4ccc(F)cc4)ncn3C3CCCCC3)ccc2n1)c1ccnc(F)c1] | N-(6-(1-cyclohexyl-4-(4-fluorophenyl)-1H-imidazol-5-yl)imidazo[1,2-b]pyridazin-2-yl)-2-fluoroisonicotinamide | 500.40 | 2.84 | B |
| 258 | 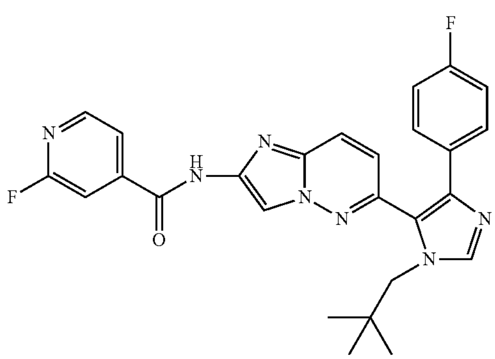 [SMILES: CC(C)(C)Cn1cnc(-c2ccc(F)cc2)c1-c1ccc2nc(NC(=O)c3ccnc(F)c3)cn2n1] | N-(6-(1-(2,2-dimethylpropyl)-4-(4-fluorophenyl)-1H-imidazol-5-yl)imidazo[1,2-b]pyridazin-2-yl)-2-fluoroisonicotinamide | 488.40 | 2.84 | B |
| 259 | 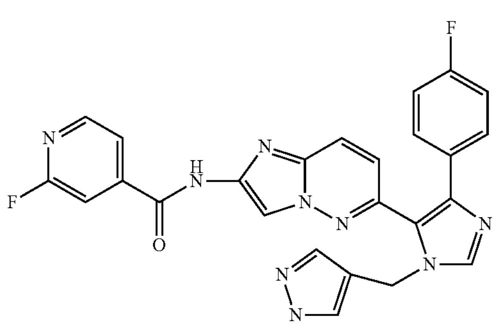 [SMILES: O=C(Nc1cn2nc(-c3c(-c4ccc(F)cc4)ncn3Cc3cn[nH]c3)ccc2n1)c1ccnc(F)c1] | 2-fluoro-N-(6-(4-(4-fluorophenyl)-1-((1-methyl-1H-pyrazol-4-yl)methyl)-1H-imidazol-5-yl)imidazo[1,2-b]pyridazin-2-yl)isonicotinamide | 512.20 | 3.60 | C |

TABLE 32-continued

| Compound No. | Structure | Name | [M + H]+ | Retention Time | HPLC Method |
|---|---|---|---|---|---|
| 260 | 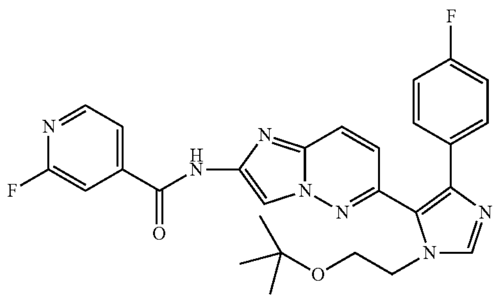 [SMILES: CC(C)(C)OCCn1cnc(-c2ccc(F)cc2)c1-c1ccc2nc(NC(=O)c3ccnc(F)c3)cn2n1] | N-(6-(1-(2-tert-butoxyethyl)-4-(4-fluorophenyl)-1H-imidazol-5-yl)imidazo[1,2-b]pyridazin-2-yl)-2-fluoroisonicotinamide | 518.30 | 2.79 | B |
| 261 | 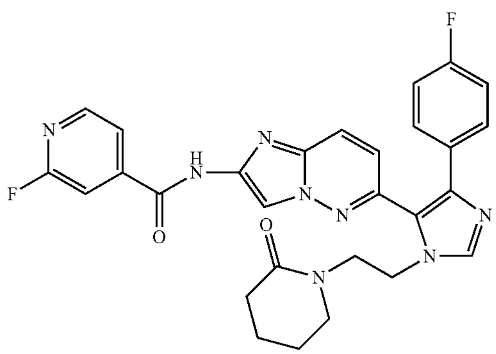 [SMILES: O=C(Nc1cn2nc(-c3c(-c4ccc(F)cc4)ncn3CCN3CCCCC3=O)ccc2n1)c1ccnc(F)c1] | 2-fluoro-N-(6-(4-(4-fluorophenyl)-1-(2-(2-oxopiperidin-1-yl)ethyl)-1H-imidazol-5-yl)imidazo[1,2-b]pyridazin-2-yl)isonicotinamide | 543.40 | 2.26 | B |
| 262 | 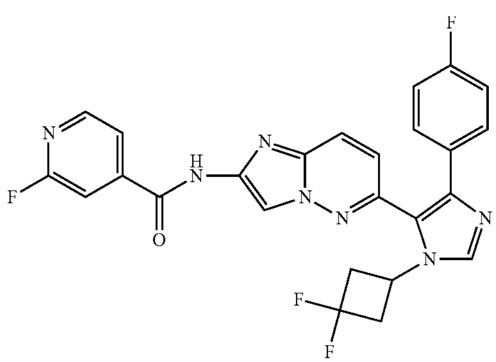 [SMILES: O=C(Nc1cn2nc(-c3c(-c4ccc(F)cc4)ncn3C3CC(F)(F)C3)ccc2n1)c1ccnc(F)c1] | N-(6-(1-(3,3-difluorocyclobutyl)-4-(4-fluorophenyl)-1H-imidazol-5-yl)imidazo[1,2-b]pyridazin-2-yl)-2-fluoroisonicotinamide | 508.20 | 2.60 | B |
| 263 | 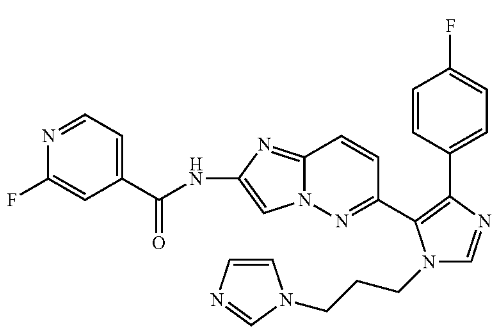 [SMILES: O=C(Nc1cn2nc(-c3c(-c4ccc(F)cc4)ncn3CCCn3ccnc3)ccc2n1)c1ccnc(F)c1] | 2-fluoro-N-(6-(4-(4-fluorophenyl)-1-(3-(1H-imidazol-1-yl)propyl)-1H-imidazol-5-yl)imidazo[1,2-b]pyridazin-2-yl)isonicotinamide | 526.30 | 2.15 | B |

TABLE 32-continued

| Compound No. | Structure | Name | [M + H]+ | Retention Time | HPLC Method |
|---|---|---|---|---|---|
| 264 | 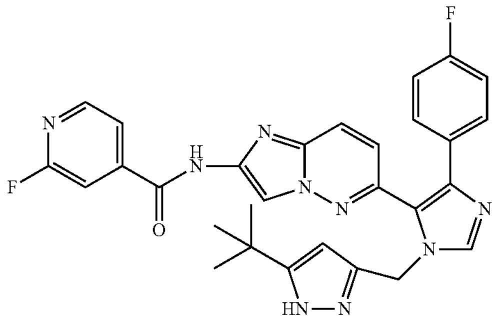 [SMILES: CC(C)(C)c1cc(Cn2cnc(-c3ccc(F)cc3)c2-c2ccc3nc(NC(=O)c4ccnc(F)c4)cn3n2)n[nH]1] | N-(6-(1-((5-tert-butyl-1H-pyrazol-3-yl)methyl)-4-(4-fluorophenyl)-1H-imidazol-5-yl)imidazo[1,2-b]pyridazin-2-yl)-2-fluoroisonicotinamide | 554.30 | 3.95 | C |
| 265 | 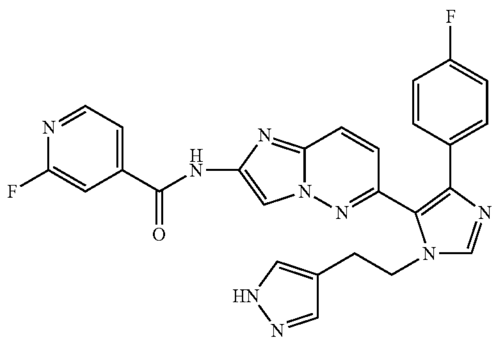 [SMILES: O=C(Nc1cn2nc(-c3c(-c4ccc(F)cc4)ncn3CCc3cn[nH]c3)ccc2n1)c1ccnc(F)c1] | 2-fluoro-N-(6-(4-(4-fluorophenyl)-1-(2-(1H-pyrazol-4-yl)ethyl-1H-imidazol-5-yl)imidazo[1,2-b]pyridazin-2-yl)isonicotinamide | 512.2 | 3.59 | C |
| 266 | 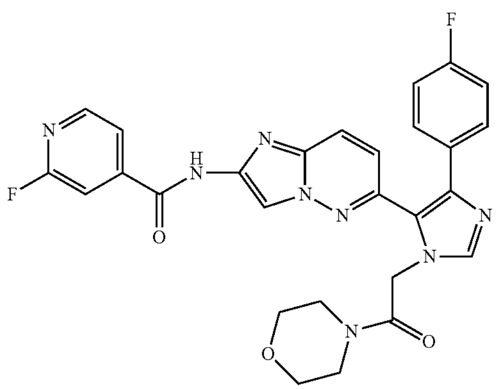 [SMILES: O=C(Nc1cn2nc(-c3c(-c4ccc(F)cc4)ncn3CC(=O)N3CCOCC3)ccc2n1)c1ccnc(F)c1] | 2-fluoro-N-(6-(4-(4-fluorophenyl)-1-(2-(4-morpholinyl)-2-oxoethyl)-1H-imidazol-5-yl)imidazo[1,2-b]pyridazin-2-yl)isonicotinamide | 545.30 | 2.10 | B |
| 267 | 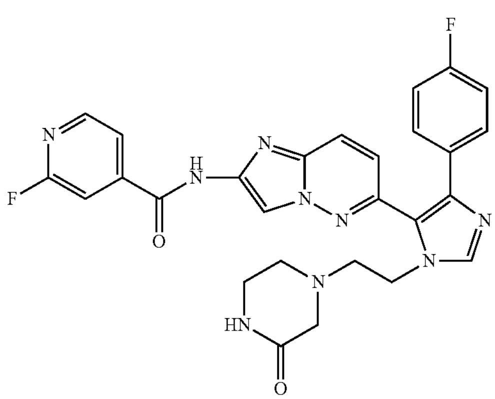 [SMILES: O=C1CN(CCn2cnc(-c3ccc(F)cc3)c2-c2ccc3nc(NC(=O)c4ccnc(F)c4)cn3n2)CCN1] | 2-fluoro-N-(6-(4-(4-fluorophenyl)-1-(2-(3-oxo-1-piperazinyl)ethyl)-1H-imidazol-5-yl)imidazo[1,2-b]pyridazin-2-yl)isonicotinamide | 544.30 | 3.49 | C |

TABLE 32-continued

| Compound No. | Structure | Name | [M + H]+ | Retention Time | HPLC Method |
|---|---|---|---|---|---|
| 268 | 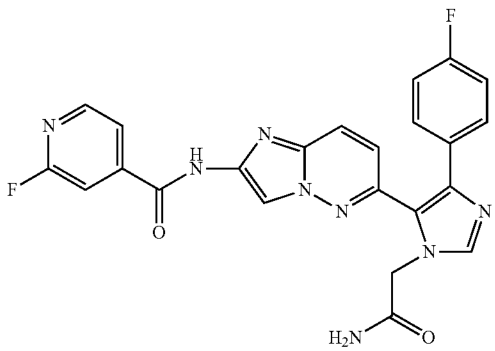 [SMILES: NC(=O)Cn1cnc(-c2ccc(F)cc2)c1-c1ccc2nc(NC(=O)c3ccnc(F)c3)cn2n1] | N-(6-(1-(2-amino-2-oxoethyl)-4-(4-fluorophenyl)-1H-imidazol-5-yl)imidazo[1,2-b]pyridazin-2-yl)-2-fluoroisonicotinamide | 475.20 | 2.07 | B |
| 269 | 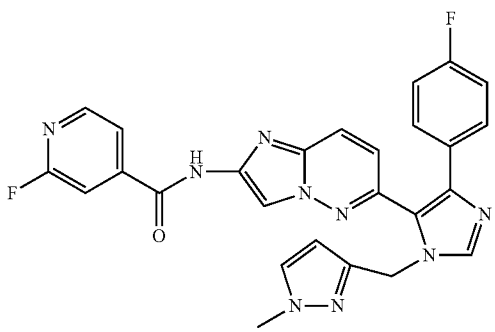 [SMILES: Cn1ccc(Cn2cnc(-c3ccc(F)cc3)c2-c2ccc3nc(NC(=O)c4ccnc(F)c4)cn3n2)n1] | 2-fluoro-N-(6-(4-(4-fluorophenyl)-1-((1-methyl-1H-pyrazol-3-yl)methyl)-1H-imidazol-5-yl)imidazo[1,2-b]pyridazin-2-yl)isonicotinamide | 512.20 | 2.29 | B |
| 270 | 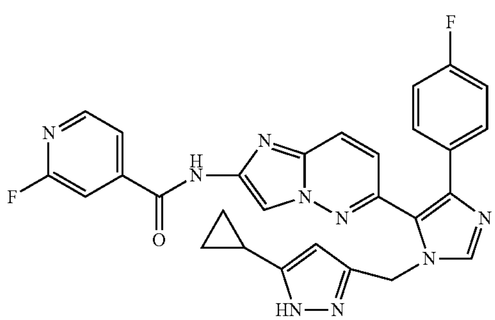 [SMILES: O=C(Nc1cn2nc(-c3c(-c4ccc(F)cc4)ncn3Cc3cc(C4CC4)[nH]n3)ccc2n1)c1ccnc(F)c1] | N-(6-(1-((5-cyclopropyl-1H-pyrazol-3-yl)methyl)-4-(4-fluorophenyl)-1H-imidazol-5-yl)imidazo[1,2-b]pyridazin-2-yl)-2-fluoroisonicotinamide | 538.20 | 3.80 | C |
| 271 | 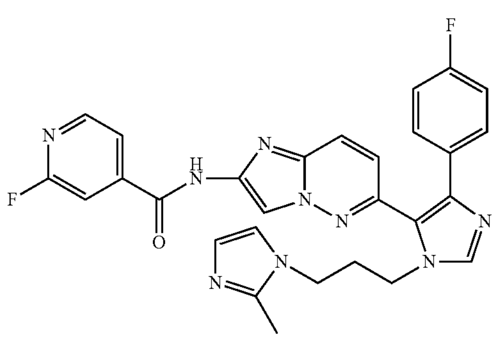 [SMILES: Cc1nccn1CCCn1cnc(-c2ccc(F)cc2)c1-c1ccc2nc(NC(=O)c3ccnc(F)c3)cn2n1] | 2-fluoro-N-(6-(4-(4-fluorophenyl)-1-(3-(2-methyl-1H-imidazol-1-yl)propyl)-1H-imidazol-5-yl)imidazo[1,2-b]pyridazin-2-yl)isonicotinamide | 540.20 | 3.60 | C |

TABLE 32-continued

| Compound No. | Structure | Name | [M + H]+ | Retention Time | HPLC Method |
|---|---|---|---|---|---|
| 272 | 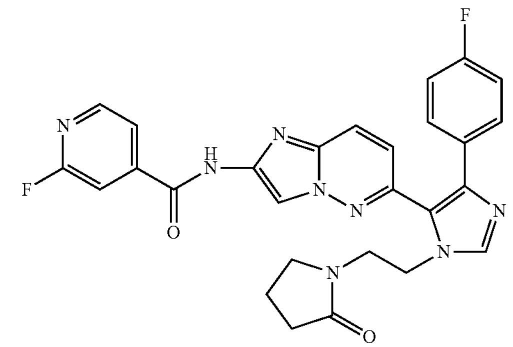 [SMILES: O=C(Nc1cn2nc(-c3c(-c4ccc(F)cc4)ncn3CCN3CCCC3=O)ccc2n1)c1ccnc(F)c1] | 2-fluoro-N-(6-(4-(4-fluorophenyl)-1-(2-(2-oxo-1-pyrrolidinyl)ethyl)-1H-imidazol-5-yl)imidazo[1,2-b]pyridazin-2-yl)isonicotinamide | 529.20 | 3.56 | B |

Scheme 15

17A

17B

17

Intermediate 17

N-(6-Formylimidazo[1,2-b]pyridazin-2-yl)pivalamide

Intermediate 17A:
N-(6-Chloroimidazo[1,2-b]pyridazin-2-yl)pivalamide

6-Chloroimidazo[1,2-b]pyridazin-2-amine (5.00 g, 29.7 mmol) was dissolved in DMA (50 mL). Pivaloyl chloride (4.38 mL, 35.6 mmol) was added, and the reaction was stirred at room temperature overnight. The reaction was diluted with water (700 mL), stirred vigorously, and the solids were filtered off and dried in a warm vacuum oven to give Intermediate 17A (6.44 g, 86%). MS(ES): m/z=253, 255 [M+H]+. HPLC retention time (Method D): 1.845 min. $^1$H NMR (400 MHz, DMSO-d$_6$) δ 10.58 (s, 1H), 8.33 (s, 1H), 8.07 (dd, J=9.3, 0.5 Hz, 1H), 7.35 (d, J=9.3 Hz, 1H), 1.25 (s, 9H).

Intermediate 17B: Methyl 2-pivalamidoimidazo[1,2-b]pyridazine-6-carboxylate

In a steel pressure reactor, Intermediate 17A (2.00 g, 7.91 mmol), PdCl$_2$(dppf) (1.158 g, 1.583 mmol), KOAc (3.11 g, 31.7 mmol), dioxane (60 mL), and MeOH (12 mL, 297 mmol) were combined. The reactor vessel was charged with ca 150 psi of carbon monoxide, then heated to 85° C. overnight. The reaction was cooled to room temperature, depressurized, diluted with MeOH and filtered over CELITE®. The residue was triturated in ether. The solids were filtered off, vigorously shaken in water (ca 200 mL) and filtered. The solids were dried in a warm vacuum oven overnight to give Intermediate 17B (1.34 g, 61%). MS(ES): m/z=277 [M+H]⁺. HPLC retention time (Method D): 1.695 min. ¹H NMR (400 MHz, DMSO-$d_6$) δ 10.69 (s, 1H), 8.12 (d, J=9.5 Hz, 1H), 7.74 (d, J=9.3 Hz, 1H), 3.96 (s, 3H), 1.27 (s, 9H).

Intermediate 17:
N-(6-Formylimidazo[1,2-b]pyridazin-2-yl)pivalamide

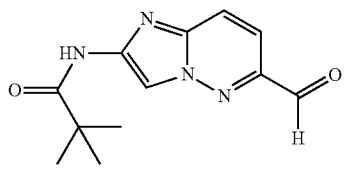 [SMILES: CC(C)(C)C(=O)Nc1cn2nc(C=O)ccc2n1]

A solution of Intermediate 17B (1.32 g, 4.78 mmol) in THF (50 mL) was cooled in a dry ice/acetone bath. DIBAL-H (1.0 M/dichloromethane) (23.89 mL, 23.89 mmol) was added slowly over 20 min. The reaction was stirred cold for 8 h. MeOH (11 mL) was slowly added (11 mL), and the reaction was stirred while slowly warming to room temperature overnight. The mixture was diluted with water (250 mL) and EtOAc (250 mL), shaken vigorously, and filtered over CELITE®. The layers of the filtrate were separated, and the aqueous layer was extracted with more EtOAc (200 mL). The combined organics were dried (MgSO₄), filtered, and concentrated in vacuo. The residue was purified silica gel chromatography (0 to 35% EtOAc/Hex) to give Intermediate 17 (583 mg, 49%). MS(ES): m/z=245 [M−H]⁻. HPLC retention time (Method D): 1.613 min. ¹H NMR (400 MHz, DMSO-$d_6$) δ 10.74 (s, 1H), 9.98 (d, J=0.8 Hz, 1H), 8.48 (s, 1H), 8.15 (d, J=9.5 Hz, 1H), 7.64 (d, J=9.3 Hz, 1H), 1.27 (s, 9H).

Compound 273

N-(6-(4-(4-Fluorophenyl)-1-propyl-1H-imidazol-5-yl)imidazo[1,2-b]pyridazin-2-yl)pivalamide

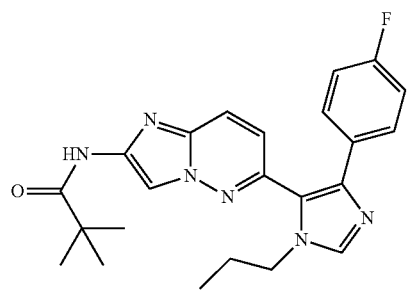 [SMILES: CCCn1cnc(-c2ccc(F)cc2)c1-c1ccc2nc(NC(=O)C(C)(C)C)cn2n1]

A solution of Intermediate 17 (50 mg, 0.162 mmol) and propan-1-amine (12.80 mg, 0.217 mmol) in DMF (600 µl) was stirred for 30 min at room temperature. 1-fluoro-4-(isocyano(tosyl)methyl)benzene (31.3 mg, 0.108 mmol) and K₂CO₃ (19.46 mg, 0.141 mmol) were added, and the reaction was stirred at room temperature overnight. The reaction was diluted with DMF (1.4 mL) and filtered. The reaction mixture was purified by prep. HPLC to provide Compound 273 (37.8 mg, 83%). MS(ES): m/z=421.3 [M+H]⁺. HPLC retention time (Method B): 2.65 min. ¹H NMR (500 MHz, DMSO-$d_6$) δ 10.59 (s, 1H), 8.39 (s, 1H), 8.00 (d, J=9.5 Hz, 1H), 7.98 (s, 1H), 7.48 (dd, J=8.7, 5.6 Hz, 1H), 7.14 (t, J=8.9 Hz, 1H), 7.07 (d, J=9.2 Hz, 1H), 4.06 (t, J=7.0 Hz, 1H), 1.59 (sxt, J=7.3 Hz, 1H), 1.27 (s, 5H), 0.78 (t, J=7.5 Hz, 1H).

The following compounds in Table 33 were prepared by the procedure described for the preparation of compound 273 using Intermediate 17 with the corresponding amines and TosMIC reagents.

TABLE 33

| Compound No. | Structure | Name | [M + H]⁺ | Retention Time | HPLC Method |
|---|---|---|---|---|---|
| 274 | 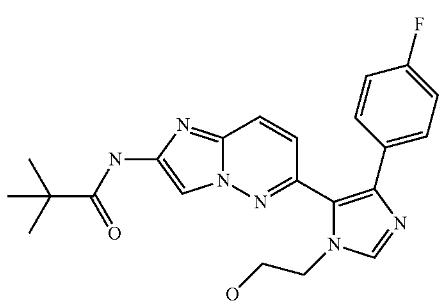 [SMILES: CC(C)(C)C(=O)Nc1cn2nc(-c3c(-c4ccc(F)cc4)ncn3CCO)ccc2n1] | N-(6-(4-(4-fluorophenyl)-1-(2-hydroxyethyl)-1H-imidazol-5-yl)imidazo[1,2-b]pyridazin-2-yl)pivalamide | 423.1 | 2.16 | B |

TABLE 33-continued

| Compound No. | Structure | Name | [M + H]+ | Retention Time | HPLC Method |
|---|---|---|---|---|---|
| 275 | 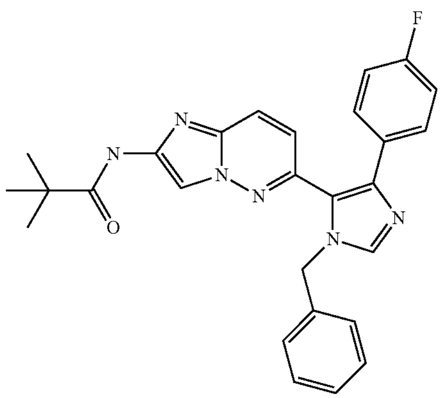 [SMILES: CC(C)(C)C(=O)Nc1cn2nc(-c3c(-c4ccc(F)cc4)ncn3Cc3ccccc3)ccc2n1] | N-(6-(1-benzyl-4-(4-fluorophenyl)-1H-imidazol-5-yl)imidazo[1,2-b]pyridazin-2-yl)pivalamide | 469.3 | 2.82 | B |
| 276 | 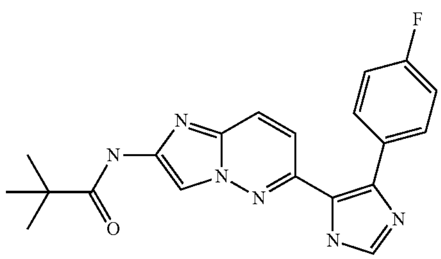 [SMILES: CC(C)(C)C(=O)Nc1cn2nc(-c3[nH]cnc3-c3ccc(F)cc3)ccc2n1] | N-(6-(4-(4-fluorophenyl)-1H-imidazol-5-yl)imidazo[1,2-b]pyridazin-2-yl)pivalamide | 379.2 | 2.28 | B |
| 277 | 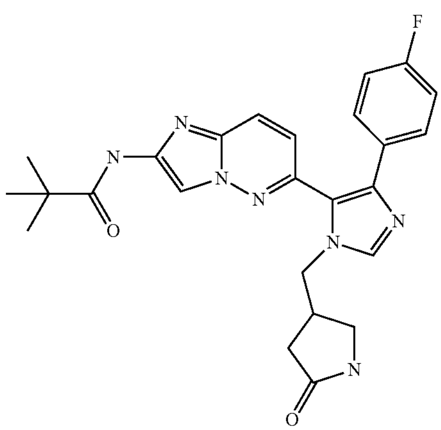 [SMILES: CC(C)(C)C(=O)Nc1cn2nc(-c3c(-c4ccc(F)cc4)ncn3CC3CNC(=O)C3)ccc2n1] | N-(6-(4-(4-fluorophenyl)-1-((5-oxo-pyrrolidin-3-yl)methyl)-1H-imidazol-5-yl)imidazo[1,2-b]pyridazin-2-yl)pivalamide | 476.2 | 2.22 | B |
| 278 | 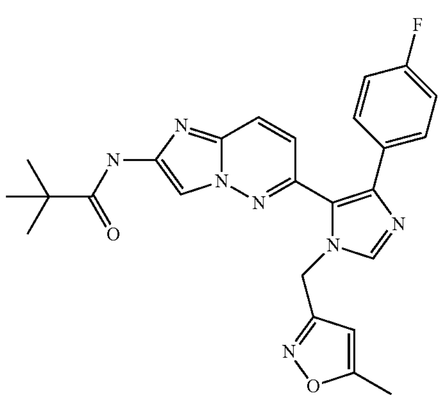 [SMILES: Cc1cc(Cn2cnc(-c3ccc(F)cc3)c2-c2ccc3nc(NC(=O)C(C)(C)C)cn3n2)no1] | N-(6-(4-(4-fluorophenyl)-1-((5-methyl-isoxazol-3-yl)ylmethyl)-1H-imidazol-5-yl)imidazo[1,2-b]pyridazin-2-yl)pivalamide | 474.2 | 2.53 | B |

TABLE 33-continued

| Compound No. | Structure | Name | [M + H]+ | Retention Time | HPLC Method |
|---|---|---|---|---|---|
| 279 | 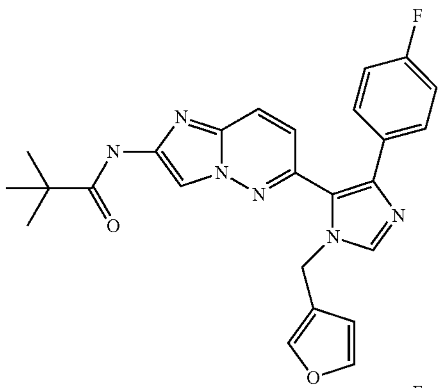 | N-(6-(4-(4-fluorophenyl)-1-(furan-3-ylmethyl)-1H-imidazol-5-yl)imidazo[1,2-b]pyridazin-2-yl)pivalamide | 459.4 | 2.66 | B |
| 280 | 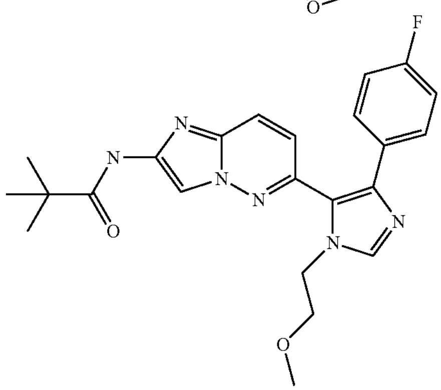 | N-(6-(4-(4-fluorophenyl)-1-(2-methoxyethyl)-1H-imidazol-5-yl)imidazo[1,2-b]pyridazin-2-yl)pivalamide | 437.2 | 2.48 | B |
| 281 | 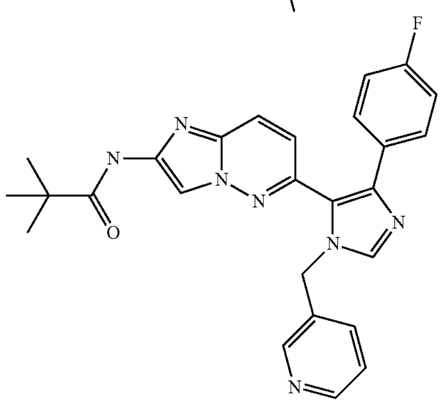 | N-(6-(4-(4-fluorophenyl)-1-(pyridin-3-ylmethyl)-1H-imidazol-5-yl)imidazo[1,2-b]pyridazin-2-yl)pivalamide | 470.1 | 2.35 | B |
| 282 | 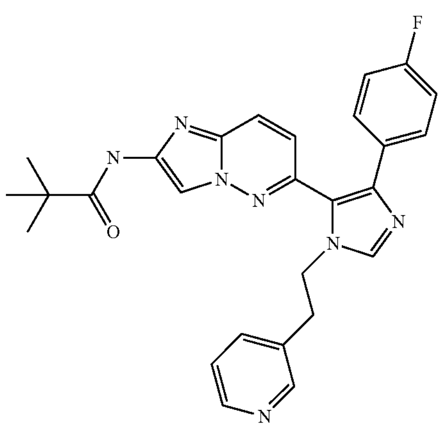 [SMILES: CC(C)(C)C(=O)Nc1cn2nc(-c3c(-c4ccc(F)cc4)ncn3CCc3cccnc3)ccc2n1] | N-(6-(4-(4-fluorophenyl)-1-(2-(pyridin-3-yl)ethyl)-1H-imidazol-5-yl)imidazo[1,2-b]pyridazin-2-yl)pivalamide | 484.2 | 2.39 | B |

TABLE 33-continued

| Compound No. | Structure | Name | [M + H]+ | Retention Time | HPLC Method |
|---|---|---|---|---|---|
| 283 | 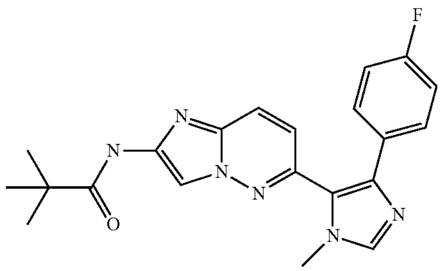 [SMILES: Cn1cnc(-c2ccc(F)cc2)c1-c1ccc2nc(NC(=O)C(C)(C)C)cn2n1] | N-(6-(4-(4-fluorophenyl)-1-methyl-1H-imidazol-5-yl)imidazo[1,2-b]pyridazin-2-yl)pivalamide | 393.1 | 2.36 | B |

Intermediate 18

N-((4-Fluorophenyl)(tosyl)methyl)acetamide

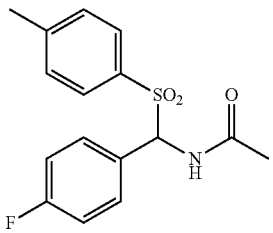 [SMILES: CC(=O)NC(c1ccc(F)cc1)S(=O)(=O)c1ccc(C)cc1]

Reference: WO 2011/051858

A solution of 4-fluorobenzaldehyde (1.5 g, 12.09 mmol), acetamide (1.785 g, 30.2 mmol), and TMS-Cl (1.699 mL, 13.29 mmol) in MeCN (6 mL) and toluene (6.00 mL) was heated to 50° C. for 1 h. More acetamide (607 mg) and TMS-Cl (0.574 mL) were added. The reaction was heated for an additional 1.5 h, after which 4-methylbenzenesulfinic acid (2.83 g, 18.13 mmol) was added. The reaction was heated for an additional 18 h at 50° C., after which MTBE (15 mL) was added. After 5 min of stirring, water (80 mL) was added and the mixture was cooled in an ice/water bath for 1 h. A white solid was filtered off and dried in a warm vacuum oven to provide Intermediate 18 (1.74 g, 82%). MS(ES): m/z=157.0. HPLC retention time (Method D): 1.023 min. $^1$H NMR (400 MHz, DMSO-$d_6$) δ 9.39 (d, J=10.5 Hz, 1H), 7.75-7.70 (m, 2H), 7.69-7.62 (m, 2H), 7.45 (d, J=7.8 Hz, 2H), 7.34-7.25 (m, 2H), 6.35 (d, J=10.5 Hz, 1H), 2.43 (s, 1H), 1.79 (s, 1H).

The following intermediates in Table 34 were prepared by the procedure described for the preparation of Intermediate 19 using the corresponding substituted benzaldehyde and the corresponding primary amide.

TABLE 34

| Intermediate No. | Structure | Name | [M + H]+ | Retention Time | HPLC Method |
|---|---|---|---|---|---|
| 19 | 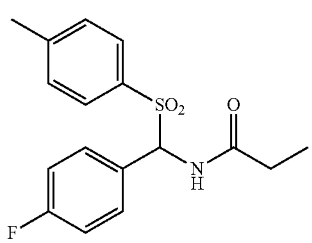 [SMILES: CCC(=O)NC(c1ccc(F)cc1)S(=O)(=O)c1ccc(C)cc1] | N-((4-fluorophenyl)(tosyl)methyl)propionamide | 157.0 | 1.035 | D |
| 20 | 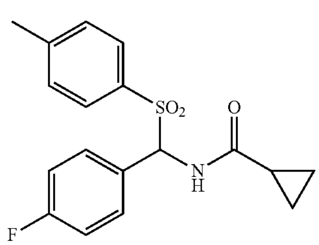 [SMILES: Cc1ccc(S(=O)(=O)C(NC(=O)C2CC2)c2ccc(F)cc2)cc1] | N-((4-fluorophenyl)(tosyl)methyl)cyclopropanecarboxamide | 157.0 | 1.037 | D |

TABLE 34-continued

| Intermediate No. | Structure | Name | [M + H]+ | Retention Time | HPLC Method |
|---|---|---|---|---|---|
| 21 | 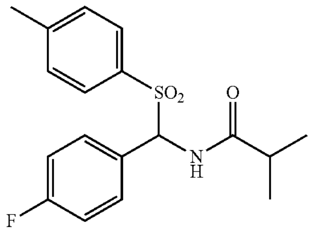 [SMILES: Cc1ccc(S(=O)(=O)C(NC(=O)C(C)C)c2ccc(F)cc2)cc1] | N-((4-fluorophenyl)(tosyl)methyl)isobutyramide | 157.0 | 1.015 | D |
| 22 | 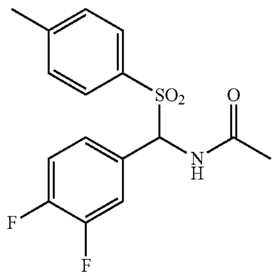 [SMILES: CC(=O)NC(c1ccc(F)c(F)c1)S(=O)(=O)c1ccc(C)cc1] | N-((3,4-difluorophenyl)(tosyl)methyl)acetamide | 157.0 | 1.073 | D |
| 23 | 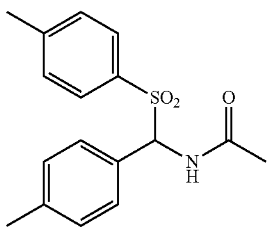 [SMILES: CC(=O)NC(c1ccc(C)cc1)S(=O)(=O)c1ccc(C)cc1] | N-(p-tolyl(tosyl)methyl)acetamide | 157.0 | 1.053 | D |
| 24 | 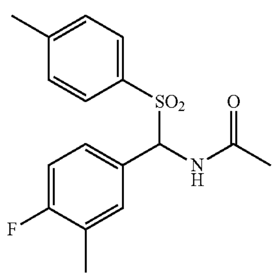 [SMILES: CC(=O)NC(c1ccc(F)c(C)c1)S(=O)(=O)c1ccc(C)cc1] | N-((4-fluoro-3-methylphenyl)(tosyl)methyl)acetamide | 157.0 | 1.002 | D |
| 25 | 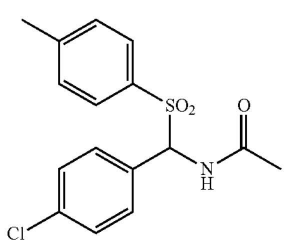 [SMILES: CC(=O)NC(c1ccc(Cl)cc1)S(=O)(=O)c1ccc(C)cc1] | N-((4-chlorophenyl)(tosyl)methyl)acetamide | 157.0 | 1.053 | D |

Intermediate 26

N-(6-(2-Acetamido-2-(4-fluorophenyl)acetyl)imidazo[1,2-b]pyridazin-2-yl)-2-fluoroisonicotinamide

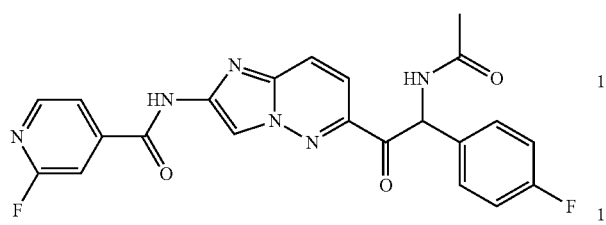

Intermediate 18 (500 mg, 1.556 mmol), Intermediate 16 (488 mg, 1.711 mmol), and 3,4-dimethyl-5-(2-hydroxyethyl)thiazolium iodide (444 mg, 1.556 mmol) were combined in a 20 mL reaction vial. Dichloromethane (4 mL), NMP (4 mL), and $Et_3N$ (3.25 mL, 23.34 mmol) were added. The vial was heated to 35° C. for 45 min. The reaction was diluted with EtOAc (150 mL) and washed with water (3×150 mL) and brine (150 mL). The organics were dried ($MgSO_4$), filtered, and concentrated in vacuo. The residue was triturated in ether to give Intermediate 26 (540 mg, 74%). MS(ES): m/z=451.2 $[M+H]^+$. HPLC retention time (Method D): 1.880 min.

The following compounds in Table 35 were prepared by the procedure described for the preparation of Intermediate 26 using Intermediate 16 with the corresponding intermediate from Table 34.

TABLE 35

| Intermediate No. | Structure | Name | $[M + H]^+$ | Retention Time | HPLC Method |
|---|---|---|---|---|---|
| 27 | 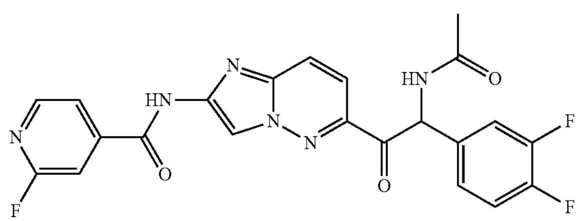 [SMILES: CC(=O)NC(C(=O)c1ccc2nc(NC(=O)c3ccnc(F)c3)cn2n1)c1ccc(F)c(F)c1] | N-(6-(2-acetamido-2-(3,4-difluorophenyl)acetyl)imidazo[1,2-b]pyridazin-2-yl)-2-fluoroisonicotinamide | 467.3 | 1.945 | D |
| 28 | 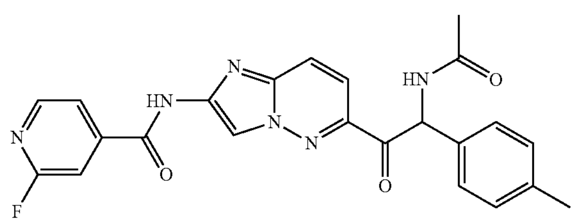 [SMILES: CC(=O)NC(C(=O)c1ccc2nc(NC(=O)c3ccnc(F)c3)cn2n1)c1ccc(C)cc1] | N-(6-(2-acetamido-2-(p-tolyl)acetyl)imidazo[1,2-b]pyridazin-2-yl)-2-fluoroisonicotinamide | 447.3 | 1.922 | D |
| 29 | 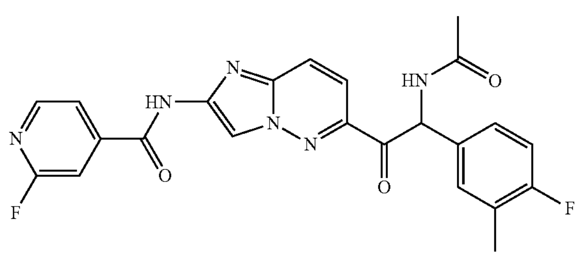 [SMILES: CC(=O)NC(C(=O)c1ccc2nc(NC(=O)c3ccnc(F)c3)cn2n1)c1ccc(F)c(C)c1] | N-(6-(2-acetamido-2-(4-fluoro-3-methylphenyl)acetyl)imidazo[1,2-b]pyridazin-2-yl)-2-fluoroisonicotinamide | 465.1 | 1.953 | D |
| 30 | 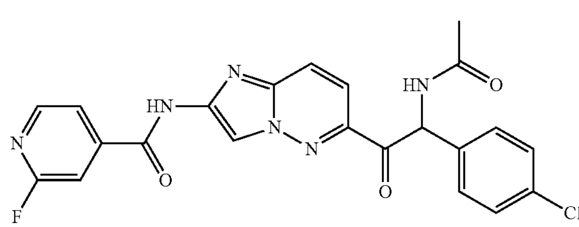 [SMILES: CC(=O)NC(C(=O)c1ccc2nc(NC(=O)c3ccnc(F)c3)cn2n1)c1ccc(Cl)cc1] | N-(6-(2-acetamido-2-(4-chlorophenyl)acetyl)imidazo[1,2-b]pyridazin-2-yl)-2-fluoroisonicotinamide | 467.1 | 2.010 | D |

Compound 284

N-(6-(1-(2,2-Difluoroethyl)-4-(4-fluorophenyl)-2-methyl-1H-imidazol-5-yl)imidazo[1,2b]-pyridazin-2-yl)-2-fluoroisonicotinamide

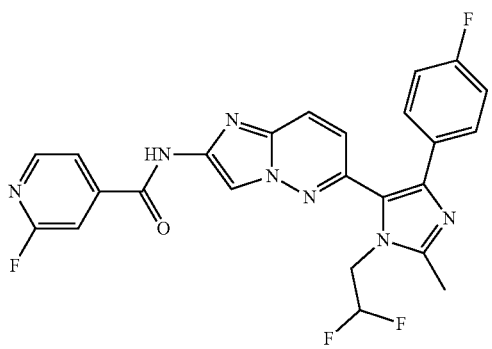 [SMILES: Cc1nc(-c2ccc(F)cc2)c(-c2ccc3nc(NC(=O)c4ccnc(F)c4)cn3n2)n1CC(F)F]

In a 20 mL reactor vial, CH$_2$Cl$_2$ (4 mL) was added to a mixture of Intermediate 18 (250 mg, 0.778 mmol) and 3,4-Dimethyl-5-(2-hydroxyethyl)thiazolium iodide (44.4 mg, 0.156 mmol), followed by Intermediate 16 (244 mg, 0.856 mmol) and Et$_3$N (1.626 mL, 11.67 mmol). The mixture was heated to 35-40° C. for 5 h. NMP (1 mL) and more 3,4-Dimethyl-5-(2-hydroxyethyl)thiazolium iodide (200 mg, 1.26 mmol) were added. The reaction was stirred at room temperature overnight, then the reaction was partitioned between water (100 mL) and EtOAc (100 mL) The layers were separated, and the aqueous layer was extracted with more EtOAc (100 mL). The combined organics were washed with water (2×75 mL) and brine (75 mL), dried (MgSO$_4$), filtered, and concentrated in vacuo. A solution of 2,2-difluoroethanamine (145 mg, 1.789 mmol) in EtOH (4 mL) was added to the residue, followed by AcOH (0.218 mL, 3.81 mmol). The reaction was heated to 90° C. for 1.5 h, then 105° C. overnight. The reaction was concentrated in vacuo, and the residue was purified by preparative HPLC to give Compound 284 (31 mg, 8%). MS(ES): m/z=496.2 [M+H]$^+$. HPLC retention time (Method D): 2.010 min. $^1$H NMR (500 MHz, DMSO-d$_6$) δ 11.90 (br. s., 1H), 8.64 (s, 1H), 8.47 (d, J=5.0 Hz, 1H), 8.02 (dd, J=9.3, 0.6 Hz, 1H), 7.97 (dt, J=5.1, 1.6 Hz, 1H), 7.81 (s, 1H), 7.50-7.45 (m, 2H), 7.19-7.12 (m, 2H), 6.99 (d, J=9.5 Hz, 1H), 6.56-6.30 (m, 1H), 4.75-4.64 (m, 2H).

The following compounds in Table 36 were prepared by the procedure described for the preparation of compound 284 using Intermediate 16 with the corresponding amines and intermediates from Table 34.

TABLE 36

| Compound No. | Structure | Name | [M + H]$^+$ | Retention Time | HPLC Method |
|---|---|---|---|---|---|
| 285 | 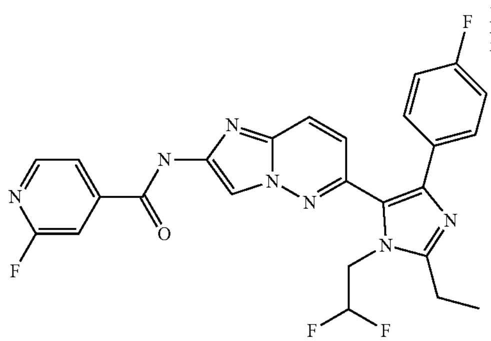 | N-(6-2-cyclopropyl-1-(2,2-difluoroethyl)-4-(4-fluorophenyl)-1H-imidazol-5-yl)imidazo[1,2-b]pyridazin-2-yl)-2-fluoroisonicotinamide | 522.4 | 2.80 | B |
| 286 | 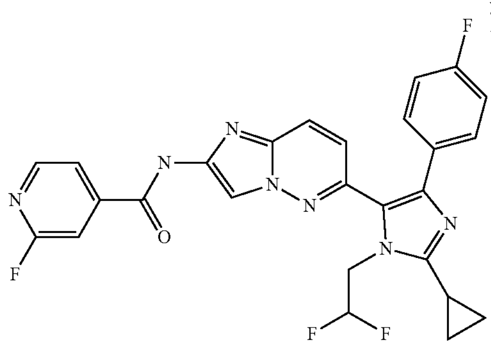 | N-(6-(1-(2,2-difluoroethyl)-2-ethyl-4-(4-fluorophenyl)-1H-imidazol-5-yl)imidazo[1,2-b]pyridazin-2-yl)-2-fluoroisonicotinamide | 510.5 | 2.66 | B |

TABLE 36-continued

| Compound No. | Structure | Name | [M + H]+ | Retention Time | HPLC Method |
|---|---|---|---|---|---|
| 287 | 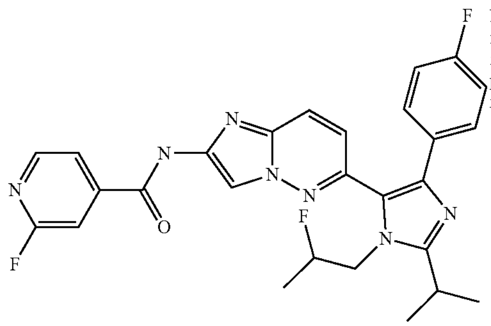 [SMILES: CC(F)Cn1c(C(C)C)nc(-c2ccc(F)cc2)c1-c1ccc2nc(NC(=O)c3ccnc(F)c3)cn2n1] | N-(6-(1-(2,2-difluoroethyl)-4-(4-fluorophenyl)-2-isopropyl-1H-imidazol-5-yl)imidazo[1,2-b]pyridazin-2-yl)-2-fluoroisonicotinamide | 524.4 | 2.83 | B |

Compound 288

2-Fluoro-N-(6-(1-(2-fluoroethyl)-4-(4-fluorophenyl)-2-methyl-1H-imidazol-5-yl)imidazo[1,2-b]pyridazin-2-yl)isonicotinamide

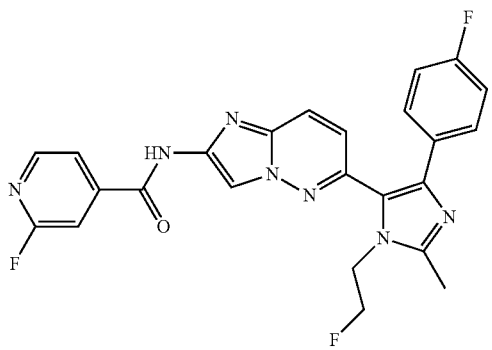 [SMILES: Cc1nc(-c2ccc(F)cc2)c(-c2ccc3nc(NC(=O)c4ccnc(F)c4)cn3n2)n1CCF]

In a microwave vial, a mixture of Intermediate 18 (45 mg, 0.100 mmol), 2-fluoroethanamine HCl (29.8 mg, 0.300 mmol), trifluoroacetic acid (0.023 mL, 0.300 mmol), and butanenitrile (0.5 mL) was heated to 140° C. for 30 min in a microwave reactor. A small amount of methanol was added to dissolve the precipitated solids. The solution was diluted with EtOAc (25 mL), then washed with water (2×25 mL) and brine (25 mL). The organics were dried (MgSO$_4$), filtered, and concentrated in vacuo. The residue was purified by preparative HPLC to give Compound 288 (19 mg, 9%). MS(ES): m/z=478.5 [M+H]+. HPLC retention time (Method C): 2.38 min. $^1$H NMR (500 MHz, DMSO-d$_6$) δ 11.90 (br. s., 1H), 8.58 (s, 1H), 8.47 (d, J=5.2 Hz, 1H), 8.02 (d, J=9.2 Hz, 1H), 7.96 (d, J=4.9 Hz, 1H), 7.80 (s, 1H), 7.46 (dd, J=8.9, 5.5 Hz, 2H), 7.13 (t, J=8.9 Hz, 2H), 7.02 (d, J=9.2 Hz, 1H), 4.77-4.60 (m, 2H), 4.51-4.39 (m, 2H), 2.48 (s, 3H).

The following compounds in Table 37 were prepared by the procedure described for the preparation of compound 288 using the corresponding amine and the corresponding intermediate from. Table 35.

TABLE 37

| Compound No. | Structure | Name | [M + H]+ | Retention Time | HPLC Method |
|---|---|---|---|---|---|
| 289 | 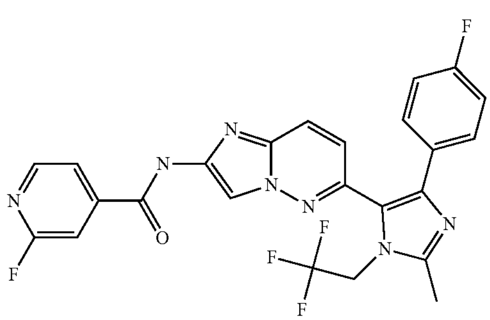 [SMILES: Cc1nc(-c2ccc(F)cc2)c(-c2ccc3nc(NC(=O)c4ccnc(F)c4)cn3n2)n1CC(F)(F)F] | 2-fluoro-N-(6-(4-(4-fluorophenyl)-2-methyl-1-(2,2,2-trifluoroethyl)-1H-imidazol-5-yl)imidazo[1,2-b]pyridazin-2-yl)isonicotinamide | 514.5 | 2.55 | B |

TABLE 37-continued

| Compound No. | Structure | Name | [M + H]+ | Retention Time | HPLC Method |
|---|---|---|---|---|---|
| 290 | 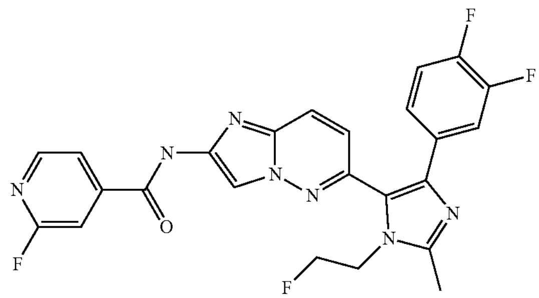 [SMILES: Cc1nc(-c2ccc(F)c(F)c2)c(-c2ccc3nc(NC(=O)c4ccnc(F)c4)cn3n2)n1CCF] | N-(6-(4-(3,4-difluorophenyl)-1-(2-fluoroethyl)-2-methyl-1H-imidazol-5-yl)imidazo[1,2-b]pyridazin-2-yl)-2-fluoroisonicotinamide | 496.5 | 2.46 | B |
| 291 | 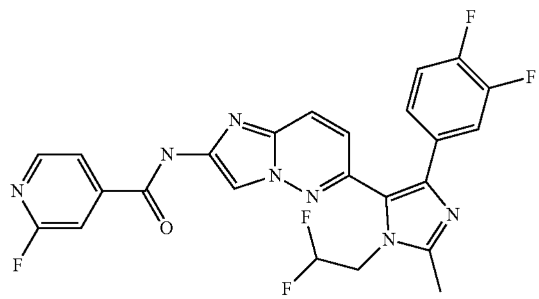 [SMILES: Cc1nc(-c2ccc(F)c(F)c2)c(-c2ccc3nc(NC(=O)c4ccnc(F)c4)cn3n2)n1CC(F)F] | N-(6-(1-(2,2-difluoroethyl)-4-(3,4-difluorophenyl)-2-methyl-1H-imidazol-5-yl)imidazo[1,2-b]pyridazin-2-yl)-2-fluoroisonicotinamide | 514.5 | 2.55 | B |
| 292 | 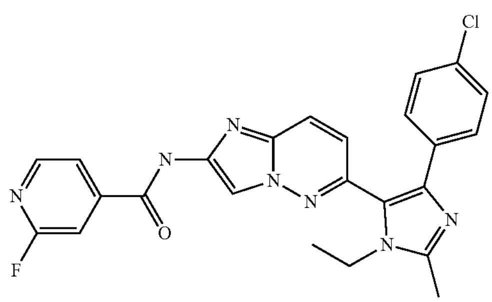 [SMILES: CCn1c(C)nc(-c2ccc(Cl)cc2)c1-c1ccc2nc(NC(=O)c3ccnc(F)c3)cn2n1] | N-(6-(4-(4-chlorophenyl)-1-ethyl-2-methyl-1H-imidazol-5-yl)imidazo[1,2-b]pyridazin-2-yl)-2-fluoroisonicotinamide | 476.3 | 2.56 | B |
| 293 | 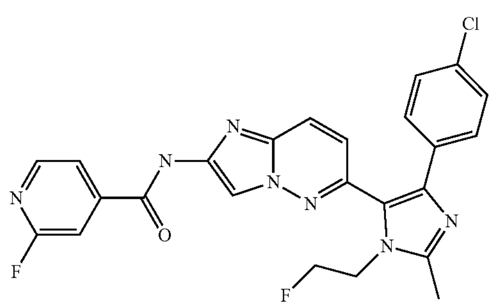 [SMILES: Cc1nc(-c2ccc(Cl)cc2)c(-c2ccc3nc(NC(=O)c4ccnc(F)c4)cn3n2)n1CCF] | N-(6-(4-(4-chlorophenyl)-1-(2-fluoroethyl)-2-methyl-1H-imidazol-5-yl)imidazo[1,2-b]pyridazin-2-yl)-2-fluoroisonicotinamide | 494.4 | 2.52 | B |
| 294 | 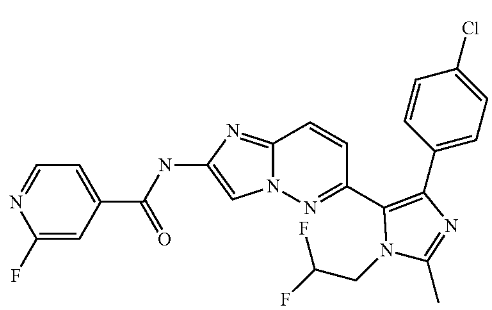 [SMILES: Cc1nc(-c2ccc(Cl)cc2)c(-c2ccc3nc(NC(=O)c4ccnc(F)c4)cn3n2)n1CC(F)F] | N-(6-(4-(4-chlorophenyl)-1-(2,2-difluoroethyl)-2-methyl-1H-imidazol-5-yl)imidazo[1,2-b]pyridazin-2-yl)-2-fluoroisonicotinamide | 512.4 | 2.61 | B |

TABLE 37-continued

| Compound No. | Structure | Name | [M + H]+ | Retention Time | HPLC Method |
|---|---|---|---|---|---|
| 295 | 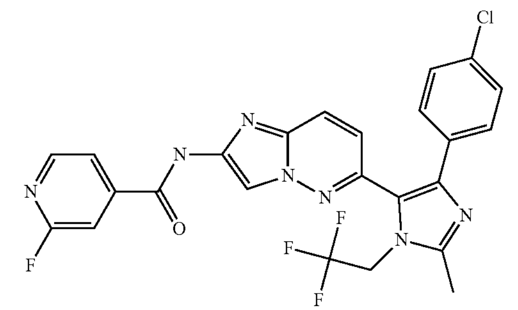 [SMILES: Cc1nc(-c2ccc(Cl)cc2)c(-c2ccc3nc(NC(=O)c4ccnc(F)c4)cn3n2)n1CC(F)(F)F] | N-(6-(4-(4-chlorophenyl)-2-methyl-1-(2,2,2-trifluoroethyl)-1H-imidazol-5-yl)imidazo[1,2-b]pyridazin-2-yl)-2-fluoroisonicotinamide | 530.4 | 2.71 | B |
| 296 | 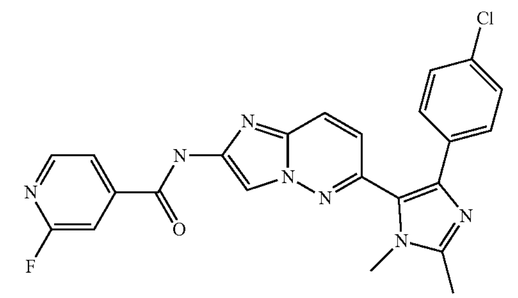 [SMILES: Cc1nc(-c2ccc(Cl)cc2)c(-c2ccc3nc(NC(=O)c4ccnc(F)c4)cn3n2)n1C] | N-(6-(4-(4-chlorophenyl)-1,2-dimethyl-1H-imidazol-5-yl)imidazo[1,2-b]pyridazin-2-yl)-2-fluoroisonicotinamide | 462.4 | 2.42 | B |
| 297 | 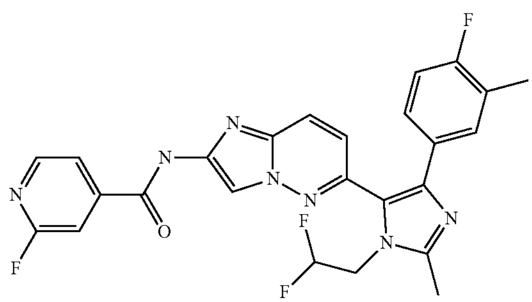 [SMILES: Cc1cc(-c2nc(C)n(CC(F)F)c2-c2ccc3nc(NC(=O)c4ccnc(F)c4)cn3n2)ccc1F] | N-(6-(1-(2,2-difluoroethyl)-4-(4-fluoro-3-methylphenyl)-2-methyl-1H-imidazol-5-yl)imidazo[1,2-b]pyridazin-2-yl)-2-fluoroisonicotinamide | 510.3 | 2.72 | B |
| 298 | 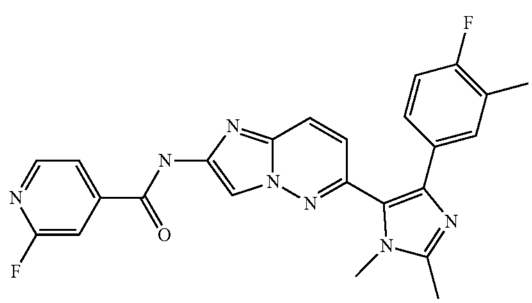 [SMILES: Cc1cc(-c2nc(C)n(C)c2-c2ccc3nc(NC(=O)c4ccnc(F)c4)cn3n2)ccc1F] | 2-fluoro-N-(6-(4-(4-fluoro-3-methylphenyl)-1,2-dimethyl-1H-imidazol-5-yl)imidazo[1,2-b]pyridazin-2-yl)isonicotinamide | 460.4 | 2.52 | B |
| 299 | 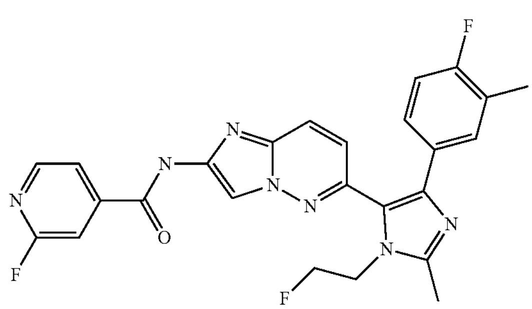 [SMILES: Cc1cc(-c2nc(C)n(CCF)c2-c2ccc3nc(NC(=O)c4ccnc(F)c4)cn3n2)ccc1F] | 2-fluoro-N-(6-(4-(4-fluoro-3-methylphenyl)-1-(2-fluoroethyl)-2-methyl-1H-imidazol-5-yl)imidazo[1,2-b]pyridazin-2-yl)isonicotinamide | 492.4 | 2.59 | B |

TABLE 37-continued

| Compound No. | Structure | Name | [M + H]+ | Retention Time | HPLC Method |
|---|---|---|---|---|---|
| 300 | 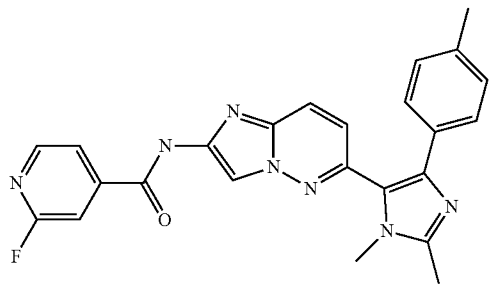 [SMILES: Cc1ccc(-c2nc(C)n(C)c2-c2ccc3nc(NC(=O)c4ccnc(F)c4)cn3n2)cc1] | N-(6-(1,2-dimethyl-4-(p-tolyl)-1H-imidazol-5-yl)imidazo[1,2-b]pyridazin-2-yl)-2-fluoroisonicotinamide | 442.3 | 2.34 | B |

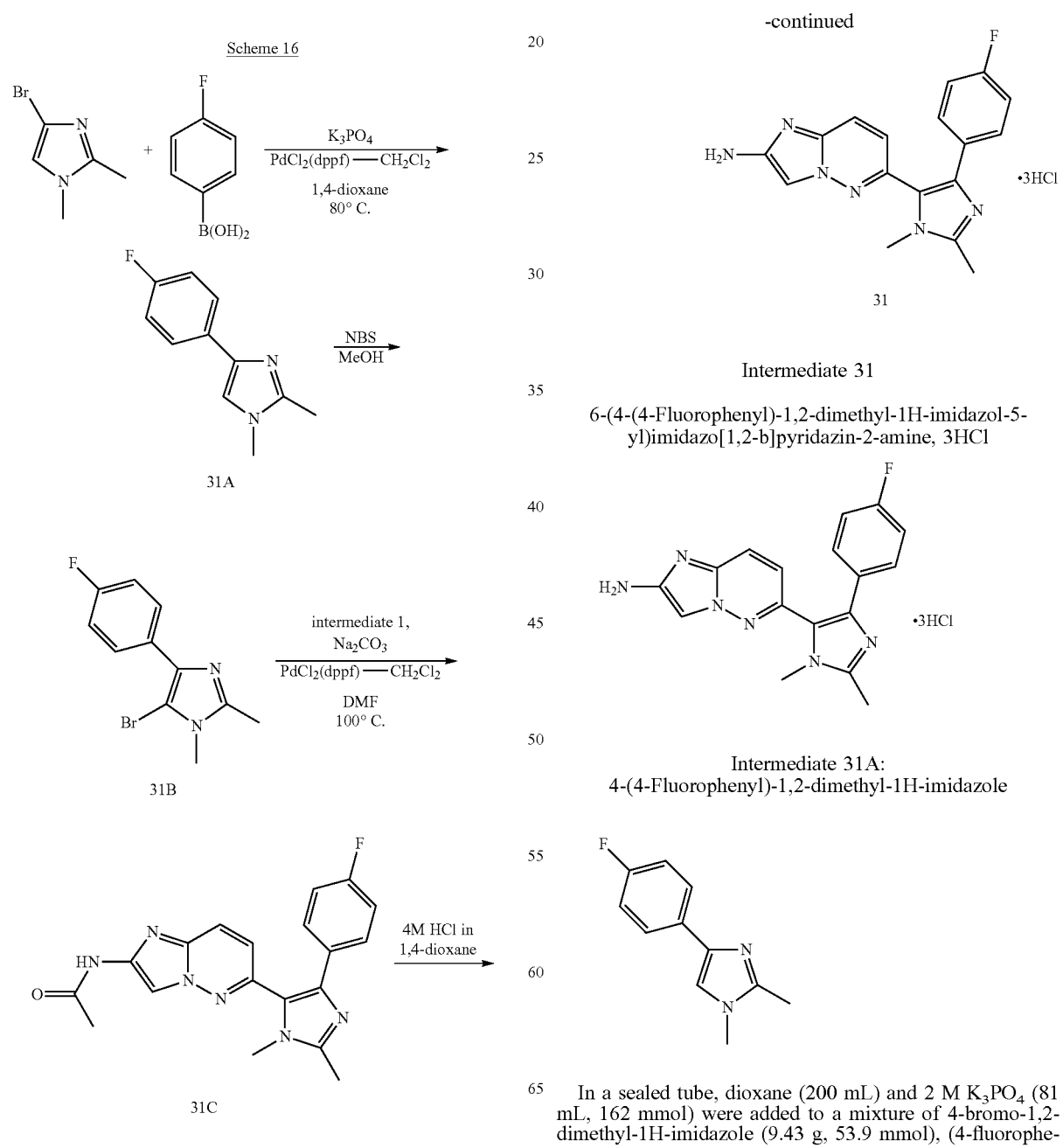

Intermediate 31

6-(4-(4-Fluorophenyl)-1,2-dimethyl-1H-imidazol-5-yl)imidazo[1,2-b]pyridazin-2-amine, 3HCl Intermediate 31A:
4-(4-Fluorophenyl)-1,2-dimethyl-1H-imidazole In a sealed tube, dioxane (200 mL) and 2 M $K_3PO_4$ (81 mL, 162 mmol) were added to a mixture of 4-bromo-1,2-dimethyl-1H-imidazole (9.43 g, 53.9 mmol), (4-fluorophenyl)boronic acid (9.80 g, 70.0 mmol), and PdCl$_2$(dppf)-CH$_2$Cl$_2$ adduct (2.200 g, 2.69 mmol). Nitrogen was bubbled through the mixture for several minutes, then the vessel was capped and heated to 80° C. for 5 h. The reaction was diluted with EtOAc (250 mL), washed with water (2×250 mL) and brine (150 mL) The organics were dried (MgSO$_4$), filtered, and concentrated in vacuo. The residue was purified silica gel chromatography (0 to 30% 90:10:1 [CH$_2$Cl$_2$/MeOH/NH$_4$OH]/CH$_2$Cl$_2$) to give crude 31A (10.04 g at 70% purity, 68% yield), which was carried to the next step without further purification. MS(ES): m/z=191.1 [M+H]$^+$. HPLC retention time (Method D): 1.637 min.

Intermediate 31B: 5-Bromo-4-(4-fluorophenyl)-1,2-dimethyl-1H-imidazole

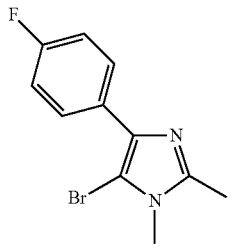

4-(4-Fluorophenyl)-1,2-dimethyl-1H-imidazole (10.20 g, 37.5 mmol) was dissolved in MeOH (175 mL). NBS (7.35 g, 41.3 mmol) was added, and the reaction was stirred at room temperature overnight. The reaction was diluted with EtOAc (400 mL) and washed with sat aq sodium thiosulfate (300 mL), water (300 mL) and brine (300 mL). The organics were dried (MgSO$_4$), filtered, and concentrated in vacuo. The residue was purified via a silica gel chromatography (20 to 80% EtOAc/Hex) to obtain 31B (8.61 g, 85%). MS(ES): m/z=268.95, 270.95 [M+H]$^1$. HPLC retention time (Method E): 1.600 min.

Intermediate 31C: N-(6-(4-(4-Fluorophenyl)-1,2-dimethyl-1H-imidazol-5-yl)imidazo[1,2-b]pyridazin-2-yl)acetamide

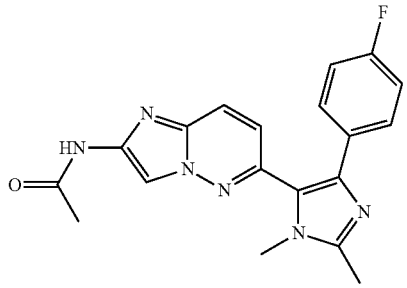 [SMILES: CC(=O)Nc1cn2nc(-c3c(-c4ccc(F)cc4)nc(C)n3C)ccc2n1]

In a sealed tube, nitrogen was bubbled through a mixture of Intermediate 1 (4.17 g, 13.80 mmol), Intermediate 31B (2.97 g, 11.04 mmol), PdCl$_2$(dppf)-CH$_2$Cl$_2$ adduct (0.451 g, 0.552 mmol), DMF (50 mL), and 2M Na$_2$CO$_3$ (16.56 mL, 33.1 mmol). The vessel was sealed and heated to 100° C. overnight. Water (1 L) was poured into the reaction, and the mixture was extracted with DCM (2×500 mL) and EtOAc (2×500 mL). The combined organics were dried (MgSO$_4$), filtered, and concentrated in vacuo to ca 500 mL, then washed with water (500 mL) and brine (500 mL), dried again (MgSO$_4$), filtered, and concentrated in vacuo. The residue was purified via silica gel chromatography (0 to 30% 90:10:1 [CH$_2$Cl$_2$/MeOH/NH$_4$OH]/CH$_2$Cl$_2$ to obtain Intermediate 31C (1.63 g, 40%). MS(ES): m/z=365.3 [M+H]$^+$. HPLC retention time (Method D): 1.798 min. $^1$H NMR (400 MHz, DMSO-d$_6$) δ 10.81 (s, 1H), 7.87 (dd, J=9.5, 0.8 Hz, 1H), 7.78 (s, 1H), 7.59 (d, J=9.5 Hz, 1H), 7.56-7.49 (m, 2H), 7.40-7.32 (m, 2H), 3.40 (s, 3H), 2.45 (s, 3H), 2.07 (s, 3H).

Intermediate 31: 6-(4-(4-Fluorophenyl)-1,2-dimethyl-1H-imidazol-5-yl)imidazo[1,2-b]pyridazin-2-amine, 3HCl

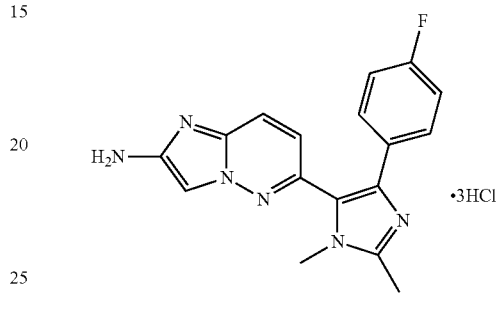

Methanol (15 mL) and HCl (4 M/dioxane) (15 mL, 60.0 mmol) were added to Intermediate 31C (1.82 g, 4.99 mmol). The reaction was stirred at room temperature overnight. The reaction was concentrated in vacuo to give slightly impure Intermediate 31 (2.19 g, 102%). MS(ES): m/z=323.2 [M+H]$^+$. HPLC retention time (Method D): 1.690 min. $^1$H NMR (400 MHz, DMSO-d$_6$) δ 8.03 (d, J=9.0 Hz, 1H), 7.65 (s, 1H), 7.62-7.54 (m, 2H), 7.36-7.28 (m, 2H), 7.20 (d, J=9.3 Hz, 1H), 3.71 (s, 3H), 2.77 (s, 3H).

Compound 301

N-(6-(4-(4-Fluorophenyl)-1,2-dimethyl-1H-imidazol-5-yl)imidazo[1,2-b]pyridazin-2-yl)isonicotinamide

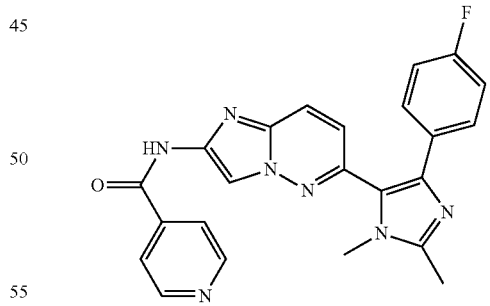

Intermediate 31 (200 mg, 0.463 mmol) and isonicotinic acid (86 mg, 0.695 mmol) were dissolved in DMF (8 mL) DIPEA (0.566 mL, 3.24 mmol) and HATU (211 mg, 0.556 mmol) were added, and the reaction was stirred at room temperature overnight. The reaction was diluted with DMF and purified by preparative HPLC to obtain Compound 301 (85.4 mg, 42.3%). MS(ES): m/z=428.1 [M+H]$^+$. HPLC retention time (Method D): 1.877 min.

The following compounds in Table 38 were prepared by the procedure described for the preparation of compound 302 using the corresponding carboxylic acids.

TABLE 38

| Compound No. | Structure | Name | [M + H]+ | Retention Time | HPLC Method |
|---|---|---|---|---|---|
| 302 | 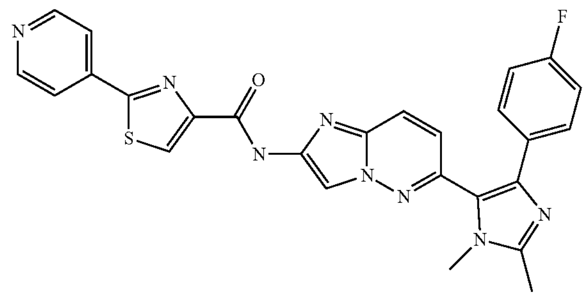 [SMILES: Cc1nc(-c2ccc(F)cc2)c(-c2ccc3nc(NC(=O)c4csc(-c5ccncc5)n4)cn3n2)n1C] | N-(6-(4-(4-fluorophenyl)-1,2-dimethyl-1H-imidazol-5-yl)imidazo[1,2-b]pyridazin-2-yl)-2-(pyridin-4-yl)thiazole-4-carboxamide | 509.3 | 2.045 | D |
| 303 | 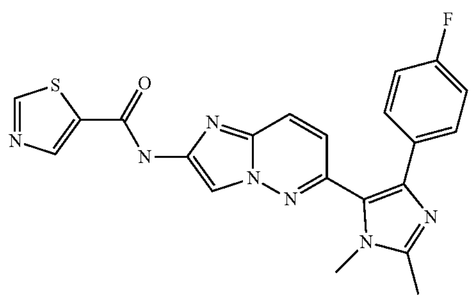 [SMILES: Cc1nc(-c2ccc(F)cc2)c(-c2ccc3nc(NC(=O)c4cncs4)cn3n2)n1C] | N-(6-(4-(4-fluorophenyl)-1,2-dimethyl-1H-imidazol-5-yl)imidazo[1,2-b]pyridazin-2-yl)thiazole-5-carboxamide | 434.2 | 2.235 | D |
| 304 | 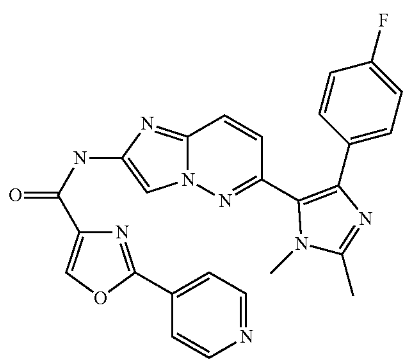 [SMILES: Cc1nc(-c2ccc(F)cc2)c(-c2ccc3nc(NC(=O)c4coc(-c5ccncc5)n4)cn3n2)n1C] | N-(6-(4-(4-fluorophenyl)-1,2-dimethyl-1H-imidazol-5-yl)imidazo[1,2-b]pyridazin-2-yl)-2-(pyridin-4-yl)oxazole-4-carboxamide | 495.3 | 2.102 | D |
| 305 | 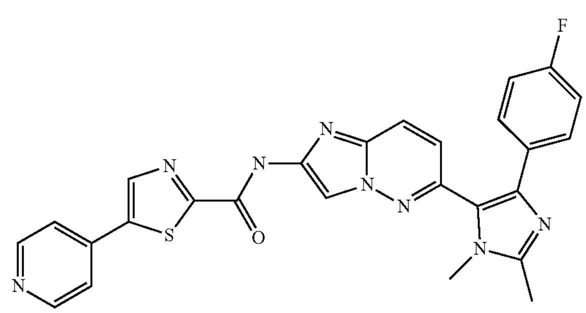 [SMILES: Cc1nc(-c2ccc(F)cc2)c(-c2ccc3nc(NC(=O)c4ncc(-c5ccncc5)s4)cn3n2)n1C] | N-(6-(4-(4-fluorophenyl)-1,2-dimethyl-1H-imidazol-5-yl)imidazo[1,2-b]pyridazin-2-yl)-5-(pyridin-4-yl)thiazole-2-carboxamide | 509.3 | 2.130 | D |
| 306 | 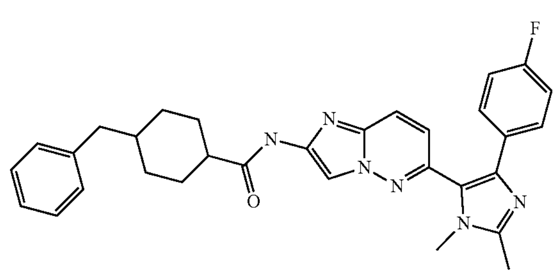 [SMILES: Cc1nc(-c2ccc(F)cc2)c(-c2ccc3nc(NC(=O)C4CCC(Cc5ccccc5)CC4)cn3n2)n1C] | 1-benzyl-N-(6-(4-(4-fluorophenyl)-1,2-dimethyl-1H-imidazol-5-yl)imidazo[1,2-b]pyridazin-2-yl)piperidine-4-carboxamide | 522.4 | 2.095 | D |

TABLE 38-continued

| Compound No. | Structure | Name | [M + H]+ | Retention Time | HPLC Method |
|---|---|---|---|---|---|
| 307 | 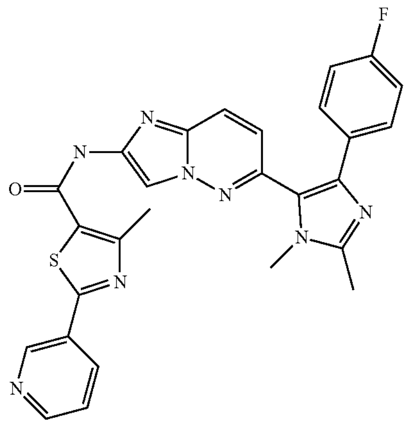 [SMILES: Cc1nc(-c2cccnc2)sc1C(=O)Nc1cn2nc(-c3c(-c4ccc(F)cc4)nc(C)n3C)ccc2n1] | N-(6-(4-(4-fluorophenyl)-1,2-dimethyl-1H-imidazol-5-yl)imidazo[1,2-b]pyridazin-2-yl)-4-methyl-2-(pyridin-3-yl)thiazole-5-carboxamide | 523.3 | 2.132 | D |
| 308 | 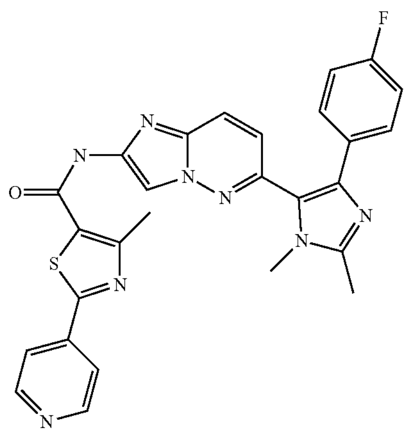 [SMILES: Cc1nc(-c2ccncc2)sc1C(=O)Nc1cn2nc(-c3c(-c4ccc(F)cc4)nc(C)n3C)ccc2n1] | N-(6-(4-(4-fluorophenyl)-1,2-dimethyl-1H-imidazol-5-yl)imidazo[1,2-b]pyridazin-2-yl)-4-methyl-2-(pyridin-4-yl)thiazole-5-carboxamide | 525.2 | 2.102 | D |
| 309 | 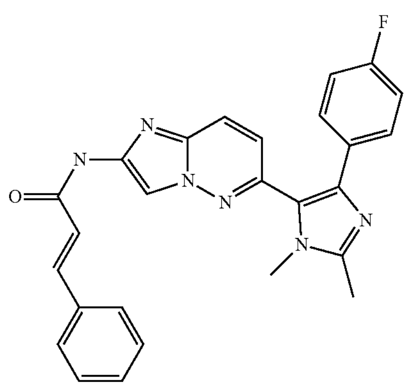 [SMILES: Cc1nc(-c2ccc(F)cc2)c(-c2ccc3nc(NC(=O)/C=C/c4ccccc4)cn3n2)n1C] | N-(6-(4-(4-fluorophenyl)-1,2-dimethyl-1H-imidazol-5-yl)imidazo[1,2-b]pyridazin-2-yl)cinnamamide | 451.3 | 2.140 | D |
| 310 | 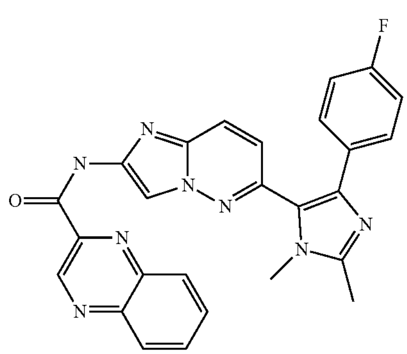 [SMILES: Cc1nc(-c2ccc(F)cc2)c(-c2ccc3nc(NC(=O)c4cnc5ccccc5n4)cn3n2)n1C] | N-(6-(4-(4-fluorophenyl)-1,2-dimethyl-1H-imidazol-5-yl)imidazo[1,2-b]pyridazin-2-yl)quinoxaline-2-carboxamide | 479.2 | 2.163 | D |

TABLE 38-continued

| Compound No. | Structure | Name | [M + H]+ | Retention Time | HPLC Method |
|---|---|---|---|---|---|
| 311 | 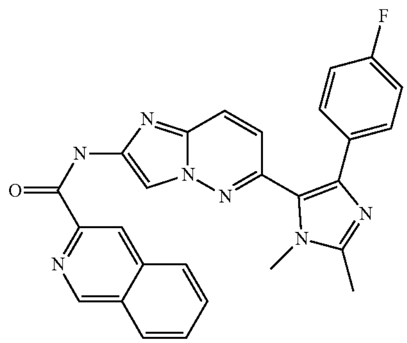 [SMILES: Cc1nc(-c2ccc(F)cc2)c(-c2ccc3nc(NC(=O)c4cc5ccccc5cn4)cn3n2)n1C] | N-(6-(4-(4-fluorophenyl)-1,2-dimethyl-1H-imidazol-5-yl)imidazo[1,2-b]pyridazin-2-yl)isoquinoline-3-carboxamide | 478.2 | 2.207 | D |
| 312 | 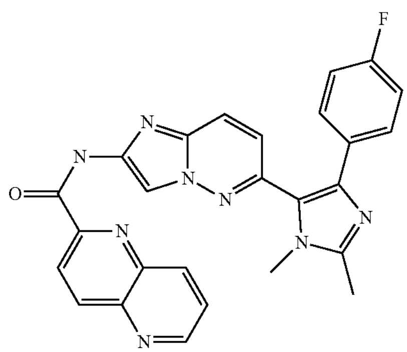 [SMILES: Cc1nc(-c2ccc(F)cc2)c(-c2ccc3nc(NC(=O)c4ccc5ncccc5n4)cn3n2)n1C] | N-(6-(4-(4-fluorophenyl)-1,2-dimethyl-1H-imidazol-5-yl)imidazo[1,2-b]pyridazin-2-yl)-1,5-naphthyridine-2-carboxamide | 479.2 | 2.065 | D |
| 313 | 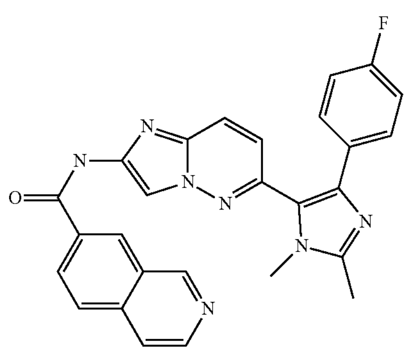 [SMILES: Cc1nc(-c2ccc(F)cc2)c(-c2ccc3nc(NC(=O)c4ccc5ccncc5c4)cn3n2)n1C] | N-(6-(4-(4-fluorophenyl)-1,2-dimethyl-1H-imidazol-5-yl)imidazo[1,2-b]pyridazin-2-yl)isoquinoline-7-carboxamide | 478.2 | 2.27 | B |
| 314 | 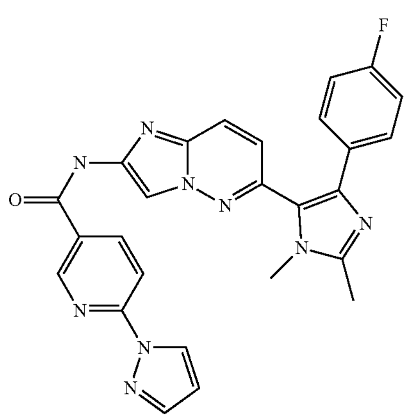 [SMILES: Cc1nc(-c2ccc(F)cc2)c(-c2ccc3nc(NC(=O)c4ccc(-n5cccn5)nc4)cn3n2)n1C] | N-(6-(4-(4-fluorophenyl)-1,2-dimethyl-1H-imidazol-5-yl)imidazo[1,2-b]pyridazin-2-yl)-6-(1H-pyrazol-1-yl)nicotinamide | 494.2 | 2.44 | B |

TABLE 38-continued

| Compound No. | Structure | Name | [M + H]+ | Retention Time | HPLC Method |
|---|---|---|---|---|---|
| 315 | Chiral | (S)-N-(6-(4-(4-fluorophenyl)-1,2-dimethyl-1H-imidazol-5-yl)imidazo[1,2-b]pyridazin-2-yl)pyrrolidine-2-carboxamide | 420.3 | 1.65 | B |
| 316 | Chiral | (S)-4,4-difluoro-N-(6-(4-(4-fluorophenyl)-1,2-dimethyl-1H-imidazol-5-yl)imidazo[1,2-b]pyridazin-2-yl)pyrrolidine-2-carboxamide | 456.2 | 2.15 | B |
| 317 | 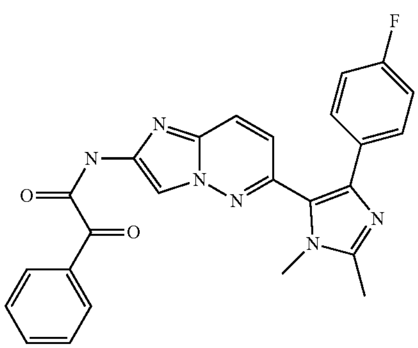 [SMILES: Cc1nc(-c2ccc(F)cc2)c(-c2ccc3nc(NC(=O)C(=O)c4ccccc4)cn3n2)n1C] | N-(6-(4-(4-fluorophenyl)-1,2-dimethyl-1H-imidazol-5-yl)imidazo[1,2-b]pyridazin-2-yl)-2-oxo-2-phenylacetamide | 455.180 | 2.61 | B |
| 318 | 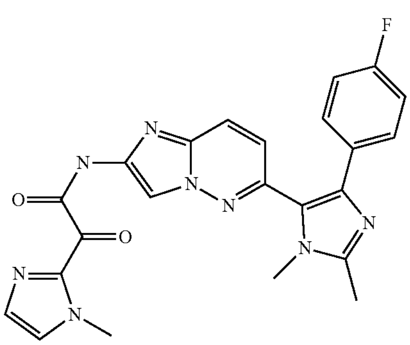 [SMILES: Cc1nc(-c2ccc(F)cc2)c(-c2ccc3nc(NC(=O)C(=O)c4nccn4C)cn3n2)n1C] | N-(6-(4-(4-fluorophenyl)-1,2-dimethyl-1H-imidazol-5-yl)imidazo[1,2-b]pyridazin-2-yl)-2-(1-methyl-1H-imidazol-2-yl)-2-oxoacetamide | 458.2 | 2.50 | B |

TABLE 38-continued

| Compound No. | Structure | Name | [M + H]+ | Retention Time | HPLC Method |
|---|---|---|---|---|---|
| 319 | 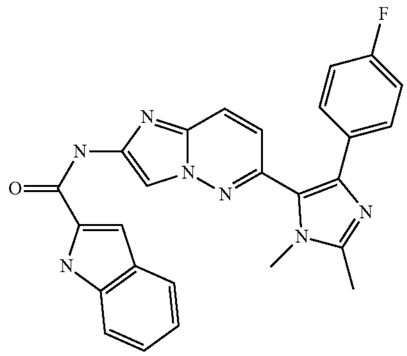 [SMILES: Cc1nc(-c2ccc(F)cc2)c(-c2ccc3nc(NC(=O)c4cc5ccccc5[nH]4)cn3n2)n1C] | N-(6-(4-(4-fluorophenyl)-1,2-dimethyl-1H-imidazol-5-yl)imidazo[1,2-b]pyridazin-2-yl)-1H-indole-2-carboxamide | 466.2 | 2.61 | B |
| 320 | 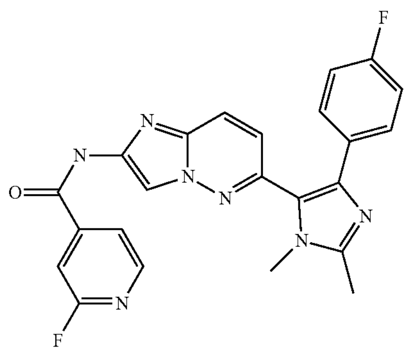 | 2-fluoro-N-(6-(4-(4-fluorophenyl)-1,2-dimethyl-1H-imidazol-5-yl)imidazo[1,2-b]pyridazin-2-yl)isonicotinamide | 446.2 | 2.28 | B |
| 321 | 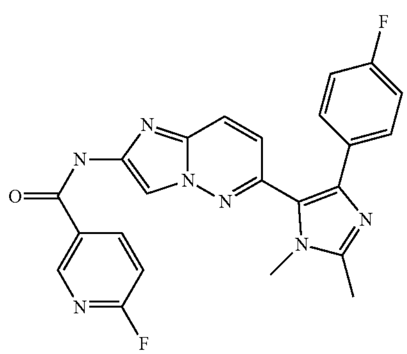 [SMILES: Cc1nc(-c2ccc(F)cc2)c(-c2ccc3nc(NC(=O)c4ccc(F)nc4)cn3n2)n1C] | 6-fluoro-N-(6-(4-(4-fluorophenyl)-1,2-dimethyl-1H-imidazol-5-yl)imidazo[1,2-b]pyridazin-2-yl)nicotinamide | 446.0 | 2.19 | B |
| 322 | 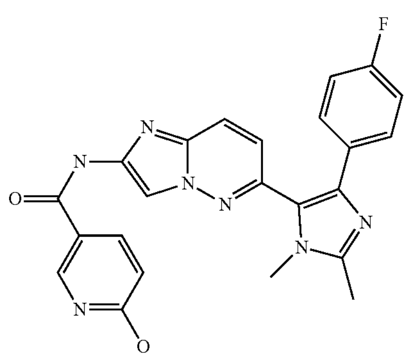 [SMILES: Cc1nc(-c2ccc(F)cc2)c(-c2ccc3nc(NC(=O)c4ccc(O)nc4)cn3n2)n1C] | N-(6-(4-(4-fluorophenyl)-1,2-dimethyl-1H-imidazol-5-yl)imidazo[1,2-b]pyridazin-2-yl)-6-hydroxynicotinamide | 444.4 | 1.79 | B |

TABLE 38-continued

| Compound No. | Structure | Name | [M + H]+ | Retention Time | HPLC Method |
|---|---|---|---|---|---|
| 323 | 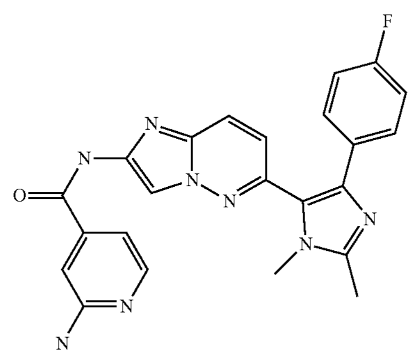 [SMILES: Cc1nc(-c2ccc(F)cc2)c(-c2ccc3nc(NC(=O)c4ccnc(N)c4)cn3n2)n1C] | 2-amino-N-(6-(4-(4-fluorophenyl)-1,2-dimethyl-1H-imidazol-5-yl)imidazo[1,2-b]pyridazin-2-yl)isonicotinamide | 443.3 | 2.07 | B |
| 324 | 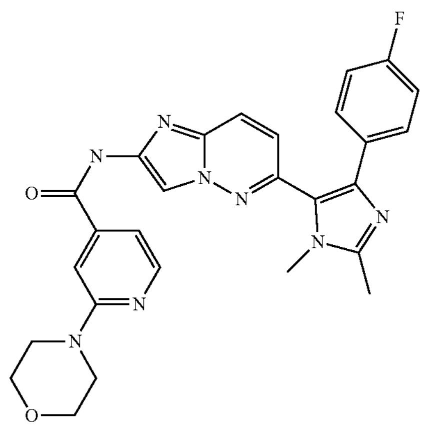 [SMILES: Cc1nc(-c2ccc(F)cc2)c(-c2ccc3nc(NC(=O)c4ccnc(N5CCOCC5)c4)cn3n2)n1C] | N-(6-(4-(4-fluorophenyl)-1,2-dimethyl-1H-imidazol-5-yl)imidazo[1,2-b]pyridazin-2-yl)-2-morpholinoisonicotinamide | 513.4 | 2.41 | B |
| 325 | 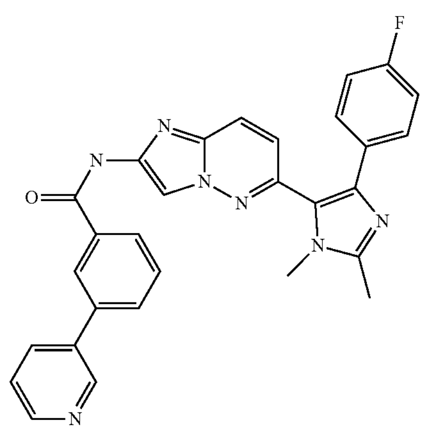 [SMILES: Cc1nc(-c2ccc(F)cc2)c(-c2ccc3nc(NC(=O)c4cccc(-c5cccnc5)c4)cn3n2)n1C] | N-(6-(4-(4-fluorophenyl)-1,2-dimethyl-1H-imidazol-5-yl)imidazo[1,2-b]pyridazin-2-yl)-3-(pyridin-3-yl)benzamide | 504.3 | 2.54 | B |
| 326 | | N-(6-(4-(4-fluorophenyl)-1,2-dimethyl-1H-imidazol-5-yl)imidazo[1,2-b]pyridazin-2-yl)-3-methyl-1H-pyrrole-2-carboxamide | 430.18 | 3.85 | C |
| 327 | | N-(6-(4-(4-fluorophenyl)-1,2-dimethyl-1H-imidazol-5-yl)imidazo[1,2-b]pyridazin-2-yl)-1H-pyrrolo[3,2-c]pyridine-2-carboxamide | 467.20 | 2.02 | B |
| 328 | | N-(6-(4-(4-fluorophenyl)-1,2-dimethyl-1H-imidazol-5-yl)imidazo[1,2-b]pyridazin-2-yl)-5-quinolinecarboxamide | 478.20 | 3.74 | C |

TABLE 38-continued

| Compound No. | Structure | Name | [M + H]+ | Retention Time | HPLC Method |
|---|---|---|---|---|---|
| 329 | | 5-(4-chlorophenyl)-N-(6-(4-(4-fluorophenyl)-1,2-dimethyl-1H-imidazol-5-yl)imidazo[1,2-b]pyridazin-2-yl)-1H-pyrrole-2-carboxamide | 526.16 | 3.09 | B |
| 330 | 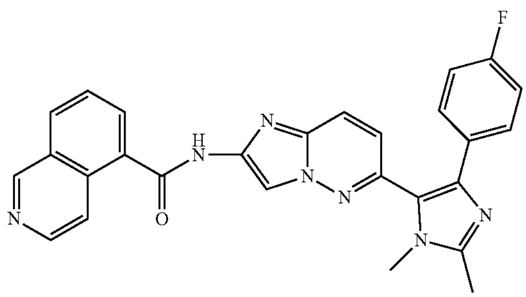 [SMILES: Cc1nc(-c2ccc(F)cc2)c(-c2ccc3nc(NC(=O)c4cccc5cnccc45)cn3n2)n1C] | N-(6-(4-(4-fluorophenyl)-1,2-dimethyl-1H-imidazol-5-yl)imidazo[1,2-b]pyridazin-2-yl)-5-isoquinoline-carboxamide | 478.22 | 3.70 | B |
| 331 | 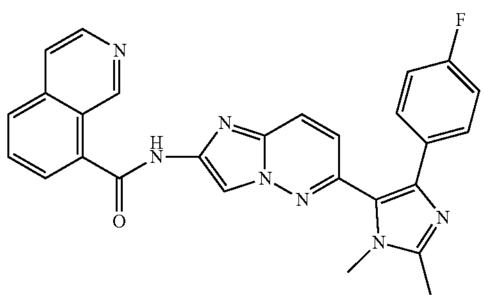 [SMILES: Cc1nc(-c2ccc(F)cc2)c(-c2ccc3nc(NC(=O)c4cccc5ccncc45)cn3n2)n1C] | N-(6-(4-(4-fluorophenyl)-1,2-dimethyl-1H-imidazol-5-yl)imidazo[1,2-b]pyridazin-2-yl)-8-isoquinoline-carboxamide | 478.22 | 3.69 | C |
| 332 | 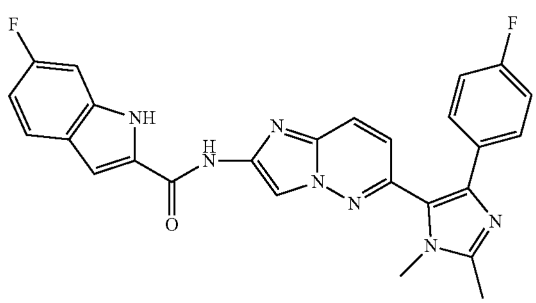 [SMILES: Cc1nc(-c2ccc(F)cc2)c(-c2ccc3nc(NC(=O)c4cc5ccc(F)cc5[nH]4)cn3n2)n1C] | 6-fluoro-N-(6-(4-(4-fluorophenyl)-1,2-dimethyl-1H-imidazol-5-yl)imidazo[1,2-b]pyridazin-2-yl)-1H-indole-2-carboxamide | 484.25 | 2.76 | B |
| 333 | 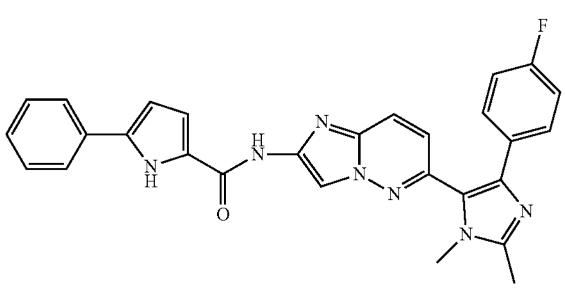 [SMILES: Cc1nc(-c2ccc(F)cc2)c(-c2ccc3nc(NC(=O)c4ccc(-c5ccccc5)[nH]4)cn3n2)n1C] | N-(6-(4-(4-fluorophenyl)-1,2-dimethyl-1H-imidazol-5-yl)imidazo[1,2-b]pyridazin-2-yl)-5-phenyl-1H-pyrrole-2-carboxamide | 492.21 | 2.83 | B |

TABLE 38-continued

| Compound No. | Structure | Name | [M + H]+ | Retention Time | HPLC Method |
|---|---|---|---|---|---|
| 334 | 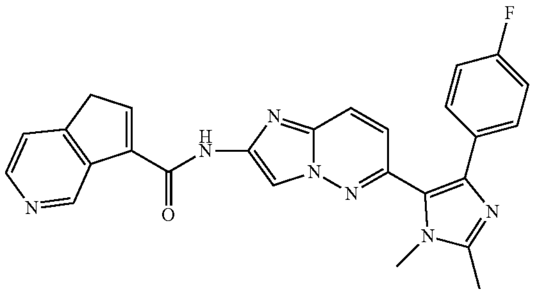 [SMILES: Cc1nc(-c2ccc(F)cc2)c(-c2ccc3nc(NC(=O)C4=CCc5ccncc54)cn3n2)n1C] | N-(6-(4-(4-fluorophenyl)-1,2-dimethyl-1H-imidazol-5-yl)imidazo[1,2-b]pyridazin-2-yl)-1H-pyrrolo[3,2-c]pyridine-3-carboxamide | 467.22 | 3.44 | C |
| 335 | 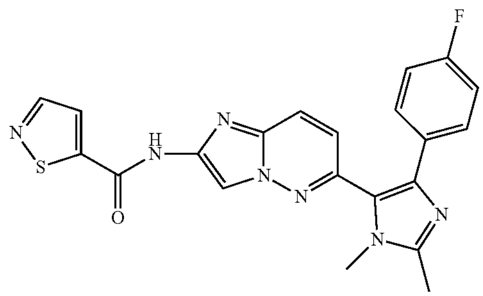 | N-(6-(4-(4-fluorophenyl)-1,2-dimethyl-1H-imidazol-5-yl)imidazo[1,2-b]pyridazin-2-yl)-5-isothiazolecarboxamide | 434.12 | 3.75 | C |
| 336 | 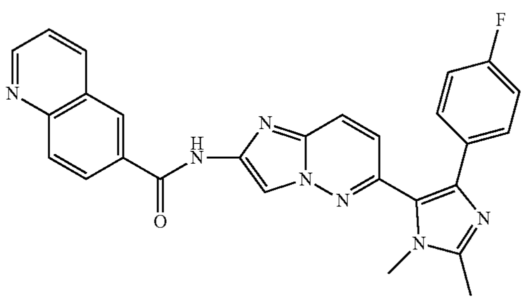 [SMILES: Cc1nc(-c2ccc(F)cc2)c(-c2ccc3nc(NC(=O)c4ccc5ncccc5c4)cn3n2)n1C] | N-(6-(4-(4-fluorophenyl)-1,2-dimethyl-1H-imidazol-5-yl)imidazo[1,2-b]pyridazin-2-yl)-6-quinolinecarboxamide | 478.20 | 3.82 | C |
| 337 | 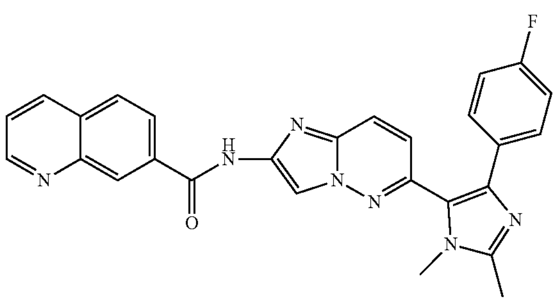 [SMILES: Cc1nc(-c2ccc(F)cc2)c(-c2ccc3nc(NC(=O)c4ccc5cccnc5c4)cn3n2)n1C] | N-(6-(4-(4-fluorophenyl)-1,2-dimethyl-1H-imidazol-5-yl)imidazo[1,2-b]pyridazin-2-yl)-7-quinolinecarboxamide | 478.21 | 3.85 | C |
| 338 | 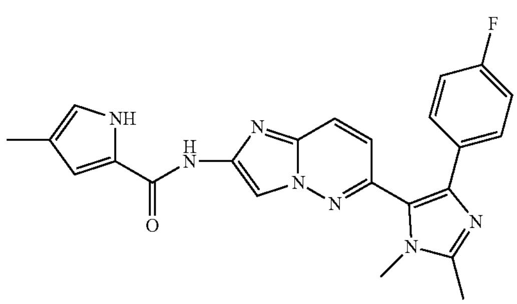 [SMILES: Cc1c[nH]c(C(=O)Nc2cn3nc(-c4c(-c5ccc(F)cc5)nc(C)n4C)ccc3n2)c1] | N-(6-(4-(4-fluorophenyl)-1,2-dimethyl-1H-imidazol-5-yl)imidazo[1,2-b]pyridazin-2-yl)-4-methyl-1H-pyrrole-2-carboxamide | 430.22 | 2.43 | B |

TABLE 38-continued

| Compound No. | Structure | Name | [M + H]+ | Retention Time | HPLC Method |
|---|---|---|---|---|---|
| 339 | 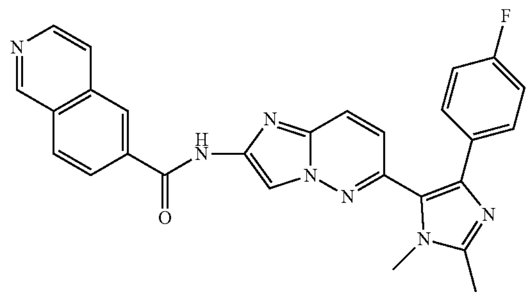 [SMILES: Cc1nc(-c2ccc(F)cc2)c(-c2ccc3nc(NC(=O)c4ccc5cnccc5c4)cn3n2)n1C] | N-(6-(4-(4-fluorophenyl)-1,2-dimethyl-1H-imidazol-5-yl)imidazo[1,2-b]pyridazin-2-yl)isoquinoline-6-carboxamide | 478.22 | 3.85 | C |
| 340 | 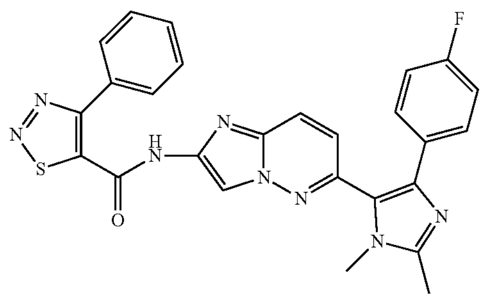 [SMILES: Cc1nc(-c2ccc(F)cc2)c(-c2ccc3nc(NC(=O)c4snnc4-c4ccccc4)cn3n2)n1C] | N-(6-(4-(4-fluorophenyl)-1,2-dimethyl-1H-imidazol-5-yl)imidazo[1,2-b]pyridazin-2-yl)-4-phenyl-1,2,3-thiadiazole-5-carboxamide | 511.17 | 2.76 | B |
| 341 | 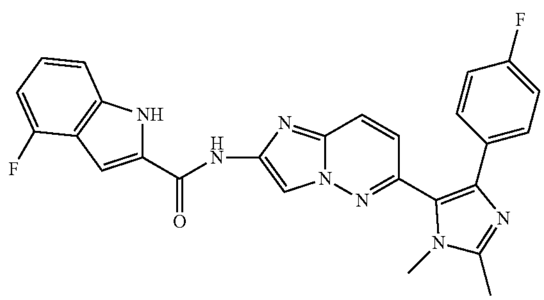 [SMILES: Cc1nc(-c2ccc(F)cc2)c(-c2ccc3nc(NC(=O)c4cc5c(F)cccc5[nH]4)cn3n2)n1C] | 4-fluoro-N-(6-(4-(4-fluorophenyl)-1,2-dimethyl-1H-imidazol-5-yl)imidazo[1,2-b]pyridazin-2-yl)-1H-indole-2-carboxamide | 484.18 | 4.09 | C |
| 342 | 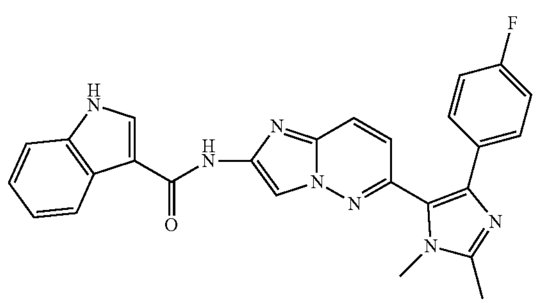 [SMILES: Cc1nc(-c2ccc(F)cc2)c(-c2ccc3nc(NC(=O)c4c[nH]c5ccccc45)cn3n2)n1C] | N-(6-(4-(4-fluorophenyl)-1,2-dimethyl-1H-imidazol-5-yl)imidazo[1,2-b]pyridazin-2-yl)-1H-indole-3-carboxamide | 466.21 | 2.48 | B |
| 343 | 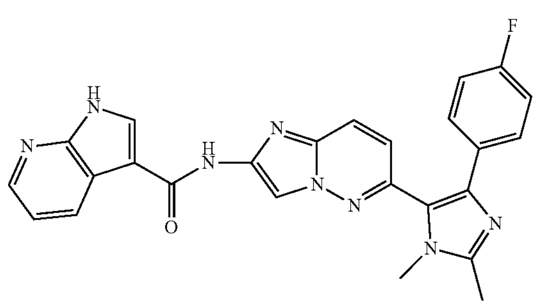 [SMILES: Cc1nc(-c2ccc(F)cc2)c(-c2ccc3nc(NC(=O)c4c[nH]c5ncccc45)cn3n2)n1C] | N-(6-(4-(4-fluorophenyl)-1,2-dimethyl-1H-imidazol-5-yl)imidazo[1,2-b]pyridazin-2-yl)-1H-pyrrolo[2,3-b]pyridine-3-carboxamide | 467.20 | 3.71 | C |

TABLE 38-continued

| Compound No. | Structure | Name | [M + H]+ | Retention Time | HPLC Method |
| --- | --- | --- | --- | --- | --- |
| 344 | 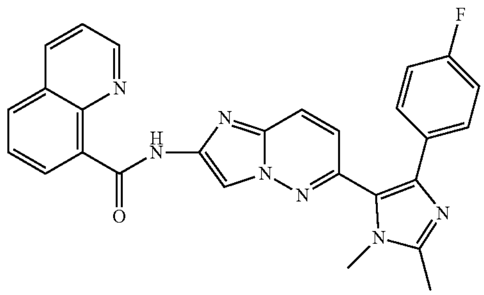 [SMILES: Cc1nc(-c2ccc(F)cc2)c(-c2ccc3nc(NC(=O)c4cccc5cccnc45)cn3n2)n1C] | N-(6-(4-(4-fluorophenyl)-1,2-dimethyl-1H-imidazol-5-yl)imidazo[1,2-b]pyridazin-2-yl)-8-quinolinecarboxamide | 478.49 | 4.16 | C |
| 345 | 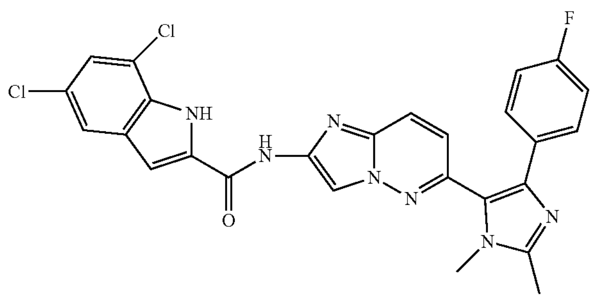 [SMILES: Cc1nc(-c2ccc(F)cc2)c(-c2ccc3nc(NC(=O)c4cc5cc(Cl)cc(Cl)c5[nH]4)cn3n2)n1C] | 4,6-dichloro-N-(6-(4-(4-fluorophenyl)-1,2-dimethyl-1H-imidazol-5-yl)imidazo[1,2-b]pyridazin-2-yl)-1H-indole-2-carboxamide | 534.40 | 4.52 | C |
| 346 | 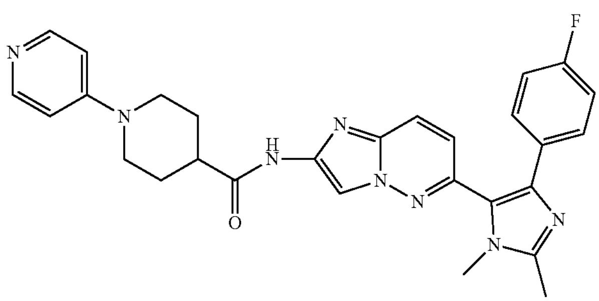 [SMILES: Cc1nc(-c2ccc(F)cc2)c(-c2ccc3nc(NC(=O)C4CCN(c5ccncc5)CC4)cn3n2)n1C] | N-(6-(4-(4-fluorophenyl)-1,2-dimethyl-1H-imidazol-5-yl)imidazo[1,2-b]pyridazin-2-yl)-1-(4-pyridinyl)-4-piperidinecarboxamide | 510.30 | 3.17 | C |
| 347 | 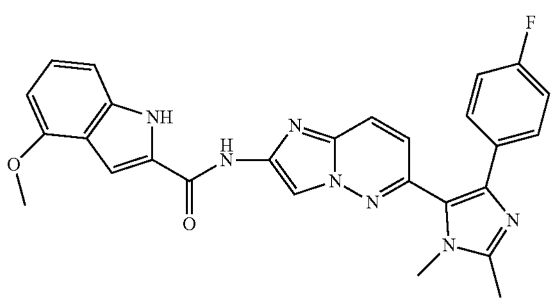 [SMILES: COc1cccc2[nH]c(C(=O)Nc3cn4nc(-c5c(-c6ccc(F)cc6)nc(C)n5C)ccc4n3)cc12] | N-(6-(4-(4-fluorophenyl)-1,2-dimethyl-1H-imidazol-5-yl)imidazo[1,2-b]pyridazin-2-yl)-4-methoxy-1H-indole-2-carboxamide | 496.22 | 2.67 | B |
| 348 | 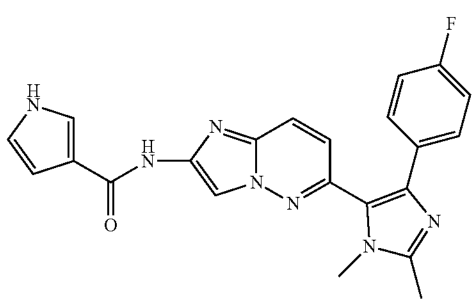 [SMILES: Cc1nc(-c2ccc(F)cc2)c(-c2ccc3nc(NC(=O)c4cc[nH]c4)cn3n2)n1C] | N-(6-(4-(4-fluorophenyl)-1,2-dimethyl-1H-imidazol-5-yl)imidazo[1,2-b]pyridazin-2-yl)-1H-pyrrole-3-carboxamide | 416.25 | 3.35 | C |

TABLE 38-continued

| Compound No. | Structure | Name | [M + H]+ | Retention Time | HPLC Method |
|---|---|---|---|---|---|
| 349 | 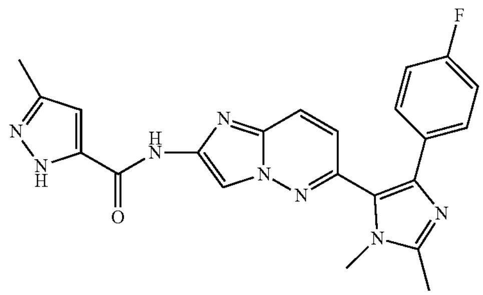 [SMILES: Cc1cc(C(=O)Nc2cn3nc(-c4c(-c5ccc(F)cc5)nc(C)n4C)ccc3n2)[nH]n1] | N-(6-(4-(4-fluorophenyl)-1,2-dimethyl-1H-imidazol-5-yl)imidazo[1,2-b]pyridazin-2-yl)-5-methyl-1H-pyrazole-3-carboxamide | 431.30 | 2.13 | B |
| 350 | 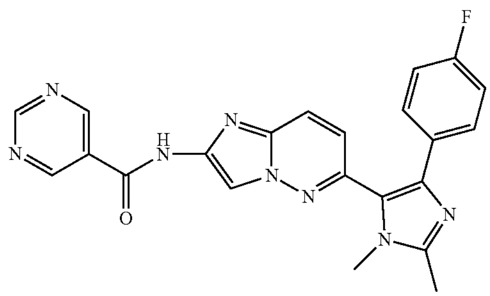 [SMILES: Cc1nc(-c2ccc(F)cc2)c(-c2ccc3nc(NC(=O)c4cncnc4)cn3n2)n1C] | N-(6-(4-(4-fluorophenyl)-1,2-dimethyl-1H-imidazol-5-yl)imidazo[1,2-b]pyridazin-2-yl)-5-pyrimidinecarboxamide | 429.21 | 3.44 | C |
| 351 | 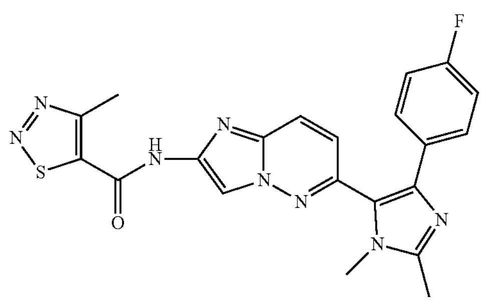 [SMILES: Cc1nnsc1C(=O)Nc1cn2nc(-c3c(-c4ccc(F)cc4)nc(C)n3C)ccc2n1] | N-(6-(4-(4-fluorophenyl)-1,2-dimethyl-1H-imidazol-5-yl)imidazo[1,2-b]pyridazin-2-yl)-4-methyl-1,2,3-thiadiazole-5-carboxamide | 449.21 | 2.30 | B |
| 352 | 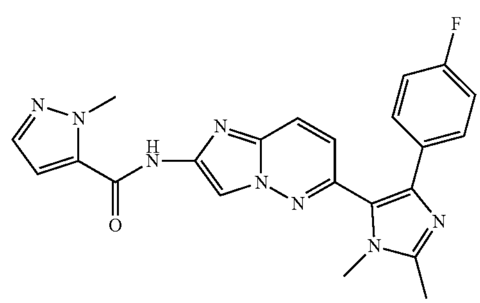 [SMILES: Cc1nc(-c2ccc(F)cc2)c(-c2ccc3nc(NC(=O)c4ccnn4C)cn3n2)n1C] | N-(6-(4-(4-fluorophenyl)-1,2-dimethyl-1H-imidazol-5-yl)imidazo[1,2-b]pyridazin-2-yl)-1-methyl-1H-pyrazole-5-carboxamide | 431.23 | 3.66 | C |
| 353 | 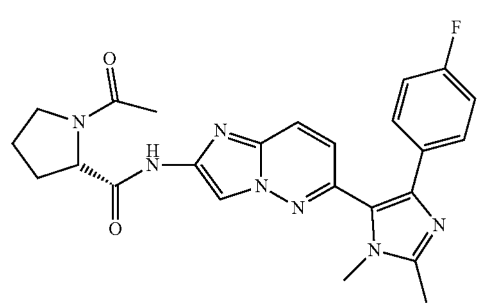 | 1-acetyl-N-(6-(4-(4-fluorophenyl)-1,2-dimethyl-1H-imidazol-5-yl)imidazo[1,2-b]pyridazin-2-yl)-L-prolinamide | 462.29 | 1.98 | B |

TABLE 38-continued

| Compound No. | Structure | Name | [M + H]+ | Retention Time | HPLC Method |
|---|---|---|---|---|---|
| 354 | 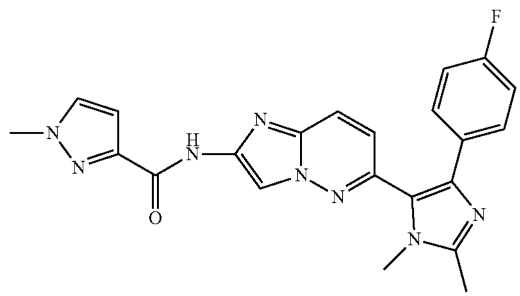 [SMILES: Cc1nc(-c2ccc(F)cc2)c(-c2ccc3nc(NC(=O)c4ccn(C)n4)cn3n2)n1C] | N-(6-(4-(4-fluorophenyl)-1,2-dimethyl-1H-imidazol-5-yl)imidazo[1,2-b]pyridazin-2-yl)-1-methyl-1H-pyrazole-3-carboxamide | 431.23 | 2.16 | B |
| 355 | 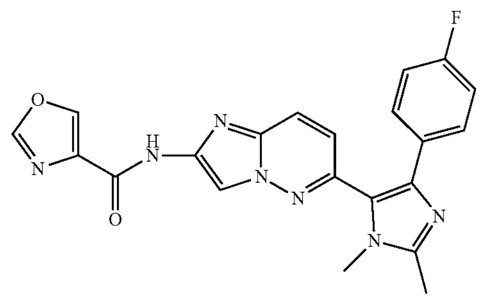 [SMILES: Cc1nc(-c2ccc(F)cc2)c(-c2ccc3nc(NC(=O)c4cocn4)cn3n2)n1C] | N-(6-(4-(4-fluorophenyl)-1,2-dimethyl-1H-imidazol-5-yl)imidazo[1,2-b]pyridazin-2-yl)-1,3-oxazole-4-carboxamide | 418.21 | 3.46 | C |
| 356 | 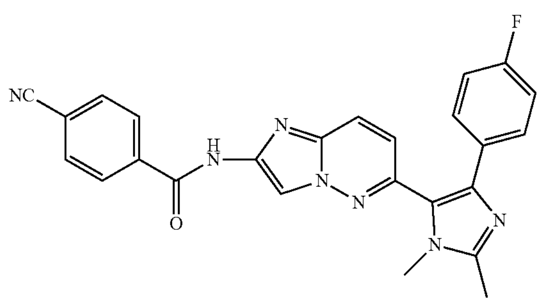 [SMILES: Cc1nc(-c2ccc(F)cc2)c(-c2ccc3nc(NC(=O)c4ccc(C#N)cc4)cn3n2)n1C] | 4-cyano-N-(6-(4-(4-fluorophenyl)-1,2-dimethyl-1H-imidazol-5-yl)imidazo[1,2-b]pyridazin-2-yl)benzamide | 452.25 | 2.44 | B |
| 357 | 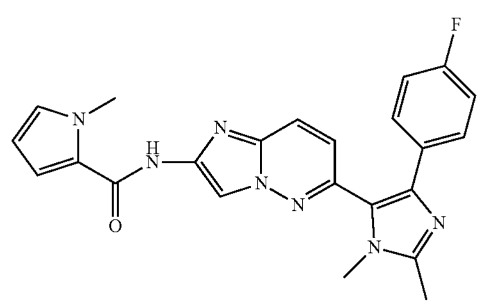 [SMILES: Cc1nc(-c2ccc(F)cc2)c(-c2ccc3nc(NC(=O)c4cccn4C)cn3n2)n1C] | N-(6-(4-(4-fluorophenyl)-1,2-dimethyl-1H-imidazol-5-yl)imidazo[1,2-b]pyridazin-2-yl)-1-methyl-1H-pyrrole-2-carboxamide | 430.26 | 2.46 | B |
| 358 | 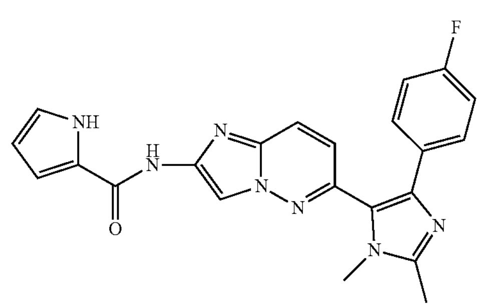 [SMILES: Cc1nc(-c2ccc(F)cc2)c(-c2ccc3nc(NC(=O)c4ccc[nH]4)cn3n2)n1C] | N-(6-(4-(4-fluorophenyl)-1,2-dimethyl-1H-imidazol-5-yl)imidazo[1,2-b]pyridazin-2-yl)-1H-pyrrole-2-carboxamide | 416.22 | 3.58 | C |

TABLE 38-continued

| Compound No. | Structure | Name | [M + H]+ | Retention Time | HPLC Method |
|---|---|---|---|---|---|
| 359 | 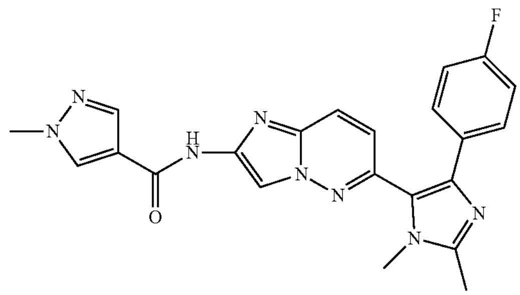 [SMILES: Cc1nc(-c2ccc(F)cc2)c(-c2ccc3nc(NC(=O)c4cnn(C)c4)cn3n2)n1C] | N-(6-(4-(4-fluorophenyl)-1,2-dimethyl-1H-imidazol-5-yl)imidazo[1,2-b]pyridazin-2-yl)-1-methyl-1H-pyrazole-4-carboxamide | 431.25 | 2.01 | B |
| 360 | 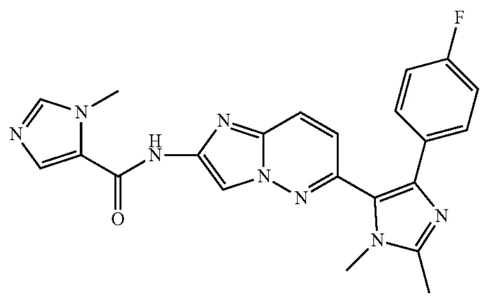 [SMILES: Cc1nc(-c2ccc(F)cc2)c(-c2ccc3nc(NC(=O)c4cncn4C)cn3n2)n1C] | N-(6-(4-(4-fluorophenyl)-1,2-dimethyl-1H-imidazol-5-yl)imidazo[1,2-b]pyridazin-2-yl)-1-methyl-1H-imidazole-5-carboxamide | 431.24 | 3.46 | C |
| 361 | 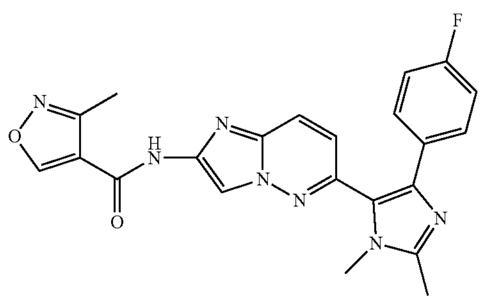 [SMILES: Cc1nocc1C(=O)Nc1cn2nc(-c3c(-c4ccc(F)cc4)nc(C)n3C)ccc2n1] | N-(6-(4-(4-fluorophenyl)-1,2-dimethyl-1H-imidazol-5-yl)imidazo[1,2-b]pyridazin-2-yl)-3-methyl-4-isoxazole-carboxamide | 432.25 | 3.16 | C |
| 362 | 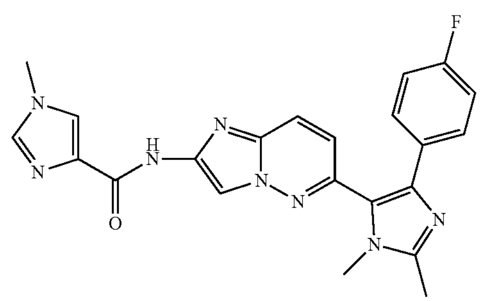 [SMILES: Cc1nc(-c2ccc(F)cc2)c(-c2ccc3nc(NC(=O)c4cn(C)cn4)cn3n2)n1C] | N-(6-(4-(4-fluorophenyl)-1,2-dimethyl-1H-imidazol-5-yl)imidazo[1,2-b]pyridazin-2-yl)-1-methyl-1H-imidazole-4-carboxamide | 431.25 | 1.99 | C |
| 363 | 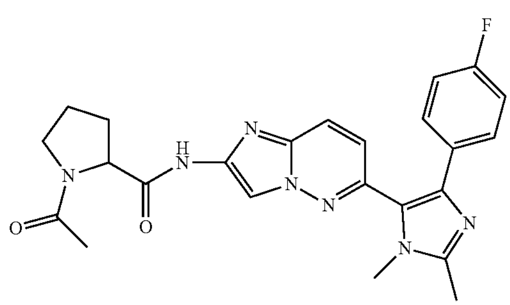 [SMILES: CC(=O)N1CCCC1C(=O)Nc1cn2nc(-c3c(-c4ccc(F)cc4)nc(C)n3C)ccc2n1] | 1-acetyl-N-(6-(4-(4-fluorophenyl)-1,2-dimethyl-1H-imidazol-5-yl)imidazo[1,2-b]pyridazin-2-yl)prolinamide | 462.28 | 3.31 | C |

TABLE 38-continued

| Compound No. | Structure | Name | [M + H]⁺ | Retention Time | HPLC Method |
|---|---|---|---|---|---|
| 364 | 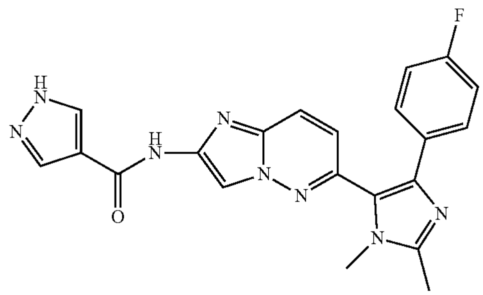 [SMILES: Cc1nc(-c2ccc(F)cc2)c(-c2ccc3nc(NC(=O)c4cn[nH]c4)cn3n2)n1C] | N-(6-(4-(4-fluorophenyl)-1,2-dimethyl-1H-imidazol-5-yl)imidazo[1,2-b]pyridazin-2-yl)-1H-pyrazole-4-carboxamide | 417.24 | 3.31 | C |
| 365 | 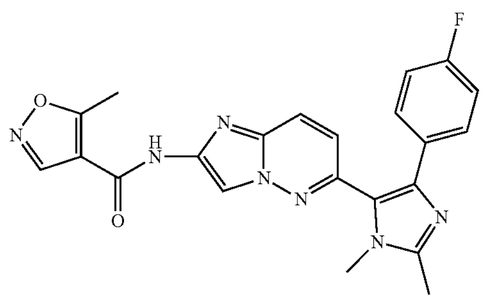 [SMILES: Cc1oncc1C(=O)Nc1cn2nc(-c3c(-c4ccc(F)cc4)nc(C)n3C)ccc2n1] | N-(6-(4-(4-fluorophenyl)-1,2-dimethyl-1H-imidazol-5-yl)imidazo[1,2-b]pyridazin-2-yl)-5-methyl-4-isoxazole-carboxamide | 432.25 | 3.16 | C |
| 366 | 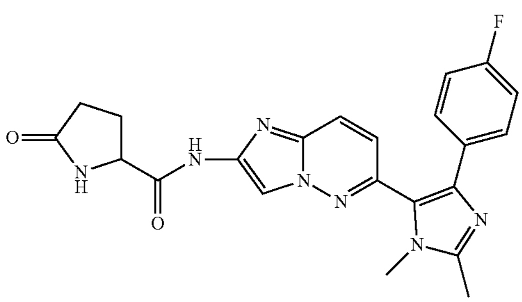 [SMILES: Cc1nc(-c2ccc(F)cc2)c(-c2ccc3nc(NC(=O)C4CCC(=O)N4)cn3n2)n1C] | N-(6-(4-(4-fluorophenyl)-1,2-dimethyl-1H-imidazol-5-yl)imidazo[1,2-b]pyridazin-2-yl)-5-oxoprolinamide | 434.29 | 1.78 | B |
| 367 | 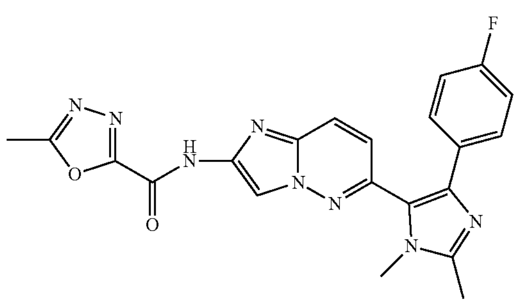 [SMILES: Cc1nnc(C(=O)Nc2cn3nc(-c4c(-c5ccc(F)cc5)nc(C)n4C)ccc3n2)o1] | N-(6-(4-(4-fluorophenyl)-1,2-dimethyl-1H-imidazol-5-yl)imidazo[1,2-b]pyridazin-2-yl)-5-methyl-1,3,4-oxadiazole-2-carboxamide | 433.24 | 3.36 | C |
| 368 | 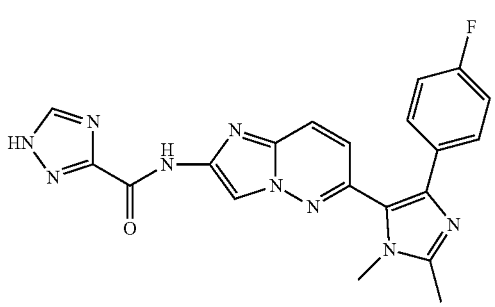 [SMILES: Cc1nc(-c2ccc(F)cc2)c(-c2ccc3nc(NC(=O)c4nc[nH]n4)cn3n2)n1C] | N-(6-(4-(4-fluorophenyl)-1,2-dimethyl-1H-imidazol-5-yl)imidazo[1,2-b]pyridazin-2-yl)-1H-1,2,4-triazole-3-carboxamide | 418.23 | 3.19 | C |

TABLE 38-continued

| Compound No. | Structure | Name | [M + H]+ | Retention Time | HPLC Method |
|---|---|---|---|---|---|
| 369 | 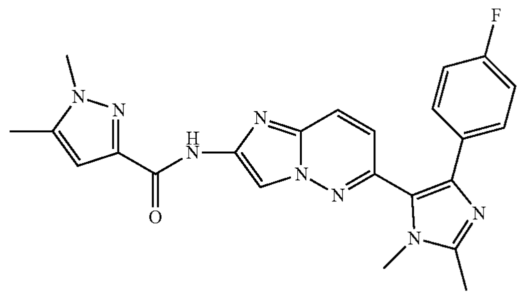 [SMILES: Cc1cc(C(=O)Nc2cn3nc(-c4c(-c5ccc(F)cc5)nc(C)n4C)ccc3n2)nn1C] | N-(6-(4-(4-fluorophenyl)-1,2-dimethyl-1H-imidazol-5-yl)imidazo[1,2-b]pyridazin-2-yl)-1,5-dimethyl-1H-pyrazole-3-carboxamide | 445.30 | 2.27 | B |
| 370 | 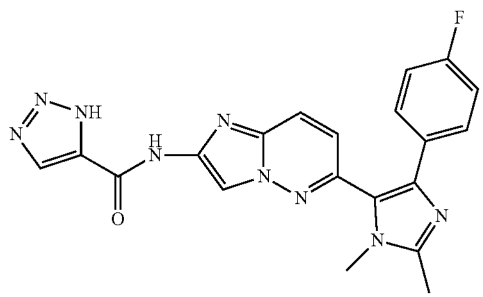 [SMILES: Cc1nc(-c2ccc(F)cc2)c(-c2ccc3nc(NC(=O)c4cnn[nH]4)cn3n2)n1C] | N-(6-(4-(4-fluorophenyl)-1,2-dimethyl-1H-imidazol-5-yl)imidazo[1,2-b]pyridazin-2-yl)-1H-1,2,3-trizole-4-carboxamide | 418.24 | 3.22 | C |
| 371 | 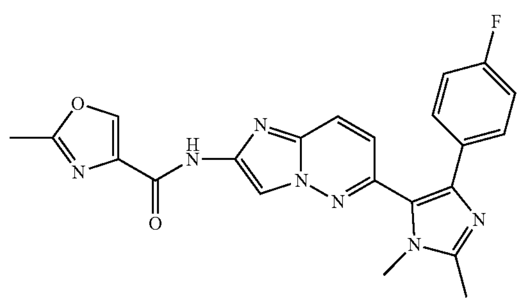 [SMILES: Cc1nc(C(=O)Nc2cn3nc(-c4c(-c5ccc(F)cc5)nc(C)n4C)ccc3n2)co1] | N-(6-(4-(4-fluorophenyl)-1,2-dimethyl-1H-imidazol-5-yl)imidazo[1,2-b]pyridazin-2-yl)-2-methyl-1,3-oxazole-4-carboxamide | 432.24 | 3.67 | C |
| 372 | 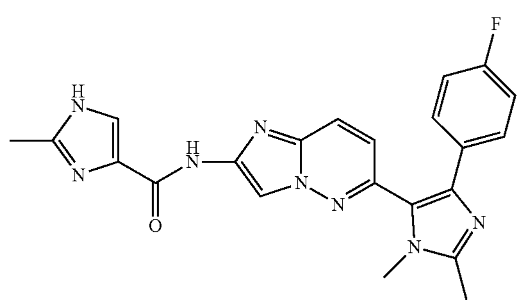 [SMILES: Cc1nc(C(=O)Nc2cn3nc(-c4c(-c5ccc(F)cc5)nc(C)n4C)ccc3n2)c[nH]1] | N-(6-(4-(4-fluorophenyl)-1,2-dimethyl-1H-imidazol-5-yl)imidazo[1,2-b]pyridazin-2-yl)-2-methyl-1H-imidazole-4-carboxamide | 431.26 | 3.46 | C |
| 373 | 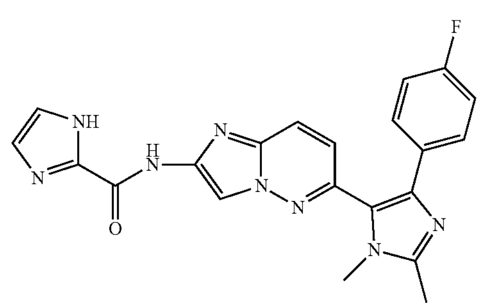 [SMILES: Cc1nc(-c2ccc(F)cc2)c(-c2ccc3nc(NC(=O)c4ncc[nH]4)cn3n2)n1C] | N-(6-(4-(4-fluorophenyl)-1,2-dimethyl-1H-imidazol-5-yl)imidazo[1,2-b]pyridazin-2-yl)-1H-imidazole-2-carboxamide | 417.25 | 3.45 | C |

TABLE 38-continued

| Compound No. | Structure | Name | [M + H]+ | Retention Time | HPLC Method |
|---|---|---|---|---|---|
| 374 | 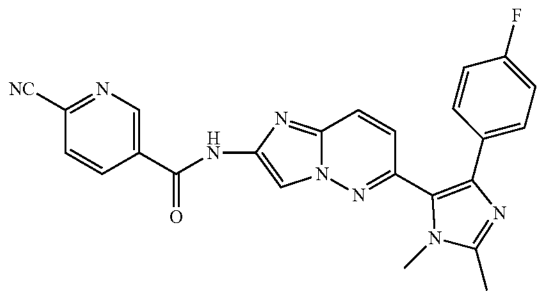 | 6-cyano-N-(6-(4-(4-fluorophenyl)-1,2-dimethyl-1H-imidazol-5-yl)imidazo[1,2-b]pyridazin-2-yl)nicotinamide | 453.25 | 3.65 | C |
| 375 | 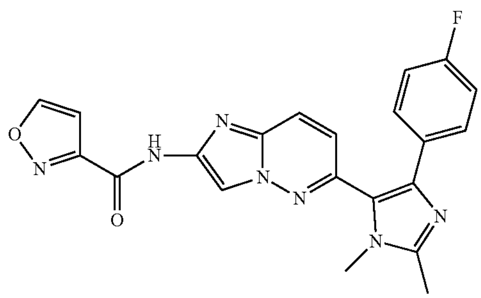 [SMILES: Cc1nc(-c2ccc(F)cc2)c(-c2ccc3nc(NC(=O)c4ccon4)cn3n2)n1C] | N-(6-(4-(4-fluorophenyl)-1,2-dimethyl-1H-imidazol-5-yl)imidazo[1,2-b]pyridazin-2-yl)-3-isoxazolecarboxamide | 418.22 | 3.57 | C |
| 376 | 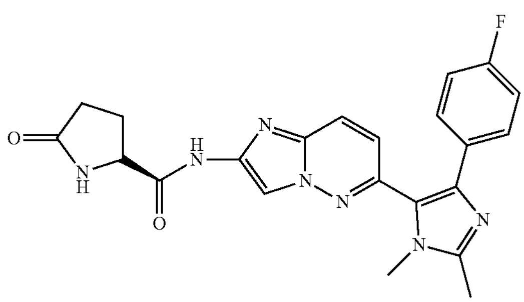 | N-(6-(4-(4-fluorophenyl)-1,2-dimethyl-1H-imidazol-5-yl)imidazo[1,2-b]pyridazin-2-yl)-5-oxo-L-prolinamide | 434.26 | 3.10 | C |
| 377 | 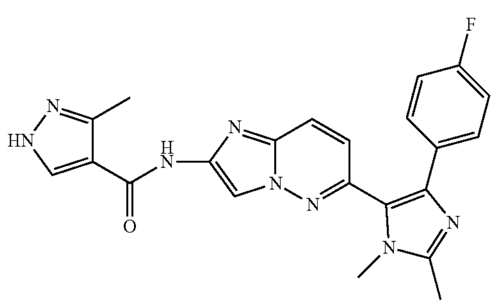 [SMILES: Cc1n[nH]cc1C(=O)Nc1cn2nc(-c3c(-c4ccc(F)cc4)nc(C)n3C)ccc2n1] | N-(6-(4-(4-fluorophenyl)-1,2-dimethyl-1H-imidazol-5-yl)imidazo[1,2-b]pyridazin-2-yl)-3-methyl-1H-pyrazole-4-carboxamide | 431.27 | 3.41 | C |
| 378 | 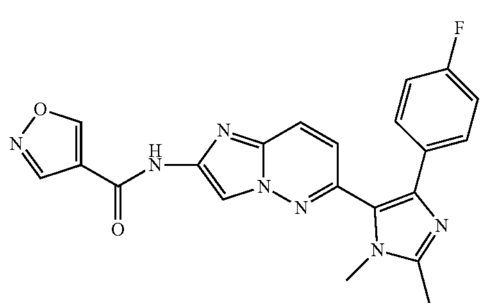 [SMILES: Cc1nc(-c2ccc(F)cc2)c(-c2ccc3nc(NC(=O)c4cnoc4)cn3n2)n1C] | N-(6-(4-(4-fluorophenyl)-1,2-dimethyl-1H-imidazol-5-yl)imidazo[1,2-b]pyridazin-2-yl)-4-isoxazolecarboxamide | 417.99 | 1.75 | B |

TABLE 38-continued

| Compound No. | Structure | Name | [M + H]+ | Retention Time | HPLC Method |
|---|---|---|---|---|---|
| 379 | 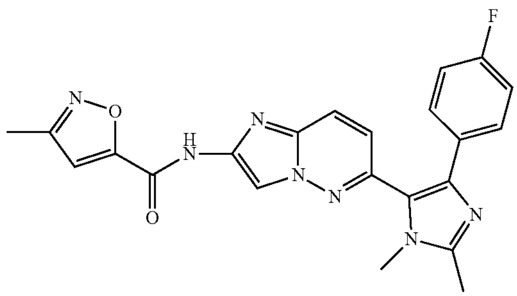 [SMILES: Cc1cc(C(=O)Nc2cn3nc(-c4c(-c5ccc(F)cc5)nc(C)n4C)ccc3n2)on1] | N-(6-(4-(4-fluorophenyl)-1,2-dimethyl-1H-imidazol-5-yl)imidazo[1,2-b]pyridazin-2-yl)-3-methyl-5-isoxazole-carboxamide | 432.20 | 3.58 | C |
| 380 | 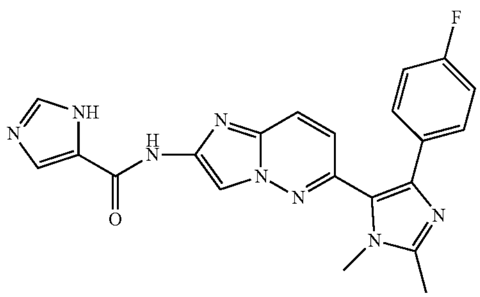 [SMILES: Cc1nc(-c2ccc(F)cc2)c(-c2ccc3nc(NC(=O)c4cnc[nH]4)cn3n2)n1C] | N-(6-(4-(4-fluorophenyl)-1,2-dimethyl-1H-imidazol-5-yl)imidazo[1,2-b]pyridazin-2-yl)-1H-imidazole-5-carboxamide | 417.23 | 3.27 | C |
| 381 | 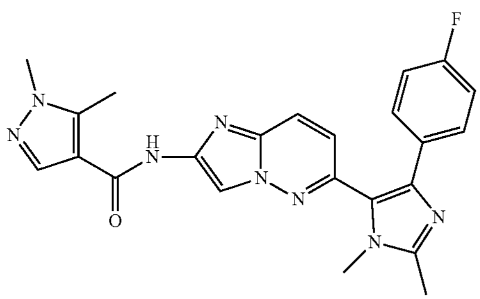 [SMILES: Cc1c(C(=O)Nc2cn3nc(-c4c(-c5ccc(F)cc5)nc(C)n4C)ccc3n2)cnn1C] | N-(6-(4-(4-fluorophenyl)-1,2-dimethyl-1H-imidazol-5-yl)imidazo[1,2-b]pyridazin-2-yl)-1,5-dimethyl-1H-pyrazole-4-carboxamide | 445.28 | 2.08 | B |
| 382 | 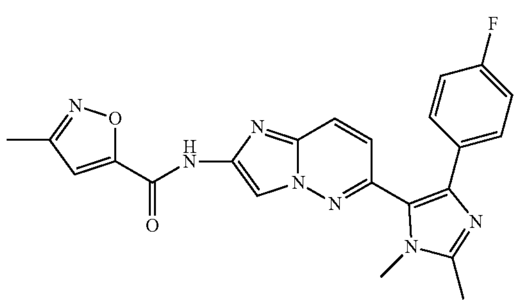 [SMILES: Cc1cc(C(=O)Nc2cn3nc(-c4c(-c5ccc(F)cc5)nc(C)n4C)ccc3n2)on1] | N-(6-(4-(4-fluorophenyl)-1,2-dimethyl-1H-imidazol-5-yl)imidazo[1,2-b]pyridazin-2-yl)-3-methyl-5-isoxazole-carboxamide | 432.19 | 3.20 | C |
| 383 | 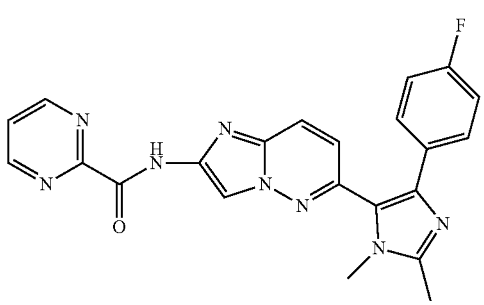 [SMILES: Cc1nc(-c2ccc(F)cc2)c(-c2ccc3nc(NC(=O)c4ncccn4)cn3n2)n1C] | N-(6-(4-(4-fluorophenyl)-1,2-dimethyl-1H-imidazol-5-yl)imidazo[1,2-b]pyridazin-2-yl)pyrimidine-2-carboxamide | 429.15 | 1.70 | I |

TABLE 38-continued

| Compound No. | Structure | Name | [M + H]+ | Retention Time | HPLC Method |
|---|---|---|---|---|---|
| 384 | 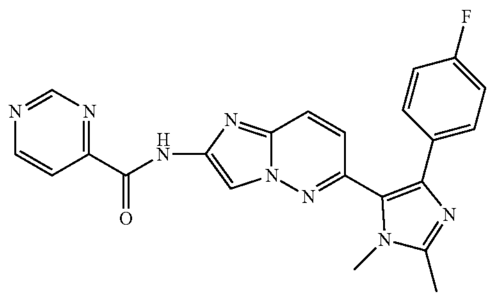 [SMILES: Cc1nc(-c2ccc(F)cc2)c(-c2ccc3nc(NC(=O)c4ccncn4)cn3n2)n1C] | N-(6-(4-(4-fluorophenyl)-1,2-dimethyl-1H-imidazol-5-yl)imidazo[1,2-b]pyridazin-2-yl)pyrimidine-4-carboxamide | 429.15 | 1.56 | I |
| 385 | 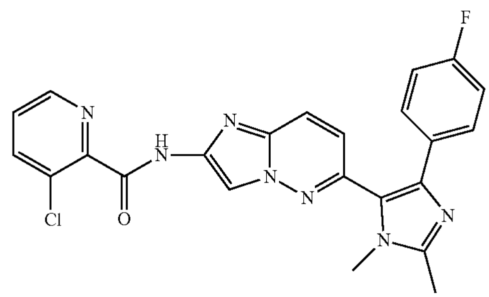 [SMILES: Cc1nc(-c2ccc(F)cc2)c(-c2ccc3nc(NC(=O)c4ncccc4Cl)cn3n2)n1C] | 3-chloro-N-(6-(4-(4-fluorophenyl)-1,2-dimethyl-1H-imidazol-5-yl)imidazo[1,2-b]pyridazin-2-yl)picolinamide | 462.88 | 1.66 | I |
| 386 | 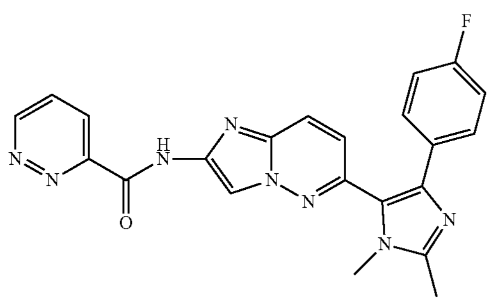 [SMILES: Cc1nc(-c2ccc(F)cc2)c(-c2ccc3nc(NC(=O)c4cccnn4)cn3n2)n1C] | N-(6-(4-(4-fluorophenyl)-1,2-dimethyl-1H-imidazol-5-yl)imidazo[1,2-b]pyridazin-2-yl)pyridazine-3-carboxamide | 429.16 | 1.59 | J |
| 387 | 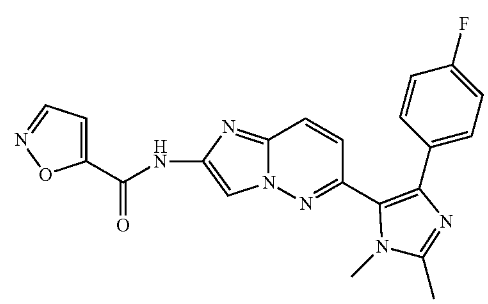 [SMILES: Cc1nc(-c2ccc(F)cc2)c(-c2ccc3nc(NC(=O)c4ccno4)cn3n2)n1C] | N-(6-(4-(4-fluorophenyl)-1,2-dimethyl-1H-imidazol-5-yl)imidazo[1,2-b]pyridazin-2-yl)isoxazole-5-carboxamide | 418.40 | 1.70 | I |
| 388 | 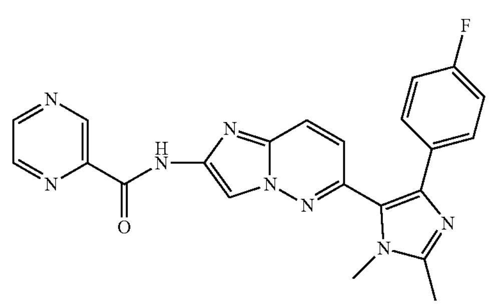 [SMILES: Cc1nc(-c2ccc(F)cc2)c(-c2ccc3nc(NC(=O)c4cnccn4)cn3n2)n1C] | N-(6-(4-(4-fluorophenyl)-1,2-dimethyl-1H-imidazol-5-yl)imidazo[1,2-b]pyridazin-2-yl)pyrazine-2-carboxamide | 429.42 | 1.94 | G |

TABLE 38-continued

| Compound No. | Structure | Name | [M + H]⁺ | Retention Time | HPLC Method |
|---|---|---|---|---|---|
| 389 | 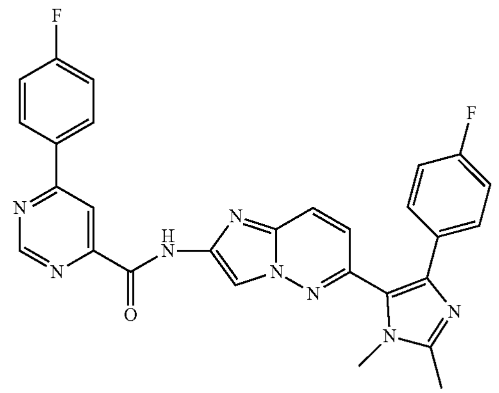 [SMILES: Cc1nc(-c2ccc(F)cc2)c(-c2ccc3nc(NC(=O)c4cc(-c5ccc(F)cc5)ncn4)cn3n2)n1C] | 6-(4-fluorophenyl-N-(6-(4-(4-fluorophenyl)-1,2-dimethyl-1H-imidazol-5-yl)imidazo[1,2-b]pyridazin-2-yl)pyrimidine-4-carboxamide | 523.51 | 1.14 | G |
| 390 | 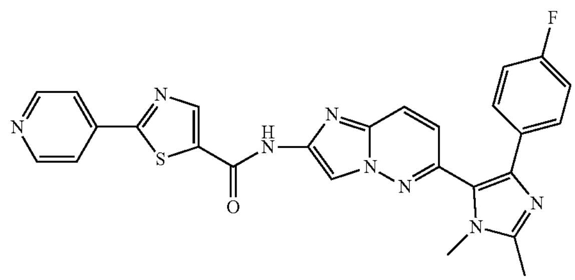 [SMILES: Cc1nc(-c2ccc(F)cc2)c(-c2ccc3nc(NC(=O)c4cnc(-c5ccncc5)s4)cn3n2)n1C] | N-(6-(4-(4-fluorophenyl)-1,2-dimethyl-1H-imidazol-5-yl)imidazo[1,2-b]pyridazin-2-yl)-2-(pyridin-4-yl)thiazole-5-carboxamide | 511.55 | 1.31 | G |
| 391 | 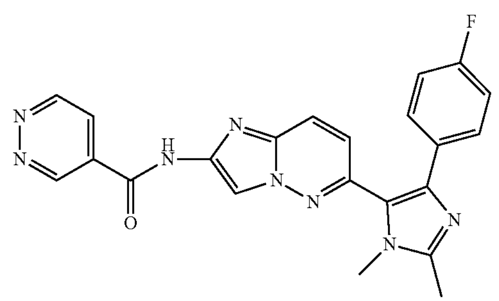 [SMILES: Cc1nc(-c2ccc(F)cc2)c(-c2ccc3nc(NC(=O)c4ccnnc4)cn3n2)n1C] | N-(6-(4-(4-fluorophenyl)-1,2-dimethyl-1H-imidazol-5-yl)imidazo[1,2-b]pyridazin-2-yl)pyridazine-4-carboxamide | 429.43 | 1.31 | J |
| 392 | 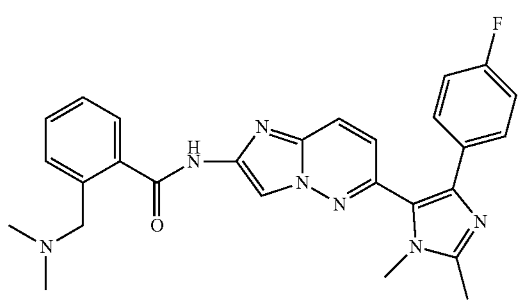 [SMILES: Cc1nc(-c2ccc(F)cc2)c(-c2ccc3nc(NC(=O)c4ccccc4CN(C)C)cn3n2)n1C] | 2-((dimthylamino)methyl)-N-(6-(4-(4-fluorophenyl)-1,2-dimethyl-1H-imidazol-5-yl)imidazo[1,2-b]pyridazin-2-yl)benzamide | 484.54 | 1.70 | J |
| 393 | 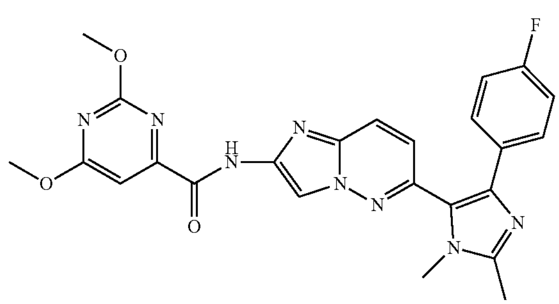 [SMILES: COc1cc(C(=O)Nc2cn3nc(-c4c(-c5ccc(F)cc5)nc(C)n4C)ccc3n2)nc(OC)n1] | N-(6-(4-(4-fluorophenyl)-1,2-dimethyl-1H-imidazol-5-yl)imidazo[1,2-b]pyridazin-2-yl)-2,6-dimethoxypyrimidine-4-carboxamide | 489.47 | 1.33 | J |

TABLE 38-continued

| Compound No. | Structure | Name | [M + H]+ | Retention Time | HPLC Method |
|---|---|---|---|---|---|
| 394 | 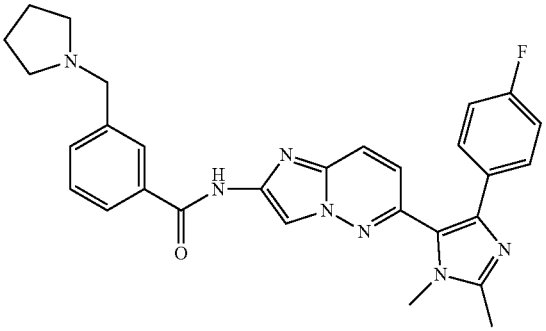 [SMILES: Cc1nc(-c2ccc(F)cc2)c(-c2ccc3nc(NC(=O)c4cccc(CN5CCCC5)c4)cn3n2)n1C] | N-(6-(4-(4-fluorophenyl)-1,2-dimethyl-1H-imidazol-5-yl)imidazo[1,2-b]pyridazin-2-yl)-3-(pyrrolidin-1-ylmethyl)benzamide | 510.58 | 1.36 | G |
| 395 | 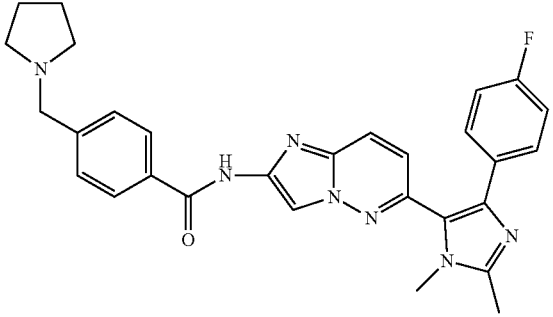 [SMILES: Cc1nc(-c2ccc(F)cc2)c(-c2ccc3nc(NC(=O)c4ccc(CN5CCCC5)cc4)cn3n2)n1C] | N-(6-(4-(4-fluorophenyl)-1,2-dimethyl-1H-imidazol-5-yl)imidazo[1,2-b]pyridazin-2-yl)-4-(pyrrolidin-1-ylmethyl)benzamide | 510.23 | 1.29 | J |
| 396 | 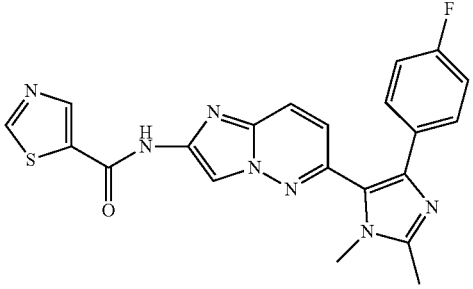 [SMILES: Cc1nc(-c2ccc(F)cc2)c(-c2ccc3nc(NC(=O)c4cncs4)cn3n2)n1C] | N-(6-(4-(4-fluorophenyl)-1,2-dimethyl-1H-imidazol-5-yl)imidazo[1,2-b]pyridazin-2-yl)thiazole-5-carboxamide | 434.11 | 1.38 | G |
| 397 | 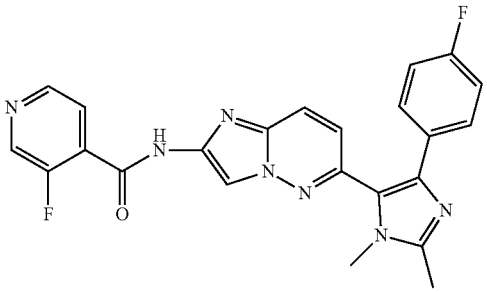 [SMILES: Cc1nc(-c2ccc(F)cc2)c(-c2ccc3nc(NC(=O)c4ccncc4F)cn3n2)n1C] | 3-fluoro-N-(6-(4-(4-fluorophenyl)-1,2-dimethyl-1H-imidazol-5-yl)imidazo[1,2-b]pyridazin-2-yl)isonicotinamide | 446.15 | 2.08 | I |
| 398 | 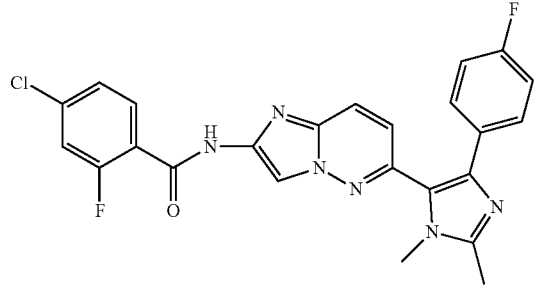 [SMILES: Cc1nc(-c2ccc(F)cc2)c(-c2ccc3nc(NC(=O)c4ccc(Cl)cc4F)cn3n2)n1C] | 4-chloro-2-fluoro-N-(6-(4-(4-fluorophenyl)-1,2-dimethyl-1H-imidazol-5-yl)imidazo[1,2-b]pyridazin-2-yl)benzamide | 479.11 | 1.08 | G |

TABLE 38-continued

| Compound No. | Structure | Name | [M + H]+ | Retention Time | HPLC Method |
|---|---|---|---|---|---|
| 399 | 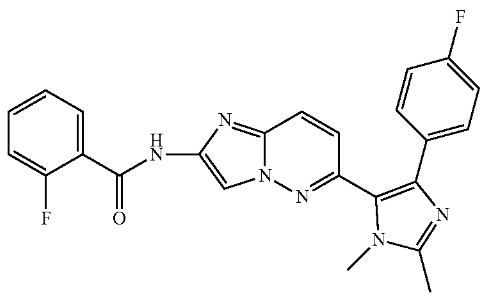 [SMILES: Cc1nc(-c2ccc(F)cc2)c(-c2ccc3nc(NC(=O)c4ccccc4F)cn3n2)n1C] | 2-fluoro-N-(6-(4-(4-fluoro-phenyl)-1,2-dimethyl-1H-imidazol-5-yl)imidazo[1,2-b]pyridazin-2-yl)benzamide | 445.15 | 2.08 | I |
| 400 | 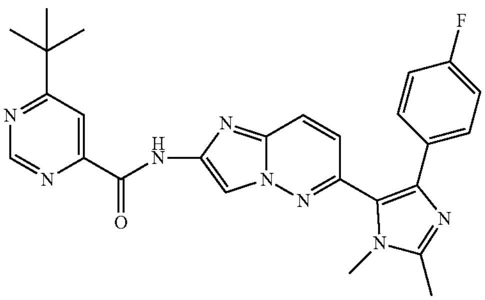 [SMILES: Cc1nc(-c2ccc(F)cc2)c(-c2ccc3nc(NC(=O)c4cc(C(C)(C)C)ncn4)cn3n2)n1C] | 6-(tert-butyl)-N-(6-(4-(4-fluorophenyl)-1,2-dimethyl-1H-imidazol-5-yl)imidazo[1,2-b]pyridazin-2-yl)pyrimidine-4-carboxamide | 485.21 | 1.31 | J |
| 401 | 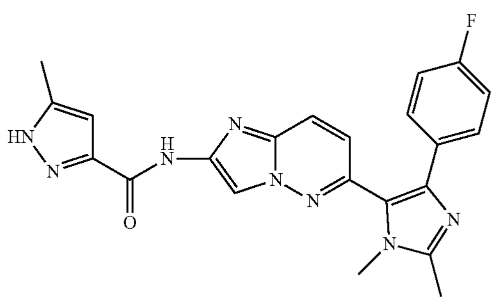 [SMILES: Cc1cc(C(=O)Nc2cn3nc(-c4c(-c5ccc(F)cc5)nc(C)n4C)ccc3n2)n[nH]1] | N-(6-(4-(4-fluorophenyl)-1,2-dimethyl-1H-imidazol-5-yl)imidazo[1,2-b]pyridazin-2-yl)-5-methyl-1H-pyrazole-3-carboxamide | 431.17 | 2.54 | I |

Intermediate 32

Methyl 2,4-dimethyl-5-(pyridin-3-yl)benzoate

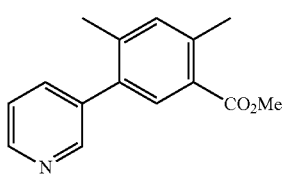 [SMILES: COC(=O)c1cc(-c2cccnc2)c(C)cc1C]

Nitrogen was bubbled through a mixture of pyridin-3-ylboronic acid (132 mg, 1.077 mmol), methyl 5-iodo-2,4-dimethylbenzoate (250 mg, 0.862 mmol), PdCl$_2$(dppf)-CH$_2$Cl$_2$ adduct (35.2 mg, 0.043 mmol), 2 M Na$_2$CO$_3$ (1.293 mL, 2.59 mmol), and DME (7 mL). The reaction was heated to 100° C. for 2.5 h, then cooled to room temperature. The reaction was diluted with EtOAc (75 mL) and washed with water (75 mL) and brine (75 mL). The organics were dried (MgSO$_4$), filtered, and concentrated in vacuo. The residue was purified via silica gel chromatography (0 to 40% EtOAc/Hex) to give Intermediate 32 (183 mg, 88%).

MS(ES): m/z=242.2 [M+H]+. HPLC retention time (Method D): 2.023 min. $^1$H NMR (400 MHz, chloroform-d) δ 8.63 (br. s., 1H), 7.88-7.71 (m, 1H), 7.49 (br. s., 1H), 7.22 (s, 1H), 3.93-3.85 (m, 3H), 2.64 (s, 3H), 2.30 (s, 3H).

Compound 402

N-(6-(4-(4-Fluorophenyl)-1,2-dimethyl-1H-imidazol-5-yl)imidazo[1,2-b]pyridazin-2-yl)-2,4-dimethyl-5-(pyridin-3-yl)benzamide

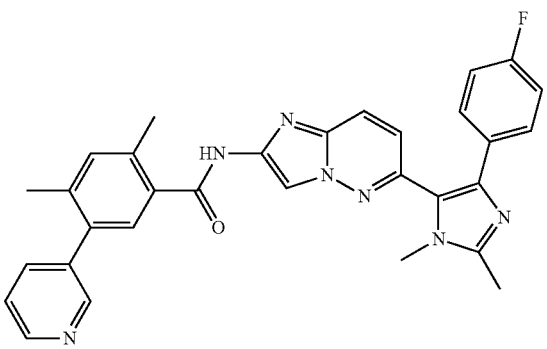 [SMILES: Cc1cc(C)c(-c2cccnc2)cc1C(=O)Nc1cn2nc(-c3c(-c4ccc(F)cc4)nc(C)n3C)ccc2n1]

THF (1 mL) and NaHMDS (1 M in THF, 0.371 mL, 0.371 mmol) were added to Intermediate 31 (40 mg, 0.093 mmol). After ca 5 min, the reaction contents were transferred to a vial containing Intermediate 32 (67.1 mg, 0.278 mmol). The reaction was stirred overnight at room temperature. The reaction was diluted with water (30 mL) and extracted with EtOAc (2×30 mL). The combined extracts were dried (MgSO$_4$), filtered, and concentrated in vacuo. The residue was purified by preparative HPLC to give Compound 402 (10.2 mg, 20%). MS(ES): m/z=532.3 [M+H]$^+$. HPLC retention time (Method B): 2.64 min. $^1$H NMR (500 MHz, DMSO-d$_6$) δ 11.43 (s, 1H), 8.72 (d, J=1.8 Hz, 1H), 8.62 (dd, J=4.7, 1.7 Hz, 1H), 8.54 (s, 1H), 8.02 (d, J=9.2 Hz, 1H), 7.93 (dt, J=7.9, 2.0 Hz, 1H), 7.55-7.50 (m, 2H), 7.49-7.44 (m, 2H), 7.32 (s, 1H), 7.16-7.09 (m, 2H), 7.07 (d, J=9.5 Hz, 1H), 3.59 (s, 3H), 2.49 (s, 3H), 2.46 (s, 3H), 2.31 (s, 3H).

Intermediate 33

Methyl 2-methyl-3-(pyridin-3-yl)benzoate

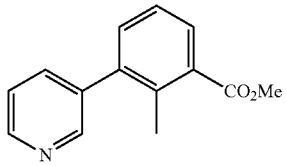 [SMILES: COC(=O)c1cccc(-c2cccnc2)c1C]

Nitrogen was bubbled through a mixture of pyridin-3-ylboronic acid (168 mg, 1.364 mmol), methyl 3-bromo-2-methylbenzoate (250 mg, 1.091 mmol), PdCl$_2$(dppf)-CH$_2$Cl$_2$ adduct (44.6 mg, 0.055 mmol), 2 M Na$_2$CO$_3$ (1.637 mL, 3.27 mmol), and DME (7 mL). The reaction was heated to 100° C. for 2.5 h, then cooled to room temperature. The reaction was diluted with EtOAc (75 mL) and washed with water (75 mL) and brine (75 mL). The organics were dried (MgSO$_4$), filtered, and concentrated in vacuo. The residue was purified via a silica gel chromatography (0 to 40% EtOAc/Hex over 10 column volumes) to give Intermediate 33 (227 mg, 92%). MS(ES): m/z=228.1 [M+H]$^+$. HPLC retention time (Method D): 1.910 min. $^1$H NMR (400 MHz, chloroform-d) δ 8.66 (dd, J=4.9, 1.4 Hz, 1H), 8.60 (d, J=1.8 Hz, 1H), 7.95-7.85 (m, 1H), 7.77 (dt, J=7.8, 1.8 Hz, 1H), 7.50 (dd, J=7.7, 4.9 Hz, 1H), 7.40-7.33 (m, 2H), 3.94 (s, 3H), 2.43 (s, 3H).

Compound 403

N-(6-(4-(4-Fluorophenyl)-1,2-dimethyl-1H-imidazol-5-yl)imidazo[1,2-b]pyridazin-2-yl)-2-methyl-3-(pyridin-3-yl)benzamide

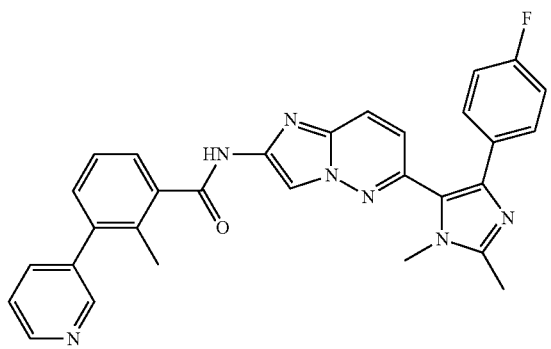 [SMILES: Cc1c(C(=O)Nc2cn3nc(-c4c(-c5ccc(F)cc5)nc(C)n4C)ccc3n2)cccc1-c1cccnc1]

THF (1.5 mL) and NaHMDS (1 M/THF) (0.371 mL, 0.371 mmol) were added to Intermediate 31 (40 mg, 0.093 mmol). After a few minutes, the reaction was transferred to a vial containing Intermediate 33 (105 mg, 0.462 mmol). The reaction was stirred overnight at room temperature. The reaction was diluted with water (30 mL) and extracted with EtOAc (2×30 mL) The combined extracts were dried (MgSO$_4$), filtered, and concentrated in vacuo. The residue was purified by preparative HPLC to give Compound 403 (5.6 mg, 11%). MS(ES): m/z=518.230 [M+H]$^+$. HPLC retention time (Method B): 2.41 min. $^1$H NMR (500 MHz, DMSO-d$_6$) δ 11.48 (s, 1H), 8.64 (dd, J=4.9, 1.5 Hz, 1H), 8.60 (d, J=1.8 Hz, 1H), 8.55 (s, 1H), 8.04 (d, J=9.5 Hz, 1H), 7.84 (dt, J=7.9, 2.0 Hz, 1H), 7.58-7.51 (m, 2H), 7.50-7.37 (m, 4H), 7.18-7.05 (m, 3H), 3.59 (s, 3H), 2.46 (s, 3H), 2.28 (s, 3H).

Compound 404

N-(6-(4-(4-Fluorophenyl)-1,2-dimethyl-1H-imidazol-5-yl)imidazo[1,2-b]pyridazin-2-yl)-2-(pyridin-3-yl)-4-(trifluoromethyl)thiazole-5-carboxamide

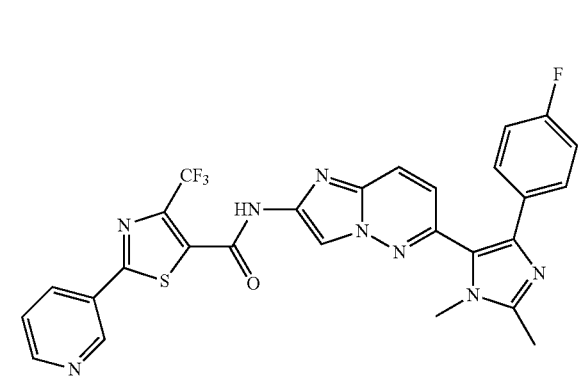 [SMILES: Cc1nc(-c2ccc(F)cc2)c(-c2ccc3nc(NC(=O)c4sc(-c5cccnc5)nc4C(F)(F)F)cn3n2)n1C]

THF (0.5 mL) was added to Intermediate 31 (40 mg, 0.093 mmol), followed by NaHMDS (1 M/THF) (0.371 mL, 0.371 mmol) and a solution of ethyl 2-(pyridin-3-yl)-4-(trifluoromethyl)thiazole-5-carboxylate (84 mg, 0.278 mmol) (prepared according to WO 2010/129497) in THF (0.5 mL) The reaction was stirred overnight at room temperature. The reaction was diluted with water (30 mL) and extracted with EtOAc (2×30 mL). The combined organics were dried (MgSO$_4$), filtered, and concentrated in vacuo. The residue was purified by preparative HPLC to give Compound 404 (5.6 mg, 11%). MS(ES): m/z=579.2 [M+H]$^+$. HPLC retention time (Method B): 2.61 min $^1$H NMR (500 MHz, DMSO-d$_6$) δ 12.23 (br. s., 1H), 9.24 (br. s., 1H), 8.81 (d, J=3.4 Hz, 1H), 8.52 (s, 1H), 8.45 (d, J=8.2 Hz, 1H), 8.07 (d, J=9.2 Hz, 1H), 7.69-7.60 (m, 1H), 7.47 (br. s., 2H), 7.18-7.05 (m, 3H), 3.61 (s, 3H), 2.46 (s, 3H).

Intermediate 34

Ethyl 2-(pyridin-4-yl)-4-(trifluoromethyl)thiazole-5-carboxylate

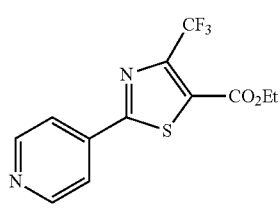 [SMILES: CCOC(=O)c1sc(-c2ccncc2)nc1C(F)(F)F]

A mixture of EtOH (15 mL), ethyl 2-chloro-4,4,4-trifluoro-3-oxobutanoate (1748 mg, 8.00 mmol), and pyridine-4-carbothioamide (553 mg, 4 mmol) was heated to 150° C. for 10 min in a microwave reactor. After cooling, Et$_3$N (1.673 mL, 12.00 mmol) was added, and the reaction was microwaved at 130° C. for 1 min. The reaction was concentrated in vacuo, and the residue was purified via a silica gel chromatography (0 to 60% EtOAc/Hex), followed by preparative HPLC to afford Intermediate 34 (449 mg, 37%). MS(ES): m/z=303.1 [M+H]$^+$. HPLC retention time (Method D): 2.035 min. $^1$H NMR (400 MHz, DMSO-d$_6$) δ 8.85-8.78 (m, 2H), 8.05-7.98 (m, 2H), 4.41 (q, J=7.2 Hz, 2H), 1.34 (t, J=7.2 Hz, 3H).

Compound 405

N-(6-(4-(4-Fluorophenyl)-1,2-dimethyl-1H-imidazol-5-yl)imidazo[1,2-b]pyridazin-2-yl)-2-(pyridin-4-yl)-4-(trifluoromethyl)thiazole-5-carboxamide

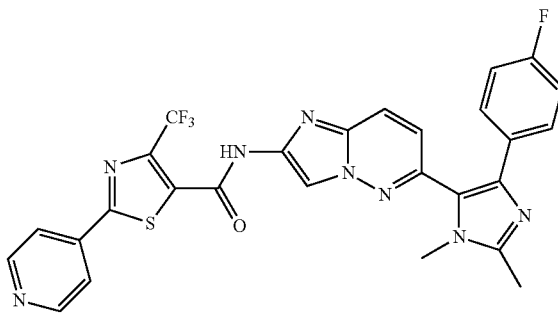

THF (1 mL) and NaHMDS (1 M/THF) (0.371 mL, 0.371 mmol) were added to Intermediate 31 (40 mg, 0.093 mmol), followed by Intermediate 34 (84 mg, 0.278 mmol). The reaction was stirred at room temperature overnight. The reaction was diluted with water (30 mL) and extracted with EtOAc (2×30 mL). The combined organics were dried (MgSO$_4$), filtered, and concentrated in vacuo. The residue was purified by preparative HPLC to give Compound 405 (6.6 mg, 12%). MS(ES): m/z=579.170 [M+H]$^+$. HPLC retention time (Method B): 2.60 min. $^1$H NMR (500 MHz, DMSO-d$_6$) δ 12.24 (br. s., 1H), 8.85-8.81 (m, 2H), 8.52 (s, 1H), 8.07 (d, J=9.2 Hz, 1H), 8.04-7.99 (m, 2H), 7.51-7.44 (m, 2H), 7.16-7.08 (m, 3H), 3.61 (s, 3H), 2.46 (s, 3H).

Intermediate 35

Ethyl 6'-fluoro-[3,3'-bipyridine]-5-carboxylate

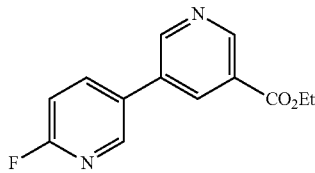 [SMILES: CCOC(=O)c1cncc(-c2ccc(F)nc2)c1]

Nitrogen was bubbled through a mixture of (6-fluoropyridin-3-yl)boronic acid (250 mg, 1.774 mmol), ethyl 5-bromonicotinate (272 mg, 1.183 mmol), PdCl$_2$(dppf)-CH$_2$Cl$_2$ adduct (48.3 mg, 0.059 mmol), 2 M Na$_2$CO$_3$ (1.774 mL, 3.55 mmol), and DME (7 mL) The reaction was capped and heated to 100° C. for 12 h, then diluted with EtOAc (100 mL) and washed with water (100 mL) and brine (100 mL). The organics were dried (MgSO$_4$), filtered, and concentrated in vacuo. The residue was purified via silica gel chromatography (0 to 100% EtOAc/Hex) to obtain Intermediate 35 (117 mg, 40%). MS(ES): m/z=247.11 [M+H]$^+$. HPLC retention time (Method E): 1.768 min. $^1$H NMR (400 MHz, chloroform-d) δ 9.28 (s, 1H), 9.01 (br. s., 1H), 8.53 (d, J=17.1 Hz, 2H), 8.11-8.01 (m, 1H), 7.13 (dd, J=8.4, 2.9 Hz, 1H), 4.49 (q, J=7.3 Hz, 2H), 1.46 (t, J=7.2 Hz, 3H).

Compound 406

6'-Fluoro-N-(6-(4-(4-fluorophenyl)-1,2-dimethyl-1H-imidazol-5-yl)imidazo[1,2-b]pyridazin-2-yl)-[3,3'-bipyridine]-5-carboxamide

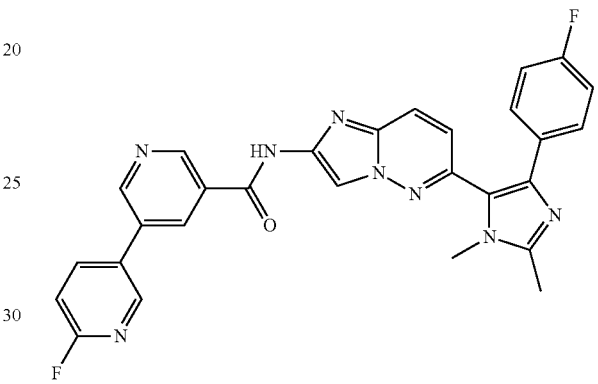

THF (1.5 mL) and NaHMDS (1 M/THF) (0.371 mL, 0.371 mmol) were added to Intermediate 31 (40 mg, 0.093 mmol). After a few minutes, Intermediate 35 (68.4 mg, 0.278 mmol) was added. The reaction was stirred overnight at room temperature. The reaction was diluted with water (30 mL) and extracted with EtOAc (2×30 mL). The combined organics were dried (MgSO$_4$), filtered, and concentrated in vacuo. The residue was purified by preparative HPLC to give Compound 406 (14 mg, 28%). MS(ES): m/z=523.2 [M+H]$^+$. HPLC retention time (Method B): 2.34 min $^1$H NMR (500 MHz, DMSO-d$_6$) δ 11.85 (br. s., 1H), 9.21 (dd, J=17.1, 2.1 Hz, 2H), 8.88 (t, J=2.1 Hz, 1H), 8.82 (d, J=2.4 Hz, 1H), 8.60 (s, 1H), 8.55 (td, J=8.1, 2.7 Hz, 1H), 8.07 (d, J=9.2 Hz, 1H), 7.52-7.45 (m, 2H), 7.43 (dd, J=8.5, 2.7 Hz, 1H), 7.19-7.07 (m, 3H), 3.61 (s, 3H), 2.46 (s, 3H).

Compound 407

3-(6-(4-(4-Fluorophenyl)-1,2-dimethyl-1H-imidazol-5-yl)imidazo[1,2-b]pyridazin-2-yl)-1-methyl-1-phenylurea

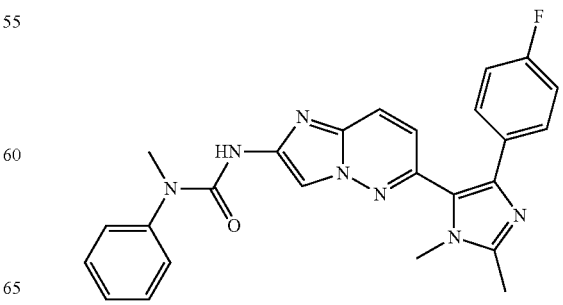

Triphosgene (0.1 M/dichloromethane) (0.324 mL, 0.032 mmol) was slowly added to a solution of Intermediate 31 (40 mg, 0.093 mmol), N-methylaniline (9.93 mg, 0.093 mmol), DIPEA (0.065 mL, 0.371 mmol), and DCM (1.5 mL) The reaction was stirred at room temperature overnight. A small amount of methanol was added, and the reaction was concentrated in vacuo. The residue was purified by preparative HPLC to give Compound 407 (14 mg, 28%). MS(ES): m/z=456.2 [M+H]+. HPLC retention time (Method B): 2.46 min. NMR (500 MHz, DMSO-$d_6$) δ 8.91 (s, 1H), 8.21 (s, 1H), 7.90 (d, J=9.2 Hz, 1H), 7.50-7.42 (m, 4H), 7.41-7.36 (m, 2H), 7.35-7.30 (m, 1H), 7.11 (t, J=9.0 Hz, 2H), 7.02 (d, J=9.2 Hz, 1H), 3.56 (s, 3H), 2.44 (s, 3H), 1.90 (s, 3H).

The following compounds in Table 39 were prepared by the procedure described for the preparation of compound 407 using the corresponding amine.

TABLE 39

| Compound No. | Structure | Name | [M + H]+ | Retention Time | HPLC Method |
|---|---|---|---|---|---|
| 408 | 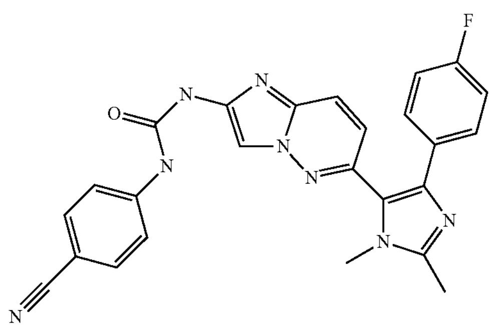 [SMILES: Cc1nc(-c2ccc(F)cc2)c(-c2ccc3nc(NC(=O)Nc4ccc(C#N)cc4)cn3n2)n1C] | 1-(4-cyanophenyl)-3-(6-(4-(4-fluorophenyl)-1,2-dimethyl-1H-imidazol-5-yl)imidazo[1,2-b]pyridazin-2-yl)urea | 467.1 | 2.44 | B |
| 409 | 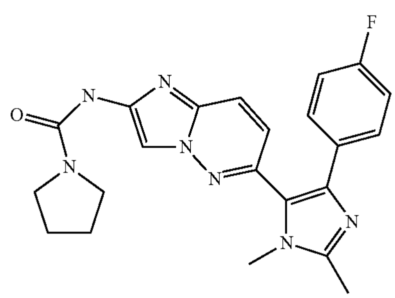 [SMILES: Cc1nc(-c2ccc(F)cc2)c(-c2ccc3nc(NC(=O)N4CCCC4)cn3n2)n1C] | N-(6-(4-(4-fluorophenyl)-1,2-dimethyl-1H-imidazol-5-yl)imidazo[1,2-b]pyridazin-2-yl)pyrrolidine-1-carboxamide | 420.2 | 2.09 | B |
| 410 | 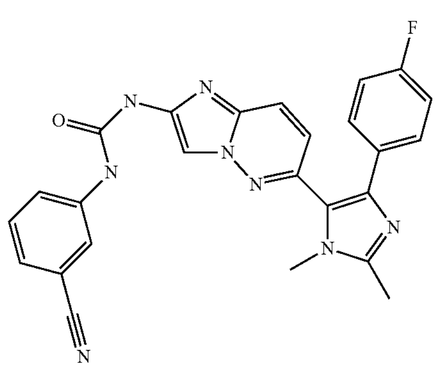 [SMILES: Cc1nc(-c2ccc(F)cc2)c(-c2ccc3nc(NC(=O)Nc4cccc(C#N)c4)cn3n2)n1C] | 1-(3-cyanophenyl)-3-(6-(4-(4-fluorophenyl)-1,2-dimethyl-1H-imidazol-5-yl)imidazo[1,2-b]pyridazin-2-yl)urea | 467.3 | 2.46 | B |

Compound 411

N-(3-Bromo-6-(4-(4-fluorophenyl)-1,2-dimethyl-1H-imidazol-5-yl)imidazo[1,2-b]pyridazin-2-yl)-2-fluoroisonicotinamide

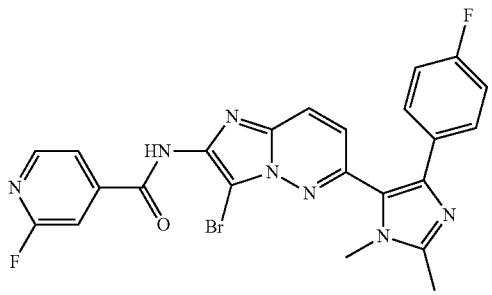 [SMILES: Cc1nc(-c2ccc(F)cc2)c(-c2ccc3nc(NC(=O)c4ccnc(F)c4)c(Br)n3n2)n1C]

NBS (17.58 mg, 0.099 mmol) was added to a solution of Compound 321 (40 mg, 0.090 mmol) in DMF (500 µl). The reaction was stirred at room temperature for 15 min. The residue was purified by preparative HPLC to give Compound 411 (24.6 mg, 50%). MS(ES): m/z=524.6 [M+H]⁺. HPLC retention time (Method B): 2.40 min. ¹H NMR (500 MHz, DMSO-$d_6$) δ 11.22 (br. s., 1H), 8.52 (d, J=5.2 Hz, 1H), 8.14 (d, J=9.5 Hz, 1H), 7.93 (d, J=4.9 Hz, 1H), 7.75 (s, 1H), 7.57-7.51 (m, 2H), 7.19-7.12 (m, 3H), 3.70 (s, 3H), 2.48 (s, 3H).

Compound 412

N-(3-Chloro-6-(4-(4-fluorophenyl)-1,2-dimethyl-1H-imidazol-5-yl)imidazo[1,2-b]pyridazin-2-yl)-2-fluoroisonicotinamide

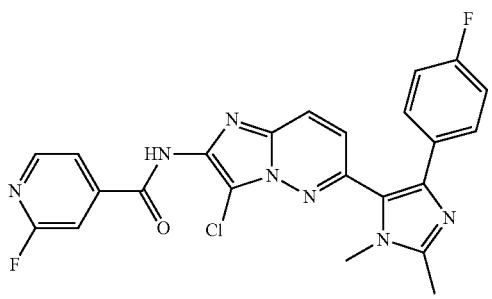 [SMILES: Cc1nc(-c2ccc(F)cc2)c(-c2ccc3nc(NC(=O)c4ccnc(F)c4)c(Cl)n3n2)n1C]

NCS (13.19 mg, 0.099 mmol) was added to a solution of Compound 321 (40 mg, 0.090 mmol) in DMF (500 µl) overnight. The residue was purified by preparative HPLC to give Compound 412 (31.3 mg, 72.6%). MS(ES): m/z=480.1, 482.2 [M+H]⁺. HPLC retention time (Method B): 2.26 min. ¹H NMR (500 MHz, DMSO-$d_6$) δ 11.30 (br. s., 1H), 8.51 (d, J=5.2 Hz, 1H), 8.16 (d, J=9.5 Hz, 1H), 7.94 (d, J=4.9 Hz, 1H), 7.76 (s, 1H), 7.53 (dd, J=8.7, 5.6 Hz, 2H), 7.19-7.10 (m, 3H), 3.68 (s, 3H), 2.48 (s, 3H).

Compound 413

2-Fluoro-N-(6-(4-(4-fluorophenyl)-1,2-dimethyl-1H-imidazol-5-yl)-3-methylimidazo[1,2-b]pyridazin-2-yl)isonicotinamide

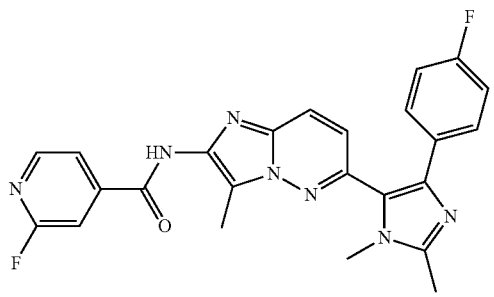 [SMILES: Cc1nc(-c2ccc(F)cc2)c(-c2ccc3nc(NC(=O)c4ccnc(F)c4)c(C)n3n2)n1C]

Compound 411 (50 mg, 0.095 mmol) and Pd(Ph₃P)₄ (11.02 mg, 9.54 µmol) were dissolved in DMF (800 µL). Tetramethyltin (15.85 µL, 0.114 mmol) was added, and the reaction was heated to 120° C. for 20 min in a microwave reactor. More tetramethyltin (20 µL, 0.144 mmol) was added, and the reaction was reheated to 150° C. for 20 min in the microwave, followed by an additional 30 min at 150° C. Heated again in the microwave for 30 min at 150° C. The residue was purified by preparative HPLC to give Compound 413 (15.8 mg, 34.6%). MS(ES): m/z=460.2 [M+H]⁺. HPLC retention time (Method B): 2.26 min. ¹H NMR (500 MHz, DMSO-$d_6$) δ 11.11 (br. s., 1H), 8.48 (d, J=4.9 Hz, 1H), 8.03 (d, J=9.5 Hz, 1H), 7.91 (br. s., 1H), 7.73 (s, 1H), 7.52-7.42 (m, 2H), 7.13 (t, J=8.9 Hz, 3H), 7.03 (d, J=9.5 Hz, 1H), 3.63 (s, 3H), 2.48 (s, 3H), 2.46 (s, 3H).

Compound 414

N-(6-(4-(4-Fluorophenyl)-1,2-dimethyl-1H-imidazol-5-yl)imidazo[1,2-b]pyridazin-2-yl)pivalamide

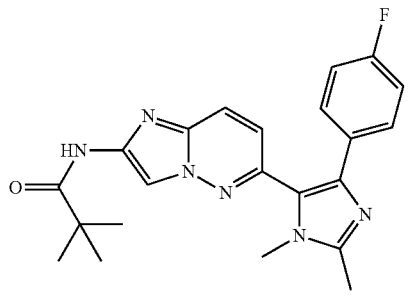 [SMILES: Cc1nc(-c2ccc(F)cc2)c(-c2ccc3nc(NC(=O)C(C)(C)C)cn3n2)n1C]

THF (1.00 mL) was added to Intermediate 31 (40 mg, 0.093 mmol), followed by DIPEA (0.081 mL, 0.463 mmol) and pivaloyl chloride (13.96 mg, 0.116 mmol). The reaction was stirred at room temperature overnight. The reaction was diluted with EtOAc (10 mL), then washed with water (10 mL) and brine (10 mL) The organics were dried (MgSO₄), filtered, and blown dry under a stream of nitrogen. The residue was purified by preparative HPLC to give Compound 414 (30.0 mg, 79.0%). MS(ES): m/z=407.5 [M+H]⁺. HPLC retention time (Method B): 2.42 min. ¹H NMR (500 MHz, DMSO-$d_6$) δ 10.56 (s, 1H), 8.37 (s, 1H), 7.99 (d, J=9.5 Hz, 1H), 7.48-7.42 (m, 2H), 7.15-7.08 (m, 2H), 7.06 (d, J=9.5 Hz, 1H), 3.57 (s, 3H), 2.45 (s, 3H), 1.27 (s, 9H).

Scheme 17

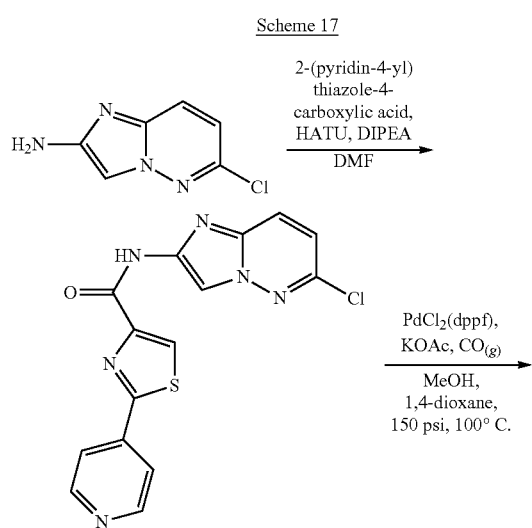

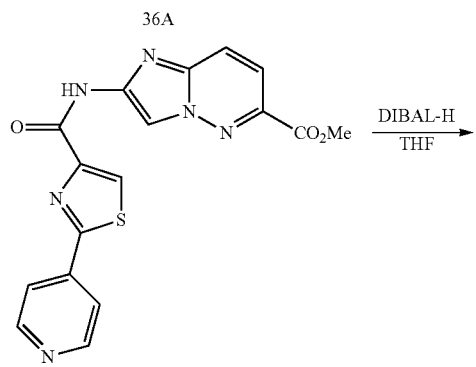

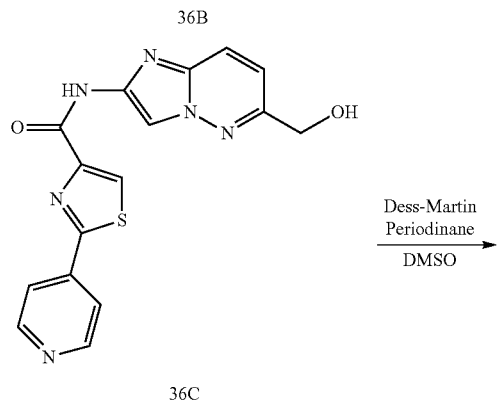

Intermediate 36

N-(6-Formylimidazo[1,2-b]pyridazin-2-yl)-2-(pyridin-4-yl)thiazole-5-carboxamide

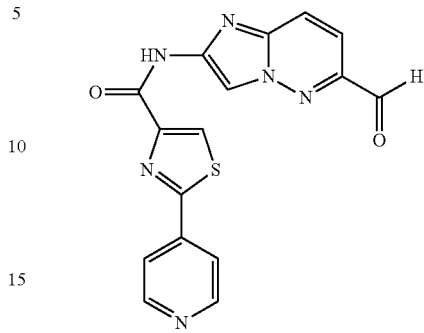

Intermediate 36A: N-(6-Chloroimidazo[1,2-b]pyridazin-2-yl)-2-(pyridin-4-yl)thiazole-4-carboxamide

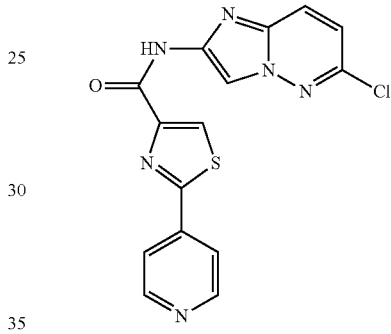

DMF (90 mL) and DIPEA (622 mL, 35.6 mmol) were added to a mixture of 6-chloroimidazo[1,2-b]pyridazin-2-amine (3.00 g, 17.80 mmol) and 2-(pyridin-4-yl)thiazole-4-carboxylic acid (4.04 g, 19.57 mmol). HATU (7.78 g, 20.46 mmol) was added, and the reaction was stirred overnight at room temperature. The reaction was diluted with water (1 L), and the resulting solids were filtered off and dried in a warm vacuum oven to give Intermediate 36A (6.36 g, 100%). MS(ES): m/z=355.1 [M−H]⁻. HPLC retention time (Method D): 2.038 min. ¹H NMR (400 MHz, DMSO-$d_6$) δ 11.32 (s, 1H), 8.82-8.77 (m, 2H), 8.75 (s, 1H), 8.53 (s, 1H), 8.20-8.15 (m, 3H), 7.42 (d, J=9.5 Hz, 1H).

Intermediate 36B: Methyl 2-(2-(pyridin-4-yl)thiazole-5-carboxamido)imidazo[1,2-b]pyridazine-6-carboxylate

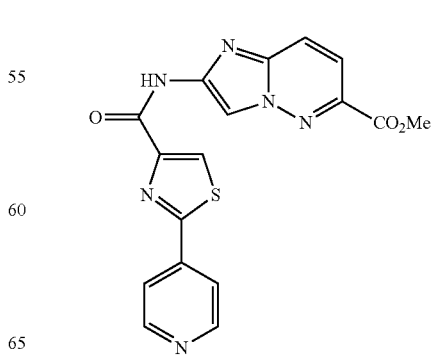

In a steel pressure reactor, dioxane (100 mL) and MeOH (20 mL, 494 mmol) were added to a mixture of Intermediate 36A (3.00 g, 8.41 mmol), PdCl$_2$(dppf) (1.230 g, 1.682 mmol), and KOAc (3.30 g, 33.6 mmol). The reactor was charged with 150 psi of carbon monoxide and heated to 100° C. overnight with stirring. Upon cooling to room temperature, the reaction mixture was filtered over CELITE®, rinsing with methanol. The solids were filtered off from the mixture, rinsed with methanol, dried, then agitated with 1:1 DCM/MeOH. The filtrate from above was concentrated in vacuo to a solid. These two solids were combined to give Intermediate 36B (1.93 g, 60%). MS(ES): m/z=379.1 [M+H]$^+$. HPLC retention time (Method D): 1.410 min. $^1$H NMR (400 MHz, DMSO-d$_6$) δ 11.42 (s, 1H), 8.82-8.76 (m, 3H), 8.64 (s, 1H), 8.26-8.15 (m, 3H), 7.80 (d, J=9.3 Hz, 1H), 3.98 (s, 3H).

Intermediate 36C: N-(6-(Hydroxymethyl)imidazo[1,2-b]pyridazin-2-yl)-2-(pyridin-4-yl)thiazole-5-carboxamide

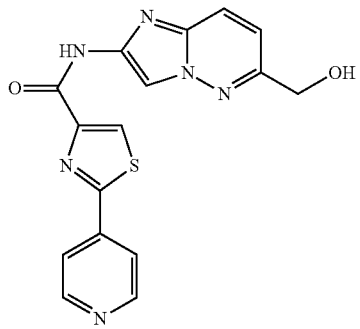 [SMILES: O=C(Nc1cn2nc(CO)ccc2n1)c1csc(-c2ccncc2)n1]

THF (13 mL) was added to Intermediate 36B (485 mg, 1.275 mmol). The pale yellow suspension was cooled in a dry ice/acetonitrile bath. DIBAL-H (1 M/DCM) (4.46 mL, 4.46 mmol) was added, and the suspension was removed from the cold bath after ca 15 min and allowed to stir at room temperature for 2.5 d. More DIBAL-H (1 M/DCM) (4.46 mL, 4.46 mmol) was added. The reaction was stirred at room temperature for 2.75 h, then 1 N NaOH (15 mL) was added. After several minutes, water (150 mL) and EtOAc (150 mL) were added. The mixture was stirred vigorously, then filtered over CELITE®. The layers of the filtrate were separated, and the aqueous layer was extracted with more EtOAc (150 mL). The combined organics were washed with brine (150 mL), dried (MgSO$_4$), filtered, and concentrated in vacuo to give crude Intermediate 36C (251 mg, 76% pure, 42.5% yield) which was used without further purification in the next step. MS(ES): m/z=353.1 [M+H]$^+$. HPLC retention time (Method D): 1.665 min.

Intermediate 36: N-(6-Formylimidazo[1,2-b]pyridazin-2-yl)-2-(pyridin-4-yl)thiazole-5-carboxamide

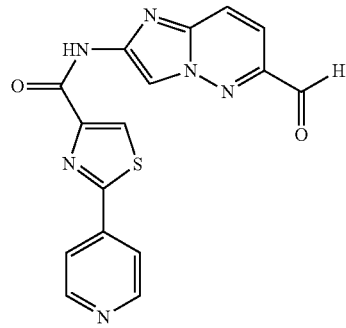 [SMILES: O=Cc1ccc2nc(NC(=O)c3csc(-c4ccncc4)n3)cn2n1]

DMSO (5 mL) and Dess-Martin periodinane (274 mg, 0.647 mmol) were added to impure Intermediate 36C (250 mg, 0.539 mmol). The reaction was stirred at room temperature for 40 min. The reaction was diluted with water (100 mL), filtered, and dried. The solids were triturated in EtOH, then filtered and dried to obtain impure Intermediate 36 (89 mg, 65% purity, 30% yield). The material was used without further purification in the next step. MS(ES): m/z=349.2 [M–H]$^-$. HPLC retention time (Method D): 1.760 min.

Compound 415

N-(6-(1-(2,2-Difluoroethyl)-4-(4-fluorophenyl)-1H-imidazol-5-yl)imidazo[1,2-b]pyridazin-2-yl)-2-(pyridin-4-yl)thiazole-5-carboxamide

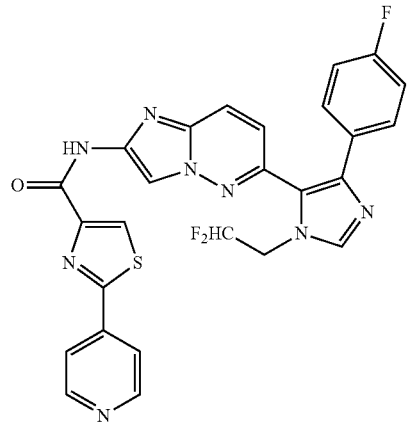 [SMILES: O=C(Nc1cn2nc(-c3c(-c4ccc(F)cc4)ncn3CC(F)F)ccc2n1)c1csc(-c2ccncc2)n1]

A solution of 2,2-difluoroethanamine (11.03 mg, 0.136 mmol) in DMF (600 μl) was added to crude Intermediate 36 (55 mg, 0.102 mmol). The reaction was stirred overnight at room temperature. 1-fluoro-4-(isocyano(tosyl)methyl)benzene (19.68 mg, 0.068 mmol) and K$_2$CO$_3$ (12.22 mg, 0.088 mmol) were added. The reaction was stirred at room temperature for 3 d. The reaction was diluted with DMF, then purified by preparative HPLC to afford Compound 415 (7.2 mg, 18.8%). MS(ES): m/z=547.4 [M+H]$^+$. HPLC retention time (Method B): 3.13 min $^1$H NMR (500 MHz, DMSO-d$_6$) δ 11.22 (br. s., 1H), 8.77 (d, J=5.5 Hz, 2H), 8.72 (s, 1H), 8.61

(s, 1H), 8.15 (d, J=5.5 Hz, 2H), 8.06-7.98 (m, 2H), 7.50 (dd, J=8.2, 5.8 Hz, 2H), 7.17 (t, J=8.9 Hz, 2H), 7.02 (d, J=9.2 Hz, 1H), 6.54-6.23 (m, 1H), 4.81-4.68 (m, 2H).

Scheme 18

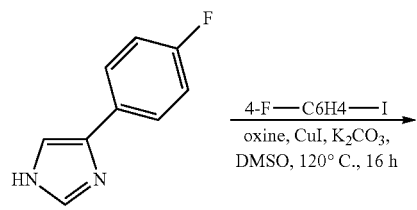

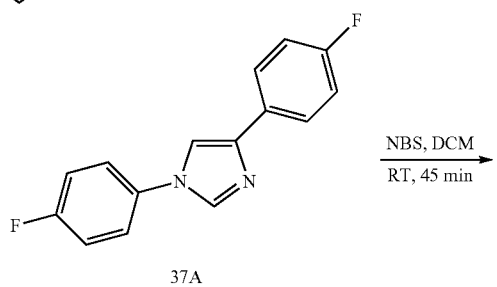

37A

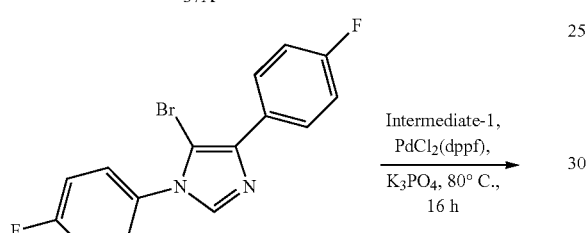

37B

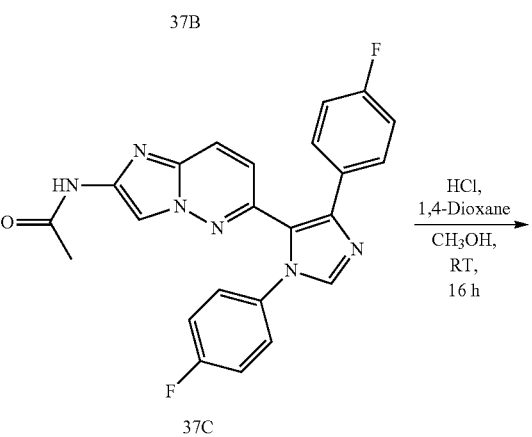

37C

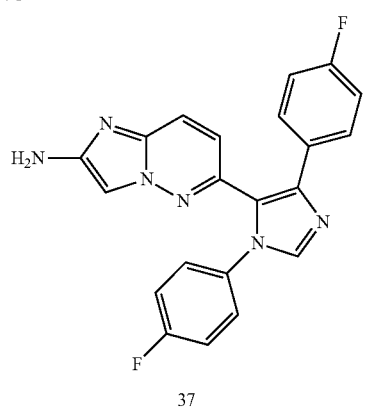

37

Intermediate 37

6-(1,4-bis(4-Fluorophenyl)-1H-imidazol-5-yl)imidazo[1,2-b]pyridazin-2-amine

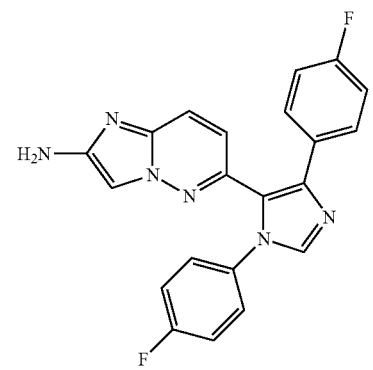 [SMILES: Nc1cn2nc(-c3c(-c4ccc(F)cc4)ncn3-c3ccc(F)cc3)ccc2n1]

Intermediate 37A:
1,4-bis(4-Fluorophenyl)-1H-imidazole

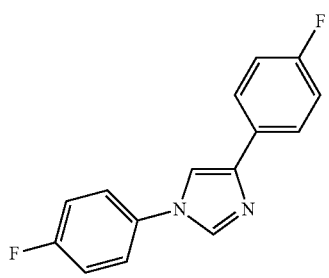 [SMILES: Fc1ccc(-c2cn(-c3ccc(F)cc3)cn2)cc1]

To the stirred solution of 4-(4-fluorophenyl)-1H-imidazole (4.38 g, 27.0 mmol) in DMSO (10.0 mL) was added 1-fluoro-4-iodobenzene (5.0 g, 22.52 mmol), oxine (0.327 g, 2.252 mmol), CuI (0.214 g, 1.126 mmol), $K_2CO_3$ (7.78 g, 56.3 mmol) and the resulting reaction mixture was stirred at 120° C. for 16 h. The reaction mixture was cooled to room temperature; water (50 mL) was added and extracted with ethyl acetate (3×50 mL). The organic layer was washed with water, brine, dried over $Na_2SO_4$, filtered and concentrated. The residue was purified by silica gel chromatography (120 g REDISEP® column, eluting with 30% ethyl acetate in hexane). Collected fractions were concentrated together to afford Intermediate 37A (4.1 g, 71%) as a tan color solid. MS(ES): m/z=257 [M+H]+; $^1$H NMR (400 MHz, DMSO-$d_6$) δ ppm 8.30 (d, J=1.26 Hz, 1H), 8.26 (s, 1H), 7.85-7.94 (m, 2H), 7.73-7.81 (m, 2H), 7.39-7.47 (m, 2H), 7.20-7.29 (m, 2H).

Intermediate 37B:
5-Bromo-1,4-bis(4-fluorophenyl)-1H-imidazole

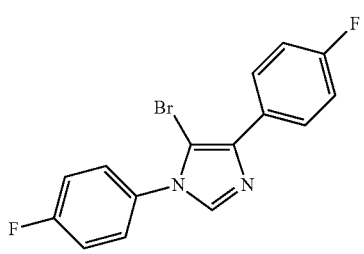 [SMILES: Fc1ccc(-c2ncn(-c3ccc(F)cc3)c2Br)cc1]

To the stirred solution of Intermediate 37A (0.65 g, 2.54 mmol) in DCM (10.0 mL) was added NBS (0.474 g, 2.66 mmol) at 0° C. The reaction mixture was warmed to room temperature and stirred 45 min. The reaction mixture was diluted with DCM (10 mL), washed with water, brine, dried over Na$_2$SO$_4$, filtered and concentrated. The residue was purified by silica gel chromatography (40 g REDISEP® column, eluting with 25% EtOAc in hexane). Collected fractions were concentrated together to afford Intermediate 37B (0.6 g, 70%) as a pale yellow solid. MS(ES): m/z=337 [M+H]$^+$; $^1$H NMR (300 MHz, DMSO-d$_6$) δ ppm 8.18 (s, 1H) 7.94-8.03 (m, 2H), 7.57-7.66 (m, 2H), 7.42-7.51 (m, 2H), 7.26-7.37 (m, 2H).

Intermediate 37C: N-(6-(1,4-bis(4-Fluorophenyl)-1H-imidazol-5-yl)imidazo[1,2-b]pyridazin-2-yl)acetamide

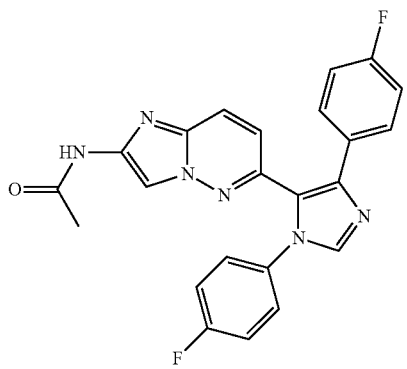 [SMILES: CC(=O)Nc1cn2nc(-c3c(-c4ccc(F)cc4)ncn3-c3ccc(F)cc3)ccc2n1]

To the stirred solution of Intermediate 37B (0.55 g, 1.641 mmol) in DMF (5.0 mL) was added intermediate-1 (1.735 g, 5.74 mmol), K$_3$PO$_4$ (2.462 mL, 4.92 mmol). The reaction mixture was degassed with nitrogen and added PdCl$_2$(dppf).DCM complex (0.134 g, 0.164 mmol) and stirred at 80° C. for 16 h. The reaction mixture was concentrated, diluted with ethyl acetate, filtered through CELITE®. The filtrate was washed with water, brine, dried over Na$_2$SO$_4$ and concentrated. The residue was purified by silica gel chromatography (40 g REDISEP® column, eluting with 2% methanol in chloroform). Collected fractions were concentrated together to afford Intermediate 37C (0.27 g, 38%) as a brown solid. MS(ES): m/z=431 [M+H]$^+$; $^1$H NMR (400 MHz, DMSO-d$_6$) δ ppm 10.93 (s, 1H), 8.14 (s, 1H), 7.92 (d, J=9.79 Hz, 1H), 7.55-7.62 (m, 2H) 7.37-7.45 (m, 2H), 7.24-7.32 (m, 2H), 7.12-7.20 (m, 2H), 7.01 (d, J=9.29 Hz, 1H), 2.09 (s, 3H).

Intermediate 37: 6-(1,4-bis(4-Fluorophenyl)-1H-imidazol-5-yl)imidazo[1,2-b]pyridazin-2-amine

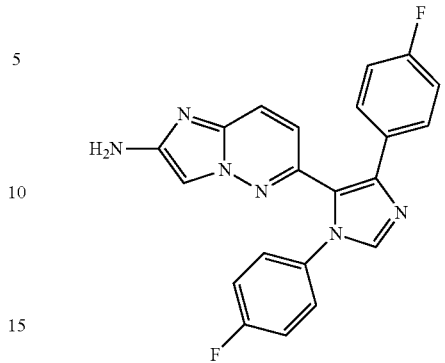

To the stirred solution of Intermediate 37C (0.26 g, 0.604 mmol) in methanol (5.00 mL) was added HCl in dioxane (8.0 mL, 32.0 mmol) and stirred at room temperature for 16 h. The reaction mixture was concentrated under reduced pressure. The crude product was dissolved in ethyl acetate, washed with sodium bicarbonate, water, brine, dried over sodium sulfate and concentrated to afford Intermediate 37 (0.175 g, 74%) as a brown solid. MS(ES): m/z=389 [M+H]$^+$; $^1$H NMR (400 MHz, DMSO-d$_6$) δ ppm 8.15 (s, 1H), 7.52-7.63 (m, 3H), 7.34-7.42 (m, 2H), 7.23-7.31 (m, 3H), 7.10-7.20 (m, 2H), 6.81 (d, J=9.03 Hz, 1H), 5.62 (br. s., 2H).

Compound 416

N-(6-(1,4-bis(4-Fluorophenyl)-1H-imidazol-5-yl)imidazo[1,2-b]pyridazin-2-yl)-2-fluoroisonicotinamide

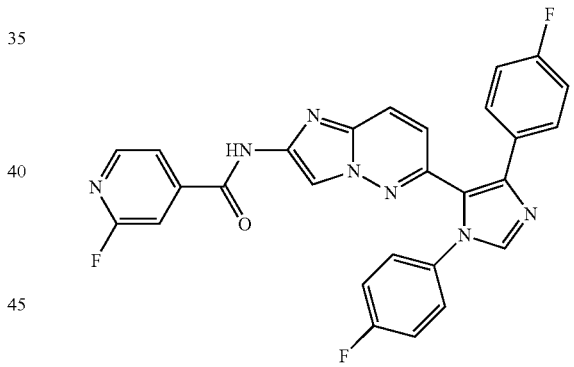

To the stirred solution of 2-fluoroisonicotinic acid (0.022 g, 0.154 mmol) in DMF (1.5 mL) was added HATU (0.059 g, 0.154 mmol), DIPEA (0.054 mL, 0.309 mmol), Intermediate 37 (0.030 g, 0.077 mmol) and stirred at room temperature for 16 h. The reaction mixture was concentrated to remove DMF, diluted with ethyl acetate, washed with water and brine. The organic layer was dried over sodium sulfate, filtered and concentrated under reduced pressure. The crude compound was purified by reverse phase HPLC purification to afford compound 416 (0.012 g, 30%) as a pale yellow solid. MS(ES): m/z=512 [M+H]$^+$; HPLC Ret. Time 9.66 min and 8.66 min (HPLC Methods K and L respectively); $^1$H NMR (400 MHz, DMSO-d$_6$) δ ppm 7.09 (s, 1H), 7.15-7.22 (m, 2H), 7.26-7.34 (m, 2H), 7.39-7.48 (m, 2H), 7.57-7.64 (m, 2H), 7.78 (s, 1H), 7.94 (d, J=5.02 Hz, 1H), 8.03 (d, J=9.29 Hz, 1H), 8.22 (s, 1H), 8.39 (s, 1H), 8.46 (d, J=5.02 Hz, 1H), 11.89 (s, 1H).

The following compounds in Table 40 were prepared by the procedure described for the preparation of compound 416 using from the Intermediate 37 using the corresponding acid.

TABLE 40

| Compound No. | Structure | Name | [M + H]+ | Ret Time (min) | HPLC Method |
|---|---|---|---|---|---|
| 417 | 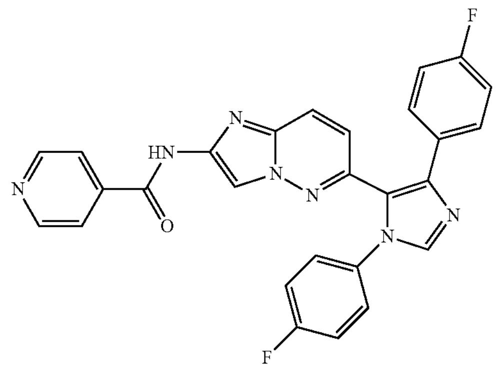 [SMILES: O=C(Nc1cn2nc(-c3c(-c4ccc(F)cc4)ncn3-c3ccc(F)cc3)ccc2n1)c1ccncc1] | N-(6-(1,4-bis(4-Fluorophenyl)-1H-imidazol-5-yl)imidazo[1,2-b]pyridazin-2-yl)isonicotinamide | 492 | 6.59<br>6.73 | K<br>L |
| 418 | 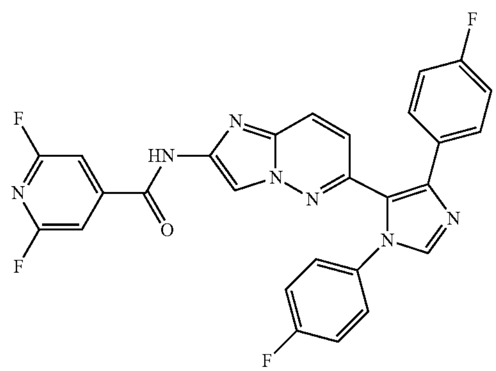 [SMILES: O=C(Nc1cn2nc(-c3c(-c4ccc(F)cc4)ncn3-c3ccc(F)cc3)ccc2n1)c1cc(F)nc(F)c1] | N-(6-(1,4-bis(4-Fluorophenyl)-1H-imidazol-5-yl)imidazo[1,2-b]pyridazin-2-yl)-2,6-difluoroisonicotinamide | 530 | 10.08<br>9.67 | K<br>L |
| 419 | 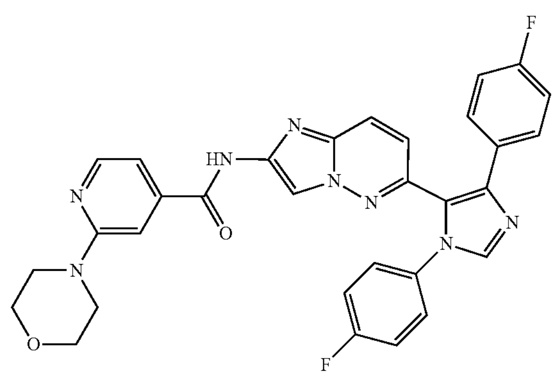 [SMILES: O=C(Nc1cn2nc(-c3c(-c4ccc(F)cc4)ncn3-c3ccc(F)cc3)ccc2n1)c1ccnc(N2CCOCC2)c1] | N-(6-(1,4-bis(4-Fluorophenyl)-1H-imidazol-5-yl)imidazo[1,2-b]pyridazin-2-yl)-2-morpholinoisonicotinamide | 579 | 6.80<br>7.31 | K<br>L |
| 420 | 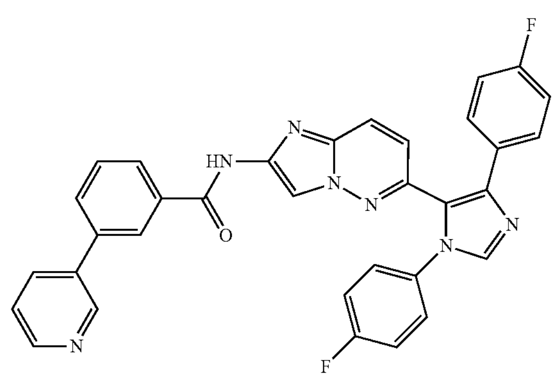 [SMILES: O=C(Nc1cn2nc(-c3c(-c4ccc(F)cc4)ncn3-c3ccc(F)cc3)ccc2n1)c1cccc(-c2cccnc2)c1] | N-(6-(1,4-bis(4-Fluorophenyl)-1H-imidazol-5-yl)imidazo[1,2-b]pyridazin-2-yl)-3-(pyridin-3-yl)benzamide | 570 | 7.48<br>7.10 | K<br>L |

Scheme 19

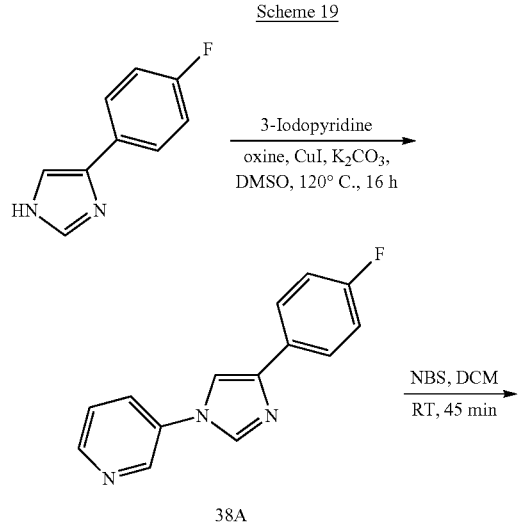

38A

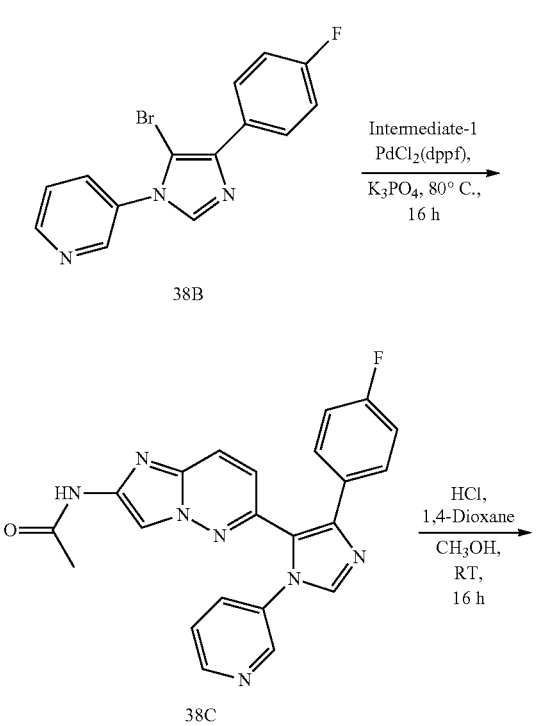

38B

38C

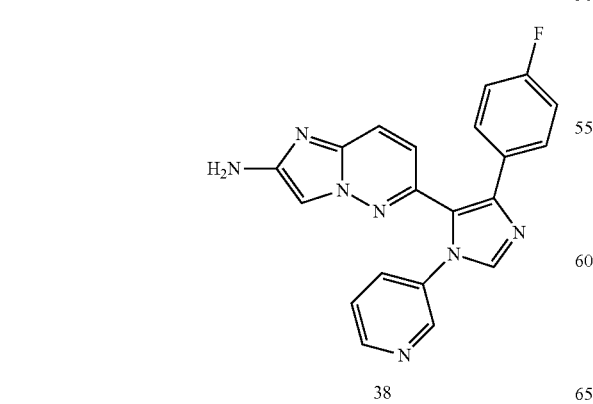

38

Intermediate 38

6-(4-(4-Fluorophenyl)-1-(pyridin-3-yl)-1H-imidazol-5-yl)imidazo[1,2-b]pyridazin-2-amine

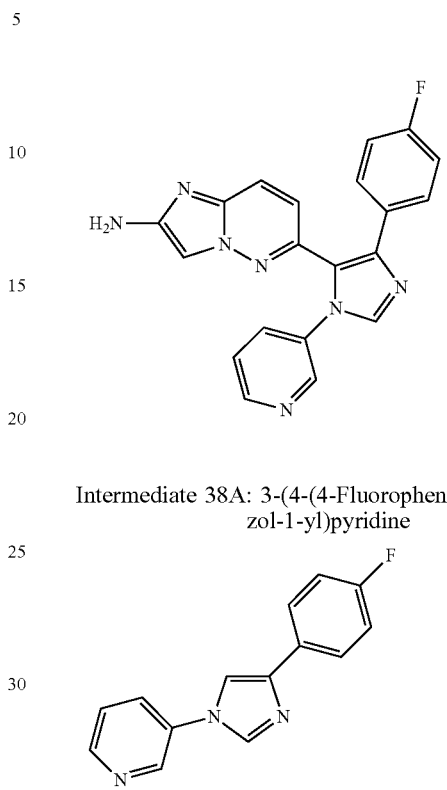

Intermediate 38A: 3-(4-(4-Fluorophenyl)-1H-imidazol-1-yl)pyridine

To the stirred solution of 4-(4-fluorophenyl)-1H-imidazole (2.85 g, 17.56 mmol) in DMSO (15.0 mL) was added 3-iodo pyridine (3.0 g, 14.63 mmol), oxine (0.327 g, 2.252 mmol), CuI (0.214 g, 1.126 mmol), $K_2CO_3$ (7.78 g, 56.3 mmol) and the resulting reaction mixture was stirred at 120° C. for 10 h. The reaction mixture was cooled to room temperature; water (50 mL) was added and extracted with ethyl acetate (3×50 mL). The organic layer was washed with water, brine, dried over $Na_2SO_4$, filtered and concentrated. The residue was purified by silica gel chromatography (120 g REDISEP® column, eluting with 5% methanol in chloroform). Collected fractions were concentrated together to afford Intermediate 38A (2.46 g, 70%) MS(ES): m/z=240 [M+H]$^+$. $^1$H NMR (400 MHz, DMSO-$d_6$) δ ppm 9.03 (d, J=2.51 Hz, 1H), 8.55-8.65 (m, 1H), 8.35-8.47 (m, 2H), 8.12-8.24 (m, 1H), 7.81-7.97 (m, 2H), 7.61 (dd, J=8.03, 4.52 Hz, 1H), 7.12-7.37 (m, 2H).

Intermediate 38B: 3-(5-Bromo-4-(4-fluorophenyl)-1H-imidazol-1-yl)pyridine

To the stirred solution of Intermediate 38A (0.5 g, 2.09 mmol) in DCM (10.0 mL) was added NBS (0.517 g, 2.29 mmol) at 0° C. The reaction mixture was warmed to room temperature and stirred 45 min. The reaction mixture was diluted with DCM (10 mL), washed with water, brine, dried over Na$_2$SO$_4$, filtered and concentrated. The residue was purified by silica gel chromatography (40 g REDISEP® column, eluting with 2% Methanol/Chloroform). Collected fractions were concentrated together to afford Intermediate 38B (0.42 g, 63%) as a pale yellow solid. MS(ES): m/z=318 [M+H]$^+$; $^1$H NMR (400 MHz, DMSO-d$_6$) δ ppm 8.73-8.82 (m, 2H), 8.28 (s, 1H), 8.07 (ddd, J=8.03, 2.51, 1.51 Hz, 1H), 7.96-8.03 (m, 2H), 7.62-7.71 (m, 1H), 7.23-7.39 (m, 2H).

Intermediate 38C: N-(6-(4-(4-Fluorophenyl)-1-(pyridin-3-yl)-1H-imidazol-5-yl)imidazo[1,2-b]pyridazin-2-yl)acetamide

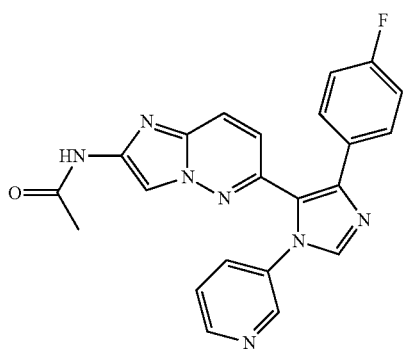 [SMILES: CC(=O)Nc1cn2nc(-c3c(-c4ccc(F)cc4)ncn3-c3cccnc3)ccc2n1]

To the stirred solution of Intermediate 38B (0.41 g, 1.28 mmol) in DMF (5.0 mL) was added intermediate-1 (0.973 g, 3.22 mmol), K$_3$PO$_4$ (0.644, 1.289 mmol). The reaction mixture was degassed with nitrogen and added PdCl$_2$(dppf).DCM complex (0.063 g, 0.077 mmol) and stirred at 80° C. for 16 h. The reaction mixture was concentrated, diluted with ethyl acetate, filtered through CELITE®. The filtrate was washed with water, brine, dried over Na$_2$SO$_4$ and concentrated. The residue was purified by silica gel chromatography (40 g REDISEP® column, eluting with 3.5% methanol in chloroform). Collected fractions were concentrated together to afford Intermediate 38C (0.24 g, 45%) as a brown solid. MS(ES): m/z=414 [M+H]$^+$; $^1$H NMR (300 MHz, DMSO-d$_6$) δ ppm 10.95 (s, 1H), 8.53-8.63 (m, 2H), 8.31 (s, 1H), 8.09 (s, 1H), 7.91-8.00 (m, 1H), 7.78-7.83 (m, 1H), 7.56-7.64 (m, 2H), 7.44-7.52 (m, 1H), 7.11-7.23 (m, 2H), 7.04 (d, J=9.07 Hz, 1H), 2.09 (s, 3H).

Intermediate 38: 6-(4-(4-Fluorophenyl)-1-(pyridin-3-yl)-1H-imidazol-5-yl)imidazo[1,2-b]pyridazin-2-amine

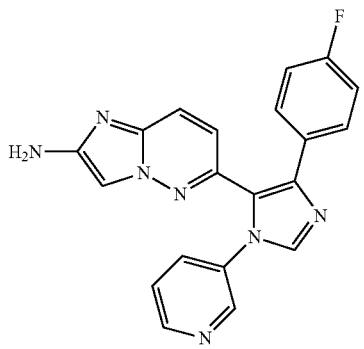 [SMILES: Nc1cn2nc(-c3c(-c4ccc(F)cc4)ncn3-c3cccnc3)ccc2n1]

To the stirred solution of Intermediate 38C (0.18 g, 0.435 mmol) in methanol (5.00 mL) was added 4 M HCl in dioxane (5.0 mL, 45.9 mmol) and stirred at room temperature for 16 h. The reaction mixture was concentrated under reduced pressure. The crude product was dissolved in ethyl acetate, washed with sodium bicarbonate, water, brine, dried over sodium sulfate and concentrated to afford Intermediate 38 (0.12 g, 74%) as a brown solid. MS(ES): m/z=372 [M+H]$^+$; $^1$H NMR (400 MHz, DMSO-d$_6$) δ ppm 8.51-8.62 (m, 2H), 8.26 (s, 1H), 7.75 (ddd, J=8.16, 2.64, 1.51 Hz, 1H), 7.53-7.63 (m, 3H), 7.47 (dd, J=8.28, 4.77 Hz, 1H), 7.12-7.26 (m, 3H), 6.86 (s, 1H), 5.63 (s, 2H).

Compound 421

2-Fluoro-N-(6-(4-(4-fluorophenyl)-1-(pyridin-3-yl)-1H-imidazol-5-yl)imidazo[1,2-b]pyridazin-2-yl)isonicotinamide

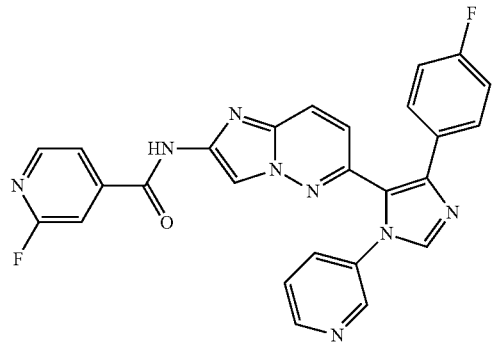 [SMILES: O=C(Nc1cn2nc(-c3c(-c4ccc(F)cc4)ncn3-c3cccnc3)ccc2n1)c1ccnc(F)c1]

To the stirred solution of 2-fluoroisonicotinic acid (0.023 g, 0.162 mmol) in DMF (1.5 mL) was added HATU (0.061 g, 0.162 mmol), DIPEA (0.056 mL, 0.323 mmol) followed by Intermediate 38 (0.03 g, 0.081 mmol) and stirred at RT for 16 h. The reaction mixture was concentrated, diluted with ethyl acetate, washed with water and brine. The organic layer was dried over sodium sulfate, filtered and concentrated under reduced pressure. The crude compound was purified by reverse phase purification to afford compound 421 (0.0165 g, 40%) as a pale yellow solid. MS(ES): m/z=493 [M+H]$^+$; HPLC Ret. Time min and min (HPLC Methods K and L respectively); $^1$H NMR (400 MHz, DMSO-d$_6$) δ ppm 11.91 (s, 1H), 8.58-8.66 (m, 2H), 8.46 (d, J=5.02 Hz, 1H), 8.32-8.36 (m, 2H), 8.04 (dd, J=9.29, 0.75 Hz, 1H), 7.93 (d, J=5.27 Hz, 1H), 7.76-7.86 (m, 2H), 7.63 (dd, J=8.78, 5.52 Hz, 2H), 7.45-7.53 (m, 1H), 7.20 (t, J=8.91 Hz, 2H), 7.13 (s, 1H).

The following compounds in Table 41 were prepared by the procedure described for the preparation of compound 221 from the Intermediate 38 using the corresponding amines.

TABLE 41

| Compound No | Structure | Name | [M + H]+ | Ret Time (min) | HPLC Method |
|---|---|---|---|---|---|
| 422 | 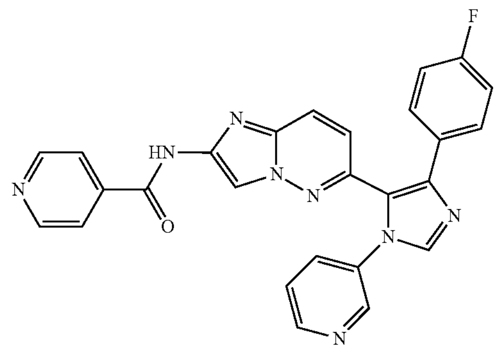 [SMILES: O=C(Nc1cn2nc(-c3c(-c4ccc(F)cc4)ncn3-c3cccnc3)ccc2n1)c1ccncc1] | N-(6-(4-(4-Fluorophenyl)-1-(pyridin-4-yl)-1H-imidazol-5-yl)imidazo[1,2-b]pyridazin-2-yl)isonicotinamide | 475 | 5.57<br>5.96 | K<br>L |
| 423 | 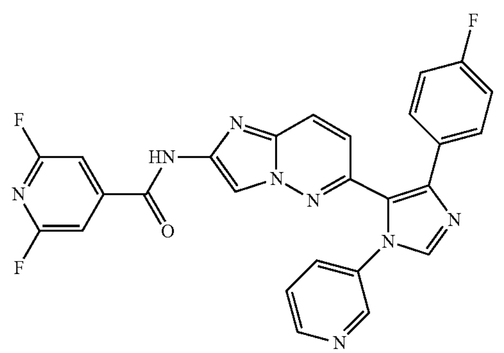 [SMILES: O=C(Nc1cn2nc(-c3c(-c4ccc(F)cc4)ncn3-c3cccnc3)ccc2n1)c1cc(F)nc(F)c1] | 2,6-Difluoro-N-(6-(4-(4-fluorophenyl)-1-(pyridin-3-yl)-1H-imidazol-5-yl)imidazo[1,2-b]pyridazin-2-yl)isonicotinamide | 511 | 8.84<br>8.61 | K<br>L |
| 424 | 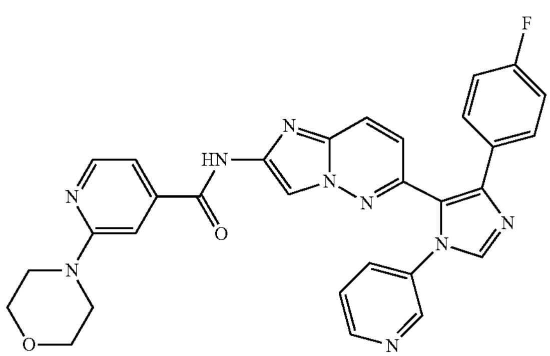 [SMILES: O=C(Nc1cn2nc(-c3c(-c4ccc(F)cc4)ncn3-c3cccnc3)ccc2n1)c1ccnc(N2CCOCC2)c1] | N-(6-(4-(4-Fluorophenyl)-1-(pyridin-3-yl)-1H-imidazol-5-yl)imidazo[1,2-b]pyridazin-2-yl)-2-morpholinoisonicotinamide | 561 | 6.09<br>6.69 | K<br>L |
| 425 | 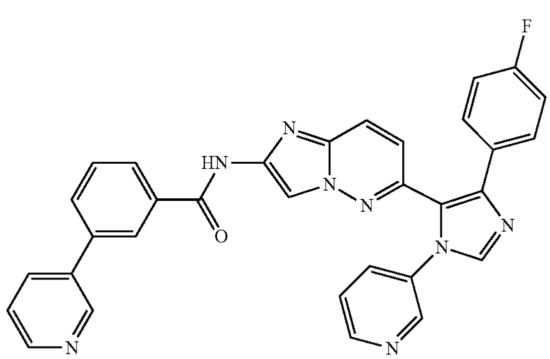 [SMILES: O=C(Nc1cn2nc(-c3c(-c4ccc(F)cc4)ncn3-c3cccnc3)ccc2n1)c1cccc(-c2cccnc2)c1] | N-(6-(4-(4-Fluorophenyl)-1-(pyridin-3-yl)-1H-imidazol-5-yl)imidazo[1,2-b]pyridazin-2-yl)-3-(pyridin-3-yl)benzamide | 552 | 5.77<br>6.51 | K<br>L |

Scheme 20

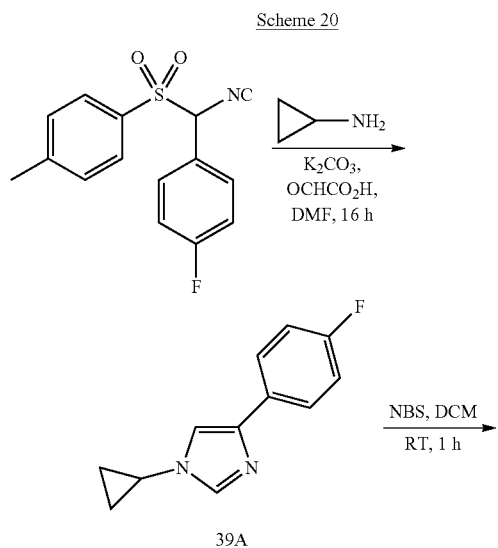

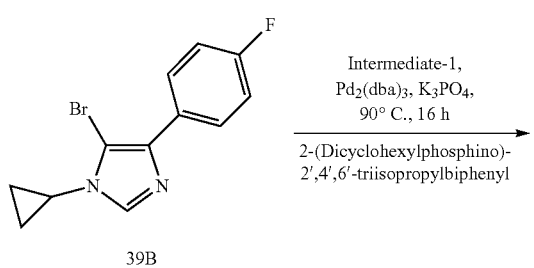

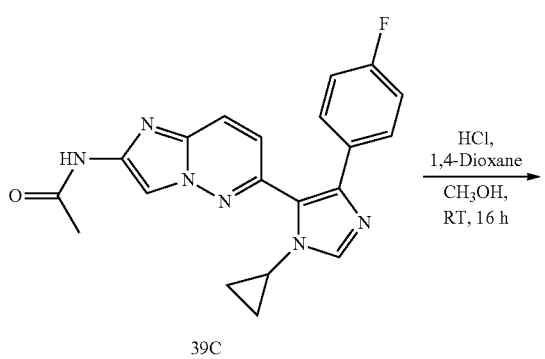

Intermediate 39

6-(1-Cyclopropyl-4-(4-fluorophenyl)-1H-imidazol-5-yl)imidazo[1,2-b]pyridazin-2-amine

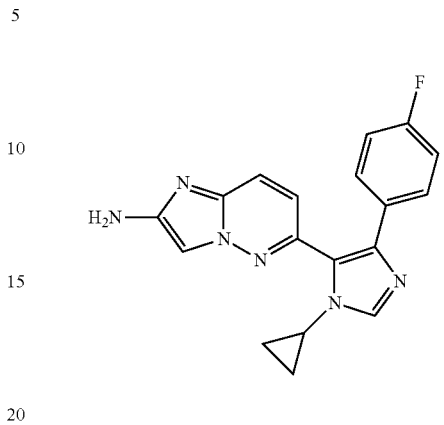

Intermediate 39A:
1-Cyclopropyl-4-(4-fluorophenyl)-1H-imidazole

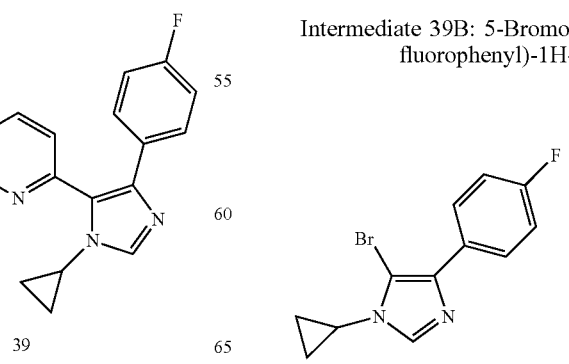

To a solution of cyclopropanamine (0.5 g, 8.76 mmol) in DMF (15 mL) was added glyoxylic acid (0.390 mL, 7.01 mmol) and potassium carbonate (3.03 g, 21.89 mmol) and the resulting reaction mixture was stirred at room temperature for 3 h. Then added 1-fluoro-4-(isocyano(tosyl)methyl)benzene (2.027 g, 7.01 mmol) and stirred at room temperature for 16 h. The reaction mixture was diluted water and extracted with EtOAc (3×100 mL). The combined organic layer was washed with water, brine, dried over sodium sulphate and concentrated under reduced pressure to afford desired product. The residue was purified by silica gel chromatography (40 g REDISEP® Column, eluting with 3% MeOH in chloroform) to afford pure Intermediate 39A (0.9 g, 50%) as a pale yellow oil. MS(ES): m/z=203 [M+H]$^+$; $^1$H NMR (400 MHz, CHCl$_3$) δ ppm 7.67-7.74 (m, 2H), 7.57 (d, J=1.07 Hz, 1H), 7.20 (d, J=1.32 Hz, 1H), 7.00-7.09 (m, 2H), 3.33-3.42 (m, 1H), 0.99-1.04 (m, 4H).

Intermediate 39B: 5-Bromo-1-cyclopropyl-4-(4-fluorophenyl)-1H-imidazole

To a solution of Intermediate 39A (1 g, 4.94 mmol) in dry DCM (15 mL) was added NBS (0.968 g, 5.44 mmol) slowly at 0° C. and the reaction temperature was slowly warmed to RT and stirred for 1 h. The reaction mixture was diluted with water and extracted with DCM (3×40 mL). The combined the organic layer was washed with water, brine, dried over Na$_2$SO$_4$, filtered and concentrated. The residue was purified silica gel chromatography (40 g REDISEP® column, eluting with 25% EtOAc in hexane). Collected fractions were concentrated together to afford Intermediate 39B (1.0 g, 79%) as a yellow solid. MS(ES): m/z=283 [M+H]$^+$; $^1$H NMR (400 MHz, chloroform-d) δ ppm 7.84-7.91 (m, 3H), 7.06-7.15 (m, 2H), 3.21 (tt, J=7.18, 3.80 Hz, 1H), 1.15-1.21 (m, 2H), 1.04-1.11 (m, 2H).

Intermediate 39C: N-(6-(1-Cyclopropyl-4-(4-fluorophenyl)-1H-imidazol-5-yl)imidazo[1,2-b]pyridazin-2-yl)acetamide

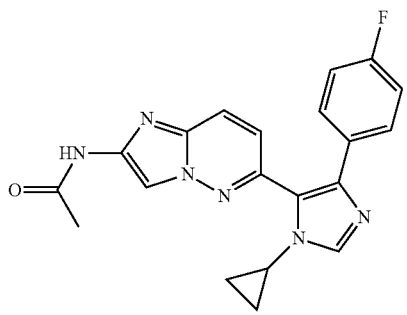 [SMILES: CC(=O)Nc1cn2nc(-c3c(-c4ccc(F)cc4)ncn3C3CC3)ccc2n1]

To a degassed solution of Intermediate 39B (1 g, 3.56 mmol), Intermediate-1 (2.69 g, 8.89 mmol), K$_3$PO$_4$ (1.452 g, 10.67 mmol) in 1,4-dioxane (10 mL) and water (1 mL) was added Pd$_2$(dba)$_3$ (0.228 g, 0.249 mmol) and 2-(dicyclohexylphosphino)-2',4',6'-triisopropylbiphenyl (0.237 g, 0.498 mmol). The reaction mixture was purged with nitrogen for 10-15 min. and stirred at 90° C. for 16 h. The reaction mixture was diluted with water and filtered through CELITE® and extracted with EtOAc (3×80 mL) The combined organic layer was washed with water, brine, dried over Na$_2$SO$_4$, filtered and concentrated. The residue was purified silica gel chromatography (120 g REDISEP® column, eluting with 3% methanol in chloroform). Collected fractions were concentrated together to afford Intermediate 39C (0.8 g, 59%) as a yellow solid. MS(ES): m/z=377 [M+H]$^+$. This product was taken to the next step without further purification.

Intermediate 39: 6-(1-Cyclopropyl-4-(4-fluorophenyl)-1H-imidazol-5-yl)imidazo[1,2-b]pyridazin-2-amine

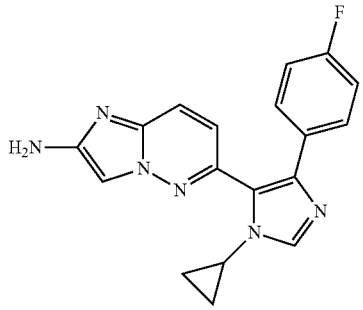 [SMILES: Nc1cn2nc(-c3c(-c4ccc(F)cc4)ncn3C3CC3)ccc2n1]

To a solution of Intermediate 39C (0.8 g, 2.125 mmol) in methanol (4 mL) was added 4 M HCl in dioxane (6 ml, 24.00 mmol) at 0° C. and the reaction was stirred at room temperature for 2 h. The reaction mixture was concentrated under reduced pressure, quenched with 10% sodium bicarbonate and extracted with chloroform (3×80 mL) The combined organic layer was washed with water, brine, dried over sodium sulphate, concentrated to afford Intermediate 39 (0.7 g, 93%) as a brown gummy solid. MS(ES): m/z=335 [M+H]$^+$. The crude product was taken to the next step without further purification.

Compound 426

N-(6-(1-Cyclopropyl-4-(4-fluorophenyl)-1H-imidazol-5-yl)imidazo[1,2-b]pyridazin-2-yl)-2-fluoroisonicotinamide

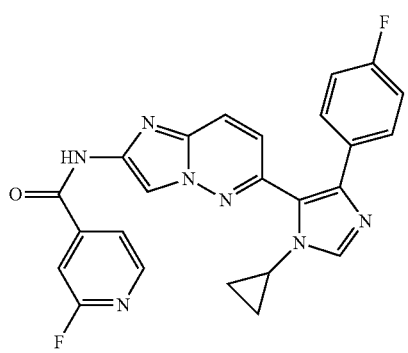 [SMILES: O=C(Nc1cn2nc(-c3c(-c4ccc(F)cc4)ncn3C3CC3)ccc2n1)c1ccnc(F)c1]

To a solution of Intermediate 39 (0.07 g, 0.209 mmol), HATU (0.159 g, 0.419 mmol) and DIPEA (0.128 mL, 0.733 mmol) in DMF (1 mL) was added 2-fluoroisonicotinic acid (0.059 g, 0.419 mmol) and the reaction was stirred at room temperature for 16 h. DMF was removed under high vacuum, diluted with 10% sodium bicarbonate solution and extracted with chloroform (3×80 mL) The combined organic layer was washed with water, brine, dried over sodium sulphate and concentrated to afford the crude product. The crude product was purified by preparative HPLC purification to afford the product 426 (0.05 g, 50%) as a pale yellow solid. MS(ES): m/z=458 [M+H]$^+$; HPLC Ret. Time 6.36 min and 6.80 min (HPLC Method A and B respectively); $^1$H NMR (400 MHz, DMSO-d$_6$) δ ppm 11.92 (br. s., 1H), 8.57 (d, J=0.56 Hz, 1H), 8.47 (d, J=5.15 Hz, 1H), 8.13 (dd, J=9.32, 0.66 Hz, 1H), 7.95-7.99 (m, 2H), 7.81 (s, 1H), 7.48-7.54 (m, 2H), 7.28 (d, J=9.29 Hz, 1H), 7.10-7.17 (m, 2H), 3.52-3.60 (m, 1H), 0.81-0.94 (m, 4H).

The following compounds in Table 42 were prepared by the procedure described for the preparation of compound 426 from the Intermediate 39 using the corresponding acids.

TABLE 42

| Compound No | Structure | Name | [M + H]+ | Ret Time (min) | HPLC Method |
|---|---|---|---|---|---|
| 427 | 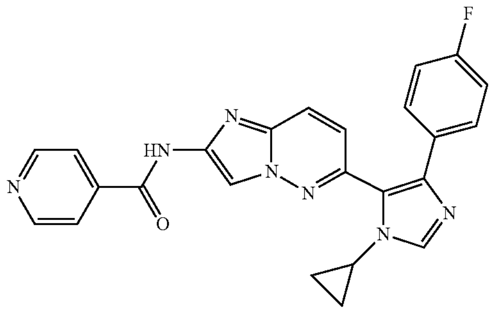 [SMILES: O=C(Nc1cn2nc(-c3c(-c4ccc(F)cc4)ncn3C3CC3)ccc2n1)c1ccncc1] | N-(6-(1-Cyclopropyl-4-(4-fluorophenyl)-1H-imidazol-5-yl)imidazo[1,2-b]pyridazin-2-yl)isonicotinamide | 440 | 9.03 9.08 | M N |
| 428 | 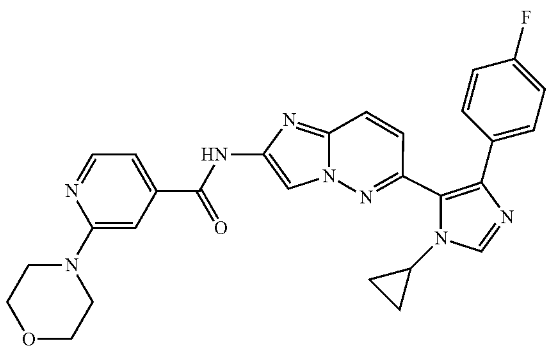 [SMILES: O=C(Nc1cn2nc(-c3c(-c4ccc(F)cc4)ncn3C3CC3)ccc2n1)c1ccnc(N2CCOCC2)c1] | N-(6-(1-Cyclopropyl-4-(4-fluorophenyl)-1H-imidazol-5-yl)imidazo[1,2-b]pyridazin-2-yl)-2-morpholinoisonicotinamide | 525 | 5.47 9.88 | L M |
| 429 | 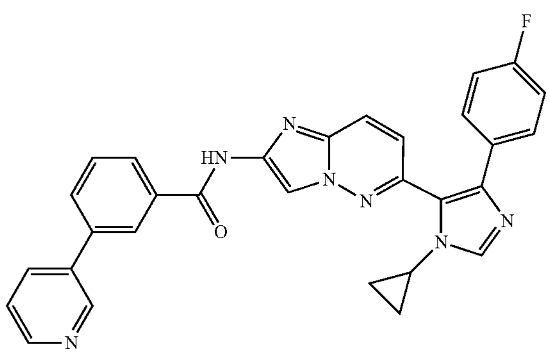 [SMILES: O=C(Nc1cn2nc(-c3c(-c4ccc(F)cc4)ncn3C3CC3)ccc2n1)c1cccc(-c2cccnc2)c1] | N-(6-(1-Cyclopropyl-4-(4-fluorophenyl)-1H-imidazol-5-yl)imidazo[1,2-b]pyridazin-2-yl)-3-(pyridin-3-yl)benzamide | 518 | 5.58 9.94 | L M |
| 430 | 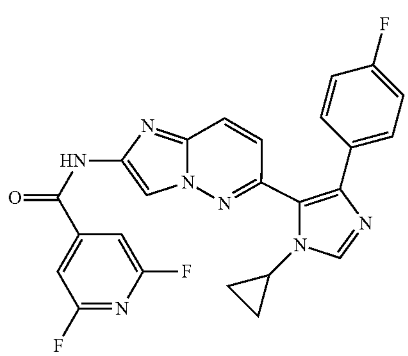 [SMILES: O=C(Nc1cn2nc(-c3c(-c4ccc(F)cc4)ncn3C3CC3)ccc2n1)c1cc(F)nc(F)c1] | N-(6-(1-Cyclopropyl-4-(4-fluorophenyl)-1H-imidazol-5-yl)imidazo[1,2-b]pyridazin-2-yl)-2,6-difluoroisonicotinamide | 477 | 7.52 8.18 | K L |

Scheme 21

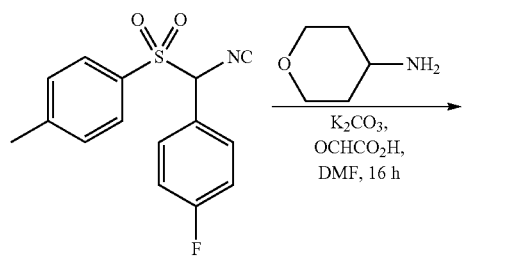

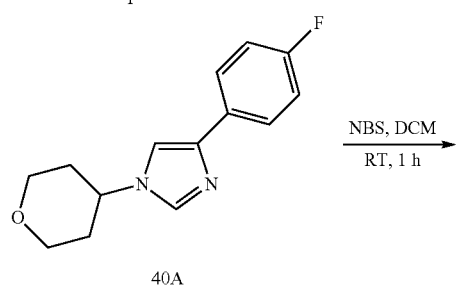

40A

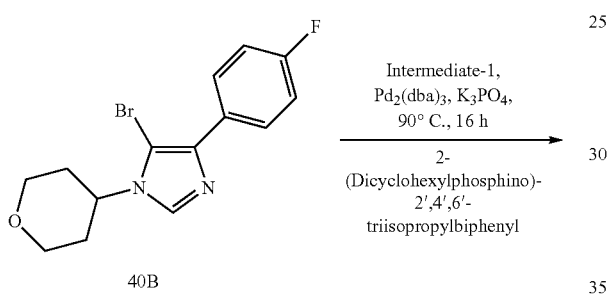

40B

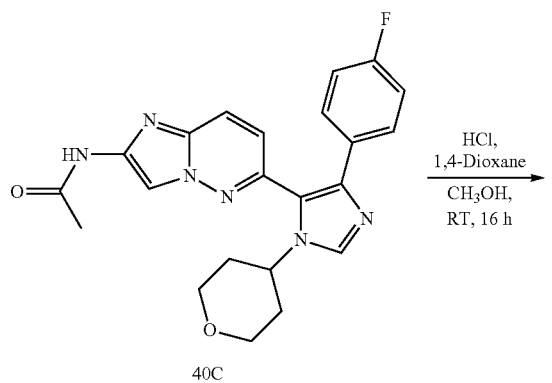

40C

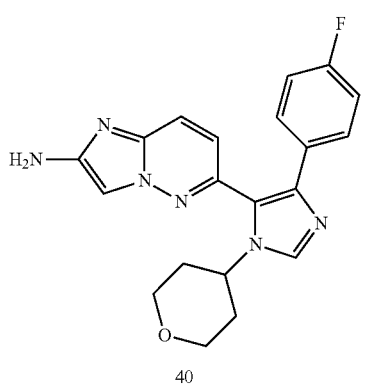

40

Intermediate 40

6-(4-(4-Fluorophenyl)-1-(tetrahydro-2H-pyran-4-yl)-1H-imidazol-5-yl)imidazo[1,2-b]pyridazin-2-amine Intermediate 40A: 4-(4-Fluorophenyl)-1-(tetrahydro-2H-pyran-4-yl)-1H-imidazole To a stirred solution of tetrahydro-2H-pyran-4-amine (1.0 g, 9.89 mmol) in DMF (10 mL) was added glyoxylic acid and K$_2$CO$_3$ (2.73 g, 19.77 mmol) and the resulting reaction mixture was stirred at room temperature for 3 h. Then added 1-fluoro-4-(isocyano(tosyl)methyl)benzene (2.86 g, 9.89 mmol) stirred at room temperature for 16 h. The reaction mixture was diluted water and extracted with EtOAc (3×100 mL). The combined organic layer was washed with water, brine, dried over sodium sulphate and concentrated under reduced pressure to afford desired product. The residue was further purified by silica gel chromatography (40 g REDISEP® Column, eluting with 3% MeOH in chloroform) to afford a pure Intermediate 40A (0.6 g, 26%) as a pale yellow oil. MS(ES): m/z=247 [M+H]$^+$. $^1$H NMR (400 MHz, chloroform-d) δ ppm 7.69-7.75 (m, 2H), 7.58 (d, J=1.50 Hz, 1H), 7.21 (d, J=1.50 Hz, 1H), 7.06 (t, J=8.75 Hz, 2H), 4.09-4.18 (m, 3H), 3.49-3.60 (m, 2H), 2.07 (dd, J=9.76, 3.75 Hz, 4H).

325

Intermediate 40B: 5-Bromo-4-(4-fluorophenyl)-1-(tetrahydro-2H-pyran-4-yl)-1H-imidazole

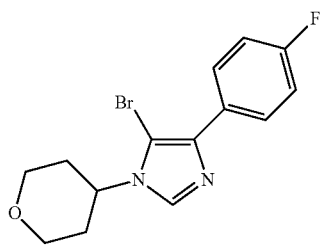 [SMILES: Fc1ccc(-c2ncn(C3CCOCC3)c2Br)cc1]

To a solution of 40A (0.600 g, 2.436 mmol) in dry DCM (10 mL) was added NBS (0.455 g, 2.56 mmol) slowly at 0° C. and the reaction temperature was slowly warmed to RT and stirred for 1 h. The reaction mixture was diluted with water and extracted with DCM (3×30 mL). The combined the organic layer was washed with water, brine, dried over Na$_2$SO$_4$, filtered and concentrated. The residue was purified silica gel chromatography (40 g REDISEP® column, eluting with 25% EtOAc in hexane). Collected fractions were concentrated together to afford Intermediate 40B (0.35 g, 50%) as a yellow solid. MS(ES): m/z=327 [M+H]$^+$. $^1$H NMR (400 MHz, chloroform-d) δ ppm 7.88-7.94 (m, 2H), 7.72 (s, 1H), 7.06-7.13 (m, 2H), 4.25-4.36 (m, 1H), 4.11-4.19 (m, 2H), 3.58 (td, J=11.82, 2.38 Hz, 2H), 2.77 (s, 2H), 1.98-2.14 (m, 4H).

Intermediate 40C: N-(6-(4-(4-Fluorophenyl)-1-(tetrahydro-2H-pyran-4-yl)-1H-imidazol-5-yl)imidazo[1,2-b]pyridazin-2-yl)acetamide

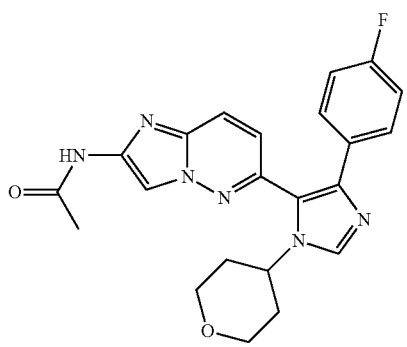 [SMILES: CC(=O)Nc1cn2nc(-c3c(-c4ccc(F)cc4)ncn3C3CCOCC3)ccc2n1]

To a degassed solution of Intermediate 40B (0.800 g, 2.460 mmol) in DMF (10 mL) and water (1 mL) was added Intermediate-1 (2.230 g, 7.38 mmol), Cs$_2$CO$_3$ (2.405 g, 7.38 mmol) and PdCl$_2$(dppf) (0.108 g, 0.148 mmol). The reaction mixture was purged with nitrogen for 10 min. and stirred at 80° C. for 16 h. The reaction mixture was diluted with water and filtered through CELITE® and extracted with EtOAc (3×50 mL) The combined organic layer was washed with water, brine, dried over Na$_2$SO$_4$, filtered and concentrated. The residue was purified silica gel chromatography (40 g REDISEP® column, eluting with 3% methanol in chloroform). Collected fractions were concentrated together to afford Intermediate 40C (0.45 g, 45%) as a yellow solid. MS(ES): m/z=421 [M+H]$^+$. This product was taken to the next step without further purification.

326

Intermediate 40: 6-(4-(4-Fluorophenyl)-1-(tetrahydro-2H-pyran-4-yl)-1H-imidazol-5-yl)imidazo[1,2-b]pyridazin-2-amine

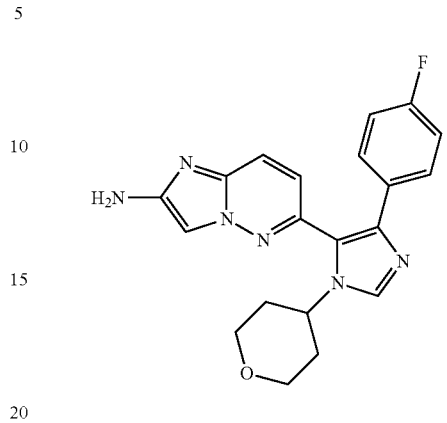

To a solution of Intermediate 40C (170 mg, 0.404 mmol) in MeOH (2 mL) was added 4 M HCl in dioxane (2 ml, 0.80 mmol) at 0° C. and the reaction was stirred at room temperature for 2 h. The reaction mixture was concentrated under reduced pressure, quenched with 10% sodium bicarbonate and extracted with chloroform (3×20 mL) The combined organic layer was washed with water, brine, dried over sodium sulphate, concentrated to afford Intermediate 40 (0.11 g, 72%) as a brown gummy solid. MS(ES): m/z=379 [M+H]$^+$. The crude product was taken to the next step without further purification. $^1$H NMR (300 MHz, DMSO-d$_6$) δ ppm 8.11 (s, 1H), 7.66-7.72 (m, 1H), 7.48-7.56 (m, 1H), 7.36-7.46 (m, 3H), 7.05-7.14 (m, 2H), 6.89 (d, J=8.97 Hz, 2H), 4.07-4.25 (m, 2H), 3.90 (dd, J=11.05, 4.34 Hz, 2H), 3.35 (br. s., 2H), 1.87-2.01 (m, 5H).

Compound 431

2-Fluoro-N-(6-(4-(4-fluorophenyl)-1-(tetrahydro-2H-pyran-4-yl)-1H-imidazol-5-yl)imidazo[1,2-b]pyridazin-2-yl)isonicotinamide

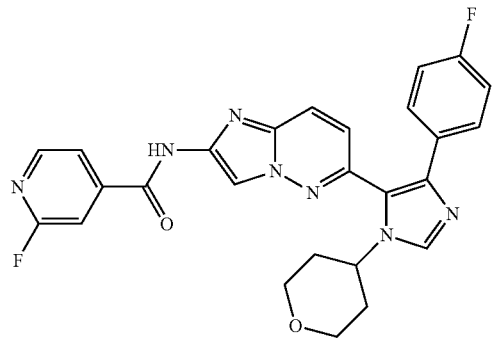 [SMILES: O=C(Nc1cn2nc(-c3c(-c4ccc(F)cc4)ncn3C3CCOCC3)ccc2n1)c1ccnc(F)c1]

To a solution of Intermediate 40 (50 mg, 0.132 mmol) HATU (100 mg, 0.264 mmol) and DIPEA (0.069 mL, 0.396 mmol) in DMF (2 mL) was added 2-fluoroisonicotinic acid (37.3 mg, 0.264 mmol) and the reaction was stirred at room temperature for 16 h. DMF was removed under high vacuum, diluted with 10% sodium bicarbonate solution and extracted with chloroform (3×80 mL). The combined organic layer was washed with water, brine, dried over sodium sulphate and concentrated to afford the crude product. The crude product was purified by preparative HPLC purification to afford compound 431 (0.011 g, 17%) as a pale yellow solid. MS(ES): m/z=500 [M+H]⁺; Time 6.20 min and 7.08 min (HPLC Methods K and L respectively); ¹H NMR (400 MHz, DMSO-d$_6$) δ ppm 11.74-12.05 (m, 1H), 8.61 (s, 1H), 8.46 (d, J=5.02 Hz, 1H), 8.20 (s, 1H), 8.07 (d, J=9.29 Hz, 1H), 7.94-8.00 (m, 1H), 7.80 (s, 1H), 7.75-7.86 (m, 1H), 7.42-7.49 (m, 2H), 7.09-7.17 (m, 3H), 4.30-4.41 (m, 1H), 3.94 (d, J=10.79 Hz, 2H), 3.36-3.43 (m, 2H), 1.97-2.08 (m, 4H).

The following compounds in Table 43 were prepared by the procedure described for the preparation of compound 431 from the Intermediate 40 using the corresponding acids.

TABLE 43

| Compound No | Structure | Name | [M + H]⁺ | Ret Time (min) | HPLC Method |
|---|---|---|---|---|---|
| 432 | 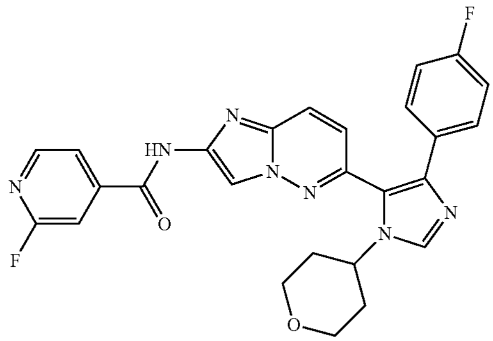 [SMILES: O=C(Nc1cn2nc(-c3c(-c4ccc(F)cc4)ncn3C3CCOCC3)ccc2n1)c1ccnc(F)c1] | 2-Fluoro-N-(6-(4-(4-fluorophenyl)-1-(tetrahydro-2H-pyran-4-yl)-1H-imidazol-5-yl)imidazo[1,2-b]pyridazin-2-yl)isonicotinamide | 500 | 6.21<br>7.09 | K<br>L |
| 433 | 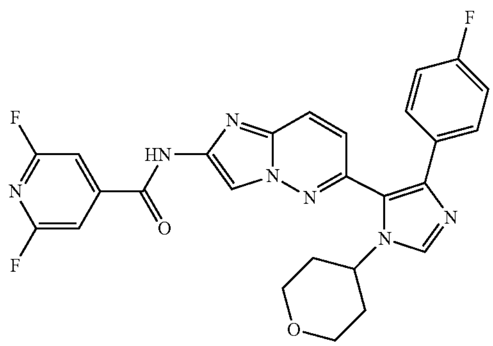 | 2,6-Difluoro-N-(6-(4-(4-fluorophenyl)-1-(tetrahydro-2H-pyran-4-yl)-1H-imidazol-5-yl)imidazo[1,2-b]pyridazin-2-yl)isonicotinamide | 520 | 7.27<br>8.03 | K<br>L |
| 434 | 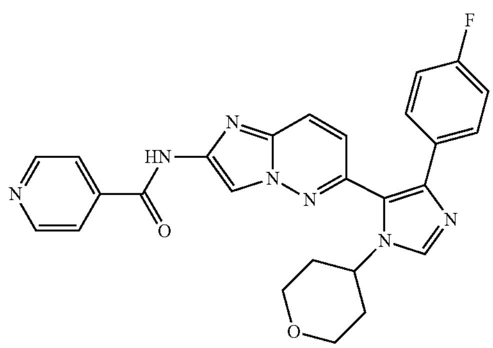 [SMILES: O=C(Nc1cn2nc(-c3c(-c4ccc(F)cc4)ncn3C3CCOCC3)ccc2n1)c1ccncc1] | N-(6-(4-(4-Fluorophenyl)-1-(tetrahydro-2H-pyran-4-yl)-1H-imidazol-5-yl)imidazo[1,2-b]pyridazin-2-yl)isonicotinamide | 484 | 5.17<br>9.42 | L<br>M |
| 435 | 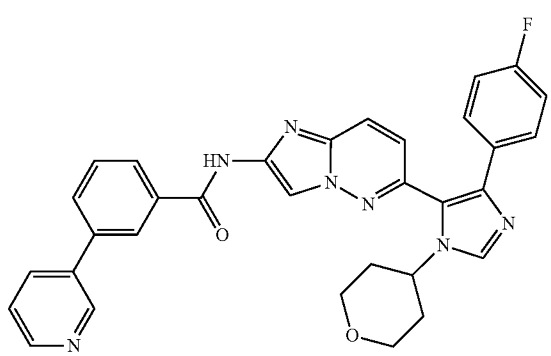 [SMILES: O=C(Nc1cn2nc(-c3c(-c4ccc(F)cc4)ncn3C3CCOCC3)ccc2n1)c1cccc(-c2cccnc2)c1] | N-(6-(4-(4-Fluorophenyl)-1-(tetrahydro-2H-pyran-4-yl)-1H-imidazol-5-yl)imidazo[1,2-b]pyridazin-2-yl)-3-(pyridin-3-yl)benzamide | 558 | 5.14<br>5.46 | K<br>L |

Scheme 22

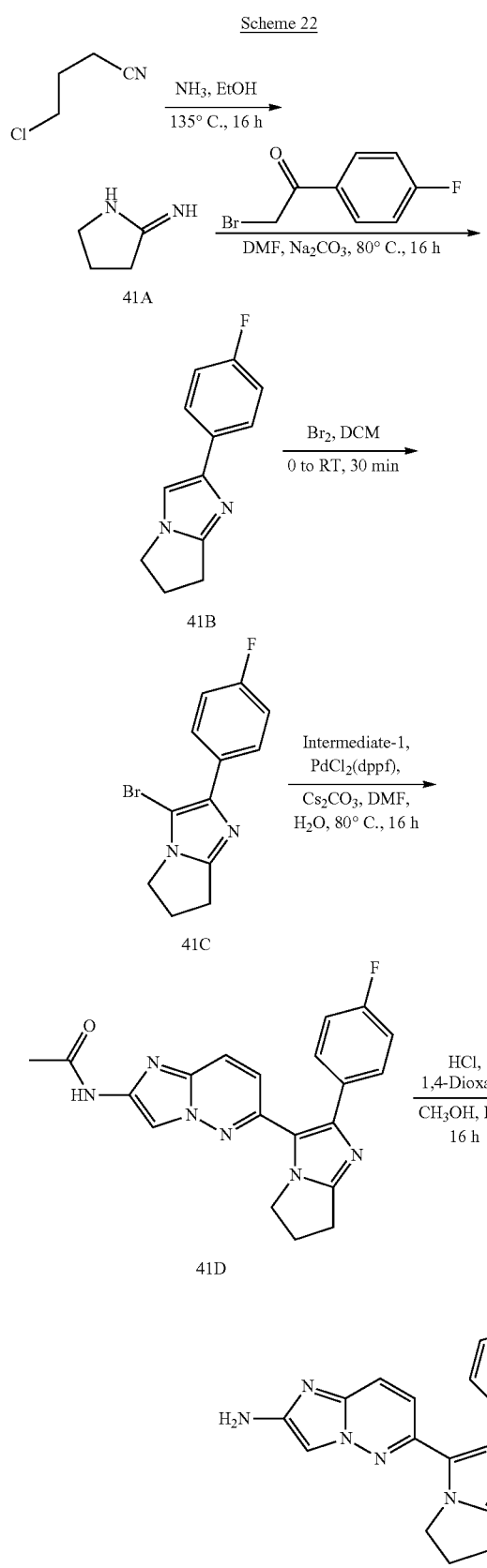

Intermediate 41

6-(2-(4-Fluorophenyl)-6,7-dihydro-5H-pyrrolo[1,2-a]imidazol-3-yl)imidazo[1,2-b]pyridazin-2-amine

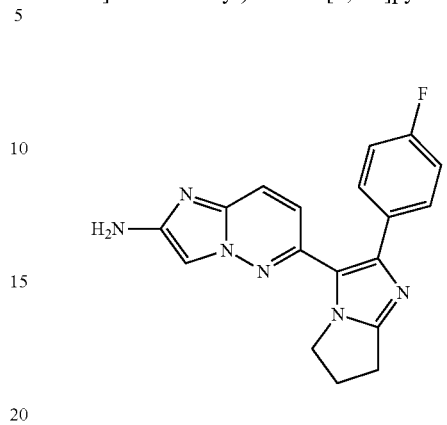

Intermediate 41A: Pyrrolidin-2-imine

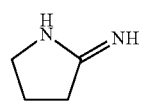

To a solution of 4-chlorobutanenitrile (9 g, 87 mmol) in ethanol (10 mL) was added saturated ammonia in ethanol (50 ml, 2311 mmol). The reaction was heated to 135° C. in an autoclave reactor for 16 h. The reaction mixture was filtered through CELITE® pad and concentrated under reduced pressure. The solid obtained was recrystallized from with ethanol and diethyl ether to afford Intermediate 41A (7 g, 66%) as a white solid. $^1$H NMR (400 MHz, chloroform-d) δ ppm 9.24-9.63 (m, 1H), 8.81 (br. s., 1H), 3.67 (t, J=7.15 Hz, 2H), 2.97 (t, J=8.03 Hz, 2H), 2.19 (dt, J=15.12, 7.62 Hz, 2H).

Intermediate 41B: 2-(4-Fluorophenyl)-6,7-dihydro-5H-pyrrolo[1,2-a]imidazole

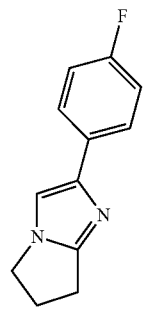 [SMILES: Fc1ccc(-c2cn3c(n2)CCC3)cc1]

To a solution of 2-bromo-1-(4-fluorophenyl)ethanone (3.6 g, 16.59 mmol) in dry DMF was added Intermediate 41A (6.00 g, 49.8 mmol), sodium carbonate (7.03 g, 66.3 mmol) and the reaction mixture was heated to 80° C. for about 16 h. The reaction mixture cooled to room temperature, diluted with water and extracted with ethyl acetate (3×100 mL). The combined organic layer was washed with water, brine, dried over sodium sulphate and concentrated. The residue was purified by silica gel chromatography (24 g REDISEP® column, eluting with 3% MeOH in chloroform) to afford pure Intermediate 41B (1.6 g, 47%) as a pale yellow solid. $^1$H NMR (400 MHz, chloroform-d) δ ppm 7.66-7.74 (m, 2H), 7.11 (s, 1H), 7.00-7.06 (m, 2H), 3.98-4.03 (m, 2H), 2.87-2.97 (m, 2H), 2.57-2.66 (m, 2H).

Intermediate 41C: 3-Bromo-2-(4-fluorophenyl)-6,7-dihydro-5H-pyrrolo[1,2-a]imidazole

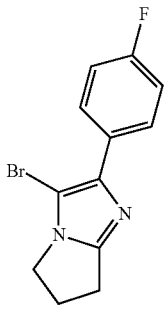 [SMILES: Fc1ccc(-c2nc3n(c2Br)CCC3)cc1]

To a stirred solution of Intermediate 41B (1.5 g, 7.42 mmol) in dry DCM (10 mL) was added bromine (0.420 mL, 8.16 mmol) slowly at 0° C. and the reaction was slowly brought to RT and stirred for 30 min. The reaction mixture was diluted with water and extracted with DCM (3×40 mL). Combined the organic layer was washed with water, brine, dried over Na$_2$SO$_4$ and concentrated. The residue was purified silica gel chromatography (40 g REDISEP® column, eluting with 30% EtOAc in hexane). Collected fractions were concentrated together to afford Intermediate 41C (1 g, 48%) as a yellow solid. MS(ES): m/z=283 [M+H]$^+$; $^1$H NMR (400 MHz, chloroform-d) δ ppm 7.86-7.94 (m, 2H), 7.04-7.11 (m, 2H), 3.94-4.01 (m, 2H), 2.95-3.03 (m, 2H), 2.59-2.68 (m, 2H).

Intermediate 41 D: N-(6-(2-(4-Fluorophenyl)-6,7-dihydro-5H-pyrrolo[1,2-a]imidazol-3-yl)imidazo[1,2-b]pyridazin-2-yl)acetamide

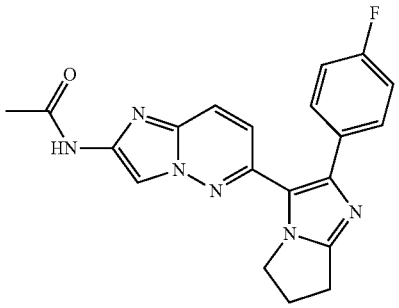 [SMILES: CC(=O)Nc1cn2nc(-c3c(-c4ccc(F)cc4)nc4n3CCC4)ccc2n1]

To a degassed solution of Intermediate 41C (1 g, 3.56 mmol), intermediate-1 (2.69 g, 8.89 mmol), cesium carbonate (3.48 g, 10.67 mmol) in DMF (10 mL) and water (1 mL) was added PdCl$_2$(dppf).DCM adduct (0.145 g, 0.178 mmol) and the reaction mixture was purged with nitrogen for 10 minutes and stirred at 80° C. for 16 h. The reaction mixture was concentrated, diluted with ethyl acetate, filtered through CELITE®. The filtrate was washed with water, brine, dried over Na$_2$SO$_4$ and concentrated. The residue was purified by silica gel chromatography (40 g REDISEP® column, eluting with 2% methanol in chloroform). Collected fractions were concentrated together to afford Intermediate 41D (0.6 g, 44%) as a pale yellow solid. This product was taken for next step without further purification. MS(ES): m/z=377 [M+H]$^+$.

Intermediate 41: 6-(2-(4-Fluorophenyl)-6,7-dihydro-5H-pyrrolo[1,2-a]imidazol-3-yl)imidazo[1,2-b]pyridazin-2-amine

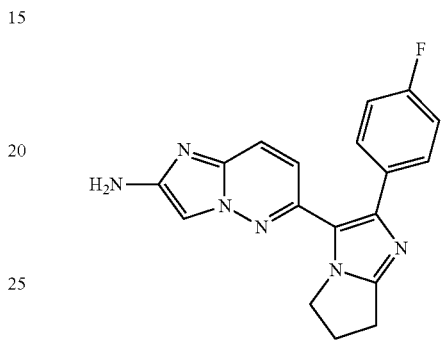

To a solution of Intermediate 41D (0.11 g, 0.292 mmol) in methanol (1 mL) was added 4 M HCl in dioxane (3 mL, 12.00 mmol) at 0° C. and the reaction was stirred at RT for 2 h. The reaction mixture was concentrated under high vacuum, quenched with 10% sodium bicarbonate solution and extracted with chloroform (3×40 mL). The combined organic layer was washed with water, brine, dried over sodium sulphate, filtered and concentrated to afford Intermediate 41 (0.085 g, 87%) as a brown gummy solid. MS(ES): m/z=335 [M+H]$^+$. This product was taken for next step without further purification.

Compound 436

2-Fluoro-N-(6-(2-(4-fluorophenyl)-6,7-dihydro-5H-pyrrolo[1,2-a]imidazol-3-yl)imidazo[1,2-b]pyridazin-2-yl)isonicotinamide

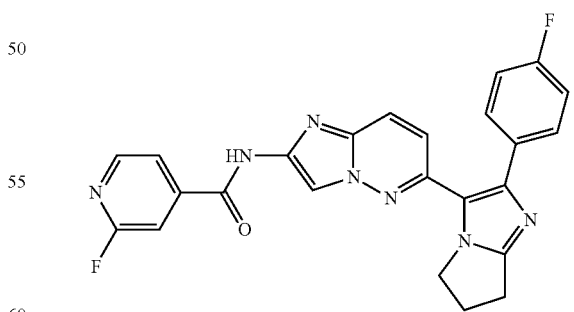

To a solution of Intermediate 41 (0.08 g, 0.239 mmol) in dry DMF (1 mL) was added HATU (0.182 g, 0.479 mmol), DIPEA (0.125 mL, 0.718 mmol), 2-fluoroisonicotinic acid (0.068 g, 0.479 mmol) and stirred at RT for 16 h. The reaction mixture was concentrated under high vacuum, diluted with 10% sodium bicarbonate solution and extracted with chloroform (3×80 mL) The combined organic layer was washed with water, brine, dried over sodium sulphate and concentrated. The crude product was purified by preparative HPLC purification to afford compound 436 (0.023 g, 23%) as a pale yellow solid. MS(ES): m/z=458 [M+H]; HPLC Ret. Time 5.82 min and 6.69 min (Method A and B respectively); $^1$H NMR (400 MHz, DMSO-d$_6$) δ ppm 8.53 (s, 1H), 8.44 (d, J=5.21 Hz, 1H), 7.92-7.99 (m, 2H), 7.79 (s, 1H), 7.55-7.62 (m, 2H), 7.21 (t, J=8.91 Hz, 2H), 7.01 (d, J=9.47 Hz, 1H), 4.27 (t, J=7.22 Hz, 2H), 2.87-2.93 (m, 2H), 2.61 (t, J=7.25 Hz, 2H).

The following compounds in Table 44 were prepared by the procedure described for the preparation of compound 436 from the Intermediate 41 using the corresponding acids.

TABLE 44

| Compound No | Structure | Name | [M + H]⁺ | Ret Time (min) | HPLC Method |
|---|---|---|---|---|---|
| 437 | 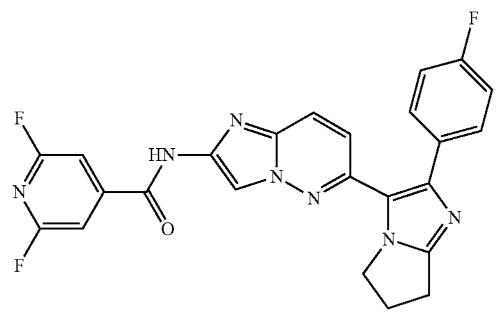 [SMILES: O=C(Nc1cn2nc(-c3c(-c4ccc(F)cc4)nc4n3CCC4)ccc2n1)c1cc(F)nc(F)c1] | 2,6-Difluoro-N-(6-(2-(4-fluorophenyl)-6,7-dihydro-5H-pyrrolo[1,2-a]imidazol-3-yl)imidazo[1,2-b]pyridazin-2-yl)isonicotinamide | 474 | 6.59 7.67 | K L |
| 438 | 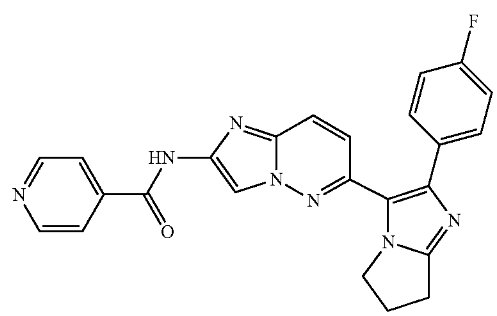 [SMILES: O=C(Nc1cn2nc(-c3c(-c4ccc(F)cc4)nc4n3CCC4)ccc2n1)c1ccncc1] | N-(6-(2-(4-Fluorophenyl)-6,7-dihydro-5H-pyrrolo[1,2-a]imidazol-3-yl)imidazo[1,2-b]pyridazin-2-yl) isonicotinamide | 440 | 9.01 8.53 | L M |
| 439 | 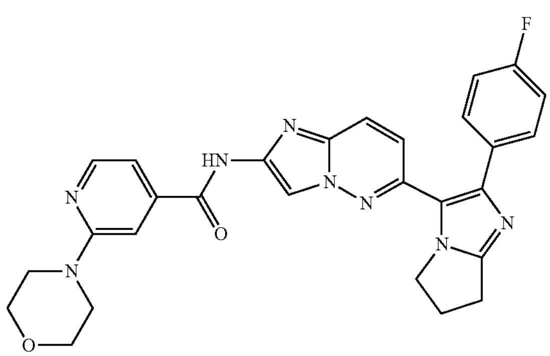 [SMILES: O=C(Nc1cn2nc(-c3c(-c4ccc(F)cc4)nc4n3CCC4)ccc2n1)c1ccnc(N2CCOCC2)c1] | N-(6-(2-(4-Fluorophenyl)-6,7-dihydro-5H-pyrrolo[1,2-a]imidazol-3-yl)imidazo[1,2-b]pyridazin-2-yl)-2-morpholinoisonicotinamide | 523 [M − H] | 9.25 5.34 | K L |
| 440 | 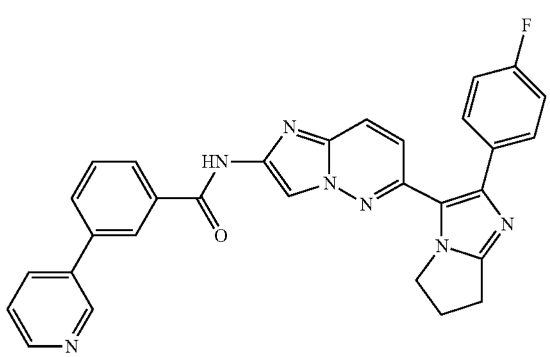 [SMILES: O=C(Nc1cn2nc(-c3c(-c4ccc(F)cc4)nc4n3CCC4)ccc2n1)c1cccc(-c2cccnc2)c1] | N-(6-(2-(4-Fluorophenyl)-6,7-dihydro-5H-pyrrolo[1,2-a]imidazol-3-yl)imidazo[1,2-b]pyridazin-2-yl)-3-(pyridin-3-yl)benzamide | 514 [M − H] | 5.49 9.39 | L M |

Scheme-23

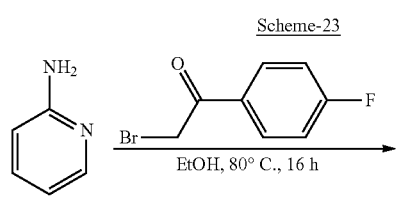

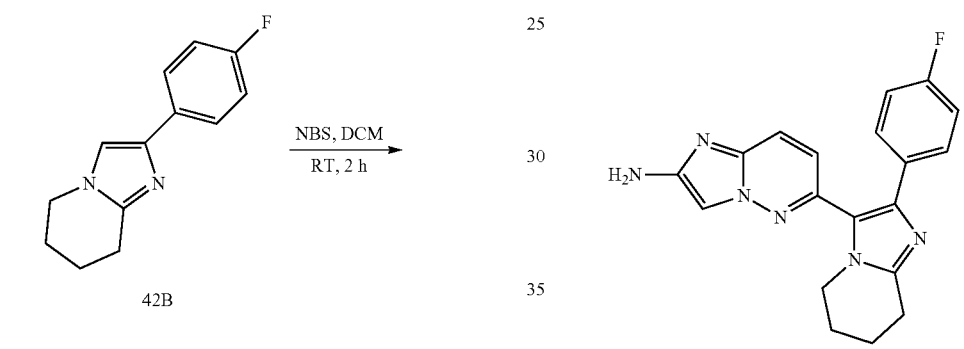

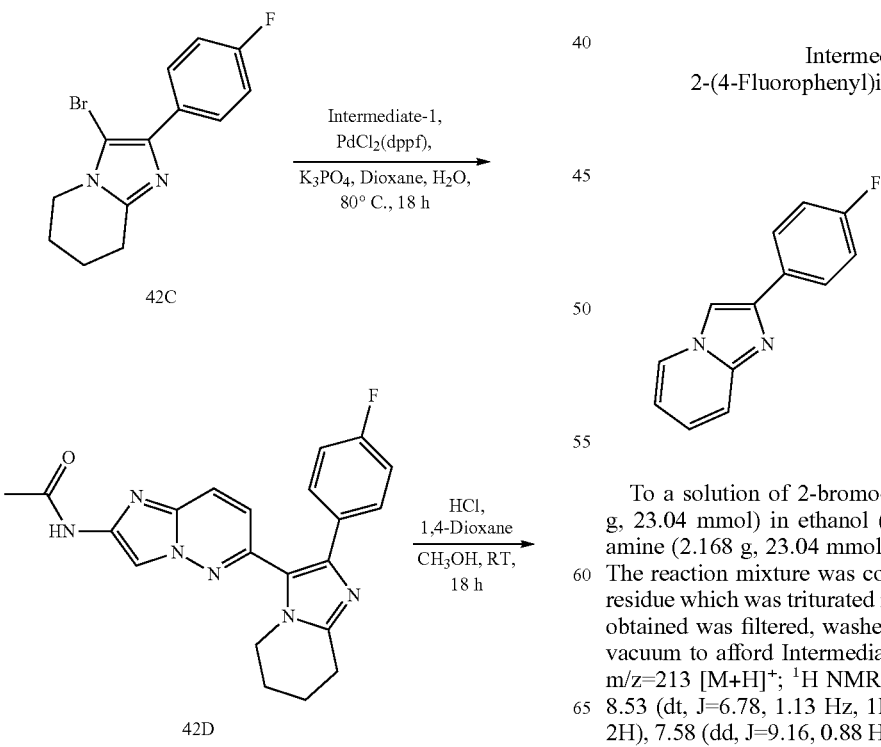

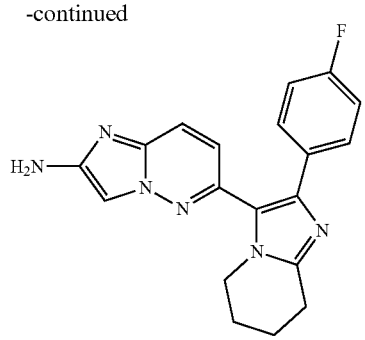

Intermediate 42

6-(2-(4-Fluorophenyl)-5,6,7,8-tetrahydroimidazo[1,2-a]pyridin-3-yl)imidazo[1,2-b]pyridazin-2-amine Intermediate 42A:
2-(4-Fluorophenyl)imidazo[1,2-a]pyridine To a solution of 2-bromo-1-(4-fluorophenyl)ethanone (5 g, 23.04 mmol) in ethanol (50 mL) was added pyridin-2-amine (2.168 g, 23.04 mmol) and heated to reflux for 16 h. The reaction mixture was concentrated to give pale yellow residue which was triturated in 3:1 hexane/EtOAc. The solid obtained was filtered, washed with hexane and dried under vacuum to afford Intermediate 42A (5.5 g, 67%). MS(ES): m/z=213 [M+H]$^+$; $^1$H NMR (400 MHz, DMSO-d$_6$) δ ppm 8.53 (dt, J=6.78, 1.13 Hz, 1H), 8.39 (s, 1H), 7.97-8.07 (m, 2H), 7.58 (dd, J=9.16, 0.88 Hz, 1H), 7.20-7.32 (m, 3H), 6.91 (td, J=6.71, 1.13 Hz, 1H).

Intermediate 42B: 2-(4-Fluorophenyl)-5,6,7,8-tetrahydroimidazo[1,2-a]pyridine

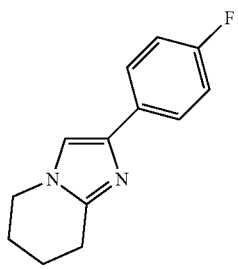 [SMILES: Fc1ccc(-c2cn3c(n2)CCCC3)cc1]

To a solution of Intermediate 42A (300 mg, 1.414 mmol) in ethanol (10 mL) was added Pd/C (451 mg, 0.424 mmol) under nitrogen and hydrogenated under 3.5 bar hydrogen pressure at room temperature for 16 h. The reaction mixture was filtered through CELITE® pad and the filtrate was concentrated to afford crude product as off-white solid. The solid was triturated with hexane to afford Intermediate 42B (0.2 g, 59%) as a white solid. MS(ES): m/z=217 [M+H]$^+$; $^1$H NMR (300 MHz, DMSO-d$_6$) δ ppm 7.66-7.77 (m, 2H), 7.43 (s, 1H), 7.08-7.22 (m, 2H), 3.95 (t, J=5.67 Hz, 2H), 2.75 (t, J=6.14 Hz, 2H), 1.78-1.97 (m, 4H).

Intermediate 42C: 3-Bromo-2-(4-fluorophenyl)-5,6,7,8-tetrahydroimidazo[1,2-a]pyridine

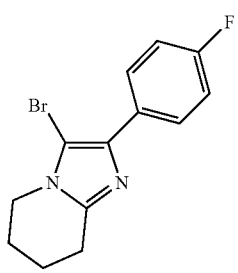 [SMILES: Fc1ccc(-c2nc3n(c2Br)CCCC3)cc1]

To a solution of Intermediate 42B (2.5 g, 11.56 mmol) in DCM (3 mL) was added NBS (2.160 g, 12.14 mmol) and stirred at room temperature for 2 h. The reaction mixture was filtered through sintered glass funnel and the filtrate was evaporated under reduced pressure to give crude product as pink solid. The residue was purified silica gel chromatography (40 g REDISEP® column, eluting with 30% EtOAc in hexane). Collected fractions were concentrated together to afford Intermediate 42C (2.5 g, 72%) as pale yellow solid. MS(ES): m/z=295 [M+H]$^+$; $^1$H NMR (400 MHz, chloroform-d) δ ppm 7.85-7.96 (m, 2H), 6.96-7.14 (m, 2H), 3.82-3.94 (m, 2H), 2.91 (t, J=6.38 Hz, 2H), 1.88-2.14 (m, 4H).

Intermediate 42D: N-(6-(2-(4-Fluorophenyl)-5,6,7,8-tetrahydroimidazo[1,2-a]pyridin-3-yl)imidazo[1,2-b]pyridazin-2-yl)acetamide

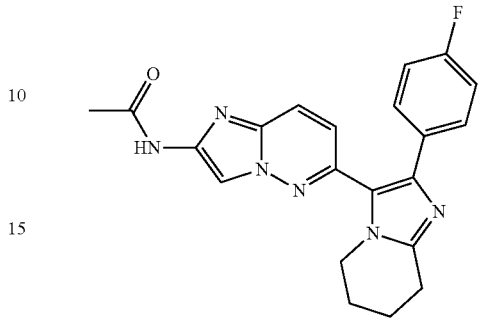

To a solution of Intermediate 42C (0.5 g, 1.694 mmol), intermediate-1 (1.536 g, 5.08 mmol) in dioxane (15 mL) was added K$_3$PO$_4$ (2.54 mL, 5.08 mmol, 2 M in H$_2$O) and purged with nitrogen for 10 min. To which was added PdCl$_2$(dppf) (0.074 g, 0.102 mmol) and stirred at 80° C. for 18 h. The reaction mixture was concentrated under reduced pressure and residue was added water and extracted with EtOAc (3×10 mL). The combined the organic layer was washed with water, brine, dried over Na$_2$SO$_4$, and concentrated to give crude compound as yellow solid. The residue was purified silica gel chromatography (24 g REDISEP® column, eluting with 2% methanol in chloroform). Collected fractions were concentrated together to afford Intermediate 42D (0.25 g, 40%) as pale yellow solid. MS(ES): m/z=391 [M+H]$^+$. The crude product was taken for next step without further purification.

Intermediate 42: 6-(2-(4-Fluorophenyl)-5,6,7,8-tetrahydroimidazo[1,2-a]pyridin-3-yl)imidazo[1,2-b]pyridazin-2-amine

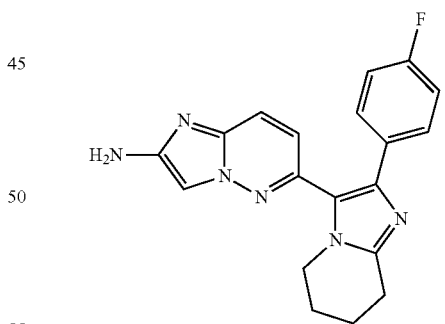

To a solution of Intermediate 42D (200 mg, 0.512 mmol) in MeOH (5 mL) at 0° C. was added 4M HCl in 1,4-dioxane (6.40 mL, 25.6 mmol) and the reaction mixture was stirred at room temperature for 18 h. The reaction mixture was concentrated under reduced pressure, neutralized with saturated NaHCO$_3$ solution and extracted with EtOAc (3×5 mL). The combined organic layer was washed with brine, dried over Na$_2$SO$_4$ and concentrated to afford crude compound as yellow solid. The residue was purified silica gel chromatography (24 g REDISEP® column, eluting with 2% methanol in chloroform). Collected fractions were concentrated together to afford Intermediate 42 (0.15 g, 76%) as pale yellow solid. MS(ES): m/z=349 [M+H]⁺. This product was taken for next step without further purification.

Compound 441

2-Fluoro-N-(6-(2-(4-fluorophenyl)-5,6,7,8-tetrahydroimidazo[1,2-a]pyridin-3-yl)imidazo[1,2-b]pyridazin-2-yl)isonicotinamide

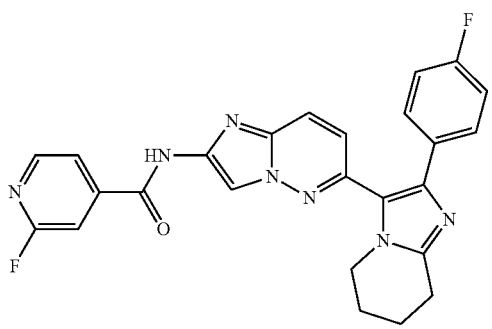 [SMILES: O=C(Nc1cn2nc(-c3c(-c4ccc(F)cc4)nc4n3CCCC4)ccc2n1)c1ccnc(F)c1]

To a stirred solution of 2-fluoroisonicotinic acid (35.6 mg, 0.253 mmol), HATU (96 mg, 0.253 mmol) and DIPEA (0.120 mL, 0.689 mmol) in DMF (2 mL) was added Intermediate 42 (40 mg, 0.115 mmol) and stirred at room temperature for 18 h. The reaction mixture was diluted with water (5 mL) and extracted with EtOAc (3×5 mL) The combined the organic layer was washed with water, brine, dried over $Na_2SO_4$ and concentrated to afford crude compound as dark brown residue. The residue was further purified via reverse phase HPLC to give compound 441 (0.01 g, 18%) as pale yellow solid. MS(ES): m/z=472 [M+H]⁺; HPLC Ret Time 6.07 min and 7.20 min (HPLC Method A and B); ¹H NMR (400 MHz, DMSO-$d_6$) δ ppm 11.90 (s, 1H), 8.56 (s, 1H), 8.47 (d, J=5.27 Hz, 1H), 8.04 (d, J=9.29 Hz, 1H), 7.97 (dt, J=5.14, 1.69 Hz, 1H), 7.81 (s, 1H), 7.47-7.53 (m, 2H), 7.15 (t, J=8.91 Hz, 2H), 7.09 (d, J=9.29 Hz, 1H), 4.04 (t, J=5.27 Hz, 2H), 2.88-2.94 (m, 2H), 1.94 (br. s., 4H).

The following compounds in Table 45 were prepared by the procedure described for the preparation of compound 441 from the Intermediate 42 using the corresponding acids.

TABLE 45

| Compound No | Structure | Name | [M + H]⁺ | Ret Time (min) | HPLC Method |
|---|---|---|---|---|---|
| 442 | 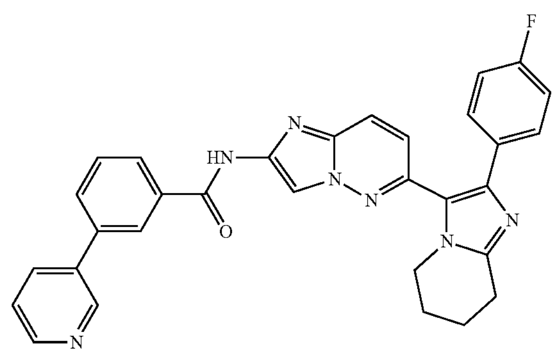 | N-(6-(2-(4-Fluorophenyl)-5,6,7,8-tetrahydroimidazo[1,2-a]pyridin-3-yl)imidazo[1,2-b]pyridazin-2-yl)-3-(pyridin-3-yl)benzamide | 530 | 5.93<br>9.85 | L<br>M |
| 443 | 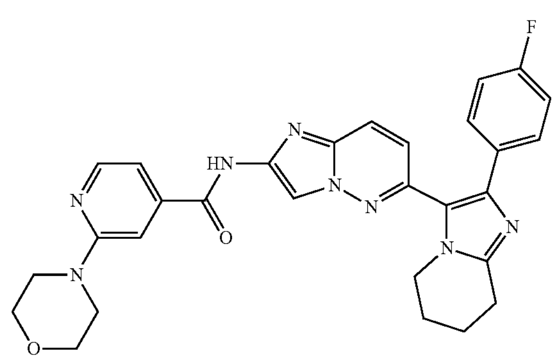 | N-(6-(2-(4-Fluorophenyl)-5,6,7,8-tetrahydroimidazo[1,2-a]pyridin-3-yl)imidazo[1,2-b]pyridazin-2-yl)-2-morpholinoisonicotinamide | 539 | 5.81<br>9.77 | L<br>M |

TABLE 45-continued

| Compound No | Structure | Name | [M + H]+ | Ret Time (min) | HPLC Method |
|---|---|---|---|---|---|
| 444 | 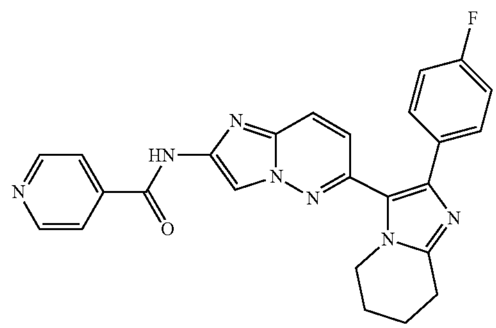 [SMILES: O=C(Nc1cn2nc(-c3c(-c4ccc(F)cc4)nc4n3CCCC4)ccc2n1)c1ccncc1] | N-(6-(2-(4-Fluorophenyl)-5,6,7,8-tetrahydroimidazo[1,2-a]pyridin-3-yl)imidazo[1,2-b]pyridazin-2-yl)isonicotinamide | 454 | 5.30 9.39 | L M |
| 445 | 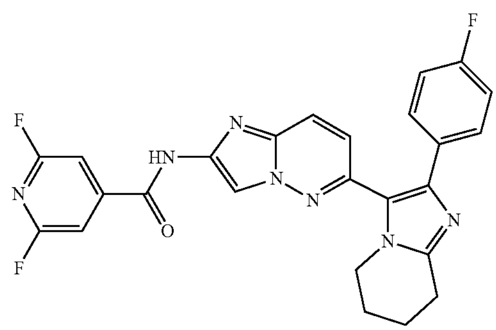 [SMILES: O=C(Nc1cn2nc(-c3c(-c4ccc(F)cc4)nc4n3CCCC4)ccc2n1)c1cc(F)nc(F)c1] | 2,6-Difluoro-N-(6-(2-(4-fluorophenyl)-5,6,7,8-tetrahydroimidazo[1,2-a]pyridin-3-yl)imidazo[1,2-b]pyridazin-2-yl)isonicotinamide | 490 | 6.75 8.18 | K L |
| 446 | 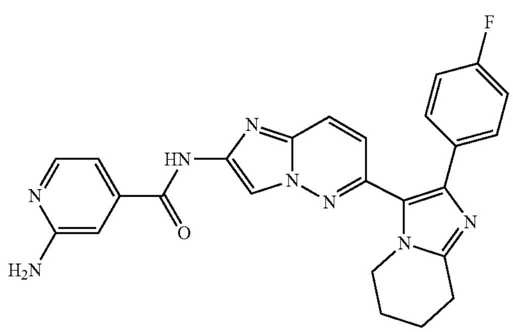 [SMILES: Nc1cc(C(=O)Nc2cn3nc(-c4c(-c5ccc(F)cc5)nc5n4CCCC5)ccc3n2)ccn1] | 2-Amino-N-(6-(2-(4-fluorophenyl)-5,6,7,8-tetrahydroimidazo[1,2-a]pyridin-3-yl)imidazo[1,2-b]pyridazin-2-yl)isonicotinamide | 468 | 7.93 9.58 | M N |

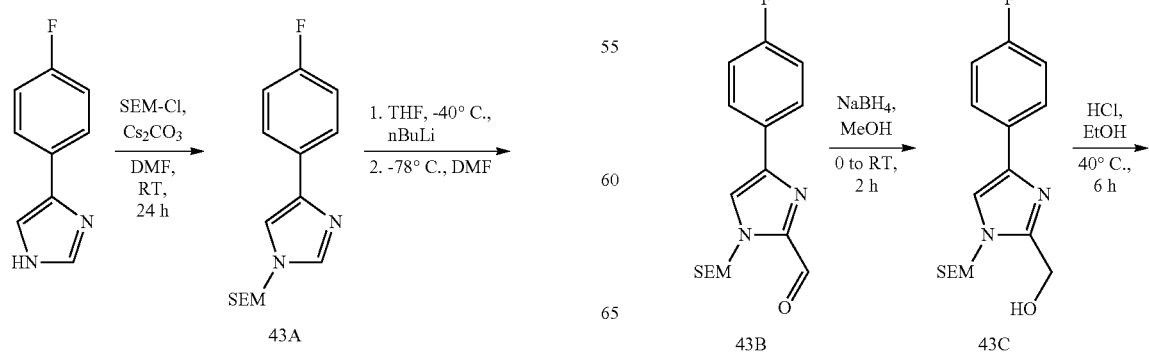

Scheme 24

343
-continued

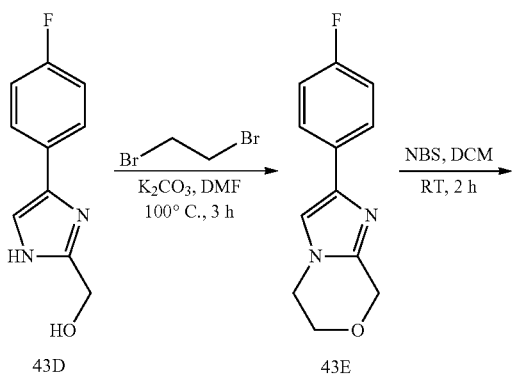

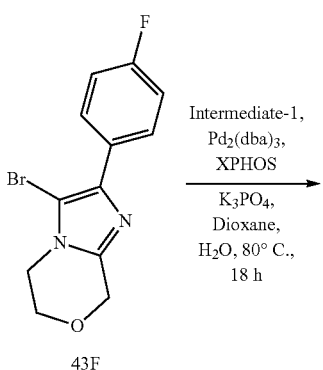

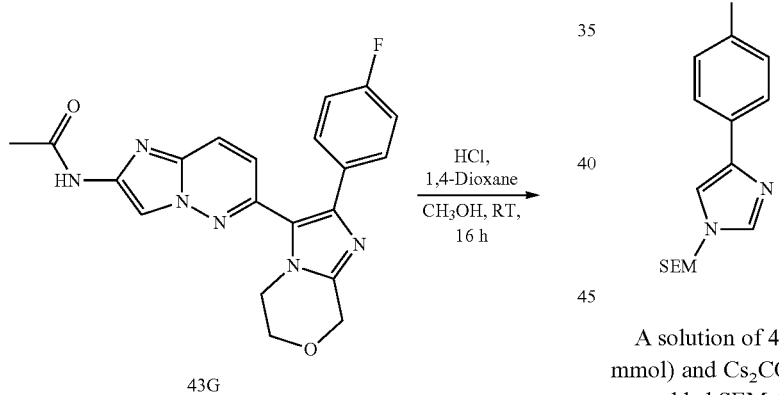

344
Intermediate 43

6-(2-(4-Fluorophenyl)-6,8-dihydro-5H-imidazo[2,1-c][1,4]oxazin-3-yl)imidazo[1,2-b]pyridazin-2-amine

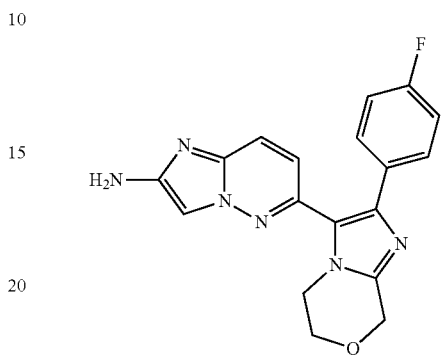

Intermediate 43A: 4-(4-Fluorophenyl)-1-((2-(trimethylsilyl)ethoxy)methyl)-1H-imidazole

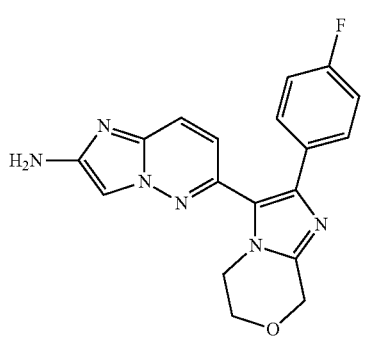 [SMILES: Nc1cn2nc(-c3c(-c4ccc(F)cc4)nc4n3CCOC4)ccc2n1]

A solution of 4-(4-fluorophenyl)-1H-imidazole (1 g, 6.17 mmol) and $Cs_2CO_3$ (5.02 g, 15.42 mmol) in DMF (10 mL) was added SEM-Cl (1.20 mL, 6.78 mmol) and the resulting brown suspension was stirred at room temperature for 24 h. DMF was removed from the reaction mixture under reduced pressure. The residue obtained was diluted with ice cold water and extracted with ethyl acetate (3×15 mL) The combined organic layer was washed with water, brine, dried over $Na_2SO_4$, filtered and concentrated to afford crude product as yellow solid. The residue was purified by silica gel chromatography (24 g REDISEP® column, eluting with 50% EtOAc in hexane). Collected fractions were concentrated together to afford Intermediate 43A (0.8 g, 42%) as off-white solid. MS(ES): m/z=293 [M+H]$^+$; $^1$H NMR (400 MHz, chloroform-d) δ ppm 7.72-7.80 (m, 2H), 7.61 (d, J=1.25 Hz, 1H), 7.26 (s, 1H), 7.02-7.11 (m, 2H), 5.29 (s, 2H), 3.49-3.56 (m, 2H), 0.93 (dd, J=8.66, 7.65 Hz, 2H), −0.04-0.01 (m, 9H).

Intermediate 43B: 4-(4-Fluorophenyl)-1-((2-(trimethylsilyl)ethoxy)methyl)-1H-imidazole-2-carbaldehyde

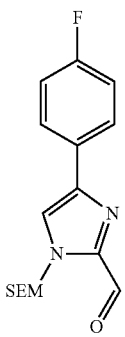 [SMILES: C[Si](C)(C)CCOCn1cc(-c2ccc(F)cc2)nc1C=O]

To a solution of Intermediate 43A (0.8 g, 2.74 mmol) in dry THF (10 mL) at −40° C. was added n-butyl lithium (1.313 mL, 3.28 mmol) dropwise and for 1 h. The reaction mixture was further cooled to −78° C. and DMF (1.059 mL, 13.68 mmol) was added and stirred at the same temperature for 30 min and slowly allowed to warm to room temperature. The reaction mixture was quenched with saturate $NH_4Cl$ and extracted with ethyl acetate (3×15 mL). The combined organic layer was washed with water, brine, dried over $Na_2SO_4$, filtered and concentrated to afford Intermediate 43B (0.8 g, 60%) as brown semi solid which was taken to the next step without further purification. MS(ES): m/z=321 [M+H]$^+$; $^1$H NMR (400 MHz, chloroform-d) δ ppm 9.87 (s, 1H), 7.72-7.80 (m, 2H), 7.61 (d, J=1.25 Hz, 1H), 7.02-7.11 (m, 2H), 5.29 (s, 2H), 3.49-3.56 (m, 2H), 0.93 (dd, J=8.66, 7.65 Hz, 2H), −0.04-0.01 (m, 9H).

Intermediate 43C: (4-(4-Fluorophenyl)-1-((2-(trimethylsilyl)ethoxy)methyl)-1H-imidazol-2-yl)methanol

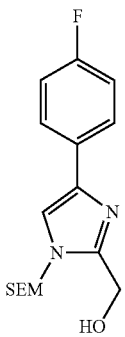 [SMILES: C[Si](C)(C)CCOCn1cc(-c2ccc(F)cc2)nc1CO]

To a solution of Intermediate 43B (0.56 g, 1.748 mmol) in MeOH (10 mL) 0° C. was added then $NaBH_4$ (0.079 g, 2.097 mmol) and stirred at room temperature for 2 h. The reaction mixture was quenched with saturate $NH_4Cl$ and the aqueous layer was back extracted with ethyl acetate (3×10 mL) The combined organic layer was washed with water, brine solution, dried over $Na_2SO_4$, filtered and concentrated to afford crude compound as brown semi solid. The residue was purified by silica gel chromatography (24 g REDISEP® column, eluting with 50% EtOAc in hexane). Collected fractions were concentrated together to afford Intermediate 43C (0.8 g, 42%) as pale yellow solid. MS(ES): m/z=323 [M+H]$^+$; $^1$H NMR (400 MHz, chloroform-d) δ ppm 7.67-7.75 (m, 2H), 7.21 (s, 1H), 7.03-7.10 (m, 2H), 5.33 (s, 2H), 4.77-4.82 (m, 2H), 3.53-3.60 (m, 2H), 3.02 (br. s., 1H), 0.90-0.97 (m, 2H), −0.01-0.01 (m, 9H).

Intermediate 43D: (4-(4-Fluorophenyl)-1H-imidazol-2-yl) methanol

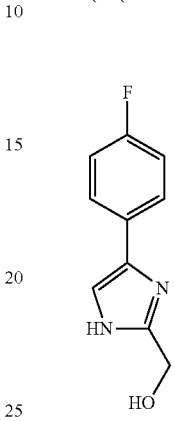

To a solution of Intermediate 43C (0.5 g, 1.551 mmol) in ethanol (5 mL) was added and HCl (2.5 mL, 27.5 mmol) and the resulting solution was stirred at 40° C. for 6 h. EtOH was removed from the reaction mixture, 10% NaOH was added to adjust pH~8.0 and the aqueous layer was extracted with ethyl acetate (3×5 mL). The combined the organic layer was washed with water brine, dried over $Na_2SO_4$, filtered and concentrated to afford crude product as brown solid. The residue was triturated with diethyl ether (2×5 mL), filtered, rinsed with hexane to afford Intermediate 43D (0.2 g, 66%) as off-white solid. MS(ES): m/z=193 [M+H]$^+$; $^1$H NMR (400 MHz, DMSO-$d_6$) δ ppm 12.00 (s, 1H), 7.75-7.80 (m, 2H), 7.50 (d, J=2.07 Hz, 1H), 7.12-7.18 (m, 2H), 5.37 (t, J=5.71 Hz, 1H), 4.49 (d, J=5.77 Hz, 2H).

Intermediate 43E: 2-(4-Fluorophenyl)-6,8-dihydro-5H-imidazo[2,1-c][1,4]oxazine

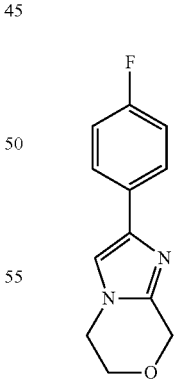

To a solution of Intermediate 43D (2.3 g, 11.97 mmol), 1,2-dibromoethane (2.063 mL, 23.93 mmol) in DMF (0.5 mL) was added $K_2CO_3$ (4.96 g, 35.9 mmol) to give a brown solution. The reaction mixture was stirred at 100° C. for 3 h. DMF was removed from the reaction mixture under reduced pressure and the residue was added water and extracted with ethyl acetate (3×2 mL). The combined organic layer was washed with water, brine, dried over Na₂SO₄, filtered and concentrated to afford crude product as brown solid. The residue was purified by silica gel chromatography (40 g REDISEP® column, eluting with 30%-50% EtOAc in hexane). Collected fractions were concentrated together to afford Intermediate 43E (0.4 g, 15%) as pale yellow solid. MS(ES): m/z=219 [M+H]⁺; ¹H NMR (300 MHz, DMSO-d₆) δ ppm 8.16 (s, 1H), 7.79-7.85 (m, 2H), 7.18-7.24 (m, 2H), 5.45-5.55 (m, 2H), 4.59 (d, J=5.76 Hz, 2H), 4.45-4.52 (m, 2H).

Intermediate 43F: 3-Bromo-2-(4-fluorophenyl)-6,8-dihydro-5H-imidazo[2,1-c][1,4]oxazine

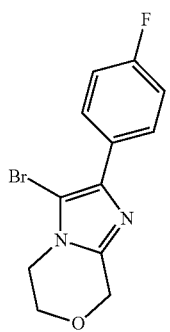 [SMILES: Fc1ccc(-c2nc3n(c2Br)CCOC3)cc1]

To a solution of Intermediate 43E (350 mg, 1.604 mmol) in DCM (15 mL) was added NBS (285 mg, 1.604 mmol) and stirred at room temperature for 2 h. The reaction mixture was filtered through CELITE® and the filtrate was evaporated to afford Intermediate 43F (0.45 g, 66%) as off-white solid which was used in the next step without purification. MS(ES): m/z=298 [M+H]⁺; ¹H NMR (300 MHz, DMSO-d₆) δ ppm 7.79-7.85 (m, 2H), 7.18-7.24 (m, 2H), 5.45-5.55 (m, 2H), 4.59 (d, J=5.76 Hz, 2H), 4.45-4.52 (m, 2H).

Intermediate 43G: N-(6-(2-(4-Fluorophenyl)-6,8-dihydro-5H-imidazo[2,1-c][1,4]oxazin-3-yl)imidazo[1,2-b]pyridazin-2-yl)acetamide

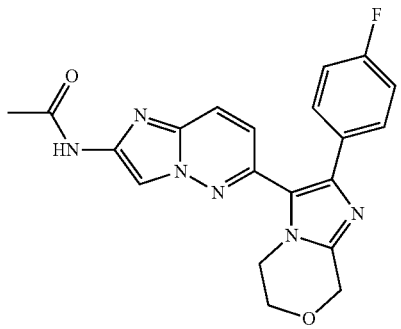 [SMILES: CC(=O)Nc1cn2nc(-c3c(-c4ccc(F)cc4)nc4n3CCOC4)ccc2n1]

To a solution of Intermediate 43F (350 mg, 1.178 mmol), Intermediate-1 (1068 mg, 3.53 mmol), X-PHOS (112 mg, 0.236 mmol) and K₃PO₄ (1.767 mL, 3.53 mmol, 2 M in H₂O) in 1,4-dioxane (10 mL) was degassed for 10 min To which was added Pd₂(dba)₃ (108 mg, 0.118 mmol) and stirred at 80° C. for 18 h. The reaction mixture was filtered through CELITE® pad and the filtrate was concentrated under reduced pressure. The residue was added water and extracted with EtOAc (3×20 mL) The combined organic layer was washed with brine, dried over Na₂SO₄, filtered and concentrated to give crude compound as yellow solid. The residue was purified by silica gel chromatography (24 g REDISEP® column, eluting with 2% methanol in chloroform). Collected fractions were concentrated together to afford Intermediate 43G (0.18 g, 37%) off-white solid. MS(ES): m/z=393 [M+H]⁺; ¹H NMR (300 MHz, DMSO-d₆) δ ppm 10.94 (s, 1H), 8.31 (s, 1H), 7.95 (dd, J=9.35, 0.66 Hz, 1H), 7.47-7.59 (m, 2H), 7.11-7.23 (m, 2H), 7.02 (d, J=9.35 Hz, 1H), 4.88 (s, 2H), 4.03-4.17 (m, 4H), 2.12 (s, 3H).

Intermediate 43: 6-(2-(4-Fluorophenyl)-6,8-dihydro-5H-imidazo[2,1-c][1,4]oxazin-3-yl)imidazo[1,2-b]pyridazin-2-amine

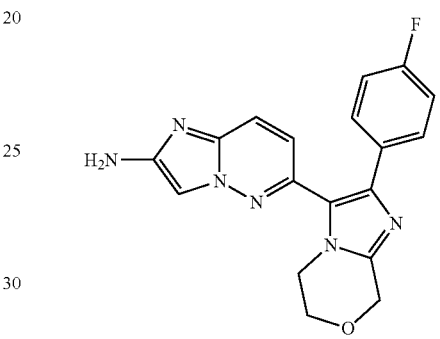

To a solution of Intermediate 43G (40 mg, 0.102 mmol) in MeOH (2 mL) was added 4 M HCl in 1,4-dioxane (0.382 mL, 1.529 mmol) at 0° C. The reaction mixture was slowly warmed to room temperature and stirred for 4 h. MeOH was removed from the reaction mixture, 10% NaHCO₃ was added and extracted with ethyl acetate (3×5 mL). The combined organic layer was washed with 10% NaHCO₃, brine, dried over Na₂SO₄, filtered and concentrated to afford Intermediate 43 (0.03 g, 79%) as yellow solid which was taken for next step without purification. MS(ES): m/z=351 [M+H].

Compound 447

2-Fluoro-N-(6-(2-(4-fluorophenyl)-6,8-dihydro-5H-imidazo[2,1-c][1,4]oxazin-3-yl)imidazo[1,2-b]pyridazin-2-yl)isonicotinamide

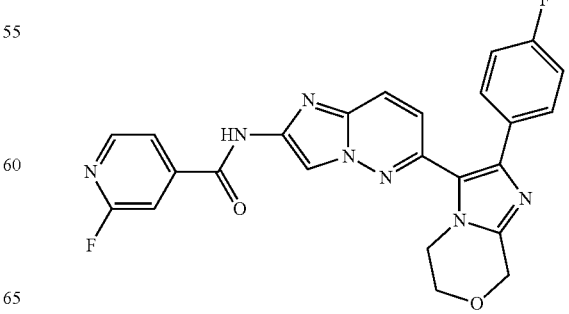

To a solution of 2-fluoroisonicotinic acid (30.2 mg, 0.214 mmol) in DMF (2 mL) was added HATU (81 mg, 0.214 mmol), DIPEA (0.090 mL, 0.514 mmol) and stirred at room temperature for 15 min. Intermediate 43 (30 mg, 0.086 mmol) was added and stirred at room temperature for 18 h. The reaction mixture was diluted with water (5 mL) and extracted with EtOAc (3×5 mL). The combined organic layer was washed with water, brine, dried over $Na_2SO_4$, filtered and concentrated to afford crude compound as dark brown residue. The residue was purified via reverse phase HPLC to give compound 447 (0.006 g, 14%) as off-white solid. MS(ES): m/z=472 [M−H]; HPLC Ret. Time 6.73 min and 7.24 min. (HPLC Method A and B); $^1$H NMR (400 MHz, DMSO-$d_6$) δ ppm 11.90 (bs, 1H), 8.57 (s, 1H), 8.47 (d, J=5.02 Hz, 1H), 8.04 (d, J=9.54 Hz, 1H), 7.98 (dt, J=3.39, 1.57 Hz, 1H), 7.81 (s, 1H), 7.51-7.57 (m, 2H), 7.14-7.21 (m, 2H), 7.10 (d, J=9.54 Hz, 1H), 4.90 (s, 2H), 4.15-4.21 (m, 2H), 4.03-4.10 (m, 2H).

The following compounds in Table 46 were prepared by the procedure described for the preparation of compound 447 from the Intermediate 43 using the corresponding acids.

TABLE 46

| Compound No | Structure | Name | [M − H]+ | Ret Time (min) | HPLC Method |
|---|---|---|---|---|---|
| 448 | 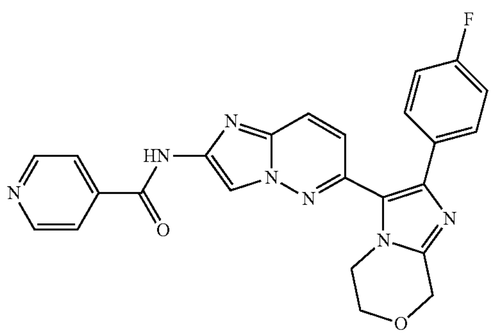 [SMILES: O=C(Nc1cn2nc(-c3c(-c4ccc(F)cc4)nc4n3CCOC4)ccc2n1)c1ccncc1] | N-(6-(2-(4-Fluorophenyl)-6,8-dihydro-5H-imidazo[2,1-c][1,4]oxazin-3-yl)imidazo[1,2-b]pyridazin-2-yl)isonicotinamide | 454 | 5.08<br>9.29 | L<br>M |
| 449 | 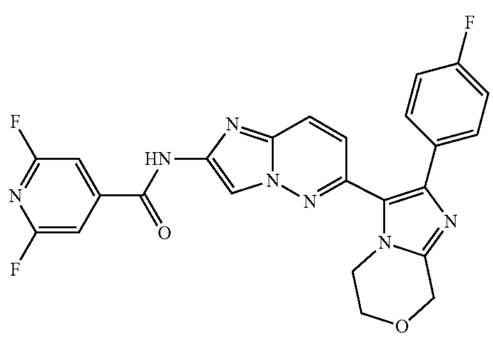 [SMILES: O=C(Nc1cn2nc(-c3c(-c4ccc(F)cc4)nc4n3CCOC4)ccc2n1)c1cc(F)nc(F)c1] | 2,6-Difluoro-N-(6-(2-(4-fluorophenyl)-6,8-dihydro-5H-imidazo[2,1-c][1,4]oxazin-3-yl)imidazo[1,2-b]pyridazin-2-yl)isonicotinamide | 490 | 7.56<br>7.92 | K<br>L |
| 450 | 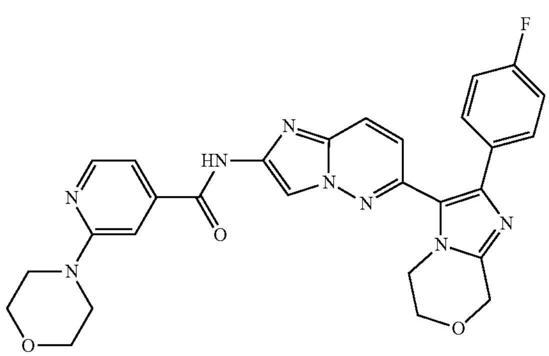 [SMILES: O=C(Nc1cn2nc(-c3c(-c4ccc(F)cc4)nc4n3CCOC4)ccc2n1)c1ccnc(N2CCOCC2)c1] | N-(6-(2-(4-Fluorophenyl)-6,8-dihydro-5H-imidazo[2,1-c][1,4]oxazin-3-yl)imidazo[1,2-b]pyridazin-2-yl)-2-morpholinoisonicotinamide | 539 | 5.10<br>5.58 | K<br>L |

TABLE 46-continued
| Compound No | Structure | Name | [M − H]+ | Ret Time (min) | HPLC Method |
|---|---|---|---|---|---|
| 451 | 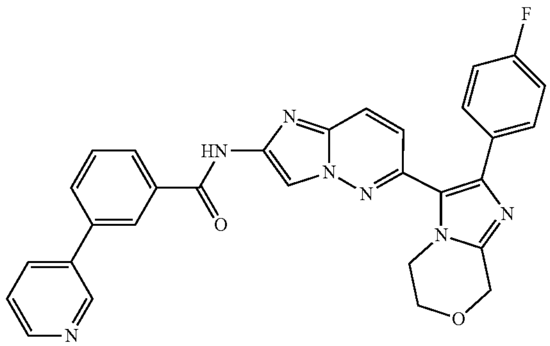 [SMILES: O=C(Nc1cn2nc(-c3c(-c4ccc(F)cc4)nc4n3CCOC4)ccc2n1)c1cccc(-c2cccnc2)c1] | N-(6-(2-(4-Fluorophenyl)-6,8-dihydro-5H-imidazo[2,1-c][1,4]oxazin-3-yl)imidazo[1,2-b]pyridazin-2-yl)-3-(pyridin-3-yl)benzamide | 530 | 5.08<br>5.72 | K<br>L |
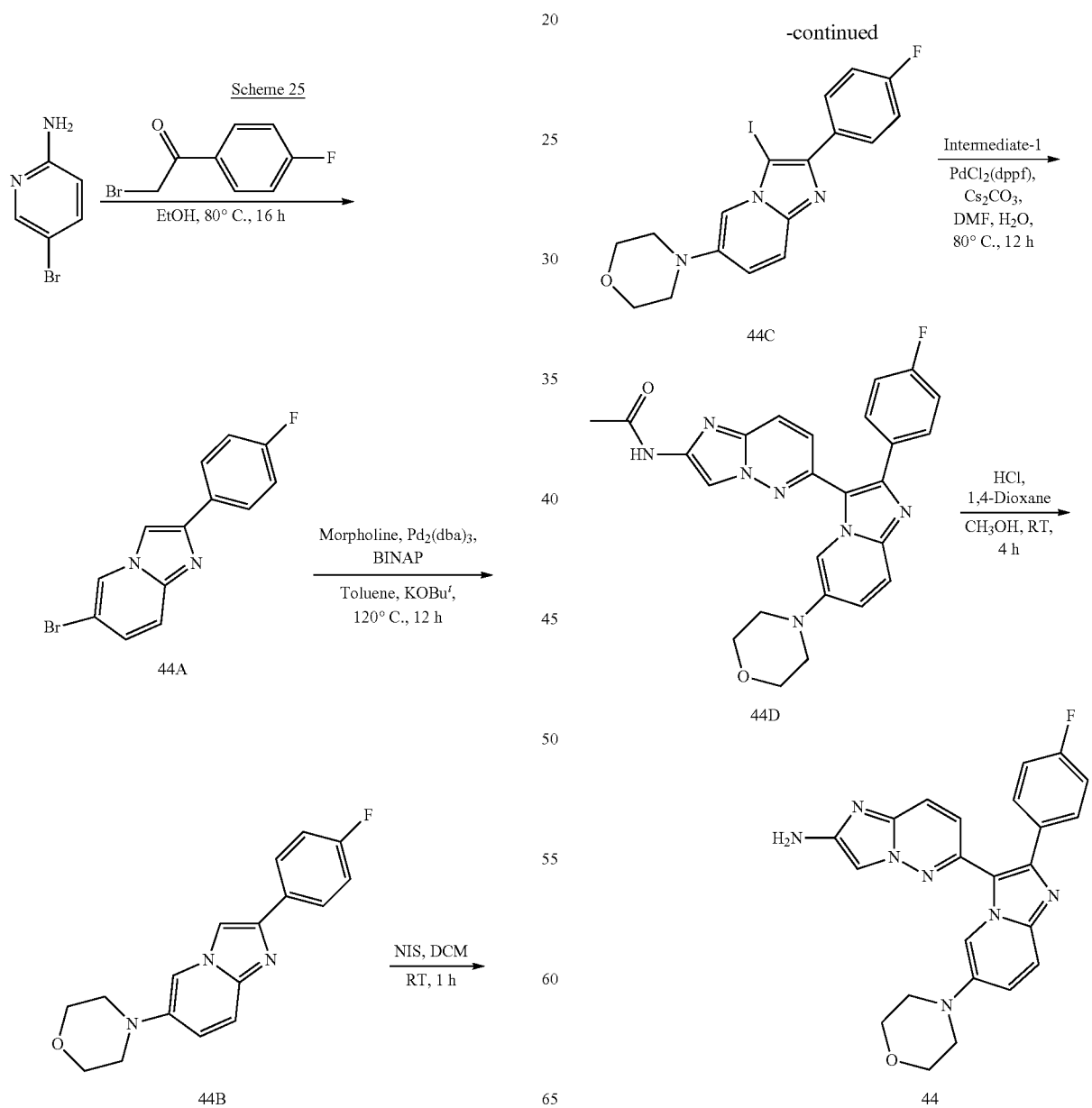

Intermediate 44

6-(2-(4-Fluorophenyl)-6-morpholinoimidazo[1,2-a]pyridin-3-yl)imidazo[1,2-b]pyridazin-2-amine

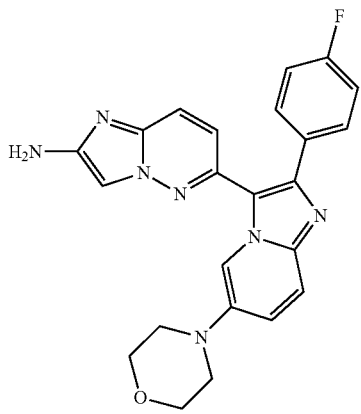 [SMILES: Nc1cn2nc(-c3c(-c4ccc(F)cc4)nc4ccc(N5CCOCC5)cn34)ccc2n1]

Intermediate 44A:
6-Bromo-2-(4-fluorophenyl)imidazo[1,2-a]pyridine

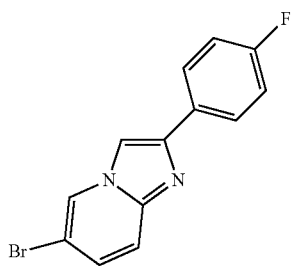 [SMILES: Fc1ccc(-c2cn3cc(Br)ccc3n2)cc1]

To a solution of 5-bromopyridin-2-amine (5.0 g, 28.9 mmol) and 2-bromo-1-(4-fluorophenyl)ethanone (6.27 g, 28.9 mmol) in dry ethanol (100 mL) was added sodium bicarbonate (7.28 g, 87 mmol) and heated to 80° C. for 24 h. The ethanol was distilled off under reduced pressure. The residue was diluted with water and extracted with ethyl acetate (3×100 mL). The combined organic layer was washed with water, brine, dried over Na$_2$SO$_4$, filtered and concentrated. The residue was purified by silica gel chromatography (120 g REDISEP® column, eluting with 15% EtOAc in hexane). Collected fractions were concentrated together to afford Intermediate 44A (5 g, 59%) as pale yellow solid. MS(ES): m/z=293 [M+H]$^+$; $^1$H NMR (400 MHz, DMSO-d$_6$) δ ppm 8.90 (dd, J=1.88, 0.75 Hz, 1H), 8.36 (s, 1H), 7.98-8.05 (m, 2H), 7.58 (d, J=9.54 Hz, 1H), 7.38 (dd, J=9.54, 1.95 Hz, 1H), 7.26-7.33 (m, 2H).

Intermediate 44B: 4-(2-(4-Fluorophenyl)imidazo[1,2-a]pyridin-6-yl)morpholine

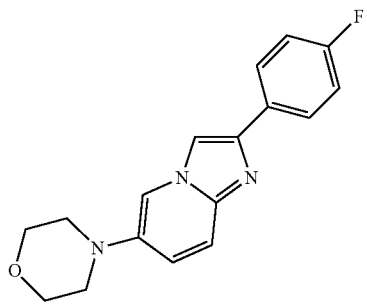 [SMILES: Fc1ccc(-c2cn3cc(N4CCOCC4)ccc3n2)cc1]

To a degassed solution of Intermediate 44A (1.5 g, 5.15 mmol), morpholine (0.898 mL, 10.31 mmol) and sodium tert-butoxide (0.990 g, 10.31 mmol) in toluene (12 mL) was added BINAP (0.225 g, 0.361 mmol) and Pd$_2$(dba)$_3$ (0.094 g, 0.103 mmol). The reaction mixture was purged with nitrogen and stirred at 110° C. for 12 h. Reaction mixture was cooled to room temperature and filtered through CELITE® pad. The CELITE® pad was washed with ethyl acetate. The combined organic layer was concentrated and purified by silica gel chromatography (24 g REDISEP® column, eluting with 50% EtOAc in hexane). Collected fractions were concentrated together to afford Intermediate 44B (0.9 g, 58%) as pale yellow solid. MS(ES): m/z=298 [M+H]$^+$; $^1$H NMR (300 MHz, chloroform-d) δ ppm 7.87-7.96 (m, 2H), 7.75 (s, 1H), 7.49-7.59 (m, 2H), 7.04-7.18 (m, 3H), 3.88-3.96 (m, 4H), 3.02-3.15 (m, 4H).

Intermediate 44C: 4-(2-(4-Fluorophenyl)-3-iodoimidazo[1,2-a]pyridin-6-yl)morpholine

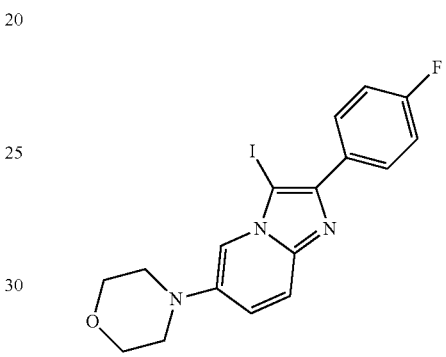

To a solution of Intermediate 44B (1.0 g, 3.36 mmol) in DCM (15 ml) was added NIS (0.757 g, 3.36 mmol) and stirred at RT for 1 h. The reaction mixture was diluted with DCM and washed with 20% sodium thiosulphate solution. The organic layer was dried over Na$_2$SO$_4$, filtered and concentrated afford Intermediate 44C (1.3 g, 91%) as a yellow solid. MS(ES): m/z=424 [M+H]$^+$; $^1$H NMR (300 MHz, DMSO-d$_6$) δ ppm 8.03-8.14 (m, 2H), 7.51-7.63 (m, 2H), 7.29-7.45 (m, 3H), 3.74-3.86 (m, 4H), 3.08-3.19 (m, 4H).

Intermediate 44D: N-(6-(2-(4-Fluorophenyl)-6-morpholinoimidazo[1,2-a]pyridin-3-yl)imidazo[1,2-b]pyridazin-2-yl)acetamide

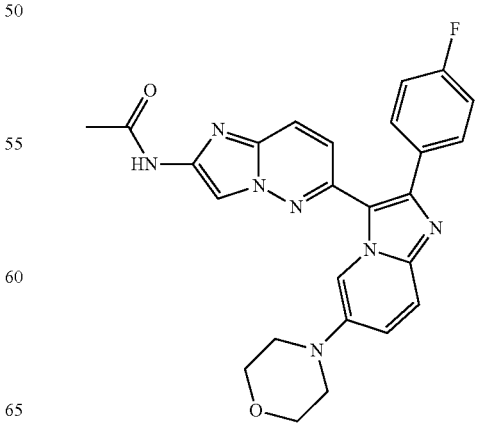

To a degassed solution of Intermediate 44C (1.3 g, 3.07 mmol), intermediate-1 (2.320 g, 7.68 mmol) and cesium carbonate (2.502 g, 7.68 mmol) in DMF (10 mL) and water (1 mL) was added PdCl$_2$(dppf).DCM complex (0.201 g, 0.246 mmol). The reaction mixture was purged with nitrogen and stirred at 80° C. 12 h. Reaction mixture was cooled to RT, diluted with water and extracted with ethyl acetate (3×30 mL). Combined the organic layers and wash with water, dried over Na$_2$SO$_4$, filtered and concentrated. The residue was purified silica gel chromatography (24 g REDISEP® column, eluting with 1% methanol in chloroform). Collected fractions were concentrated together to afford Intermediate 44D (0.85 g, 58%) as brown solid. MS(ES): m/z=472 [M+H]$^+$; $^1$H NMR (400 MHz, DMSO-d$_6$) δ ppm 10.96 (s, 1H), 8.40 (s, 1H), 8.26 (d, J=1.69 Hz, 1H), 7.98 (dd, J=9.35, 0.63 Hz, 1H), 7.62-7.70 (m, 3H), 7.49 (dd, J=9.79, 2.26 Hz, 1H), 7.19-7.28 (m, 2H), 7.03 (d, J=9.35 Hz, 1H), 3.73-3.82 (m, 4H), 3.03-3.13 (m, 4H), 2.14 (s, 3H).

Intermediate 44: 6-(2-(4-Fluorophenyl)-6-morpholinoimidazo[1,2-a]pyridin-3-yl)imidazo[1,2-b]pyridazin-2-amine

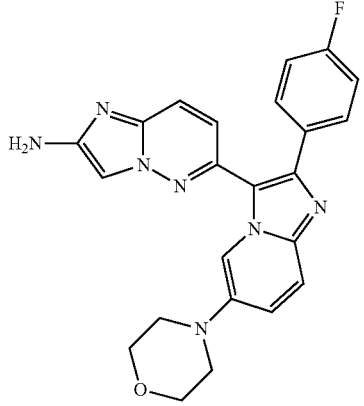 [SMILES: Nc1cn2nc(-c3c(-c4ccc(F)cc4)nc4ccc(N5CCOCC5)cn34)ccc2n1]

To a solution of Intermediate 44D (200 mg, 0.424 mmol) in MeOH (2.5 mL) was added HCl in dioxane (2.121 mL, 8.48 mmol, 4 M). The reaction mixture was allowed to stir at RT for 4 h. Reaction mixture was concentrated to remove dioxane. The crude product was dissolved in water, basified with saturated NaHCO$_3$ and extracted with DCM (3×20 mL). The combined the organic layer was and washed with water, dried over Na$_2$SO$_4$, filtered and concentrated to afford Intermediate 44 (0.18 g, 99%) as a brown solid. MS(ES): m/z=430 [M+H]$^+$. The crude product was taken to the next step without further purification.

Compound 452

2-Fluoro-N-(6-(2-(4-fluorophenyl)-6-morpholinoimidazo[1,2-a]pyridin-3-yl)imidazo[1,2-b]pyridazin-2-yl)isonicotinamide

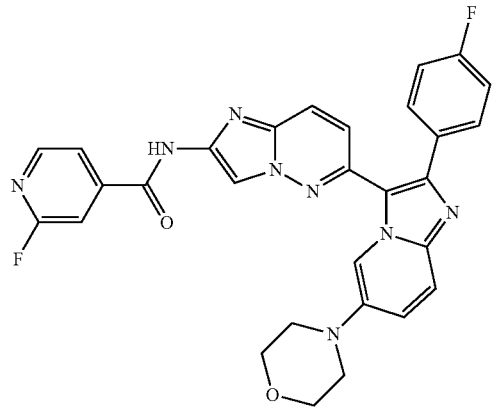 [SMILES: O=C(Nc1cn2nc(-c3c(-c4ccc(F)cc4)nc4ccc(N5CCOCC5)cn34)ccc2n1)c1ccnc(F)c1]

To a solution of Intermediate 44 (25 mg, 0.058 mmol) and 2-fluoroisonicotinic acid (16.43 mg, 0.116 mmol) in DMF (1 mL) under nitrogen atmosphere was added HATU (44.3 mg, 0.116 mmol) followed by DIPEA (0.041 mL, 0.233 mmol). The reaction mixture was stirred at RT for 12 h. The reaction mixture was diluted with water and extracted with ethyl acetate (2×15 mL). The combined organic layer was washed with water, dried Na$_2$SO$_4$, filtered and concentrated. The residue was purified via reverse phase HPLC to give Intermediate 452 (0.09 g, 27%) as a pale yellow solid. MS(ES): m/z=553 [M+H]$^+$; HPLC Ret. Time 6.73 min and 7.39 min (HPLC Method A and B respectively); $^1$H NMR (400 MHz, DMSO-d$_6$) δ ppm 11.92 (s, 1H), 8.67 (s, 1H), 8.49 (d, J=5.27 Hz, 1H), 8.33 (d, J=1.63 Hz, 1H), 8.04-8.10 (m, 1H), 7.96-8.01 (m, 1H), 7.83 (s, 1H), 7.65-7.72 (m, 3H), 7.51 (dd, J=9.79, 2.32 Hz, 1H), 7.21-7.30 (m, 2H), 7.10 (d, J=9.41 Hz, 1H), 3.74-3.81 (m, 4H), 3.06-3.15 (m, 4H).

The following compounds in Table 47 were prepared by the procedure described for the preparation of compound 452 from the Intermediate 44 using the corresponding acids.

TABLE 47

| Compound No | Structure | Name | [M + H]$^+$ | Ret Time (min) | HPLC Method |
|---|---|---|---|---|---|
| 453 | 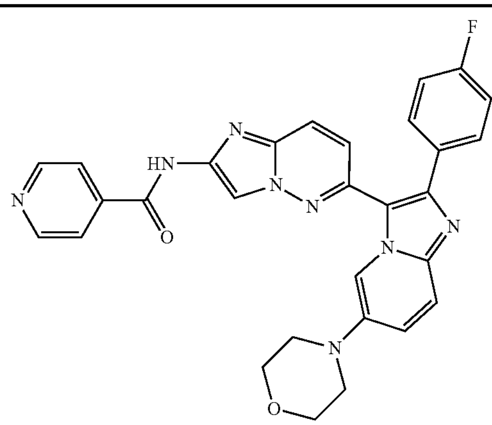 | N-(6-(2-(4-Fluorophenyl)-6-morpholinoimidazo[1,2-a]pyridin-3-yl)imidazo[1,2-b]pyridazin-2-yl)isonicotinamide | 535 | 5.24<br>5.76 | K<br>L |

TABLE 47-continued
| Compound No | Structure | Name | [M + H]+ | Ret Time (min) | HPLC Method |
|---|---|---|---|---|---|
| 454 | 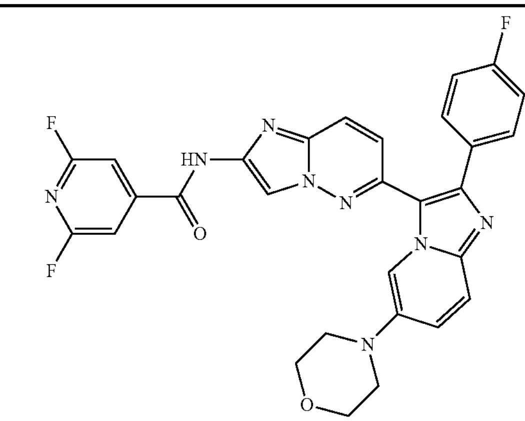 | 2,6-Difluoro-N-(6-(2-(4-fluorophenyl)-6-morpholinoimidazo[1,2-a]pyridin-3-yl)imidazo[1,2-b]pyridazin-2-yl)isonicotinamide | 571 | 7.51  8.03 | K  L |
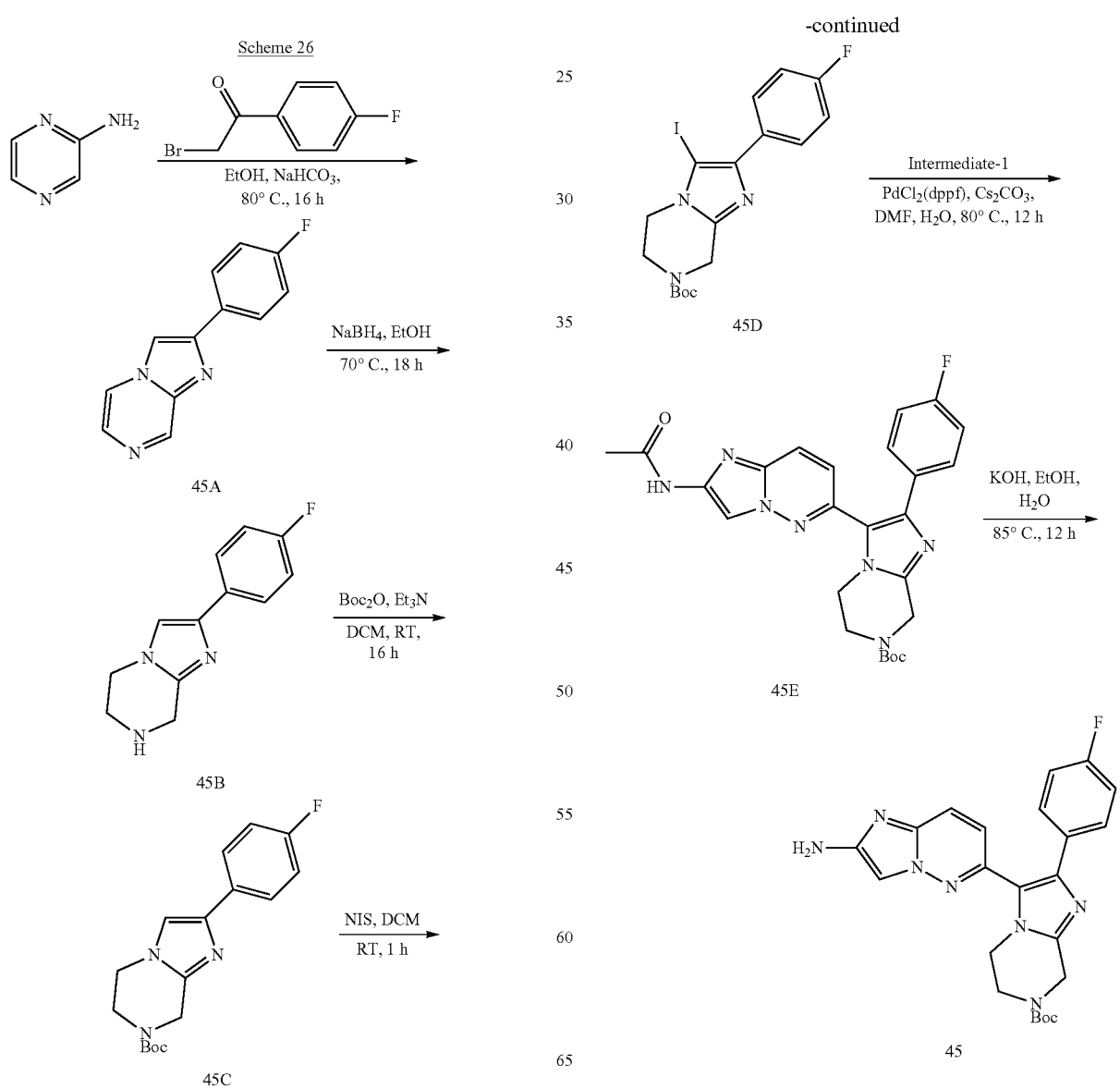

359

Intermediate 45 tert-Butyl 3-(2-aminoimidazo[1,2-b]pyridazin-6-yl)-2-(4-fluorophenyl)-5,6-dihydroimidazo[1,2-a]pyrazine-7(8H)-carboxylate

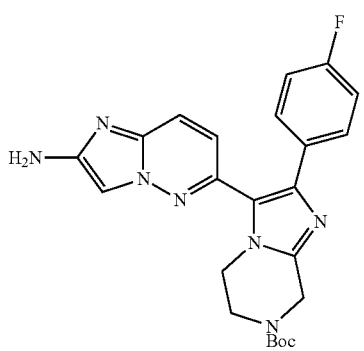 [SMILES: CC(C)(C)OC(=O)N1CCn2c(nc(-c3ccc(F)cc3)c2-c2ccc3nc(N)cn3n2)C1]

Intermediate 45A:
2-(4-Fluorophenyl)imidazo[1,2-a]pyrazine

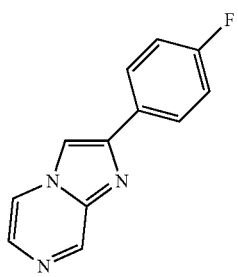 [SMILES: Fc1ccc(-c2cn3ccncc3n2)cc1]

To a solution of pyrazin-2-amine (10 g, 105 mmol) in dry ethanol (250 mL) was added 2-bromo-1-(4-fluorophenyl)ethanone (22.82 g, 105 mmol), sodium bicarbonate (26.5 g, 315 mmol) and stirred at 70° C. for 24 h. The reaction mixture was filtered through CELITE® and concentrated under reduced pressure to remove ethanol. The residue was extracted with EtOAc (3×150 mL). The combined organic layer was washed with water, brine, dried over sodium sulphate and concentrated under reduced pressure. The residue was purified by silica gel chromatography (80 g REDISEP® neutral alumina column, eluting with 30% EtOAc in hexane) to afford Intermediate 45A (2 g, 9%) as a white solid. MS(ES): m/z 214 [M+H]$^+$; $^1$H NMR (400 MHz, chloroform) δ ppm 9.10 (d, J=0.75 Hz, 1H), 8.07 (dd, J=4.52, 1.51 Hz, 1H), 7.86-8.00 (m, 4H), 7.16 (t, J=8.78 Hz, 2H).

360

Intermediate 45B: 2-(4-Fluorophenyl)-5,6,7,8-tetrahydroimidazo[1,2-a]pyrazine

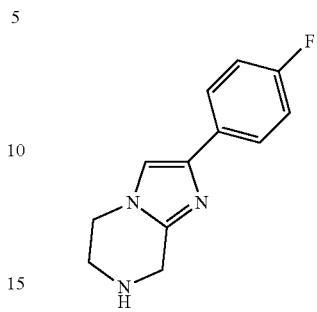

To a stirred solution of Intermediate 45A (3 g, 14.07 mmol) in dry EtOH (50 mL) was added sodium borohydride (5.32 g, 141 mmol) and the reaction mixture was stirred at 70° C. for 18 h. After completion of the reaction, excess of ethanol was removed under reduced pressure. Water was added and extracted with ethyl acetate (3×250 mL) The combined organics were washed with water, brine, dried Na$_2$SO$_4$, filtered and concentrated under reduced pressure to afford Intermediate 45B (3 g, 98%) as a white solid. MS(ES): m/z=218 [M+H]$^+$. $^1$H NMR (400 MHz, chloroform-d) δ ppm 7.64-7.72 (m, 2H), 6.98-7.08 (m, 3H), 4.13 (s, 2H), 3.97 (t, J=5.63 Hz, 2H), 3.26 (t, J=5.50 Hz, 2H), 1.78 (br. s., 1H).

Intermediate 45C: tert-Butyl 2-(4-fluorophenyl)-5,6-dihydroimidazo[1,2-a]pyrazine-7(8H)-carboxylate To a solution of Intermediate 45B (3 g, 13.81 mmol) in dry DCM (50 mL) was added BOC-Anhydride (6.41 mL, 27.6 mmol), triethylamine (5.77 mL, 41.4 mmol) and the reaction mixture was stirred at RT for 16 h. The reaction mixture was diluted with DCM and water and extracted with DCM (3×100 mL). The combined organic layer was washed with water, brine, dried over Na$_2$SO$_4$, filtered and concentrated. The residue was purified by silica gel chromatography (40 g REDISEP® column, eluting with 30% EtOAc in hexane) to afford Intermediate 45C (3.2 g, 73%) as a white solid. MS(ES): m/z=318 [M+H]$^+$; $^1$H NMR (400 MHz, chloroform) δ ppm 7.64-7.75 (m, 2H), 7.00-7.11 (m, 3H), 4.75 (s, 2H), 3.99-4.07 (m, 2H), 3.85-3.92 (m, 2H), 1.50 (s, 9H).

Intermediate 45D: tert-Butyl 2-(4-fluorophenyl)-3-iodo-5,6-dihydroimidazo[1,2-a]pyrazine-7(8H)-carboxylate

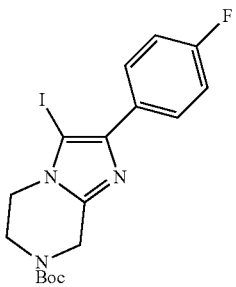 [SMILES: CC(C)(C)OC(=O)N1CCn2c(nc(-c3ccc(F)cc3)c2I)C1]

To a solution of Intermediate 45C (6 g, 18.91 mmol) in DCM (100 mL) was added NIS (5.53 g, 24.58 mmol) and stirred at RT for 2 h. The reaction mixture was diluted with water and extracted with DCM (3×100 mL) The combined the organic layer was washed with water, brine, dried $Na_2SO_4$, filtered and concentrated. The residue was purified by silica gel chromatography (120 g REDISEP® column, eluting with 20% EtOAc in hexane) to afford Intermediate 45D (7 g, 84%) as a pale yellow solid. MS(ES): m/z=444 [M+H]$^+$; $^1$H NMR (400 MHz, chloroform-d) δ ppm 7.88-7.84 (m, 2H), 7.09 (m, 2H), 4.75 (s, 2H), 3.90 (s, 4H), 1.49 (s, 9H).

Intermediate 45E: tert-Butyl 3-(2-acetamidoimidazo[1,2-b]pyridazin-6-yl)-2-(4-fluorophenyl)-5,6-dihydroimidazo[1,2-a]pyrazine-7(8H)-carboxylate

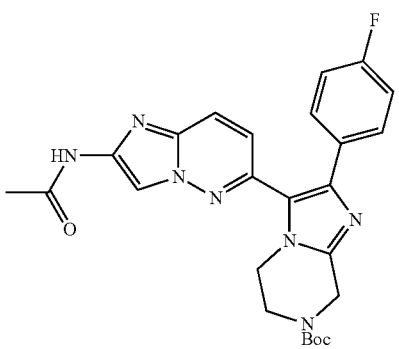 [SMILES: CC(=O)Nc1cn2nc(-c3c(-c4ccc(F)cc4)nc4n3CCN(C(=O)OC(C)(C)C)C4)ccc2n1]

To a degassed solution of Intermediate 45D (3 g, 6.77 mmol) in DMF (30 mL) and water (3 mL) was added intermediate-1 (5.11 g, 16.92 mmol), $K_3PO_4$ (3.54 g, 20.30 mmol), $PdCl_2$(dppf).DCM complex (0.387 g, 0.474 mmol). The reaction mixture was purged with nitrogen for 10-15 min and stirred at 80° C. for 14 h. The reaction mixture was diluted with water and filtered through CELITE® and extracted with EtOAc (3×100 mL). The combined the organic layer was washed with water, brine, dried $Na_2SO_4$, filtered and concentrated. The residue was purified by silica gel chromatography (120 g REDISEP® Column, eluting with 3% methanol in chloroform) to afford Intermediate 45E (2.8 g 84%) as a pale yellow solid. MS(ES): m/z=492 [M+H]+; $^1$H NMR (400 MHz, chloroform-d) δ ppm 8.44 (s, 1H), 8.20 (s, 1H), 7.64 (d, J=9.38 Hz, 1H), 7.47 (m, 2H), 7.03 (m, 2H), 6.89 (d, J=9.38 Hz, 1H), 4.84 (s, 2H), 4.25 (t, J=5.41 Hz, 2H), 3.90 (t, J=5.38 Hz, 2H), 2.26 (s, 3H), 1.59 (s, 9H).

Intermediate 45: tert-Butyl 3-(2-aminoimidazo[1,2-b]pyridazin-6-yl)-2-(4-fluorophenyl)-5,6-dihydroimidazo[1,2-a]pyrazine-7(8H)-carboxylate

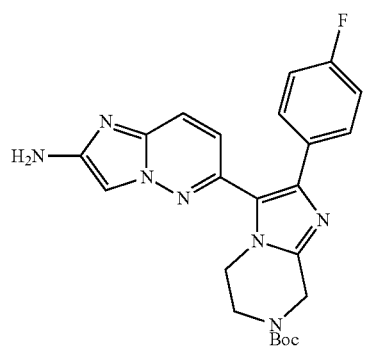 [SMILES: CC(C)(C)OC(=O)N1CCn2c(nc(-c3ccc(F)cc3)c2-c2ccc3nc(N)cn3n2)C1]

To a solution of Intermediate 45E (2 g, 4.07 mmol) in EtOH (20 mL) was added KOH (1.141 g, 20.35 mmol) in water (10 mL) and the reaction mixture was stirred at 85° C. for 12 h. Ethanol was removed under reduced pressure. The residue was reconstituted in ethyl acetate and water. The organic layer was extracted with EtOAc (3×25 mL). The combined organic layer was washed with water, brine dried over sodium sulphate and concentrated under reduced pressure to afford Intermediate 45 (1.8 g, 98%) as a pale yellow solid. MS(ES): m/z=450 [M+H]$^+$; $^1$H NMR (300 MHz, DMSO-d$_6$) δ ppm 7.66 (dd, J=9.06, 0.57 Hz, 1H), 7.44-7.53 (m, 2H), 7.38 (s, 1H), 7.08-7.18 (m, 2H), 6.88 (d, J=9.06 Hz, 1H), 5.61 (bs, 2H), 4.68 (s, 2H), 3.99 (dd, J=12.51, 6.47 Hz, 2H), 3.80 (d, J=5.29 Hz, 2H), 1.46 (s, 9H).

Compound 455

2-Fluoro-N-(6-(2-(4-fluorophenyl)-5,6,7,8-tetrahydroimidazo[1,2-a]pyrazin-3-yl)imidazo[1,2-b]pyridazin-2-yl)isonicotinamide

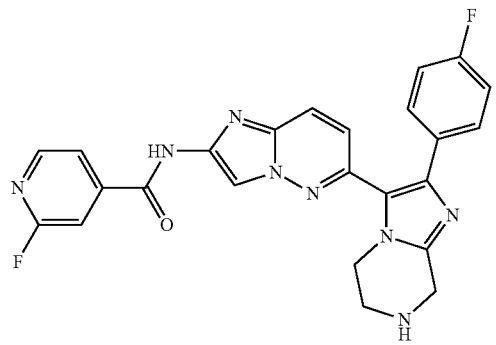

363

Intermediate 455A: tert-Butyl 3-(2-(2-fluoroisonico-tinamido)imidazo[1,2-b]pyridazin-6-yl)-2-(4-fluoro-phenyl)-5,6-dihydroimidazo[1,2-a]pyrazine-7(8H)-carboxylate

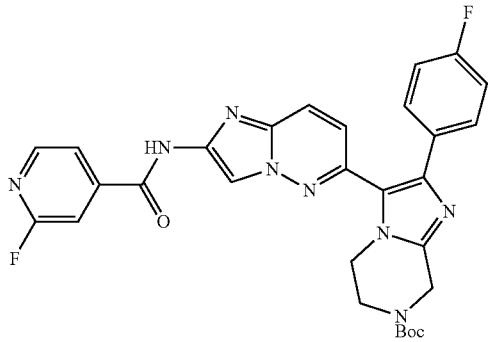 [SMILES: CC(C)(C)OC(=O)N1CCn2c(nc(-c3ccc(F)cc3)c2-c2ccc3nc(NC(=O)c4ccnc(F)c4)cn3n2)C1]

To a solution of Intermediate 45 (0.035 g, 0.078 mmol) in dry DMF (1 mL) was added HATU (0.059 g, 0.156 mmol) and DIPEA (0.041 mL, 0.234 mmol), 2-fluoroisonicotinic acid (0.022 g, 0.156 mmol) and the reaction mixture was stirred at RT for 16 h. DMF was removed under high vacuum and the residue was diluted with 10% sodium bicarbonate and extracted with chloroform (3×10 mL). The combined organic layer was washed with water, brine, dried over sodium sulphate, filtered concentrated to afford Intermediate 455A (0.04 g 90%) as a brown solid. MS(ES): m/z=573 [M+H]$^+$; $^1$H NMR (400 MHz, DMSO-d$_6$) δ ppm 11.89 (s, 1H), 8.57 (s, 1H), 8.47 (d, J=5.02 Hz, 1H), 8.05 (d, J=9.29 Hz, 1H), 7.93-8.00 (m, 1H), 7.81 (s, 1H), 7.50-7.57 (m, 2H), 7.07-7.20 (m, 3H), 4.71 (s, 2H), 4.13 (t, J=5.27 Hz, 2H), 3.83 (d, J=5.27 Hz, 2H), 1.47 (s, 9H).

364

Compound 455

2-Fluoro-N-(6-(2-(4-fluorophenyl)-5,6,7,8-tetrahy-droimidazo[1,2-a]pyrazin-3-yl)imidazo[1,2-b]pyridazin-2-yl)isonicotinamide

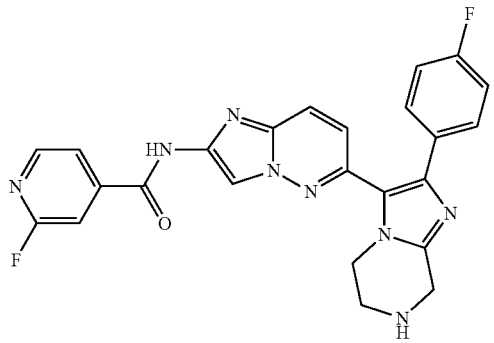 [SMILES: O=C(Nc1cn2nc(-c3c(-c4ccc(F)cc4)nc4n3CCNC4)ccc2n1)c1ccnc(F)c1]

To a solution of Intermediate 455A (0.04 g, 0.070 mmol) in DCM (1 mL) was added TFA (1 mL, 12.98 mmol) and the reaction was stirred for 2 h. Excess of TFA was removed under high vacuum, quenched with 10% sodium bicarbonate and extracted with DCM (3×30 mL). The combined organic layer was washed with water, brine, dried over sodium sulphate, filtered and concentrated to afford the product. The crude product was purified by reverse phase preparative HPLC purification to afford Intermediate 455 (0.012 g 36%) as a white solid. MS(ES): m/z=471 [M+H]$^+$; HPLC Ret. Time 5.70 min and 5.44 min (HPLC Method K and L); $^1$H NMR (400 MHz, DMSO-d$_6$) δ ppm 11.90 (s, 1H), 8.58 (s, 1H), 8.41 (d, J=5.02 Hz, 1H), 7.93-8.02 (m, 2H), 7.77 (s, 1H) 7.52 (dd, J=8.78, 5.52 Hz, 2H), 7.15 (t, J=8.91 Hz, 2H), 7.01 (d, J=9.29 Hz, 1H), 3.99 (br. s., 3H), 3.10 (br. s., 2H), 2.79 (br. s., 1H).

The following compounds in Table 48 were prepared by the procedure described for the preparation of compounds 455A and 455 from the Intermediate 45 using the corresponding acids.

TABLE 48

| Compound No | Structure | Name | [M + H]$^+$ | Ret Time (min) | HPLC Method |
|---|---|---|---|---|---|
| 456 | 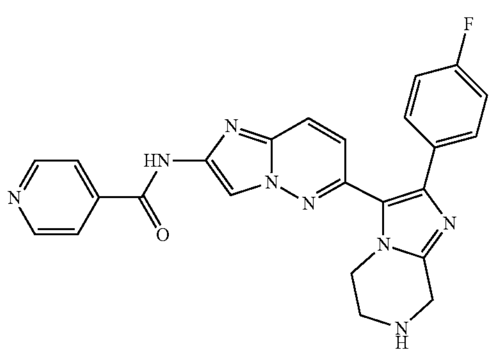 [SMILES: O=C(Nc1cn2nc(-c3c(-c4ccc(F)cc4)nc4n3CCNC4)ccc2n1)c1ccncc1] | N-(6-(2-(4-Fluorophenyl)-5,6,7,8-tetrahydroimidazo[1,2-a]pyrazin-3-yl)imidazo[1,2-b]pyridazin-2-yl)isonicotinamide | 455 | 8.51<br>9.29 | M<br>N |

TABLE 48-continued

| Compound No | Structure | Name | [M + H]+ | Ret Time (min) | HPLC Method |
|---|---|---|---|---|---|
| 457 | 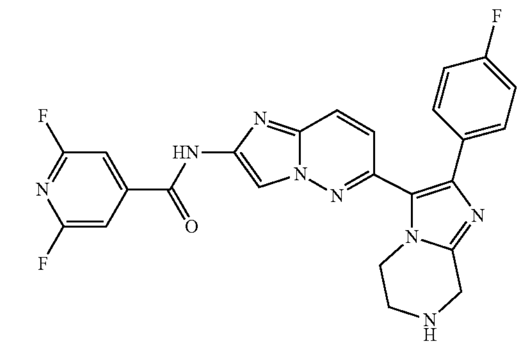 [SMILES: O=C(Nc1cn2nc(-c3c(-c4ccc(F)cc4)nc4n3CCNC4)ccc2n1)c1cc(F)nc(F)c1] | 2,6-Difluoro-N-(6-(2-(4-fluorophenyl)-5,6,7,8-tetrahydroimidazo[1,2-a]pyrazin-3-yl)imidazo[1,2-b]pyridazin-2-yl)isonicotinamide | 491 | 6.30<br>7.24 | K<br>L |
| 458 | 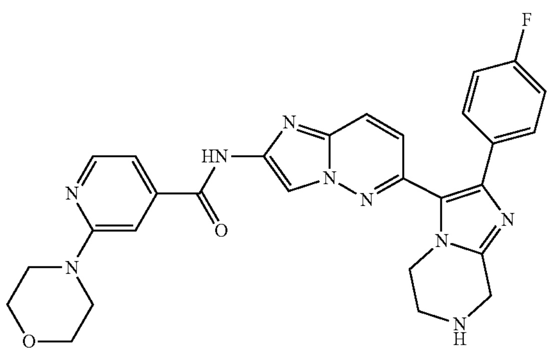 [SMILES: O=C(Nc1cn2nc(-c3c(-c4ccc(F)cc4)nc4n3CCNC4)ccc2n1)c1ccnc(N2CCOCC2)c1] | N-(6-(2-(4-Fluorophenyl)-5,6,7,8-tetrahydroimidazo[1,2-a]pyrazin-3-yl)imidazo[1,2-b]pyridazin-2-yl)-2-morpholinoisonicotinamide | 540 | 8.92<br>9.27 | M<br>N |
| 459 | 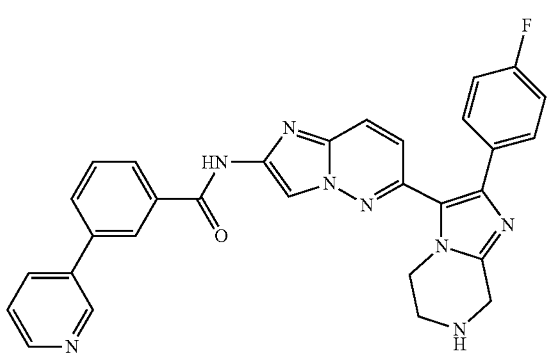 [SMILES: O=C(Nc1cn2nc(-c3c(-c4ccc(F)cc4)nc4n3CCNC4)ccc2n1)c1cccc(-c2cccnc2)c1] | N-(6-(2-(4-Fluorophenyl)-5,6,7,8-tetrahydroimidazo[1,2-a]pyrazin-3-yl)imidazo[1,2-b]pyridazin-2-yl)-3-(pyridin-3-yl)benzamide | 531 | 9.44<br>10.64 | M<br>N |

Compound 460

N-(6-(7-Acetyl-2-(4-fluorophenyl)-5,6,7,8-tetrahydroimidazo[1,2-a]pyrazin-3-yl)imidazo[1,2-b]pyridazin-2-yl)-2-fluoroisonicotinamide

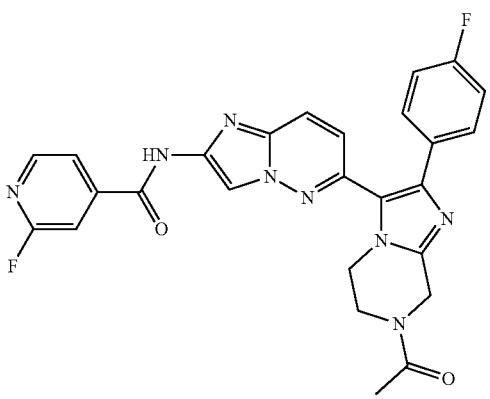 [SMILES: CC(=O)N1CCn2c(nc(-c3ccc(F)cc3)c2-c2ccc3nc(NC(=O)c4ccnc(F)c4)cn3n2)C1]

To the stirred solution of compound 455 (0.025 g, 0.053 mmol) in DMF (1.0 mL) was added acetic acid (6.06 µl, 0.106 mmol), DIPEA (0.037 mL, 0.212 mmol) followed by HATU (0.040 g, 0.106 mmol). The reaction mixture was stirred at RT for overnight. The reaction mixture was concentrated. It was diluted with ethyl acetate, washed with water and brine solution. The organic layer was dried over sodium sulfate, filtered and concentrated under reduced pressure. The crude product was purified by reverse phase preparative HPLC purification to afford compound 460 (9 mg, 33%) as a yellow solid. MS(ES): m/z=514.7 [M+H]$^+$; HPLC Ret. Time 6.19 min and 6.48 min (HPLC Method K and L); $^1$H NMR (400 MHz, DMSO-d$_6$) δ ppm 11.92 (br. s., 1H), 8.56-8.59 (m, 1H), 8.48 (d, J=5.02 Hz, 1H), 8.06 (d, J=9.04 Hz, 1H), 7.98 (d, J=5.02 Hz, 1H), 7.82 (s, 1H), 7.50-7.59 (m, 2H), 7.15-7.22 (m, 2H), 7.10 (d, J=9.54 Hz, 1H), 4.79-4.92 (m, 2H), 3.91-4.25 (m, 4H), 2.18 (s, 3H).

The following compounds in Table 49 were prepared by the procedure described for the preparation of compound 460 from the Intermediate 455 using the corresponding acids.

TABLE 49

| Compound No. | Structure | Name | [M + H]$^+$ | Ret Time (min) | HPLC Method |
|---|---|---|---|---|---|
| 461 | 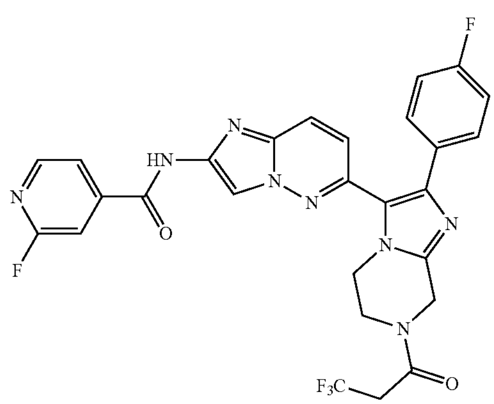 [SMILES: O=C(Nc1cn2nc(-c3c(-c4ccc(F)cc4)nc4n3CCN(C(=O)CC(F)(F)F)C4)ccc2n1)c1ccnc(F)c1] | 2-Fluoro-N-(6-(2-(4-fluorophenyl)-7-(3,3,3-trifluoropropanoyl)-5,6,7,8-tetrahydroimidazo[1,2-a]pyrazin-3-yl)imidazo[1,2-b]pyridazin-2-yl)isonicotinamide | 582 | 7.75 8.15 | K L |
| 462 | 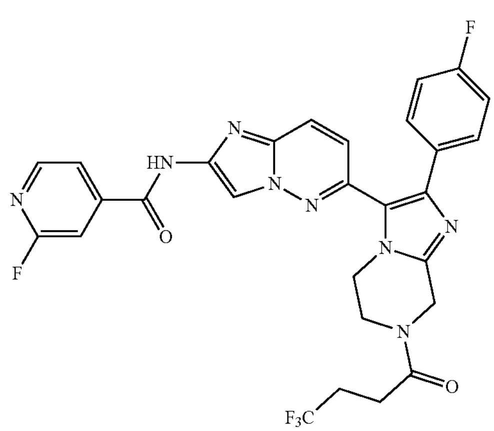 [SMILES: O=C(Nc1cn2nc(-c3c(-c4ccc(F)cc4)nc4n3CCN(C(=O)CCC(F)(F)F)C4)ccc2n1)c1ccnc(F)c1] | 2-Fluoro-N-(6-(2-(4-fluorophenyl)-7-(4,4,4-trifluorobutanoyl)-5,6,7,8-tetrahydroimidazo[1,2-a]pyrazin-3-yl)imidazo[1,2-b]pyridazin-2-yl)isonicotinamide | 596 | 7.93 8.41 | K L |

TABLE 49-continued

| Compound No. | Structure | Name | [M + H]+ | Ret Time (min) | HPLC Method |
|---|---|---|---|---|---|
| 463 | 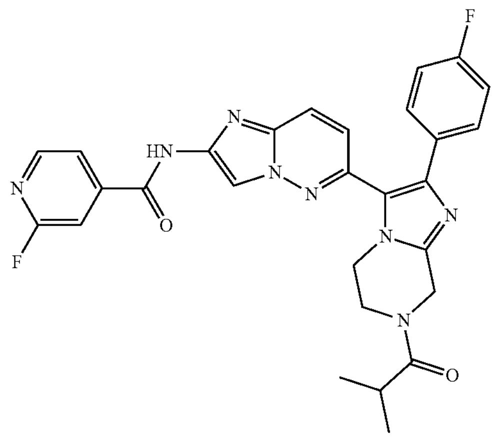 [SMILES: CC(C)C(=O)N1CCn2c(nc(-c3ccc(F)cc3)c2-c2ccc3nc(NC(=O)c4ccnc(F)c4)cn3n2)C1] | 2-Fluoro-N-(6-(2-(4-fluorophenyl)-7-isobutyryl-5,6,7,8-tetrahydroimidazo[1,2-a]pyrazin-3-yl)imidazo[1,2-b]pyridazin-2-yl)isonicotinamide | 542 | 6.54 6.75 | K L |
| 464 | 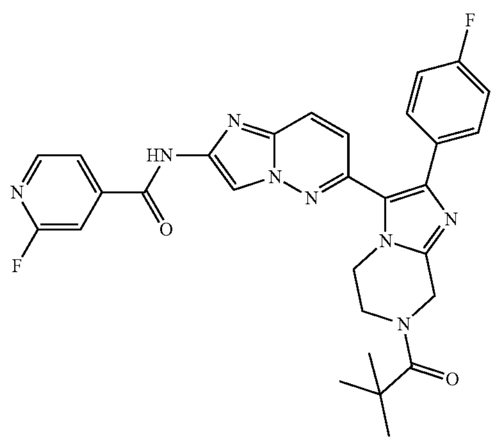 [SMILES: CC(C)(C)C(=O)N1CCn2c(nc(-c3ccc(F)cc3)c2-c2ccc3nc(NC(=O)c4ccnc(F)c4)cn3n2)C1] | 2-Fluoro-N-(6-(2-(4-fluorophenyl)-7-pivaloyl-5,6,7,8-tetrahydroimidazo[1,2-a]pyrazin-3-yl)imidazo[1,2-b]pyridazin-2-yl)isonicotinamide | 556 | 7.81 7.90 | K L |
| 465 | 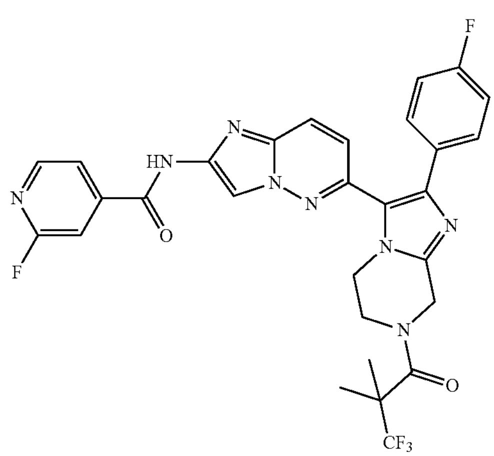 [SMILES: CC(C)(C(=O)N1CCn2c(nc(-c3ccc(F)cc3)c2-c2ccc3nc(NC(=O)c4ccnc(F)c4)cn3n2)C1)C(F)(F)F] | 2-Fluoro-N-(6-(2-(4-fluorophenyl)-7-(3,3,3-trifluoro-2,2-dimethylpropanoyl)-5,6,7,8-tetrahydroimidazo[1,2-a]pyrazin-3-yl)imidazo[1,2-b]pyridazin-2-yl)isonicotinamide | 609 [M − H] | 8.67 8.95 | K L |

TABLE 49-continued

| Compound No. | Structure | Name | [M + H]+ | Ret Time (min) | HPLC Method |
|---|---|---|---|---|---|
| 466 | 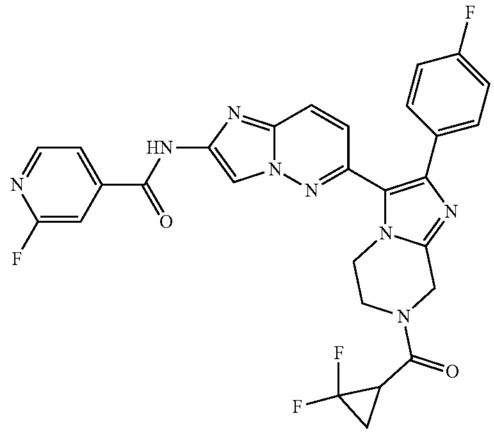 [SMILES: O=C(Nc1cn2nc(-c3c(-c4ccc(F)cc4)nc4n3CCN(C(=O)C3CC3(F)F)C4)ccc2n1)c1ccnc(F)c1] | N-(6-(7-(2,2-Difluorocyclopropanecarbonyl)-2-(4-fluorophenyl)-5,6,7,8-tetrahydroimidazo[1,2-a]pyrazin-3-yl)imidazo[1,2-b]pyridazin-2-yl)-2-fluoroisonicotinamide | 577 | 7.78<br>8.20 | K<br>L |
| 467 | 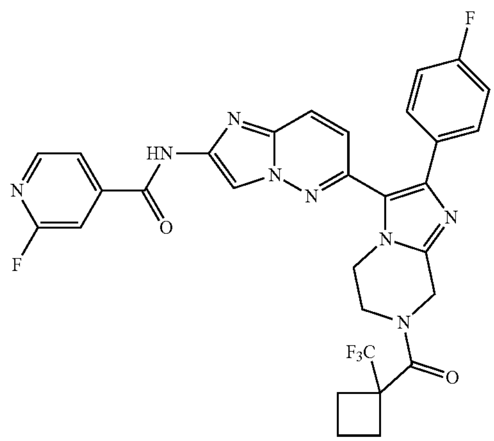 [SMILES: O=C(Nc1cn2nc(-c3c(-c4ccc(F)cc4)nc4n3CCN(C(=O)C3(C(F)(F)F)CCC3)C4)ccc2n1)c1ccnc(F)c1] | 2-Fluoro-N-(6-(2-(4-fluorophenyl)-7-(1-(trifluoromethyl)cyclobutanecarbonyl)-5,6,7,8-tetrahydroimidazo[1,2-a]pyrazin-3-yl)imidazo[1,2-b]pyridazin-2-yl)isonicotinamide | 621 | 8.90<br>9.13 | K<br>L |
| 468 | 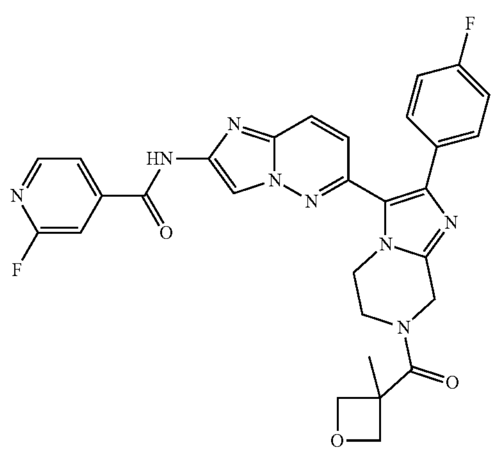 [SMILES: CC1(C(=O)N2CCn3c(nc(-c4ccc(F)cc4)c3-c3ccc4nc(NC(=O)c5ccnc(F)c5)cn4n3)C2)COC1] | 2-Fluoro-N-(6-(2-(4-fluorophenyl)-7-(3-methyloxetane-3-carbonyl)-5,6,7,8-tetrahydroimidazo[1,2-a]pyrazin-3-yl)imidazo[1,2-b]pyridazin-2-yl)isonicotinamide | 569 | 7.07<br>7.14 | K<br>L |

TABLE 49-continued

| Compound No. | Structure | Name | [M + H]+ | Ret Time (min) | HPLC Method |
|---|---|---|---|---|---|
| 469 | 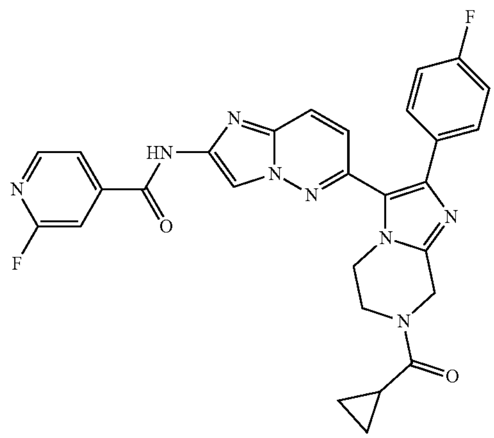 [SMILES: O=C(Nc1cn2nc(-c3c(-c4ccc(F)cc4)nc4n3CCN(C(=O)C3CC3)C4)ccc2n1)c1ccnc(F)c1] | N-(6-(7-(Cyclopropanecarbonyl)-2-(4-fluorophenyl)-5,6,7,8-tetrahydroimidazo [1,2-a]pyrazin-3-yl)imidazo[1,2-b]pyridazin-2-yl)-2-fluoroisonicotinamide | 541 | 7.04<br>7.60 | K<br>L |
| 470 | 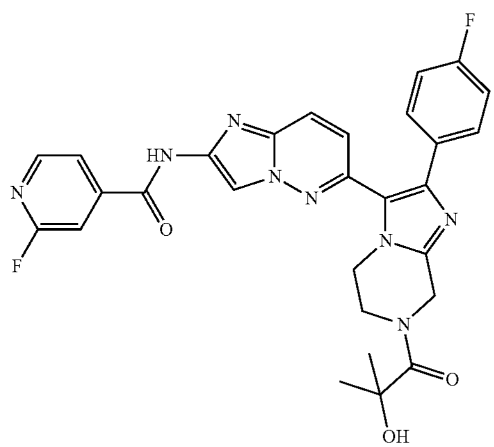 [SMILES: CC(C)(O)C(=O)N1CCn2c(nc(-c3ccc(F)cc3)c2-c2ccc3nc(NC(=O)c4ccnc(F)c4)cn3n2)C1] | 2-Fluoro-N-(6-(2-(4-fluorophenyl)-7-(2-hydroxy-2-methylpropanoyl)-5,6,7,8-tetrahydroimidazo[1,2-a]pyrazin-3-yl)imidazo[1,2-b]pyridazin-2-yl)isonicotinamide | 559 | 6.67<br>7.26 | K<br>L |
| 471 | 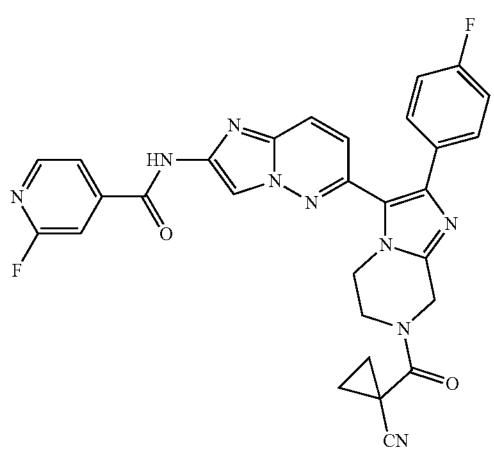 [SMILES: N#CC1(C(=O)N2CCn3c(nc(-c4ccc(F)cc4)c3-c3ccc4nc(NC(=O)c5ccnc(F)c5)cn4n3)C2)CC1] | N-(6-(7-(1-Cyanocyclopropanecarbonyl)-2-(4-fluorophenyl)-5,6,7,8-tetrahydroimidazo[1,2-a]pyrazin-3-yl)imidazo[1,2-b]pyridazin-2-yl)-2-fluoroisonicotinamide | 566 | 8.17<br>7.83 | K<br>L |

TABLE 49-continued

| Compound No. | Structure | Name | [M + H]+ | Ret Time (min) | HPLC Method |
|---|---|---|---|---|---|
| 472 | 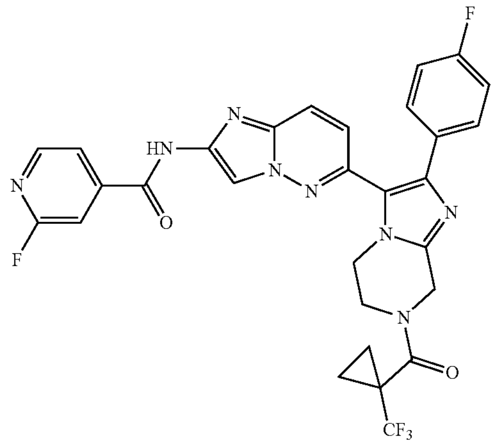 [SMILES: O=C(Nc1cn2nc(-c3c(-c4ccc(F)cc4)nc4n3CCN(C(=O)C3(C(F)(F)F)CC3)C4)ccc2n1)c1ccnc(F)c1] | 2-Fluoro-N-(6-(2-(4-fluorophenyl)-7-(1-(trifluoromethyl)cyclopropanecarbonyl)-5,6,7,8-tetrahydroimidazo[1,2-a]pyrazin-3-yl)imidazo[1,2-b]pyridazin-2-yl)isonicotinamide | 609 | 8.48 8.71 | K L |
| 473 | 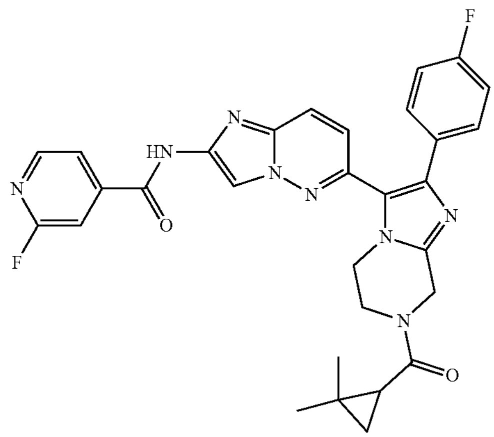 [SMILES: CC1(C)CC1C(=O)N1CCn2c(nc(-c3ccc(F)cc3)c2-c2ccc3nc(NC(=O)c4ccnc(F)c4)cn3n2)C1] | N-(6-(7-(2,2-Dimethylcyclopropanecarbonyl)-2-(4-fluorophenyl)-5,6,7,8-tetrahydroimidazo[1,2-a]pyrazin-3-yl)imidazo[1,2-b]pyridazin-2-yl)-2-fluoroisonicotinamide | 569 | 8.08 8.49 | K L |

Compound 474

Methyl 3-(2-(2-fluoroisonicotinamido)imidazo[1,2-b]pyridazin-6-yl)-2-(4-fluorophenyl)-5,6-dihydroimidazo[1,2-a]pyrazine-7(8H)-carboxylate

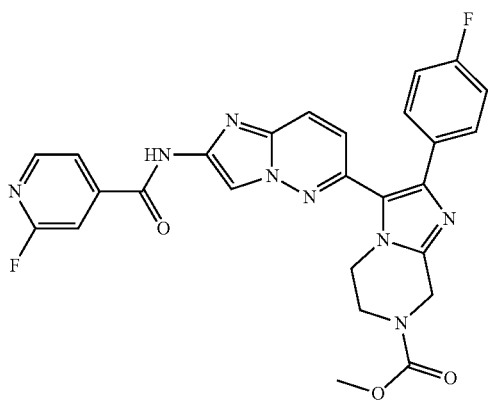 [SMILES: COC(=O)N1CCn2c(nc(-c3ccc(F)cc3)c2-c2ccc3nc(NC(=O)c4ccnc(F)c4)cn3n2)C1]

To the stirred solution of compound 455 (0.025 g, 0.053 mmol) in DCM (3.0 mL) was added DIPEA (0.028 mL, 0.159 mmol) followed by methyl chloroformate (0.015 g, 0.159 mmol) and the resulting reaction mixture was stirred at RT for overnight. The reaction mixture was diluted with DCM, washed with water, brine, dried over sodium sulfate, filtered and concentrated. The crude product was purified by reverse phase preparative HPLC purification to afford compound 474 (15 mg, 53%) as a yellow solid. MS(ES): m/z=531.2 [M+H]+; HPLC Ret. Time 7.04 min and 7.40 min (HPLC Methods K and L); $^1$H NMR (400 MHz, DMSO-$d_6$) δ ppm 11.82 (s, 1H), 8.57 (s, 1H), 8.48 (d, J=5.02 Hz, 1H), 8.06 (d, J=8.53 Hz, 1H), 7.96-8.00 (m, 1H), 7.82 (s, 1H), 7.50-7.56 (m, 2H), 7.15-7.20 (m, 2H), 7.11 (s, 1H), 4.76 (s, 2H), 4.15 (d, J=5.52 Hz, 2H), 3.88 (d, J=5.02 Hz, 2H), 3.71 (s, 3H).

The following compounds in Table 50 were prepared by the procedure described for the preparation of compound 474 from the compound 455 using the corresponding reagents.

TABLE 50

| Compound No | Structure | Name | [M + H]+ | Ret Time (min) | HPLC Method |
|---|---|---|---|---|---|
| 475 | 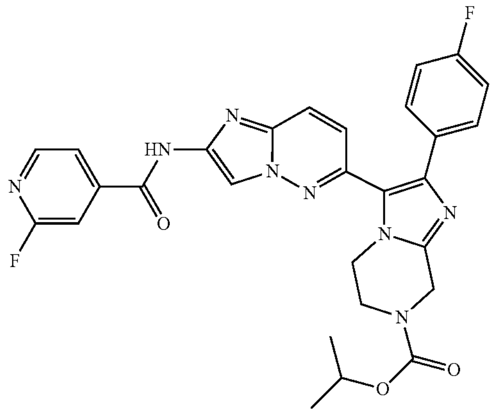 [SMILES: CC(C)OC(=O)N1CCn2c(nc(-c3ccc(F)cc3)c2-c2ccc3nc(NC(=O)c4ccnc(F)c4)cn3n2)C1] | Isopropyl 3-(2-(2-fluoroisonicotinamido)imidazo[1,2-b]pyridazin-6-yl)-2-(4-fluorophenyl)-5,6-dihydroimidazo[1,2-a]pyrazine-7(8H)-carboxylate | 557 [M − H] | 8.03 8.32 | K L |

Compound 476

2-Fluoro-N-(6-(2-(4-fluorophenyl)-7-(methylsulfonyl)-5,6,7,8-tetrahydroimidazo[1,2-a]pyrazin-3-yl)imidazo[1,2-b]pyridazin-2-yl)isonicotinamide

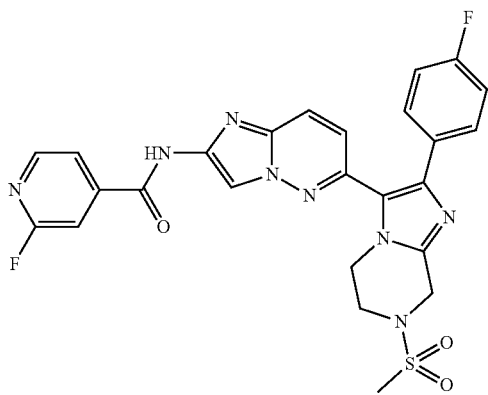 [SMILES: CS(=O)(=O)N1CCn2c(nc(-c3ccc(F)cc3)c2-c2ccc3nc(NC(=O)c4ccnc(F)c4)cn3n2)C1]

To the stirred solution of compound 455 (0.025 g, 0.053 mmol) in DCM (3.0 mL) and DMF (0.5 mL) was added DIPEA (0.028 mL, 0.159 mmol) followed by methane sulfonyl chloride (0.018 g, 0.159 mmol) and the reaction mixture was stirred at RT for overnight. The reaction mixture was diluted with DCM, washed with water, brine, dried over sodium sulfate, filtered and concentrated. The crude product was purified by reverse phase preparative HPLC purification to afford compound 476 (10 mg, 34%) as a yellow solid. MS(ES): m/z=551.1 [M+H]+; HPLC Ret. Time 7.79 min and 7.89 min (HPLC Method K and L); $^1$H NMR (400 MHz, DMSO-$d_6$) δ ppm 11.91 (s, 1H), 8.59 (d, J=0.56 Hz, 1H), 8.48 (d, J=5.15 Hz, 1H), 8.06 (dd, J=9.38, 0.60 Hz, 1H), 7.94-7.99 (m, 1H), 7.82 (s, 1H), 7.51-7.59 (m, 2H), 7.16-7.23 (m, 2H), 7.11 (d, J=9.35 Hz, 1H), 4.60 (s, 2H), 4.25 (t, J=5.40 Hz, 2H), 3.71 (t, J=5.36 Hz, 2H), 3.13 (s, 3H).

The following compound in Table 51 were prepared by the procedure described for the preparation of compound 476 from the compound 455 using the corresponding sulfonyl chloride.

TABLE 51

| Compound No | Structure | Name | [M + H]+ | Ret Time (min) | HPLC Method |
|---|---|---|---|---|---|
| 477 | 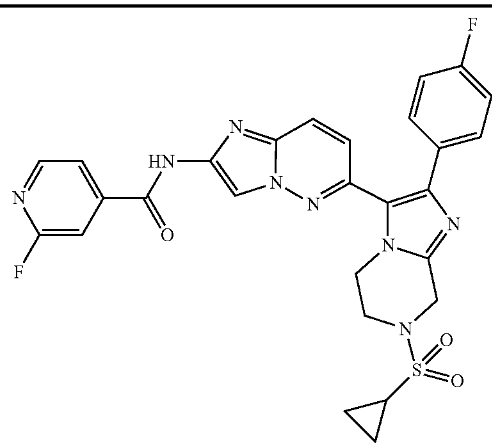 | N-(6-(7-(Cyclopropylsulfonyl)-2-(4-fluorophenyl)-5,6,7,8-tetrahydroimidazo[1,2-a]pyrazin-3-yl)imidazo[1,2-b]pyridazin-2-yl)-2-fluoroisonicotinamide | 575 | 8.17 8.39 | K L |

Compound 478

2-Fluoro-N-(6-(2-(4-fluorophenyl)-7-(3,3,3-trifluoropropyl)-5,6,7,8-tetrahydroimidazo[1,2-a]pyrazin-3-yl)imidazo[1,2-b]pyridazin-2-yl)isonicotinamide

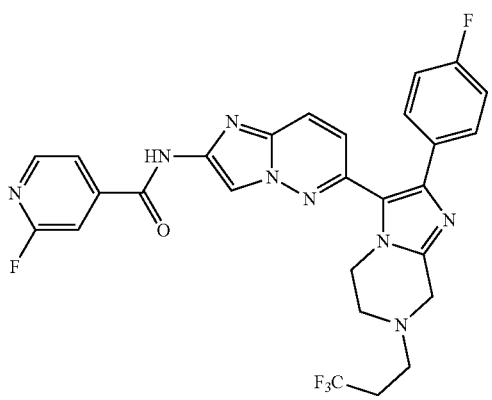 [SMILES: O=C(Nc1cn2nc(-c3c(-c4ccc(F)cc4)nc4n3CCN(CCC(F)(F)F)C4)ccc2n1)c1ccnc(F)c1]

To the stirred solution of compound 455 (0.025 g, 0.053 mmol) in DCM (1.0 mL) and MeOH (1.0 mL) was added 3,3,3-trifluoropropanal (0.015 g, 0.132 mmol) and sodium cyanoborohydride (9.98 mg, 0.159 mmol) and the reaction mixture was stirred at RT for overnight. The reaction mixture was concentrated, diluted with DCM, washed with water, brine, dried over sodium sulfate, filtered and concentrated under reduced pressure. The crude product was purified by reverse phase preparative HPLC purification to afford compound 478 (10 mg, 33%) as a yellow solid. MS(ES): m/z=568.7 [M+H]$^+$; HPLC Ret. Time 6.96 min and 7.42 min (HPLC Method K and L); $^1$H NMR (400 MHz, DMSO-d$_6$) δ ppm 11.90 (s, 1H), 8.57 (s, 1H), 8.48 (d, J=5.52 Hz, 1H), 8.04 (d, J=10.04 Hz, 1H), 7.98 (dt, J=5.15, 1.69 Hz, 1H), 7.82 (s, 1H), 7.49-7.56 (m, 2H), 7.13-7.20 (m, 2H), 7.11 (s, 1H), 4.12 (t, J=5.52 Hz; 2H), 3.83 (s, 2H), 2.97 (t, J=5.27 Hz, 2H), 2.80-2.89 (m, 2H), 2.57-2.72 (m, 2H).

The following compounds in Table 52 were prepared by the procedure described for the preparation of compound 478 from the compound 455 using the corresponding ketones.

TABLE 52

| Compound No | Structure | Name | [M + H]$^+$ | Ret Time (min) | HPLC Method |
|---|---|---|---|---|---|
| 479 | 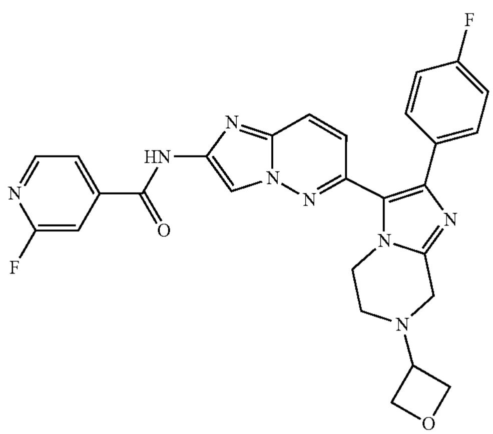 [SMILES: O=C(Nc1cn2nc(-c3c(-c4ccc(F)cc4)nc4n3CCN(C3COC3)C4)ccc2n1)c1ccnc(F)c1] | 2-Fluoro-N-(6-(2-(4-fluorophenyl)-7-(oxetan-3-yl)-5,6,7,8-tetrahydroimidazo[1,2-a]pyrazin-3-yl)imidazo[1,2-b]pyridazin-2-yl)isonicotinamide | 527 | 6.22<br>6.77 | K<br>L |
| 480 | 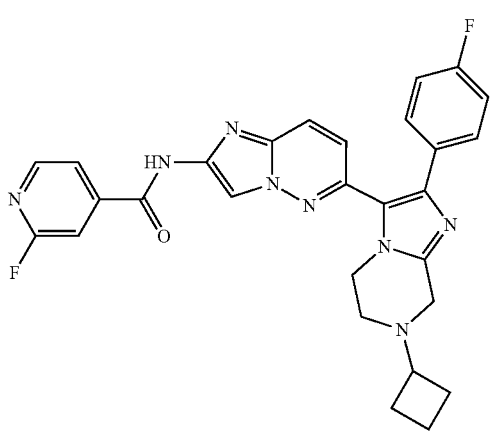 [SMILES: O=C(Nc1cn2nc(-c3c(-c4ccc(F)cc4)nc4n3CCN(C3CCC3)C4)ccc2n1)c1ccnc(F)c1] | N-(6-(7-Cyclobutyl-2-(4-fluorophenyl)-5,6,7,8-tetrahydroimidazo[1,2-a]pyrazin-3-yl)imidazo[1,2-b]pyridazin-2-yl)-2-fluoroisonicotinamide | 525 | 6.35<br>7.14 | K<br>L |

Compound 481

N-(tert-Butyl)-3-(2-(2-fluoroisonicotinamido)imidazo[1,2-b]pyridazin-6-yl)-2-(4-fluorophenyl)-5,6-dihydroimidazo[1,2-a]pyrazine-7(8H)-carboxamide

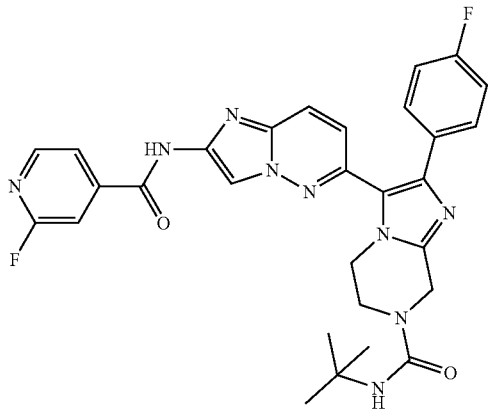 [SMILES: CC(C)(C)NC(=O)N1CCn2c(nc(-c3ccc(F)cc3)c2-c2ccc3nc(NC(=O)c4ccnc(F)c4)cn3n2)C1]

To the stirred solution of compound 455 (0.020 g, 0.042 mmol) in DMF (2.0 mL) was added tert-butylisocyanate (6.29 mg, 0.063 mmol) stirred at RT for overnight. The reaction mixture was concentrated, diluted with ethyl acetate, washed with water, brine, dried over sodium sulfate, filtered and concentrated under reduced pressure. The crude product was purified by reverse phase preparative HPLC purification to afford compound 481 (7.2 mg, 29%) as a yellow solid. MS(ES): m/z=571.7 [M+H]$^+$; HPLC Ret. Time 7.68 min and 8.14 min (HPLC Method K and L); $^1$H NMR (400 MHz, DMSO-$d_6$) δ ppm 11.90 (s, 1H), 8.57 (s, 1H), 8.48 (d, J=5.15 Hz, 1H), 8.05 (dd, J=9.41, 0.56 Hz, 1H), 7.98 (dt, J=5.11, 1.65 Hz, 1H), 7.82 (s, 1H), 7.44-7.56 (m, 2H), 7.14-7.24 (m, 2H), 7.10 (d, J=9.35 Hz, 1H), 6.22 (s, 1H), 4.69 (s, 2H), 4.06-4.12 (m, 2H), 3.76-3.83 (m, 2H), 1.31 (s, 9H).

The following compounds in Table 53 were prepared by the procedure described for the preparation of compound 481 from the compound 455 using the corresponding isocyanates.

TABLE 53

| Compound No. | Structure | Name | [M + H]$^+$ | Ret Time (min) | HPLC Method |
|---|---|---|---|---|---|
| 482 | 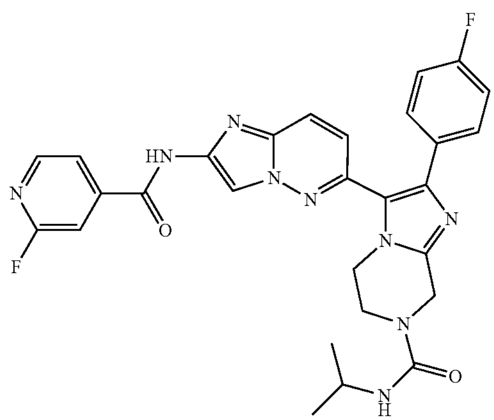 [SMILES: CC(C)NC(=O)N1CCn2c(nc(-c3ccc(F)cc3)c2-c2ccc3nc(NC(=O)c4ccnc(F)c4)cn3n2)C1] | 3-(2-(2-Fluoroisonicotinamido)imidazo[1,2-b]pyridazin-6-yl)-2-(4-fluorophenyl)-N-isopropyl-5,6-dihydroimidazo[1,2-a]pyrazine-7(8H)-carboxamide | 558 | 6.80<br>7.42 | K<br>L |
| 483 | 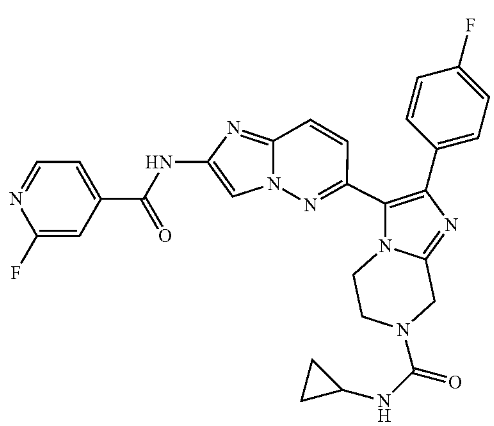 [SMILES: O=C(Nc1cn2nc(-c3c(-c4ccc(F)cc4)nc4n3CCN(C(=O)NC3CC3)C4)ccc2n1)c1ccnc(F)c1] | N-Cyclopropyl-3-(2-(2-fluoroisonicotinamido)imidazo[1,2-b]pyridazin-6-yl)-2-(4-fluorophenyl)-5,6-dihydroimidazo[1,2-a]pyrazine-7(8H)-carboxamide | 556 | 6.53<br>7.42 | K<br>L |

TABLE 53-continued

| Compound No. | Structure | Name | [M + H]⁺ | Ret Time (min) | HPLC Method |
|---|---|---|---|---|---|
| 484 | 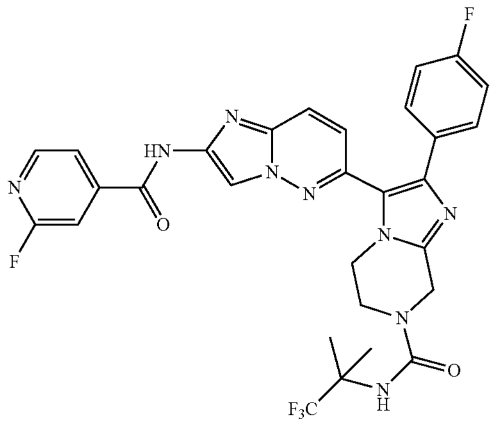 [SMILES: CC(C)(NC(=O)N1CCn2c(nc(-c3ccc(F)cc3)c2-c2ccc3nc(NC(=O)c4ccnc(F)c4)cn3n2)C1)C(F)(F)F] | 3-(2-(2-Fluoroisonicotinamido) imidazo[1,2-b]pyridazin-6-yl)-2-(4-fluorophenyl)-N-(1,1,1-trifluoro-2-methylpropan-2-yl)-5,6-dihydroimidazo[1,2-a]pyrazine-7(8H)-carboxamide | 626 | 7.89 8.96 | K L |
| 485 | 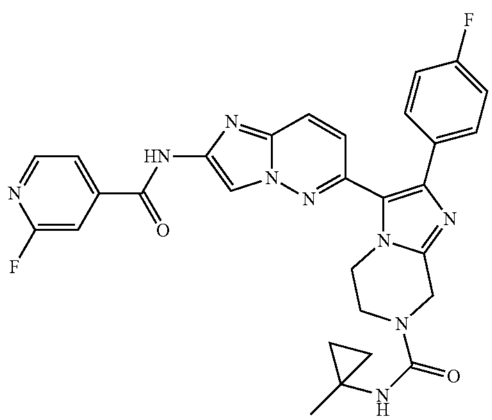 [SMILES: CC1(NC(=O)N2CCn3c(nc(-c4ccc(F)cc4)c3-c3ccc4nc(NC(=O)c5ccnc(F)c5)cn4n3)C2)CC1] | 3-(2-(2-Fluoroisonicotinamido) imidazo[1,2-b]pyridazin-6-yl)-2-(4-fluorophenyl)-N-(1-methylcyclopropyl)-5,6-dihydroimidazo[1,2-a]pyrazine-7(8H)-carboxamide | 570 | 6.83 7.49 | K L |
| 486 | 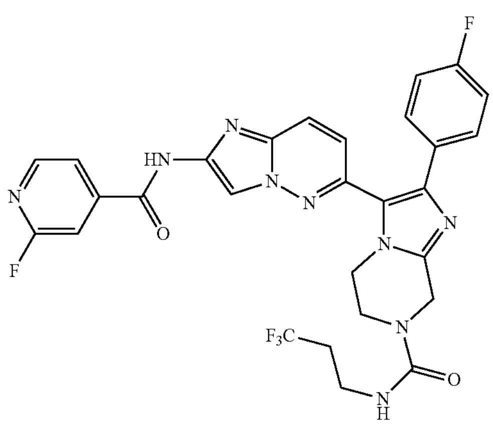 [SMILES: O=C(Nc1cn2nc(-c3c(-c4ccc(F)cc4)nc4n3CCN(C(=O)NCCC(F)(F)F)C4)ccc2n1)c1ccnc(F)c1] | 3-(2-(2-Fluoroisonicotinamido) imidazo[1,2-b]pyridazin-6-yl)-2-(4-fluorophenyl)-N-(3,3,3-trifluoropropyl)-5,6-dihydroimidazo[1,2-a]pyrazine-7(8H)-carboxamide | 612 | 8.16 7.60 | K L |

TABLE 53-continued

| Compound No. | Structure | Name | [M + H]+ | Ret Time (min) | HPLC Method |
|---|---|---|---|---|---|
| 487 | 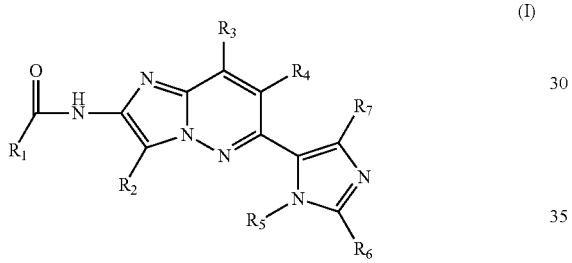 | 3-(2-(2-Fluoroisonicotinamido)imidazo[1,2-b]pyridazin-6-yl)-2-(4-fluorophenyl)-N-(1-(trifluoromethyl)cyclopropyl)-5,6-dihydroimidazo[1,2-a]pyrazine-7(8H)-carboxamide | 622 | 7.50<br>8.10 | K<br>L |

What is claimed is:

1. A compound according to Formula (I):

(I)

or a pharmaceutically acceptable salt thereof, wherein:

$R_1$ is selected from $NR_aR_a$, $C_{1-4}$alkyl optionally substituted with OH, CN, and aryl, $C_{2-4}$alkenyl optionally substituted with OH, CN, and $C_{6-15}$ aryl, $-(CR_dR_d)_r-C_{3-13}$ carbocyclyl substituted with 0-5 $R_{11}$, and $-(CR_dR_d)_r$-4- to 14-membered heterocyclyl comprising carbon atoms and 1 to 3 heteroatoms selected from N, $NR_{12}$, O, S, and substituted with 0-5 $R_{11}$;

$R_2$ is selected from H, $C_{1-4}$alkyl, F, Cl, Br, and CN;

$R_3$ is selected from H and $C_{1-4}$alkyl;

$R_4$ is selected from H, $C_{1-4}$alkyl, F, Cl, Br, and CN;

$R_5$ is selected from H, $C_{1-4}$alkyl substituted with 0-4 $R_e$, $-(CH_2)_r-C_{3-6}$ carbocyclyl substituted with 0-4 $R_e$, and $-(CH_2)_r$-4- to 14-membered heterocyclyl comprising carbon atoms and 1 to 3 heteroatoms selected from N, $NR_8$, O, S, and substituted with 0-4 $R_e$;

$R_6$, is selected from H, $C_{1-6}$alkyl substituted with 0-3 $R_e$, and $C_{3-6}$carbocyclyl substituted with 0-3 $R_e$; or $R_5$ and $R_6$ together with the nitrogen atom and the adjacent carbon atom to which they are respectively attached form a 4- to 14-membered heterocyclic ring substituted with 0-5 $R_9$;

$R_7$ is aryl substituted with 0-3 $R_e$;

$R_8$ is selected from H, $C_{1-4}$ alkyl substituted with 0-3 $R_e$, $-(CH_2)_rOR_b$, $-(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rC(=O)(CH_2)_rNR_aR_a$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_2NR_aR_a$, $-(CH_2)_rNR_aS(O)_2NR_aR_a$, $-(CH_2)_rNR_aS(O)_2R_c$, $(CH_2)_r-C_{3-6}$ carbocyclyl substituted with 0-3 $R_e$, and $-(CH_2)_r$-4- to 14-membered heterocyclyl comprising carbon atoms and 1 to 4 heteroatoms selected from N, O, S and substituted with 0-3 $R_e$;

$R_9$ is selected from $C_{1-4}$ alkyl substituted with 0-3 $R_e$, $-(CH_2)_rNR_aR_a$, $-(CH_2)_rC(=O)R_b$, $-(CH_2)_rC(=O)OR_b$, $-(CH_2)_rC(=O)NR_aR_a$, $S(O)_pR_c$, $(CH_2)_r-C_{3-6}$ carbocyclyl substituted with 0-3 $R_e$, and $-(CH_2)_r$-4- to 14-membered heterocyclyl comprising carbon atoms and 1 to 4 heteroatoms selected from N, O, S and substituted with 0-3 $R_e$;

$R_{11}$, at each occurrence, is independently selected from H, F, Cl, Br, =O, CN, $NO_2$, $-OR_b$, $-S(O)_pR_c$, $-C(=O)R_b$, $-(CR_dR_d)_rNR_aR_a$, $-(CR_dR_d)_rC(=O)NR_aR_a$, $-NR_aC(=O)R_b$, $-NR_aC(=O)OR_b$, $-OC(=O)NR_aR_a$, $-NR_aC(=O)NR_aR_a$, $-(CR_dR_d)_rC(=O)OR_b$, $-S(O)_2NR_aR_a$, $-NR_aS(O)_2NR_aR_a$, $-NR_aS(O)_2R_c$, $C_{1-6}$ alkyl substituted with 0-5 $R_e$, $-(CR_dR_d)_r-C_{3-6}$carbocyclyl substituted with 0-5 $R_e$, and $-(CR_dR_d)_r$-4- to 14-membered heterocyclyl substituted with 0-5 $R_e$;

$R_{12}$ is selected from H, $-C(=O)R_b$, $C_{1-6}$ alkyl substituted with 0-5 $R_e$, $-(CH_2)_r-C_{3-6}$carbocyclyl substituted with 0-5 $R_e$, and $-(CH_2)_r$-4- to 14-membered heterocyclyl comprising carbon atoms and 1 to 4 heteroatoms selected from N, O, S and substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-4- to 14-membered heterocyclyl comprising carbon atoms and 1 to 4 heteroatoms selected from N, O, S and substituted with 0-5 $R_e$; or $R_a$ and $R_a$ together with the nitrogen atom to which they are both attached form a 4- to 14-membered heterocyclic ring comprising carbon atoms and 1 to 4 heteroatoms selected from N, O, S and substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-4- to 14-membered heterocyclyl comprising carbon atoms and 1 to 4 heteroatoms selected from N, O, S and substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and 4- to 14-membered heterocyclyl comprising carbon atoms and 1 to 4 heteroatoms selected from N, O, S;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —(CH$_2$)$_r$—$C_{3-6}$ cycloalkyl, F, Cl, Br, CN, NO$_2$, =O, CO$_2$H, —(CH$_2$)$_r$OC$_{1-5}$ alkyl, —(CH$_2$)$_r$OR$_f$, S(O)$_p$R$_f$, S(O)$_p$NR$_f$R$_f$, and —(CH$_2$)$_r$NR$_f$R$_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

2. The compound according to claim 1 having Formula (II):

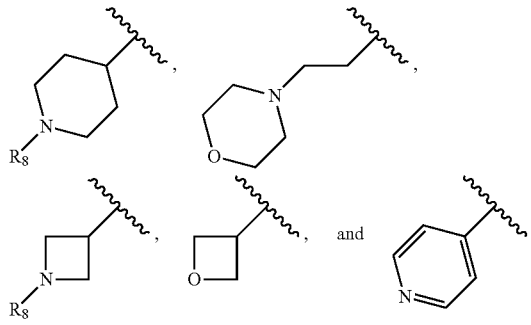

or a pharmaceutically acceptable salt thereof, wherein:
$R_e'$ is selected from F, Cl, Br, OC$_{1-6}$ alkyl, and $C_{1-6}$ alkyl substituted with 0-5 $R_f$;

$R_5$ is selected from H, $C_{1-4}$alkyl substituted with 0-3 $R_e$, —(CH$_2$)$_r$—$C_{3-6}$ carbocyclyl substituted with 0-3 $R_e$, and —(CH$_2$)$_r$-4- to 14-membered heterocyclyl comprising carbon atoms and 1 to 3 heteroatoms selected from N, NR$_8$, O, S, and substituted with 0-3 $R_e$;

$R_6$, is selected from H, $C_{1-6}$alkyl substituted with 0-2 $R_e$, and $C_{3-6}$cycloalkyl substituted with 0-2 $R_e$; or $R_5$ and $R_6$ together with the nitrogen atom and the adjacent carbon atom to which they are respectively attached form a 4- to 14-membered heterocyclic ring comprising carbon atoms and 1 to 4 heteroatoms selected from N, O, S and substituted with 0-4 $R_9$; and $R_8$ is selected from H, $C_{1-4}$ alkyl substituted with 0-3 $R_e$, —(CH$_2$)$_r$S(O)$_p$R$_c$, —(CH$_2$)$_r$CN, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, (CH$_2$)$_r$C(=O)NR$_a$R$_a$, —(CH$_2$)$_r$C(=O)(CH$_2$)$_r$NR$_a$R$_a$, —(CH$_2$)$_r$NR$_a$C(=O)R$_d$, —(CH$_2$)$_r$NR$_a$C(=O)OR$_b$, —(CH$_2$)$_r$OC(=O)NR$_a$R$_a$, —(CH$_2$)$_r$NR$_a$C(=O) NR$_a$R$_a$, —(CH$_2$)$_r$C(=O)OR$_b$, —(CH$_2$)$_r$S(O)$_2$NR$_a$R$_a$, —(CH$_2$)$_r$NR$_a$S(O)$_2$R$_c$, —(CH$_2$)$_r$—$C_{3-6}$ carbocyclyl substituted with 0-3 $R_e$, and —(CH$_2$)$_r$-4- to 14-membered heterocyclyl comprising carbon atoms and 1 to 4 heteroatoms selected from N, O, S and substituted with 0-3 $R_e$.

3. The compound according to claim 2, wherein:
$R_5$ is selected from H, $C_{1-4}$alkyl substituted with 0-1 $R_e$, $C_{3-6}$cycloalkyl, aryl, and —(CH$_2$)$_r$-heterocyclyl selected from pyridyl, pyrimidinyl, pyrazinyl, pyridazinyl, triazinyl, furyl, thienyl, imidazolyl, thiazolyl, indolyl, pyrrolyl, oxazolyl, isoxazolyl, pyrazolyl, triazolyl, tetrazolyl, indazolyl, 1,2,4-thiadiazolyl, isothiazolyl, azetidinyl, pyrrolidinyl, piperidinyl, piperazinyl, and morpholinyl.

4. The compound according to claim 3, wherein:
$R_5$ is selected from H,

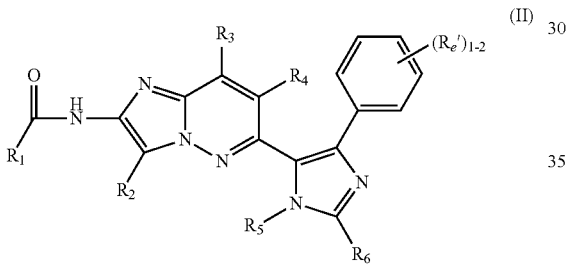

$R_8$ is selected from H, $C_{1-4}$ alkyl substituted with 0-3 $R_e$, —(CH$_2$)$_r$S(O)$_p$R$_c$, —(CH$_2$)$_r$OR$_b$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$(C=O)CH$_2$NR$_a$R$_a$, —(CH$_2$)$_r$NR$_a$C(=O)R$_b$, —(CH$_2$)$_r$NR$_a$C(=O)OR$_b$, —(CH$_2$)$_r$C(=O)OR$_b$, and —(CH$_2$)$_r$-4- to 14-membered heterocyclyl comprising carbon atoms and 1 to 4 heteroatoms selected from N, O, S and substituted with 0-3 $R_e$;

$R_a$, at each occurrence, is independently selected from H, $C_{1-6}$ alkyl substituted with 0-5 $R_e$, —(CH$_2$)$_r$—$C_{3-10}$carbocyclyl substituted with 0-5 $R_e$, and —(CH$_2$)$_r$-4- to 14-membered heterocyclyl comprising carbon atoms and 1 to 4 heteroatoms selected from N, O, S and substituted with 0-5 $R_e$; or $R_a$ and $R_a$ together with the nitrogen atom to which they are both attached form a 4- to 14-membered heterocyclic ring comprising carbon atoms and 1 to 4 heteroatoms selected from N, O, S and substituted with 0-5 $R_e$;

$R_b$, at each occurrence, is independently selected from H, $C_{1-6}$ alkyl substituted with 0-5 $R_e$, —(CH$_2$)$_r$—$C_{3-10}$carbocyclyl substituted with 0-5 $R_e$, and —(CH$_2$)$_r$-4- to 14-membered heterocyclyl comprising carbon atoms and 1 to 4 heteroatoms selected from N, O, S and substituted with 0-5 $R_e$;

$R_c$, at each occurrence, is independently selected from $C_{1-6}$ alkyl substituted with 0-5 $R_e$, $C_{3-6}$carbocyclyl, and 4- to 14-membered heterocyclyl comprising carbon atoms and 1 to 4 heteroatoms selected from N, O, S and;

$R_e$, at each occurrence, is independently selected from $C_{1-6}$ alkyl substituted with 0-5 $R_f$, —(CH$_2$)$_r$—$C_{3-6}$ cycloalkyl, F, Cl, Br, CN, NO$_2$, =O, CO$_2$H, —(CH$_2$)$_r$OC$_{1-5}$ alkyl, —(CH$_2$)$_r$OH, SH, and —(CH$_2$)$_r$NR$_f$R$_f$;

$R_f$, at each occurrence, is independently selected from H, $C_{1-5}$ alkyl, and phenyl, or $R_f$ and $R_f$ together with the nitrogen atom to which they are both attached form a heterocyclic ring.

5. The compound according to claim 1, wherein:
$R_5$ and $R_6$ together with the nitrogen atom and the adjacent carbon atom to which they are respectively attached form a 4- to 14-membered heterocyclic ring having 1 to 3 heteroatoms selected from N, O, S, and substituted with 0-3 $R_9$.

6. The compound according to claim 5 having Formula (III):

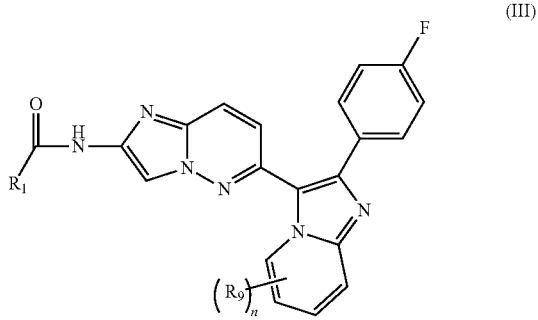

or a pharmaceutically acceptable salt thereof, wherein:
$R_9$ is selected from $NR_aR_a$, $SR_c$, and —$(CH_2)_r$-4- to 14-membered heterocyclyl comprising carbon atoms and 1 to 4 heteroatoms selected from N, O, S and substituted with 0-3 $R_e$;
$R_a$, at each occurrence, is independently selected from H, $C_{1-6}$ alkyl substituted with 0-5 $R_e$, $C_{3-10}$carbocyclyl substituted with 0-5 $R_e$, 4- to 14-membered heterocyclyl comprising carbon atoms and 1 to 4 heteroatoms selected from N, O, S and substituted with 0-5 $R_e$; or $R_a$ and $R_a$ together with the nitrogen atom to which they are both attached form a 4- to 14-membered heterocyclic ring comprising carbon atoms and 1 to 4 heteroatoms selected from N, O, S and substituted with 0-5 $R_e$;
$R_c$ is $C_{1-4}$ alkyl substituted with 0-5 $R_e$;
$R_e$, at each occurrence, is independently selected from $C_{1-6}$ alkyl, F, Cl, Br, CN, $NO_2$, =O, $CO_2H$, and OH; and
n, at each occurrence, is independently selected from zero, 1, and 2.

7. The compound according to claim 5 having Formula (IV):

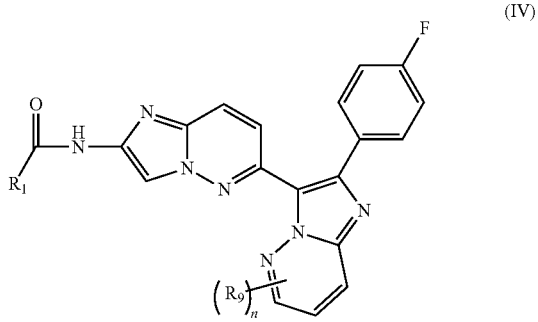

or a pharmaceutically acceptable salt thereof, wherein:
$R_9$ is selected from $NR_aR_a$, $SR_c$, and —$(CH_2)_r$-heterocyclyl substituted with 0-3 $R_e$;
$R_a$, at each occurrence, is independently selected from H, $C_{1-6}$ alkyl substituted with 0-5 $R_e$, $C_{3-10}$carbocyclyl substituted with 0-5 $R_e$, 4- to 14-membered heterocyclyl comprising carbon atoms and 1 to 4 heteroatoms selected from N, O, S and substituted with 0-5 $R_e$; or $R_a$ and $R_a$ together with the nitrogen atom to which they are both attached form a 4- to 14-membered heterocyclic ring comprising carbon atoms and 1 to 4 heteroatoms selected from N, O, S and substituted with 0-5 $R_e$;
$R_c$ is $C_{1-4}$ alkyl substituted with 0-5 $R_e$;
$R_e$, at each occurrence, is independently selected from $C_{1-6}$ alkyl, F, Cl, Br, CN, $NO_2$, =O, $CO_2H$, and OH; and
n, at each occurrence, is independently selected from zero, 1, and 2.

8. The compound according to claim 5 having Formula (V):

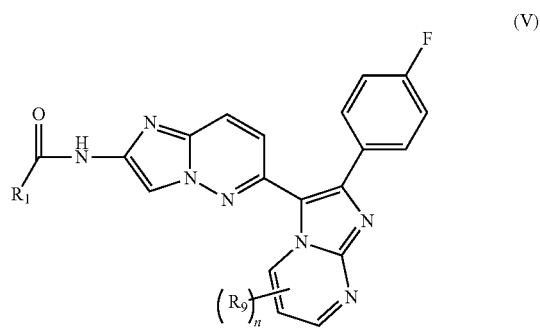

or a pharmaceutically acceptable salt thereof, wherein:
$R_9$ is selected from $NR_aR_a$, $SR_c$, and —$(CH_2)_r$-4- to 14-membered heterocyclyl comprising carbon atoms and 1 to 4 heteroatoms selected from N, O, S and substituted with 0-3 $R_e$;
$R_a$, at each occurrence, is independently selected from H, $C_{1-6}$ alkyl substituted with 0-5 $R_e$, $C_{3-10}$carbocyclyl substituted with 0-5 $R_e$ 4- to 14-membered heterocyclyl comprising carbon atoms and 1 to 4 heteroatoms selected from N, O, S and substituted with 0-5 $R_e$; or $R_a$ and $R_a$ together with the nitrogen atom to which they are both attached form a 4- to 14-membered heterocyclic ring comprising carbon atoms and 1 to 4 heteroatoms selected from N, O, S and substituted with 0-5 $R_e$;
$R_c$ is $C_{1-4}$ alkyl substituted with 0-5 $R_e$;
$R_e$, at each occurrence, is independently selected from $C_{1-6}$ alkyl F, Cl, Br, CN, $NO_2$, =O, $CO_2H$, and OH; and
n, at each occurrence, is independently selected from zero, 1, and 2.

9. The compound according to claim 2 wherein:
$R_1$ is selected from $C_{1-4}$alkyl substituted with OH and CN, —CH=CH$(CH_2)_r$-aryl substituted with 0-4 $R_{11}$, —$(CH_2)_r$—$C_{6-15}$ aryl substituted with 0-4 $R_{11}$, —$(CH_2)_r$—$C_{3-6}$ cycloalkyl substituted with 0-4 $R_{11}$, and —$(CH_2)_r$-4- to 14-membered heterocyclyl comprising carbon atoms and 1 to 3 heteroatoms selected from N, $NR_{12}$, O, S and substituted with 0-4 $R_{11}$;
$R_{11}$, at each occurrence, is independently selected from H, F, Cl, Br, =O, CN, $NO_2$, —$OR_b$, —$S(O)_pR_c$, —C(=O)$R_b$, —$(CH_2)_rNR_aR_a$, —$(CH_2)_rC(=O)NR_aR_a$, —$NR_aC(=O)R_b$, —$NR_aC(=O)OR_b$, —OC(=O)$NR_aR_a$, —$NR_aC(=O)NR_aR_a$, —$(CH_2)_rC(=O)OR_b$, $C_{1-6}$ alkyl substituted with 0-5 $R_e$, —$(CH_2)_r$—$C_{3-6}$carbocyclyl substituted with 0-5 $R_e$, and —$(CH_2)_r$-4- to 14-membered heterocyclyl comprising carbon atoms and 1 to 4 heteroatoms selected from N, O, S and substituted with 0-5 $R_e$;

$R_{12}$ is independently selected from H, —C(=O)$R_b$, $C_{1-6}$ alkyl substituted with 0-5 $R_e$, —(CH$_2$)$_r$—C$_{3-6}$carbocyclyl substituted with 0-5 $R_e$, and —(CH$_2$)$_r$-4- to 14-membered heterocyclyl comprising carbon atoms and 1 to 4 heteroatoms selected from N, O, S and substituted with 0-5 $R_e$;

$R_a$, at each occurrence, is independently selected from H, $C_{1-6}$ alkyl substituted with 0-5 $R_e$, —(CH$_2$)$_r$—C$_{3-10}$carbocyclyl substituted with 0-5 $R_e$, and —(CH$_2$)$_r$-4- to 14-membered heterocyclyl comprising carbon atoms and 1 to 4 heteroatoms selected from N, O, S and substituted with 0-5 $R_e$; or $R_a$ and $R_a$ together with the nitrogen atom to which they are both attached form a 4- to 14-membered heterocyclic ring comprising carbon atoms and 1 to 4 heteroatoms selected from N, O, S and substituted with 0-5 $R_e$;

$R_b$, at each occurrence, is independently selected from H, $C_{1-6}$ alkyl substituted with 0-5 $R_e$, —(CH$_2$)$_r$—C$_{3-10}$carbocyclyl substituted with 0-5 $R_e$, and —(CH$_2$)$_r$-4- to 14-membered heterocyclyl comprising carbon atoms and 1 to 4 heteroatoms selected from N, O, S and substituted with 0-5 $R_e$;

$R_e$, at each occurrence, is independently selected from $C_{1-6}$ alkyl substituted with 0-5 $R_f$, —(CH$_2$)$_r$—C$_{3-6}$ cycloalkyl, F, Cl, Br, CN, NO$_2$, =O, CO$_2$H, —(CH$_2$)$_r$OC$_{1-5}$alkyl, —(CH$_2$)$_r$OH, SH, and —(CH$_2$)$_r$NR$_f$R$_f$; and $R_f$, at each occurrence, is independently selected from H, $C_{1-5}$ alkyl, and phenyl, or $R_f$ and $R_f$ together with the nitrogen atom to which they are both attached form a 4- to 14-membered heterocyclic ring comprising carbon atoms and 1 to 4 heteroatoms selected from N, O, S.

10. The compound according to claim 9, wherein:

$R_1$ is heterocyclyl selected from pyridyl, pyrimidinyl, pyrazinyl, pyridazinyl, triazinyl, furyl, quinolinyl, quinoxalinyl, dihydroquinolinyl, tetrahydroquinolinyl, tetrahydropyranyl, isoquinolinyl, thienyl, imidazolyl, thiazolyl, indolyl, pyrrolyl, oxazolyl, benzofuryl, benzothienyl, benzothiazolyl, benzoxazinyl, isoxazolyl, pyrazolyl, triazolyl, tetrazolyl, indazolyl, 1,2,3-thiadiazolyl, 1,2,4-thiadiazolyl, isothiazolyl, purinyl, carbazolyl, benzimidazolyl, indolinyl, benzodioxolanyl, benzodioxane, 1,5-naphthyridinyl, imidazopyridinyl, azetidinyl, pyrrolidinyl, piperidinyl, piperazinyl, and morpholinyl.

11. The compound according to claim 9, wherein:

$R_1$ is selected from

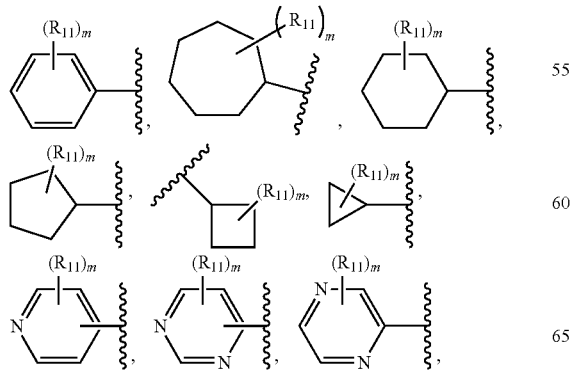

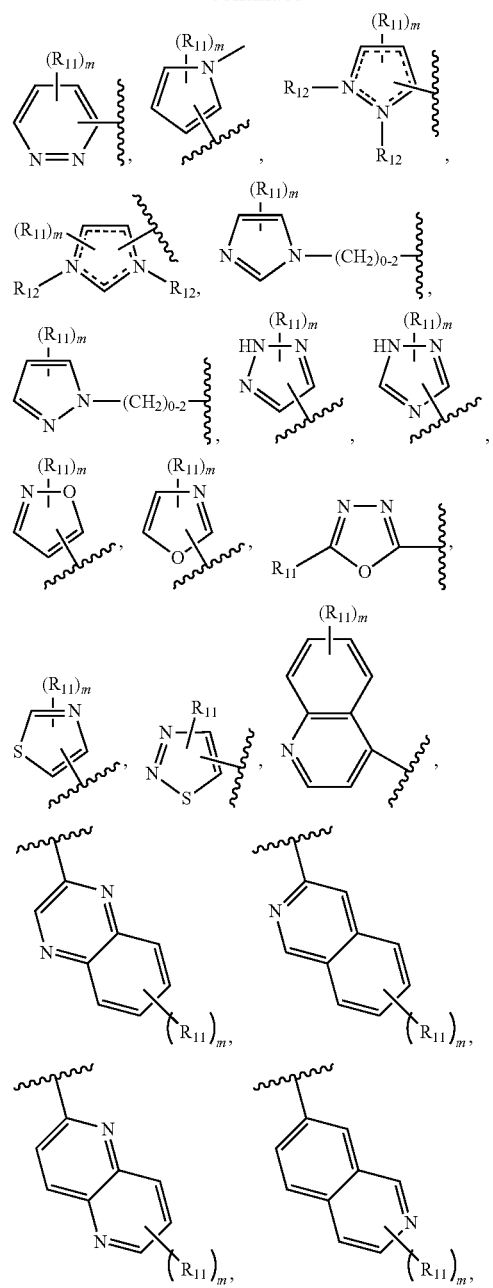

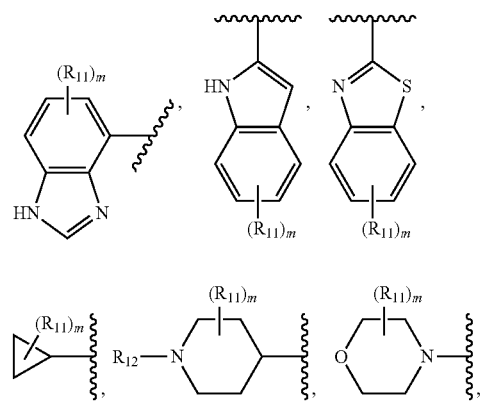

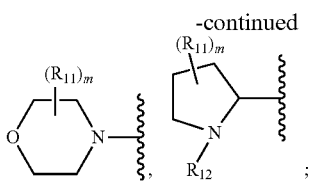

---- represents an optional bond;

$R_{11}$, at each occurrence, is independently selected from H, F, Cl, Br, =O, CN, —$OR_b$, —C(=O)$R_b$, —$(CH_2)_rNR_aR_a$, —$(CH_2)_rC(=O)NR_aR_a$, —$NR_aC(=O)R_b$, —$(CH_2)_rC(=O)OR_b$, $C_{1-6}$ alkyl substituted with 0-5 $R_e$, —$(CH_2)_r$—$C_{3-6}$carbocyclyl substituted with 0-5 $R_e$, and —$(CH_2)_r$-4- to 14-membered heterocyclyl comprising carbon atoms and 1 to 4 heteroatoms selected from N, O, S and substituted with 0-5 $R_e$;

$R_{12}$, at each occurrence, is independently selected from H, —C(=O)$R_b$, $C_{1-6}$ alkyl substituted with 0-5 $R_e$; and m, at each occurrence, is independently selected from zero, 1, and 2.

12. The compound according to claim 2, wherein:

$R_1$ is selected from —CH=CH(CH$_2$)$_r$-aryl, aryl substituted with 0-4 $R_{11}$, $C_{3-6}$ cycloalkyl substituted with 0-4 $R_{11}$, and —(CH$_2$)$_r$5- to 10-membered heterocyclyl comprising carbon atoms and 1 to 3 heteroatoms selected from N, $NR_{12}$, O, S and substituted with 0-4 $R_{11}$;

$R_5$ is selected from H, $C_{1-4}$alkyl substituted with 0-3 $R_e$ and —(CH$_2$)$_r$-4- to 14-membered heterocyclyl comprising carbon atoms and 1 to 3 heteroatoms selected from N, $NR_8$, O, S, and substituted with 0-3 $R_e$;

$R_6$, is selected from H, $C_{1-6}$alkyl substituted with 0-2 $R_e$, and $C_{3-6}$cycloalkyl substituted with 0-3 $R_e$; or $R_5$ and $R_6$ together with the nitrogen atom and the adjacent carbon atom to which they are respectively attached form a 4- to 14-membered heterocyclic ring comprising carbon atoms and 1 to 4 heteroatoms selected from N, O, S and substituted with 0-5 $R_9$; and $R_8$ is selected from H, $C_{1-4}$ alkyl substituted with 0-3 $R_e$, —(CH$_2$)$_r$O$R_b$, —(CH$_2$)$_r$C(=O)$R_b$, —(CH$_2$)$_r$NR$_a$R$_a$, —(CH$_2$)$_r$C(=O)NR$_a$R$_a$, and —(CH$_2$)$_r$-4- to 14-membered heterocyclyl comprising carbon atoms and 1 to 4 heteroatoms selected from N, O, S and substituted with 0-3 $R_e$;

$R_{11}$, at each occurrence, is independently selected from H, F, Cl, CN, —OR$_b$, —(CH$_2$)$_r$NR$_a$R$_a$, —NR$_a$C(=O)R$_b$, $C_{1-6}$ alkyl substituted with 0-5 $R_e$, —(CH$_2$)$_r$—$C_{3-6}$carbocyclyl substituted with 0-5 $R_e$, and —(CH$_2$)$_r$-5- to 10-membered heterocyclyl comprising carbon atoms and 1 to 4 heteroatoms selected from N, O, S and substituted with 0-5 $R_e$;

$R_a$, at each occurrence, is independently selected from H, $C_{1-6}$ alkyl substituted with 0-5 $R_e$, —(CH$_2$)$_r$—$C_{3-10}$carbocyclyl substituted with 0-5 $R_e$, and —(CH$_2$)$_r$-4- to 14-membered heterocyclyl comprising carbon atoms and 1 to 4 heteroatoms selected from N, O, S and substituted with 0-5 $R_e$; or $R_a$ and $R_a$ together with the nitrogen atom to which they are both attached form a 4- to 14-membered heterocyclic ring comprising carbon atoms and 1 to 4 heteroatoms selected from N, O, S and substituted with 0-5 $R_e$;

$R_b$, at each occurrence, is independently selected from H, $C_{1-6}$ alkyl substituted with 0-5 $R_e$, —(CH$_2$)$_r$—$C_{3-10}$carbocyclyl substituted with 0-5 $R_e$, and —(CH$_2$)$_r$-4- to 14-membered heterocyclyl comprising carbon atoms and 1 to 4 heteroatoms selected from N, O, S and substituted with 0-5 $R_e$;

$R_e$, at each occurrence, is independently selected from $C_{1-6}$ alkyl substituted with 0-5 $R_f$, —(CH$_2$)$_r$—$C_{3-6}$ cycloalkyl, F, Cl, Br, CN, NO$_2$, =O, CO$_2$H, —(CH$_2$)$_r$OC$_{1-5}$alkyl, —(CH$_2$)$_r$OH, SH, and —(CH$_2$)$_r$NR$_f$R$_f$; and $R_f$, at each occurrence, is independently selected from H, $C_{1-5}$ alkyl, and phenyl, or $R_f$ and $R_f$ together with the nitrogen atom to which they are both attached form a 4- to 14-membered heterocyclic ring comprising carbon atoms and 1 to 4 heteroatoms selected from N, O, S.

13. The compound according to claim 12, wherein:

$R_1$ is selected from

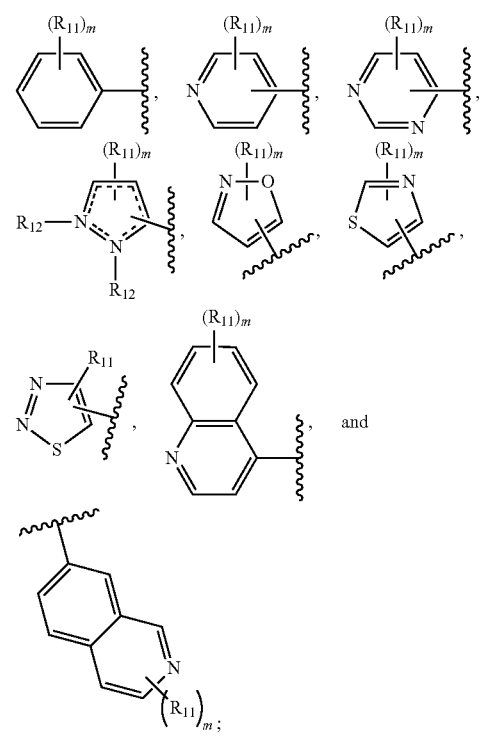

$R_5$ is selected from H, $C_{1-4}$alkyl substituted with 0-3 $R_e$,

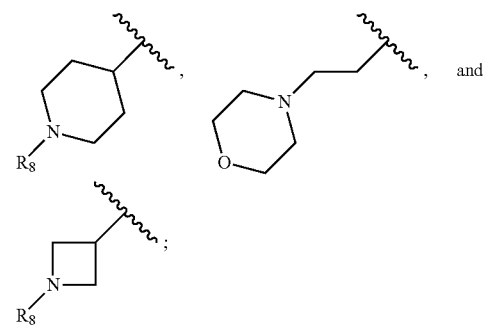

$R_6$, is selected from H, $C_{1-4}$alkyl, and $C_{3-6}$cycloalkyl; or $R_5$ and $R_6$ together with the nitrogen atom and the adjacent carbon atom to which they are respectively attached form a 4- to 14-membered heterocyclic ring comprising carbon atoms and 1 to 3 nitrogen atoms;

$R_8$ is selected from H, $C_{1-4}$alkyl, —$(CH_2)_rCN$, —$(CH_2)_rOH$, —$(CH_2)_rC(=O)NH2$, —$C(=O)CH_2NH2$, —$C(=O)CH_2CN$, —$C(=O)CH_2CF_3$, $C(=O)CH_2OH$, and $C(=O)$-isoxazolyl;

$R_{11}$, at each occurrence, is independently selected from F, Cl, CN, —$NR_aR_a$, —$NHC(=O)R_b$, $C_{1-4}$ alkyl substituted with 0-5 $R_e$,

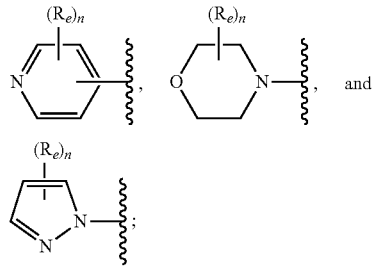

$R_{12}$, at each occurrence, is independently selected from H and $C_{1-4}$ alkyl;

$R_a$, at each occurrence, is independently selected from H, $C_{1-4}$ alkyl substituted with 0-5 $R_e$;

$R_b$, at each occurrence, is independently selected from H, $C_{1-4}$ alkyl substituted with 0-5 $R_e$;

$R_e$, at each occurrence, is independently selected from $C_{1-6}$ alkyl substituted with 0-5 $R_f$, —$(CH_2)_r$—$C_{3-6}$ cycloalkyl, F, Cl, Br, CN, $NO_2$, $=O$, $CO_2H$, —$(CH_2)_rOC_{1-5}$alkyl, —$(CH_2)_rOH$, SH, and $NH_2$;

m, at each occurrence, is independently selected from zero, 1, and 2 n, at each occurrence, is independently selected from zero and 1; and r, at each occurrence, is independently selected from zero, 1, and 2.

14. The compound according to claim 1 having Formula (VI):

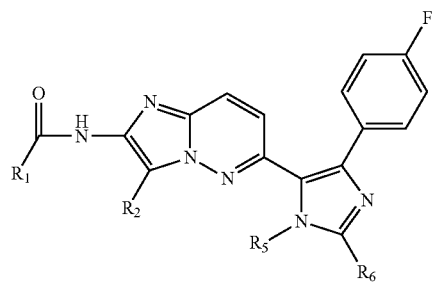

or a pharmaceutically acceptable salt thereof, wherein:

$R_1$ is selected from aryl substituted with 0-4 $R_{11}$, $C_{3-6}$cycloalkyl substituted with 0-4 $R_{11}$, and —$(CH_2)_r$5- to 10-membered heterocyclyl comprising carbon atoms and 1 to 4 heteroatoms selected from N, $NR_{12}$, O, S and substituted with 0-4 $R_{11}$;

$R_2$ is selected from H, $C_{1-4}$alkyl, F, Cl, Br, and CN;

$R_5$ is selected from H, $C_{1-4}$alkyl substituted with 0-3 $R_e$, —$(CH_2)_r$—$C_{3-6}$ carbocyclyl substituted with 0-3 $R_e$, and —$(CH_2)_r$-4- to 14-membered heterocyclyl comprising carbon atoms and 1 to 3 heteroatoms selected from N, $NR_8$, O, S, and substituted with 0-3 $R_e$;

$R_6$ is selected from H, $C_{1-6}$alkyl substituted with 0-2 $R_e$, and $C_{3-6}$cycloalkyl substituted with 0-2 $R_e$; and $R_8$ is selected from H, $C_{1-4}$ alkyl substituted with 0-3 $R_e$ —$(CH_2)_rCN$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rNR_aC(=O)R_d$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_2NR_aR_a$, —$(CH_2)_rNR_aS(O)_2R_c$, —$(CH_2)_r$—$C_{3-6}$ carbocyclyl substituted with 0-3 $R_e$, and —$(CH_2)_r$-4- to 14-membered heterocyclyl comprising carbon atoms and 1 to 4 heteroatoms selected from N, O, S and substituted with 0-3 $R_e$.

15. A pharmaceutical composition comprising one or more compounds of claim 1 and a pharmaceutically acceptable carrier.

* * * * *